United States Patent
Seth et al.

(10) Patent No.: US 11,149,264 B2
(45) Date of Patent: *Oct. 19, 2021

(54) MODIFIED COMPOUNDS AND USES THEREOF

(71) Applicant: Ionis Pharmaceuticals, Inc., Carlsbad, CA (US)

(72) Inventors: Punit P. Seth, Carlsbad, CA (US); Michael Oestergaard, Carlsbad, CA (US); Michael T. Migawa, Carlsbad, CA (US); Xue-hai Liang, Del Mar, CA (US); Wen Shen, Carlsbad, CA (US); Stanley T. Crooke, Carlsbad, CA (US); Eric E. Swayze, Encinitas, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/172,333

(22) Filed: Feb. 10, 2021

(65) Prior Publication Data

US 2021/0261945 A1 Aug. 26, 2021

Related U.S. Application Data

(63) Continuation of application No. 16/968,701, filed as application No. PCT/US2019/017725 on Feb. 12, 2019.

(60) Provisional application No. 62/746,511, filed on Oct. 16, 2018, provisional application No. 62/742,265, filed on Oct. 5, 2018, provisional application No. 62/739,088, filed on Sep. 28, 2018, provisional application No. 62/713,698, filed on Aug. 2, 2018, provisional application No. 62/686,632, filed on Jun. 18, 2018, provisional application No. 62/629,632, filed on Feb. 12, 2018.

(51) Int. Cl.
 *C12N 15/10* (2006.01)
 *C12N 15/113* (2010.01)

(52) U.S. Cl.
 CPC ............ *C12N 15/10* (2013.01); *C12N 15/113* (2013.01); *C12N 2310/315* (2013.01); *C12N 2310/3231* (2013.01)

(58) Field of Classification Search
 None
 See application file for complete search history.

(56) References Cited

U.S. PATENT DOCUMENTS

| 3,687,808 A | 8/1972 | Merigan et al. |
|---|---|---|
| 4,751,219 A | 6/1988 | Kempen |
| 4,845,205 A | 7/1989 | Huynh Dinh et al. |
| 5,034,506 A | 7/1991 | Summerton et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,185,444 A | 12/1993 | Summetton et al. |
| 5,367,066 A | 11/1994 | Urdea et al. |
| 5,432,272 A | 7/1995 | Benner |
| 5,434,257 A | 7/1995 | Matteucci |
| 5,457,187 A | 10/1995 | Gmelner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,587,470 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,808,027 A | 9/1998 | Cook et al. |
| 5,811,534 A | 9/1998 | Cook et al. |
| 5,830,653 A | 11/1998 | Froehler et al. |
| 5,948,903 A | 9/1999 | Cook et al. |
| 5,994,517 A | 11/1999 | Ts'O |
| 6,005,096 A | 12/1999 | Matteucci et al. |
| 6,166,199 A | 12/2000 | Cook et al. |

(Continued)

FOREIGN PATENT DOCUMENTS

| WO | WO 1994/022890 | 10/1994 |
|---|---|---|
| WO | WO/1997/020563 | 6/1997 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — Tracy Vivlemore

(74) *Attorney, Agent, or Firm* — McNeill Baur PLLC

(57) ABSTRACT

The present disclosure provides oligomeric compound comprising a modified oligonucleotide having a central region comprising one or more modifications. In certain embodiments, the present disclosure provides oligomeric compounds having an improved therapeutic index or an increased maximum tolerated dose.

29 Claims, No Drawings

Specification includes a Sequence Listing.

(56) References Cited

U.S. PATENT DOCUMENTS

| | | |
|---|---|---|
| 6,268,490 B1 | 7/2001 | Imanishi et al. |
| 6,300,319 B1 | 10/2001 | Manoharan |
| 6,383,812 B1 | 5/2002 | Chen et al. |
| 6,525,031 B2 | 2/2003 | Manoharan |
| 6,525,191 B1 | 2/2003 | Ramasamy |
| 6,620,916 B1 | 9/2003 | Takahara et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,034,133 B2 | 4/2006 | Wengel et al. |
| 7,053,207 B2 | 5/2006 | Wengel et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,582,744 B2 | 9/2009 | Manoharan et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,851,615 B2 | 12/2010 | Manoharan et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,137,695 B2 | 3/2012 | Roxema et al. |
| 8,153,365 B2 | 4/2012 | Wengel et al. |
| 8,158,601 B2 | 4/2012 | Chen et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| RE44,779 E | 2/2014 | Imanishi et al. |
| 8,642,752 B2 | 2/2014 | Swayze et al. |
| 8,796,437 B2 | 8/2014 | Swayze et al. |
| 8,957,200 B2 | 2/2015 | Seth et al. |
| 9,005,906 B2 | 4/2015 | Swayze et al. |
| 9,012,421 B2 | 4/2015 | Migawa et al. |
| 9,175,291 B2 | 11/2015 | MacLeod et al. |
| 9,523,094 B2 | 12/2016 | Hung |
| 9,550,988 B2 | 1/2017 | Swayze |
| 9,695,418 B2 | 7/2017 | Seth et al. |
| 9,752,142 B2 | 9/2017 | Oestergaard et al. |
| 9,914,922 B2 | 3/2018 | Freier et al. |
| 9,926,556 B2 | 3/2018 | Wan et al. |
| 10,017,764 B2 | 7/2018 | Freier et al. |
| 10,202,599 B2 | 2/2019 | Seth et al. |
| 10,415,038 B2 | 9/2019 | Guo et al. |
| 10,426,789 B2 | 10/2019 | Murray et al. |
| 2003/0077829 A1 | 4/2003 | Maclachlan |
| 2003/0119724 A1 | 6/2003 | Ts'o et al. |
| 2003/0158403 A1 | 8/2003 | Manoharan et al. |
| 2003/0175906 A1 | 9/2003 | Manoharan et al. |
| 2005/0164235 A1 | 7/2005 | Manoharan et al. |
| 2006/0148740 A1 | 7/2006 | Platenburg et al. |
| 2006/0183886 A1 | 8/2006 | Ts'o et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Monahan et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Aking et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0230938 A1 | 9/2012 | Rozema et al. |
| 2013/0004427 A1 | 1/2013 | El-Sayed et al. |
| 2013/0109817 A1 | 5/2013 | Yurkovetskiy et al. |
| 2013/0121954 A1 | 5/2013 | Wakefield et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2014/0107330 A1 | 4/2014 | Freier et al. |
| 2014/0303235 A1 | 10/2014 | Oestergaard et al. |
| 2014/0309279 A1 | 10/2014 | Oestergaard et al. |
| 2014/0323707 A1 | 10/2014 | Seth et al. |
| 2015/0051389 A1 | 2/2015 | Swayze et al. |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0276208 A1 | 10/2015 | Oestergaard et al. |
| 2016/0138014 A1* | 5/2016 | Kordasiewicz ........ C12N 15/111 536/24.5 |
| 2016/0160280 A1 | 6/2016 | Burel |
| 2016/0186175 A1 | 6/2016 | Seth et al. |
| 2017/0044526 A1 | 2/2017 | Wan et al. |
| 2017/0191064 A1 | 7/2017 | Costa et al. |
| 2017/0327824 A1 | 11/2017 | Oestergaard et al. |
| 2018/0002701 A1 | 1/2018 | Iacone et al. |
| 2018/0023081 A1 | 1/2018 | Hagedorn et al. |
| 2018/0161356 A1 | 6/2018 | Olson et al. |
| 2018/0273577 A1 | 9/2018 | Revenko et al. |
| 2019/0055564 A1 | 2/2019 | Sanchez et al. |
| 2019/0111073 A1* | 4/2019 | Kammler ............... C07H 21/02 |
| 2019/0265230 A1 | 8/2019 | Gubler et al. |
| 2019/0383797 A1 | 12/2019 | Olson et al. |
| 2020/0010831 A1 | 1/2020 | Hagedorn et al. |
| 2020/0109451 A1 | 4/2020 | Gubler et al. |
| 2020/0354720 A1 | 11/2020 | Olson et al. |
| 2020/0362337 A1 | 11/2020 | Dodart et al. |
| 2020/0362347 A1 | 11/2020 | Olson et al. |
| 2020/0385727 A1 | 12/2020 | Moller et al. |
| 2021/0017513 A1 | 1/2021 | Seth et al. |

FOREIGN PATENT DOCUMENTS

| | | |
|---|---|---|
| WO | WO/1997/046098 | 12/1997 |
| WO | WO/1998/013381 | 4/1998 |
| WO | WO/1999/014226 | 3/1999 |
| WO | WO/2002/043771 | 6/2002 |
| WO | WO/2004/024757 | 3/2004 |
| WO | WO/2004/101619 | 11/2004 |
| WO | WO/2004/106356 | 12/2004 |
| WO | WO/2007/134181 | 11/2007 |
| WO | WO/2008/098788 | 8/2008 |
| WO | WO/2008/101157 | 8/2008 |

(56) References Cited

FOREIGN PATENT DOCUMENTS

| WO | WO/2009/082607 | 7/2009 |
|---|---|---|
| WO | WO/2009/126933 | 10/2009 |
| WO | WO/2009/134487 | 11/2009 |
| WO | WO/2010/054406 | 5/2010 |
| WO | WO/2010/088537 | 8/2010 |
| WO | WO/2010/129709 | 11/2010 |
| WO | WO/2010/144740 | 12/2010 |
| WO | WO/2010/148013 | 12/2010 |
| WO | WO/2011/038356 | 3/2011 |
| WO | WO/2011/100131 | 8/2011 |
| WO | WO/2011/120053 | 9/2011 |
| WO | WO/2011/133876 | 10/2011 |
| WO | WO/2011/163121 | 12/2011 |
| WO | WO/2012/037254 | 3/2012 |
| WO | WO/2012/068187 | 5/2012 |
| WO | WO/2012/083046 | 6/2012 |
| WO | WO/2012/083185 | 6/2012 |
| WO | WO/2012/089352 | 7/2012 |
| WO | WO/2012/089602 | 7/2012 |
| WO | WO 2012/170347 | 12/2012 |
| WO | WO/2012/177947 | 12/2012 |
| WO | WO 2013/022966 | 2/2013 |
| WO | WO 2013/022967 | 2/2013 |
| WO | WO 2013/022984 | 2/2013 |
| WO | WO 2013/022990 | 2/2013 |
| WO | WO/2013/033230 | 3/2013 |
| WO | WO/2013/075035 | 5/2013 |
| WO | WO/2013/165816 | 11/2013 |
| WO | WO/2013/166121 | 11/2013 |
| WO | WO 2014/059341 | 4/2014 |
| WO | WO/2014/179620 | 11/2014 |
| WO | WO 2015/021457 | 2/2015 |
| WO | WO/2015/106128 | 7/2015 |
| WO | WO/2017/015555 | 1/2017 |
| WO | WO 2018/165564 | 9/2018 |
| WO | WO 2019/032607 | 2/2019 |
| WO | WO 2019/032612 | 2/2019 |
| WO | WO 2019/138057 | 7/2019 |
| WO | WO 2019/157531 | 8/2019 |
| WO | WO 2019/169219 | 9/2019 |
| WO | WO 2019/200172 | 10/2019 |
| WO | WO 2019/245957 | 12/2019 |
| WO | WO 2020/160336 | 8/2020 |
| WO | WO 2020/201339 | 10/2020 |
| WO | WO 2020/219983 | 10/2020 |
| WO | WO 2020/227691 | 11/2020 |

OTHER PUBLICATIONS

Biessen et al., "Novel hepatotrophic prodrugs of the antiviral nucleoside 9-(2-phosphonylmethoxyethyl)adenine with improved pharmacokinetics and antiviral activity" FASEB J. (2000) 14(12):1784-1792.
Biessen et al., "Synthesis of Cluster Galactosides with High Affinity for the Hepatic Asialoglycoprotein Receptor" J Med Chem (1995) 38(9):1538-1546.
Biessen et al., "The cholesterol derivative of a triantennary galactoside with high affinity for the hepatic asialoglycoprotein receptor: a potent cholesterol lowering agent" J Med Chem (1995) 38(11):1846-1852.
Braasch et al., "Novel Antisense and Peptide Nucleic Acid Strategies for Controlling Gene Expression" Biochemistry (2002) 41(14):4503-4510.
Burel et al., "Hepatotoxicity of high affinity gapmer antisense oligonucleotides is mediated by Rnase H1 dependent promiscuous reduction of very long pre-mRNA transcripts" Nucleic Acids Research (2015) 44(5):2093-2109.
Connolly et al., "Binding and endocytosis of cluster glycosides by rabbit hepatocytes. Evidence for a short-circuit pathway that does not lead to degradation." J Biol Chem (1982) 257(2):939-945.
Crooke et al., "Pharmacokinetic Properties of Several Novel Oligonucleotide Analogs in mice" J. Pharmacol. Exp. Ther. (1996) 277(2):923-937.

Crooke S.T., Ed., "Antisense Drug Technology, Second Edition" CRC Press (2008) 163-166 and 442-443.
Dieckmann, et al. "A Sensitive In Vitro Approach to Assess the Hybridization-Dependent Toxic Potential of High Affinity Gapmer Oligonucleotides" Molecular Therapy: Nucleic Acids (2018) 10: 45-54.
Detmer et al., "Substrates for Investigation of DNA Polymerase Function: Synthesis and Properties of 4'-C-Alkylated Oligonucleotides" European J. Org. Chem (2003) 10:1837-1846.
Duff et al., "Intrabody tissue-specific delivery of antisense conjugates in animals: ligand-linker-antisense oligomer conjugates." Methods Enzymol (2000) 313:297-321.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
International Search Report for PCT/US2019/017725 dated Apr. 15, 2019.
Jayaprakash et al., "Non-Nucleoside Building Blocks for Copper-Assisted and Copper-Free Click Chemistry for the Efficient Synthesis of RNA Conjugates" Org Lett (2010) 12:5410-5413.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259: 327-330.
Kasuya et al., "Ribonuclease H1-dependent hepatotoxicity caused by locked nucleic acid-modified gapmer antisense oligonucleotides" Scientific Reports (2016) 6:30377, 1-12.
Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11:821-829.
Khorev et al., "Trivalent, Gal/GalNAc-containing ligands designed for the asialoglycoprotein receptor." Bioorg Med Chem (2008) 16:5216-5231.
Kim et al., "Oligomeric glycopeptidomimetics bearing the cancer related TN-antigen" Tetrahedron Lett (1997) 38:3487-3490.
Kornilova et al., "Development of a fluorescence polarization binding assay for asialoglycoprotein receptor" Analyt Biochem (2012) 425:43-46.
Koshkin et al., "LNA (locked nucleic acids): Synthesis of the adenine, cytosine, guanine, 5-methylcytosine, thymine and uracil bicyclonuleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kumar et al., "Design, synthesis, biophysical and primer extension studies of novel acyclic butyl nucleic acid (BuNA)" Org. Biomol. Chem. (2013) 11:5853-5865.
Lee et al., "New synthetic cluster ligands for galactose/N-acetylgalactosamine-specific lectin of mammalian liver" Biochem (1984) 23:4255-4261.
Lee et al., "Facile Synthesis of a High-Affinity Ligand for Mammalian Hepatic Lectin Containing Three Terminal N-Acetylgalactosamine Residues" Bioconjug Chem (1997) 8(5):762-765.
Lee et al., "Protein microarrays to study carbohydrate-recognition events" Bioorg Med Chem Lett (2006) 16(19):5132-5135.
Lee et al., "New and more efficient multivalent glyco-ligands for asialoglycoprotein receptor of mammalian hepatocytes" Bioorg Med Chem (2011) 19(8):2494-2500.
Lee et al., "Preparation of cluster glycosides ofN-acetylgalactosamine that have subnanomolar binding constants towards the mammalian hepatic Gal/GalNAc-specific receptor" Glycoconjugate J (1987) 4(4):317-328.

(56) References Cited

OTHER PUBLICATIONS

Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77:7564-7571.
Lee et al., "Synthesis of peptide-based trivalent scaffold for preparation of cluster glycosides." Methods Enzymol (2003) 362:38-43.
Letsinger et al., "Cholesteryl-conjugated oligonucleotides: Synthesis, properties, and activity as inhibitors of replication of human immunodeficiency virus in cell culture" PNAS (1989)86:6553-6556.
Leumann et al., "DNA Analogues: From Supramolecular Principles to Biological Properties" Bioorganic & Medicinal Chemistry (2002) 10:841-854.
Maier et al., "Synthesis of Antisense Oligonucleotides Conjugated to a Multivalent Carbohydrate Cluster for Cellular Targeting," Bioconjugate Chemistry (2003) 14, 18-29.
Maierhofer et al., "Probing multivalent carbohydrate—lectin interactions by an enzyme-linked lectin assay employing covalently immobilized carbohydrates" Bioorg Med Chem (2007) 15(24):7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan, "Oligonucleotide conjugates as potential antisense drugs with improved uptake, biodistribution, targeted delivery, and mechanism of action." Antisense Nucleic Acid Drug Dev (2002) 12(2):103-128.
Merwin et al., "Targeted Delivery of DNA Using YEE(GalNAcAH)3, a Synthetic Glycopeptide Ligand for the Asialoglycoprotein Receptor" Bioconjug Chem (1994) 5(6):612-620.
Mishra et al., "Improved leishmanicidal effect of phosphorotioate antisense oligonucleotides by LDL-mediated delivery" Biochim. Biophys. Acta (1995) 1264:229-237.
Morvan et al., "Sugar modified oligonucleotides. III (I). Synthesis, nuclease resistance and base pairing properties of α- and β-L-octathymidylates" Biochem Biophys Res Commun. (1990) 172(2):537-543.
Nishina et al., "Chimeric Antisense Oligonucleotide Conjugated to α-Tocopherol" Molecular Therapy Nucleic Acids (2015) 4(1):e220.
Nishina et al., "Efficient in vivo delivery of siRNA to the liver by conjugation of alpha-tocopherol." Molecular Therapy (2008) 16(4):734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oestergaard et al., "Rational design of antisense oligonucleotides targeting single nucleotide polymorphisms for potent and allele selective suppression of mutant Huntingtin in the CNS" Nucleic Acids Research (2013) 41(21): 9634-9650.
Oka et al., "An Oxazaphospholidine Approach for the Stereocontrolled Synthesis of Oligonucleoside Phosphorothioates" JACS (2003) 125(27):8307-8317.
Pavia et al., "Synthetic TN glycopeptide related to human glycophorin AM. High-field proton and carbon-13 nuclear magnetic resonance study." Int J Pep Protein Res. (1983) 22(5):539-548.

Pujol et al., "A sulfur tripod glycoconjugate that releases a high-affinity copper chelator in hepatocytes." Angew Chemie Int Ed Engl. (2012) 51(30):7445-7448.
Rajur et al., "Covalent Protein—Oligonucleotide Conjugates for Efficient Delivery of Antisense Molecules" Bioconjug Chem. (1997) 8(6):935-940.
Rensen et al., "Design and Synthesis of Novel N-Acetylgalactosamine-Terminated Glycolipids for Targeting of Lipoproteins to the Hepatic Asiaglycoprotein Receptor," J. Med. Chem. (2004) 47:5798-5808.
Rensen et al., "Stimulation of liver-directed cholesterol flux in mice by novel N-acetylgalactosamine-terminated glycolipids with high affinity for the asialoglycoprotein receptor." Arterioscler Thromb Vasc Biol. (2006) 26(1):169-175.
Rensen et al., "Determination of the Upper Size Limit for Uptake and Processing of Ligands by the Asialoglycoprotein Receptor on Hepatocytesin Vitro and in Vivo" J Biol Chem. (2001) 276:37577-37584.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J Am Chem Soc. (2004) 126(43):14013-14022.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 4: 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J Med Chem. (1999) 42(4):609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tomiya et al., "Liver-targeting of primaquine-(poly-γ-glutamic acid) and its degradation in rat hepatocytes" Bioorg Med Chem. (2013) 21(17):5275-5281.
Toyokuni et al., "Synthetic vaccines: I. Synthesis of multivalent Tn antigen cluster-lysyllysine conjugates" Tetrahedron Lett. (1990) 31(19):2673-2676.
Valentijn et al., "Solid-phase synthesis of lysine-based cluster galactosides with high affinity for the asialoglycoprotein Receptor" Tetrahedron (1997)53:759-770.
Van Rossenberg et al., "Stable polyplexes based on arginine-containing oligopeptides for in vivo gene delivery." Gene Ther. (2004) 11(5):457-464.
Wan et al. "Synthesis, biophysical properties and biological activity of second generation antisense oligonucleotides containing chiral phosphorothioate linkages" Nucleic Acids Res. (2014) 42:13456-13468.
Wang et. al., "Cytotoxic and Mutagenic Properties of C3'-Epimeric Lesions of 2'-Deoxyribonucleosides in *Escherichia coli* Cells" Biochemistry (2017) 56(29): 3725-3732.
Westerlind et al., "Ligands of the asialoglycoprotein receptor for targeted gene delivery, part 1: Synthesis of and binding studies with biotinylated cluster glycosides containing N-acetylgalactosamine." Glycoconj J. (2004) 21(5):227-241.

(56) References Cited

OTHER PUBLICATIONS

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

* cited by examiner

SEQUENCE LISTING

<160> NUMBER OF SEQ ID NOS: 154

<210> SEQ ID NO 1
<211> LENGTH: 14836
<212> TYPE: DNA
<213> ORGANISM: Mus musculus

<400> SEQUENCE: 1

```
cctcccccgt gtctccccac acccgggttg gggttgtttt ggttgaccag agtggaacac      60
aacgatctat tggcagggct gaacaccaat gggtctattt gtaaagcgcc aatgaccact     120
ttctgaagca gggttttagg gagcggggcc ttagggaact ctttggtcct ttttagaaca     180
ctggactttc ttctggaaag gcaggaaaca ctgaagttta agaagttgtt tccagcttcc     240
attaactgaa cacacattaa aaccaagcac agagaatcag gacgtttcgc gggagtgaga     300
cccagtcatt tctcctccgt ttccattctg cagggtgaga gttgtaatca cccacccact     360
attcgtacca tccacccacc cccagtcgag agaatagggg tacagagggg aggtggcaaa     420
gaaaattcac gatactgagt atctctggga gacctgtttg gtctctttgc tcggtagcgc     480
agccctacgt tagaatgcat ctttcccggga atgactgtag tgagactttg gctgggaatc     540
```

```
caagttattc taactgtaga ttggtccacg ttgccctaag cctagcagtc cactgcggca    600
cagacaccct ggacatgagg tgggtcagct taagttcctg gcacgaaaga aagggtactc    660
tggcaacttt tggatgcggc gaaacagact gtttcgtctc tcaggttctt atttcacggc    720
ttgtgccttt gacagcccct tagtttctct atctgcagga tgggagcatt aagctctacg    780
acccagcctc tttacaattc aggtccaaag agcccgccca agttggggac tgggaagatc    840
aaaggtctca gcacccagcg gagccgcgga cactgagggc gccaagaagg gggtgggtag    900
gtagggaact ggaagggcgg ctgctccgca ggggatgcgc gtcagagacc ccagccacac    960
tccaggcccg cccttgatg agcccgccc cgccccgcct ggttttcgcc tctaaagcgc    1020
ccagcgctcg cctcccgctg ccgcactttc actctcggtc cacctcggtg tcctcttgct    1080
gtccagctct gcagcctccg gcgcgccctc cgcccacgc catggacgcc aaggtcgtcg    1140
ccgtgctggc cctggtgctg gccgcgctct gcatcagtga cggtgagtgc aatccgcggc    1200
cgggcccggg aaaggctcgc agctctgcgc cggagctcct tcgggtccgc ggttcctctg    1260
cccgcgccga agtcgcggag aaagaactcg gtcggcgccg ttcactacaa gcgaacttgg    1320
ggcagtccac tttgcagggc gcactcccac cgggtgccct ttcccgtgtc ccacgggtcg    1380
caccgaggtt ttgtgctctg cgaagtgcgg ccataggacc tagagagggc tgcaggggag    1440
gacccgcagg attgttgggc aagagtgggt tcggcgcgga atggaagcgt gggcgattgt    1500
gtccggggct tgggccccgg agcgcgccag ctgcactcag ctagtgtcta ccggcgccca    1560
gatgtttcca gaggcgaagg gcagcgcggt cccggagttg accgtgcaag aggttcactc    1620
gggtggtgcg tgtgtcagca aactctcaaa gaccggtcaa gtagctcgaa gtgcatggct    1680
tggctatagg ttcagtggtg aggctgagtt tcgtcccctg cgggtgtagc gtgttctctt    1740
acagcaccct cgagggctc agggccacca gcagcgcagc gcagctcttg aactcgcgct    1800
gccagccagg gccgcgcttc tgcacagttc gttggtccgt agcgacgcgg acctgagcac    1860
gcgtctcttc actgcccctt tttcttctta cccgggtcac tagacaaagg ctcagcagtt    1920
acccaagcta tatgcacacc tctccccaac ccccaaacac acctgcaaac gggcgctttt    1980
gtagccagcc ccggagtcct cagctctgga atgagagctg cagcggagtt cagtctccca    2040
gacccagggt ggtgtcttct ttcactggga aagggctttc attttgtttt ctttttttga    2100
cactgaagag aaaactctca gcgctgttac aagcaccgt tgctgcaaaa caaacaaac    2160 cattgcctct gaacacaaaa caaaatccta ctagtcgatc ccctgccttc ctccgcagtg    2220
gtgtttcctg gagagaactg agggacagtc ggggctcttg gtgagactga gctctaaatg    2280
ctgcccaagt acaccaactc gttcgtttgg gttctttccc tgtgacaacg gggtacggga    2340
atggttggag ttgcctagtc cgagggaaat gttctgtaaa agaatagtca gttgctgatc    2400
ggagtagtaa aaaaaagaa atgaaaggca gtttcgattt tttttttttt tttttttttt    2460 tttttgtta ccgagaacac ccggaggct gagccttccc actggtcccc cagtgccccg    2520
tcatggagca cattgatttg gcattaata attgaatgag ctggtgatgt tgcaagggtc    2580
acagcctctg gcaagttagg tatggggcaa gaatgtagga ctcaggtcct caaggttgga    2640
gtgcaattat ccagagtaaa agttgtctca ccctcaacat attctgaccc taggaagagt    2700
cggattgttg acagtgtctg gatcagacct gttctctagg caggacccca ttgtgctgcc    2760
cgaatgaact ttttacctc ctagtgcctg tgtgccctct gatcttacac agccctcaag    2820
ttgcagcacg gctaaccttg ctgtggttcc tgtcttttcc catcagctac tccaactcag    2880
```

```
aagctagata gtagacaccg gaggcttctt tggttaaacc cagagcagca ggcttgccag    2940
gcttgttaga ttgaatggac ccctggttcc ctaagccaag ctctctagat tcccaagtcc    3000
agggtggcag cagagctgga ttagactttg gtctgtacct gaagtctggt tttcctatgc    3060
tttagagtct aaagacacta cccttcctgg ggcatgcatc ccttagctaa ataatgcttg    3120
cagaagaaga taatcccatc atatatttaa ttcggtccac ttctccagct gcttcccaaa    3180
ggcagtgaac ttcagaatac ccagaagtct cctggaactc taaataagca aacttaaaat    3240
cctggggcta actattctca gtcatacttt taaactttgg tgaaaagacc cataaattga    3300
aacatttggg gatgctcagt agagctagga taaaaccctg ttgttggggg agcagctaca    3360
aatccagcag tcctcagggt ttgcaattct agacttaaag ggtggttctt aagggggggt    3420
tctaaaggag ccccttgcta atttacacta atgagtgtca attatagcat tttgcaaatt    3480
ggtgaattgg caaacaaagc tggtaatagg atccaggagg cctaggcatc caggtagtga    3540
ccataaaagc cacggttgac cccagctttt gggaaaagct ggatagaagg taaatccggg    3600 tcctccccctc tggattcttt tgtgatttcc agggcttagg ataggtgag tgggaggagg    3660 gaaaactgca ggtggtagaa gtgaagcccc ccacctccag gcctgcacca gagggccaca    3720
agggagccca gaactctgcc accccacttc tcctgggtcc ttttgtcctt tagaggctga    3780
gcccagtcag atctcactgt gatccctggc cgaggggatg gtctttgcaa gaaactttct    3840
gtaaccattc ctgctgatgt tcctgagtct tccccacaag agccaccaaa cccctgcac    3900 caggcagata atgactggcc ccactttttct ctctacacct cctctaggta aaccagtcag    3960
cctgagctac cgatgcccct gccggttctt cgagagccac atcgccagag caacgtcaa    4020 gcatctgaaa atcctcaaca ctccaaactg tgcccttcag attgtgtaag tcctagccgc    4080
catcccccaa agaggagcat ggtatagaag cctcggactt ggcataacta ggggcagctg    4140
ttaccaccac caccacgggg acactgatat gccatcagac atgggtttca aaggatactt    4200
ttgttcccca gagccctgat gtcctcagtg tttctcactc ttgctttcca agctgtttct    4260
tgcagcacag tgggccgcct ctctacagaa aaagccatgg acttgatgga ggtcagccct    4320
cagctgacag ttgggtctgt cttgtcagtt tcaaggttct ggtgtccaaa gttaatcctt    4380
tctcacatag aaaaaaaaat tacaagaccc ggatggcacg ggggggggg gggttcagtt    4440 ttactcactt gcactcactt gctcagaggt cattttttgtt ttagagtttt agagtttgct    4500
ggagtgtgat ggtagctgcc agtatttgat ttaaatttac ctgggaaata agaaaagccc    4560
aaaaaaggta taaatgatgt gaatatctca ctcagagtct ggtagacttg cagagatgt    4620 gtcctgtgct agtctgtcct gctcactgcc ccccagcagg ggttcccatc ctcgggagac    4680
tcaacactaa caacagtata aggatgcagc agctggagca atgctagcct gacggctttg    4740
tcacccaacg gtgactgctt cagactttct gtgctcatca gccttcctct ccagcctccg    4800
ctgctgtgtt atgtacagta ggctttagag acctagatga tgaatattat ttttgctgtt    4860
ttgattaaaa tacaatactc tcccgagaaa gggattttaa agatgatgag tttacgtttg    4920
aataggctgt gctggtgcac tgtcccggga agggcccttg aacttagagg gtcaaataca    4980
actattgatt ctgggtgatc actaagttaa taaatggcag gatccagact gacacccctg    5040
atccctgttg aagttacatc cctctgaacg actggtcaac tgcagggcag cctgcttgaa    5100
gagggttacc tgtccctagg acactgaaca ggcatttgtt tttcctagaa gacagttcac    5160
cagctggaga ggagtcgtct cccgtagttt ctgtttggtt gcttttggtt tttgtttggt    5220
tttggttttt taattatctg gcatccagga cttgatggaa aataaccaga gctaagctca    5280
```

```
ccggttcatc tgcccattag gaagttctag ggatgggaga agaacacgg cgtcaattaa   5340 caaatccaca aagctaagac cttgaagcat tctgtgaact tgtaaacgcg ctcaggcaac   5400
cattggacaa tttgtctaga ctgctccttg cccacctgaa ctgccctgtt cctcccttc    5460 tggactcctg ccgtcttcct ccagagctac ctttaaggtt gtcccatgta ctatcaaggt   5520
gctctgtcaa aagttcttag gctgcttctg gcactctcca gaattttcca agacctcccc   5580
cccaccatga tatcagtcat ccgcgccttc tgggtggttc ttcctccaca cccttgggc    5640 actttgactc ctgtgggata ttcgtccttc ctttcctttt agctttcctc acttgccaag   5700
ctccaacttg gccagaagct caaatgcctc cactgtggtc tcttctctgt gtccctggg    5760 agacatcctt agcacgtccc taactctgcg gtggtggtcc caacacgatt caagtgctat   5820
gtcttccaaa actgaagctt ccgggagcag cagctgggcc ctgcagtgag gacctttagc   5880
tgggtgtgtt gggtgagccc acaggatcgc tttctcccgc ttggctgtac agcgtctctc   5940
cccttgtgtt ttggcagtgc acggctgaag aacaacaaca gacaagtgtg cattgacccg   6000
aaattaaagt ggatccaaga gtacctggag aaagctttaa acaagtaagc acaacagccc   6060
aaaggacttt ccagtagacc cccgaggaag gctgacatcc gtgggagatg caagggcagt   6120
ggtggggagg agggcctgaa ccctggccag gatggccggc gggacagcac tgactgggt     6180 catgctaagg tttgccagca taaagacact ccgccatagc atatggtacg atattgcagc   6240
ttatattcat ccctgccctc gcccgtgcac aatggagctt ttataactgg ggtttttcta    6300
aggaattgta ttaccctaac cagttagctt catcccatt ctcctcatcc tcatcttcat     6360
tttaaaaagc agtgattact tcaagggctg tattcagttt gctttggagc ttctctttgc   6420
cctggggcct ctgggcacag ttatagacgg tggctttgca gggagcccta gagagaaacc   6480
ttccaccaga gcagagtccg aggaacgctg cagggcttgt cctgcagggg gcgctcctcg   6540
acagatgcct tgtcctgagt caacacaaga tccggcagag ggaggctcct ttatccagtt   6600
cagtgccagg gtcgggaagc ttcctttaga agtgatccct gaagctgtgc tcagagaccc   6660
tttcctagcc gttcctgctc tctgcttgcc tccaaacgca tgcttcatct gacttccgct    6720
tctcacctct gtagcctgac ggaccaatgc tgcaatggaa gggaggagag tgatgtgggg   6780 tgcccctcc ctctcttccc tttgctttcc tctcacttgg gccctttgtg agattttct       6840 ttggcctcct gtagaatgga gccagaccat cctggataat gtgagaacat gcctagattt   6900
acccacaaaa cacaagtctg agaattaatc ataaacggaa gtttaaatga ggatttggac   6960
tttggtaatt gtccctgagt cctatatatt tcaacagtgg ctctatgggc tctgatcgaa   7020
tatcagtgat gaaaataata ataataataa taataacgaa taagccagaa tcttgccatg   7080
aagccacagt ggggattctg ggttccaatc agaaatggag acaagataaa acttgcatac   7140
attcttatga tcacagacgg ccctggtggt ttttggtaac tatttacaag gcattttttt    7200
acatatattt ttgtgcactt tttatgtttc tttggaagac aaatgtattt cagaatatat    7260
ttgtagtcaa ttcatatatt tgaagtggag ccatagtaat gccagtagat atctctatga   7320
tcttgagcta ctggcaactt gtaaagaaat atatatgaca tataaatgta ttgtagcttt    7380
ccggtgtcag ccacggtgta tttttccact tggaatgaaa ttgtatcaac tgtgacatta    7440
tatgcactag caataaaatg ctaattgttt catgctgtaa acctcctacc gtatgtggga   7500
atttatttac ctgaaataaa atctactagt tgttagatgg agtgcacata catttctgaa   7560
gatggagaaa aacaggtgtg cctgctgatc aggtgctgtg ggctgccctg cagtcctggt   7620
```

```
gagcgacaga cactgaggca ggcttgtctc atgaacaggc tgcctctgca gtgaaagttt    7680
ttgtgtattt ttttttaaccc aagctagttt tctaatgaat aatacttgac tcactaattt    7740
cccctcctcc tccttctcct cagttctcct aacatcctca tgtgatcccc agactcaact    7800
ccagtaatat caagctttcc tatttttccca tgtaaaaaaa tcccatgact ctgggccatg    7860
ttaatatcag gcttttgtgg gaacaggtgg cctcaccccca taaatcatta ataccattc    7920 agcttgaatc atttttaatgt gacagtcaca aaccagttgc tctaataaaa actctgctaa    7980
ccatccttct ccttagctct ctagaacaat ctcagttatc cctagggatg ctccccagca    8040
tccagaaaag agaagtggga tcaatcatcc tgcctttctc cccctcctct cttggagggc    8100
tgcctgagcc cgtggcctcc acctcccctg ctttgtataa tttgaaatgc agatttgtag    8160
tgaaggcaga gttcacctct gcattgaaag ggaaggcagg cccagagctt ccttccctgc    8220
cctctgagat gtgcatttat gtctcaggat ggatgagctt tggtaggaat gctcaaaacc    8280
aggaccagcc agacaaactg gcagtccctg taagcggttc ccgggtcata gggttagggc    8340 accccctgttt aactttgggg tggggaaagt atctggtttt ctttgataaa ttgcttgtga    8400
accacatttg ccaagtggcc tccaggcctc aaactcaaag accgagctaa atcgactcgg    8460
aaggcaatgc tgaatgaaga ttgtgggaac tgagatagat acactcctct atgttgcaat    8520
gtgattaatg gttctactaa ttttatctaa gggggcgcag agaagaaaaa gtggggaaaa    8580
aagaaaagat aggaaaaaag aagcgacaga agaagagaaa ggctgcccag aaaaggaaaa    8640
actagttccc cgcttcctgc cgatggaccg cagtgcgctc tgctctggcg ctttgtaact    8700
cgctcctccc tcttcggggg cagaccccac actccgggca ggtgctcaaa cctgacggta    8760
aactcttccc tcttcggggg cagaccccat accccggggc gggtgcttag gctttcctgc    8820
cctggtggcc acaccagctg ctgtatttat gtgcttcata aggccctgct ctgtctgcta    8880
aagctatgaa gaaagatgtg cagagactgg ggtggagact aagccaaaga ggagctgcct    8940
agcctggcag cattgccccg agctgagccc ccttggccag gacttcacaa ggctcacacc    9000
tacaatccca tgaaggccag ggtggtctgc ttagccagga aagggcaagt gccttcccct    9060
cggccacact gccccttgtg gccttctcgg gacatgtggt aactgacttg ctctcaggcc    9120
cacccgcagc ttttccaaat acctgcagcc ttcagccctg ctgccctgcc tgtgggagca    9180
gctttgactc cagtccagaa gggtttctgc agactgtgtt gggtgagacg cagaaaggat    9240
gaaatctcag aacacatgtc agctgcttct caggaaatct tttctttgga caattcactt    9300
tagagtcttt aaacgggtct ctcgtgggga ggatagatgt gctctggaac tttctgaagg    9360
accagcagct tcagggactc ttagtctgtc cttccccact tttggtccca acatccctgg    9420
gatggtgtgc tgtctgggca ccacggtctc catcctcact cctgagagat ttctgccttc    9480
tgtgagttgg gttaaagctc tggaattatc tactatccca atccactacc ctcacctggc    9540
aatatttgtc tgtttttgtt tgtttgtttg tttgttttttg tcttttgcca gtttgaatta    9600
gaaggcaagg ctctgatttt agtagtgttt tggaaaagga ctttttttctt caccttcctc    9660 tttgcctcat gtgtacacac acacacacat cttgtacccc agacctctgg gtataatttt    9720
cataattggt gcagaaagaa gaaatgatct gaagatgtgt taaatggatt gcaggggaag    9780
gaaggcccag ggccctgtgt gtcatgccct cttgggttcc taagttctat gttccttaga    9840
ggttctagca ttaaacagat aaagcccttc atggtcctgg ctgaggaaga gtcttgctag    9900
ggggattcag ggaagacccg tgttaccagc tcttaccctt tatctggaca gctctcctac    9960
cctgtatctt ctcctcagat ctgaggatag caggctggac tattggtggg cacctttcaa   10020
```

```
gcccagggct actgtttgtc ctgtggcagc cggctacagt ctcgtctgag tggcctcatc    10080
tggacccttc ctgttattaa taaaacgctt ctggaggcca gatctgtgct caagccatag    10140
ttctgcttag aaagggatgc cccacccttα ccggacactg ggaagaactg ttggcccta     10200 gaaaccaaag gccaaactga ggctgccctg agttggaaga ccactttctg aaatgcccat    10260
ggactctgcc tcccaaccat tcgtctctca ctcctagcag agctgtctgt gcagactgtt    10320
tcttaggagg cacagcaagc tccagggaac cctctgtgct tatgaagctc gtctggtggg    10380
caaccccagc ccactggaca gagtcctcat ggaaatgcct gggaagctga tttcatctaa    10440
ggatgggttg aagtaggatg tgctcctgcg acttctcagg caggtgagag gggtagtcct    10500
tacactgtct agcataaacg ccttccggaa ggacctgcag ctccagagac cacctcctga    10560
gcaccaagac ctcttctggt ggtgtggaac cagccaagag atttcaagga agagtgatta    10620
tttgatgaat gctatgggaa tggcctcttc tcttggagtt ctgaggcctg ggatgccca     10680 ggaacactgg gcacctgctg ctgttagggc caatgcatag tctcagcacc ggtgtcctaa    10740
ggttaaggcg gtgcgccttg tcatgtgctc cttgtaccat gccatctgtg ccagtgtgtg    10800
tctgcctcac cctgtgcttg acatgttcac ccatcttctc tgcttcccgc caccatccag    10860
atcctcagcg gccgccccgg ctgtgccctt ccctgctctc ccgctctctc aggcctcgga    10920
aggaagatcg gtgctgcga gctgaactaa ggagtagggc ctgtggctca gcgctaggcc     10980
acgcacgcag catcccaggc atgtggtgag aaactgcctt aatgtgtctc ctctgttctt    11040
gtcaacagga ggctcaagat gtgagaggtg tgagtcagac gcccgaggaa cttacaggag    11100
gagcctaggt ctgaagtcag tgttagggaa gggcccatag ccacttcctc tgctcctgag    11160
cagggctgaa gccgtttgca agggacttgc tttgcacagt tttgctgtac tttcacattt    11220
tattatgtag caagatacat ggtgatttt ttttttttca tttagcctga ttttccaacg     11280
tcattggtga caggccaagg ccactatgtt atttccttttg ttctggtatc cttcccttgg    11340
aggaccttct ctgagtagtg gctccccagg tttgtccttt gagctgaggc aggaggctca    11400
cccattcttc tgaataggaa ctgggtgttc ccaccccca aggactgcag ggctttccca     11460
agctgaggca ggaacgtgag gccagggaag agtgagcttc accctcatcc cacgctgtcc    11520
tcctcaaccc accatgctca tcattctgtc tcatccatcc atccatccat ccattcatcg    11580
ccatgtgtcc gcaagactgt ctccatgacc ctgaaaaagg actctcgaga tgaaatcctt    11640
tattcaaatg ggacagcaag aaggaaaagc caatgtctgg tgtctctccc cccgcccta     11700 ccctgcgcgc atctatgtct tgtttggaat attgtctctt caacccctg ttcatgtcct     11760 tctcactcat gatcgatgtc ttgtctgtgc actgtctcta acccaaatgc aaaggctgag    11820
tgtgaggtga tggccccgag gtccaggttg tagtcatgga aagagccctg ctgtctccct    11880
tctcaggggg cccattttag acacacaaag cccaaagaaa ggtggtttgc aacagtgctt    11940
agctcgagcc tccatatttc cataactgtt agcttaaaac tgtggggttt taccttcctg    12000
gaaccaaatg cattcttctg ttgaggagta acaggtctca attcttttca attaatttta    12060
aaagtcaatc actaagagca tcggcttttgg gccctgatgg gcaggcattt ccctggaaag    12120
ggggtgaact acctacctct cctcaagaca gccgaagggt gggattggtg ccgctctggg    12180
aagcgtggcc ccaggagttt tgtcctctgc agtttttaat gcaagttcac tgccactttg    12240
acaaaagccc aattagaagc cagtctctag ttccttaaac aaaacagaca gagtaaggaa    12300
aggaaggagg gtggcagcca gctggctgga cactcgagaa agacgggaa gtaagctaca     12360
```

```
gaaagatagt cttcaaaaac aggtgtttga gagtgaatac tctgtagaat tgttagtggg    12420
gtgtgtgtgg tggtggtggg gggatttcta caaaatagtc ctttaagttg agtttacagc    12480
agatgaaaaa tccaaccagc aaaattttga tcaaatttga acaaaaaccc aaaaacctaa    12540
aactgttgag caggttgcga tgaggagcac agggctagct gcagagctgg atcctcagga    12600
ggatagcgaa ttattttcaa ccctggaata gaaaccacac actggcttgc tgtgcaccag    12660
ccactttgca tctaatccaa gctttgaagg gtgttgcttg ggaggaaaca aatacagcct    12720
tccatcttca ctccagttag ggatcctttc aaagtctcct tcacagtgag gaaaagaga    12780 agggtagaaa ctttagggag ccggatttgt gtatcaattc ctccgctgac agtcagtttc    12840
tagatggaga cagcctgctt aaagcaaatc cgaatttaaa taggacattt acatcggaaa    12900
agtctctccc taccttaatc ccccattctc ttgctttcaa aatacaagca cagcagtcct    12960
tgaatggctg ttgacccagg gcacctagct gtccctgctg gtcctggggc tgccagaatt    13020
cccttgggcg ccaagcaacc tgccaggtag ccagtccctc tgttacaagc ctttgcatct    13080 ggataggaa aggggtggag acatacagtc tgctttgtgt tgaaacccag atttgtaccc    13140
tgtgtttata cactgctgct ggctcccgag gacagtggga ctttagcaag gaagtgcagc    13200
cgaggggtaa agagccctct ggttcattgc ctgatcggct ttgagagagg gtttggaggg    13260
caaggggctg cattcctctg agggacttgg cctgaggcct ttcgggcctc tccagtgggt    13320
tctgtttatc ctctcatggg tgattatctc agtggtgtca ccaggggctt cctcccagaa    13380
gtcagtcatc cccaggccgt gcaccctttt cagctggatg agagccaggg atgcattctc    13440
tccaaacagc taccctggcc cattttaagg taatctcatt cttcaaaatg ttccatagaa    13500
tcctccaaat tcccccagca gacttctacc ctcgccaagt tcccaaaacc cactcagcaa    13560
agttgccaac ctcgacgggc tagcagtgtc taagcagcga tgggttcagt gttgtgtgtg    13620
gtgaatactg tattttgttt cagttctgtc tcccagataa tgtgaaaacg gtccaggaga    13680
aggcagcttc ctatatgcag cgtgtgcttt cttattctta ttttttaatat atgacagtta    13740 tttgagaagc catttctact ttgaagtcat tatcgatgaa agtgatgtat cttcacctac    13800
cattttccta ataaagttct gtattcaaat atagctgcca agcatcctca gtgaatgtta    13860
ccatgtggaa ttttccacac ttggttttac ccctcaaac ctgactctga ccgtgcagtc    13920
ttagcagaag agcttagcag gtcctagtgt tcactcttgg tctaactgct ggtgtcagaa    13980
gatctctaca gggagaggtg ttccattttc tccacatgac ctggattgct ccttagaggt    14040
cagacagcct tgcactgtac aaggcaatgg cttagggtaa agtcccagga gttttcccta    14100
cagtcccaag aatttggaag aggaaggccc acactacaca tgcaggtcat ggtggaaggt    14160
gacagaggaa ggactctgtc cctgtaagac agctggaaac cacaatattc tgcatgttcc    14220
tatcctgggt gaggacgcta atggaagtca aaggggaatt tgctaactgc tgttggccag    14280
cttcctccaa gaatcctgct tccccaacag acagagcctt tgtctcttat agttggtct    14340 tcagattctc tttatcccac attcagccat ttttgtaaaa gagaggctag caccagctcc    14400
aaatatccaa atctgcagtg tttgagatct cactgcgcct cctccatacc aacacatttg    14460
ccattactta tagggtagtt ttcatgtgag ttctaagttg attaacacac aagaattaga    14520
agggtgggag gctctaggaa aggcactgtg ggactatttg actgcatggg tgtgaaaatg    14580
taaggaacag gcaagagctt ggatcccatt ctctctgccc acattgtgac ttgagatata    14640
ctaattgctc ttgggggtct cagtcatata ccatccataa cagagttaaa ctgagagaga    14700
tacaggatca gctagaatga aaagcccacc ccatgcttcc agaaagtccc ctctttatac    14760
```

```
ctcctgtgat atgaactaga ggaaaagcaa ttgactttgc ttctcaaaca gcctacggca   14820
aagccctgtg agtttg                                                   14836

<210> SEQ ID NO 2
<211> LENGTH: 25001
<212> TYPE: DNA
<213> ORGANISM: Mus musculus

<400> SEQUENCE: 2
aagggtttct ttggcttaca cttttcttat tgttgttcat tattgaagga agtcaggaca     60
ggaattcaaa caagtcagga tcaaggaggc aggagctgat gcagaggcca tggagggatg    120
ttacttacta gcttacaccc cccccccccc cccggcttgc tcagctttct tttttttttt    180
tttttttttt ttttttttag atattttcta atttacattt caaatgctac cctgaaagtc    240
ccctatacca tcccccaca ctgctcccca acccacccac tcctgcttcc tggccctggc     300
attcctctgt attgttgctc agctttctta tagaacccag gaccaccagc ccaggaatga    360
caccacccat agtaggctgt gccttcctcc actgatcacc aacggagaaa tatgggcaac    420
agcttgccca taggatgggt cactagttgg gttggttact gttgggccat tccctcagtc    480
tctgctccat cccccatctc tacatttctt gtagacagaa tcaattttgg gtcaaaagtt    540
ttgcaggcag gttgttgtcc ctcttacatt tctcatggag gcatttcctc aacttatttc    600
ctctctctga tgtctccagc tcatgtcaag ttgacacagt tgttcgggac ccacatgaag    660
accaagctgt tcatctgcta catgtgtggg gaggcctagg tccaacccgt gtatgctgtg    720
gtagttcagt ctctgagagc caaaacagtc caggttagtt gactctattg atcttccttt    780
ggagttccat ccccttttggg gccctcaatc cttcccacaa ctctaccatc agagtcccca    840
agcttcatcc actgtttggc tgtgggtctc tgcatccgtc tgagtcagct gctgggtgga    900
gcctctcaga ggacaggctt tctagactcc tgtctgcaag catagcatta atagcatcag    960
ggattggtgc ttgcccatag gatggatcac tagttgggtt ggttactgtt ggccattccc   1020
tcagtctctg ctccatcccc catctctaca tttcttatag acagaatcaa ttttgggtca   1080
aaagttttgc aggcaggttg ttgtccctct tgctccactg aggttcctgc ctagctacat   1140
gaggtagcct ctttaggttt gatatcctca atgctgtgaa tcccaactaa gatcaccccc   1200
cattcattcc tggtgtctcc cctatctcag gtctcagata tgccttcaag atgccccccc   1260
cccacctctc cacctctgcc agctgcagat ttccattcat tctcatggcc atctggctat   1320
ctctcctgtt cctccccata cctggtcctg aaccccttc accccactcc catcccctc    1380 tcccacccag ttcctttcct ccatcttcct cctatgactc ttttattccc tcttctaaat   1440
aagattcaag catcctcgct tggacattcc ttcttattta gcttctttgg gtctgtggag   1500
tggagcgtga gtattccaac ttctaaggca cacagacaac ctcagattct ccagcccttt   1560
gtgtgtgttg cttatttgaa caaacgggtg aagaaaaca cacaaagttg gcgtgttgaa     1620
agagttagtc gatcttctgg ggtaggtttc agtacagaga ccaaagggac attctcagac   1680
actagacaca ctatgcaaag acaggatgtc acatgacaaa ggataacggc acaagtaaac   1740
atttaagcaa cagtgttcca taccggctca cgtagaaaaa ggacaagact ataggaaaga   1800
aagcaaacac tccgccgagg actacagcaa agacagaaag tatctgcagg tacggcttca   1860
aaaggagcat ttctctcagc aacttatatc tgttaatgcc ctgtcttctg gaataagggc   1920
ttagttttta tcagtagaga gagattgatt tttaagatgt atctgatttt acattgtaga   1980
```

```
tctccttagt caccccctgt agtaaactaa ggaaaacttc cgtggaggga gaggggaaga    2040
ttagtaactc gtagtgagta agaattctct ttcaagaaaa agattcaaga gcaatacaag    2100
gcctagatat gaaggtgtgt gtgtgtgtgt gtgtgtgtgt gtgtgtgtgt cttaacagcc    2160
tgttcagaat ttagtaggtc acatacactt acaagtaatg aagacaatat attaatgaat    2220
ttgcagtaat ttttgttttt agaaatagaa actgttgtaa ggaggataat cattcagagc    2280
tctttgatat gtatcactca cattcacata catgcataca cacagagaga gagaaagaga    2340
gatacagaga tagacagaga gagaacccaa aaatgtaaag agaggaaatg agttgaaaga    2400
aaaaatggga aactgggtta gggaggggtt cagatgacag tgactggggg ctttcagagt    2460
tgggagtgag gcagcgatgg agagagggca gggaggaggg agtgtccatt gtgacctctg    2520
cagaactctg actagactga gcagctcaca ccgtgttgga gctgtcctaa cactaccaag    2580
gggacggggg agaccccatg aacaccacct agggagttgc tcctttcatt ctgtgtaaag    2640
tctgatgtct tcaaacttgt tgtaaattta tactctgttc taaaaacagt gacattcttc    2700
tctttgtagg atgacctcat tacatcaggt gttatatttt atctttttg cctcagtttc     2760 tagtggtaag ttgctgtatt tattttcccc taacataata ttttttatta cttgagagtt    2820
tcatacaatg caccctgatc acactcactt tccattcctt ctaagttcac cctcccactc    2880
ttgagccctg ccagctcact ccccccttct tgaaaaaaaa tcatcaagtc aatcaatttg    2940
tgttgagaat atatactcgt tgggaatgtg atcaaactcc caatggtcag ccccttaaag    3000
aaaagtgagt cttttcctc ccccacttct ctccccactc ccttacccag ttggaagcca     3060
tcaactgtga agagttatac ttcagcatct ttactacaat tttaaaggac tctcttcagt    3120
atttaagtat ggcttagaaa tagctcattc cttgacctgt aatgtaggaa acagcctaag    3180
tccacaaaaa gaaattacac ttcagacccc atatattgtg gaataattcc atgctgtgaa    3240
ctccagggaa ggaaatagag tcgtttattt tccagtgaaa gctcccttt aatacatcaa     3300 agaaagaaag agatttaaat atagaattac aaagagtctt cacctatatc atctgaatgc    3360
tagtaatatc tgtctataga gttgcatctc tatctaccta cacaacacat tgccatgatt    3420
cctaggagca agattagaaa gagaagactc gactcacctc attgattatt attccataag    3480
ggattcagtc tagtatctct ctctgtctct gtctctctgt ctctgtctct gtctctctct    3540
gtctccgtct ctctctctct ctcttttctct ctctctctct ctctctcacg cacacacaca   3600
cacacacaca cacacacaca cacactcacc aattcctgac tgaaaatgtt atagaaaaat    3660
taatgtgtgg cttacacatt tggttaattt accccttgca attatgcttc cattctacat    3720
tacatccagt aaatacattg cttaccattc agtagaatga aatgggaagt tacctcacca    3780
atactgatct taacaactta gtgtaagcac ttcttaaaat aatttattta tgttatattg    3840
aatgcctgag actgccattg acatattaag catagttagt tcttttggt gtgacacatg     3900 tgaacagtag cagatctaaa ataaaataaa catatgtaac atattaaatt atacagatta    3960
tagcttaatt tttctttgtg attagattga ttttcaggtt attccttcat tatcaatgtt    4020
ttgaaatccc attgttattt gtactgtctt gttcagtact gttttgacat gttgttgttg    4080
ttgttgttgt tgttgttgtt tgacacagag tttctatgtg tagccctggc tgtcctggag    4140
cttgatttgt agaccaagct gacctcaaac tcagagatct gcctgcctct acctccaagg    4200
gctgggattg aaggtgtgca ccatcatcgc tcggcagcct gtcttaacat cttaaacact    4260
gagttcaata actgtgtcga ttcacaagga cattctgaga attataagac ttttttgctt    4320
atgaatatat atatgcaaat gtaactgaca aaatattatc cattgtggtt gtatcacact    4380
```

```
taaaaatctc agagccgaga aagttggggc aagatgatta aaagttcgag gacaggatgg    4440
gctacataac aaggttctgt ctcaaattgg ctataccaaa ccgtccaaca catattttaa    4500
agaaaaataa atgggaggct agagagatgg ctcagtagtt aagagcactt agtgctcttg    4560
catgggatca gttcaattct cagcgcccat gttagatagt tcacaacttc ctatgactct    4620
aacttccagg aatacagcac cctcttctgg cttctgtagg tacacacaca cacacacaca    4680
cacagacggc atacgtacat acatacatac atacatacat acacatac atgcctacat       4740 acacatgtac atgcatacac aataaaaaag ttttaaaat cttttttttt aaagaaagaa      4800
aattaaaaga ccaattacat tggcatattt tggccaagtt tgcttaattc taggaacaag    4860
gagttacttt aatctaagaa aaacaatcaa tggatgcaat gtagatccaa aggaagtgaa    4920
agaagagagt cctacagaga tttgtcattt gtcttcctgc tatcgggcag agaaccagca    4980
agagagaaac gtgggcattt gaagcccact cagccgtgtc atagcacaag ttgggtcttc    5040
accaatggac agaaggttaa acaaaatata atatcacagt atgcacatgc aacacaaaac    5100
aggatattac tcagcgtgtg aggaagaaaa ttctccctca tactggggca tagctgagcc    5160
ttcgtggttt tatactcaac gaaatgagtc atttacaaat gaacacatga ctgaacccct    5220
aacgtttggt tcccagagat gccgatttca ggaaaacaaa agaccgaaga gaactgacca    5280
ggggctaatg ctaatgacta tttaatgggt acaagttttc agttgaaaa gctgaaggaa      5340 ttctagaata gtggtggaaa ttgtacctaa ggtacatact tcattccaca actctagaga    5400
cctgaaaagg gccggagtga caaactttat gtcatatata ttttgccata gaagaacaaa    5460
attaaaataa tctaacacat cgaagatttt aaagattttc ataataaat agtttagcaa      5520 actcagaact ttcccaatga ctaagtagta ctgtaaaaca acaacaacta gaaaaacatt    5580
caaaccaaaa gttttcaaga aatctcatat gtaatggtga ctgaaatagt gtttccctga    5640
ggtactgggg taaggcagga gtatccacaa cttggctcct gtgaatagga aacaaggaac    5700
agagagatgc aagcatcttc aaaaagttgt cataggatcc atcatggaca ttccaggagg    5760
ggttcagttc tactttagt tttctgtgac atctcattac aggttttgat ttttt ccccc        5820 catagcttcg ccagcatgga aatttattca caagtaccaa gtcagggagt ctgcctatgt    5880
gtccatcaat agatgaatgc aaagagcaaa cactggatgt aggcacagtg caggggg cag     5940 ggaggggtgg catgttctgc atttagctaa atggttgtt ttagttttta ctaattcttc        6000
aagaatgcca tataccatat tttgctaatt tttacctcga ctccccaaac tccatccaga    6060 acccccatt ctgtacccac ctaactctgt gttctccctg tttcatttgg ccacagtgag      6120
gaatgaaatc gtgccatttg tgtaacaatg gctgtgactg ggcatcatca ttattcagtg     6180
agataagtca gattgaagaa gataaatatc ccattttctc aaatttgtgg attctagacc    6240
ttatatggat acataaaatc cagtgtgtgt gtgtgtgtgt gtgtgtgtgt gtgtgtgtgt    6300
gtgtgtgtgc ttgagtgaca cactctaggc tccagtgtct aggggaatga cagagactag    6360
aaggaaagag ggaaacgaaa agatatgaag aataaatata gtcgaagcac atgatacatg    6420
cctatgatat tatgatgtat acacacctat gcaggtgtcc catgaagccc cctgctatgc    6480
aacgaatacg tgtcaataaa tgtgttgaga gactatctac tgtcacttcc cttaaacatt    6540
atattagaga tcctgtgtag cacagtaggg aaggtcgaag gacctaagag tcaggagaaa    6600
gatggaaatt aactgactct tcccataaat gtggttatgt acatagaaaa attcaaagta    6660
atgaatgcac tgattatttc aggcagatca gcaaggagtt tacaaactcg atggaccccc    6720
```

```
gggagtggag gcacacactt gtaatctcat gactcaggag gcagagggca catcagagac    6780
cctaactcca gctcttccgt tcaaaatctt caatatacaa acagtagcca actctcgcca    6840
gtactaggaa ctgtactgag attatgaaag tcaatattat aggttaaatg attcaagtag    6900
tggctacatc ctaatcaaaa ctgcacattt attaatcctt taaaaatcaa ttcaacttat    6960
caaatcctgg tgttgtgctt gataagaaca ttttaatgtg ttatgatggc ttaatagtaa    7020
aatgttgcat ttcttagagt taacaggtaa actgtgaggt gggaatagac tgccaattag    7080
ctggaaacag acgcagtatg gtttggtggg agacaacact gaacttggaa aaagaagtcg    7140
gatctctatg tagctcctgg gatacttgcc tgtagtggag aaaaccatgt tccctaccaa    7200
gtctctgctg aattttggaa atggatctgt agtgaggttg ctcttcctcc ccacaaatcc    7260
cttccgaggc cccatggacg cagcggagcc tatccttgga ataacttttc taaaggcatg    7320
gactaaaaat atatagggtt gctggggaaa ttaattatat tgaaatatga gtagctaaag    7380
tggaaaatac tcagtacaga attagttgtg gctcggagtt aacaccttac atgacattag    7440
tggcatgccc aaaactgaat agaaataacc aacaaattat cgacaaatca taatgatgtt    7500
atatctcatc atcacataca tgacaaatac taatcatgtt aattgattac attaataata    7560
caggtatgta tgtaccacat tttggttagg gaatcaatga aaaaccacat gaggtttttt    7620
tgagctcgtt ggttatctag gtcctacaag cctcatagga gggttttgag actgctatgc    7680
acctacaatc ctctcaagac atgactgatg gctgttacag tagtctatat ttgagttaaa    7740
ttttattctt ctggaagtac ttccacgtga gtctggtaat gttttcaagt tataaagaga    7800
aatgggctag caaaccctct ccatgggcat gtatggctgc atgaagtaat cttttattca    7860
gtcactaggc aacctactgt gtgaattatt agctatctct tctagcaaca gagcactttt    7920
gaatttttat gcattttggc tttttaaaaa ctaaagctga tgtaaggttt tcgctaaata    7980
gaactcagta agtttttccct ggtaaatgtt ggtcatgaga ccatttttaa tgttcgcatg    8040
acatcataca agggccccctc agtcttggct tttagtttgt ggtagtgtca aaacaataaa    8100
tgaacgtaaa cacagcacac ccttgctgac cccctagagg ggtttcatgg ggaccgtgtt    8160
cttcttgccg gtcaacagct gagaaatcac tgagttgctc ctgcagcctt cccaagacaa    8220
tcactcataa atgtgacaac acggagggcc cccatgttgt ttgtgattta gttccatc     8280 tggggctgtt cactgaagag cgttgcccga tctgatgtcc gaggtcaggc atatttagca    8340 ctgactttt aacaaaccat gtaacgaggt aagtgcccac caacatctgc agtaatgtgc    8400
gcccgcgtgt ttttttcttc acagaatgcg ttactaaggt cttcaaagac atcagctttc    8460
aaggaggtga cctgagtact gttttcacac cgagcgccac atactgccgc ttggtctgca    8520
ctcaccaccc acggtgcttg ctcttcacgt tcatggctga gtcatcttcg gatgatccta    8580
ccaaatggta acagtttctg tttctctgaa gaggaactga tttccagtgc cagttactca    8640
ccaatgcaga ttaccttaca accccacttt tgtcatttta caaaggggga tgttagtggc    8700
tggaaagtga gtttccttcc acggaaatac taaatattac aggaaggata gcgcttaggc    8760
atattggtgg aaaaccgtaa taactcctgg gacctcaatc ttaaagtcac gttttgctc     8820 ttcatccatg gtttgtctta cattcttttt ctgtcgtggc tattggctaa caatggtggg    8880
gttatctaga gcttccttct aacctttcaa ttaggggaa aatgtttaaa aagctacttt    8940
aaaaattatt acaacaattt tctacccct ccaatatcct gtcatattat gtggctttct    9000
cggctcccat cagtggttca ataaggcatg cagactttta tataaaactt aaggcccttc    9060
attggggcag gcagactctc agctctcttc tctaatctta gatcgtctgc caagtagcta    9120
```

```
atgatttatc tcgtttccat tcctttccct atctgcctct gaatctccca cctctgcttt    9180
agttctctct ctctctctct ctctctctct ctctctctct ctctctctcc ctctctctct    9240
ctctctctct ctctctctct ctctctctcc ccctctctct gtcccacccc cagaagtccc    9300
acccttgtac ttcccgtccc actttaggca atatgagtgg gtgaggaagg acaagcactt    9360
acaaatcaga agctggtgat gggccataga catgacgata ccaaacatct gccagaactt    9420
agctctttgc cagtacagta atcaacaatt gcacaattga agtacagag acacgcctta     9480 atacaatata aggaaggtca tcgcaacact gtcatatttg ctttacctac ctgtatatgg    9540
tcacagataa atactgaaag tgagtttaaa atatcatcga cctgcatatc taaatacttc    9600
aacatgaatt tcccaataag gaaactgtaa gaagcccaac aaagttaaac atacttgaaa    9660
tgttaatttt agctgttaat taaattctca tcaaatttca caggttccta tggctgtttt    9720
tccctctcta tcttattttt aaaatattgc atccatttct gtctctatgc taagcttgaa    9780
attttaatat ataaccttta atgcaaaatt aagctgccaa tatctttgtt attgctgttt    9840
tctcagatgg ttacatattg ctgtcaacat taaatattct tctgaaatct agaacagaga    9900
tcggcaagac aggaataaaa ctttaggctt tgttgaacca aatgcaaaaa gaacattctg    9960
tgtttctaac actgttttag aatgtaacca tgtgtgggct ggagggattg ctcagtggtt   10020
aagtttgctg gctgctcttc taaagggccc taggtttgtt accccaactt acagagattt   10080
gcaatcattg gtaactccag ctctagatgc catcttctgc ctttctcatg catgtgatca   10140
cacacacaca cacacacaca cacacacaca cagagagaga gagagagaga gagagagaga   10200
gagagagaga gagacagaga gagacagaga cagagacaga gacagagaca gagacagagg   10260
cagaggcaga gagagagaca gagagaggca gaggcacaga ctgagagaga gtgtgtgttt   10320
aaaatttaaa atgtagccat gtaaaaaata gaaaaccatt tctatctcaa ggataacaca   10380
aaaatggcag atttttaagca acatttttagc aataggttaa agtccttcca ttcttattca  10440
tgtcctgttg gaaaggaggg ccgtgtgtgt tcttttagat gtagggatgt tgtaataaaa   10500
aacaaagtca atcttgcta attaaacatt tgttttggca ggaaacccag tcgtttgtct    10560
ccttctcttt gaccttagga tcccctcttt gaaagcatga attcctgctg aataatgtta   10620
ttttcatttt attttactat tttattttt aaaaagaac aggtttgcct gcatcctgaa     10680
ggacagcgtc acagaaatat tgccaatggt aaacatgaca ggcgcgatct ctggatattc   10740
cttcaagcaa tgcccctcagc aattaagtag taagattttt tttatcaaat acaattaaaa  10800
ctagccatta gagtatatac gtgtaatcgt ttcagataca ggtttgtggc tataaaataa   10860
aatactacca cctaggacta aacttcccac caaggaacca tcttcctatg tagagtagag   10920
gacacagttt tctcccttcc tctccccata agcacactgt ctcgctttac catttcttag   10980
cctcataaag gcatgtcagc acctcagttc ttattattgc acacgaaagc cctcgttata   11040
aaagctaatt caaatcaaga ggagaaatgc agactgaagt ggcacatgtt ttaatagtgg   11100
aacgggcact tttcagtaag ttaaggggtg aaccagttgg tcagtgcggt ttgaggtcag   11160
aaagtcaaaa ttcaaattca caagcttctt atttgttaaa aaatttttt atttatttta    11220 tatgcattgg tgttttgcct ccatgtgtgt ttgcgtgagc gtgtcagatc ccctgaaact   11280
agagttacac acagttgtga gctgccatgt gggtgttggg aattggaccc aggacctctg   11340
gtagagcagc cagtggtttg aatcgctgag tcccctctcc agtctcaaat gtacaagctt   11400
aaagcggttc cagtctaaga ggcacattgg cttcctcgga atacctccta gtggaagtgg   11460
```

```
gaatcacagc tgagtgaaac aaaacataga acttccacgg gagagtgggc gagaagcgag  11520
cagtttccac gcgagagggc cagcagcgaa agcagcgtac tgtagttgcc cctcgcttct  11580
ggtgacgcct agattctccg cctttatttc cagcttgcag caaagatgtg tacgtgaacc  11640
tagacatgaa gggcatgaac tataacagct ctgtcgtgaa gaatgctcga gaatgccagg  11700
agagatgcac agacgatgcc cactgccagt ttttcacata cgcaacaggg tattttccca  11760
gtgtggacca tcggtgagtg agcgggagtc cgagccgctg gatataagcc tgcccaggga  11820
aagaaaaccg ctggttccgt aggtattttc atcaatttga agcctaaact tctttttta   11880 aaccccaaga tatttgcata acaacaatca ctgttttgtc atgaaaaggt catagcgtgt  11940
ctaacacaca tttacgacat attcaaattt cagaactgga ggatggctcg gtgggtgcgt  12000
aaacacactg cttatgcagg gaccctgagt ttggatccca gcatgcacat aaaagccaga  12060
tatgggtgtg tatgccttta accccagtgc ttgggacatg ggcacgggac agaggagga   12120 tggttggagc tcactggtta gctccaggcc tttattatta ttattattat taaatattgt  12180
ctttatttac atttcaaatg ttatctcctt tccctgcccc cccccaacc ccctctccca   12240 tcccctccc atttctacta ggttgtttac ccacacacca acccactcct gcctccctgc   12300
cctggcattc ccctacactg gggcatagag ccttcacagg accaagggac tctcctccca  12360
ttgatgcctg acaagaacat tctctttagc tccaggctta gggagagatc ctgtctggag  12420
gggaaaagac agagaggtca tagggcagga actctaacac ccccccccca cttggacttc  12480
ctattctcac ttgcatacc acaccccac accccacaca caccatatac aatacataca    12540
gcgtggcctc acagattctg tgtatgttgt aaagcataca caagcttacc ctatctaact  12600
tcaaaaggca ttacattttc acgcttgtgg ttctgagagc tcggtttgct tggccatgct  12660
cttcccagtc taacaaatgt cctaacctaa aaatcatcaa aacttaaagt tgtttctct   12720 atctacctac atgtacagtt ctgtccctta cccaagacga agtcattgga acccatgtgc  12780
aaagttttct cctgtttgat gtgggattcc aaactcctcc aaggaagaaa tctgttatat  12840
aaactaacga gagggaatga ctaaatctgc atcttcagtt taaattgttg ttagaaaagt  12900
atatgacttg ttcttttaca aacattttaa ttttgtgtgt gtgtgtgtat gtttatgtat  12960
gtgtgtgcct gtgcgtttag acacacacgt gtgcagataa ctatatagcc agaagagaca  13020
tctctcaatc tctcaaggtt catttttaga cttaggaatc tttgacatta tctagatttg  13080
cacagtaaac aacaggtatg tggtagttgg attttaacat tggctattcc tacttcactt  13140
tccataattc tgggggggaa aagatgaatg ggaagtgaaa cattaaagat gtcttttaga  13200
atgaataata aaaaatgga aagtagcctt ctatggctct ctttagctct cctcagagga   13260
catgttttat gtcttagact tcacagaatg ccaactgcag gctaggaaaa tgttcctagg  13320
gcttacacaa aagcgtattt ggagggctaa cgtgaacccg ttcacacaac cacctcacac  13380
cacatcaggt cttctgtgtt gtcctctcac tgatgagata acattattcc tgagtccaca  13440 gagcctcct gtggttagaa gagctgccag gactcatgca gccacctggc tctgcaggtg    13500
aacactcctg ggcagttcct ctgttattac agtcatttcc cccctgcgga ccgtaacttc  13560
ttatcctctc gtgtttttat acacttggaa agaacaatat tttgccattt ttgtttgtat  13620
tcagtaaaat gtgtctttg aagtacaccc gaacggggac gccaaccaca ataacgaagc    13680 tcaatgcgt ggtatctgga tttcactga agtcctgtgg actttcaaac ttgggtaact    13740
atcatttttc tcaatgagat attggtacca ttaagcctga gtgaagcaga gactatgtgc  13800
aatgggtcta acttaaaaa cagctgatgg ttatacatga agcgaaccca gtaacctttt   13860
```

```
actgtcttca aagtgaaatg gttcactatg tcctggaaag catttccttc ttaaatttca   13920
aatttgttct ttttataaac aacaacaaca acaacaacaa cagcataaat aaataaataa   13980
ataaataaat aaataaataa ataaataaat aaataaggtc ttcggatgaa ctttccattt   14040
ataatacaat ttacaaaccc tgtctgggat gtctatgatt ttgctggtgc ccctgccttc   14100
ctaacacagt ttcttccctt ggacagcttg tatcagggac attttcccta acacggtgct   14160
ggcagacctt aacattgaca gcgtggtggc cccagatgct tttgtctgtc gtcgcatctg   14220
cacgcatcac cccacttgtt tgttcttcac attcttttcc caagcatggc cgaaagaatc   14280
tcagaggtaa ggcgttgtca ttaagggtca tctggtcttt ttaaaaaaac ggccaataaa   14340
aatgtgctgc acaatcaaga taggaaacgt ctaggcagca ggacacttct ggactccttg   14400
agatagattt gaattgcgga aaggaatggt accagcagga ggaaagactg ggaccacgga   14460
caatagggca aggttcaaaa gtgttttgaa aagttcttag tgacattaca atttacagaa   14520
cgcgacttgg tgattcaaga agcaatgtta ggatgaggtt gctattaaat gcttctctga   14580 gctacccttta tttgctatac ttgtaccaag tggtctttct ctttgctata ttttatctga   14640
tttattcata cactcccttt ggtccttag acatctttgt ctccttaaaa cctctgaaag   14700
tggattacca agcacacgca ttacaaagag ccacgccctt tcgggcttca gtctccagca   14760
ctgcaggcac agtgtcccag gtaaacaatg caggctgtcc ctctctctga gctccacagc   14820
cccaaggaac tggatggctg tgaaggctac acacttcaaa cctggcgtgt gctttgttgt   14880
ctagtattct gccatccgtc cttttacaac gacactgatt tcttgggaga agagctggac   14940
atcgtcgatg tgaaaggcca agaaacctgt cagaaacgt gtaccaataa cgcccgctgc   15000
cagttcttta cctactatcc atcgcacaga ctgtgcaatg agaggaagta aggcacaagt   15060
taggtggatg ctcttggagc atctccttgt aggatgagtt ttgcttacag agttttgttt   15120
tcagccgcag gggcagatgt tacctaaagc tttcctccaa tggatctcca acgagaatac   15180
ttcatgggag gggaggcatc tctggatact cactgaggct gtgcaaaatg gataatggtg   15240
aatacttgaa aaaatacaac tgaagtggaa tagtcaacct aacgttgcta gtctactaca   15300
cgaggctagt ctacaacaac catagagaga tggagacagc agcacaagga ggttgaggca   15360
ggagaatcag aaatttaata ccagattgga ttaaaaggca aaatcctgta taaaaaatga   15420
caacaaaata gacatggaag agagaacaaa gttaacaaat ttggaggttt tcccttacat   15480
atatgtatgt catatatata tatatactta tatatatatg tatatgtgta tgaatatgta   15540
tatgtatata tgtcatttca agtggcattt cctgtagaga cagacccaga gggccaattt   15600
ttgttttcaa gaagtgtttt ttttaattat cagagattaa actattaaac agtccattaa   15660
ataaattatt cattttcttc ccacttaata tttcagtgag ccatgattag atgctatgat   15720
atatgatatg atatatacac acacacatat atataatatc tctcatatat atatatatat   15780
atatatatat atatatatat atatatatat acatacacat acatacacac atgcatatat   15840
ataattccag atgttaagct atcctgtaaa ttgtgatgag atttcatcaa taagtgtga   15900 ccctaattac tcctcgtgaa agtttcaaaa gtataaaacc ttttcatca gtcatttgc    15960 tattctagaa ggtgactcta tccttagttt cagaggacct gatttacagc acattgagat   16020
gttttatccc aacaactgca gtgccctaaa cagaaaacat gccttcctag aattcactgg   16080
tttgatagca atctctgggt ggcctgagcc tcttaagaca gttaattaag ttatagttca   16140
tacacactgt gttttgctca tgataaactt acctaataag aaggaacatt caagacaagt   16200
```

```
attgtcttaa ttctacttct tcatggtaga aggggcaact agaaagacgg ctaagtcatg   16260
tgagcatgct ttaaaaactg ggatccagaa cagatagctt gatacactga agattacatt   16320
tctcacccac ttctgccttc attatgtttg tctctgttga atttatagcc tggtctgtac   16380
aggtgacaga atggatcagt tgtagattga cagaagagaa aatgtggagg gtaataaacc   16440
tgtctgcctt ctcatgcata gagaagtggt tacactgtac aatattgggc tacaatactt   16500
acctttatgc aagagagaag atcgaactca gttgtttttc gtatttactc tgttgttggt   16560
ctctaatgta acttgacttc ctaaagacac ctagcaatgg acaccactaa aagaagtatt   16620
tcttcatccc caatgcaaag ttgagcacta aagttttca gcattctgtt caagttgatg   16680
gagcagacat cgagatagaa ctttttctga aggcttgcat tgggcttact gataatgtgt   16740
cctacttact gcttgcctgt taactttcta aaggttacct ttctgctgat ggactgaaag   16800
gtttctgagg gatttctcag aagcctttca ggacgaggga cattgaagcc taggtaactg   16860
ctaaccacac tctctctgtt gtagtgtgca caactaaaat caaccccaga gtggtaggag   16920
gagctgcgtc tgttcacggt gagtggccat ggcaggtgac tctgcacatc agccagggac   16980
acctgtgtgg aggctccatc attggaaacc aatggatact gacagcagct cattgtttct   17040
ctgggtgagt attattgcta ttctcctggg attgccatca tgaaggtgaa atctgggact   17100
atcataagag tcaataaaca ctttgaaaat gtaaatgatc ctgtttccta aattaattct   17160
ctctgtgtgg gcagggacga tggtgtagaa gagaccagtc ctcatcattt ggccacaata   17220
gaacaggggc aggagcagag cagattgccc acctctgcct tttcattcaa acgcaaatta   17280
tttccattgt cttcctgatg gtgcctggtg gcgaagcaca gggccagagt gaagcttaca   17340
atcctcagct ctctgaatcc tggttaccct agtctctctt tctctgcctc cgaatgctta   17400
gagttcagca cacaccatca gaccagatcc ccgcacttag cattgctttt cgatattggc   17460
caaatgtgaa catcttagcc ggggaagtgt gtatctcgag gaaattcggt tgagtgaaac   17520
cttttctgtg tactttagt gcctctgttg cttccagaca caggtttaga ggctaatcgt   17580
tttgttaatt ttttccatg catggatgca ttatgcacat aattcaatgc tacacttgag   17640
atcaatagtc cccttgcaa gcacatatga aaaaacacag aaagtcccag tgactttct   17700 ttaaattctg cccaagacaa ggttgagact aatacccaac tctcctgagc ttggagatgt   17760
gctggggagt agaaagacca tttatttaaa gtgtccaata ttagtgcaag aactaatcca   17820
gtgatttcac tgtagaggaa atatgtgact aaaagttttg agaataaaat cactttttt   17880 accacctaaa ggtagaaaca gacacagagt ataaataact gtgaaacaca aatatttgga   17940
aattgcctag tgatagattt tttttccat tctgtttgtt ccttaggata gagacaccta   18000
aaaagctgcg tgtctacggt ggcattgtaa atcaatcaga aataaatgaa gggactgctt   18060
tcttcagggt tcaagaaatg ataattcatg atcagtatac gacagcagaa agtgggtatg   18120
atattgccct gttaaaactg gaatcagcca tgaattacac aggtatatat atagagagag   18180
agagttttag gtgacctaga taaaacattc acgttaggag actcacagtc tcatctatgg   18240
ggtctaatca acagacagac aaggaaggtc tgaaagatg gcctcactct gttgagacag   18300
agagtttgcc ttagaatact agattagcga tccatactta tctccttgta ctaaggtcaa   18360
atctaagtgg atcaaggaac ttcacataaa accagagaca ctgaaactta tagaggagaa   18420
agtggggaaa agccttgaag atatgggcac agggggaaaaa ttcctgaaca gaacagcaat   18480
ggcttgtgct gtaagattga gaattgacaa atgggaccta atgaaactcc aaagtttctg   18540
caaggcaaaa gataccgtca ataagacaaa aagaccacca acagattggg aaaggatctt   18600
```

```
tacctatccc aaatcagata ggggactaat atccaacata tataaagaac tcaagaaggt   18660
ggacttcaga aaatcaaata accccattaa aaaatggggc tcagaactga acaaagaatt   18720
ctcacctgag aataccgaa tggcagagaa gcacctgaaa aaatgttcaa catccttaat    18780
catcagggaa atgcaaatca aaacaaccct gagattccac ctcacaccag tcagaatggc   18840
taagatcaaa aattcaggtg acagcagatg ctgtcgtgga tgtggagaaa gaggaacact   18900
cctccattgt tggtgggatt gcaggcttgt acaaccactc tggaaatcag tctggcggtt   18960
cctcagaaaa ttggacatag tactaccgga ggatccagca atacctctcc tgggcatata   19020
tccagaagat gccccaactg gtaagaagga cacgtgctcc actatgttca tagcagcctt   19080
atttataata gccagaagct ggaaagaacc cagatgcccc tcaacagagg aatggataca   19140
gaaaatgtgg tacatctaca caatggagta ctactcagct attaaaaaga atgaatttat   19200
gaaattccta ggcaaatgga tggacctgga gggcatcatc ctgagtgagg taacacattc   19260
acaaaggaac tcacacaata tgtactcact gataagtgga tattagccca aaacctagga   19320
tacccaagat ataagataca acttgctaaa cacatgaaac tcaagaaaaa tgaagactga   19380
agtgtggaca ctatgcccct ccttagaagt gggaacaaaa cacccatgga aggagctaca   19440
gagacaaagt ttggagctga gacgaaagga tagaccatgt agagactgcc atatccaggg   19500
atccacccca taatcagcat ccaaacgctg acacctttgc atacactagc aagattttat   19560
cgaaaggacc cagatgtagc tgtctcttgt gagactatgt cggggcctag caaacacaga   19620
agtggatgct cacagtcagc taatggatgg atcacagggc tctcaatgga ggagctagag   19680
aaagtaccca aggagctaaa gggatctgca acccaatagg tggaacaaca ttatgaacta   19740
accagtaccc tggagctctt gactctagct gcatatgtat caaaagatag cctagtcggc   19800
catcactgga aagagaggcc cattggacat gcaaacttta tatgcccag ttcaggggaa    19860 cgccagggcc aaaaaggagg agagggtggg taggggagtg ggggtgggtg ggtatggggg   19920
acttttggta tagcattgga aatgtaaatg agctaaatac ctaataaaaa tggaaaaaaa   19980
attaaaaaaa aagaatacta gattagactt tgagagtgca gacggagaga cttgccttca   20040
ggcttcttca ggtacataga atgacatcgt tttataaaat accgaagcaa taagaataat   20100
gattgatatt ttgctttagt aacaaagggc ttgacagcac agttgagcaa atgctacaga   20160
atattaaacc acattaaaaa tgaaaggtgg tgtaaagagg gcctgtctta cccttttccct  20220 tgtcccttct gcttgggaca tttcatatgt gccactgaac acatgacatg aaacacatga   20280 gaaaagata acgaatatca taagaaaga gagcatgatt aatgtcaggt gagataacac     20340 cccttttctgg gacaaatgat tggctttctt tctgcttcgg tcagctttc gctactgtga    20400 caaaatgcct gatgtaacca ccctgtaaga aagaaaggtg atatgggctc tcttgatgtc   20460
agaggcttca gcctgcagtt gtgtgtgtgt gtgtgggggg gggggtcca ctgctttgta    20520 gcccttggta agaaatgtgc agaggagcaa attttcacct cctggatgct gggaagcatt   20580
aatgaaggga cggggctcct gatagcccct tcaaaggccc accctcaatg acgtcacttc   20640
cttcctacac cttcccccccc aacacacaca cacacacaca cacacacaca cacacacaca   20700
cacattctcc attatctcta agtagtgtca caggctggga tggagtcttt gaacatgggc   20760
ctttggggag acacctcaga tccaaaccgt agtggcctct gatgactaaa ctgtgatttt   20820
caaaattaga ttttcagcgg ccaatatgcc tgccttccaa aggagataga aacgcagtgc   20880
acacagaatg ctgggtgact ggatgggggt acacagcact aagaggtaac aaaccatgcc   20940
```

```
ttctatctct gctttattct gaagtcaaag aacagagctt aaccattgcc tctgttttct   21000
atctagtcat atggcccaaa cgtgagtcaa gtcacctact caataacagg aagactgata   21060
acaaagatca atacatctga tcagaaacgt taaatatgat taaacccctc taaagaccat   21120
tttaactgga gacttttagt ttgggaccta acactctatg taaaagttct agcctggttt   21180
ctaattattt tgtctgaaaa gaaattctac ttagtgtcag ttaattttga acttaataac   21240
attaatgaaa ttatgtacac aatagtagaa acaatgtctt ctttatactc catacttaca   21300
aaaattactt atgaatcaag cttagtaata ccaccccccc ccaggatttg tatgtacaat   21360
tttggctttt aaatataatt gtatataaac ctatagtaat tattcctcta aaacactaat   21420 atgaccettt tcaggtgaag tacaaagtac tcttcagaaa gccaaggttc cattggtgtc   21480
aaatgaagaa tgtcagacaa gatacagaag acacaaaata accaataaga tgatctgtgc   21540
aggctacaaa gaaggaggga aggatacgtg caaggtaagg cagtctcaag caatcagtca   21600
tgccagattg aagtgagagc ttaatgcatt tgtacaaacc actgtaccat tgagcagtgt   21660
ccgagtgtgc ttcctgttgc tgtgataaaa cactgaccaa acacaactca gggaaggaaa   21720
gggtttatca agcttacagg ttacacagtc caccatagcg gaaagtcaag gtaggcagga   21780
actgcagtag agacgtggga ggagtgctac ttcctggctt ctgtttagtc ttgtgttccc   21840
tactttcttt ttgtgacaat gtggttaaca attagcagtg gagaaagttc cccacagtcc   21900
aggctgatgg cagaggtgcc tcagctgtgt tccctcttcc caggtgtgtg aggttgacaa   21960
ctcagattag ccatcgcaag cagatcactt ggtgggttta ttttaggtaa actaaactct   22020
acaggaggaa ggaaagctgg ataaaggaga acaattggat gtttggatgc ttgtgagagg   22080
gccagaatat tatgtaaaat tgctgtgagc aatacttact taactcagga aatgcctacc   22140
atgatcccgg catgtgtctt cttttctcc cctttgaca gggagattct ggagggcccc   22200
tgtcctgcaa atacaatggg gtctggcact tggtgggcat cacaagctgg ggtgaaggct   22260
gtggtcagaa ggagagaccg ggggtctaca cgaacgtggc caagtacgtg gactggattc   22320
tggagaaaac tcaaacagtc tgaaagagtt caactggtat cactttgtgg ccctggaaga   22380
ttattccata gaaatgagct tgacgtctct gatgaagaca ctgggatact gactcttcca   22440
ctgtaaccaa ttgaatggcc ttgatgtacg taagaacacc cagaaagaaa actattattt   22500
tcagaattcc tgatctggga gaaccactgg ttgttttctg catccagcta ctactcaagg   22560
aaacaaatac agcaaggaga ttttaaaaat aaaaacacat cagatatata aggaaaatat   22620
caagtaaggg tgctgtctgc ctttttagtc tctgtgacaa atacctaaag tagttcacaa   22680
aaggaaaaat ttcttttgca cacctttcct caggtttcag cctacgatct ggttggctgg   22740
ccccattgct ttagcctgag gtgaggcaga accatatatc cataggaggc tgtggagaag   22800
gagtctgctc agttcatggt aggcaggaag caaatggaaa caggaatgta ttggggacac   22860
gaatggtcct tcaagaatat actgtcaatc atttacttct tccagagaca tcctgctccc   22920
taacctccct ttccttccca gataacacct ctgtcctagc tggccccaag agatcaggta   22980
gaaaggcaga ggaaaccata taaagagttg ttaagtgcaa aatcaaaacc agaaggaatg   23040
cagacaggag ctcaaaatgt ccatttataa gaatcttttt ttttctctgc ctatatgaat   23100
ccccctcctg tataaaggac tgactcaatt cagtgatggg ttttgagaag tctgtttgtg   23160
tgtgtgtgtg tgtgtgtgcg cgcgcgcgtg tgtgtgtgtc tgtctgtctg tgcacattca   23220
tgtttaggta tgtgcaggta cctggtgggg gcgatcaacc ttgcattatt tctcatgtgc   23280
catctaccct agcttttcaa agacagagtg tcttactggg attggagact tgggctaagc   23340
```

| | |
|---|---|
| tagctatcta gcaagtccag ggaccattct gtctctacct cccccaaactg aaattaagaa | 23400 |
| gacatgccat ggtgcttaat ttaaacctct ctctgtcttt gtctctgtct ctgtctctgt | 23460 |
| ctctgtctct gtctctgtct cgctctctct ccttcctcct tctctccctc ccactctctc | 23520 |
| tttgggtgtg cacgtgcgca tgtgcaagtc atagtgtgtg tgcagggcag tggaccatct | 23580 |
| tcaggagtca atgctctcct tccatcatgt aaggtccagg gatggacatt aggtgttcag | 23640 |
| atttggtgac aaatgtctgt accttcttag ccacgtcaca agccagctgt tccgatttcc | 23700 |
| tacagatgct gggaatcaaa tctgagtcct cggggttgcc tggcaagcat cattactgac | 23760 |
| tgagctctcc agtggccttg tcagtcttct ctctgcattt tcccaaactg gcttggacaa | 23820 |
| gcaccattgc aggtgttaag tgcacacttc ctaatttcca catgggccga gtataggagg | 23880 |
| agcaattttc caggaagtgg tcccttgaag acacaccgta ctgatttgct tgcctcggaa | 23940 |
| agtatctcag cgtagcctgc actcttttg cagtgttagg ggaaagtaca ggtggatgga | 24000 |
| gataaggaag acaagccaaa acctaccaag atctgccagt gagtgggagt ttacaaagct | 24060 |
| gagtaatgaa tgtgctggac ggaaatgtgt gttgaaatcg tacatactac gggggggggg | 24120 |
| ggggggtgg ataatttggg agcaaatgtg gtttcaatag aggctgcagc ctcctcaaac | 24180 |
| agttctctgt attctgagta cctgactttt gtcctcacat ggggcaataa tgtagtattt | 24240 |
| ggactttgtc cccgtacttt tcagtcagcg ttgataacta tacaagttgt ccaaatgaaa | 24300 |
| agtatttatt gtgcccaatt atgtcagagt gtcttgttga gcttgggaa ctgaagcgcc | 24360 |
| agccaataaa ttatgaaggt ttcataaggt tttctgttga tttagtacga accgaagaga | 24420 |
| ggagctgcac aaaatctata ctttcaaaca aagatgacca tgacacaaag ggttctaaga | 24480 |
| aatgacaacg aagaagagtt agcagaagct aagagagtgg catggaaagg aagtggcccc | 24540 |
| aagcaagaca aagcaaagac agcaaacaag caaaagccag agatcgatgt cactgaaatg | 24600 |
| gcacgagcag gctggattca aaatgcttct agagtaagac agaattgaca tcaaatgggg | 24660 |
| tcacaacttc acaacccatg aacaagcagc gcctttata acctatttat tacatttcac | 24720 |
| ataggaaatc ttttataacc tatttattac atttcacata ggaaattgag gaggcattgc | 24780 |
| tgtcttctct gagaagtatt taaggaatgt tttcgtctta atttttttc agaacaagtg | 24840 |
| caacatctta attctgaata tctagtacct agaaaatgct atgagctata aggaataaga | 24900 |
| aattacgctg agcagattca catctccaca ccaacaagct gcgaatctgt atactttctg | 24960 |
| gcactttct cacttaatct tctctctcct ggagctagct c | 25001 |

<210> SEQ ID NO 3
<211> LENGTH: 74000
<212> TYPE: DNA
<213> ORGANISM: Mus musculus

<400> SEQUENCE: 3

| | |
|---|---|
| tgtaaactag atctccatct tagattaggc tgtgtgaacc gaatttattt acatcgttag | 60 |
| aaaccaaata gaggcctctc ggctattgtt ctcagattgc tctcattggt catccctgcc | 120 |
| ctccctctac tgaccagaac cttgccccaa aacagcctgt aataaacatc aacgctggct | 180 |
| tagcttgggc tgctatctct ggcggagaga tcttaaagg atgtatctaa atgcaatgtt | 240 |
| tgagtagctt cagagagctc taatagaact gtaaatatcc ccggtttaat tagcagtcct | 300 |
| gcagttcggt aatggcccat agctctctga gccgagcctc ttgaggtttc tagacttcag | 360 |
| aggctgcctg caactatgct gtgtggacct atgaaatttt ccttctcctg tactctaaac | 420 |

| | | | | | |
|---|---|---|---|---|---|
| ccccagctag | cctttcctag | acacctactc | gcaattattg | caaatccata | actgactact | 480 |
| atcctccgga | tttctaaaat | gatccagtgt | ttcagcttag | gtctcaactc | agagatactt | 540 |
| tagggctcag | attggcatcc | tgagaattaa | gtccctggga | aaagaacaa | taaggaagaa | 600 |
| aactctacct | acattggagt | tgatgtcatt | ttttttttcc | ctccaagctc | aaggtgatcg | 660 |
| cttgctttgt | ggctggttgg | tgggggagga | ggggctgtac | gctagttatc | agcatttctg | 720 |
| aaccagctct | ctcaaccgcg | acaggtcagc | caatcccggc | agtaagcttt | tacttgacag | 780 |
| gtttgttctg | ggctgacagc | cattgactag | gtgctcagat | aagtcacttg | gctgagtcta | 840 |
| cggtaggtgg | ggcgcgctca | ccagttcagg | ggcagtgact | ggaagtttgt | tgcaacatcg | 900 |
| gtaagcctaa | ccagccagca | gcaacaggag | atacccttt | gccccgcgag | tacagatcta | 960 |
| gaaagggttc | acctcattaa | gcgaaggaga | tgcgtcaatc | ccccccaccc | ccgccccgcg | 1020 |
| cctcccccta | gggcccggcc | tcttctccca | cggttgggaa | cgcgcggtgt | gggcagatcc | 1080 |
| agaacaggag | tctcgtgtcc | cggccttctg | gctagctcta | tgggttacaa | gcgaagggga | 1140 |
| ggaacagctt | ggggactctc | cgcgtcagcg | tgcacaaacc | ggcggcggcc | agcagagagg | 1200 |
| ggtggcgggg | gcacgtgctt | ggatgtggct | gcttgtgtaa | ccagctcccc | aggcgctcgg | 1260 |
| ccccgacagc | gctcctgcgg | acggctcgtg | gatgctattc | tctgctccga | tccggcaaga | 1320 |
| gaggggtcca | gcagaccaca | cgggagaagg | aggcgggggc | gatcacctaa | tagagcagag | 1380 |
| gggaccaagc | tcctgcccca | ggagcacaca | gatagggaa | tgggaatttg | gaaagttccc | 1440 |
| caactaggac | cacacgtgac | ctcctcctga | aagtagttcc | gaccgcggct | catgtatcct | 1500 |
| tccacctcgc | ctttgagccc | tcccaggcct | gctcgccccg | cccactcgct | ggctgcagct | 1560 |
| tccgaacgtc | ccatactcca | cacccgggct | cagtaaccgg | gtcctcgaac | atgcaaggtc | 1620 |
| cgacagggtc | agaacctggc | catcgcgatc | caattctgcc | gggttttcat | agcggccacg | 1680 |
| aagtggggat | tgggggtggg | ggcttagctc | tttgaagact | gagcttggct | gtgatccggt | 1740 |
| agacccaccg | ctgcggggag | ctgcgggtct | catcaccggg | cggtggaggg | gtgtgtgtga | 1800 |
| ggtgcactct | attcacggag | acccactttg | tccaaccagg | ggtgtccttt | gggccctgga | 1860 |
| aactcagggg | agatgtgaat | gtacacgccc | cgtatgcaca | atcatcatgc | ttggctggga | 1920 |
| gcgttcatct | ttcgggcaaa | tgaacccagc | tgcctgggaa | gcaagaggcg | gggcagggaa | 1980 |
| ccggagcccg | atgaggtgac | ccacgcggga | gacacaatag | gggttgttct | ttgtgcaaag | 2040 |
| actgacacct | tgaggacacc | gtgaggggga | gaggtgtgtt | atctaggtaa | agactgtcgc | 2100 |
| cgacaaatcc | tagcgaagca | ctgcaatctg | accacagcgc | agggcaggga | atgaaagccg | 2160 |
| ttccgaagaa | acgcagggac | agacgcagga | aggataatcc | tgcccctgag | gctcccggag | 2220 |
| caccgaccaa | ggcggtcagc | tagtgcgatc | cacctgtgag | cggtcagcga | ttgtgctcag | 2280 |
| cgcaccctca | ctcggcccca | gcctgttgta | cctttgccgg | gtctctctgc | gctgaggcca | 2340 |
| aagccggcgt | agctccggga | gcgagccgcg | gacacactgg | gcatgctccg | cggcgttccc | 2400 |
| cgcccctgtc | ccttccgacg | cccgccccg | cccgccccg | tccccggctc | agcgcccgcc | 2460 |
| tcccgcccgc | ctcccgcctc | cctccggct | ttccgaggcg | ccctgctctc | ccggcggggc | 2520 |
| ggcgagggg | gcggctggc | cggcgcacgg | tgatgtggcg | ggactctttg | tgcactgcgg | 2580 |
| caggatacgc | gcttgggcgt | cgggacgcgg | ctgcgctcag | ctctctcctc | tcggaagctg | 2640 |
| cagccatgat | ggaagtttga | gagttgagcc | gctgtgaggc | caggcccggc | gcaggcgagg | 2700 |
| gagatgagag | acggcggcgg | ccacggccca | gagcccctct | cagcgcctgt | gagcagccgc | 2760 |
| gggggcagcg | ccctcgggga | gccggccggg | cggcggcggc | ggcagcggcg | gcgggcctcg | 2820 |

```
cctcctcgtc gtctgttcta accgggcagc ttctgagcag cttcggagag agacggtgga   2880
agaagccgtg ggctcgagcg ggagccggcg caggctcggc ggctgcacct cccgctcctg   2940 gagcggggg  gagaagcggc ggcggcggcc gcggctccgg ggaggggggtc ggagtcgcct  3000 gtcaccattg ccagggctgg gaacgccgga gagttgctct ctccccttct cctgcctcca   3060
acacggcggc ggcggcggcg gcacgtccag ggacccgggc cggtgttaag cctcccgtcc   3120
gccgccgccg caccccccct ggcccgggct ccggaggccg ccggaggagg cagccgctgc   3180
gaggattatc cgtcttctcc ccattccgct gcctcggctg ccaggcctct ggctgctgag   3240
gagaagcagg cccagtctct gcaaccatcc agcagccgcc gcagcagcca ttacccggct   3300
gcggtccagg gccaagcggc agcagagcga ggggcatcag cgaccgccaa gtccagagcc   3360
atttccatcc tgcagaagaa gcctcgccac cagcagcttc tgccatctct ctcctccttt   3420
ttcttcagcc acaggctccc agacatgaca gccatcatca aagagatcgt tagcagaaac   3480
aaaaggagat atcaagagga tggattcgac ttagacttga cctgtatcca tttctgcggc   3540
tgttcctctt tgcttttctg tcactctgat aacgtgggag tagacggatg cgaaaaattt   3600
ctgtagttgg ggtgactata acgtttaatt ctgggcgcat ttctagatcg tgcatattgt   3660
gtctcttcca gtgtattcaa cctagggagt gttcggctag acggaactca tgcctccttg   3720
caagtgtcaa ggcacggatt gttttcttgt cgagctctgt ggtctcttct taaaatctat   3780
tgtccggtaa tacagagtac tgtacactgg attagcgagc tcgtcaatcc agccttctaa   3840
atgaactaaa aaaaaaaaaa aaaatagacg ctttgggttg tgcatatttc gattagatcg   3900
tgacttgggc cctagatcta gggtgtagat gagattaaaa tgaaagtccg tgctgcacgt   3960
aggcatgttg cctcagaatc ttgcagtgat tgttttttagt ttcctgggtt gcattggaag   4020 attttttctga aatgtgactt gtggactgat ttgcataact ttataagcat agtcatcgtc   4080
agcatggacg gtgcacattt gagggtagaa gtagttttgt gtgtttaaac cgacgtaatt   4140
acaaatttgg agcctgcatt tggaagtttt gtagtttaaa atcaatagtg ccagaatata   4200
tatcattgga gcttttaata gaactttgtt aaattagact ttctttcctg atgagatgtg   4260
ggataggata tgaaatttgc atttcagtgg tatgttccat tcatttgacc tcgccacact   4320
tgatagaatg gagatcgaat agttttgat  cccagatgat gatgtctgtg agtccaggga   4380
tgcttgctgt gtgtggcaaa tgactgcaga ggttaaactc agttctcaca tgaaatttaa   4440
gtagtagcgt gaattcgctg ctcatatttt ttgtttcagg tgctctgact cgttggctta   4500
tcagtgggtt ttagcctgat ttgtgcagaa cgtcaagtat aatttagccc gctaatatcc   4560
agacaaactg gcaggaatgg atcactggct ccagattgta ggtatgctag ctctctgcat   4620
gcagtaattt actgagtcag cttgttgaat aagacagaaa cccaagaatt ttaacgttgt   4680
atagttctga ttgtctaaaa gttaggcctt tgtacttcaa aagttcgtgg tttaaagcat   4740
ttatctttgc agtttcaggt atggtgctgg ttatgatcag gggtaggaaa gagagccctc   4800 ctctttttgca gagtgggaag tgttgacaga aattgagagc tttggggagg ccagtgtgca   4860
aggtgtgcga aaacacaagt tgcaggtctg aagtgactga gccttttaaat gattgggcct   4920 tttggtacaa cccaaaattt tgttatgtga cttgtagcat tgaacagtat ttagttaaaa   4980
ttatgtaatt ttataattgg tggtaaggta ttctttgtaa aaattatttt ttagttaata   5040
ttagtagaca ttttcttaag gtggaagggc agcagcaact tgtctataca tgtcctgcta   5100
atagatcact atggagaact ttgttttatta attaatttat tattttttttt gaagaaatat   5160
```

```
tttcatttgg aagaggtttg atggattaca ttagtggcat ataaaatgca tagctaatttt    5220 tgattgagtt ttttgttctg acatgaagat gaaactctca ctgaagagct ggcttcacac    5280 aggctaatttt tcttttcgagc taaaaataca gtttgaaagg aatctttaat ttccgagttt   5340
gcgttaattg agaagcttta ctcaggatga acttgaccaa aagataattg gtgagcattc    5400
tgagttgtca cttgcttcaa ggcagtttac tgttggtgtg aattaatgtt aataatctcg    5460
atctagaagg aattagtcag gtatctattt aattaaaaaa aaaaaaacat tcaaagaaaa    5520
gtctagaatg cctggtaggc agacttcttg tagagtccaa agtacacttc tgctttgcct    5580
tcctttcccc aaaggacttc aagattattt tgtaaatttt ttttttttgt ctgagcagtg    5640
acgtgattgc agttccttat ttgatttcat actgcatggg cttctgcacg tgcagtttat    5700
gtggctgaag aaatccaaag ctctcccttt agttatggta tgcgtagaaa gcagcatcaa    5760
atactgcatc aaatgactaa taacaaactc ttaatttcta gagctgtggt ttgatggagc    5820
caaatgttga tgtgagaacg agtcaggagg ggaaaaagtc agcgagcctt gctcttctga    5880
gaggtgtgcg ccccttagtt ctgagaagct agggagaggg cttgcttggt tcctcatcag    5940
ggttttctgt gtttggggca gggattaaaa tggtcattga agatttgtgc tggtcagtgt    6000
tggcaatgag gttggccaag ttaaatttca ttatgaaagt agtaagttga atattttcat    6060
ttgctgaagg cacaattgaa ttactgtagg aatgtgttgg ttggaaatta ttattttttt    6120
tttaatatat aaaactctga agtcttttt tttttaaaga tttatttatt tttatttata    6180
caagcacgct gtagctctct tcagatacaa agaagaggg catcagaccc cattacagat    6240
ggttgtgagc caccatgtgg ttgctgggaa ttgaactcag gacctctgga agagcagtcg    6300
gtgtgctctt acccgctgag ccatctctcc agcccaggaa attttttctta ccgtctggaa    6360 agtaggctga atgtgagaca gcaagagtta atgatgttaa agcacagaga aggttcaggt    6420
ttctggtaca gcttttttgt ttggtatatt tacttttcag atactgacca caggaatatt    6480
agtaccttgc agagagaata gtgattattg atattagctc ttttgttaaa ggcaagtgat    6540
tgttgcaggt aattatggtt tttctttata agtgactcta caaacttcat cttgcctttt    6600
tcatagtcat ttgtgtcttt cctgaaaaat acaactagta tagtaagttg caaatttcat    6660
ttttcctaaa acttaagagg agtaaagtgc atcaaaagga gtaattttca gttatgtgta    6720
attcaatata aggaaaagaa attttattac tgtcaatttt agaagtttac acagcaatag    6780
agatgtagac tgagattcct tataacgtat taaataaaga ttaaatgttt caagttaaat    6840
atgatgaata taatctggtt atttctagac atagatttag aaagtggaga ttcatggcct    6900
ttaaaaatct ttattttagt aacaggagaa aggcagatag tgtattttca ttttttttgtg   6960 tggaacatta tgtctaatttt atcataatta tataaaatat atacctaagt attatgaaat   7020
agcttacctc ctggaaatga attcagttct tatttttaaa tgttacaaca tgagttgttg    7080
gttttttttt tttttttttt tttttttttt ctgttcattt gtttatagag tgacagtatt    7140
tttttttttt ttttcccgag acagggtttc tctgtgtagc cctggctgtc ctggtactca    7200
ctctgtagac caggctggcc ttaactcaga aatccacctg cctctgcctc ccgagtgctg    7260
ggattaaaag cttgcgtcac caccgcccgg caagtgacag catttaagc cacttctaaa     7320 atagtcactt taatgacttg attagaaaat tgttcatgta ggaaaataga aagtttgaac    7380
attcacttta gtaaatattc agttttcaat actttatgtc tcagtaagct ccaaatgtag    7440
gcagtgtttt tctattgata acttatgtaa attcagagtt gacagggata agtttagagt    7500
cctgagtatg taggtcaggt tttcatttct gtaggcctat tccatttaga agtattctgt    7560
```

```
tctatgaggc agtgttagtt attagtacag cttaaaaagt ttacttgctc gcatttttg     7620 ttttccatg ataaactact ggctcataaa acagaagttt ggctgcacag agctggtggc     7680
tcgcgttttg ttcccctttc ttctccctgt agataaaaaa gttgattttc agaaccagcg   7740
ttggagagtt ggttttgtga tccactcttt tgaaaagtta caggacttgt tccaaagatc   7800
atgatttagg tatgacactt tgtgtggttt tatcagaagt gatttctgta aatattcagg   7860 gttttttgt agttgatttg tatgtggtag ttttgaagtt catgcagttg ctgagctatt    7920
agtgatgttg aatacagatt aaatagcttt atgttagtat ttgctgattt ttttttttat   7980
aggtcttgct gctgttgctt aaaagtgtct aattgtggga tgatggttct caggtcctga   8040
agctattggc agagatgaaa ttaggatcct ggctttgatg tcttaccttc ccattctgta   8100
ttctctgcta tggtttcaga agggacgata tagcagtttc agcttctaaa ataatttata   8160
ctggaacaaa aagcctgttt cttggaggaa ggttactatc agagtaaaca actaattttg   8220
cctgggaagt tttaattaca tttagaatag tcaggtatac tcttctattg caacggacat   8280
ttgtggacat cttttggagta ctaagactta acacttgttt gtggtgttaa ctttggagag   8340
atgcaaactg cagttgcacc cactaatgac ctgtatgtgc gtggtgtgga aaagcttgca   8400
aatctgctgt tttgtgtaat tagtcaaaca gttataatca gaaagccaac gcttaatacg   8460
aacagtgact ttaacgtaaa tatttgaatt tttctatgtg taggcatgca tgtgagtatc   8520
aagttaacaa acttactagt ctggaaaatg gattttctcc ttaaagaaca gactactttg   8580
gaagccattt taaccataa ttgagtcttt taaattacat tgaaatacgg ctggtcttat    8640
ctatactctg aagttataat tatttatctt agttttaggt agacagggtc cctgtcttgg   8700
ctctgtcaca gagctgggta actatgctat ttaatttctc ttagtcttac tttacctgaa   8760
ataaaggaag gataatgata cccaccacaa aagtttatct aataccagca aggcagagga   8820
aggaggctat tgctaattcc taggcagtag ccttcagtac tacatagtga atttgaggtc   8880
cactatagtt ctatactgtg agttccaagc cggctaaggc tccatagcga gaccatgtct   8940
gaacaagcaa caatcaaatc acatagttaa tcccctaca gggtttctct gtgtagctct    9000
ggctgtcctg ggactcactc tgtagaccag gctgacctcg aactcagaaa tccgcctgcc   9060
tctgcctccc gagtgctggg attaaaggcg tgtatcacca ctgtctggat gttttcaact   9120
tttaagggaa catgaaaact tccttagttt tcacataata actttaagaa ctatctgttg   9180
taagattaaa ttttcttagt attcaatata gatgaatata aatagcatga catttataat   9240
atgtgtgctt atatgatacg atacatagca tatatgatct atgatacagt tatggtatgc   9300
ttgtccttag gaggcagagc ctcaccatgt agccctggct tgtctggaac ttgtggccat   9360
gcttggtcag tatcacagtt cttttcaca aagagtattc ctcaccacta agaagtagga    9420
cttcgaatat gtaactcagt tatataaact ctcaggaaag gtacattagc atttcctttc   9480
tgctcttcca gctcacatac atacagcaga caatacagtc tgcagtgagc tactatagga   9540
atttaaagtt actgttaaac cttgccctca gtttcacagt gagccaggat tttcagtata   9600
actacaactt tgaaatggga agaaagagct agagagattt ttttccttcc catactgcat   9660
ttttaaaaat tactcattta tttggggttg gggatgggag gaatggaaca gggcatacgt   9720
ttggaggtta gagaacagct ttcgggagtt gattctctca ttcctctctt tgacactggg   9780
aatggcagtc aggttgttag ggtagcagga agtgccttt agccagctga gccatcctag    9840
aagctcacat gcttttttct tatctagggg agggaagaac ggagtaagct taaggctcac   9900
```

```
ctacctgcac gtgacaggga ctagtttttc cttcctgtgc ttgtggtttc ctgggaatgg   9960
agcgccttaa tttccagggc tgtttcttat ttattttgaa atgcagagtg gatgctgctg  10020
taattattca tgactgcgct cttgtaattt ttatttattt tttgctgagc tttccctgag  10080
tattttagct gtttttttt tttgtagcag attataaaat tgagttgcat atctttatat  10140
ctgaacctat ctcactgtct gaacgagttt ctatctttct cttctgtctg tgtacctgta  10200
ctataagcac ataggtgtta tatcactaga ggaccagtga ctttcattgc atggtaacac  10260
tcatgtaggt tttcaggctg aagtagaata atttcctccc tccctccctc cctccctccc  10320
ttttcttcc ttcctagtga tgcagacctc atttgtatgt ttgttcttga ccctaggagt  10380
aggatgcagt tactcaaggt gtatggaagg gtatgaattc tgctttgaaa cagcttatct  10440
tttaaggaga tatatttcta aaagtgaatt gtaaaaatca atatttgttt aacaacgcta  10500
gaagcaaatt tttgctttga aacaaaatgc agatttttc caataaattt tttctcttta  10560
atgagacttt aaaaaaaaaa aaggttggtt tattagtgta tatgagtaca ttgtagctgt  10620
ctacagacac accagaaggg ggcatccaat cccattacag atggttgtga gccaccgtat  10680
ggtttctggg aactgaactc aggacctctg gaagagcagt cagtgctctt aaccactgag  10740
ccatctctct agcctgagac ttgttttttg aatgttttat gtttctctca actaaataga  10800
attaaatttt ttcttttatg ttgagaatga gtttgggga gatattatta agttgtcct  10860
taggactctg tattacatta tctcctatca acaaaccttt aatgtactat attctctgtg  10920
tatgtgtgtg tttatagttt ataggctagc aatcaacatt ggtgtctcct ctgttgctct  10980
gtgccttgtt tattgagaca gggtctctca ttgaacctgg agcttgccaa tttggcaaga  11040
ctgtcttctg tctgtgccct ccagtgctgg gatcacaggt gtacacacca tacatggttg  11100
tacacaccac acatagctgt acatactata catgggtgcg taccaccata catggttttg  11160
acattggtgc tagggctctg acctcagatc tttgtgcgtg catagtaaag tactttatcc  11220
actgagccat tccctcagct cccatgctat atactcattg agttaatagt atttacaggt  11280
gcattatatc aatagacata agtcctaaat accctaatgt aagaaatatg ttgatttgtt  11340
ttgtagacaa ggcccagtga attagaaagg cagcctgcta gaatgcaaag aacatagcct  11400
ggcattagcc aggccctgga attagattcc tgccctagtt cccatctttc taatgagggg  11460
taaagctgtg acttgtaggt gtttcttttt gttgatctga acttttggta atgtctagaa  11520
acattttggt gaacatggtc atacctgagg tgacagaagg cctacttgca cttagtgggt  11580
tgaggctact gggctcttag acatttgcag aacctgggat ctgtttaatg ttaggggaag  11640
tgtttgatat gtagatatag taccttttgcc aaggtcaact gttgctgggt ggtaaaaact  11700
gggcccacat aggttttctg actattgtgg ggcctttctc tctctctccc cccccccctc  11760
tcttttcttt cttcctttct tccttccttc cttccttcct ttcttccttc cttccttcct  11820
tccttccttc ctttctttct ttcttttctttct tctttctttc ttttctttct  11880
ttctttcttt cttttctttct ttcttttctttct ctttctttct agacatggtt tctctgtaaa  11940
gacctggctg tcctggacct cactttgtag accaggctgg cctcgaactc agaaatccgc  12000
ctgcctctgc ctcctgagtg ctgggattaa aggcgtgtgc caccaccgcc cagcgggct  12060
tatgtttctt ctaacaactt tgtccactaa agatatctct aataagaaaa agatttattt  12120
gacaaggtct catgtctttt agcatttgt gggagtttga acctctgctg aaatgctgtc  12180
tttgtcgctt ttctgaagag tatgacaggg aatgcaaggt ggatgtgcag tcaggtgttt  12240
tgctccttga agctgaagca ggaggattat ttttatgttt gaggacagct tgggcaacct  12300
```

-continued

```
catactacac cttgagttct agggccaggt cagactgtct caaaggccag gttcgcgctc    12360
accccactc agtgtttgaa cagttttctt tgtaattgtt tagggagtta ctttgctgct    12420
agtgtcttta atgttactgt tgtttaactg cttctttagt cttagatttt ttttttttt    12480
tttactctaa acctttgttt cttcagatgg ggtgaagtta aatgtgctca tgtgaagaag    12540
gggcaggttt ctgacaaaga ataagaaaaa tcatgaaatt tttccagatg aagagaatgg    12600
gttggcctga ctgaagttcc cgggtgctgg tcacctgctt ttctgagcct tacattggtt    12660
gttagcctgg ttactggaaa ttaccgtgat gctcctgaat tgggcatgcg agtttgcatt    12720
agtccaaaga tgcacagaaa ctaaagcagt aaaaaggaca gagaatttct tggtttattt    12780
ttagggatca caagcataat tataagtgtt ctaggaatag attagttgct atgttggttt    12840
cttttttcctg tttaatttta caatttcatt tgctgctcac tttacaacag aataaaatgt    12900
ccaaggcctt aattttttaat ttcttaggaa acttaagtac tgatttagag ttttggttct    12960
tgaagttgag ggcagtgttt aggtatgtat actgataaat gttttgaaac cgacatgact    13020
tgtcatgata gcttcatatt caccaagaaa agcaaatagt atccattgct actaaatact    13080
atccattgct aaattgaata gattaacagt gattaagtct gaattaagag ctcatttgct    13140
tactaaagaa aattcctttt ataaagagat tactaagaga aaaattttgt tgtttgctca    13200
tttgttttt catttcttca aaacttcaag ttgttttcta attcttggtg aactcaaaga    13260
ggtatctttt ttgaataatt tatatagtgc ttcataattg aaattatcaa aaatacatat    13320
ttacctataa attaagattt ctccattttt ttctcttact attttttat atagtggact    13380
taaagtttca ataggggaca attttttatga ttgagatttt acacaaatca caatcaacaa    13440
gaacaaaaaa aacaattgaa atattagagc tttgaaatgc cttcatctga aattacttct    13500
aggccatcta ttgcacattt aatacttaat gtttatatta cttatgtgag atagcacaca    13560
cacatataat gttatatgtt acatataata tatattaaat atttgggaca actttccagt    13620
ttcctagacc atgctgccct cgaactcatt ataaacatcc cattttttcct gcttctcaag    13680
ggctatggtt ataggtttat attagaattc caggctccaa atactttttga tatattaatt    13740
tcatttattt tggagtatt tgctgatttg aaattgaaat ggaatagaaa taatttgaac    13800
aattttcata ctaaagtggg catagctttg ttgctgtacc tttgaatcca taattattgg    13860
cttgccatga tgttacagtt gcagtttgaa taatgtggtt tatatttgta tagttggctt    13920
gtatttgttg tactatcaat taatcaatgt gcactgataa ctagtactag cttttggtga    13980
aaaatctgca tttaacagtt tgtcagattt tattttttaag tcagatacta aaagagaatc    14040
ttttttttcat agatttttat tatttaaatg catttttatt atatcaaaca taataatact    14100
gagtatttta ggaatcaaat aatacataaa aatttgttca attttttatat tcatatctaa    14160
aagagaatct ttaaccatat cagctaacca ttaattcttt atcaataaat tatattaata    14220
tttttttgtat aaacaattta aaacaaagtg atagaaacat cgttttttat tttataaaca    14280
aagttactac taggtgtgct ctgtggcctg tgaccttagc accctggagc tgtccccaag    14340
gaaaccagaa gtgcagttac tcttggccac attgtaaggt gaagcttagt ctagaccaaa    14400
agagacagaa ccaagacaga aaaacaaatt acctgcttat tattaagtac gattctttcc    14460
caaataaagt gaaacttaag cttgaaattt tcatctaggc ataaggttgc tatcttgggt    14520
tctaataaaa attagtggtg gcaaaaatct tttgttactg ttttcttgtt gctgcctggg    14580
gactgaagac ccagtcttca gtagctttgg tggtctggtt tgtagggcat ttgatgaaag    14640
```

```
aacagtattg gaaaactgtg aagcactttc tcctgcattg tgtccggatt gtggtcatga    14700
ttgcgtgagt ttgaaaatat gagaaggtcc ttagaaagat gtttgtttgt tattactgca    14760
aaggtcatag gttgtggttg tgccgtgtcc agatacccag gcctgccatc tgttcctcag    14820
atgtaggaaa aagttaaggt aatttagtgg tagtaagtgg ttttgacacc tttgtttttg    14880
gaatcatcta attataagtt ttaagaccta agattaagtt ttaggccttt gtaaaaatga    14940
aacttacaca gtatgctatc atttgtgcaa aaccactaag ggcctgcttc agagctgaag    15000
atggctgctc cgagcccaac tctttactga agtgtctgca tgcttcagca caggagtgtc    15060
acgtgtcacg tgtcatgctt tcacctgacg tactaaatta cacaaaatgt tggggttttt    15120
taaactaggt tttctaacac gttatgtaag aattgataat acagaactca gtgagggcac    15180
tgacttagta agcagtttta aacatttctt ttaagtattt ttttcaagcc ctgtgctttt    15240
tttctctcct acaacttaat tcttaatttt catctgcgtt tgaaggagct tcctcaggta    15300
aaccttttct cttgcattat acttgcatga aaatgatgtt agctatgctg tatttaaaat    15360
ctttaaaatg cctctatatg gcttaatata atctgatgag ttttgtatta tagttggagt    15420
ttttgatgtg ccaagtggtt attgtaaaaa taatgtctga agtttaaata tttgaatttg    15480
tatttttttt taaagattta tttattgtat ttatatgagt acactgtcac tgtcttcaga    15540
cacaccagaa gaggacattg aatcccatta gagatggttg tgagccacca tgtggttgct    15600
gggatttgaa ctcaggacct ctggaacaac agtcagtgct cttaaccact gagccatgtc    15660
tccagcccga atttgtattt tcaaacccaa cttcgggcct ggggtctata gttttgagt    15720 gcaagcttct tgtcaggtta atgtctggga ggaagaaggt tttgtcagta aagtttctga    15780
acttttgact agaataactg actttctgtg atgaagacta aactacaggc catgactgca    15840
caggagtcag ggcgtacata gatgatcctc agattttggg cagcttttac ccaaacattg    15900
agtttagaaa ctgttctcca ttcggctcac ttcgtatttg gatagcatgg agtattaaag    15960
gagttctcat tattgtcatt tttattgctt ccatttaact ggtattttg tcttttgtgt    16020 attgagctct ctttctgtct ccccctctc tgttagggcc tcactgtgta ggtctagttg    16080
gcctgaacct cacaagactc ccactgcctt tgcctcctg ggttacagga gggtgccacc    16140
tcacttcagc caaacaaacc ttgtatgttt cagcacttta tttatcagtt gaaaatactg    16200
actttcttct tttttaaat tttagccttt ttttctatgg ctttaaaata tattctttga    16260
acataaggat gataaattac aaaggtgctt tctcccacag agccagtaat tattttctta    16320
taaaaattgt accctccaa tcaatttctt taaaaagtag tttatttaaa tgtgcaccaa    16380
agactcattt cttttttttc caaatatttt tgtatttat atgtaagatt gttctgtctg    16440
catgtatgcc tgcatcaagt ccagtggttg tgagccacca tctgggtgtt gggaattgaa    16500
ctcaggatct ctgggagagc agccagtgtt cttaactgct gagctatgtt cccagcccct    16560
aaagacttgt tcttactttc catctatcaa tacagttaaa atgttaatag aaaagtttca    16620
tattctaaag tgaattttaa ctagcatatt ttaaaataca atttcacagt tcagggaata    16680 atttttataat tcaaagttga ttataatgat ttaaatgttt tcagtgggaa taggaatcct    16740
tttacaatat taaaacaagg caattataaa atcatcaata tgactctact ctagtaatga    16800
gtgacagtat atatgtcttc atgatttaaa atctacataa ttacttccgg ttcatttat    16860 ttttcttcag tccaaaacag tccatagggg caaatttatt tataccactt gcaatagaaa    16920
cgaagccatt tcatttgatt tctatgttag taatacaggg taaagaaaca ttttatttca    16980
tgtattacat caaagtcata tgtaaagtga actaattcag cccacagatt tggagttttt    17040
```

```
ctgttttaaa tagtctcaaa gtctgctttg aagggtaaaa ttttgactgt taaaagcaac   17100
taaaaatttt gcaattttgg ctaaattgaa ggagactggt ccatcggcag gcaggacata   17160
ctgcgtgagg accctgagtc tcttcattct cagtgctgaa cttgctaagg cattgcaggt   17220
gaatgttttg ggtttttttt tatttttgca agatgcagct actactaagt taattggcac   17280
taaatatgac aggggctttg ttctcaagtt actggtccat ccttcaggca cataggaata   17340
tctctcctgt cgtaagttag agactttaat atctttgaa tgattataaa gtagctaaaa   17400
cttagtgttt tgtttctaag cagcctgttg caggagtaac ttagaaatct aatatcaaat   17460
atgaagatta gagcattaga gagatatctc ttatagcttt atgttagtgt tgaatcaatt   17520
acagctttag tttttatagt cttgtgtgta ccattatgat ttttctgtag acagtttgga   17580
gtttgtgttt gccttagttc tcataaagtt gttaatatgc ctgatacatg ttgggcttct   17640
gcacttttgt gcatattttg tcattagtgg tcaatcttag atggcttttt tagtggcaag   17700
aaaaccaaag agatgccggg ctggtggcgc acgcctttga tcccagcatt tgggagctag   17760
aggcaggcga atttctgagg ccagcctggt ctacaaagtg agttctagga cagccagggc   17820
tacacagaga aaccctgtct cgaaaaacca aaaaaaaaaa aaagaaaacc aaagagtgtt   17880
atgcataaaa gtgtgtatgt gtgtgtgaac caaagagaca gcgttgtgtg tggatgtgtg   17940
cgcacacttg aatgtagtgt aaatgcagta gagctttgaa acaggaaacc agtcttttca   18000
tattttccag agacctagga agaagctaat tgttctatat aaactcatta gaaattaaaa   18060
gttttagagg ctcacatatg taggcttttg agcagttgca ggtacattat ttcataatta   18120
acttctagga agaaaaactg ggtgggaaac tagtagggat gactagtaag caagccatcg   18180
gtaaatatgc ccaataaacc ttactttgga tttcggagtt gctgacttta aaaggaactt   18240
aataaactaa gtaaaccctta tttgaaattc agaatacttt tttcattgaa aaattgaaag   18300
ttttattgaa agttttttcat tgaatttatt catatccaga tataaataag attggaatca   18360
cttttaaaga gattctaaaa cttaaggatt cagtggaaaa aaatgtgctg gggatacccca   18420 gggacttcca gatgtaaggc agagtgctct accattgagc tatgaaacca ttcctttctt   18480
tctttacttt ttttttttaaa gagatttatt tattttatgt atatcagtat accattgctc   18540
tcttcagaca caccagaaga ggtcatcaga tcacattaca gatggttgtg agccaccatg   18600
tggttgctgg gaattgaact caggacctct ggaagaacaa gcagccagcg ctcttaaccg   18660
ctgagccatc tctccagccc tcttctttta cttttgagtc aagttttcct tcactgaccc   18720
aggctagtct taaaccctgg aggcccagaa cttgtgatcc tccagtctca ccctaccaaa   18780
tagctaagca ttatatagcc ctgcaccacc atgccaggtt gattctgttt caagggtgt   18840 tactggcact gggtgtggt gcctgtaatc ccagtattta gggaagacag gaggaacaag   18900
aggagttaaa ctttcctgct ggcaagttgc agaccagttc aggctaagac acccctcttc   18960
ccacaaaaag aaagtttgtc actggaaatt aagttagtta atgtatatgc ttacattctc   19020
atgtatgttg ttattgcata gccattgtca gtgtttgata cggttttctt ttcacaaaga   19080
gttttttttt tttttttggt ttttcgagac agggtttctc tgtgtctggc ctagtatttg   19140
tttttgtttg tttgtttttt ttttttttta ctttatttat tatatgtaac tacactgtag   19200
ctgtcttcag acactccaga agagggagtc ggatctcttt acggatggtt gtgagccacc   19260
atgtagttgc tgggatttga actcggaact ttgaaccttt ggaagagcag ttgggtgctc   19320
ttacccactg agccatttca ccagccctta tttatttatt tatttattta tttatttatt   19380
```

```
tatttttttga gacagggttt ctctgtgtag ccctggctgt cctggaactc actcggtaga   19440
ccaggctggc ctcgaactca gaaatccgcc tgcctctgcc tcccaagtgc tgggattaaa   19500
ggcgtgcgcc aacacaccca gcttgccctt tctttcttaa gcattttctt tgtaatatgt   19560
tacatgcatg ttagggcttt cagtgtccct tgttgaaagc actccagtaa tggtaaatgt   19620
aggttgttct tgatgtctgc tgacttgaca ggccatgacg aggcttttcc ccttcaggct   19680
ttcccttgtt cttgactatg accccattta tgcatatatg cctgagtaaa ttgaactact   19740
tgacaggcat ccctaaacct gtgtctgttt tatgtaaatc ctgtcctttc tgtgtgtctt   19800
tatgagttgc attgggctct tgttcctgga tagatttctg tctcttttcct gcagttctct   19860 gcttggactg ttctagccac ttaagtatat cttttctaat ataaatctta ttttttatgt   19920
gtatgagtgt tatgcctgca acatgtctc tttcccgtat gcgtgtctgg tcttcacttt   19980
gatatgggta cagggaacca aaccggatgc tctttctgca agagcagcaa gtatgtttaa   20040
ctgctgggtc atctctccaa acactcctgt gttttcttct gtcaccagaa ggcgtgtgtg   20100
agtgctaccc aacataatac tcacttggtg atgcttatac atacttccac ggatccctct   20160
gaaaacatct tcatttaaaa aatacagtag tactttttagt gccatggtag gtctgtgtgc   20220 ctgtcttttct tgaggacggt aaccactgcc cggcccctaca gacttttttaa tttgtctcat   20280 ttattcttgc ataatattat ttagcctgtc cctctatatt attcctataa gttaacattt   20340
tttttctcaa aggctttgag agttggtgtt aaagattctt ggccattaca gatgatgctc   20400
tgcctttgta gtacctatgg ccaaagcctt ctcatgactt ggagatcaat tactgagtta   20460
tatgtagaag gcaaatgtat ccagaatatg taggcggagg tcttaagtgg ttgttttaaa   20520
ggaggtaact tggtatagtt gatgtgaaaa tcttgtaggt agttatgaga tggaacccca   20580
gaacaaatga gagctagaaa gatggataaa attcatggaa gtgtagattt ttagttaatc   20640
ggaaataaat tctcccagaa tatagagatg ggttttttatg ttaactggtt ttgaattgaa   20700
actaaggaca tgctaaggac taattacact gatgagaaga aagcatgtag gcttgagcct   20760
cagtcgcgta ttctgacatc acagctgtca gggatgaggt tatcactgcc cgccgagtca   20820
ctgtgggcag taggaactta tagaagtcta aggatagtga gtggctgact gtccaggcta   20880
tagctcaagg agcagacaag tacatttgac gacctttttat aatcacagct agcgtgggaa   20940
aagctaatgt tttcaaatgc atgcatattt gtgtcattgt atattctagg tatttccttta   21000 acttaataat ttagatattt atccaaatat tattgctatg ggatttcctg cagaaagact   21060
tgaaggtgta tacaggaaca atattgatga tgtagtaagg taagcattct tgatttttcta   21120 tttcttatat taataaaatta ttttgatgtg ttttatttag aaaagatccc gaaaacacag   21180
accagtattt gcattttgat gtgtttttggt aaaactctga aagttttaac ctaaagcacc   21240
tgacagctct cactcggctg gatgcgtcac tggatgagaa ctggctagtt atatagtcgt   21300 gtttgttttat gtcatgaaga ttttttttttt tgtattccat aatatgtctc ttaccaggtt   21360
attctctggc ttgtattaca gtacaaggtt ttgacttttgt atttgggtta ggccttgctt   21420
aagtaggttt gtttagttat tcaccctgcg gtatgagtga ccgatgtgtt ttatgtagca   21480
cttatacctg tagcagtgtt tgatacaatg attttggaga gacttgctgg acattcattc   21540
aaaagagtaa atgaagagta tcataatttt acaaaatttc caagtgtgat tgttgcttag   21600
ttcagaaaag tgtttctcaa ggcccactta aaaaatttag tttcagaata aaaatgcaat   21660
tgtatgagta aatgaacatt aaattttgt tgcaaactat catagttttt aacaattcat   21720
taatactgag tcttgctgta tttgctatgc tggttctgaa gtactttaat gaatttaaaa   21780
```

```
gttaaaattc tggattattt cctttttact cataagtgag catctttcct ggtgctttta    21840
actatgtgtg attatgcaga tttaaatagg tgggagagtg ctttgtaact tagagtgtca    21900
tgcagatgta ggatgctttt gtggtactgc atgactttat gtctttagat gagctagtag   21960
tcagtttcct aagtggctaa tttttactgt tttaaattgt gcttgtttgg ataatttatt   22020
ataatattgt ttatgttttg ttcaggttta aatttcacca tctataaaag tctaccaaaa   22080
ctaacaccaa accccttact gctttgtagt ttccattaaa ccttaggtta tcctgttaga   22140
ggtaactgtt taaaagcctt taacaatagg gaaatacatt tgccttctta taattaggta   22200
gaacacagtg gaaggatact tagcatggca ggcccacagg aacacagctc gataggaaca   22260
cagtgatgat gcagagaaaa tgaaatacgc cacagaaaaa aagtaagaga ggaaatttt    22320
tcattgaaag ttgcagagta tggttaagtg gcagtttggc cagataatta ttttctgctt   22380
tgatgcagaa ttgtttatgt ctttcatgtt atgcctcata agatacacta tttcacatca   22440
attttatatt cagccaagga ccaatttaac caaaccaaat tcagctgtat tgaaaagggg   22500
agcaagttct ttctttaagt ggaggggatc ttttctggcc atgtaatgtt cttttgacta   22560
atctggcatg ctaattttat attgatttct cttaagtatg aattagtaag tgagggtgat   22620
tagattatct ttaaggttac aattccagtt tctagacctt taccctggt tattagacct    22680
tatactacag taacttagcc aaaaatatgt tgtgttgaaa aattagtttg gtcctgagtc   22740
ttctggtttc atgattccta tacttttgct tgcaaattaa gagaattgca cattcatttt   22800
tataattagt aactaagacg gaattaatt ctatctagct ttatctatct agttttttta    22860
tttagcctta ggtgttctct ctcttttaaa gaaatctatc tgtattattt agcttgttct   22920
tttagcttct tactttaatg ttttataaa actgttctgt gtttggtttt tgttgtttgt    22980
ttgttaagat aaatgaccat taaggcctgg ataacttctg tttatcagtt ccccacccac   23040
ttttatagta aagtatgaat agtgactaga aaggaagata ggccttttcc tacaaactaa   23100
agtgactaaa aataacttttt tgtgatttg tttgtttgtt tgcttttttt tttttttttt   23160
ttgagatagg gtctgaatta agtaagtagc cttggctagc ctggaagtcc ttatgtagaa   23220
ctgtcttgtt ttgaactcat aggcatttgc ctctctgtct ccgcctcgga ggactgggat   23280
caaagccaac accattacat tagcccctac aaataatgaa ttacaatgcc ttttaggatt   23340
gccttctcca aagaacactt gtgtctaata tctaaataac tgattacttc agtttgttca   23400
cactatattg gtgatgttag ttttaatcaa tagtgagtgc ttccttttgc tttaaagttg   23460
ataacatctc agtacaagta ttttttgtttt catatcacca gatagcccag aagaagcagg   23520
tgatgtaaga gggggttcgt ttgcctcatt gtttgagaag gcttctggc tgtggagggt    23580
gaggagggag ggcagaggcc ctccatccct ccatccatgg cttcctgagt ttggggcaga   23640
gttcatggtg gaaggagtgg aggcagtaac tcctcatggc tgtgaaagga agcaggaacc   23700
agagaaacct gcagataatt tgccctgact gactgatttc tgtcagccag atttcacttc   23760
caaaggctcc acaaccgggc tgggaggagg atttcagatt gaaactataa catgtttgct   23820
ttcttattaa taaacttttt ttttgcagtt aattttctt tgctttgtct agtagggtat    23880
ccaaaagata tttaactta ttttctttt atctaattcc atattttct tatatttccc      23940
ccaaacaaga aatatataaa acttaaatct tgctattgt actatagcgt tacctggagt    24000
gaggtaaact taaattgcaa atattttcat gcttaaattg tcctatgcag aaaggtttgg   24060
aagatatagt gtgctatgat aagtaaaatt tcatagctga gatctacaaa atttgagaaa   24120
```

```
aatatttagc ttcttcattt gagatctggg attcatgtaa aaaatggaaa tggaggaaca    24180
ctgggcttgg aatttgcttt ctaattacag atgatttgct ttttttaatc taaggagtga    24240
gctgacaggg caggcagggc aggagggact gcggaggctc ccacagtagt tgttgtcgtt    24300
cctcttaact gcttccttct tttttttttt cctcattttt tgcaatgaag aggggtgat     24360 gcaccaccag cacttggctt gatttgtgct tttccagtgt cctttaggct ggtgggaaag    24420
ctctgtggct ttaaatctaa gcagtcgtga acagactggg gcatagtgtg tctaaggagc    24480
ttgtcttgta atctcttctg cccaatgact caggaaaatg tagatgtaac agaggcaaac    24540
tactttttac acaaaatgtt tagtacagtg ccaccaggta gacctttccc caccttatg     24600 ttttctcttg gtttccttt ataatttgct aactctcatc ttcctagaca gtgtttcatg     24660
gagctcaatt tggaaaatgt tgaaaatgaa aaagttatgt gtacagaatt gttctaagtt    24720
tgatatgttt tgaggtggag gcatgctata tgacccaggc tgacttatgt atagtccatg    24780
ctggtttcta attcatgatt tttacactcc tgcctatggg tgtccatcaa gcccagtttg    24840
tctatagctt ttataaggaa atgattagag ctcagtcttg tgcataatg atttaacaaa     24900 aagctattac tgttttgtaa acccatgtat aacctgttac aggttcaaga gtcttattgt    24960
ttcttgactg ctggcatata tattttcttt ctgaagaaac tttgcaaatg ttcaattctt    25020
tttttttttt tttttttttt ttttggtttt tttgagacag ggtttctctg tgtagctttg    25080
tttgtactgg aactcactct gtagaccagg ccggccttga actcagaaat ccgcctgcct    25140
ctgcctccca gtgctggga ttaaaggcgt gcaccaactc tgcacagccc tattcattac     25200
ttaatggccc tctgaataat gttttcaagt cttatttta attgatagtc aataatgatg     25260
ctagaataac aaatagttct ttctcattga aaatcaagaa aaaaaatgt tgagcggtgg     25320 tggtgcacgc ctttaatccc agcacttggg aggcagaggc aggcggattt ctgagttcaa    25380
ggctggcctg gtctacagag tgagttccag gacagccagg gctacacaga aaaaccctgt    25440 cttgaaaac aaaaaaaaaa aaaggaaat aattaataat aataataata aacaggaaag      25500
attacttctg ttttccatt ctaacatttt tttgccct ttcctcattt gccttcctct        25560
tttccatttt aaaaaaatta gtgagttaac ataaatagtca ctgttttaaa ctgtaatttg    25620
agtgacattt aatattttca cagtatagcc agaggtaatg cagtcaccac cgataccaaa    25680
ttccagaacc ttttatcac tcctgaaagc tcctggctgc ccttcccttc tgctggctgt     25740 cttcctgca catggggaga tttagtgtgt tggacaataa taatgttatg ggcacaaact     25800
agctttgcta tttaatagcg gatactgttt tctgtacatt tatttattta ctatttatat    25860
ctgttaacta ttgtataacg agcttgcata taccatctta ctaagtttgt agacggaatc    25920
taatccctat ttcacttta taagtgcctt aaaagaaatt agaatcttca gttgccacag     25980
cttagaagta gcaagaagct ggaagttgag tccgtgtctg tgagattcca agttgatt      26040 ttttctttt ttgtttgtta ctgtatttaa ggcaaggtct cactgtgtag ctaaggccag     26100
tcttgaactc aaggtcctcc tggttccata ttctcagagt gctctgtgta taatcttatg    26160
gtgatctggc cagcaaaaat tcaatttta aaagttttt taaccagggg agggatgcag      26220
tctggagttt gaactcagtc attactaggt acttcaccac tgggcattac ttaaagctgc    26280
ttcccttaat atctttttc tgtacatcaa aggacaaaat ctagaaacac ttggacaaat     26340
cgagactata cttaaaaatc atgaagcctc gtgcaaaacc ctgtatttct agcttatttt    26400
taaaagctga aagagctgtc aaaactgaat tcaacattcc tgtgtgatgg atcaagtatg    26460
gttgtgtaat gctctctggc attaaattgt taccatttct ccattaagga ctgtttctta    26520
```

```
gtgaggtttc cattgctgga aatgtgcctg gcccaaggaa tggcactatt aggaggtgtg   26580
gtcttgttga gggatgtgtg tgtgtcattt tggggttagg ctttgagacc ctctcataac   26640
tgcctgagga cagtctgctc ctggtgtcct ttggatgaag atatagaatc ctggacacca   26700
ccatgcttct tgctgtgata actttcatta tattgaaagt tgttatattt taataatact   26760
gttaatgttt taccttgcct agtttattca acttcattga taagtgtgta tatggaaaat   26820
gtacatacag tttgtcgctg tccaaagttt caggcagcca tatggaaggc gtgtgtatag   26880
tgtaaggttt cagctgagga tacattacat tccttgttaa accttagtgc tgcagatgtt   26940
ctctcacttc cacttgaagg gctgtctata gcatttcttt taagttttcg taacttttgt   27000
ttctctggga atatttcaat ttatttctca tttttgaag acagttttg ctggatattt     27060 tttatttcta ggaccttaaa tgttatattc ttacttcctg ttctgagggg gaaaaatctg   27120
ctgataccaa cgctcctttg tgacatgttc cttctctctg tatttgagac tgtgggtctt   27180
tctcaggaga gggtcttgca taatacaggc tagcctggag tccttgtata tatgcaagga   27240
tgtactaact gactttgat cctcctgctt ccacttgact agtgctctga tttcaggagt     27300
gcaccaccat caaaggttta tgtagagatg gggacagatt tctcagagct ctgtttgtgt   27360
tatccaatga gatatgcccc cagcctgtct ttgtcttgtg atggtttgat tgcgatctgt   27420
cttagtaagt ctctgagttt ttgtgaattg tggttcattg agccagaagt tctttatatt   27480
cttttatcaa atttgagaag ttttgactgt acttctgtat ataattattt ttctggaact   27540
ttaaagatcc ctaaggtagt ccagttgctg ttgtctcaca ggttggttaa tctcttacg    27600 tttcttcagt aagttgcttt ctgtattttg atatttatcc tcctacccta gttcctgggt   27660
gtggaatgtg gttactcca ggaaagaaga ttgactttct cactcttggt agccaatagc    27720
tccttagccg gggatgggac tttggtcatc acttttcttt gcttggcttg tgctttcaca   27780
ggtcttgtgt atgctgttag ggttgctgtg agttcatatg tgcatctggc ctgttgtgtc   27840
tagcaagcgc tgtctccttg aagtcaccta tcattcttgc tcttacagcc ttcctgccct   27900
cttccacata gatgcctgag ccttgaaagg aagggtatga tgcagaatac catttgctct   27960
gaacattttg aagtctttct ttgcaggttg tatgtactaa ttgccatcaa cagaagcttc   28020
tctgatgagg gttgagctgt gcactgtctg tggtttattt agcagtagtc attagcaatc   28080
attctattgc tgtgtccact tacccgagga atattggtag gttttcccta ggctccatgc   28140
ccatctagct acaggctttt ggcctcattt tgacaatgtt agatgtggct tccatcttat   28200
agaacagacc taaatctaat caaaggtgg ttggttattc ctataaacat tttattcca    28260 cttgactgta cttttcagcc atggctagga ttacaagtat gaactactgt attgttctat   28320
ttaaattttt attaagagtt ttttcatata tcttgatgat attctttccc attcttcaac   28380
tcctcccagg tctttttccca cctcccattc cgacaaatgt catgttcttt ttttctttcc  28440
ttctcaagaa gaaaaaaaag aaaatcaaca aaacccaata agacaaaaag tgacaaaaca   28500
aaacagaaaa gcacaaaaac catggagtcc attctatgtt ggccaactac tcctgtgcat   28560
gagcgctgat tggagcgtag ttgatatgtt ggagaaaact gatcttctgt ttctcagtag   28620
gaatcaactg caaatcgttt cttggttaga ggcagggctt tgtgtctgct tcagatttag   28680
tgctgagatt ttgtttggtt tgacttgagc agatcttgca catgctgaaa caatctgtga   28740
gtttgtgtga caccccttgtt gtgtctggaa gatgctgttt gcttagactc atttactacc   28800
tctagctctt cccatctttc ttcccttttcc tcggagtaga tccctgaacc ttgaggggag  28860
```

```
gggttcaata aatgcatccc atttagtact gagtgttcca aagcctctcc atttgtacgc   28920
tgtgttgatg tatatgctta atttcatgtg ggggttactg ctttagatca ttcagtttcc   28980
agataaaaaa cacaaacttt taaaaattat ttataagcct taatgagcac taaagctggg   29040
ctggtatcta ccttctaggc tattagtatc tacttcctta ttggtagccc tgagttataa   29100
cttgccatat ttcatctggg ccactcttaa ctccaattgg ccagccttca tgaccgagtt   29160
ttcatgaatc acttaacccc actgtggctt ctcctctctc tattgtttcc tgatcttctg   29220
cctcagaccc caagcctggg aacccaaacc ccacctaact ctcttcagcc tagctataag   29280
ctgtaggcat cttcattcac caatcaagga tagctttcag ggttatagag cattatttga   29340
tgtatgtgag gatcaccttg gcccagaggt aaccagggcc aatatttagc attacaatat   29400
ataacaacag accaaacctt aacggtttta aattaaggtg taaggtttat acagcaaagg   29460
ctggtaaatg tgaaattcac ttgtaggtct aaatctttta gtacagaatt cagcattgct   29520
atacatagca acagaccaaa cctcaacaca ctcttcagtt gtgggtctct gtgttaatca   29580
ccatctactg caaaaagaat tttctctgat gagtgacaca ctcatctata gggagagcag   29640
tatgttagga atatttctgt ttcttttaata gaataatagt agtagtaggt tttcccctag   29700
gctcatgact tgtctagcct taaattctta gcctcactag cagtggcagg catgggttct   29760
attttaagga atgggtctta aattcagttt ttaaaagtg gttgtttgtt cccataacat   29820
ttatgccaat attggatcaa tatatatgcc cgcgagcatg caggtctttg ttgtgggtca   29880
cagagtttgt agctgggtta tattgatgac tactttatc ttccagtcgt gtgcaaaagt   29940
accttccagc accacgagtg ctagtcagta gtgctgaatc tctagttggc tgtcagctca   30000
atctctctgt gctcgatgac acaagtaagc agtatcttaa gcaacaggac taccatctgg   30060
ttgtggagga aaacagtagc cttggcagta gccatgatgt tgggattgca agtatgtgct   30120
atcgcacttt gttctttttt tcaagacagg gtttctctgt ataccccttg cttcctggaa   30180
ctcactctgt agaccagaaa tccacctgcc tctgcctccg aagtgctagg attaaaggcg   30240
tgtggcacca ctgcctggcc tgtgctttgt tctttatgtg ggttctggga ccctaaactt   30300
agactaaggt gccttcctag tcctggaatt ttcctttta aaatttttt atttgttttt   30360 gtatgttggg gtgtgtgtgt gctatgccat gccacacttt tagaggtcag aggacaactt   30420
ataattcttt ccttttactg catggttcag tttggtggca gttatctttt ttttatcttc   30480
tcagctaccc atcttgttaa taactcagaa gctgcacttt cctgcctcag ccttccgaat   30540
gctggcggac aagtgtgtac cactacacct agctctttgt ttctcttca ctttattgat   30600 acttctgttc atcatttttc ttgatcttac ccgtgtcttt tttttctttt tttgagacag   30660
ggtttctctg tgtagccctg gctgtcctgg aactcactct gtagatcagg ctggccttga   30720
actcagaaat ccgcctgctt ctgcctccca gtactgggga ttaaaggcgt gcgccaccac   30780
gcctggcata cccctgtctt tcattagctt tctgagtatc attaagacca cacaaatctt   30840
tgcctagtaa atttgctttc tggttttct gagagacagt tgttgactt tttaacttat   30900 tcgattttg agtatccaca catcttattt tggggtgtga gtatgcacac ttgtgtatgc   30960
atgtatgttt ttgtcttggt cttgtaaatg tgtgtatg tgtgtgtgtg tgtgtgtgtg   31020
tgtgtgtgca tgtggtgtgt gtgtgtgtgt gtgtgtgcat gtgcgcttgt gtgtgtgtgt   31080
gcatgtgtgt gtgtgtgcat gtgtgtgtgt gtgtgtatgt gtgtgtgtgt gtgtgtgcat   31140
gtgtgtgtgt gtgtatgggg ggaggtagct aaaaacaatc tggatcttgt agggtcgaag   31200
atcctctctc ttttcttgat ggcccagctt tcccttgttt tctgtattgg gtatctacta   31260
```

```
tgctatacct atgcaaagat taccatgcta aactcatgca aacttaagat ctttggggct    31320
ggagcagtgg ccgagtgttt ggggacactg gctgttctca caactgcctg ccaatctagt    31380
ctgagggtac ccgatagcct cttctaaact cgggtggcag gcactacatg ctagtggcat    31440
gcaagtggtg cacagacata cattcaggca aaatactaaa tacacaaaat cataataaat    31500
taaagatctt ttaggcttgg gctttttttc taggtatagg gaatgacttc ctaaatttt     31560
tttgtatgtg taattaatct cagttgttat tatctttaaa tgttgggttc tttgaaagat    31620
ccaaaggaag gaaaaagaag tgggcagggc gagtagattt aaaatcccct gatgtcttca    31680
gttggtgggc gacagcttcc tccatctacg tatgcgtgtt caaaagcagc aattagtgac    31740
cagcacacag atttaaaata ttggaacgta cggcatttat tattaacttt ggcttttgaa    31800
agttgtttgt aagtctctat agaggtatat caatgactgt atgagaagtc cttgttgtat    31860
aagagctaaa atcagggctg tggagatggc tcccttagta aagttcttgc tattctgagt    31920
tcccattgtt ctttttttt ttttaataga agaaaaggtt tatttactc acagttccat     31980
ataacagttc attatcaaaa gtaatgagga caggaactga acagggcag gaacctggag     32040
gcaggagcca atgcagagag catgaagggg cactcctgac tggcttgctc agcatgcttt    32100
cttttctttt ctcttctttt ctttctttt ctttctttt ctttctttt ctttctttt        32160
aatattttt attattacgt atttttcctca attacattta gaatgctatc tcaaaaatcc    32220
cccataccct cccccacca ccacttccct acccacccat tcccatttt ttggccctgg      32280
cgttcccctg tactgggca tataaagttt gcgtgtccaa tgggcctctc tttccagtga    32340
tggctgacta ggccatcttt tgatacatat gcagctagag tcaagagctc cagggtactg    32400
gttagttcat aatgttgcac ctacagggtt gcagatccct ttagctcctt ggatacttc    32460
tctggctcct ccattggggg ccctgtgctc catccagtag ctgactgtga gcatccactt    32520
ctgtgtttgc taggccccgg cctagtctca ctgagttccc attcttagaa ctcatacaaa    32580
agccagcttg ctcagcatgt ttctgcgacc tctgtgacag gaagcaggca gagaagacta    32640
tcctggggc ttgctggcca gttagcttag ccaaaataac tagctccgtg ttcagtgagg    32700
gaaccgttct caaaaacaga ctagttgcaa agtcatagag aaatacctgt tgttcccatg    32760
acacacacac acacacacac acacacacac acacctaaaa ttgtttaagt taaccttcat    32820
tttctgtcag agctgactca ctgaaagtgt cagcgttttgc ctagattccc tgggaaaggt   32880
tccgcaagtg cagtcggtgg tcagggctgg cttctggggc tgcttctctg tcctcttgaa    32940
ctactttggt ttctttgttt ctgttttgtg gggtttttta agatttgttt ttgttgtttt    33000
gttgtggatt tttggtaata ctttctagca tttgaaatac atgtttatat aaaataaatt    33060
taaaattcac tattgtggct tatctagatt tatttcctaa gaaatctttc atgctctatac   33120
atcagcctca gtttatctca gtgagacaga cacacagaca cagcacagtt ggaaaggagg    33180
ctcaacaggg ataggagggt gagagtggtg aggcgatgtg agacagacac acagacacac    33240
cacagttgga aaggaggctc aacagggata ggagggtgag agtggtgagg gcgatgtgag    33300
acagacacac agacacacca cagttgggaaa ggaggctcaa cagggatagg agggtgagag   33360
tggtgagggc gatgtgcagt cagttccttc aaggaagatg cagttctagg aggtgtctta    33420
ggtcgtgcag ggttagggag cattgcctct cactgctgtc taatattta gcctctacta    33480
tctaaataca tctctgtagg caagtttgcc cattctctt tggaatgtgc tgtttcacttt   33540
gtctttcctc acttgtcttt ctatgtgtca gactgagaga acagtggggg aagtgcggaa    33600
```

-continued

```
tgtgtccctaagtaatcagttctctttgagacagttatccccccaccccttcaaatgatg  33660
gaatgatgtactgtacccattaaagggctgcttcttctgttagacttgctgttgctcac    33720
atgctagctaagaaatcagaatgttcaactgttaaggggcacacagatagatttccccta    33780
agcctaaggtaaacacacggtaggaaagactcttgaaagaattatgagttttagttgca  33840
aatgacataaaatgtctttaccagaaaggaataatgctctggaggaagttcccattgtgg    33900
aaagcagaagtttaggaaacgtggtgtaggggctacagtctgcttagacaccaatgcatg    33960
gtcctacatcctggttgctgtctgtgaattcccaggtcttccagtgagatcttgaagaa    34020
tctactgttctcttgtaccttgctgcccactctgtaggagtgagtgtctcacaacaaggg    34080
aaagagaaaagaaatacctgcctctgatctcagtgtttgctaactggttgacataagggt    34140
ggcacaattccttatgaaatttttatacttcatcccccttcagaaaatttgtagctgtg   34200
tttacatataagaagccgtggtctttgttttgtttggtgttcttggactttctagc    34260
ttccaaagctcggacagttaacttctgtgggcattgtgtgcatacgtggtgtttactt    34320
tgtgttgactttcttttcaactgagttttcttttaaattgtttaaactgctttgattcct    34380
tttgtagacacagctttataatgctttataagtcctttcttatgcctttataatatagc    34440
ctttataaatcccttctgtgcccttagattcagataaatgttgactaaagaaattgatgg    34500
gttatattttgctcagaataactgattgctaactctgcttatgttgtatataattact   34560
atattttctattgctagctcttaaataatcaagaagcagctttgcttaaattcaagta    34620
gaaaagatttaacttatgaggaattgttaatatatctcctactactgactcggcattttt    34680
cttttggacagagaatagagaagtgaaaggtttagggctccctgccttttcctgtttcc    34740
agcattatacaccagtcaagcgtatggaatctagttctttttgttctgttgctccact    34800
ccaacctttagttgatactgttttgtgttccttcttatacaccactttgtgctgttctg    34860
atttcatctctgagcactccttctgccattgtgatgaccgtgttttaaaatggagctttg  34920
tgagctctctgcagctaagtgttttttcctgaataatttgttcattacaaagagaattc    34980
tagagaatcctaccaagtccatagcattgttactgtgattgctgttttgatggtgtcc  35040
aactctaatccagctgacttcaaactcagttctatagacctggctgtgtttacatgtgt    35100
gcggtggtaacatgcatggcacatgtcacttagtgggcttgacctttcttctctctctt    35160
tctttctttctttctttcttctttctttctttcttttctttctttctttcttttctttctt    35220
tctttctttctttgaatcatcaaagtatgacttcatgttttgtctttttaaaaattacat    35280
ttccctctgtgttaaacaaatgagcctagtttatagttccccatggattacagttaaat    35340
cctctctgtagtcttcttttagattgggttgtagattcctaggctgctgctgaggcgaag    35400
catttgcaatgctttacagtccagtatggtatctcactatgccagcatttccttccttgt    35460
ctgatgtcagctctagaatttacatgaacactttccctctgtttcctgacatttccagagt    35520
tgtagtttccttctaaaaattattttataaaagagaactaaccaaccatttcaagatttt    35580
ttttttaaagaaaaacctcagaagttaaaagaaccagattcctaatatttttgctctattt    35640
ttcttgtaattttataatgtattccgaggatgtgcccacttggtaaccgactgtgaca    35700
caaatgtattgtgtcatactgcttggttttcttctttaattgaaaataaaaatagata    35760
tttttcataaatattctgattatggtttctcctatcccaactcctcctagtttccctc    35820
ccttctcccatacagattacacccctttctgtctctcattagaaaacaggtgtctaaaaa    35880
ctaatagagtgaaataaagtaagcaaacaaactggaatagacaaaacaaacaaacaaga    35940
aaaacacaagacccacgtaggctcagagacacgtgtttgcacacatagaactcttataaa    36000
```

```
atcacaactg gaaaccgtac tatgtgtcca ggagatctat gttctcggtt ttaatttaca    36060
cgcacacaca cacacacaca cacacacacc ctgctctgta aatctcacag tgattgagca    36120
catttggtgc tcatcagttt ctcgtactcc tgggtcttcc tgaccgacct aactctgacc    36180
taattgcctt ctgtgtgtgc agcctgaggt accccttgcg atcctgggg tcctcacttc     36240 ttttacaggt tgggctccct ggttcccaga accgattatg attttcact ctcaacatct     36300 tttacaactg agatagtgta tgggaaacaa atgacttgtt gtagaacagt gcctttattg    36360
tattatatac tcacccacga tttatagtct gtcttgtata gcattctagg ctggaagtaa    36420
attttctgaa aaatcaaact ttgtataatt gtttttagga agctagtgtt aatggcagtg    36480
cgtttgtcgt tttgtcttat gctgtctact ttccatgcca actttagggt ctggtgttct    36540
ctttggcact tagaaataac gtagatatat atggctccat ttgcggctcc cctagacccc    36600
ctttttaaag tcaattttat tagctattta tgtcttcatc ttgggaactc atgttggacc    36660
tggagatgta aactgacaga atgttttgct gaggctctag gttaattgc cagcactgca     36720 taaacccagg ttggtgatac agacctgtag tcccagcacc ccagaaatgg agggaggagg    36780
gtcaggaatt cagggccagc ccgggctaca tgaaactatt ttctccttt gtctcattat     36840 taattcttca ccattatacc ttgctgagtc ttctgtttca ggcctgaagg ttaaacaaat    36900
ttacatacat aaagtactta aataatacct ggcatgtaat aggtgctttg gtacctgtga    36960
tcactgtgtg gtttcacagc tggttggaag gagtggcccc tgctctgact cttcatttac    37020
tagcttcaca ccttggacaa gcttcataat ctcttgaggt ttacttcctt ttcctgtaaa    37080
atgtaaattc catctctgcg atgttggtca gggacaagag aaagtataca tgtatacatg    37140
tgaaaaatgc ttacagaact acattgctat tgtacttttc agattgtggg ttttttttt     37200 tttccctgct aggaagatta catttaagc tttttttttt tttcatgga agtctgtgag      37260 ctgggtacac ttgaactgct aatatcgttt tgtcaagacg tgattgtaat ttattagact    37320
gaagacatag atatgaaaac agtttttgat aaagtcagct ctacttcaga atgtataaat    37380
ctgtgtaatg taataactat taatgaatga ggggatatgt atttgtgtta ttaatagtat    37440
gtgagataag ggtaaataaa tctgttttag tcctgtgcag cattaatgta atttgaaata    37500
ttagctcatt tttgttaatg gtgttttttt tgtttgtttt gttttaaggt ttttggattc    37560
aaagcataaa aaccattaca agatatacaa tctgtaagta tgcttttttt atttgtctct    37620
gttaaaataa ctaaataaaa gttatttctt tgttgaagat aaaaatatat ttagatattt    37680
ttatatttga ggaactggat tcctgaaaac agttgcagtc tgatagagag agttgttggg    37740
tctcgaagcg tggtgatgag gtgcagcagc ttggcacagc ctccggttac ttgatctgct    37800
tttacagact tggcacctcg cccatccttg agcccataat catgtgataa tttgaaatgt    37860
aatccacagc ggagctgctg ttagtattaa cgatggcttc taaggagaca gactccaggg    37920
tggatggaca gacttttgtt tcctctgtgc ttgttgatca atatactgaa acagctattt    37980 gaatatttc tgtgtataac ctagtaagtt atgcagcatt gtttagttat ctagtatagg     38040
atttgaggga ttgctcatta aaacttattg gcctatcttt aaaccttcac tttcttttga    38100
cttttggagt agtgacatga aaacaggaaa ggaagacaaa tcattaaaca ccctttgtct    38160
ttcaaaacca ttttattttt ccccaaatac tgagcatttt taaaaattta aagataaat     38220 taccatgttt ctattatgtc ctttaatttt ctatgtctat gatttatata acaggagaat    38280
gttatgcaat ggtagaatac caattagtaa ttaaccattt tctgtagact ttatcaaata    38340
```

```
taactacaag tgttttctgt tctgcttcga gtggctattt gaattgctac ccagaaggat   38400
ggagaatttt ctatgtcttg ttatagtgct agatgttact tttatttttt cagtctttaa   38460
tgatatttct gttttgataa gacttcaaag tattcatgtg caatagttac caatattatt   38520
tctcttcgct tttgctgact tcagatcaga aaggtgcagc catggtgaaa catgcagata   38580
gagtgctcat atggctagtt ccagccctct agtagcctat agcttgatgt gaaagtagga   38640
gggagcagga gagaagtgtg gacaaagtaa ctggccccac aggaggcctc tgtaaaagac   38700
cagatgtgtg ggctgtgatt aacttctgat accttctttc ttctatccct gcttgttata   38760
tacttgtaag actaagagga gtttctgttt tatttctttt aattttaaga ttatttcttt   38820
gcaaacataa atttaaagat cttgaaatat ttccatggct tttctactaa tgaaaatcaa   38880
taggagttat ctattagacc tgggaggatg agccaaggca agtcagaaga ttgatagtat   38940
aatggtattt gaaatatggc agataactca ttttgggcag gtggtggtgt atgctggctt   39000
aggtggggtt gtgctaataa aaggtggata ggagaaccac aagactgttt ctgaacagct   39060
gcattcagaa ggtgactgaa aaaggacaag aactgttgaa agctggaatt gatgaaatga   39120
atcatttcag actcacactg tcaggtttgg ggatttagag aggtcccaat agggaagtag   39180
aaagacatta aagacacat ttctgcctga gctgaaatct tatgcctgtt taacatatct   39240
aaagcacagg gaggaaattc ttttcattcc tgcctatagt gacttcctgc ccctagaatt   39300
tagggattag gtttatgctg tctcctttgt tgtatttcag tatagttaga ggtggcattg   39360
ggtggaccta ggaacttgat ttgagtttcc aagcatttga ttcccaattt aatgaaccat   39420
ctctttatta gttgagagca gcctttagtg catatgaact tattcccttg tcatttggaa   39480
ctgaggcttt cagaatggca aaggatctga agggtccttt tagcagtgcc ttcttatctt   39540
atagacaggg cattaggcct aggaagttaa atgaggtagc caaagacagg taggtgcata   39600
ataacagact acccactgtt tgcaccagaa tccctttttgt tgctggtta gctcttcgtt   39660
ttatttactt caaaagtttt taaacatata caaaattgag tgtttaatt tgagtacccc   39720
ctctccctg cctactgtgt atctgatttt aggcaagtga gactagccac aacagatgtt   39780
tttgttttat ttcttttgt cttaggatag gaattacagg tagtatgtat ttttttttc   39840
ttggaaatgt agatgtttga aggtcctaaa gtatttttca ctggacatct gtatagttag   39900
tagtttgtga gaccttttat agcagcagtg ttgcacatga atgaagaact atcagcctaa   39960
gctttctgat aatctagctt atctattatt attaatcagt tattttgaaa aagggcaaca   40020
ttaattaatc agttttatat gagtgttttt aaaatttctt tgttgctccc tgttcagaga   40080
atacaagatt ttaagttttt attatatttt agtgaatatt tgctgtactt ggcaaacatt   40140
taactgtgtt atttttctgt taagatttcc tttgtaaaac actgtagagt gaagaagaga   40200
gctccctacc atgtagttct atggcaaggc ctagttgtct gcaagtttgc ctttctggtt   40260
tcactcctcc tcttaatttc tgttgccacc ttgggaaacc tcatttttcct tgttttttt   40320
tttttcatt tctcttttca tataagccaa tttaagataa ggacaaaaat atcgtttgag   40380
ttttaattac aaagaaaaat ttaaatccaa attgttattt gctatcttct attttagtat   40440
gtggagtgac ttactgctaa tatgccataa gaaatttaaa agaaactccg ctgtgaattt   40500
tggctatata ccagagattc taactaaggt ggaaggtttc ttcttgaccc tgtgacccct   40560
tctttctctt gagcactgtt tcacaggcag ccctagcatg tcctcccaaa gcccctccgc   40620
ttgcctataa ggagctgcat gctcccctcc ccccccaagt caattgttag gtctgtcttc   40680
agtgacaaat actgctcatg tttgtgctgt aaaatttgtc actgctttt catttaagac   40740
```

```
ttgaatgttt ctgttatgtt gaatgaaact gtaatagaag ttgttggatt tagttgagca    40800
aggatactaa gcttgagttc ctgtctcacg gtgacttcat gttgttatta ggaaagcttt    40860
taagggcctt tctaaatctt agcttttcca tatatacata tgcctcacat atacaatggg    40920
gatgtaaact gttacatgat tgtgagggtg aaaacatgga tgtcagctgt aaggtgccca    40980
tatcctgtag acttcagttg ttactgtgtt cctttcacct taactgatga tacatgacaa    41040
ccagtttgta atggtgatct taagcagtgc ttattaaacc aaacttttca gagtgtttgt    41100
tccatctttc tctggggtgg gaccctccct tcccctcctc tccccttccc tgcatcacct    41160
ccgcaggcaa ttgggatccc tgaccctaga ccagaaagtg tggcaaactg aaaaatctga    41220
cttgtaggac actaacaacc ggcttcttag ggtatgtgcc tagcttcctc ttgtttcctg    41280
attgtatcct taattcttga ctgtcttcca ctgtgggctc ttcaccacac agcacctctc    41340
agaagagcag aacctggctt ccctgtgtgg agttctaaca cttggaggtg gagggagaag    41400
ggaattcaga gccagtcttg ggtatatgag atcctgactc aaggaaaacc aaagaggaag    41460
ggaggaaaga gaatatagaa tatgtgatct tttgtatatg tgtcagtttt cttcttccta    41520
tctcattttt aggtaagcag acatttagca gagtatttag caaggatgca tacgtcatct    41580
aataaatttt ctcttttcaa aaacagtaca tcaggtaata cactaaaaga aaaacacatg    41640
tgtgtgtccg tgtctgtgtg tgtgtgtgtg tgtgtgtgtg tgtgtaata cagaagttaa    41700 ttcccctcag gtctgctcca ttgggctgta gtttatggat aatttgttca atctttgtgt    41760 gaactggggtt ttgaaataca gttgagttgt acaaattcca gatgcccagt gcaggcccac    41820
agctatttat ttggaagtct tggatcagtt ttattttggt acatagaaaa tttcagttttt    41880 caaaaaacta aaaactaaa taaaacaaga aaatccatat cttttgtgtt actctagtat    41940
ccactgtggt agactagtcg gtactcagca ggtatgttgg ttgaacaacc tcagattggg    42000
tcctgttcga gttgagatta cctatttata actttggagt ttgagatttg ggctaaggaa    42060
taatggaact ttgttttaaa acactaactt ttatttttca gtaatttctt tttgtttgtt    42120
tgtttgtttt ttttgagaca gggtcttgta tcccaggctg gcctaggact cactagatag    42180
caaaggctaa tcttaaagat ataatctttc ccagtaactc ttctgaagtg ctaggattac    42240
agcctgtggt aacactccta gcttatttga ataatgctta agtgtctgat ttccttagta    42300
gttggagtca ccaggatgct tctgacccca ctaatatgta ggataccctt catagtatca    42360
ctgattagtg ttattattga aaagctaagt gtttgtctta atgtgtcagt attttactat    42420
cagtgggttt tagttatttt attgtgatct ggtattaaat tttgtactct gagagattat    42480
tggaaatgag atttgtatat aaaagagtaa aggtctggct tacaattttt agtaagcatt    42540
gtgttaataa ttaaattagt atcattcagt tgtcttttac atttcctttg ttcttttct    42600 ttatttttaa catgtatgtt ttaagtaatg gtttaagatt gtatgtgatc atctgtcagg    42660
taaagataat agtaagagta gctatttatt cataggtatt tgtgaaataa aaatacatt    42720 ctaaagccat gtatagtctt tatccaagaa attacagggt cagtgcagtt gaatttacag    42780
tgttgcatgt tgatgtcaca aattctgtga acaaatatat gcacacaaat tgcatgcatg    42840
cgtttaactt ttattaaagc tttggtctcc ttaattataa gaatgataat agtacctact    42900
tcagaattct tgaagttaac ggaaatagtg actgtaaaaa cacttagcgc agtgttttta    42960
catgatagaa aaggtggtat gatagaaagg gtggataaat attgctaata ttgatactct    43020
tccttccagt gtgaaaggta actttatgcc acatttaaac tttcttgtag atgtgctgag    43080
```

```
agacattatg acaccgccaa atttaactgc agaggtatgt ataaacataa ccacagcata   43140
ctgtataact aaagaccaat agacttgtct tttactgcct ggtgataatt atcaagatta   43200
gtgagataaa aatcttaaga atggcctttg acaattaaaa aaagtgtatt taatgttaga   43260
gttgttcttt aagacctatc tattgtcagg aaaactaaat cacagaatac ttggagaggt   43320
cccaagacta aactaggatt ggaggtgctt attgacggtg tgggacagct agcgctgctg   43380
gaaacaatca caagaagaga gcagaaccat tttaactttt ctacatcgaa gaatggcata   43440
aagttaggaa aagatgtagc attggtctgt ctgtctgtct gtctgcctgt ctgtcttctc   43500
agaatcatga agcactaagg agtaagtaag aacagtttct ggggaccgac agacctaggc   43560
tactgctcat taggaaacat gccatggttg aaggtcactt agctttaaat gtacatttta   43620
acagactctt gaatgttctt gtgtgccact ggggaaatga ggtcgggagc acagttagac   43680
agatggttaa gtaaaagctg gcctgcagcc tcttggtgaa tgtagtttgc cattgtttac   43740
cacagagctt tcctgtcatg gaaggagta  aatggatgga ttgttcttgt accatttac   43800
gatggcttgc tttaggataa gtcagagttt ttacatatta gataatatgg cagataatca   43860
gaacagtaat atcaccagga ttttttgttt taattttaag acaagggtct cagggtctca   43920
gtgtcccaga gtgaccctga actcaatgtt tagctgaggg tgacttgaa cttgtgatcc    43980
caattctcct gcttttactc ctcaagtatt aggattacag acttgcacca catcctcagt   44040
tgtgtgttta ctcaaggcag ggatgagccc agagctgagc atcctaagca agcactctgc   44100
gaactgagct acatcccaga gttcatacca ggatttaagg atctcaatag gatagaatca   44160
aaacagatac tagtaagata aaaaccagta gtgatagaac ggaagtcttg cttctagata   44220
atagcatctt gccttcaaaa acttaactct gactatagag aacaaagaca tcttagattc   44280
ttaattcatg tgaaaaaaat ctgaaactta atttgctata aactttactt cagttgtatg   44340
tttttctgtg agtgattaat ctcatgtata tggaaatata atgtttgtga gaccatttta   44400
aaaacaagtc actgggtaat tttattatgg gataggaaaa gtcagtcttt tccatagttg   44460
actctattag taattatact ttcttcggag catgtctggc aatgctgtag taatatctgc   44520
tattggtcct gatagaagtt actacttgac aagaggcctg ggtgacgtgc atttggattc   44580
agttgtactg ataggctatg acgtgttccc ttcatgcaca gattcatcct ccctggagtg   44640
aagagcacaa tgcttgtttc catgtctaat gaatgcattt aagaattaat aaaagacttt   44700
cttttaaatc taggtttaat tagtaataaa ttaaaatttc ctgaaagtta ggcttctttt   44760
aagaaccagt aagtttatat ataacatttt gaaagttaac ctatgttttt aaataaaaaa   44820
tttaaaattt tcttacactg ggattatctt tttgcaacag ttgcacagta tccttttgaa   44880
gaccataacc caccacagct agaacttatc aaacccttct gtgaagatct tgaccaatgg   44940
ctaagtgaag atgacaatca tgttgcagca attcactgta aagctggaaa gggacggact   45000
ggtgtaatga tttgtgcata tttattgcat cggggcaaat ttttaaaggc acaagaggcc   45060
ctagattttt atgggaagt  aaggaccaga gacaaaagg  taagctgttt acttttttcct  45120
tcctccctct tgtgggacca agaatttatt gggaaacagg ttttctccct cttgctttat   45180
tgaggtataa ccaacaaagt cttaatctac ttacagtgtg atgctttgag aactgttata   45240
ttgtggttgt atccacttag tgtatccctc atccctggta tccccaccct cttccttagc   45300
tgtactgaga acatccaaga cctacctgga gtaggtgcta ggcacacagt atggattttg   45360
atgacaactt gaatgccatt acctagtaaa gcaaggtatt taatttgatg gtaaataaaa   45420
cattttctga tgggggtatt cactagtata gttaactaat caaagattca ttggttattc   45480
```

```
agaaaactaa agactgttga attagtggca tgttttgtct atggtacaat tgaaaacaaa    45540
agcaaattct tggactgctt tttcagagga ctcgtttagt tagtgtaaca ccaagattct    45600
ttgcatgttt ttcttctcc aagcacagca cctatagtac ttcagatgaa ttgaaagctc     45660
agggtagcag tgaaagtgcc ccaacataag gtcataaact cacttaacct ttgagttggt    45720
ttgcagtctt ttttgtagac attgtaagtg acaacatcag tttgcaatgc caagggttgg    45780
acatggctgc tctggggagt aagacatttg aaacttgatt ctagtattaa atttggactt    45840
gtgccccacc cccgcttctc ttctgcctcc tctcccttct gtctttctcc tcctctactc    45900
cattcttccc ccttctcctt tttttgagcc ctgattttat ctggatcaac tttgggccat    45960
gcccatcaca ctaaggtctg tggctgcagc ggtcctgggc cctgtacttc tctttcacct    46020 gcttttaaa aaccctgtcg ttataactct tttgagtttg tacaagaata tcaagactgt     46080
ttgttcattg gtgggagttc acaaaattac atctttaatg cagtaaaaaa gtcatgtgtt    46140
agaaaatcag atttaagcta gagactcctc aactctgact cccgatgaag tgttcagatg    46200
ttctgttatt cgatgtatgt ggtatataca taaccataaa ttgttgttgg tagcttccat    46260
ttgccttcag acaaaatata aaggaacttc taacaaatta tgtctcattt ctcccattta    46320
aaaaatcagt accccttacc tgagaacagt aggtatctaa atgggttgat tctgttcaat    46380
agtgaaattt atgataaaca gttttaaaa acaagttgaa agcttgccat tgtttgactc     46440
ttacatcatc cttgctctca gtgttatttt tattcttgtt tagtgaaaat aaattatgaa    46500
aactcttatt tcacctatga gagaaatatg gaacataata tgttttgac caattaaagt      46560 aggctgtgtc agataaaatc tctaagacta gatacgatca tctattagtt tctttgcctt    46620
caagatcatt atctctgtgg ggcaggaaaa gattatggac cattttaatt ttcaggttaa    46680
agcattaaac tgcttgacag cacagcgttg tctggcttct agatatcagt ggacctgtgt    46740
gcagtgaaga gctttctagg tccttctgtc tgttgacaaa gcctcttgag attctcttgc    46800
ttgaaggtct tggctctctc ttgtgaattt gggtctttca cagcagtagg ttttcatga     46860 caaatcatca gcagggaac ttttcacaac tgtagaagag agtctcctag gattaatgtg     46920
atcttgctac ccagtgcagc agtgagggcc agggcagaga tatcatccac ttttaccagt    46980
gcagggaaac cagaggagct gcagggaaag ctgctagagt gtggaggact cttagggcca    47040
gcgatgtgct cagccatttt tatttaactt ttttacatta agacttttca gttctttgag    47100
actgtaataa attatatcat gagtatgtat gtatgtgtag tacaacctgt ggatatgttt    47160
ttagggctta ccatttggat aacaaattgg catgctctct tagcatttct tagttaccag    47220
tagatctttg tctagggttg aggcttggtc agctttctcc cattctggca tgtcttttgt    47280
tctccttgct cagctcatgt ttggtagtca tgttgatgag actttatggg tgtagcttct    47340
gacattgcca gtagacaatc tcacagcaaa ctcccagatc ctctacctct tacagtctct    47400
aagccttcgt ctacaatggt ccctgagctg taggtgcagt tattgtgttg tagatggctc    47460
agttggaact gagttccaca actctgtgtt ttgaactgtt gtggttttct gcaatgtttt    47520
ccttatgcta caaagagaaa tttccttgat gagggataag cactatgctt atctattggt    47580
ataaatttag agcatagtta tggactatat atattattta gtaaattagt ggttgtaggt    47640
tctctgtcaa gaagcatgac ttccctagcc caaggtagtt ggctaggttt ccaataccag    47700
gcagtttctc tgtctttaag gggatttaaa atttttattt gtttatctgt ccatccatct    47760
gtccatctgt ctgaaatcta tctatccgtc cacccattta ggtgaggcct gagagacaga    47820
```

```
gtcaaggaaa tgtcaccatc tttaaaaaaa aaaattaaga aggaccettt cttaaaaga    47880 ccttaaatta tttgctgatt atttattcat ttgttttat tgccatgcat aattttgatg    47940
gaaactttga actgattaca ctaagagctt aattactagt aagtggtact cctgatactt    48000
ctatggcctg tcttgtattt tgagagagca atgtttgctt tggagaaatg gatgagaata    48060
tttgaagtcc tgcgactctc tcagccattt cctgccagga atctcagcta cttgacattt    48120
ttttctgttt ctgtttgttt gtttattgtt gttttgatgt tttcattttt ctctctttct    48180
ctcattcccc ttttgtaatg gtaaggattg agcctagggc cttgtacatg gacacatatt    48240
ctaccagtaa gctatatccc tcagcccttg tttgactcat tcatcatgtt aaactacatg    48300 acctttgtt ttgctttgtt tctgtttgtt tgctagttca gacaaggatt ttcacttgag    48360
acaaataatg gttgtgaaat ggtttaggct tctctaagct ctgctgtcaa tctccattct    48420
ttttccttca cttcttcaga attgccagcg tgtgtataga gtgataagat gctggggtgg    48480
tctgtttcct tatgttcaag ggtaagagca agacttgggc acttgaactt tcctgtaaat    48540
ttctctgttt ccaggccagg gtaaatgcag gaatccaggt tagacgcagg agtcaagtta    48600
ggtgcaggag acccatgtca gaaactgagg tcttgacaca ctagtcatta cagcctggtg    48660
gcaacagttc tgtttccctc tagaagggag gggagggtgt ttgtggaagt gacaagaagt    48720
cttgggaaat gttacaaggt aggggtatt tgtgagtgaa atgtgaagcc tctagtgtca    48780
tttggtaaaa tgtaataata atacttgtgt cctccataga acttttcttg gcactctcca    48840
tctcttgacc atttcttcca tgtgaaaatg atagactaat ggacatagaa gatgcagggc    48900
tgtgcacatt gttagagctg tagctggtgc atttgatgtt tagccattgc attatactaa    48960
gactccttaa gtaatttagc atcttacagc cacatcagta ggatctactg tacctgttgc    49020
atagttaata tacctagaca agtgttttgg ataagtttat acacggacct aaagcagaat    49080
ccttatgtgt atcctacctt tattctttcg attatttaaa aaacaagaaa gaacttatga    49140
acagatactg ttgaccaagc tgtgttttac taatggttgc ttttgcattt taagctacaa    49200
tagtattaga aacctacatc cagataaaag ctttcagata tccctactcc aggaatgctt    49260
ctttacagat gacatcaagg cccagaaaag tgaactgtag tgatcagaat tcgtgacggt    49320
gtcaatcagt tcatgacagc atttacagta aaaacaagtc ccttggtgtg ttgttaaatt    49380
tctttgtata ttatcaagct tacagattct gaactgcaaa aggttccata tttattgctg    49440
atggttttga aaggcttctc agttttatgc ttttctttac aaatcgtagt gtttaataac    49500
cctccaggtt aaaatcttgg agtgtttaac ctccagtcta agtttaaaat ctccagagag    49560
agattgctag ttttgtaact ataatgctgt gcatttcctt aaaatttta caatttaatt    49620 ttctcaaagc ttttaaatgt aaagaaaaat aaaatcatgg catttatagg aagagaatgg    49680
aactagaagt cattacttta agtaaaacaa atctgatcag aaaaacgtgt tttctctcat    49740
gggaagaacc tagcttggag gtatgcatac cctttggggg agggagatct gaagggaaga    49800
tggtgaaagg aagagtggaa cctgctccac acagaaatgc agaagaggaa ctgtttaggg    49860
agggaggtga ctcagaagga agtacaacgg tacctctatg aggaaatgtc atagtgaaat    49920
gcgctagtaa caaagaaaaa taataaaaca aaccttaaaa ggcaccgggc cttgggctgg    49980
tagagtggct gtggaatgat ggatgtgttt tagcttgctg agtataggaa agctgcttta    50040
gtacagctga ggaagtcttc ctagaagaat cttagagaat tgatgactca gtgtggcagt    50100
gtagacacac agtggacttg cagacttgta gactagctag gagtccctgt ggctacgttc    50160
gtgctgcttg ttgtgtttgc tgtttctgga tttatacttt gtgattgtaa atgtgaactt    50220
```

```
ctggagatta atacttaaat ctgctttgta gttaatcata ttagaattgt ctgtattatt   50280
ttgtttatat ttgtaatttt aactatggag ggaccataag aagctgaaga aatttgtgtt   50340
ctggtacaga atcctcatct tctttctttt atgttaaagg aggaggcaat tggcctgttg   50400
tgaaaaaatt gtagactttg cctaaaatgt gtgtttttt tttttttggct tttacttata   50460 gtactttctt tctcagagtc ctgtagttag gtcttgatat gatgcaggtt ggatttgcaa   50520
gctgaccata aaatgtagca ttgtgttctt aatgctggaa caatacttca ggttttgaat   50580
attgcaatga agttcaacag ttgctacttc ctataaagaa aaaatatctc aagggcgaag   50640
taactgctca agggaacaaa gacccatacc cttattcagt caaagaagtg tgttgcccac   50700
tttactggga attatttact tgtatagttg atattttcct ttgtgaaaag gtggcaaatt   50760
atccaaatcc aaagtcactg agggtgaatc ccgactgact gcacatgcgc gcgcgcgcac   50820
acacacacac acacacacac acacacacac accccgcgcc agcccctcct gctgtaaatt   50880
accttctggg gttggtttcc acgtgtgcct tgctgtttgc aaatgcactt agggttcagt   50940
gctgcaatac atggtttgcg ggatgtaaac tatgaggaga gtgtaagaaa gaccttttca   51000
gaatggcaat gagcgcaggt tttggagtaa cttttccaaac ttgagggaag acactgccac   51060
taaccatacg tagtgtctgt tctccctggc ctccagcagt ggcaaggaaa gtaaccttaa   51120
tgcttagttc tcttattaaa cttaggggag ggattgaaac gtttcagttt gccttttctt   51180
tgcttacaag ttggttatta ggtaggtgtg tgtgttttga ctacgtgagt gtgtgtgaga   51240
gagaatgtgt gtgtgtgatt agtttactac ctcagtttgt caactttact aaaataacaa   51300
tgccaagctt aattttaaga gatttcatta ttttctgtga gaagtgaact tttataaccct   51360 actatcaagg ttatccccct acccctgttt tacttattaa atcccctcat cataaaattt   51420
tcttgcttag tccttatttt taaatcaaac aagttgtggt tgctgttgct aaaacaaaaa   51480
actcagtata attttcttgt aatgtcaatt atcatgtgtt ctcttctgat gcatactgtt   51540
tgggctatta tctactatct agcagtccac tgattcataa agctgtgcag ttttaggctt   51600
tgaaagattt aagcagttac ttaatacaaa cccatttgca aagaccacac tgccctgatt   51660
catagtcttt ctttgtcata ctcaacacct ggcttcctaa ttttgttcct tggattctct   51720
ctgctgtact aagctctact taatttttc cttttcttt tgattcctaa aatagaaacc   51780
aacaccaaaa aaaaaaaaaa aaagagagag agagagagag aaaaattgct gttttgaatg   51840
tgtgagtttt tcagttttag gtaagagaaa cccaagtagg agaaggagac agaagacaa   51900 caagggagat gtttattgac taatagaacc taaaaggtca ggtctggatc taaatgctca   51960
ataagtgtca ggaacctctc ctttctacac tcttcccttt tctttcttgg ctatgtttat   52020
tcagaaagga tctttgcaag taataccaag ctatggtccc gtagctttag gcttacactc   52080
ttgactaact gcagtggtaa aagaacaccc atttgactag aggttcctag aataggttct   52140
gatttccctg gcttaaaggg tgtgtctttt tatttttta ttttttgta agatttgttt   52200 atgtatatga gtatactgtc actgtcttca aacacaccag aagagggcat cagacccccat   52260 tacagatggt tataagacac catgtggttg ctgggaattg agctcttaac cactgagcca   52320
tttctccagc ccacatctac ctctttttg aaacaaatac ttttgctagt gagtggaatc   52380
ctcttacaaa ttcatatatc tgaattgaag aataggccca acaccccaaa ccacaaaact   52440
gtcattatag cttctaaaga aaatccaggt gaggaaagag tgttggccag aaatgatctg   52500
tgtcactttt gtcacagaga ttctgtaagt taccatagaa ctcgaagcat tatgtattcc   52560
```

```
aaacttcaga ggttcttcat aaaggggaaa aactgaatta agagaagtta tggcttcatt    52620
cagatcgcat agcattcctg ttttcaggtc acctgagtca gattcattta ggtcctgtac    52680
tgcatttgag caagataaac atgtatagtc ctacttgttt cttattaaag tagaggcagc    52740
agggctggcc tcagtgtgcg tgggacccag cagttggcag gtagagttag gaggatcaag    52800
agtcaaagcc accatcagat cctgcagtgt gtttgaggcc agctctcccc tggggggaaa    52860
ttgaggttgt aatggttggc tgtggtgtca cagaggccta taatctccac tgttggagcc    52920
tgaagcaata gaatacctat tttgagacca ttctgggta cataatgaga ccctgtctta     52980
aaacataaga tatgtgataa tatataccct gtaattttat gggaataata gaaatatgtt    53040
ttgaatatta gaaatatct acaataacta ctattgtcat agtattagta accacattct      53100
tttgtttatt gaattactgc cttgtttatt gtggtcattc agaatgtagg ttttcctct      53160 tcaagcaaat acttttagg ttgaaacttt tatttatgag tttagacttg gaaaatattt       53220
tccagtttat taagaaagtt tgctcaaata gaaaattact tctttaagga ctctaagttg    53280
tgaatttacc ttctagaaga tcatctagaa tctgaatgca tagaggatga acatacatta    53340
tatatacata tatatataca cacacacact gtgttgttcc gtgctaatcc cgtatagtag    53400
tcttatgaca gtagtataga tctcaaagat gtatgtcctc catataagtc tgttttcaa     53460 agagccagcc aggcatggtg aacacacct taaatcccga gcacttggga agtatgagtt     53520
tcaagacaca aagaaactct tatcttgaaa accaaaaaga gaaaagtaa ttagcatcaa      53580 gtagccaagg cttataaaag aagaattaat gaaaaataca ctaggaaaat gtaaaattcc    53640
aaggcaggct tttcttatcg gaatagcatt ataataaaaa ccataaaact gatcaaagat    53700
gtcattttac actcacacag gagacacttc atacggacac tgagctgtta cgaacgtctg    53760
tgccaaaagg agtcaacttt gttaagcaaa tgctagagaa ggaaaataaa aagctagact    53820
cggaggaggc gcaaagtaaa tatgtgcaca ctgaagacag tgatagagtc ggcacctgag    53880
tgctttgcag tgcccacttg cttaggttaa taactcacca gattaactac aaatcccaca    53940
agcttggaaa gtagagccct gttacctgtc ttgacagttg agtggaacta tagtttgaag    54000
tttaattcag gtcattatgg aaatttaaag ccatttcctt caataatttt tgagccattt    54060
gaagaaagat acattgatta ttcaccagta gaaaatgaaa caaaaatata aaggagtgaa    54120
ctgaggaaat gctgaactat ttgggctagc aaatcgaaca ttgactacaa gaaagagaac    54180
tggtgttttt tttaatagtg tttagggtta aatctggtt tttgtaactg tctcaaagat      54240
gaataatgta gcacatgttt gtgtttagct aggcagttaa gtcctagggg tgtacgatgc    54300
tctggcctcg ccttgctgcc taggccttag tatggtgcaa gcttccctct gtatcaccac    54360
tgcctgtgag ctctgtgagc tctattcaca caactgctgt tgatctgaga attgtttact    54420
tacatatcaa cccagctttt ttcaaaagga tgagcatata aatgcttgtg ataataggtg    54480
tccttcccat cacttgagaa tctgtttatt gctgtacaca agtgtgaaat gtgtaccaaa    54540
agctagagag caggagaaat gccatctgaa cattatcagc tactatattt ttttgtttat    54600
tttaacttct tttatataac tgaatttgct ggtttatcct catgtaaatt ctattaagga    54660
ggtttgtatt attgtattaa tttttttaaa gaagcaaatt ggaagtttat attttctcag    54720
aattcaaata taagctttga ctatttagta tgtgattttt cactctagcc aaagtcttaa    54780
attgccaatc atgatttcaa gtggtttata tccatttttg tttgtttgtt tttgtttttg    54840
agacggggtc tctctttgta gccctgttgg cttggaatgc acagagatcc accagcttct    54900
ttcttcctcc tgaattctgg aattaaagtt gtatactgcc acttatccat tttgatacac    54960
```

```
atatggagca gagaaacaga gaaagacaga gagaggggaa gagggtgggg tcagagttca    55020
tatacctgta tttgctagac atcgtattcc ttctatactt cttagcttgt atgctgtctt    55080
cttccccagc agaagggtgt ctgtgtctag agtccttatc acagtagaag ttgagaggcc    55140
atcagtaaac taaagagcat tgtaatacct ttttcttatt aacataaaat acctattttc    55200
tgcaattctg tttgttgaga ctgggcctca cataggtcaa gctggcctta aacttacgat    55260
tttggttgta cccaagtacc gagattacaa gagggtactg ccatgccaaa actgctgttt    55320
actttaaact gttagattaa atgcttatta tttgccttat attgactttt ttactgttat    55380
attgtgaata gaaaaatatt aactcattag tgaatgaatt gttacacata tggtatgtat    55440
gtctttgtgt gtgtgtgtct atatgtatat atgtatgtgt ctgtatgttc cttggatgtc    55500
catcctctgg tgccatctat cttgttcaga cagggtctct aattggtctg gaattcacca    55560
agtaggctag gccagcctgt gaatcccaag aatctgcctg tctctgctcc cccatgccga    55620
agttttaggc atatatatgg ttacgtggta ccttaaaaaa tgtatatagg catgggctag    55680
gttggctgaa gtgatagctg gtttaaagca ctgttgttct tgcagaggac ccaggttaac    55740
tcccagtacc cacacaatgg cttacaaaca tctgtaactc cagtttcatg gcatgccttc    55800
tggtttctgt gggcaccagg tatacatatg gcaaacact cacaaaatat ttcaagaact    55860
aagaaaaaaa catatgcatg ggttttgggt catacatgcg attgattgat tgattgactg    55920
gtttccggct ggcctggaac tatataaacc ctgggctggt tcggaacagt cctctgcttc    55980
atcccctta gtggtaggat tacaggtgtg ggacaccatt cctggttagg gtccccttt    56040
aaatgtcata tgaattatgt ctttaaata tttgtaatat tttctaagcc attttatgct    56100
tccctaatgt ctgcaaggag tggatatagc acaaggatac cgatacccct tactgcctct    56160
gttaacaagt tgtattgaat atgtttatca ttcagctgca tactctctct tttccttttt    56220
tttttggact ctaaggtcag aatctcattt ttcctgcaca gaggcaacac gtttctctag    56280
tgtactgatt ctgatatgat tttgcttaga aagtatgtaa acaggtttgt gaagacttgc    56340
ctagtaaacc catctttgag aggagacttg ggtatgtgta gctgcagtac agagaccatt    56400
gactgtctgt ttgaatacac agtggccttt gcttattggg ttcatagatc agagcattat    56460
ttaatatttg aataaatgag gtatttaata actacatttt aagaatattc ttttgttatt    56520
gctcttattt attctaatac tgagttagat ttgattgtta gccacttaaa ggagaaactt    56580
tgggataacc cagttatagc aattttgtat aataacttta atgaaacttt ccttttgaat    56640
ttgacttctc ttttctttt gtctccctcc tccctctgcc ccctgggcct atcagggagt    56700
cacaattccc agtcagaggc gctatgtata ttattatagc tacctgctaa aaaatcacct    56760
ggattacaga cccgtggcac tgctgtttca caagatgatg tttgaaacta ttccaatgtt    56820
cagtggcgga acttgcagta agtgctctaa attcttagct gtctgtgtgt cggaaaactt    56880
tttaaaacca tatctaaatg tatatgtaaa tgtttagaaa tacatttacc aggttaaaag    56940
gagtatattt ctgaagttgg aattaattag ttcagttgtt caactcactg ggttaagaaa    57000
gctaacccaa tgaattttgg tgttcttttt ttgtttgttt gttttatgt ttttcgagac    57060
agggtttctc tgtatcgccc tggctgtcct ggaactcact ttgtagacca ggctgtccct    57120
gaactcagaa atctgcctgc ctctgcctcc caagtgctgg gattaaaggt gtgagccacc    57180
acacctggca attttggtgt tcttcaagtc aattatattt atgggagaaa tattctatgt    57240
tataaccacc agatgcagtc tctgttctga caaaataacc gagagactct tgacagatca    57300
```

```
gtgtgagaat ctgagagaca ctcttgacag atcagtgtga gaatggcctc tggctacaac   57360
caggtcctca tcagagggaa acatgttcac tgtcagagac agaaagagag gagcccttca   57420
aatatagaga ataaaagggt gtgtgaattg ggatgtgtgg agaaaaccta agtgtagctt   57480
tgaagtcaag ctctcagcct gtggcttgga cttgtcatct cctcactgag tttgcttgtt   57540
agtaaaataa agaaatcttg gtaagtatga cgtcatgaca tcagtgtgtg cttgtagtaa   57600
tttctcttac cttagtgaca cctgggagtg gtcagtcatg ttttacactt aagatatttt   57660
atttgtattt tcaatataac gtcatagtat cagatgtcac ttattagaat cccttgatat   57720
tattttatgg atgtttgcag tttgtcagtg attttagttt ttcgcctcca tgaaatactt   57780
cattaaatta acttgttctt tctaaaataa tttttatgta gagaatcagt ttcttcgtca   57840
gataggtgtg attgcccatg agtatggcaa ctttgttaag ggcccctaat ttatttatat   57900
agcttgttgg aaagttctaa ggaacttcca tactgattaa gtatattagt ataattttaa   57960
aagtgtgagt acaaggcaca atggactatt gaaagcaatt gacctaggaa cttcactagg   58020
ttcattgaga aggaaagggg ataggaactc atgttcttcc tatagtttag gcatcaatat   58080
agagctgtaa aggcggtatg gaggcaatac ggaaaagctc tgctcaggaa tctcactagg   58140
tactgacttt ttgtcagctc tactttgctt attgattaaa ctgctgttgg gcttttagtc   58200
ggacaacatt atgtttgcat ctctacgctt aaaaaatatt gactactaaa ttcttttttaa   58260 tctttaaaaa tttctagtta cttatttatg tgctgggatt taacactata tgttgaagtt   58320
atattaaaat aaagctcatg agattcatat gtataaatta taactgccat gttcacaaaa   58380
ggttttggaa acaatttcat gaagaaagtc ggtcactgga gaacacatgc agtttggatt   58440
ggcattgagt gtgaaggaaa tattacaggc agtagaaata aggtgaccga aacacagcag   58500
aagaactgga cgagaaatag aagatgtgat tggctgtcac aggatcttga atgggatgta   58560
atagacttgg actattggtg tcacgataat tctaggaact tcagctgtgt tttaaggaca   58620 gcccatgtt gtatagacag ttgtgatgta ggaggggtag tacagccagc tctgtgactt   58680
ggcagatgtt gctagagcga tggaatgtac tttgtttgga ttttctttag ttgttcatac   58740
ccagagtgca tttgagattt ggagatataa atattatcac tttgctttta agttatttta   58800
aatctgatga gatcaaggta cttgtgagga tctgcagtgg ggctgcagct ctgtcttggt   58860
ggtgtagtgt ttttctcaag ctagagtgca ggattgcctt cagtctccag cccgaggagg   58920
aggaggcatg agtgaaacag acagaactag tgataaaagg tttagtgtct tctgcagagg   58980
gaccaggaag tgtttgccaa gcgtttgtct tattaccttac cttttctac gtgaagagaa   59040 gttgctgtat aataaaaatg atcagtttgc ttttgtgtca ggatgcactc tcatccttgt   59100
ttttgtcaag tccagatcct gtcatttctt cagaacatag ttaattaaca tagcatatat   59160
ttcagatgtg catctcagaa gtcaagagga ctgtactaat attagaatat tgatgttaga   59220
acttccatcc ctcctgctgg gcgtggtggc acacaccttt aatcccagca cttgggagac   59280
agaggcaggc ggatttctga gttcgaggcc agtctggtct acaaagtgag ttccaggaca   59340
gccagagcta tacagagaaa tcctgtctcg aaagaccacc aaaaacaaaa acaaaaaaga   59400
aacaaacaca caaacaaaaa aaacaatttc caactcaatg ggaaactcat ggtctatagg   59460
aggtcgtttt gtctcagtgg tcttagaaaa agctgctgtt ttttcattac tgtacactac   59520
agctggggac attgtcaagg aaagatgcca tgacaaggca attcttataa aagagttaat   59580
tgggacttgc ttcacttttc agaggatttg tccattatca acctatcagg aagcatggtg   59640
gcacacaggc agatacgctg agagttctac atccagaggc tggcagcctc tacctcctga   59700
```

```
gtgccagcac tttaaaagc acgggctacc atcacccagc tatacatgtt ttttattttt    59760
ttaaacatat tatttttatt aattccttga gaatttcaga taagcattca gtgtatcttg    59820
atgtaactca tttcctactt ctcccaacag ccttgtctag ttccaggaca gccagggcta    59880
actaaacaaa gaaactctgt cttaaaatgc caaaccaac aaacaaaaac ttgtgaactg    59940
gaggtcaaaa gaaagatgat cagtattgta tatttctata ttataaaggc ttaggtttac    60000
atcgtttatt aaaatattct tgtaaagttg cctctatgca gttcacaaaa gtcccaggaa    60060
attgttaaag ttatttatg cttaaagtag tttgtgatgt gtcttttgca tgttaatgta    60120
aagctttaat tgttaatatg ctgctagagt ctagtcttag aacttactgt ttgtgaagta    60180
gcaattgatt atcatatctg taatagaact ttacttaagg attcagattg aagaagtcct    60240
tacatgggtt ggtatgttt ttacatattt tatttctact gatttgtttt agataagcag    60300
tcaatatgaa gagttatcat tttgtgtata tttctgttta ttttatcatt aaagtagttt    60360
ttgataagtt gaagacattt cttgtgaaat gatcctatat gtatttaacc acacagatcc    60420
tcagtttgtg gtctgccagc taaaggtgaa gatatattcc tccaattcag gacccacgcg    60480
gcgggaggac aagttcatgt actttgagtt ccctcagcca ttgcctgtgt gtggtgatat    60540
caaagtagag ttcttccaca aacagaacaa gatgctcaaa aaggtttgca attcagttct    60600
attgtgtaga aatagccatt cctcaatgag taaccacaga cctttgctt aaagcctttg    60660 gttaggaaat tattctgtaa ggagagacta tttctctgcc atctaccaaa ctgattactc    60720
ttttgttaga ttggcagact cttcatttct gtggcattga tgagacatgt aagcagactc    60780
acctgccccg accccttagtt tgttggcttt tttggtttgt tctatgttct tatgttgcac    60840
aagccatgtt ttacccattt gggtttatgt ttcttgagag tagactattt tatattttgt    60900
ttccccaggt tactgagtat ttagtcagta ctgagtattt agtcagtact gagtatttag    60960
tcagtattac ttagttgaaa gaagtggttg tgaagaagta atagtaatta aaaaaaaaaa    61020
aaaaaacata ccaaaaaaca aaagggtgga aacagctaag catatcctct gtccagggtt    61080 gctgggggctt gagatacact tgggaggagg agagagctca ggtgcagtgt ccttggtgtg    61140
aacatttatc cttggtggct ttagtaccct tagttgaatg tgaacattaa aatgagtctt    61200
aaggtgtaga agttttagct ggatcagaag aagataccag ttttgtgcag aatcaattcc    61260
cgtgaagcac atagagcagt acatagtccg gaaggggggtt ttataaaag cagtaaaagg    61320 agagcttact tactataaaa ccttgcaatg tcagatcaat ttatcaggag agataatttc    61380 tttttttctag gatctacata gctaaagaag aaaaaaaatc acaaagttaa ccaaattaat    61440
gtttttatca tggacctctc atgaaacaaa aaagctaaat ataaatatct ttgagttact    61500 ggttttttttg tttattttct gagaccacaa taaatgtgag caaacatttc aaaaattagg    61560
tatttggaag gctttagttt ttttccctct tacttcattt gtttgtttgt tgtttgttt    61620 gtttgagaga catggtctct ctgtctagct ctagctgtct cgaacttgtt ttgtagacaa    61680
ggctagtctc aaactcagag atcgattgcc tctgcatcct aaatgctggg attaaaggcc    61740
tgtgccatcc ctgcccgcta tctcttacat cttgtaagac tctgattcac ataagagtgt    61800
gtgtgtgctc acacttgtgt gtgtgcgtgc gctcacacat gcatatgttt ttcttttcctt    61860 gtttgtttga agacagattc ttactctgta gctcaagctg gtctggaact cactaagtag    61920
ctcaggttgg cttcatataa aacagtcttt ttgctttaaa ttcccaagac aggagccgcc    61980
tctcttggct ttatattgct tgtaaaaaga gataattacc tcactgtctc cttgtagttt    62040
```

```
tagagatgtg ctgtttctta ctccagatct ctgaagattg atatttata atatatttgt    62100 atattttaga ttactttcca taaatttcca tttatcatag gttttcctta ctaattatat    62160
gcctgttctg atttaaataa aaacagtttt agaaaatcag tgcacatcag tgagctacat    62220
ttgcaagttt aaataatatt accgtgtttt cttctaagta aaatatgatt gccaactgaa    62280
caactttgtt aaaataattg agatcaataa ggtttgaaaa gggctggaaa cacgactcag    62340
cagttaggag ggagcgctgg atgttctgga ggacacaggc ttggtcctca gcacccatct    62400
gttgtcttac agttgtctgt aataccagac ctgggggga atctgagtcc tacctcgggc    62460
ctccatggac actggacaga tacaggggcc agaaatgtag ttgccatagg gatcaactta    62520
ctagggcttc tgttgaagta gcaacacctg atctttgttt atatttacat atgcataaac    62580
tcagaatatt tttaaaatcc agtattagaa taagaagtag ttttcttagg attttaagat    62640
aaaagtaaga taccagattt tacatgatta tattttttat ttgaaatttt agaaaagata    62700
acttagtgaa taagaatatt ccacaaggtg tttgccttca cttaagaata tcaaataata    62760
tatggtttat atgttgacta tttgtggtac attttttaaat aagtgaaata catcttccat    62820
ttcttttctg tttaggacaa aatgtttcac ttttgggtaa atacgttctt cataccagga    62880
ccagaggaaa cctcagaaaa agtggaaaat ggaagtcttt gtgatcagga aatcgatagc    62940
atttgcagta tagagcgtgc agataatgac aaggagtatc ttgtactcac cctaacaaaa    63000
aacgatcttg acaaagcaaa caaagacaag gccaaccgat acttctctcc aaattttaag    63060
gtcagttaaa accatttggg ggtgggaggg tgtgttttat tctgattgtg aagctaagag    63120
ctagacattg ttctagtatt gttcaatatg taacattccc gagtggttgc gtagcctttc    63180
cttttctgtt tattactcca cttgctctcc ttatttcttc tcctcccccc tccccatctt    63240
gagtctttcc tctttccttt ttcctttta aattctttt tcattccatt gtatttgttt    63300
cattcacatg taacaaactc aaccatagat tattatatta ttattataac ataataatac    63360
tcctaatatt taaaatagaa aatgaccttc acacatgtta agtgaacata gacctaatat    63420
tcagtgcctt tggatctcaa gtatgtttta agtttccttt agaatcttca acttttcatt    63480 ttttccttttt ctctaaattt acatttctat caaccacctg cttcctgatt tttattttag    63540
ataggatctt ggtatatagg ctcaggctgg ccttgaactg gcatgtctct gcctcagcct    63600
cacctggcaa ccatttgctt ttaaaatgta tttctctcta gttttactgt tttaatatttt   63660 ttctggcaat gtgcctcaat gcttgtctaa catgagaaat gccttgagtt gaacaccaag    63720
tcctacaaaa caaccagtaa aaaataaag cataaaatag ttcgtgtaga taaaagctgt    63780
tttcattgtc actgtaaggt aagtcctatg aagcatgcag ctggcaaaga aagtctggtc    63840
aagtggatgg tctgtaaaga gggttgtctg cgtgaaatgg gtgcatttaa ttatgcaaat    63900
tgtatgcgac ctacagaaca gttatgtggg ggaaggagga agagtagaaa tgagaatctg    63960
aggcatgaat gagcttggta tattcagtgg ctgaagtcat ttccactgag tcacaggaac    64020
ccagtcttga tgtagcagtg tggagtgctg aacacagaga aggtataatc tgagcttttt    64080
aaccttccag ttcacttcct aaattgagac tggctcagaa actagggaga ggagaggccg    64140
tggggctgta gtggcaagga gcagtggtaa attactaact ttgaagggg attttttaaag    64200 caaatgttgg ttataagaaa aacttataat gacttgcata atgggaaaag agcaaagata    64260
tgatttaaac ctggtctctg ccaattgttc actagagatt gtcctttagc atgtggccta    64320
gacttcaggg tttttgtttc ttacctttta aaatggaaat aacctaagaa ctgcagccat    64380
gcatgtaaag gctactgatc aatcctcaca gcacagagtg ctctgttagc ttgcaccatt    64440
```

```
ctctcgtcag atgactgttg tagagctagt tgaccttatt aatcagtatt gtgtagtgtc   64500
actaatgtaa acatagagtt gtctcagaga ttgcaagaga aatgtttttg aaacataagc   64560
acttgtaaat tgaattttgt gatttagtga gttcattgcc ttcagtttgc acttttatag   64620
aattatacag tgcttatggc tgatgtattt taaaaatagc tttcaactca tcattgtgtc   64680
ttttgagagc acagtagtca atcttcaggt catctgaaaa gcagtgccct tcagaattca   64740
ttttgttata gtactttcaa gtaaatctgc aaaacagaat gtctttgcta atacagaact   64800
cattctaatt gttcattttc atcttaaact ttctttctct aggtgaaact atactttaca   64860
aaaacagtag aggagccatc aaatccgagg gctagcagtt caacttctgt gactccagat   64920
gttagtgaca atgaacctga tcattataga tattctgaca ccactgactc tgatccagag   64980
aatgaacctt tgatgaaga tcagcattca caaattacaa aagtctgatt ttttttttct    65040
tatcaagagg gataaaatac catgaaaaaa aaaaacttg aataaactga aatggacctt    65100 ttttttttt tttttttttt aaatggcaat aggacattgt gtcagattgc agttatagga    65160
acaattctct tctcctgacc aatcttgttt taccctatac atccacaggg ttttgacact    65220
tgttgtccag ttaaaaaaag gttgtgtagc tgtgtcatgt atataccttt ttgtgtcaaa    65280
aggacattta aaattcaatt aggataaata aaagatggca ctttcccatt ttattccagt    65340
tttataaaaa gtggagacag gctgatgtgt atacgcagga gtttttcctt tattttctgt    65400
caccagctga agtggctgaa gagctctgat tcccgggttc acgtcctacc cctttgcact    65460
tgtggcaaca gataagtttg cagttggcta aggaagtttc tgcagggttt tgttagattc    65520
taatgcatgc acttgggttg ggaatggagg gaatgctcag aaaggaatgt tcctacctgg    65580
gctctggacc atacaccatc tccagctcct tagatgcacc tttctttagc atgctccact    65640
tactaatctg gacatccgag agattggctg ctgtcctgct gtttgtttgt gcattttaaa    65700
gagcatattg gtgctagaca aggcagctag agtgagtata tttgtagtgg ggtacaggaa    65760
tgaaccatct acagcatctt aagaatccac aaaggaaggg atataaaaaa agtggtcata    65820
gatagataaa agacacagca gcaatgactt aaccatacaa atgtggaggc tttcaacaaa    65880
ggatgggctg gaaacagaaa atttgacaat gatttattca gtatgctttc tcagttgtaa    65940
tgactgctcc atctcctatg taatcaaggc cagtgctaag agtcagatgc tattagtccc    66000
tacatcagtc aacaccttac ctttatttt attaatttc aatcatatac ctactgtgga    66060
tgcttcatgt gctggctgcc agtttgtttt tctccttaaa tattttataa ttcttcacag    66120
gaaatttcaa cttgagattc aacagtaagc aggttttgtt ttttttttttт cctagagatt   66180 gatgatgcgc gtcctcagtc cagtggctgt cagacgttca gcccctttga ccttacacat    66240
tctattacaa tgagttttgc agttttgcac attttttta aatgtcatta actgttaggg    66300
aattttactt gaatactgaa tacatataat gtgtatatta aaaagtcat tgtttgtgtt     66360 aaaaagaaa ttagagttgc agtaaattta cagcactgca cgaataataa ggcattgaag    66420 ttttcagta gaaattgtcc tacagatgct ttatcgactt gctattggaa gaatagatct    66480
tcttaaatgt gcagtgttga gtcacttcgt tatagtggta gagttgggat tagggcttca    66540
attttacttc ttaaatatca ttctatgttt gatatgccca gactgcatac aatttaaagc    66600
aagagtacaa ctactatcgt aatggtaatg tgaagatgct attacaaagg atctcctccc    66660
aacccctcgg gaatttggtg tctttcaaat tatatcttga ccttgacatt tgaatatcca    66720
gccattatta gatttcttaa tggtgtgaag tcccattttc aataacttat tggtgctgaa    66780
```

```
attgttcact agctgtggtc tgacctagtt aatttacaag tacagattgc ataggaccca    66840
ctagagaagc atttatagtt tgatggtaag tagattaggc agaacgccat ctaaaatatt    66900
cttagaaaat aatgttgatg tattttccat acctcatcag tttcactcaa ccaataaagt    66960
ttttaaaatt gtaacaaagc tcttaggatt tacacattta tatttaaaca ttgatacatg    67020
aatattgact gactgttgat aaagtcagag acaactttc  ctgagatctc accatggaaa    67080
tctgtacacc cccttgtctt tcctaaaagc tgaaagtggc tgactaaaat gcaaagcagc    67140
tgttgatgtt ttgaagatag tgataaacac tgttctttgt tagttttggg cacagcatgc    67200
taaactataa cttgtattgt tccaatatgt aacacagagg gccaggtcat gaataatgac    67260
attacaatgg gctgttgcac tgttaatatt tttcctttgg aatgtgaagg tctgaatgag    67320
ggttttgatt ttgaatgttt cagtgttttt gagaagcctt gcttacattt tatggtgtag    67380
tcattggaaa tggaaaaatg gcattatata tatattatat atatataaat atatatatta    67440
tacatactct ccttacttta tttcagttac catccccata gaatttgaca agaattgcta    67500
tgactgaaag ggttttgagt cctaattcaa actttcttta tgacagtatt cacgattagc    67560
ctgaagtgca ttctgtaggt gatctctccc gtgtttctgg aatgctttct tagactcttg    67620
gatgtgcagc agcttatgtg tctgaaatga cttgaaggca tcacctttaa gaaggcttac    67680
agttgggccc cgtacatccc aagtcctctg taattcctct tggacatttt tgccataatt    67740 gtaaagggt  agttgaatta aatagcgtca ccattctttg ctgtggcaca ggttataaac    67800
ttaagtggag tttaccggca gcatcaaatg tttcagcttt aaaaataaaa gtaggttaca    67860
agttacatgt ttagttttag aaaatttgtg caatatgttc ataacgatgg ctgtggttgc    67920
cacaaagtgc ctcgtttacc tttaaatact gttaatgtgt cgtgcatgca gacggaaggg    67980
gtggatctgt gcactaaacg ggggctttt  actctagtat tcggcagagt tgccttctac    68040
ctgccagctc aaaagttcga tctgttttca tatagaatat atatactaaa accatccagt    68100
ctgtaaaaca gccttacccc gattcagcct cttcagatac tcttgtgctg tgcagcagtg    68160
gctctgtgtg taaatgctat gcactgagga tacacaaata tgacgtgtac aggataatgc    68220
ctcataccaa tcagatgtcc atttgttact gtgtttgtta acaacccttt atctcttagt    68280
gttataaact ccacttaaaa ctgattaaag tctcattctt gtcattgtgt gggtgtttta    68340
ttaaatgaga gtatttataa ttcaaattgc ttaaatccat taaaatgttc agtaatgggc    68400
agccacatat gattacaaag ttcctgtgca ttttctatt  tttcccctc  cttgctatcc    68460 ttccaagcaa agcatctttc tgtcatcttg gtagacacat acctgtctac tcatggttaa    68520
gaagagcact ttaagcctta gtcatcactt aataagttat tccaggcaca gtaaaaagtt    68580
caaggttctt ggaaaacggt gcttatttct cttcttataa gccagatgtc tgaagatagc    68640
cctaacccca agaacgggct tgatgtctca ggtctgttct gtggctttct gttttttta    68700 acactgcagt tggccatcag cacatgggag gtttcatcgg gacttgtcca gagtagtagg    68760
ctcaaatata ctatctcctt tctaatattc ttaaaggcta aggagtcctt tcaatataac    68820
agtaagataa cttgtgatgt tttagaagta agcagaccat taatgtcaat gtggagtctt    68880
aatgttacat gaagttgata gtttctctgt gacccattta aaaatacaaa ccgagtagca    68940
tgcaattatg taaagaaata tgaagattat atgtagtcac acatttttctt tagaattctt    69000 agtttggtga aaacttgaat ataaaggtat tttgatttat atgacatttt gatgatattt    69060
gaaaaaaagg aatttcctga cattttgctt ttagatcatg tccccccattg tgctgtaatt    69120 taagccaact tggttcagtg aatgccatca ccatttccat tgagaattta aaactcacca    69180
```

```
gtgtttaaca tgcaggcttc tgagggctcc cggagaatca gaccttaagc ccagttgatt   69240
tacttctaac gtgaaacttc gagttcctgt atactttgct agataatttg tggtacatct   69300
aaagcttagt cttaagtggc ttgtgtgtgg attttattca acattcttgt tgctagggta   69360
gagagaaatg ttgctgagta gaaacaagag tacccagttc aatgtggtac agagagcagt   69420
ccctaaaatc tgtacacagt gtaatggacc actttaggag tcaagaggct gattttcct    69480 atgaaattac attgcaacag gaagccttct agtatagttc cttttactgt tagaatatgt   69540
ttttatgcat acgctatagc tgctttccca tcttccaaca acaggtatca ggatgtaagc   69600
aagctttaaa cagtgtgaag atggcaggat agtgtcatcg gtaacagtcc tctgactcta   69660
aatgtagttg ctctgtaaca ctttgtgaat ataacatcac aattctcatg tccttggggg   69720 ggggggggcat acccagtatt agtatgtttt agtgactaag caatcatttt tctgtttact   69780
catgtacatt ttctctttaa aactaaaacc tgtactgtgt atgtctccaa agccttttag   69840
cttagttttt aggaaatgaa cactgaatgg atcacttttt agtgtagcag gtatgggata   69900
tgtgcattat agagagacct tgtcagctct ctgggcctat ttgaatgttt attgttggtg   69960
tgaggatggt aggggaatca gtaaatacaa gttacgttgg tttagcagag caagctcagt   70020
gtgggtattt ctcttttgaag cgtggtgcgt gacgcactgt gagtagagaa tttggtcacc   70080
ctttgagtcc tcttgcattt tgcaaacttg ctcagcaaat gcgtacctac cttgcccct    70140 aggtaaaagc aggaactact actgatttat ctgtcactca gctgtcttta tatgtgtgct   70200
tctgtgactt gtatcacaca agaatcttaa agatttcaca aattgttacc ttttagctct   70260
gaatgttgag tattctggtg ggctaacaac aagacaaact cttgacagtc atttgagaat   70320
tttcatgaaa catttagctg aaaacatttt ataatttatg aaaaaaatgt gttaccttaa   70380
acttttacat atgtgggaga cattaactgc catatttgag catactgaat tttaaattta   70440
aaataaagct gcatattttt aaatgaaatg tttaacaagg attcatattt tttgtttttt   70500
aagattaaaa ataatttatg tcttctcatg tggaacctca tctgtcacaa tggttagatt   70560
atacagaatg gagcaaggct tgtagtggtt tagcttacag taaaattctt aatgtttaga   70620
tgtgtttact tactggctgt tatgtatact tttgagattt tccacctgtt ctgtgtagtt   70680
ttctaaatga tactcctact taaaaacagc attttagtat ctattttctg tctccattaa   70740
atggtcctca ttttctattg agtttggaag tgtgcacatt gtgtgtgtgt gtgtgtgtgt   70800
gtgtgtgcac acgtgtgcgc gcccgtgcgt gtgtctattt gtggagtttg tatgggagaa   70860 ttagtttga aagtgctaga atagagatga aatttggttc aagtaaaatt tcccactgg    70920 gattttacag tttattgtaa taaaatgtta attttggatg accttgaata ttaatgaatt   70980
tgttagcctc ttgatgtgtg cattaatgag atatatcaaa gttgtatatt aaaccaaagt   71040
tggagttgtg gaagtgtttt tatgaagttc cgtttggcta ccaatggaca taagactaga   71100
aataccttcc tgtggagaat attttttcctt taaacaatta aaaaggttca ttattttga   71160 tgatttgctt cttagctttt tattcatccg agaatcaatc cctgctatgt gtaacaggta   71220
tttggactat attacttagt gaaagaggaa catcctgatc ttactgttga aaagttata    71280 cttcaccaga gtaaactacg taaaagctgt ggggtgtgct aggaagtatg agacctcatg   71340
gctcccttgc atgtccatcc tcagagttta gattctgttt actagagcat tactagagtg   71400
aaatagccat gaaagtgcag agaaacttcc aagtaaaggc agtgagagat ccctgtaccc   71460 tcctgtctttt ttccttccct agtgcagtgt cctgaagtgt gtcctagtgt gtgtcatggc   71520
```

```
tctgccagcc caggtcttga ggtaacacct gcagtggagc tcctgagggt cttcctctac    71580 ccccttttcaa cacaagcaag aaacaataat attttgggtt gctattctaa ccaatatgct    71640
ttgaaaaact tagctttctt gagcagcaaa gggaattaat aataaaaccc aacatattta    71700
gattagtttg tccaattaac aggatgcaag atgtccaaat gttttttttt ttgatgagta    71760
gttattgcgg tacgtcaggc attgtgaacg ctcggcatgc acttgggtga acagcagttt    71820
cctgtctgtg aagtttgcat tctagcaaga aaaatagagc aaagataaat gtgtcagctc    71880
acctcaagca gagtgacttc agtgttggat aggttatttg agagtggctt cagcaggtgt    71940 gggggggtttc agtagactgg tgcaatttgt acccagaaac ttccacaaaa ctttactcag    72000
acttggagtt tgaaaatgtt tagtatatct aaggagaatt tatagtaacc tcatcttaag    72060
tagccatgac cattctgttg tctaaattgg tttggtaaag cctgttttaaa caattggttc    72120 ctctttattc tcagagttaa ctttttagtg ttctctgtgt atgtttcaaa aacactaagt    72180 cattttttcag aagttaaagg ctctatttttg accttaaata gttttgtaat gttgaagagt    72240
catgccattt atgatttgtt gttggacagt gagttataaa tgttgagtta ctcaggatat    72300
gggtgtgatt tatgacctgg tgctctatgt attagttcct aacccataac caaacatcct    72360
gaaaaatacc attatctaag tatcagaagc agcatttcca cacaaagata aaaatcccca    72420
cctctcctgc ttcatctcaa agattgaagt caaagtgttt aataatctgc tacaatggac    72480
acttgaaaca ttttattcat tacatcatta acatttttagt agtggcaggg tccactcctc    72540
agatcaggcc caggactaag gggtgaggtc ttttatttat ttgtttatttt ctgtgtatac    72600 acgttcacat gtgtgggagc atgtatgca cgtgtatgta tatgtgggtg gagtcagagc    72660
ttaatgttag ttgccttcct ccatggctat tgaggaagcc atctcttcct aaaatcttcc    72720
taaatctctt cctaaacttg gtgcttggtg attcatctgc aattacagtt ggatgtacag    72780
cccagcatgt agtgttggga tcataacact agtcctcata gttgcaaagc aagtactttg    72840
ctcagtgagc catctcccca gtccctaggg aggaaatctt gaaagaaaat gttgactttt    72900 ttttttttaat tcttgatttt aaaataggtt taaaagaatt tgatagtcat ctatagatag    72960
accatgaatc tgagcaagga gaggtatata ggaagatttg gaagggagga aggcaagggg    73020
agaaattatg taattaaatt acattatcgg gctggtgaga tggctcagag gttaagagca    73080
ccgactgctc ttcggaaggt cctgagttca aatcccagca accacatggt ggctcacaac    73140
catccgtaat gagatatgat gccctcttct ggtgtgtctg aagacagcta cagtacttac    73200
atataacaat aaataaatta aaaaattaca ttgtctcaaa aaataagaaa ataactaaaa    73260 attttaatttt tacttaatgt tttcctgtga atattattga taagaaacct ttttgtgtgg    73320
ctgcctttaa cagaggagcc acaagctata ttcttgttac ttattacgtt tgtgtgtttt    73380
tgtatatgca aatgtttgcc atgatactcc atgtaggtta agaggacaac ttgtcaggag    73440
tcttttttct ccttccacta tgtaggtccc agaagttaaa cttaggttgt caggcttggt    73500
gctcatctcc tgagccttct catctgccca taccaggtat tctttagcaa gtacttcagt    73560
aagtacagcc attgtaagtc acaagagcaa ttagacttct tcatggtaga ataattagc    73620 tgatggaaag attatatttt aggattataa atgttcttgg ggggggtttg ttttttgttttg    73680 ggagttttttg gtttgttttg agacagggta cttaggctgg cattatactc acgatatagt    73740
tctggctgac ctgcagcaca tgatcctttg gcttcagtct cccaggtaag aatactggaa    73800
ttacagatgt gttgccaaca cctctggtta ttagtgatgt gtgtgtgtgt gtgtgtgtgt    73860
gtgtatacac acacagtgaa tgtttttactc tttttggtaaa aatggaggtc tgaggtaaaa    73920
```

-continued

```
gtttcctatg tcagctgtcc atagggaaga cttaaaagac tttgcttcaa aagattgagg   73980
gctggtgaga tggctcagca                                               74000

<210> SEQ ID NO 4
<211> LENGTH: 9001
<212> TYPE: DNA
<213> ORGANISM: Mus musculus

<400> SEQUENCE: 4
ggcagatttc taagtttgag gccagcctgg tctacagagt gagttccagg acagtcaggg     60
ctacacagag aaaccctgtc tcgaaaaaaa aaaaaaaatc cctttctctg gctataagga    120
tggctcagtg gttaagagca ctgactgctc tgccagaggt cctgagttca agtcccagca    180
accatctgta atgggaaata atgcactctt ctagtgtgtg tctgaagaca gctgtagtgt    240
actcatataa ataaaaaata aatcctaaaa aaaaaaagaa ttcccttcct cttattgata    300 cccctttcttg tctctaggga cccccatat atctttctag acatttctga gaactcatgt   360
aaatacatgc tgagccccct ctttgtagtt tgtaacccttt gctcattcca taccatttta   420 acaaatatttt tccttgaaac actatttctc acccattgca tggaggtatc acataggact   480
ttatcaggca tcctgttctc cagtgtgtgg cttagagcca gtggaatgca cggcgtgtcc    540
gagaaccact tcacacaggg aagagaatac agattttac tcagcaagta acaccagctg    600
ggaatggtgg ggcagacaag caatcctagt tactagggat gctgaggcag gaggatctta    660
aattcaagtt tagtccctat ctcaaaaatt aaaaagaac ccctctaacc ccagcaactg     720
agaggcagag gccagggaga tctctgtgag ttcaaggtca gcctgtctgt tctacacaat    780
gagttccatg agagccaaag gtacacagtg tgatatttttt aaaaaggtat gtgtgtcttt   840
ttttttttca aatttttatt atttttcttca tttacattttc aaatgctatc tggggagtcc   900
cctataccac gccccctgc tcccctcccc acccactccc acttcttggc cctggcattc     960
cactgtactg aggcatataa atttgcaaga ccaagggcct ctcctcccag tgattgtcga   1020
gttggccatc ttctgctaca tatgcagcta gaaacgcgag ctccggaggt actgggtagt   1080
tcatattgtt gttccaccta tagggttgta daccccttca gctccttggg tactttctct   1140
agctcctcca ttaggggccc tgtgttccat ccaatagatg actgtgaaca tccacttctg   1200
tatttgccag gcactggcaa agccttacac gagacagcta tatcagggtc ctttcagcaa   1260
aatcttgctg gcatacgcaa tagtgtctgc atttggtggc tgattatggc acggatctcc   1320
aggtggggca gtctctggat ggtccatcct tttgtctcag ctccaaactg tgtctctgta   1380
actccgtcca tgggtatttt gttcgttatt ttaaggagga atgaagtatc cacacgttgg   1440
tcttccttcc tcttgatttt cttgtgtttt gcgtgtgtgt gtgtgtgtgt gtgtgtgtgt   1500
gtgtgtctta actggcagag cacttgtctg tcatgcaggg ggcggggtgg gggtgggga    1560 ctgtctaatc tccagctcta gtaacaaaaa taaagaagt aaaaaataag taagaaacgg    1620
gggtgtgtct agagatagaa catgggcttt acacatttta gacatcatga gaaaataaag   1680
ctggaaatga cactgggcat ccatcttggc gcatctcaac tttcacactg caaccgaggc   1740
gcgctgtgca aagtcagtga caatccgcat ttccagacac agtgggttca gaccttccag   1800
gcgcgcacgc gggcctcgtg ttctcggtttt ccgcggcgac tcggccgacg tcacagttag   1860
aagacaatag cgactttccc cgctcaggct cctcgggaac tttctcagtc cgcacgctcc   1920
aggagccgga gctaccctcc gccccgcccc cagcgtgccc cgcggccagg gagctccacg    1980
```

-continued

```
aagggcgggc ggaggccgcg ggtagcgatt ggttccgtgc caaggtgggc gtggtcagac    2040
tcaggcctat aaaagctccg tggcgccagg gcctcgtttt tttgcgcggt cctttcctgc    2100
ggcgccttcc gtccgtcggc ttctcgtctt gctctctctg gtccctccgg aggaggccgc    2160
cgcgcgtctc ccggggaagc atggcgatga aagcggtgtg cgtgctgaag ggcgacggtc    2220
cggtgcaggg aaccatccac ttcgagcaga aggcaaggcc cggggcgcgg ggcgcaggcc    2280
gcggtgacgc ggcgcacctg tgcgggagca cgccacgccc ccgccacggc ctgagcccgc    2340
taagtgctga gtcaccgtgg cctggggcag gggctgggcg ccgggaagcg aggcccgggg    2400
cgccgcgggg ccttccggcc gggcggggc ctccccgcgc ccggagcgg ctgggcctgc     2460 ccgggagagc cggcttggca tccgttatcc ttctggggct gctgcttttc cggtgtccgt    2520
gtcccacagg ctcagagccc cgtggccacc ggctgcgatt gttgtaagaa tatttgaacc    2580
cggtggtgcc agaccggact aaggccgcag gacgcgtttg cggcacttta aagcaaagtc    2640
ctgggctgtt ctgtactagg tcagggtcgt gtcgcaaggc ggaaagaaag agatggcctt    2700
ggacagccgt cccttgcttt gcactccaga gagagaccccg gctgtgggtt ttttctacca    2760
cagcgagttt ctgagcacat tttggaaaag tacatagaga tattttcgaa atactgtga     2820 ccctgcaaaa acacatgcgt cacagggaag atgtgtgtgg taaggttgtg tccagagcct    2880
tagggaggtt accgttgttg tattcacctt aatcccgaga gaatatttga taaatgagcg    2940
ttatgtgctc tctgaagtgg tggacatacg tgtgagaagg cagacaccat agtgaatccc    3000
aagtgtttgg tttacgacga gaactgataa cggcaattta gagttttcg taactagcct     3060 cgttccagc agtttcttgg cattgaaatg cgttttgttg ttttcctgtg gaagttttt     3120 gttttttgtct ttttctcctc cccacgtaat tcactgtgag aaagacgaag ttcggctggg   3180
tcttacccct gtgtgtgggt ttctgtcatc ttccaccatg ccatgccaga gcagctcgca    3240 ctattttgt gacgctgcaa actacacatc gctggtgccc tttgtaccca atgaaacgat     3300
agttaagcat tccagattgg cagttgtaat caaagctggt tgatttaacc tgttgccaac    3360
ttttcagaat cagattttc tacccaaagt tcatattccc ttattctgtt gcaaaagttg     3420
gacatttaaa aaaaaaaaaa cctaaaaaat gattgtcctt gcttgttggt cggttgctct    3480
tacattttct ccctattgct acactttctg gagcagtact aatttgaatt ttgggtgttc    3540 ttttctttt tgttaagtgg caaatttct agatttggat agctaatgag attttttttt      3600
taaggtagct ctggttagac ccaaatggat ctccacaggc agtaggacaa aggcattttc    3660
tgaccactaa ataaaaatag gggaactgat aaaatcactg aatgtggaga acagggttct    3720
cggcagccag tgttctgtaa gagtcaagtc tgacagtgca gtagccatct cttccccagg    3780
cctggcattc agtagcccct gtttgttcca cctggtgctt tctaaatgct gttcagtcca    3840
ggtgcctgca cacatggcat ctggcagcaa gtgttaggag aagtgtgaca gggagagaga    3900
ggcctagagc tgagcgtctc cagagccacc ctgtaggaag tgggtctact tggatctgaa    3960
cataggtttg attttcactg ttgtgtgttt tgacttgagc ttttactgt gcttggttag     4020 ggtgtaaccc agcaacagcc ctggtgcagg agtatttaca ctcaaacttg atgtcttcat    4080
ttttgtattt tttaaatca aggcaagcgg tgaaccagtt gtgttgtcag gacaaattac     4140
aggattaact gaaggccagc atgggttcca cgtccatcag tatgggggaca atacacaagg   4200 taggtcctag gctggctagt gaccagtgat ggaaaggaac tgagtcagga cccaattact    4260 aaccattta aactatctcg tttgtttct ttttctttta gataaagtta aaatgaccac      4320
ttaggtcaac cttggaaagt agccacaaaa gtatttatt tagtatcaag tattgcttgc     4380
```

-continued

```
ttccttaagt gtgggaaggt aaagaaggtg attttcttc attgtaatta taattaagca    4440
gcaccttgct tattctgggt gtttattggg tgcttatttg ggtgtttgga gctgggcgtt    4500
gaggatggat gcattaggca gagtgtctaa ggacaaccat gccttagcat gagaggcata    4560
gcgggacaga agtgacaaaa actgaagatt caatataaat gcttaagtaa gatttatttt    4620
ctctatttgg gattagaatc aagtcagtaa aaagtagtgg cttaaattgc agttagtgaa    4680
cttttaccat attggagtaa tgatctgaat ttgcttaccg tcatttaaga gcctcatcca    4740
tgttgcgaga gccttttcct ttcctctcct tctccctgc cttcttccct tctccacata    4800
gcccacggtg gcctggaatt tagtcttgtg tgtgctgtgt taaaggcatg taccatcaac    4860
ctgtgtgcta tgtgccataa tttgttctac agttacttag gattgggttt gacccatttg    4920
ataattacta aagttacccc gagttgcctc tggcctggta gctttgattt gttaagctcc    4980
ttccagaatc ctgcccagtt cctattttct tggtctgagt aaacactgga agtcctgcat    5040
ataaaaggac ttgctgcatt gttgagctgt gccttgtgac tggcatccct tagcccacat    5100
gagtagtgtg gtacacctcc tggagttgag acaccagcc ctggcccttg ggaacaagcc    5160
atctaacagt ctgcctgccc caagtaaaag ctagacaggt gagctgtttg gtggcacatg    5220
gtctagaaag ataagtattt ttatcatgaa gtatgctccc ttcttaaaag ccaaggtctt    5280
taaatgtggg actttaactt tagaagtgcc attaaagatc acatctgttc cagttacaag    5340
gaaggaacaa gagccaggca tgctgtcctg acactgccat ggcccaagg ctaaggtggg    5400 agggtcatag gtcgcagata tcctgagctg tagtagtgag acactgtctc aaaactcaaa    5460
agcaaacaaa aagaaaaatg tgacagtcta ggaaaaaaag gtagcctgag aatgtaaggc    5520
tatacagtgc agctacttac accagggcgc tgctgcctgt ttttatcgcc ccagcacata    5580
ccaggtcagt gtttgctatg ttggaggttg taagaatgcc tgtgttgtta catatagggg    5640
tttacttcat aatctgactg ctggtttctg gtaaataggc tgtaccagtg caggacctca    5700
ttttaatcct cactctaaga aacatggtgg cccggcggat gaagagaggt gagcagcacg    5760
ctctgtatgc atggtggagg agaggggtct gtggaggacc ccagtaagac agaactgcat    5820
ggcctcctgc ctctgctttt gtgtttgttt ccattcaccc aactcactcc cacaacccca    5880
cgtgctagaa tagcttctgt tgggtgaagg agctgacaaa tgtggactct taaagtgatt    5940
tggttttgta gcatttattg aagatgaact aatacaagtg ccaaaaggaa ccaatacaga    6000
aaatatcatg gataacagta ctgtcagtca ctggcaaagt aaatcattgt ataataggac    6060
gctaatgcag ataatgaaaa ctagttgaga ttccatttgt atgtgaaacc ttaggaaagt    6120
cctaaataaa gaagggctag cctgttttta gaatggggc ctgggagcaa acctttgcta    6180
actcaggagc tggcatactt tactaaagcc ccagattatg actcttctca gagcactacc    6240
tttaaacttg aagaactgtc tgtcaaggta tcctgtagct acctgttttg aactttgtgt    6300
ttccagacct ttgccggtct ggaaaagcca tcatagttga taatgtatgt gtactttttc    6360
atccactcat acgtatttga cttagtcaga ttttaactta gttattgaac tctagtgatg    6420
tgaaatagac atcattgttc atccacctga tgctgtttta atgttaggca tgttggagac    6480
ctgggcaatg tgactgctgg aaaggacggt gtggccaatg tgtccattga agatcgtgtg    6540
atctcactct caggagagca ttccatcatt ggccgtacaa tggtggtaag ttttcatat    6600 aaggatatat acataggatt tcttctaaca tagttatgta ccttcccatg actttatggt    6660
ggttaaacta gtttctaaag agtcacataa attgttaaga gttcagggta ggaaaaagt    6720
```

```
tcttttattg gctgtgatag taaagaatta atttgcctag gtcagttaag aacactgttg    6780
tgctgaaatg cagtagaaag cagttacatt tgatgagact ggatctgagt tgaggataca    6840
atagtcttta gtctaaaaca gccggatttt cttgccatga ttgcccccce ccttgcaaca    6900
tttcgttgag tctaaaatct gcgatggatg gcagtattca agtctgtagg ttatcgcttg    6960
gttaccatat gggagccgtc ttcccaagtt accctcggga gatgcatctg ggtcatgcag    7020
aacaccaagt agtaaaggct cttgcccacc tcgggcagct aacttttcag taggcacttc    7080
cttccttgca gttgacccttt tatccttaga atgctcttca gccctattgg tgaagcagaa    7140
cagtcattca taagtgttgt aaaataaagc tttagagtct tgttgctaag tagagatact    7200
tagaattgcc tcttatgtgt aggcctatag ttctttcaac atgagatttt gatagagaaa    7260
tttgtaagaa tgactactgt gtagttgggg aggagctaag atcagcatgt acctggtagt    7320
tacttgggtc ttagtatttc atctagaaat agccactagc aaggaaaaac ttagtggtct    7380
gctcttaact gctagtattt aagtctgtag tattgctggg aagaagtact agttacttga    7440
tcattcaaac ctaaatgttc ttcttttcaa aggtccatga gaaacaagat gacttgggca    7500
aaggtggaaa tgaagaaagt acaaagactg gaaatgctgg gagccgcttg gcctgtggag    7560
tgattgggat tgcgcagtaa acattccctg tgtggtctga gtctcagact catctgctac    7620
cctcaaacca ttaaactgta atctgaagag ttgtaactgt gtgactcctt tgactgggct    7680
aaggacagca atgacagctg atggagactg tgtacaactc actgaattca aatctgtttc    7740
tgtgcctttc catattttgc cagactacac aggtgataag ctgaaattct catttgagcc    7800
tgttagtaaa tatgtgtggc acttattttg agcctattaa tgtgtacaaa aaaaaatttt    7860
aagttagctc tatacattga gcatcaataa cagactcaat gatgctaact catagtattt    7920
cattttgaaa gtgttttatg tgataccatc aaaatggtgg gtggtagccc aaacaaaatt    7980
tgagcagaaa atttctgccc cttatcaga gaaattattg aaagctctca agattcagag    8040
tacttaacct tatattttaa aattgtatta ggattagatg tcatgattta agaaaaagcc    8100
ctttagtaaa cttgtatcaa actcatagaa ggcaaacatg gagcctcagc tagctctact    8160
agccaagtga agttggtacc acccatcttt aaggttggca ctcagggaaa acacaatagc    8220
tcggggaatg acaccaagtt tgactggagg ttctggctaa atcgactttt atagcccag    8280
gtaatgaaat tgagtgcctt aatacccaag aaagagtgcc tttgaaagga atattaaca    8340
ggcttgtgac tatctgaaat agttcaattg aagtattttc aacaaattgg gtgtaaacca    8400
tagttctcac tgatatactg aagtcactga agaagagaca actaaattgg aaaagcacat    8460
aatttggtgt ttccaacctt aaaattttta agtttagatt tccaatctaa gattgctcat    8520
aatgcttttt caagtagtta tgttgaagtt ccaggtaaat cctatgtaac tgatttcctt    8580
aatgtagttt tgatgtgggg gatgactcaa tgcggattaa cttggtaatc acaaaccatt    8640
tagtggctca cgtctcagta tttttagttg gaaagacaag ctgcaagtct gtccttggaa    8700
tctgacattg gatcatcgtc ggatgcatgt tttatgatac tctaataagg acttaaaagc    8760
ctaagtaggg tcaccagaaa gctgaagcct ggcaaagcta cagacacatt tcttccatca    8820
ttaggaagag ctcagatcta aatgtcaaat gggaacatac aaaaaggaac ttctaggtac    8880
gataaagcta agtttgacaa gttttttgtt taacctagca ccttgtagtt ttaaaaatca    8940
ttttttagggt gtgtgcacta agaggaaaac aagttcatat tcttccacct tttattgtcc    9000
c                                                                    9001
```

```
<210> SEQ ID NO 5
<211> LENGTH: 66001
<212> TYPE: DNA
<213> ORGANISM: Mus musculus

<400> SEQUENCE: 5
ggccttggcc tcactgagga aggaagtcac cccatgcctc agggtttttt tttttttttt      60
tttttttttt tttttttttt ttggctgtaa cacgaagcat ttagaattaa aggcttaaag     120
gctctggctg tggtctgaga acgagctaac tgggcactgg gcagagcagg gaaagacaga     180
gtccctacca ccctgctggt atcctgagtg gggttcatgg ccaaagaacg cataactgag     240
ctcaactgag ctggtggtgt ctctgggtga taaggaagag tcagcagaga gcatagccgc     300
caggcagtct gataagcccc tcgaacacat tcctggatgg agtcaggggc ccagcgcgtg     360 tctgggcct ggagtttga gtggagggta tgcttaaggc ctcgagggac acagaattct      420
gtacgaaggg tgtgcaaagg tcccgggaga catggaattc cgagggaca gtgtgcaaag     480 gccacgaggg acacagaatg gagggtgtgc aaaagcccaa agggatatgg aattccgagt     540
gggggaagtg caagggccc cgagggacac ggaattttga gtggagggcg ttcatggccc     600
agaggctggc ccgggctgac tgcaactgat tttaatgcag gggagcggga ggcattcgca     660
ggagtccgga agaaagaaga ggtcgcaggg gcggggtag tggatgcaga cggtgccagg      720
gtcttctgcc ctctgtagag ggcacatcgg ttcccaccta gaccagcaac caccaggaaa     780
gcccagcagc tcggagggc ggcgcccaaa ggaagccacg cccacgcctc accatcagag     840
caccgcccac tccccgcctc ttcccacccc tcgccggaat cccgcgccga actcgggggc     900
gggctgcccg ggccatggcg cataaagcct ctggccacct gcagggctac tgctgctccg     960
gccaccgcca ggcacacacc ttgctgctga gggagtctcg gcttctgtca tctctgtggc    1020
ctccgtcacc tctgtctccg tctccttcag gtcctgagcc ccgagagccc cttccgcgca    1080
cgcggacatg ggcggcagct ccagggcgcg ctgggtggcc ttggggttgg gcgccctggg    1140
gctgctgttt gctgcgctcg gcgttgtcat gatcctcatg gtgccctccc tcatcaagca    1200
gcaggtgctc aaggtgagtg aagtgtcttg gggagatggg ggttgggat cgggacgcag     1260 ggtgggacgg tggagctacc tcctcaccac cagggaggcc caggctcacc ccagaggctt    1320
ggtctgagtc accagcgtcc caggagccta aacctcactg aagcagaagt atggcctggt    1380
tgtccctgag tttcgactgt agctgtcgcg acctccagcc cttctgaacg cgccggccgg    1440
tgactgtacc tagtaacctc agagctgcgc gaaaccctg tacatctgtg aggctcccac      1500
gggctccagt tctttgggtg ctctgcctgt ttcctcccgc ccagatgccc cagagatgcc    1560
ctggctcgcc cccacactgc ctgccagtct cgagagttaa gctgctttct gccccccacg    1620
ctctggcaga ggtagacacg actcaggtct gccgaggata ggcagcccag cctctcccctt   1680 gatctcagcc ttaggccctg ttttgccctt tcaaccgggc accgatatta ggcgggtggt    1740
gccggtccag ccacagactc tgccctggga tccgtgtcc ttctatttga gccgggagct     1800
cattaagtcc tggagattac cgagtaattg tgttttctga gacgcagggt tactgcggaa    1860
ggggaaacgg gggctggctc tcagggaaca tccagttaga actggatctg ggatccagaa    1920
ggggctgttg tcacagggtt tgactgacat ctttcctctt agcgggtttg tttactggga    1980
gtttaagaat ggcttcgtgt cccatgtccc atcgcccgct gaaaggaggg aatgaatgag    2040
ggatactccc tcttgggctg gccgctacct gccaggtcct ggcgggtctt caggatggag    2100
ccacaggtgg cttttcctgga gttgtggtgg gtatttccga gttctcttgg ccacactgtc   2160
```

```
atttctcttg cttagaattt tcaacccttg tacatgaagg tcccaggagt tgccctgtct    2220
tgggtagagg gaagatcctt cttgttggag catcagaatt gctctgggcc tttctgttag    2280
gtttggcaaa gtagtggtga cagccttgtc tcagtggcag cctgtggttt cagtaagaac    2340
ccagccctgt gcactccgca cgtggactgg gtttcctgct cagccagcct gtagtgggta    2400
gagtgagcag atatcccctg ttcttcgatt tgggggtgag ggggaatctg agctggttcc    2460
ttctcaaact ccttcggga atgttttctt tggggttg gcacagagac taaggatggg    2520
gggggttggt gtgtgtgggc gtgcacgtta gcgttgggac tgcgcaggcc tgctccatca    2580
gtcagggtcc catctgcccg tgcttgagaa agaccacgac tggcagaatt gccccatagc    2640
tggtagcttg gggcttcacg tttgagcgag cggcttccac aatcttactt gtgaaaatcc    2700
caaaggcgat tggttggggg ctgagtggcg tgaaggaagg aagagcctaa gacacgccta    2760
gcccaaaaca gcctcttctt agaggccctg gctggaagcc gacctcttga gggaggaaaa    2820
aaaagttcac ttcaggggat ggtgggagga tggcagcgag gggagcaggg agggaccctg    2880
gagttgactt tggattcttg cgttctgtgc tacttgaatg gaagccttgt ctttgtgtgt    2940
gtgtgtgtgt gtgtgtgtgt gtgtgtgttt cttcttcc ttttttttt tttttgtaa    3000
gttaaagaag ttgatttata aaagtcagga atactaggtt gtttaagaaa acaagttcag    3060
gacttggggt gtagctcagt ggtagagaac ttaccttgca ttcaacaggc cttgggttcc    3120
aacacacaca cacacacctt gcattcaacg gccttgggtt ccaacacaca cacacacaca    3180
gagagagaga gagagagaga gagagagaga gagagagaga gatttcactc ttattttctt    3240
ctgatgatat cattttttga cataaattgt gtgtgtgtgt gtgtgtgtgt gtgtaggtca    3300
cctgatttct tcccttacag atagggtctc ttgatgagct agacagccat cccctgtct    3360
ctggggttac aggtgcaatc ctatcgatgc acaatattgt atatgtcact gggagtttga    3420
actcaggtcc tcatgtttgc ctagcgtgga catcttttac aaaacccgag ttggatagta    3480
tgtggttttc ttcttttctt cctcctttct ttccttcctt tcttcttctt ttttctcctt    3540
tctcttgatt cgtggtctca ctagatagcc caggaactca gtgcatagtc caggctggcc    3600
tcaaactcag agatccacct acctttgcct cttgagtgtt aggattaaag gtctgtctac    3660
catgcctggc ttaaatagta tggttttcct gttcagtgtt agtattcaaa ggggtgtgtg    3720
tatgcctgtg tgtgtatgtg tgtatacacg cacacgtgta cacacacata catgcacgta    3780
tactcatgca cctgtatgga cgtgcttgcc acgcggtgag accagaggtt gaagtgcagt    3840
gtcttccaca gtgtctctcc accttattt tttgagacag gctctctcat taaatatgag    3900
gtgtgccttc tctgctagcc actgaacaac aggtccctgg aatctgcctg tctccgcctg    3960
tcctggtact gggggtccag acatgtatca gacgtgctca gctattttt tttctgcgtg    4020
tccctggcca tcctagaact ccctctgtag gctctccctg cctcctgagt gctgagacta    4080
aaggtatagg ccaccacccc tggctctgtg ttgagctttt gtttgggttt tgagaatcag    4140
aactcagatc ctccagcgag cactttaccc actgggcgat cttcccagcc cctttcaaag    4200
gttttgacag gccgaacatg ccaagtctgt tactgccttt tcccccctta ctgtgctggg    4260
attcctttgt ttacagttcc tctgttgact ggccatgtct ttgtctcaga ctccagagaa    4320
cacatagcgt cctgtgtgag tccaggaaca cttgcacggt ctgagcctta gctgtggacc    4380
cacaggtgcg ctctgtttgg aatttggaat tctctactat tgctcccgct gtcaagctgt    4440
gggaccatcc acttcgatgg caatgaagtg tcatttctaa accccatcac cctctttggc    4500
tacctgtggt tttgatttca catcttcagc gccacaaggt tgggcaggag gaacgtgatc    4560
```

-continued

```
cccgtgtagg tgacagtttt cagagctcag gggctcaggc ctactgtacc atgtgctagc    4620
tggagccggt tcatcactca agagagccaa gttttccccc cagcagtgag acaggggtca    4680
gatctggttt gctgtccctg agggattagc aagttgcaaa ggagattaca agcggccttt    4740
ggaaatgccc tgtgagcttg cctgcttctg gactcaatct aaccacggca gcgttgtgaa    4800
acaggcagag gctgcgaatt cttcctctct acagataagg gatctggccc atagcaaagg    4860
tcggcagctg gttattaaac atggcctgtg gtgggctggg agggacttca agcggccatg    4920
ctcggtttac cttccatagg gaagtaggaa gcaagcaaga gccctctctt tctgtacagt    4980
gagctgctgg gcagtccaag aaaagaatta agaagggcca ggtttcagga agacatgcat    5040
gatagaaaaa aggctctgtt actattaaag tccctcttcc ccagcctctt acccggcatc    5100
ccagctactt ggagtctgag gcaggaggaa tgaatattca aagccggagg aagttcagag    5160
cctgcctggg ttgcacagga agctcagggg agcttagtga gaccctgtc tttatatcaa     5220 atgtaagcaa ggtgcattag tgcatatttt taaatcccag cgctcagaag gcagaggcag    5280
gcagatctct gagtcaagtc aagtgcctgg atagccaggg ctatagagag agatcctgtc    5340
tcataaagaa acaaacacac aaataaataa cacataaata agtaagtaaa taaataaata    5400
ggtaagtgga aaactgaaga tagagctcac tgattgatag actgcttccc agtatgtgca    5460
catccctggg ttcaatcccc agcactgcaa aacataaaga gaaacacaca cacacacaca    5520
cacacacaca cacacacaca cacacaccaa aatccctcag ccagtcggtg gtcgcagcgg    5580
cggctcatac ctttaatccc agcactcggg aggcagagac agagtgatct ctgtgtcagc    5640
cagggttaca cagagaaacc ctgtctcaag acaaacaag tcaaccaacc aaccaaaccc     5700
aaaatgacaa gaatgacatc aaaaccctaa cagtattcta tattttcaac agactcgtgt    5760
tagtgccaaa atggtttaga aaaaggtgcg gaagggtgcg tgccagacac acaaggtaga    5820
taatgctggc tgcacgactc tctgtacatt tttgttttat tttatgtgta ggggtgtttt    5880
tcctgcatgt acctctgtgc atgcagtgcc cttgtagacc agacaggaca tcagatcctc    5940
tggaacttgg acttacagat ggttgtgagc caccatgagg gtgctaggaa tttcacgaac    6000
ccaggtcctg tatcagagcg gccagcctgg ctcttaacca ccgagcaatc tccaaaccat    6060
catgattctt tttgtaaaat attatgtgta tgtatttgtt ggtgtgtgag tggaggggtg    6120
gtgctgcaac atgcctatgc aggtcatggg acaactttga ggagtgattt ctctcctgct    6180
cctaagtggg gtcctaggga ttgaactcag gtcgtcaggc tgccgagccg tctcactgag    6240
cccaatggtt actatcttgt ttgtagttct ttagggcaag gtttcgttgt attactcagg    6300
ctttatttga aatcctcctg cctcagcttc ttgttcatca ctgttcatca tggaagggag    6360
tcagggcagg aactagaaca agggagggac ctggaggcag gagctggtgc agagaccatg    6420
gagggatgct gctacgaact ttctcttat gacttgctca gcttgctttc ttacagaacc     6480
gaggaccacc agctctgggg agaccccctcc cacaataggc cacgcccttc ccatcaatc    6540 actaattaag aaaatgttct acaggcttgc ccattgccca gtcttttttt ttttttttaa    6600
gatttactta tttatttaat gtatatgagt acaccgtagc tgtcttcaga cacaccagaa    6660
gagggcgtca gatctcatta cagatggtta tgagccacca tgtggttgct gggaattgaa    6720
ctcacgacct ctggaagaac agtcagtgct cctaaccact gagccatctc tccagccccc    6780
cccccccccc cccccagtct tatggaggaa tttgtcttaa ttgaggttac ctcctctcaa    6840
atgacaatag actgtgtcaa gttgacgcaa agctagccgg cacaggcagc gtggttgaca    6900
```

```
caggtccttg tcagttaagg aaacagctga aaatggtaag aagtaccccg tgactttctt    6960
ggagtgtgtg taagtgtcac acggagggaa acccaccagc cctggaaccc ctgtgtgtct    7020
cacctagaac ccagcctggc acgcggcttg cccgtccaca gggccaccgc cttcagcaca    7080
gagcctcata atcttttccca agtctgggtc tgcatcagct ccactgtcct gacgtggcat    7140
ttcctgttgc actgtgcgtg atctgttcat ctgctgatgc ctccctcctc tgtcccatgt    7200 gtccccttagg tgcaaagcgg aagcctcagg ctgccctcac ctgctccgtt gttctttctg    7260
ctacctcata cctgcttcac cattacccttt tatgacccct ctaccccat ggccttactg    7320 cctgcttgga cccgtgtggt agtctatcct gctcttctag tgagggatgg tgcccaccct    7380
gctcagactc tctaacattc ccgtcttttt ctgagtgaac cccaaattcc tctcagcagc    7440
ttgaaggctc ccaatttgtt tctctttccc accctcaatt cagcacccca ccccacacc     7500 actatgctcc tggtttgagc ccattagacc tagtccctct tcagaggccc tggcgtgtcc    7560
ctttggtggc acatgccttt aattcccagc acttggaagg cagagaggta ggtggatctc    7620
tgagttcaag gccagcctgg tctatagagt gggttttatg acagccaggg ctacacagag    7680
aaaccctgtc tcaaaacgcc ctatccccct aaaaaatga tttatttatt attttcagtg    7740
ttttgtctgt attcacgtgt gtggtgcttg aggagggtca aaagaggtgt caggattccc    7800
tggaactgtg acctgtcatg tgggtgctgg aaccgaact cagattctct atgggtgcag     7860
ccagtgcttg taaacctcgg agccatccct ccagcccacc atccttattc tgtcacaggc    7920
ttggatgtgg ctcgctcttt ttcctgattg agaagttggt cagccaggtg aagggctagg    7980
gagctgactg gatgctggcc aatagctggc tctctacccc tccttgcctc aattctaatc    8040
tgatcccttc tcccacagct aggagttggg ctagcctggg atatctactc tgttcctgag    8100
ttgttttgtg acctctggca gagcccattg gcttgacact tggaaggtgt ccctgatggc    8160
agatagctcc ttgtagatag atactgtgtt acgatgctcc tcagagcctt ttattaagta    8220
tctaaacgac tacagttgct ctctgcttca tctaggagga gggacacaaa gagagattaa    8280
gtaaaacttg tcccctggtg tcccatgtct ccccaccca accctctacc tccgcattcc     8340
agatttaggt gacagaacca agatgtagcc tctgctaaaa gattgtaacc cttgaacagc    8400
tggccttgac tggccgttcc ttcttttttct cccttctctt ccatcgatgt gcatggctag    8460
cgggtgtatt ccagggtttt ctcccacaag agaaggctgc agattcagca ccccttggta    8520
cctcctcagg aggactctta agtgggaagg tctgccttttt cccagtttgt accaccctgt    8580
gaccttggga tcaaggtctg cctgggccat cgtgggctgc tccccaagtg agactgggg    8640 ccccagatgt caggatgggt gtccctgcaa gttccctgtt ctctgggccc tgggtaagaa    8700
tgcttgggtg tgctgggatt tcttctgttt tcttcctctt tcctgatgcc tggtttccgg    8760
ttcccatggc ttccggtccc cctggcatgt gtggaactat tttagttccc ttcagggtgc    8820
agctgtggct atagactacc tatttttagt cccaagcatt tatttctgtt cctttctggc    8880
tcctcgtaca tccacaagtc ctcatagctt cagtgtgtgt gtctgttggt atacacacct    8940
tttggtgcgg gtccacgtaa tagtgtcccc caggtatagt agcacacaga cagagcttgg    9000
tgtatgtatg gtccagtgct gacatccatg gatgtgagtg tttctgtgta ccgcacgagc    9060
tacaacctat ccacatggag aaaagccagg aaggggatgc aggcacatgg gtcattgtct    9120
gggcccatgt agacacatgc acatatgttg atgcctgttc catttgctgg ggtgggcag    9180 tggacatggc tgcatggcag aatgatggcc ttcgaggtgc aagccactgg gctccgacct    9240
tagcactgca gcagacagaa ggggtcacgg gcactgcatg gtcactgtgt gcagtagtta    9300
```

-continued

```
ggtgctggta ttttgaagcc agactctcct gttgcattcc tggaaggaag ttaccctggg    9360
acccttcctg gaaggatgga ttctttgcta tcttcccaca gtgactcatc ccctcattcg    9420
ctccaattcc tggagttcgg ctaccaggaa tcctgttctc tggccttgga tcccagcagc    9480
cgactctggg gccagtcctg gagagagcca cttggttctc tgcagagctt atcctaggtg    9540
catcttggtt cctaggaggc ttggcccagg ctgccagctc tgtggccttc tgtggctttt    9600
agggtacaga ggagtattca aatgtccttc cttggccagc aaaagagagg ccctgggcta    9660
ccgtgagctt ctccccaggt tgccactgga tgtttgacat ttcactctta aggaccatga    9720
gttcagctga gaggccttct gaatgagaga gggggggggg agagagagag agagagagag    9780
agagagagag agagagagag agagaagaaa acatggatgc tcttgggtat agtggaggag    9840
aaggtttatt gtagataaaa gggagaacgg gagaacatag ctagaggcag agaccgctgg    9900
aagagtccag agtggacatg accttgaacc ctgagctaga tgaggggagg gggagggaaa    9960
aggagaggag agaggggagc caggtgcaac tgccaagaag gagggagggc aatcaaaatg   10020
gttggattat cctggggaga gtagcccagc cctctgggct atagagttca gggtaggggg   10080
cagggtatgc cagcctgaag gggttctgaa actggtaggg actgagggat gctgggagaa   10140
cgtggcagcc aggtctgctt tgatatgtta actagccacc taaccatttt gtgcagggtt   10200
tgaaactcaa taccttcagt gccagatcct gtgccatcaa tttagtttga ggaggattta   10260
gcctggcagg ggtgggtggg ggtgtaggtg gggctctgcc caaaatagaa acaggttagg   10320
aggctaaagc aggggattg ctagttctag gccagcctgg gctaccctcc ccccaaaata   10380
aataaaaaa attccataaa aatgaaaaac cagaaaacaa aaacacttga tccttttacc   10440
tctctcctct ctcctcactc tctccctcac tggtgacctt ggcctccact ggcctagggc   10500
agggtcaggc caggctgagc tacaaagaga aacaacaaca acaaaaaaac ccaggtctgg   10560
ctcagcctgg ctctgagtcc cagtggctga ggaggttcca tggctgccga gggaagattt   10620
ccacccctct cctcagatcc cgggcttct ggcctctccc cagctcccat ctcctctgct   10680
ttgtgatctt cagctgccta gggagggaa ggaataggag tgacctgacc cttgcttgct   10740
tcctggcttt tcaatgaagt tccttccacc ctctctggaa gcttctagaa aagggtcttg   10800
gctgggccct ctctggctgt gggttgtctc catggttctc gtggggcagg ggttctcttt   10860
ccccctttgc ctcagccaga ctctggtgga atatgcccag gcccaattca cagctcaggg   10920
ccttaacttc ccccccaacc cccccacccc caccccctgc tcagcccaa actgtcccct   10980
cctgggcctt gacctcaaag gagtctggtg tgccaggtgg ctcaactttt tcctgacctt   11040
ccccttcaac tccaggcctg tcccccttca ccttcctggt tagcttggcc tgtggtcttc   11100
tagcttgtgg cggcagcaag ccacgacctt ggcagcggcc ttcctcgcc ctctctgctt   11160
cccacacgtg agccctgggg aagtgagcgt ctcccacctt tttgtccgtt tcccgaggct   11220
gacttctgtc attttcttat ctggatcctt aaattccttt cctctgtctc ttgtgttcct   11280
cccagctccc agtacagcag ccagaaacag accctaggtc cttcccatgt gtcaagaggc   11340
cagtaccttg ccctctgata cctttctggc ttgcacaccc caccccttga ttcctctcgt   11400
gcgtgggcta ggtctatagt ctaatgtctg acatttccaa gtgggactcc gctgaggtca   11460
attcagaccc aatatgccac actagttaca tgtacattgg gcttttttcc ttctgccacg   11520
ttgtccccat ggggagtccc caggctcagg agggcaagga cctctgtggt gtttgttctt   11580
tgtccccagc gttggaactg atgccagaca ctgggccttg ggttcccaaa tgtttaccca   11640
```

```
aagtggacag ggtcgaatca cagggtgttc tggtaccctg gcactaggaa gtcctgtgcc   11700
aggctagacc atgggtgccg tggtgctact gtcctgccat gggtgatccg gctgatccgg   11760
cacttccccc tgtcacagac agagtgctct ttcgaagaca cagtgcttta gtttaaagct   11820
gtttcaggat ccagctaggt gagatgatgt ggatttgatc cccagagccc acgtcaaaca   11880
agctggtaat tccatccctg ggaggcaga  gacaggagac tccatggggc tcccgggatt    11940
cattcctgca acgcaactgg ggagctccag gctttagaaa gaatcgatct taaaaaaaaa   12000
gatagatagt gctggaggga gcacacctga ggttggattg gcctctggcc tctacatata   12060
tacatacaca cacacacaca cacacacaca cacacagaga gagagaggga gagagagaga   12120
cccacaccca cagaggcaga cagacagaca aacacacaca cccagagaga cagacagaca   12180
cacacaaaga gccaaacaca tacacccaca gagacacaca catagagaca tacatgcaca   12240
cagaggcata gagaaagata gacacacaca cacacacaca gagacggagg agagacatat   12300
agagacacac acacacacac acacacacac acagacacac atacaaagac agacagacag   12360
acagacagac acacgcacac actcactcac tcttgccccg atccatcagt cctttcttca   12420
caggctccaa cctgtctggc cagtcagcgg ttctgttcta agcccacaag tctctctcct   12480
cctccattct cacacgcgcc ggaagttcct tctgcccaga tacttttccc cttggctctt   12540
tcactcagtt cctctcctgt gtttcaaaat aaatgacacg tatttgtatt ttggggtgct   12600
tgggagggac acagagaggc actcatacta gacaagtgtt ctcacaccag tacacccaaa   12660
gcctgtgtgg ggatgttttt gaagacactt cctggtccca gcttccctga cctcccttga   12720
cctttggaag tttccttgcg cccatctcta gtgaactcat tcctttggtt gatgtcctac   12780
caggatgggg atctggtgtg ttttgtacat agctttactc ctgcagtggt ggcctggctg   12840
gggtgggacc ctagcagcca tcgctgaggt cacaagcctt gctgactgcc tctgctccat   12900
tggggggggg ggggctgtgc ctctgttttg cttttttgtt tttgtttttt tgttttgtt    12960 tttgttttg  ttttgtttt  ttttttttt   ttttttttgg ttttcgaga  cagggttct     13020 ctgtgtagcc ctggctgtcc tggaactcac tttgtagacc aggttggcct tgaactcaga   13080
aatctgcctg cctctgcctc ccgagtgctg ggattaaagg cgtgcgccac cactgcccag   13140
caagggctgt gcctctgtct ccaggggct  gcctcctgat gccactacct aagcctcaga   13200
ccatgagcct ctgtccctg  gatgccattt cttgaagcca cctgggtgag ttggtgttca   13260
tatgtcccag accacaccca ctggcccgag tctctggcag gtgaccctag atccagggtc   13320
tgagtctctg catgttttct cttgactcca gcaactcctc actggtgtct gtgccagggc   13380
tgctggcttc ccccagtaac ctcttcctgt cccaccacaa aggcagtgga ccagaaggaa   13440
gagacccagt tctcagccat gtcatcggga tggctgtggg cggtggataa ataaatcaca   13500
cctgtcttag ccaagggcgg gagagaccag gaggtggggt gcaggtttgc aatgcacggc   13560
cttcgggagt gaacgggagt cttcagcagc cttggtttga cgtggtccgt gtacagtcct   13620
ccgcagggga caagtttagg tttatgaata aagcgaagtc acttcctccc cggagttcca   13680
gataacctgc cccagtgcgg gatgcagtgc gggatgcagt gcgggatgca gtgcggggtg   13740
cagtggacag ctgctttctc ctgccagtga tctatataga aggacctggg aggtgtggct   13800
cacaggtgcg aagaacaaaa ataaactggg tgccattaca cacctgtaat cctggcattc   13860
cagaggcgaa aacaagagaa ccaggtgtta agtcatcctg actacagagg gaattggagg   13920
ccagccctgg ctaaagaggc tgtctaaagg gttcagtgag taatgcttgc caccaagcct   13980
gttgattggc gttcgatcct gggacccaca cagtggaaga aaagaacagg ctctttcaag   14040
```

```
ttgtcctctg accgctgtgg gtgtacctca ggcacattca cactcctcac acatacactc  14100
aaataacaaa tgcaaaaaac aataacaaat gcaaagcaat gacgttaagg gctgggagaa  14160
ggggcgggg cttggggctg tccattgcct ctgattggct taggtcacat gctcatgttt  14220
gagccaatca gtgtgtgtca agaaagcttt ctttggaaag aggcgctctc tctgaggact  14280
caggagggga tggagcgatg ttctatgggt tggcaggagg caagggagac aggtagccag  14340
agtaaggaca gaaccettgg cccctagtta gcaccggatc accccaggtt ccgctcgctg  14400
cctcttatgt acgtacatgg gtgcttttt tgacgctggc tccaggcttt tttgattggg  14460
gaggcagcgc gccagggtaa attttataaa tcttaggttg ttgggtcttc aagtacttac  14520
ttgggtttct ctcttttat tttatttcat tcttatcctc attgttattt tggttttttg  14580
aaacagggtt tctctatgta gtcctggctg gcctggaact tactttgtag accaggctgt  14640
cctcgaactc atagagatcc atctgcctct acctccctcc tgagtgctag gattagagta  14700
tttcaccacg cccagatttt gctacgggct acggctgctt ctgcttctcc ttcctattta  14760
ttattattat tattattatt attattatta ttattatttg aggcaggggc tcacactgta  14820
gcccaggctg gcctcacact tttggcaatc cttctgcctc tgcttcccaa atcctgggag  14880
taaagacatg tgccgtagtg cctggcccat ctttttgttt gttaaaatca catgtttgtt  14940
tatttgtgtg tattgtggag ggtaggggtg ccatatgtgt actacacatg tgtagagggc  15000
agaggacaac ttgcaagagt cagttttctt cttctaccat tatgcatggg gttgaactca  15060
ggcaggcttg gctgctgggg ctttattggc taagtcatct ctcctgccct catgcttttg  15120
tttttgtttt tattttgttt cttgagactg ggtttctctg tgtagccctg actgtcttag  15180
aactcaatca gtagaccagg ctggcctcga actcacagag atctgtctgc ctctgcctcc  15240
caagtgctgg aattaaatgt gtgtgccatc accgcccagc ttagcgcctg tgttttattt  15300
ttctctttaa ggacccagat ctcagaggga gctgtgatct gttcaaggcc atagttggta  15360
gccagtgtta gctggtcgtg ggccaggtta actgccaggc tggccgggga agtggggtgc  15420
tgggctaggg aaagataaga gatctcggta agtgagggct agtcatgttg ttttctggtg  15480
acttcgggca gtctcccagc tccctcccac ctacctcttc tttgctctca tctgactgta  15540
ggagtgggag gaggtgtttt gataaagtag gagagatgtc aggacccggt ataccaaagt  15600
tcaagctcta tgcgccttct ctgaggctct gagtgcgccg taggatgcaa acagcgagaa  15660
ccagcccaag cctccgcgcc cttcactaca ctcggcatca ggctcagatg cagaggaggt  15720
aatctgctct ggacgtgttc tgcaatatag ctcaggagtc ggctcacgcc ccagacagag  15780
cagctgttgg ctcttaccca agactctgag gtacgccatg tccttctgga gcagtatggg  15840
gactgaagct gagcttctgc tagtgtctct ttgtaagccg agctgggctc tctggctacc  15900
cacatgtttg ccgtctgcct ggaggagagg tgggaggtga gtgtgttcct ggagggtcac  15960
tgccaaggtt gtaaacccat tggaaagtct ctgggcttga gccttgcggg ggatggctct  16020
gccaattccc tgctgggtaa cctcgggcaa gtgccttaat tcctctgtgc cttttcaccg  16080
tgttcttaat agtgtcctgt gtctgaggag atcatacctg ttaaacacct agaataacaa  16140
gctgctgagt atcgctcagt atgctgatgc acacatcctc ggggacctgt catcaatgct  16200
tgcaactgac ttctcttcta catcctgctc tgagatgtca cagggcatgc tcatggcaca  16260
cccagctttc ccaccagcct taagagtggc tgggatgtc tcaagactga ttctgcagtt  16320
gcccaagtac cttgctggct agccatgtcc cagtaaactc agccaccggc tgttctccct  16380
```

```
ccccacgtct aggttttcct tttaaaaatt attgttttgg aaaaatcgct gacacaatgg   16440
gacagtgggt cacattggca ctcacccaaa cctcttggcc ctgcagagaa tgtgcgtaga   16500
cctctgttag agtcaaggtc acttatcctc ctgcccacag cctgcagcta caggctggcc   16560
cctgtgtgtg aggcctctgc ctccagctct gtccttttc cattcaaatc tgtcttactt    16620 atttctgcc agggtaggaa ctgaacctgg ggtctcctgc ttgatgtgcc atatccccag    16680
tcctttctcc ttaaaaacct ttttacactt acttatttaa agatttttt ttaaattat     16740 gtgtctttgt gtgggtatgt gcacatgagt gcaggtgcct gtggaggcca catgaaggcg    16800
ccagatcccc tggagcaaga gttctagtga gccacctgac tatagggtac tggaaatgga   16860
acttagggtc tctgcaatag cactccatgc ttttaactgc taagcggtct ctctggccct    16920
tatttttgtt tgtttgtttg tttgtttgta tagcgattag aggacatccc tagtttgtca    16980 gttcccttt ctgtcatgtt gacagcaagc acctttactt gctgagccat tttgaaagcc     17040 caactcttc ctaatattat tattaaagtt agtctcacta agtgtcccag gctagccttg      17100
gatgttcagt cctcctgctt tagcctgggg tggcaggctt gcccacagag tccatattg     17160 gttgtagctg ttaagtttag aggtttgtcc tgtgtggatc tccttcctcc tatcagtggt    17220
acaaccaggc ctctcttgcc acctgttctg caagccttgt ttcccaggag ctgatggcca   17280
ccttctaggc agggcgccct ggttgtggtt gctatgtgct cttcccacag accctgcaca    17340
taaactgcct agggttatcc tggctgagca ggcagtgcga gcagcgggc ttagagttc     17400 ttgcaccagc ttctgcttga gtttcctggc tttcccagcc ccacctccat gttcggagag   17460
gtgttgatcc ctctgacgac caggctgagg ccagctcagg gctcccaccc accettgcag   17520 ctgtaggagt cctggcatgt cagagctggc cttctggagt tggaggccca ggaaggtggg    17580
acctgggggc tcatcctgct ctgctcccta ccgccacccc aacccccatc ctgacctctg    17640
agccctgcag aaattctaag ccctggccct ggtcccctca tctggcctct tagcccagga   17700
ggctcccctg ggctgagagc ccatcttagc cagtgctcca ttgtagctgg ggtcctgacc   17760
tgcgctggcc tcgggatctc cttctcctgt ctgttcccag ccctcactgt gcctcttgcg    17820
cttcctttct tattattgtg aaatagtaca aagttctaac aaaggtcata atacacatcc    17880
gtcaggttaa atcagcccca ggtgaaaaga tggagcctca tggtcccgag gccctgctgg    17940
agggagccac cacccttggg tgctccttgc cttttgtaga accatcccta tatatccgac    18000
ttggtctggt tttgaacttc ctttagtgtc tacaaactct gactttattg ctgtggcatt    18060
ttgctttcgt tgctttgttt gtttgtttgt ttggagacca agcctgctct gtagctcaga    18120
ctaacctggt atcagtcttt ctgtctcagt ctctggcatg caaggcccac agatgcgcac    18180
cgccaagcct gaccacattt gcatcctggc tgtggcccgt ttttttcaag ttcatctatg     18240
taatagcgta tacctgtgcc tcctaactct ctgtgactga acaatgtttt gtgtgtgtgt   18300
gcggttttta atggtataga tgtcacattg tgtttatctg tctttagccg gtggcagcag   18360
gtagctagtg gctcttgtgg gtgtggggag cgtggtgctg tggggtgtgg acacatgctc   18420
acttgtcatg tcctctctct ctccttccct gtctcctcct gtcagtgtct ccctctgtgg    18480
ctcatcctct ctctggcttc gatcttgagt acgttcttcc atctgcttca gtcccatcca   18540
tccacatcac tgtgggtgag agcttacgtt ccgaggcctt gggctggggt ccaggtgttg    18600
gctcagcctt ctcccagcta tgtgacctag tgccattggc tcacctctct gccttaggtg    18660
acttgcttta ccaggccatc atcgtgaaag gccatcagct gtgtgactta agcaacatcc   18720 gcttccttc tggctcttct ggaggctgca tgcccttggc tgccatggct gctcctgctg    18780
```

```
tctagcttgc agccactgcc tgcctttccc tgtctccctg ctgctatcct cagtatctct    18840
ctcctagctc ttcttgctgt agactccggt cacaccgcat cagggaccat cctgactaat    18900
ttattgcctc cttttttttt tttaacctac tgtggcccca tcatgggctc tgaatccagt    18960
acattccaat acagtttgag gcatgggggt ggggtagaca ggtgggagtg gttcggcacc    19020
tggaacgctt caggcaatga cgctatgtgg acaccttgaa atcagagtct ctgtgattag    19080
tggctgggac ccttgaaaga ctgggtcttg tgggaatgaa gaggtgccct ggagtagcca    19140
tgcagtaagc agttgctagg gatggggtgg ggtcacacag ctgcctttga gtcatccgtg    19200
cttctataag tgacccagt atcattgctg caccccatct gatgggccag aatctcctct     19260
taggtcaggt gtcactttgg ggtgaataga aagagtctca aggaaaaatc acacaagaac    19320
agggggtttg ctgggcagtg gtggtggcgc acgcctttaa tcccagcact gggaggcag     19380
aggcaggtgg atttcagagt tcgaggccag cctggtctac agagtgagtt ccaggacagg    19440
cagggctata cagagaaacc ctgtctcaaa aaaccacccc ccccaaaaaa aacccaaaaa    19500
aaaaccccag ggggttttat gtttattttg tttatgtatt tacttgtgtg tgtacgtgca    19560
catgtatgtt tgtgtgtgtg tgcatgagtt tttgcgtatg cacgagtgtg tgtgtgtgtg    19620
tgtgtgtgtg catacagacc tacagaccca aagatgacat caggtgtctt cttttctgt    19680
cattttctgt gggaataaag gtagattcta gtattctggt tacagtgtcc agggaggtgg    19740
tggcatatcc cagcactggc caatcactta gccaggtgtt accatcttat ctgggttgcc    19800
cgtgtgcata tctggctcct ggctccttgc tgttgcctgg tctccctgtt taatgtctgt    19860
gagagcttgt ctgttaccat ggtgacagat gccctggttt ttccaactct atcaaccata    19920
tacagcatac gcaacacact tcctgggacc tgccacattg ggtggcttca gattggtccc    19980
tgggatgttt gagtaggcag ctggctgcct actgttagca ggctggttac acaagtgtcc    20040
attcaccctc tcagagttct gtgtgaccag ccttcttgaa gaagacgacc tgtgggtgtt    20100
tcagtttgca tttctgaggt gtgtgtgtgt gtgtgtgtgt gtgtgagcat acatctatga    20160
gtgtgtgtat atgtgtaggt gggtgcattt ctgtgtactt gtggatacca gagtctaggt    20220
tgggtgttct cccccatgat tctcaagttt gcatgtttgt ttattctgag gcaagctctt    20280
attgtgtagt gtaggctgac caggaactca ctgtgtagat caggctagcc tcggaactca    20340
ctatgtagat caggctagcc tcgaacttac agagatgcac ctgccttttc ctcctaagtg    20400
ctgggattaa tggcatgcac caccacactt gatcgtaaat tatgtgtgtg tatataaatt    20460
atatatttat ataaatctac aaaatgtata ctatatttat gttatatata tttatatata    20520
taagtaaatg tatatttggt ggtgccggag tttgagccca gagcttcgta ggtgctagtt    20580
aagctctctg ccactctcct acctcccatg ccagtttatt tatttattta tttatttatt    20640
tatttattat ttatagattt atctttagat ttatttattt tatgtaagta cactgtagct    20700
gtcttcagac actccagaag agggcgtcag atctcattac ggatgggtgt gagccatgtg    20760
gttgctggga tttgaactca ggaccttcag aagggcagtc agtgctctta cctgctgagc    20820
cacctctcca gccctgccag tttatttttg actcagggtc tctcactgaa tctgagctt    20880
gctgattgtc tagactgtct gaccatcaag cttcaggaac cctccttctt ccactgatcc    20940
caatgcccag agtgctgtag ttatagacct gtatgtctgg gtttgatgac ccacttggct    21000
ttttcatggg tgctggggcg agggtccgca ctcgggtcct cagcttgaac ggctggtact    21060
tgtgtctaga gccgtctgtg cagcctgctg agcctcgctg gcttgtgagt aaggctctga    21120
```

```
gaacttgaag gactttaaca ggctaacctg aggtttgggc ttcacttctt cagagcattt   21180
gtgttgcgct gagcatgtgg ctcactttgt agctgcttgc ctggcacaca cgaggccccg   21240
ggggcagccc ccaggacccc atgaacttta tatgatggtc cctatctgtc atctcagatt   21300
ctgcttggct actctaggga gtaggaagcc aatctgggct agagagacac tggcccccaa   21360
aaaggaatct gtgatgaagg tcatggggct caggagtgtc tgcatcttgc ctgggatgac   21420
agtttgatag aggccagcag aaacgtcccg ccaagggcta gaggccaagg acagtctgt    21480
cccatcacca gagctgaaat cagggtgtgt ttctttcagt ggtggtgccc cagcctccta   21540
gagaggcctg tgttagtcac ctaggtctaa acttgtgtcc ttaagccgtg gaacttcat    21600
ggctaggctg ggcgcttcta gtgtcttgag ggctcttggc tctctccatt cctggaggtg   21660
ttcaccgttc ctcagttgac ggcatcaatg ctcctgtttc tgtctctatc tctgtctcaa   21720
cgtggcctcc tttgtatttt ccatttcctc ttcaaaactg agttattagt attatttatg   21780
tgtatgtgca tatgcctgca tgagtttatg tgcatagcat gcgtgcttgg tccccatgaa   21840
ggccggagga catcagagcc cctggacctg agttacaga tagtgtgagc caccacgtag    21900
ctgctgggaa ccgaacaccg atgcctgcat ccatcgagcc atctttccag ctcccctgct   21960
cttctttgag acccaaccta agtccaaaca ctttgacatt cattcctatt ttgagttaag   22020
agtctcaccg tgcagcccag gcaggcttta aattcacaat cctcctgcct cagcttccca   22080
agtgctgaag tgacaggcct gtgccactgc gctgatctga tatttttaac ttgacatctg   22140
gccagaccct atttccgatt aaggtcacac agggcacagt caagtatctt aggatcacca   22200
cctacataga tgcatggcag agtacctttt gcccagacag cccctactgt gaaaataaac   22260
tacaggacaa aaatcaccag tctgtcctga tagccggctc tcagcacttg aaggtaggaa   22320
gcaagaggat cagaagttca aggtcatctc tgctaatagt gagtttgaag ccagtccaga   22380
ggggaatgac cctctgggaa gacaaaggtg acatgacact cgcgtccccc agcgtcccaa   22440
gcacagaggt aactttggtt catggctctt tgttccttgc tgcaaaaaac atgtttgtgt   22500
ttagaagagc ccctccctgc cctccctggc ctccctctcc tggccccgg tacccgtgcg    22560
cacttcctgc actttgcagt ctcggattgg gcactcagat ggctctgggt ctccccttc    22620
tttccagagc gctggaggga tcagccgtgt ttcccatcag ccaaggccgc ggggaatggc   22680
tgtgcattca atagcatgtc tctgggaaat tgggcctatt ccagcaccat cttcccgtgt   22740
cttccggagc tttctcagga gatatatttg tttctacaga cgccactaat tactcctggc   22800
tgggtgcctg gaaatcacat ctgtggatta aggtgccacc agatctgagc ttcctctagg   22860
gccccaggag tcctgacata tcccccattc agcatacttg ctcgcttgct tgcttgagct   22920
cagtttgatt tctccactca tacagcccag gaccccttgc ctagggaatg gggccgccaa   22980
tggtggacta ggtcttctca ggtcagataa gctaatcatt tagacaatcc ccacaggcca   23040
atccaaatgt aggcaggccg tccttcactg agaccctctt cccagggaa tctacgttgt     23100
gtcaggttgc cagagctaac cgctgcaagg ttataatttt aaaggacaag acacatcatt   23160
gggcgtgctt agctcaaagt tgtggcttaa gtacgtaaaa gagtaaaggt taatcaacac   23220
agaatttggt ccccgaagtc acttgccgtg tttagtcacc ctcagagctt cacagtaaga   23280
actttttctca aagaaaaaaa aaaaaagaac agccgggcag tggtgtcgca tgtctttaat   23340
cccagcactt gagaggctca tatttctgag ttcaaggcca gcctggtcta ccctccaggt   23400
accatgctgt gtgaggtcca ggcaagctca ccagatccag atccgctccc atctactgag   23460
gtccactcaa ggcatttct gcaagtggag gctcacaggc actgaggtag aggtacccgt    23520
```

```
gtgaggccag atgagtgaac cttgactcaa atccccatgt ccaggaactt gctgtgcatc   23580
aagatggcag gatttatgtg gcagccctg gcagagctgt cccttaagg atcttgatct    23640 ttagaccatc tcctctctgg atggtcatct ctggtgtgtg gctgagggca agaacttgat   23700
tccttgcgcc tttggtttcc tgcttgtcag tggggctggg gctgagagag ataaatgggg   23760
atcattgggg aatcagagag gtgttgccgg gatcggatcc agctgctggc tggcatgggt   23820
agcaaggtgg ccaattcaaa tcgacagtga agagggccag agagacggct catcacgggg   23880
aagggttctt gctgctaagc ctagtaaccg gaattggatc tctggaaccc acatggtgga   23940
aggacagaca gactcctata agttatctat cctctggctt ccacacgtgt gctgtggtgc   24000
atctgtgcct gtgcacataa taaataaata cacaaataag taaatgtgat ttaaaaaaat   24060
aattgaaagg gtctaagaag tgtcctgtgt tttctgtaat tctccactaa gtttatggcc   24120
gatggccgta tggagtagaa tggaggaggc gggcccaggt ctagcttccg actcagtcag   24180
ggtctcatct cccaaggact cagtttcccg gtctgcagag tggttggtgt taattcctgt   24240
atccagttgt caggacttag gggtcagccc acctacctat aaggctgttg tctggggtgg   24300
gagtcattga tgatgatgaa ggtgtccccg gggacctctc acacaagggg acgagtcaaa   24360
gaaaggtgag gagaagaggc cagccaggga aatggccatg gctgtgggcg ggaggctgca   24420
gtggactgag cagcctggcc ttcgaggtct ccccacagct gaccttccca gtctgggctt   24480
tcatggtgtg tggtccagga gcagataagt ggaccgagct atcagcagtc agggtcaccg   24540
agtcctcatg tggaagtgga ggcgggggag aaggggaagg gagatataga atgggctttg   24600
tttcaaggta gaggccaatg gagagccatt gtggaagaac cctatatgta tagcctggcc   24660
tcagagagtg ccattgcccc ctacccagac ccacagcggg gtctagctga gctctggctg   24720
aaaaaaaaaa ccaaaacccc ccaaacaaca ataacaacac aaaacctgtg ggattggaag   24780
gtgcctgtct cctagcagct gggatacccca caaactccag ctctaagtgt cgatttaaga   24840
cacttggtgc cttaagtcac ctccaggtgt cttttcagtcc caccaaaacc ttggggatta   24900
ttgatctggc agatgggaca gacacagagg agcagggtag agaggaggag gagtctgagg   24960
ctcttctggg gaagcaggtg ttccctcttc ctgttgagct gactgccccg ttgcatgctg   25020 ggccccctccc aggccctgga gttgcatggt gggcagagaa acagggtctt gatggactgt   25080
ctgcaggact tgacacctgc acaagagggg cagtgtgact ggcctgtggt gagtgtggct   25140
aacaaggcca ctggtgaggg aggggcctct ggtgctgagg agaagcaggc ccctctgagg   25200
gccaggcaag gagcatttcc acctgacaga aaacgaaatg agtatccgaa gtagtttaca   25260
ggtggtgaga gccctggagc agatagatgc tcaggacacc tgtcactggg ctgcaggttg   25320
ctgaaggtca aaggtcgtgc aaacccacaa ggacagcctc tgttgaactt agtaggtcgt   25380
aggtgatgtt gctggtactg taaaagggtg cagctgccat gagaagctgg tgtcaggtca   25440
ctgtcccgtg cagccgtcct cctggggagt ctggacacca cacaacagct gaaggtagaa   25500
gggtcccaat acttagtgat gctggatggg cagataggaa aagcagatga aatacagaga   25560
ggtgagctgg agagggtttc agaggtcagg agctcacatg gctcttccaa aggaccagag   25620
ttcagttccc tgcacccaca tcaggcgagt cacagctact tgtaatatca gctccaggag   25680
atctgacacc cttctgggag cctctttagg gactgtgctc atgtgcacag agcaacacac   25740
acattaataa aattaagatt aaatcttcag aaatgaaaag agggctctcc aagagggaat   25800
agtatgcagc cgtataaagg aagagagaga ttccatttat ttatttattt atttatttat   25860
```

```
ctatctatct atctggagac agggtttcat tatatagtcc ccaggtaaat agttcaaact  25920
cgtggtcctc ctgcctcagc tttaaagtcc tgcgatagct gctgcagagg agagaattct  25980
cccacacact ggaacatgga tgaatgctga agttagattc tgagagacgg caggatggtt  26040
gcagcgtgat ttcgtttact ggggcccta gagtacctat tgatgaggtt ggagaaatgg  26100
gacactaagg aggtagtggg aggggaaagg ggccagggag agtgttaagt ggagacaggg  26160
tctcagaagg acatggaagg gcgtggccat tggtggggac agttgcccaa gccatgggtg  26220
tacttaacac catcagaatg gatgctataa aatggcactg cctttaatcc tagcagtgga  26280
agcagaggca ggcagatctc tgagttcaag accagcttgg tctacagatg gcgttccaag  26340
acagctgagg ctacagagaa accatgtctg gggttggggg cttggggga gagtgacaaa  26400
acaaacccca agtctggaga ctttagcatg ataaaaatga ataaatcatt atggctgatg  26460
tcccctgaag ggacatgggt cacagccctc cttactctgg tttgtaaaag ggggacccag  26520
tggccatagt gactatgttc cagcctgatg agtgtcttag aaaaaaccca gttccctgga  26580
aatatggccc tgagctgata gctgatgctg gctgccactg cccttcctct gaggtttggc  26640
agggctctgg gattgttctt gaaccccagc cagtctacag ctggaggctc tgtgatatgt  26700
cttccttgaa gtgtctggga gttggtatct tcctagggac agccttgtgc cccaggctat  26760
tgcatgcagt gccactggaa ggagccctaa ggggaccagg caacagcctg gggattaggc  26820
tgtagagacc tgaggatggg gcccctggcc aaccccaacg gccttgtgtg gcactggctc  26880
aatggagaac tcacacgttt ctaatgtctg tagctgctac tgaaagcatt ctctagaagt  26940
ctcccaaaga cttctcactc agtctaaagt cagggctacc ttccctgtat ggttgggctc  27000
tacccaacag gtgaaccaca tgtgtttcta gaggggtagg aggcagagag gccttgggtg  27060
ggcaacaagg taatctgctt ctgtgtcaat ttcttatctg gcatgtggct gtcgagaagc  27120
agagaccgga ggatcatggg catgagctat acactgaggt ccaggctagc ctgggtgaca  27180
taacctgtca gaaaaactac aagaaaagat tcgcattcac catctggctt ggaccttggt  27240
taagtgataa ccattgtcat tagcctgaca cttaggcgcc aggatcaaga aacaagaact  27300
cccagaatcc tttggggcac cagaaagcct ttcattttga gataggctct ggctgtgtct  27360
ctggctctcg tggaagtcac acagcaatcc ctttgcctta gcctaagtgc agagattgta  27420
gacgtgagtt atactagcct cctctgcatg gattggcttg acctaaactg agctgggctc  27480
tccatcgact tgcttctgcg atttcagagt ggcagcctga cctagctctg cagtggcttg  27540
gtgcagctca gcctgaggct ggtgagatgc ttacaagtca tagctggttg ctgcttggtg  27600
ctggtggtca tgttatgagc aaactggtcc ctggtcagtg ggctccggat tagggctgtg  27660
atggaggcct ctaggaatct cgctaagtct ctcactggtt gttttcatct ctctgagcga  27720
tgtgtaggat tgagtgacag atggcagata attgggagtg ggtgacaggc ttcagtattc  27780
tactttaatg gctgttaccc ggtgatgccg gcataggcgt ctgatgctct gagtacttcc  27840
tctcatgtcc ctgagtcatg cagacttagg aggcctcttc tccactcaca accgtttccc  27900
tgagggcaga atccagttcg gttaactttg cttcgtagta ctaaatacca gtttggggcc  27960
tcgacagtgc gggggagtgg ggcgggttag aatgaaaaaa aaaggagcaa acaggttcat  28020
taacagctaa atgaatgaat gactgatgaa aggatgaatg aatgaagtgt tctcagcctg  28080
tgctgttctg ggtcagggct gagtgggaat gtcaaagggt gtggccacta tgtgagccat  28140
ggagttgggg ttagagggaa ggctgcctgt gggctgcacc agtgttgggg tgcaacccctt  28200
gttgggcagc acctagtttt ccaaagggag tcagaaacga ggcttttgag actaaccttg  28260
```

```
gttatgtctg acagggtttg ggggtggggt gggcacatag acactcttgc tttttgtttg   28320 tttcctttc ttttctgggg agtgtgtggt gtcaacttga cagggtctag aatcaccttg   28380
gagacaaatc tctggatgtg tctgtgatgg agccatccta actgctggag cagagaaaaa   28440
ggagaaagat cctagcagtc attcacccct ccctgcttcc tgactgtgga cacagcctgg   28500
caagctgccc ctggcttctt cctctattgc cttcaccacca agatggactg cggctttgat   28560
cagtgagcca gattagcctt ccttaagctg cttctgtcct acgtatgtat gtatgtatgt   28620
atgtatgcat gtatgtatgt atgtagcaag ccaggggcct gtgcacatac cacacaagtg   28680
ctccgatgtt agcatttggc ccttgagact tgagcgttgg agtttctatc gagtctggga   28740
aaattactgc acaccagaag cctgttaaac agtaacaggc cccagagcga gagccaacct   28800
cacacgcctc ccgtaagctt ctcccactga cagctgtctg tgggccagac acggttgata   28860
tgcgcacctg ctccctggtc agcatggtag gggttctcct ctgagggact ttattggggt   28920
agcccttggg agcagaagga atatggtccg gggattgaca tacacatagg tgcccacgtg   28980
tttgcgtcca gtccagtcca accagggagc ttcctaagaa ccctggagtg gctctcactc   29040
cacttgtctc cagggaaact cactaggtcc tgatgttgcc ctagaggatg ctgggacctt   29100
ctgatggagc caccttagcc ctctttcctg gggctctgac ttttatagct ggacaggctc   29160
tctgctttgt caagctgggg tcaaagtgag gtcacaaggc ttataccttg aggacacctt   29220
tctacttctg tccctaagat gtatctgcct gctctggtgt gtcaccggag cagaaaccag   29280
tttccccata gcccgaggga ctcaccggcc acaccctttg acgtctaggg atcatttgag   29340
gatgagatta tgcatctccc agccactcaa tcggacgtcg gcttcaccct tgtgtattaa   29400
gctactgtag caaaccctt gaaaacattt atggataacc agcgggcagg tgctggcgtt   29460
tccccaggat gtacagtgaa caggtactta gctctagcag gcaaaccatg cgccgacac   29520 agttccaccg acatcgtgca tgcattctgg ttgccccaga gccttgccaa cacttgtgat   29580
tatcaatccg tctccttttg gctgtgctgg tatacgtcat agagattctt gtgaatttgg   29640
gggatatgtc cagagttggg gagggcttta tgatgtcaca ggccaccagt ctttatgctc   29700
tgtcatcctt tgggtatggt tttcagtctc aaagcttttcc catgatccaa ggtagctctg   29760
tagctctctc catcaggacc gaatttctgg gtggggtgg cgggtgtttc actgaaacca   29820
ccggaacttt tagtgtggtg ggagggctg ctgttacaaa gattggtcct gtccattttc   29880
ttttttcttt ttttaagatt tatttattta ttacatgtaa gtatactcag acacctacag   29940
tatgcatagg gcatcagatc tcattacgga tggttgtgag ccaccttgtg gttgctggga   30000
tttgaactca ggaccttgg aagagcagtc agtgctctta actgctgagc catctctcca   30060
gcccttgtcc attttcttcc ctgctgtggt ttaggcctag cacacagcct cttgtgcact   30120
gggtgctcag cagaggcctc gtggatgcca ggaactgaac ccaggtcctt tgtaagagca   30180
gccagtgctc ctaaccactg agccatctct ccagccattc ctggtgtgtt cctggtgtgt   30240
ggtgtcttca tgcctaggc tggattgtcc tttggggccc atccttcctg tatacatagt   30300
aactctacag ggctagtaca ttgcgactgg ctggctggct cagagctgac aggatatgtg   30360
tctcaaccca gatccagggc tggtgaaccc agtggcaatg accagaactg tttcctctcc   30420
ctcctcctcc tccctctcct cctcctcctc ctcctccttc tcttcttctt cctcttctct   30480
ccttcctctt cttcctcctc ttgtttggag atagggtttc tttctgcatc cctagctgcc   30540
ctggtagacc accaggttag ccttgaacac agagatccac ctgcttctgc ctcctaagag   30600
```

```
ttggattaaa ggtgtgagcc gacctctgtc agcctggctc aaaaacctgg tttttttttg   30660
aacctgaaat gtgtttgctg tgattcttgg gggaggaggg actggatttt gcaatttccc   30720
aggtcagatt aatgattgct ttgcgagggc tgcagcacct gagctgagcc acactgagca   30780
gggcctggag aggctaggta cagtgtcctg gagatcctgt gcagtcctgt gtggggatag   30840
aggctggggg agcttccatc tctgtgatct tcatgaacca gaggcctctg agcctgatgc   30900
ctgtgcacct gggatatatg gtcagagagt taaagaggtg tagtgaccag aagtgtcctg   30960
ttacccacac agagggtctg ttgggtccct agcacctcat gtggcggcct tgatcagctc   31020
cagctgcctt tttgtttgtt tttcttttga atggagcctc tgatgtccaa gtgtgttcgg   31080
ttcctgcaga ctgacctata tcctggccat cagagaaccc gctaaccccc ggattatggt   31140
gctcactccc agtttggctt gcccagaccc cacctcagac tcaaagccct tgtttctctg   31200
atgcccagcc accctaccca atccctctct ggaaggcaga tggcttattc tgtgcttatt   31260
ctgtacccag gtcactgctg ccaagcacat gcctagtatg tactgggtc gtggggagc    31320
aggggtccaa gcaaatgatc agaatgctca cagacctttg tggtgtggag catggagatt   31380
gctccagttt tcctgtctct cgggcacttg gtgtgcattt tggacatccc caaggcttgc   31440
agaatggagt cgaggtagcg tatggctccc cacggaagga ggaaacctca gtgcattagt   31500
ctgtcggtat tgctgtaatg aaagacacag gcttggtgtt agcatcacat ctgatgggc    31560
cacttcatgt tgttgcgaac tgcttggagc agctatgagc cgagagatta cagtggggaa   31620
gccagaaggc aaagaaagtc tgcaccatcc ccaccaccaa tccccagccc tttcccagtg   31680
gggctaagcc tcctgagggt cccctcccaa ggcttcatgt cagagaccaa gtctccaact   31740
gccaccgaaa gcacgagaat aaagtgtttg cagagcagac attttttaagg taatgatctg   31800
gtgggccaat gagtgtcctt tagagaagac agaaaagaat gtgcagtgga gaggagggga   31860
cagagaagca ggggtgggag ccaagaggct gtacgaggct gagaggctca ccgctggagc   31920
tcagggatgc tttggtgaca gctggcccag gaagtgggag ctgtggtcat ttatttaga    31980
aatataaatg tgtgtgtgtg tgtgtgtgtg tgtatctgtg cacatgtgca tactcggtga   32040
cttt ggaggc cagaggatga tgtcatatcc catggaacta gagttacaga tgattgtgag   32100
ccaccaagtg ggtcctggga tttgaacctg ggtcctctgg aagaacccag ccaatgctct   32160
aaccaatgaa ccacctcact ttgttgttca aaggcagggt ctctcactag gatgtgagtc   32220
tcgccatttt taggctagcc tggctggcca gcaagccctg ggcattatcc cgctgtctcc   32280
acctctccag agctgggatc acaagcatac accaccatgc ctggctttgt atggggccca   32340
aactcggctc cttccactta tgaagcaagc actttatggc tgagccatct ccctagaatt   32400
ccaaactctg ttctcaagaa cacactatgt caaaggtgcc cacaggatgc tgggggtttg   32460
tttcctacaa tgatggatta tggcgctcca gaattggctt gggctccttc ctccaagtcc   32520
tctgaggtcc ttccaggtgc ctggcactgc tcagagttca cggatccagc atgagcatca   32580
ttggtggggt ttatggcctg gcagagagac gtgagcacaa tacacaggat gagtcattaa   32640
cgtaatcggg aagaaggcag ggagagcctc ggaataaaca agagtttaag agggagccca   32700
gggctcgggg tgggctctgt gggggttcct gagcacagac acaggatccc aggaggcttc   32760
ctctgcaaac atggaaggca gaagaagcga cgaccagtgc aagggcctgg tgggtgagag   32820
tgtgtgaaca gcaaggcag agcaagcatg ccaggctggt ctaaaggact aatgggggta    32880
tcagtaagac acagccctag agatgccact gagccagatg ggcaaaggct tataggtcag   32940
tgttagcatg gtaaaattta caataaataa ataaacaaac aatccatttg gtttggggat   33000
```

```
ggccatacat atgccagggt gcatgtagaa gacacagaac aatgtcttgg agtcttctgt   33060
tctgttgtgt gggtcctggg gatccagctc tggtccttag gcttggtgat taagctcctt   33120
tattttgcag gccacaatct gaaagatgct gggccctggg cttcagatag gggaaggcca   33180
ctccccacag gcattccatt ccccactctg gtggctgtac atgaggtacc tcgtggttca   33240
gcctcccgca acaccccaac cacctgcttg cagagggaac cgcccatcac cccatggttt   33300
tcagtgagat tctgcctagt cctctgtgcc aaaaaagcca agcagaatct ttggggaggc   33360
tgcctttcct gctctcctga gagttctctg ggtggcgaag ggagacaatc tgtctgagat   33420
gaggaccttc gggcgctctc caccgctctg ttggcctctc aaaccttgag aatccctccg   33480 ggcagagtt ttcaaactgg gatgttatct ttctgatatc ggttgtgaca tccctggggt   33540
gtgtgggcaa ctgatgttta aaacatggcg ggagtgtgct ggtgatgatg gggtgataaa   33600
gaaatggctc agaggttatg aggagtatgt ctcatctcac acacacacac acacacacac   33660
acacacacac acatacacac acacacacac acgcgcacgc acatttgagt gtggggtgct   33720
aggaactgaa ttcagtctcc tggaacagcc tcaagtgctt ttaaccacta agccagctcc   33780 ccaccccac cccaccccg caaattaaaa acaagcaaat atataaaagt ctaaaacaca   33840
gtgtgagcca ggtgtaatga taccccaggc tccctataat ctggacattg aagaggcgga   33900
ggcagaaaga tcaggagttt cagagtcatc ctcagctaca tatcaaatca gaaatcctgg   33960
agttggggtg gaaatcattt tgtactggag aggttgccct gggtggcagg cagcatttgg   34020
gagctggtat tcggggtgtt gtcccaggta gaggctccgc agagccatag ggcactgcac   34080
agatatgatc tatgttagaa gtgcacacaa gtacccgctg gctgcccggg ctgtgtacct   34140
cacccatgcc ctcacttatt tagcttcagc ttcctattgc agtgttctgg ggaagtatag   34200
tctacttgac tttacagctg accttttaaa aatgatgggt gcatttcagt ttcggtattc   34260
aatggagggc gcagcaagat ggctcagtgg gtgaaggcac ttgctgccaa gcctaatggc   34320
ctgagttcga tccctggggc ccatatggtg gaaggaggga gaactgtcct ctgacctcca   34380
cacatgcacc ctggcgtaag caaacccaca cacatacccca tatacacaaa taagtaactg   34440
cagagattaa aagaatataa aaacctttat tgagacacgc cagccttgtt tattctggaa   34500
tttctcacag taggactcac aacgcccctgt gcatatttcc ttctgtattc tctccccag   34560 tagtatactg agtccttccc cttcccctcc ctttttcttt ttgagatggt cttacgtagc   34620
ccaggctagc cctgaattca ctatgtagct gaggatggcc tgggactcct gctcctcctg   34680
cctgtgcttc tggagggctg gggtggcaga ggtgggcact gtgcccactt tgttcagggc   34740
tggggatgga tctaatttaa tccaccaggt cacacacaca cgagtggagc catgagcacc   34800
cgtgggactt gtctcgtgtt ggcagaggca ggttggtaat ctcccagcag ctccacagat   34860
gtttcctaga gtctcggttt ataaacactc ctgtcatggg tggacacgga gccccgcacg   34920
cttgctcggc aggccagcct ttgctggaac accctcctgg gacctttttcc tggcaaagcc   34980 tgttttgtct ttgttttgtc ctcttgctgt tgtgaagcgg gtgattgcca tgcagcaagg   35040
ctggcctcag aaagccagtc aaccctctgc cttagctgcc tgagcgctaa agtgactggc   35100
gtgtgctcca acagcgtgca ccccgagagc cagctcttaa tttttttttt tttttagttt   35160
tccaccatgt gttgatttgg ttgtggtggt agggattgaa cccagggcct tgcacgggct   35220
gggtaagctc ttttccactg agctgcatct atgtcttctc ttcttttaaa tgtaaaatcg   35280
tttattcagt ctttgagaac cacaaacattc atacaacgta tttcaatgat acacgcttgc   35340
```

```
tactcctccc agatccccct acaggccact cctgatttta tatccatttt ggttttggtt    35400
ttggttttgt tcaccccttc gagacaggat ctcactagat agtgctggct ggtcttaaac    35460
tcacatagat ccttgtgcct ctgcctccca agcgttggaa gtaaagtcac gtgccaccac    35520
agccagtact ttcttcttgt cttttctttt tcccccttat ttacccactc aatccaattg    35580
ctgtggccca tatacatatt gtaggggcag ttttacactg tgtggcagta agcaaaatag    35640
tagttctggg gtcatggggg aacagcaccc ccagagcctg tctcagccat ttgattctca    35700
gccagattta tagtatcggg catgttttc gtcctatgga gaaggcctta aatccagtca    35760
gagagtattg gctaaaccca taatatccgt gccactaatg cgtccgtggg cagatcttac    35820
caggctgata agctgcaggg tagtttgcag gagtcacagc tgcctaaggg tgccagggtc    35880
ttgaaatgcc tctctgtttt tgccagatgt tcaggctgtg ggtgaccaac ggaaggtgcg    35940
gcaggacatc tcttaggtgg actcagcagg ggattttct ttcagtgggt cccgaggagg    36000
acaggccaga cccagccatg gctttcatga ctccggcctt gcagtactca aggacaaacc    36060
ccaggcccag agagccaagc taggcctgag agagtgtggc ccagtgtccg cctgcctcgg    36120
agtctactct gacgtggggc tgggcttgac ctgccagttc tggcttgcca cctcccctgg    36180
agcctctgcc tgttgtttct ggctgtttgg ggacagtggg gtggttgtct ttgtcctggc    36240
aggtcgagtt caaagtcaaa gctgtttggc ttttggacac tgctatctct gatgagctgg    36300
gggtggtgac tcttagctct gtggcattag cagaggtccc aggtcaggga atggtccacc    36360
tcttcctcct agccttggag aaaatcagta gttctgtttt gagacagagt gtctcattca    36420
ctgtgtatcc caggctgacc tcaaagttac catctaactc cttcagtgtc ccaagtgcta    36480
ggatgacagc cctgcatgac tggacccagg gctgcctgca cactaggcaa tcactaagcc    36540
ccgcccccgg tcctgcttac tgtcttctgt ccctcactgc tggtgactca agaatcatcc    36600
tcttccctct ccctgctcct cagtacatca cacagcactg gctctgcccc cgctccaccc    36660
ccccccaccc ccaccccccc acccggtgca taaagccctt gtcttcccga tttggtaaaa    36720
gcttcacggg actggagaca gccagcctgt ctacttccca ctcctgtctg ctactgcggg    36780
aacctcatct gtcaaaaatg aatgaatgag tgaccaaatg aatgaatgaa gaaagaacaa    36840
aaagaatgcg ggagtaaatg tgaaatgatc agtgaataat gaatgaatga acgaacgaac    36900
ggctttctgg atgagttatt gactgaaaga atggagagac agccacctgt gcagagctcc    36960
agccctagga gcacctccct cgatgagcac tacctagcca gtgttctgtt ttgctgtgaa    37020
gagagaccac aacgaagaca actctgtatt ataaagcatt taactggggg cttgtttaca    37080
gtttcagagg cttagtccgt tatcctcatg gcagggagca tggtgcaagt taggtggagt    37140
tagtgttgga gcaagttagt gttggagcag tagctgagat cacaggcaga gagggagaga    37200
gagagacagg gagggaggga gaccaatgga ccctgtgctt ggagtgagct tttgtaacct    37260
caaaccctgc ccctagcgac acacctcctt caacaaggcc acacctcctc cgacaaagac    37320
acgcctcttc ctccgacaag gccacacctc ctccaacgac acaccccta atccctgccc    37380
atagcgacac gcctcctccg acaacgacac acctcctaat ccttccaagc cgttctccaa    37440
ctaaaggcta agctgcaaat atctgagcct gtggggcctt tctcattcag accaccccag    37500
acacccttcc agatgagcct tggagggtcc atggcgcagg ccaagtctca ggcagctgtt    37560
gcagagccgt aaagtgggga agcccctcct cacactcctc cctgtgtctc cccacagaat    37620
gtccgcatag acccgagcag cctgtccttc gggatgtgga aggagatccc cgtcccttc    37680
tacttgtctg tctacttctt cgaagtggtc aacccaaacg aggtcctcaa cggccagaag    37740
```

```
ccagtagtcc gggagcgtgg accctatgtc tacaggtgag gccaggcagg gtggggtggg    37800
actgtgtgtg ggtgtgtggg tgtggagggg ggtgttctgc catgctgagt tttggagatt    37860
gattgctcca gagacagaag tcggacagac accgcctctc cacagactgt cagccacaca    37920
gagaagccgg aggccacagt ggctgacagt ctgtggagag gcggtgtctg tccgaggcga    37980
gtgcatactc gcatgcgtgt cctggggtga gggctaatgt gagtgtaaat gtgttgtcat    38040
gggggcgggg cacagaggac ccaacagcgc acaaaatggg caaaatggct gctgttgagt    38100
cagaaaagtc aaacaaacat gcagaagtga agccagttac gcagcatcta agaagtgagc    38160
ggtgctgggt agtggtggca cacaccttga atcccagcac ttgggaggca gaggcaggtg    38220
gaattctgag ttgaaaactg gatccaggag cggctgcctg gtcctccacc ttggacagag    38280
agttttaact tccataatgc ctattttagc cccatctgtg agacagaggt aatggtaccc    38340
actgtgggta ggttcaagga taagatgaga tagttagttg gagccactta agctctgtct    38400
gccatgccat aaactctcag taaacgctgc ctgtgtggat atctgctcca tgctggttgt    38460
caagtgaaag ggagacgtgg ggggtggggg cagcagttgg agttgttttc cagagaggct    38520
caaagagcct tatggctcac cagggaaagc agagaagagc tgattggtgg tggcagtgtc    38580
ttgccctgga cagacagcga ggatataaac aagaggtggc aagcttgatt tggtggcctt    38640
ggtgctgttg ggtatcagtg taccatcacc ccagggcatg ctgggagatg atgggtgctt    38700
tcatgtgacc tcacagagcc acagctgact caatgccttt ttacagggag ttcagacaaa    38760
aggtcaacat caccttcaat gacaacgaca ccgtgtcctt cgtggagaac cgcagcctcc    38820
atttccagcc tgacaagtcg catggctcag agagtgacta cattgtactg cctaacatct    38880
tggtcctggt gagactgtgg ccctgtgtca accccatgcc aaccctgctt cctcccagct    38940
tagccttcag gagtcagaga gcaagggcca cctcagcccc actgtctcca tggtgaccat    39000
cccctccttc tcattgcctt acctcccatc tgagactccg ggacctccac tgtggtccct    39060
ggggaagcat gaaggtcaga gccactgggg gccagagggc aggtgggagt ccggaagagc    39120
aggcatttat tgagcacact gtgtggggtc gctgagtctg tcctttggtg tatgcgggga    39180
tctactcaac cctgctgttc aggggaggaa gcaaaagcca ggcagaggca gggaatttac    39240
acagggccca gaaggaccct ccccaaggac aaaatcccag ataccaattg ggccagtgtt    39300
accaaggcag gatcggatcc tgtggtcaga catcacggcc ctcgctggaa gtttgaggac    39360
agggtacacg gtggttggta gtgggggggac agtcaaggca tgatgtcacg aggtaagcat    39420
taccattccc agtgacacta acttgagaga ttggaactgt gagctttgtg tgattttcat    39480 gcttttttaga agattcttct gatctccccc cacccccacc ctcaaccata ggaaactgtt    39540
gaaaacacca gctttcctgc agttgatgcg ggccgatgct gactggattg gtcctttagc    39600
caccttgcct cgagtccatt ttcagaggtg tcccccgggt ccgatggggc tggagggaca    39660 cttttttgttt ttattaattt attatattac tactatcatt atcattattt tgagataggg    39720
tgttactggg cagccatagc tgccctgtat ctcattatgt agaccaggcc agccttgaac    39780
tcacagagat ctgccagcct ctgcctcaag tgcctgggtgt gagccaccac atttgtcata    39840
ttaattccag ttttttaaaaa ttattttattt tatgtatatg agtacactgt agctggcttc    39900
agacacacca gaagaggtca tcggatccca ttacagatgt ttgtgaacca ctttgtggtt    39960
gctgggaatt gaactgagga agtagtactt taaccactga gccatctctc cagcccttaa    40020
ttccattttt gatattgaaa aagcaacagc attctgtgct gggccagcag gatggctcag    40080
```

```
taggtaaaag gtgcctgtca ctaagtcgga tggcctggct ttaatctcca ggacccacat    40140
gactgcctca cattgtcctt tgacctctat acgtgcacta tagcacccct caataaatat    40200
aataaaagcc ctgtgttgaa ggagacctgt aagtgttggt gggtaggcat catgcgcttg    40260
cttgatggaa agaacctgga gacaccagcc atgcgttgcc caggaggtgg aaggtggctt    40320
ttggttgaat ggcctttggg aaaaacaag agcccagatg ctccatacgg aggaagaaca    40380
aacaagaaaa ctataaactc aactgaactt ggggcagtta gaccctgggg gggcttcggg    40440
ggagtagata ttctgggctc ccagtgttga ggtggggcag ggacatgaga agtgaggtgg    40500
aatccctgtg aggagactgc ggcaggagaa tgctgatttc caagccagcc cagattaatc    40560
attgagacct tgctgtaaac atgttcaaaa ggaggccacg gggagtcggg gaggctttct    40620
ccatatgctg tgtttctagg ctcatgttac tgatagaata gggttcacgt cctagctata    40680
aaccgggtat ccaaggggct ggcgagatgg ctcagcgggt aagagcacta ctgactgctc    40740
ttccagagat cctgagttca atcccagca accacatggt gactcacaac cacctgtaat    40800
gagatctgac accctcttct ggtgtgtctg aagacagcca cagtgtactt atttataata    40860
ataaatgaat ttgggaacaa gaagaggccc taaaaattca attcccaaca acatgaaggc    40920
tcacaaccat ctgtacaact acagtgtagt catatacatt aaaataaata aataaatctt    40980
taaaaatcaa aaacaaaaca aaacaaggta ttcatatctt tgctggcccc cttctgtgtt    41040
aggttttctc ttaaccttgg ctccagcctc atccgttcgc ttggtgaggg atggcatggg    41100
agcctccttc tctgtgcccc ggctctgcgg agtgtctctg gtggttcact ggttccattt    41160
aggcctcagg tgtggctcta cagacacagt ggctcaggaa ggcttccgga ggtcaggcct    41220
gagcttcgtg tatgcctctg agtccttgta gagttcactc aatctgaacc catcatcggg    41280
tgttctcgag agtacaggtt accctggcaa caaggaccag agaaaggtcc atcctgaggg    41340
cctgagctct ttgcctgaag cctggttgaa agtgggggat ggtgtcctac catgtccttt    41400
accctaatcc catgtccttg gcttttccagg ggggctcgat attgatggag agcaagcctg    41460
tgagcctgaa gctgatgatg accttggcgc tggtcaccat gggccagcgt gcttttatga    41520
accgcacagt tggtgagatc ctgtggggct atgacgatcc cttcgtgcat tttctcaaca    41580
cgtacctccc agacatgctt cccataaagg gcaaatttgg cctgtttgtt ggggtaagtg    41640
tcttctgtcc cttcagagag tcaggttatc tctcaaggac cctaactcaa accagcttaa    41700
acaaaaattg ggaaattatc agctcatata acaggagatg ccaggattac attcaggtgc    41760
ggcttgatcc agttcgagtg gggggatatg ctgggggttt aacttagaag atttgaggca    41820
cagcttgcgg ggaggaggag gaggactgga tcttcgaagc acacctctca aatgtcccca    41880
tcagtgtgac ttagaggcac ccactatttc tcacagttga cctttggtaa cctgagctaa    41940
ggtttggtct ctgacccctg accccaactc tctggttcag ctcagctttc tctgtgggga    42000
tctactgacg gggtgtgctt gcagtaacgt tacccacacc ctccaggacc tgttattact    42060
gagttcacgt gagatttact acccagtggt tagagcactg gctgttcttc aagaggaccc    42120
aggttcgatt cccagcaccc acatgacggc tcacacccca tctgtagctc cagttccagg    42180
ggatctgaca ccctcttctg gctcactcag gcactgcagt gcaggcaatg cacagaccta    42240
catgcaggca aaaagactca gacacataaa ataaaaatat gtccaatctt gtggagagga    42300
gacggggtaa ggcactgtgt ctcccagtga ccagatgggg accccatggg gtgaacacat    42360
aacgagggcg gcaggctgaa tacccagtct taaagctttt acagagttag aggccctggg    42420
taaagccctg tacctgtctg tacctgccct tcccagtacc ccatagagac tgccatccct    42480
```

```
ctcttcctga caattgaggt ggggcccttc tactgagctt ctagatcgtt cctgtcagaa    42540
atttgtatta aattctttct ttcttttat ctttgtttta ttatttttat tgagtcaggg    42600
tctctctatg cagtcctggc tgtcctggaa ttcactttgt agaccaggct ggcctcaaac    42660
agatgtctgc ctacctctct ctcctgagtg ttgggagtaa gggtgtgtgc cactaaaccc    42720
ccgctaaaat gccttttac tttattagct gttggccctg attgagtaga cttgtcatct    42780
gtgtacatgg gagtatgagg caggagtatg gcaaattcaa aaccagcctg acaaccctg    42840 tctgaaaatg tgcaataaaa aagaatgctg gatggagggt ggagctggag agatggctca    42900
gcagttaaga gcactgactg ctctaccaga ggtcctgagt tcaattccca gcaaccacat    42960
ggtagctcac aaccatctgt aatgagatct gatgccctct tctgatgtgt ctgaagagag    43020
ctacagtgta ctcacataaa attttttaaa gggtgggggg aagctggggg tgtgactcag    43080
tggatgagta cttgcccaca tgtgtaaggc actgggttct gtccccatca tttatgcagc    43140
aacagtgagg ggacatacct atagctgaag aataggtggg cttgtgccta tgttgtgatc    43200
tatgcccagg gctaaaggtg ctgttccctg cctgtctgta gatgaacaac tcgaattctg    43260
gggtcttcac tgtcttcacg ggcgtccaga atttcagcag gatccatctg gtggacaaat    43320
ggaacggact cagcaaggtg agcaggaggg cagacagtcc ccatcgattg gtgtggggac    43380
tacaccagaa caagccttgg cagagggtgt ccgggtcacc cgaggacttc acggatccca    43440
caactgtccc tgcggtattt ctgtcgggaa ctcttttctg ttcctgagtt gtcatttcta    43500
aggctgacag gaagacattc ccataaagat aagacaatga ggtccagcac cttgcctagg    43560
cccacccgga aatcccccaa cactgcttat agaacccagc ttcctggcca tttacccacc    43620
accacgcctc tgtgtaccca gagaaatgtg ttttccttcc ttcttcgaat acacagaaat    43680
cctgtcatgt gctatttgc tgctggcttt tctccttagg ggcatcttta tggataatgt    43740
gtttttgttc tgttgtgttg tccagaggcc caggtactaa agatggaacg caggccatgt    43800
gaatctttga caaggacacc actgctgagc tagacttctg cccttcactg ggggaattct    43860
aggcaggggc tctaccactg agccacgccc ccagcccctc actggggat tctaggcagg    43920 tgctctacca ctgagccaca cccttaaatt tttttattct gaaataaggt ctctgtgtat    43980
cccaggctag cttcaaaaat tcaatcctcc tgtctctgtt gccttgtaag tgtttaattc    44040
atagatgtgt gttaccacac ccagccaaca gctattctta gtgggtgctg ttcacattaa    44100
ccagctgctg ttttatatgc attggcattt tgtctgcatg tatgtctgtg tgagggcctt    44160
ggatcccctg gaactggaat tatagacagt tgtgagctgc catctgggtg ctaggcattg    44220
aacctgggtc ctctggaaaa acagccagtg ctcttaacca ctgagccatc tctccagccc    44280
ctaatcgtct cctttctact atgagaaggg ctgattgaaa gctcttacgg cagagtggga    44340
agtgcgttta gttttgctgt tgctgttgct gttttgtttt gtttttgtttt ggaagcaggg    44400 tctcagtgta gtcctggcta gcctggaact cgatattgta caggtgactt aactgagtcc    44460
ccacaatact gtatgttctg tccccactgt ggggaacagg aagctgggct agaacctctg    44520
tgcacacagc ctgctcacgg gcttggatat gatgatgtct gtactagggc acacattggg    44580
tgtagatctt ggctgtccct caaggctata tctcatcctg tcctgcagat cgattattgg    44640
cattcagagc agtgtaacat gatcaatggg acttccgggc agatgtgggc acccttcatg    44700
acacccgaat cctcgctgga attcttcagc ccggaggcat gcaggtaagc cctgtgtagg    44760
gactccctgc ctcctaccag gaaactctgc ttctgagatg gttcagggtc cactcaggta    44820
```

```
gctccctgga agtgtgctca aagtgtctgg ccttctgtgt actatgcctc aatggttttt   44880
cttgtcactg tgacaagata cctgacagag gtgacttgcg aggtgtctgg ggactcagtc   44940
atggtggcag tggtgaaggg tactggtagg aaagtgttaa agtcttgtag cttgggctcc   45000
accatcccca gggtcctaac tgtggcctag gaagacatgg tgggtcttca gagacccatt   45060
tccaggtggt gccctagcct gtgcatccat tctggccaca ccagagatga ctctggcctg   45120
gggactcact gggctgatct ttgagccctc ttcctctcta gctcacacag gcagccatgc   45180
ttcatgccag gtgtgaacac agccacgacg gggtgagcaa agtctgtgtg ctctggtgga   45240
ctttcaaaag cagaacttcg ggtttggttt tgttttgttt ttacatttta tttattactg   45300
gttttttaat tttgtgtatc tgtgtgtgtg cacatgagtg caggtgcctg aggaggccag   45360
cagagggcgt cagatcacct ggagctcctg taagaggtgg ctgtgagctg ccctacgagg   45420
atgctgggac tcaaacgttt tgttttgttt tgttttgttt tttgagacag ggtttctctg   45480
tatagtcctg gctgtcctgg aactcacttt gtagaccagg ccggcctcga actcagaaat   45540
ccgcctgcct ctgcctccca gtgctggga ttaaggtgt gctgcgccac cacgcccggc   45600
tgctgggact cgaacttaag tgttgctcta aactactgag ccacctctcc agcccattta   45660
tttgtgtgtg tgtgtgtgtg tgtgtgtgtg tgtgtgtgtg tgtgtgctga taatggaacc   45720
cagggcctca cacactctaa gtaagtggcc tgatactgag tcatgccgca gacactaaat   45780
aggatttcag cctggcagaa ttatatgaga gcagggtgca ggccaggtgt ctctttcctt   45840
cagtccttca tgggttatc tccagaaaca aaggcctctt cttacacaat cacaaggatc   45900
gaaatcagag aatttaacat cgccctaata agagcctcta agctggtgct gctgcataaa   45960
ataacaaaac aaactgtgct tataatttca gattaggggc catctttgtg gctggtggtg   46020
gggggagatc aaagcaggaa ctccaggcag ctaatcaatc cacttacagg aacagagtca   46080
cactgaatgc actcatgcct atagctcaga tggctgtctc cattcttata cagtccatga   46140
gccaaaccta gggaatagtg ccgcccacag tgggctggct cttcccacat caattagggg   46200
aatccagaca atttcacaca gtgagagtct cttcacagga gattctaact atgtcaaatt   46260
gacatttaaa aacttaccac cagactgtgt gaaaagattt tctgagaaga gcttttgctt   46320
agtgttgggt cttagaaatc tgggtgtcgg tcaggtgtgg cagtgcttgc atttaatcct   46380
agcactcaag gcagaggcaa gggaatcctt gggagtctaa ggccagcctg gtctacatag   46440
ctatttccag ttctttacat agagagacta tagaactaca taaggaaggg gcagagggag   46500
ggagggaggg ggagagagag agagagagag agagagagag agagagagag agagagagag   46560
agagagagag agagcgccaa tgtcttatcc tcttttttt ggttcatccc aattggtttc   46620
ctcttgtttt gctttgttgt tttgagttgg ggggggggt ctcactgtgt agcctggcaa   46680
aaaagtatcc tcctgcctca gcctgcacag tcctaggatt gaagccatga gccacagacc   46740
gagttctgcc ctggactctc tttgttttga ggattgagca gacatgtgtg tgtgttatgg   46800
tgttgaccat ggacagtgtg ggtcacccgg gccttgtttc ccatcagaag agtgtttgag   46860
gccagacagt gggagtgaat ggatgaagag gagtcagggt ggacaaggga gactgggaaa   46920
gccgaagtct gggctgaggg agaggtggga tccggaggtt caggggcagg aagggacatg   46980
actaaggccc tggcaggtac agtgagacag gaagtggaga gggaagctgt ggatggcatc   47040
tgtggatggc atcgcactgc agggtgactg cagggccatg gtggttgctc atccctccgc   47100
atgcacagaa aaccattgcc caaagccttg gtttccacag tcctcatcag ctctcaagcc   47160
cctatcaaga gaacatggca catcgttgta agtgtaaggg aactctgtaa acttcagatt   47220
```

```
atctcaagtg actgacacag ctactgcaga catgtgctgt gcatgtttta gcttgctttc    47280
tttctttctt tctttcttcc tttctttctt tctttctttt tttttgtgtg gttttttcgag   47340 acagggtttc tctgtgtagc ccttgctgtc ctggaactca gtctgtagac ccaggctagc    47400
ctggaactca gaaatccgcc tgcctctgcc tcccaagtgc tgggattaaa ggcgtgtgcc    47460
accactgccc ggctgctacc gtactgttat gaatcataat ggaaatgtct gcgttttcca    47520
gtgggctttt gtgggcggtt acgacccaca ggttgagaac ctccggccta gggcatgctg    47580
gccaaactgt gctaaactgt gctgagttct ggttttttaat ttgcctcatt gggaggatgg   47640
attagtgagt ggggagccaa gggagcaggc agaacattga gggaccgctg aagtttcctc    47700
agcaacaggt gactagtgtc attgctggtc cctgtggttt cttctgcagg ggtgccccag    47760
cctctgtgct caaggcacag ttctcaccct gcctcccctc tgcaggtcca tgaagctgac    47820
ctacaacgaa tcaagggtgt ttgaaggcat tcccacgtat cgcttcacgg ccccgatac    47880 tctgtttgcc aacgggtccg tctacccacc caacgaaggc ttctgcccat gccgagagtc    47940
tggcattcag aatgtcagca cctgcaggtt tggtgagtgt cctctaagtg ttctccacct    48000
ctaggctgag gtgagagggt ggtaccggga ttttatctgc tgccagcttg ctgtcccatt    48060
aatctctggt ctctgcaccc atgatgatct cagtgctaca gatagggagc taaaggtaac    48120
tgaaaaaaag ataacagcca ccctgataaa tgtcccaccg gcacgcgtta tccacaagcc    48180
gtgtcgctcc gaagtccgaa gggtcctgcc ccgaggttaa gattccatca gtgggcactg    48240
cttcttggcc aaggagagga gcctgccctc atcctttcct gcttccggag gcaccacatt    48300
ccttggcttg tggtcccttc ctttctcaac ctagcatcca gcttgagact gggtagcgcg    48360
ttgtggccca agttagcttc aaacttgcgc atccttcctg cctctgcctt cagaggtatc    48420
gggatagaag gcatgtaccc agacaccaga tcccccaaa acactccgtt ctatgaccac     48480
ctcctcctcc tctatccagc ccatagcttt caggaccccca gagactgact gggtagaggc   48540
cactgggata acctggtctg ttatcctggt ggctctaact tctttgccca ctaggacgag    48600
gctggaaaca ttccctgtgg ccattcacct gctgggagca aaagctagag tcctgcccctt   48660 cactcaaact ggccacgctc ctattgtgtc aaactctcct ctttagccaa gttgggtgtg    48720
aatcttggta ctggctgtgg cccccctggca catctgctct gtgttctaat cctgggccct   48780
accctgctgc tattgctcaa gtctgctccg tgcctcaccc ctcacctggc agtcaggccc    48840
aggctgctct aagcacctcc cacacagtct ttctccttcc cacccacctt cttcccgtgt    48900
cactcgggtg cccttgctct ctcgccagct cgtattgcac cagatgtcaa tcaaactcaa    48960
atgaaatgct tcctctgatc ctgatcagat cctcccagac actctccctg atcttccgtc    49020
ccctctggct ctccagccgc tctctggtac actctctctt atgccttcct gttgctgct    49080 catggctgtc gatgttattt actgaaccct cccctgcttg tctcctcctt ggactgcaaa    49140
ccctgtggcc atgtcccagt aggatattgg gagtcaaact tctaaggccc ctacacagac   49200
gtgggatcca gggcttgcct gcggacagga agtttcactc acaactgcac ctccgccttc    49260
ccctccttgt accagcaaaa atcccagggc ttggttgaac tggtccagct ctgacctagt   49320
cattaggctg tgttaattgg ccaggctggg tcccacacac cgcaggggca gcaacaggcc    49380
cacatcacac agaactctgc tgtcaggaac agaatttcag ctgtgaaaga gaatctaagt    49440
gtagttgtgt ctgtagcttg ttctttttgtt ttgttttgtt ttgttttccg agacagtgg    49500 gtttaagtat gcgtgtgcgt gtcgcacacg cgtggaggga ggtataaaca ggtgcatcga    49560
```

```
tggatggaga ccggaagtga gtgtcttcct tcatcactct ttgtttgttt gtttgtttgt    49620
ttattgatgc agatttttca atcactaatc ctggatcttg ggaggtccag ggatccacct    49680
gtctctgcct cccagttaca gatgtggcgc tgctgggaac ccgaattcgg gtcctcacac    49740
ttgcacagga ggctcttaac tgactaaact gttttcccag ccctaaagc ttgccccttg     49800 taaatcgggt gagaacaaga aaggggaaga ggaacaggga ttcgagtgat agggaacacg    49860
gccatgtgac caacaacccc acaaagaggc aactcttacc acacccaaca tctccccttc    49920
ctgctcctcc tgcccactgg cctgactttt ggtctctcgg ctctctgcct ggcattactg    49980
tttacataga tggagtcaca actgttcttt ctccctcgat ccctgatgcc tcccatgatg    50040
gctctcatga ttatatggta aatctgcaag atagcgggtg atagcctaga ttgttgggtg    50100
gtgttccatg gtggggctaa ctctgcttgc cttactcctt cctggctcac ggagctttct    50160
tttggcattt caccactaca aggatgcttc tagaacattc tcgcacctgc tgtaggagga    50220
gtgcacctga gttcgaattt ctgtggcatt ttatcttaag ataaagaata cacataggtt    50280 tcccttctg ggtcacgaga cttcttgga ctcaggactc cccgtgtttc ctgtccttgt       50340
cttgggagca ccttggatct tccctgaagt ggtccttaat caccacgcgg gtaatcctga    50400
gcagttaagt ctggatacac gggccataaa gctataaatt aattatactt attgcccggg    50460
tgcgtctctc tgagggtgtt tggaaatcaa aagaaagat gagccacacc tattgttaga     50520
aagccacggg catgccacct gcagcaggtc tgtgctggca gccttgacat cctgttggaa    50580
tctgtgcttc caggtctggt taggtggggg cttcatctcc cggggatcca tggcatccct    50640
ctgaaagaaa tgggttctc tctgatcttt gctggtgtct cctttcacag tatggttgga     50700
aggatgggta gggttttcca agtagaaggc agcatatctc agcgtgactt tagaagggtc    50760
cacagaggtg acgttaggcc tcagggattg atcaggtctc ttttctgttc tgttgtatcc    50820
ttggtgttgt gtttccatga gggcttgaag gccaccctga ggatccttcg cctgtctttc    50880
tgacaggacc aggtgtgtct ctggagcctc gaaggtgcta gggttcacct ggactctcag    50940
tgatccgggt tctctgctgc atccctgccc acgtgcacct cctggctagg ccatttctct    51000
gccaaggctg tcacaggtgc agcactcttg tgtctgacac ctgcacttga agatgcccat    51060
agcagccggt tcaggggttg ggagcaagag gtaggggttg ggggcttcaa gcagtggatg    51120
tcctggagac cagactcgga tggaactcag agatccacct gcctctggct cccaattaaa    51180
gaggtatgct agcctgtctg gctttggatt ttaaagaaat gttttctttt ttttaaaagg    51240
tttattattt attttatttta tgagtacacc atagctgtct tcagacatgc cagaagaagg    51300
catcggatcc ccattacaga tggttgtgag ccaccatgtg attgctggga attgaactca    51360
ggacctatgg aagagcagtc agtgctctta accactgagc catctctcca gccctgtttg    51420
ttgtgttttt gagacagagt ttcttttgt agtcttagct gtcctggaac tcactatgta     51480
ggccaggctg gcctcaaact cagagatctc cttgcctctt cctccaggt gctgggattc     51540 aaggtgtgca ccaccagacc cagctaaaac acaatgcccc cctgtggat ctgttgccct     51600 gggagcctct tgtggcctcc ccagggagac tcagaactcg gaactcccca ggcccttgtc    51660
ctgagatctc tgggttgagc cactttggct ggttggtggt aaagtcccac ctcagggccc    51720
tgggtgggaa tatctcattg gtgctgtccc ttccattcct gtgatgtcag agacccactc    51780
acgtgtaccc ctgagctaca atgtctccaa aagcagtctg tgtgcctggc ttgacattca    51840
gactccgctt ccactcctaa attcatatgg tgttaatttt cctttccact ttcatctccc    51900
atgattccct gctgcacctc cagacctgga ggggtggggg tgggggggttg aaaatcacgt   51960
```

```
ccaagctctc acctcttgct acactcccac ccggaatgcc tttcccttgc cgggtagcag   52020
ctgctctctc ccttcctcca cccacccacc cacccacccc caacactgta atcggccact   52080
ctggctccat ccaccctctcc caggtcctgt gtgtgctcag cttggtcccc agtgttagca   52140
tccctgcatc cctggcaccg aggcaggcca acgtgacgct cccgtcttct aacgcctctc   52200
ttcccctcct ccaggtgcgc ctctgtttct ctcccacccc cacttttaca acgccgaccc   52260
tgtgttgtca gaagctgttc ttggtctgaa ccctaaccca aaggagcatt ccttgttcct   52320
agacatccat ccggtaagct ccgtgtcctg ctagtggctg gggcccattc ccagagattg   52380
ccactggccg ctgggcaccc gccccgctcc ccccaattcc ccaggacaga gcgggttcca   52440
actgaggcag gggagttcag ttccttccac agcggctgct cctagaactt caagtcatca   52500
aagtcttact ttaccccaat tccagagttc agtgatatca ttaccttttt tattggggcc   52560
tataaaaaga tataagatag taaattaatt aagacctatc agccgggacg tctccttcac   52620
cagagacaga tacccttgac agtgtcaaga cactaaagac atcatcgtgg gccagtgtct   52680
cacagagaaa tcagggggag gaatttgtcc tctgttaact tctctctgcc tctggtcact   52740
gtaagatgtg tccagtccag ggttcctgcc ctacgtgacg ccctgaaggc attccgtgaa   52800
gaactctttt ttgtttttact gggtggggat ggaagcctgg gttttgaaca cacaaggccc   52860
caggctctga tgccgagctg tgcctgcagc tggccttgaa cttgcaaatc ctcctgcctc   52920
ggcttccagt gtttcttcac acctggctca tagctgaggg ttatcgcaga ggaagggtgg   52980
gcacatgggg cacagtcgtc tgaagtcttt cccaggttgt gcctagctcc ccagcaagga   53040
acttgacata gaggtgtttt atatcaggaa agcccctcag aataggggg cctagttgtc    53100 gactggggac ctgtcctgtg agcctctctc cctgggcag atccatgctt catcccagag     53160
gacgaaggtg tttggtatta ttaactgtct atgcaaatgg cacagtgagg ccaacacact   53220
agcttagaga atggggcacc ctcacctcac cccccagaac ttaggttcca agaccaacac   53280
tgggcaccta ccctggacga cttctaggga gggttgccgg gcccacccat ggtatgcgtg   53340
gttatcacat ccatgcctct gtccaaaagt cataccaggt ttctggaggc ctttgccctg   53400
ggggcaggag ggatctgggc gtcctgggca aaacgtgtcc tggccttcta ctgtgggtga   53460
ttacaatctg agaggtggcc tccggcctcc catcaatctt tcaagagtct catgatctgg   53520
gcagggctaa aggcatcaaa cggtggtctc ttttcaccaa cctttccat tctagaactt    53580 tcttcctgat ttaaataata cctgtgaatt ctcctagtga ttttttggtt gttgttgttt   53640
ttaattttat gtatgtgagt acactgtcac tctcttcaga cacaccagaa gaggacattg   53700
gatccaattc cagatggttg taagccacca tgtggtggct gggaattgaa ctcagcacct   53760
ctggaagagc cgtcagtgct cttaaccgct gagccatctc tccagcgaga ttttttttta   53820
aaagcatcac attttaaaaa gagagctgca agcaggcagc tctctgtggc tacctctgtt   53880
agggagcgcc aggatgctac atagtgggaa actggctcga ttaaacctac tcaccctgga   53940
ccaggccctt cctttggttc cctgggctat taggaaatgt aaacaggaga aaaaagacat   54000
ccttactgcg catgccccac acttgggagg cactgtctta ggcagcttcg tgagggctgg   54060
gaggatagct tagtaggtag ggtgctcccc tgccctgcac agagccctgg cttccatccc   54120
agcaccatgt aaagttaggc ataagccagt cctcagaagg tagagacagg aagatttgga   54180
gttcaaggtc atccttggct acatagcaaa ttggagtcca acctggacca catgaaatct   54240
gtccccaaac gaacatgcag atgtggggg cgggggtgt catccctctg gcaacaagtg     54300
```

| | |
|---|---|
| tctagagagg ggatcttgcg atagctgatc cctttgggag caggtatttc ctgagggaga | 54360 |
| gcccagtggg tgtgtgggaa atttctagaa gggtggatgc cccagcaggt attatctggt | 54420 |
| ttaagttgga taagaaaccc cagggctgga gcaggctgga gcaggctgga gcaggctgga | 54480 |
| gcaggctggg aggctcccca caggatctta catctcctca ctgtatttat gctctaggtc | 54540 |
| actgggatcc ccatgaactg ttctgtgaag atgcagctga gcctctacat caaatctgtc | 54600 |
| aagggcatcg ggtgagtgga gttgggacgg gagcttctga aagcttcagg ggccaggagg | 54660 |
| tttcatgcat tggtgatgca aggcacagga cagggcgagg cccaagcgtt gggatccaac | 54720 |
| cacctctttt cctgggattg catcattgct ctggatggag actcagaccc aggctgcatc | 54780 |
| ctgacactac ctccatcctc cacgcccaag ggctcttctg ccattagtcg cattggtaat | 54840 |
| cttgtctccc ccacagtagg atggatttgc ctgcttgtat gtctgtgcac catgtaagtg | 54900 |
| caagagccgc cgaggccgga agagggcata gggacctgga gttagacgga gttgtgagcc | 54960 |
| actgaatgga tgctgagact tgaacctggg tcctgccagt gttctcaacc acaattccct | 55020 |
| gggtttactt tatgtttagc tttgtgtaac gtacagagtg agactgagag tcctcctgcc | 55080 |
| cccattccct gcttgcccgg cagaaacatg gtggtaggag tccagccttg gggctggaga | 55140 |
| gatgtcttag cagttaagag cactgacggc tcttccagag gtcctgagtt caattcccag | 55200 |
| caaccacatg gtggctcaca accatctcta atgggatctg atgccctctt ctggagtgtc | 55260 |
| tgaaaacact aaagtgtact tatgcaaata aaataaataa ttctttgaac gaaaggaccc | 55320 |
| acatgctggt cactcctcag catcgcagat cacatgcctg ggaaccactg aggaagaggt | 55380 |
| ggactctggg cttcatggtg aaaactaagt ccgggaattg ctggactcag ctaggcttct | 55440 |
| gtacacacac acaccctggg actcctgcat gccagaaaac actctttcac tgaattacat | 55500 |
| cccagccctc ttcactttt aggtctcact agattaccca ggctgccctt aatctctctg | 55560 |
| tagcccatca tggccttgaa catgcgccac ttgatctgac tcatctgggc tcttgaaacc | 55620 |
| ggaggccaaa gtgggctggc cacgggcttg agttcctgag gtcagcagcc aaacattgat | 55680 |
| ttgctccact gcctcaaata ctctttagaa atctttatag atttatggag aggtgtcaga | 55740 |
| gacgcaagca aatctttgtt ctctgtcccc ggtgcattca gtactgtccg ctcctggcag | 55800 |
| tatctgtcac ggtaaggaac caaagtctag tgcagcgtta ttgccacaac tgcagcttct | 55860 |
| cagcacgaga tgccgcccgc tcacgcctca cgcccggctc ccgtggctgt gatgggttgt | 55920 |
| tttgttttgt ttttttcttt taatctttgt ttcttgttgg tgttgtgagt tttgggattt | 55980 |
| tgttttggtt tttggagggg aaggtggttc atacagaggc caaaagagga tgccatgtgt | 56040 |
| cctcttttat ccctcttccc tttcttccct cgcggcagga attctcaccg aagccccagc | 56100 |
| tagcttctac ctgtctcagc cctggggtca caggttcaaa gccacacaca gcttttagcc | 56160 |
| tgggttcagg ggtctcacct cgggttcatt tgcttgagca gcaaatgctt tccccactga | 56220 |
| accatcccca gcacagtgat agtttctcct ctagcttttg gggtgttaaa gtacttgctg | 56280 |
| gacctgggtg tgtgtggtgc gatcaggttc ccctgtagat agtaacaggg gcagccaccc | 56340 |
| aggctttggt gggaggagac tcattattat tttattatta ttggtattat tattattatt | 56400 |
| attattatta ctactactac tactactact actactacta tttggctttt tgagacaggg | 56460 |
| tttctctgtg ttaataacct tggctgtcct ggaactcact ttgtagacca ggttgacctc | 56520 |
| aaactcacag agatccacct atctctgcct tcccaagagc tgggattaaa ggcattgtgc | 56580 |
| caccacatac acagatatta ttatttattt ttaaagttgt atttatgtat tttatgaatg | 56640 |
| agtggtctgt ctgaatgtac acctgtgagc cagaggaggg catcagatgc catgatagat | 56700 |

```
ggttgtgagc caccatgtgg tggctaggaa ttgaactcag gaccttttaa ccgttgagtt    56760
atctctctag ccccattttt agttgtgttt agtgtgtgtg tgtgtgtgtg tgtgtgtgtg    56820
tgtgtgtgtg tgtgtgtata ggtgcatgcc acaatgaaca tgtgaaggtt gggacaactt    56880
tagggagcct gttccacctt ctgggtcccg gggatggaac tcaggtcttc aggcttagca    56940
gcaagcactg tcacccactc agctgagcct tgccacgccc cttaattaat ttttgcatc     57000 aggtttcct  gtagcccagg ctagcctcaa acttggctaa ggatagtcaa ctgtacgtag    57060
cgttacaggc tccctttat ctttctgtct cattttcttg tgaagtggtt tcgactgagc     57120
gaaggccttt cacatggtaa ccagtagctc tcccactgac ccccaagcc  ccaaacatag    57180 ctccattgcg agggtcacat cacccctggt cactcacttt gtgtcccatg tttccaggca    57240 aacaggaag  atcgagccag tagttctgcc gttgctgtgg ttcgaacagg tgagtctatg    57300
aaggtagaag ggagtctggg gtctctgtat gttagctgag gcttttagtt cgctttgatg    57360
ctaatgttat gttaacttcc ggtacctaaa tttagctatt tgtatgttta gcctgcccat    57420
atgtatgtat gtatggttat catgtgagtg cccggtaccc gcagaagccc agagagcatc    57480
aggtctccta gaactggaat tacagatggt tgtgagccgt caagtctgaa acgtgggctc    57540
tcttgaagag cagccagcgc tcttaaccac agagccattt ccaggttttg ttaatggccc    57600
ctgagagggg ggagtggaga tggaattccg caccaggcca ccctgcaggc atcctgatct    57660
cgtcgccctt caggtcctaa gactagattc taaccagcga aagagatgac tgttaggcga    57720
ggaggcttgg ggccagatcc acctcccatt agccagtgcc tcatttcatg ggcgtgccaa    57780
cagcaagggc gtctgggaaa tgtagttctc tttggacttc tagccaaagc gcccgaggct    57840
ctctgttctg atttggggcg gggcacggca cagtgggatg ggtgccttgg agacgcagcg    57900
tgcagcccga cctttcttct gcagagcgga gcaatgggtg gcaagcccct gagcacgttc    57960
tacacgcagc tggtgctgat gccccaggtt cttcactacg cgcagtatgt gctgctgggg    58020
cttggaggcc tcctgttgct ggtgcccatc atctgccaac tgcgcagcca ggtaagtagg    58080
aggggcggcc acgcctcgga ctcggctcgg gtttcagccg acctctgttt cctgcagcta    58140
gctcttgttc tacctcctct ctcgcaccct gcagtaactt ttctctacaa gtcctggaag    58200
gcccaggacc ctcccaggtc ggggctaggc tgaggctagg tacccagtca tttggccaac    58260
aagtgggtgc cacttggtgc ccgctctgga aagtgcctgc cgaaggtaga ggtgggggt     58320 cagggctggg ctggttagag aagcaaagga aagccaggtt aaaccaaaca gagaagatag    58380
tttttcccaa ggaaaatgct ctgggctgga gttgggtgtg agatggaagt gggaggagcc    58440
acgtgtggaa ccatgaactt agattttcta agtccagaga aaaagtgaa  agaaattagt    58500 tataaattt  gcttgaccca aatatatcag catatgaggc tgaagtttta catcagccat    58560
agagcacttg tttagccagt gtgaggcctt gtattcaggc ctcagcgctg acaggaaaaa    58620
aaaataatca aaaataatga aaatatttaa aaagaagaa  gaaagaaaa  gaaggtctgg    58680 agagatagct cagtgattat gagcacttac tgcttgcagg gacccaggtt cgattcccag    58740
cacctacctg tgttctgca  accaactgta accccttgttc tgtaaccccta gttctgtaac   58800 cctagttcca ggtgatctca aggcacacac acagtgcata tacttgcatg agaaacactc    58860
atacacataa actaatacag gtgcctataa tcccagcact caggaaggaa ggaggccagg    58920
ggagaaggat ccggttcaaa atcatccctg gttacatgta gggtttgatc aaggccagcc    58980
taggatacgt gacatcttgt ctccgaaaat caattaaact tcaaaaaaag aatagtgtgg    59040
```

```
gcgactggag agatggctca gcagttaaga gcactggctg ctcttccaga ggtcctgagt    59100
tcaagtctca gcaaccacat ggtggctcac aaccatctgt aatgggatcc gatgcctgca    59160
gagcaacagt gtacttgtat acataacata aataaataaa tcttaaaaga caagaatagg    59220
gctggtgaga tggctcagtg ggtaagagca cccgactgct cttccaaagg tcaggagttc    59280
aaatcccagc aaccacatgg tggctcacaa ctatccgtaa cgagatctga ctccctcttc    59340
tggagtgtct gaggacagtt acagtgtact tacaataaat aaataaataa ataaataaat    59400
aaataaataa atctttaaaa aaaaacttta aaagaaaaa gacaagaata gtgtggttca    59460
gacaggggta ggggtcactt ccataaagaa aggatgactg aggaatgtaa catcagggca    59520
tgcagcccct gaaagcagga agcaaagggg tcatgactag aaccttcgtt cccttctggc    59580
ctcaggagta ccggctcgtg catgagatct tggggttacg acattggtca agtcccctgg    59640
ggtgcttgct gatagctgta gttgtgaagc agggaatttg aggacaggac tgtgatcagc    59700
tgtgattcaa gagggctgct gtctgcaaac aggggagcca ctggccacct ttgaacactc    59760
gtacaagagc cactcacagg gtcccacctg agatgtcctg gggccacagg ctgggctttc    59820
tgtgcgtgct tggtgtgtgt gttgggggg tcttcccacc tgctctcctg cagtcagcca    59880
gctgctgcc tttcttcttt aaggcttgct tgcttgcttg cttgcttgct tgcttgcttg    59940
cttgcttgct ttgggaagaa cggatccctg tggagtcccc agcacccggc ttcccttttcc    60000
aaacacaggc cccaagtctc ttgtcatcac caaggggtgt ctggttgcct ctggctctcc    60060
atgttgactg tagctatgag gatctggagg acatcacggt ctgggcttcc gggctggtgt    60120
tcctccctgc tgctgcccag tgagaactga gccaggctttt tcagtcaac cattggagga    60180
gagacccaa aatagaaggc aggcgtctcg ctggggtctg ggggcaaggt tgtttgtcct    60240
gcgggtttca tcagagagag gccaaagaag ccttgtcctg acaaagctag gcctcacctg    60300
tgtgttcctg tccttgagca tctggggggcg ggggggttaa ctgcttgctg gtaaagaaca    60360
tactcagtca tacgccattc ataaatcaag agtatgttaa tgtttccctc agattgacaa    60420
ataccatgga cttggagaag aggttaagag agagattgta cccagtaggc tccaggccct    60480
aggttcaaat ccagccccac cagaccagac cagagaaatt caaacactca gcaggccagt    60540
cccgctgtgg ccacctccgc cactctcttc ctgtcggtga cttttctgctt gccggacttc    60600
cggggcgctt cgcccacagt gcagggtgga acaagactct gcaatcttgt tctcttctgt    60660
cccttttgctt ctggggggac ccagcgtcac cccagtgaca cggcatgcca tataaactag    60720
cttggttgtc ttccaggaga aatgcttttt gttttggagt ggtagtaaaa agggctccca    60780
ggataaggag gccattcagg cctactctga gtccctgatg tcaccagctg ccaagggcac    60840
ggtgctgcaa gaagccaagc tataggtgcg taccaggtaa ccccccctct tcaccccacc    60900
tactcatagc cagtagacct accgtctcta cctatagcat cttcctggat gttattcaca    60960
tggagagcag ttaccctcct gcctctcacc ctcctgcgag atgggaatct tgcctcggtt    61020
tcttggaccc tttcagtcat tgactctcat ttacaaagtc ctgttagaag atgacagtta    61080
gggctggtga gatggctcag tgggtaagag cacccgactg ctcttccaaa ggtccggagt    61140
tcaaatccca gcaaccacat ggtggctcac aaccatccgt aacgagatct gacgctctct    61200
tctggagtgt ctgaagacag ctacagagta cttacatata ataataaat aataaatct    61260
ttaaaaaaaa aaaagaaga tgacagttag gccagttgct tctcagtgtc ctatcccctg    61320
caggttgcta aatacaggtc cctgggcatc ccggaaagcc aagagactct cctagccaa    61380
aaggtttgaa aactttttttt tttttttggac ttcaagggca tgtaaaagga cacactgact    61440
```

```
ccagttcaga atagagagac tgaaaatgaa gacgtttaaa catcagttaa gcaccagcta   61500
catactcagt cagggcctga ggatagaatt tcatggtcaa gtacacaggg tgtgcgacag   61560
actgctcaat acagtctgaa tttagatgga gtcgtgtgtc cgccctgtgc tttgctgcga   61620
tgggtggtcc agtggtgag ccaccgagtc aggtatagct ggcgtcctgg tttacttagt    61680
agccatctcg caaggatcca ggaccgtact tctccaagat ctccaggtcc tgtagggatc   61740
aaggctcagg agagaggctg agccctacag ggtgtgtccc tgcctgggaa gggactggaa   61800
gagctgtggt ccctgcaatt tggggttagc agaggtgagt gagtgtctca atagaagctg   61860
ctattttagc ttgtgagcca acttgggtgt gagcactttc ttggagggag ctgggggtgg   61920
ggggtggagg cggggcttgg gggggcgggg aggggaggcc acagctcagc tcctggaggc   61980
cagctgacta tttgctgcaa tgtcatttgc ttgagaagca aataaggcag aactctggtg   62040
actgtgtgat tgtcctggtg agtgccacct ccctggagga ggaagaagct ctgcagctca   62100
gtgggtcccc atatgtccct ggagctgaga aagggtcctg ccaggaagag gtggggagat   62160
ggttagtgtc tgccagtcat ggtgatgttt gggtattgcc agagtgcgag gggacaaatg   62220
taggctccga gcagaggctc cgcagtccct ttagcccaga tggagcccat aggtacacag   62280
ccatagccct gtccagaccc taatagaatg aacaagattg gcttacctc tttactttcc     62340 cagcttggtc taatcctcgt ttggcttcaa gattcccctg ggtgcccct agtcctggcc    62400 atgtgctagg gagggcagtg tcctctgagg atcagctaca gcacatgggt ccttgcatag   62460
ggacctcacc ctccccccc cgaccccca gtgcctggct aagtgaaatt cggtggggcc      62520
ccacactctg ccatgcacct gggtgtgggg gtggtccta gaggctgctg ctgattgcta    62580
tagaatggaa acagacgtgc cgctagacca aagggtatta ttatatgaat aacgtccctc   62640
tgggtggatg ggcatttctg taaggcaagg gggttggggg ttggcaggca gggttggctg   62700
tccggccagc tgctgtgaac acagtagcct ttaagaaaat gacctgatcc tctgcttctt    62760
tttggtctgt ctctcattct gaattctcct ctgtcagaca cagtacaggg aggagccagg   62820
acagaggagg ggaaatctgc ccacccgccc tggctgccca gagccttgtg gctttgtgtg   62880
tgttttcatg ggagagacca agctacagag ttaactcttg ctttattctc tggcaacaag   62940
ggcgttctgg gccactcacg ctggcttcga acttgtggac atcctcctgc ctctgtctcc    63000
cgagtgcgga gattccaagc atgcaccact actgtgcctt gtgtcccctt ccccatttta   63060
cttctgtttt ggttttggtt ttgtgttttg ttgttttcgt ttttgggtt ttggttttgg     63120 gttttgaga cagggtttct ctgtgtagcc ctggctgtcc tggaactcac tctatagacc    63180
aggctggcct cgaactcaga aatctgcctg cctctgcctc ccaagtgctg ggattaaagg   63240
cgtgcgccac cactgtccgg cctttactt ctgttttttt gtctgtccat ttgtctgtct    63300
gtctgtgtgt ggtgaagcca gggccttttg cttagtgtag tccacctctg agcttcaccc   63360
cagcacttcc tgttttactt ctgagtgaga ctatctggaa tgctggggtg ctgtgtcggg   63420
ggtggaggag tgggatgggg ggtgctcgtt ggctttgatc caaagagaag acgcctccct   63480
gcagtttcct tccctgccac tagggggatc ggtatggggg ttgcagggca ggggtgccca   63540
gtgttcttaa acccggcctt ccattcattt tcctaagttg ggaagtcttt tcaagtcaga    63600
gtctcccaac ttaccaagcc atcctttcct gttctgcacc ctttgcccaa catcctactg   63660
tccctaaggc ccgaggccac cattacagca gtctggtgag agtgtgtctc tcttacctct   63720
atgaacaaga gccagttta atagctgttc ctggcccgtc aggtgacagc attttaaaca   63780
```

```
tgtgggcaga catttaagcc attcctagtt tctttgtgcg gcggtgttat ctacccactc    63840
cggactctgc cccccttcact gtaacaggcc agtctccctg gcctcagttt tcccatctct   63900
aaagggagag gttggaacca agagacctac atgactgagg agtccccgtg tctatagagt    63960
ggcatctctg ggttcatggc agacagggct ggatgtgtca ggaagtggtt tctgtgctgg    64020
tgggatgtgc ggtgggacta ggggaggtag gcagggcagg gctaggtgac aggcttgtga    64080
ctcagcttcc ttttttctcc acagggtcct gaagacacta taagcccccc aaacctgata    64140
gcttggtcag accagccacc cagtccctac accccgcttc ttgaggactc tctcagcgga    64200
cagcccacca gtgccatggc ctgagccccc agatgtcaca cctgtccgca cgcacggcac    64260
atggatgccc acgcatgtgc aaaaacaact cagggaccag ggacagacct gctgccaagt    64320
gagcctgatg ggccacaggt gtgctcttct aaatggcctg tgagccaggc tgtgggaact    64380
ctagctgctg tcagcccctc ctgtaggagc tggccctgcc caggctcctg acttccctca    64440
ggaagtcttt ctgtctttct ccatcagtct gaaagcctta gttcccacag aggacggatc    64500
tgtcactcct aggggctggg catatgtcgg cctcttgtgc caaggccagg caagcagctc    64560
caggtcctga ccagtttgca cacacactct ggagctgtat ctggcgcttt ttctatcgtc    64620
tctgctatgt cactgaatta accactgtac gtggcagagg tggcaggccc ctcagggtcc    64680
ttatttttca ggcatggggt caaagctaga ggtatgggcc gtctacaccc ccccgccccc    64740
cggcatctag tgtacctcac cagagggtat tcggaggccc agcatcctgc aaccgacccc    64800 tttttttctac tggaagagaa attttatcat cttttgaaag gaagtcatga ctgaagcaat    64860
aaaccttttc actgattcaa caacactggc ttctgtgact gttttctggg cagggctggg    64920
tctccagaat ccaggccaca tcagtaggtg ttcccatgac tgccagcgag tctcctggtg    64980
tgaggccagc accggccact agccatgttt ccacctcaag gctaatgtgg tatgtggctt    65040
ggatgcacca ggacaggcta gctctgtcct ttctctgtcc cgtggaacct tctgggcctt    65100
ccagcagtct gtgtccaaga tcagaacatc cttgtgaccc caagtgacaa gcctgcagcg    65160
tctgggggag ggctggaagg gagggtctaa cttttgtccc aagttcaagc aggggttcta    65220
cctggcatct ctgagagtaa aaccatgttt tgcccttaag ggaccactac ggaactgggc    65280
aatagatttt cactgtgaac attaaaaact acatagccgg gctggagagg tggctcagtg    65340
gttaagagca ccgactgctc ttccaaaggt cctgagttca attcccagca accacgcgat    65400
gactaacaac catctaatgg gatctgatgc cctcttctgg tgtgtttctg aagacagcta    65460
cagtgtactc atataaaatg aataaataat taaaaaaaaa actacataga cactcactcg    65520
gtggttgtaa tggtcttcac ccttcccttt cttagaaaag aatttgaatt attgtgtgtg    65580
ggtccatgcc atggcataag tcagagggtg agctctaaga gttggttctt ttctcaccat    65640
gtgggtcccg ggcatcgaac tcaggtcccc aagtttggca gcaagctcct ctagctgcgg    65700
agccatctcg ctggccttgc acttccttaa tgagcactgt tctctacctg ccctggaagc    65760
attgaaagtt tcctacctca tactataaac tgcattataa tcgtgagaca taaacttcta    65820
tataaggcaa acattttag tcttgtaaga cggggtctag ctttgtaggc caagctgggc    65880
tggacctcat catccgcttg ccttctgctc ctaatgctgg ggtgacaggc acccctcac    65940 catagccaga tttcttttttt tccaagacag gatttctctg tgtatcctta gctgtcttgg    66000
a                                                                    66001
```

<210> SEQ ID NO 6
<211> LENGTH: 70000

```
<212> TYPE: DNA
<213> ORGANISM: Mus musculus

<400> SEQUENCE: 6
agtgtcctca gaggccagaa gagggtatac ggtccctcat aactcaagtt acagaggatt      60
gagagccacc aagtggaggt gaaacagagt ccaggagctg gatcctcagc aagagcagcc     120
tctgcccata actgttgagc ctcgtcttca gccctttcat tttccaccc aagaaaaatg      180
aaaaatgaaa ggcctagggc agccacacag taaacctcag cagaagaccg gagttcagtt     240
cccagaatct atacagagcc gctcacaacc acctctaact ccagctcctg agacctagtg     300
ccctcttcta acctgagggc acccacacat ccgtgaacac agataaaaag ctttaaaatc     360
tttaagaata aataaataaa tagatagata ttttaaaaac aaaactccta atgacagagc     420
ttcttgcctc acctgtttcc tctaccccca gaggctctgt cacctaccta ggcatcaact     480
gggcacagcc cagacttatc tgaggacata acatgagggg aattgcctca ttcaattggc     540
ctgtggcaca tctgtgggag tagctcaatt ggtagggtac tcaacatcct ggccattgtc     600
tccagcacca cacagacctg gcacaatgga gcacatctgc agtcccagta tgggcaggta     660
gtggcaggtg atcaggagtt caaggtcact cttggctacg tcacgagtac cagaccaaca     720
tgcactactt ctcaaagaat ggtagggtgg aggggcagga gcactcactg gacactcttg     780
ccgaggaccc aagttcaagt attcctagca tccagatggt agttcacaag catttgtgca     840
tggagcctta tctgtgtatg ttcgtgagtg tgtgtgtgta ccatttcctg ctgagccatg     900
tctctggccc tgacttcatt tcctagggta ggaaactgag gcttacacgg gaccaggagg     960
ggctcacact gacacaccta gccctggtct tgtggcttcg attgtttctt ctctgggata    1020
gtaaacactg ccaactttcc tttcactggg tgctcgggaa ggcaaggcag aagaaaacag    1080
tggagtggcc cccaaagtgg gacaggcagg gtacatttca caggacattt tcactctctg    1140
gtgggaacag cgggacacag aagaagcctc atggactcca gtttcttttt cccacactcg    1200
ttggcagcct tgggtttgtt atccttgcga caatgccact gtcctcatga aacctggtga    1260
cgttggctga gcaaatacta cctccgatat tgactcaaaa cgtgtacagg ggctcaaagt    1320
tcaagttcag tggggcctga ggcttggagg aggagggaa acactgcct cctgtgatta     1380
caacattctt tagtatgaag tagagttccc tcaaaactag gtctcatagc caagtcccca    1440
aacgtcttaa gcactttgga tagatatcta ttgagtcctg ccaaccggaa aggaggctag    1500
agagaatgac catggagcag ccatcctctt ggcaaaacag tgggggctgt gaaaattccc    1560
tgtcacatat attaggtggg atagttaggg ttgggatgtt gtttggcctt ctacacataa    1620
gaccttggct tccagctcta gtactgaaaa aaaaaccaaa ccaaaacaaa acaaaacaaa    1680
caaacaaaca aacaaaaaaa cgagggctgt ggtagctccg tggcagagca cctgactagc    1740
atgcatgcaa ccctacgatt aatcagctta tcttattctt tccattgtcc tcaaacttga    1800
tatgtggcca aggacaattt gaacttcttg ctggatcac aagtgtgcat cattataccc     1860
tctttatgtg gtgtggggga tgggatctag gacttcatgc ctgctagaca agcgctgtaa    1920
tactgagcca catccccagt tgtggttttg tttttagatt aaaaataatg tgtatgggaa    1980
tgtatgaaca tataaatgca ggtgcccatg atggccagaa gggggagcaa gatccccagg    2040
agctggagtt ataggtgttt gtgaacattg agacttggat gccgggaacc aaactgtggt    2100
cttgggcaag agtagtattc gtacttagtt actgagcaat tcctccaac tctgtttttg     2160
ttttgttttg ttttgttttg ttttggtttg gtttggtttg gtttggtttg gtttggtttg    2220
```

```
gtttggtttg gttttttgaga caggctcacg ctgtaaccca ggctggtctc caactcatat    2280
atgatcctcc tgcctcagtc tcccaagtaa tgaaattaca gatgtgagcc accacacagg    2340
gcaaacgtat ccatcgtgag cagctggcac agtctatggg attgaaactg agaaagaatg    2400
tgaaaaataa acaggcgagc ttgagaaagg ttattctagc cttggtgcca gttcctggta    2460
tattttcagc gctcagggag tttaggttaa tgccccaagc ttccccatcc ccaccccgag    2520
gggcgagggg gaggttaagc tctttattaa tagccactcc gggagctaca gtccttggga    2580
aaagggctat ggtgagggta gaggaaggaa aatgaggtcc ccacaggata aaccaggtg     2640
caggcggctc tggctcatta tggtgcctcc ccaaggcacg aggtgtctga gagttccttc    2700
tgatgttgtc tccgcccctg ctcctgtccc tcctggccgg cagggagggc ctgctgtcaa    2760
ggccgctgag cctcctggac agacagggca cagggccaat ccagagggac gcaaagcagg    2820
acgccaagaa aagaggaagt gtccttgggg aggggaccgg ttaggactgg ggttctaggg    2880
agagaaggaa gggcatttaa ggtgagtcca acagtccagg acttaaaagg agccttaagt    2940
aggggggcagc aagaggtgac actagagcca tcgaggccga tgaggcccgg gggacagcag   3000
aaagtgtttc cagatagcac ctctgcagtg ccagccacat gtcacactgg tctctgcttc    3060
cacgctcagg aacaggtgct cagataagga tgcttaagaa gatggaaggc gtttgggtgt    3120
gtcagaacaa tgaaggcaag tgaaagaccc cgattctcta tgagtcccTT cacataaact    3180
aaaaatctca agttacacc caacaatcgc ctgtcctttt aaataataga ggtgtagggg    3240
gagatgagat acagcaacag ttaactacag ttggggggcgg gatcaagggg aactttcatt   3300
ttctctatgg aaaccttcca cggcaaggca gagaaagatg gaggcaaaca gggctcttcc    3360
atgaccaggc gtgcttgacc tcagagctgc gactcttcct tcttcagcgc atttatggag    3420
agcttgctac acgcagggcc tggagctgca gcctgggagg gcgccccatc tggcgggtag    3480
agtgctttgc catgtctggc ccgacttctc tacaccctgt tcacaactca ccctgcaacc    3540
ttcgttcccc gtgtgctgcc agcgatcccc ctccagaagc cactctgtcc gaggttccaa    3600
tcactcccct attgacacct attcgttctc agcgttcaaa gagtacttcg attccgttgc    3660
ttttgggcgc agagacttga atccaggacc ttacacaggc aaggaatgca cggcattgtg    3720
agctacccac acaccctaat tgttccgcag atgagggttc ccccgccccc tgacgatttt    3780
atcccaggga gactatgagt gtgttggcct ctggcgccaa cctgcccccg gatgtcaaac    3840
atctgttctc aaacttggaa cctgagctta cttcttcatt ctctgatgtt agacaagccg    3900
ttcttcccaa caccacccca agcgtcccac tcccctttTT taaaaaaaaa aataatcaac    3960
caaacaacca aacaaaccaa aagtctggag caaaatcagc ataactcccg cagggttgca    4020
gagaagtta cgggcggatt agtgtaaacc gcgagtgtaa gccaagtatg gtgcaaagag    4080
ctgttttgga catggcttta atgagttggt cccttttgta tatgaagaaa ctgaggctct    4140
cagggtaagg aatgttgtcc taggtctgcc gttggcaagc tcgggactta gcctcagttt    4200
ccttactgac ctcctccccg cagccccgcc cgtccaggc cccgcccgt cctgcccgcg      4260
ctgcagccca gctgggctca gccaatcacc cgcggcgcgc gtcggtgagc ctggcctcgc    4320
ccgcccggc ccggactccg ctcgctcatt ccgccgccgc cgtctgcaga ctcggtaaga    4380
caccgcgagg gcagcgctgc ggcaccgccc tgggctgggc gcgggtgt cattcttaag     4440
agtgtggagg gagacccaga ctgtgcccgt agggtacgcg tgagccgcgc attggagaag    4500
cagagggcac tccctccccc gcgcagtgac ggatctgggg gatcccggga cgggaggaaa    4560
gatgcttggt ccccagactg ggcaaaatgc ctccactcgg gacgcgtggg acctcggctc    4620
```

```
gtggtgtccc gccccacggt ggattcactc accgcgtggg tttggggtct tcattgctct    4680
gtgaaagatg cttatgatta ggcgtgactc cttggtccct gaccagtagg agtgtcaact    4740 cccttctga ccctgctca ctccccactc cgcgggtggc ttggggccag tgtggacgcc      4800
gagcgttctc caggctcttt ccaccgcta ctctgcaggt ggattggttc tcggggtccg    4860
tgagggtcgg gctcggcagt aggaaggatg ctcgcacagg ggacttggca ggtggccggt    4920
gccctctctt cgtgcgggtc cctgcagtat agccttcggg acacacctt ggcgcagaga    4980 cttaagtgtt ttgcacccct caccgcggtt ttgcccgggg ttcaagggca ggtgggtgtc    5040
agagactgcc caaggtcgcg ccgggaccag agcccgggag ggtgggggcg tcacgtgacc    5100
tggcctgagc gaacttggcc tgggacagcc ggacagcacg gtctgggcaa ccaggctgtg    5160
cggtaacagc gggtacccct cgttttctt catcttattg tgaatcgggt ctggttttcg     5220
ttgatgtcac agaacacaga tgaacgctca agttttaag gagttaaaaa gttcctagtg     5280
tgaaccaggc tacatacaat caagctcagt actctcagct ctgggccgac tctcgttccg    5340
tgcatttaaa tagttgtcca aaaacagatt ttagtcggaa actgctaact ttggaagttc    5400
gcaaataaaa tgaaagtgag tttagaagcc tttcggaacg cgtatttagt tacagcattt    5460
tgttgcacag gcgtctggtt tctggtcatt cctgatattc aagcgtgttt atcactgtca    5520
aaaccacaag ccaaatgact aaaacacagc tttggccttt tatttgtgcc agcaagcata    5580
catcaccacc ccccttcc tagtcggtcg actcaggact cagtgaggac ctaaagcaga     5640
ggactgtggt gtggggagga cagtgcttgc tccggggcag tgcagagtag taggtaggtc    5700
tgggcagcgt ccgcattcag agtcctgggc tagactggtt ttgctgcagc acccggagct    5760 ctttttgtcat gtaaattatt gcttttctta actaaagcct cgctagactt aaccttacac   5820
ttgaattttc tcttttatct atttatttac ttttaaaaaa tgagatagga tctcatgtaa    5880
cacaggctgc cctccagcct gctctgtacc caaggttggt tttgaacccc cgatctcctt    5940
cctgcaccca cccataagtg cggtgattat aggcgagcac caccacgccc ggctttgaac    6000
tccttaaccg tctttggaat caagctccgg ttaggttttg tatcaaaagt ggccgaagcg    6060
gcttcctgca caagacaaaa cctttcgagt ttgagctaga aagccacctg actgcagatg    6120 agggggtggaa cgcctccctt ccgccgccgc tgcgcttggc cctgacccag tggtcacgaa    6180 accgcagge ctgattctct cgggagtttg gggcgctggc cggggtttag ccaaccctga     6240
ttcctcttgc ccattttgcc cattcataaa agcgctgcaa ttttactttt attttccct    6300 tgggttcgc agcgaaaccc ttcgaggcac ggtgccggct ggctgttttg ttgtatgcga     6360
cagctgtcct cggacaaagc ggatcggtga ctccgggatg gcagcggcga cgcgtcgctc    6420
cggaaggcct gcgtgggctc ggccggtgga acaggatccg agcgcccgg acgcgccagc    6480 acggggcgg ggcacccgta acctttcccc tacttttctc agccgtcacg tgacccggct    6540
gggtagggga aggggcgggg cgggaagccg ctgttgttag tgcccttccc ttccccagcg    6600
ccttgaactt gcagtctgga tctgcaggcg gctagagcca cgcgactttc ctgtactttg    6660
accgtttgaa ggttttttt ttttttggt tagaaaatat gtttagtcac tcttcagtca      6720
ctcttcatag atatttaccg gtaggcccga gtcttaaagc tggtggaagt ctgcatttga    6780
actagtttag aataaaatgg tagtccaagg tggataattt taaagtgtgt ttagcagact    6840
ggacagtccc ctgaaggagg gagagtcgct cgaatctggg agttaaggga cagcctggga    6900
ataggcaaag atccatcctc agctcgggaa agaagaaaaa gggaggtggg gttttaagcc    6960
```

```
ggtggcggtg gcgcgcctag taggcttaaa aaggattact gcacacttga attaatgcca     7020
atttaagctc ttagtgcaag aatttttgtt gtttggaaaa taagcctgct gccaagcctg     7080
actaccctaa ctcgaagggt gaaaatgatc ccgacttctg cacaccgtgc tatagtgtgc     7140
actcaaccgc caccataaat aaataagata catggttttg ttttaagtaa aaagcaatac     7200
aagcatattg tgcaaaatta gaaaggcaaa aatgggggtgc gatgcagtca cctacttact    7260
cagtagttac tgcaaaggcc accactgtga gcagttcatt caggactgtg atggtgtgta     7320
cctgtaccat ctagctcttc ggaggtggac agaggagagc cggacttaag gccagctacc     7380
accatccgtg agttggagtc ctgtgtggga tacacaagaa cttgtctcta aaccaaacct     7440
agactgcaaa gtttgtttat tttttaatc tcttacctaa cacaaggagt gagttctcct      7500
tgttgatttc aaatatctgt tgccttttgt actcttcacc ttgaaccccg tgcaaatatt     7560
gaggcggaca ttgggtcccc acaggccctg ggctaaggcc agctttgctc tgttgaggta     7620
acgtggcagc ctggttctga gaagtgccca ccctttgccc tttttgtgcg agttgttctg     7680
accttcagga atgtttttcg gaagttaata gcagcaggca cactgcccgt tcgcgcccc     7740 gacacctggg taactgccac tttagaaggt tgggaaatag gatggctact gaccttgcct    7800
ctgaggagtg ttgcacaccg accatttagg tagaaatgta agagaagctt ggtgtggtac    7860
aaaacactta taatcctagg gtttgggggga tggtgctgag gcaggattcc gtgactccat   7920
agtgagacct tgactcaaaa aacaaaatta accaaaccaa acccagcaaa gaccggatta    7980
ggctgggttg tccatgccta taatcccagt ccttagtagg tggagacaaa attagtagtt    8040
caagatcagc atcagtgatg tacctggttt agggctagca tggactacat aagacctgtc    8100
tcaaaaacaa gacaaaatac tgtatgcact ggtattaatg cactggtgat atatattgga    8160
gttatgcact ggtgctgtgc actggtgtga atgcactggt gctgtgcact ggtgctgtgc    8220
actggtgtga atgcactggt gctgtgcact ggtgtgaatg cactggtgcg aatgcactgg    8280
tgctgtgcac tggagttgtg cactggtgtg aatgcactgg tgctgtgcac tggtgctgtg    8340
cactggtgtg aatgcactgg tgctgtgcac tggagttgtg cactggtgtg aatgcactgg    8400
tgctgtgcac tggtgctgtg cactggtgta aatgcactgg tgctgtgcac tggtgtgaat    8460
gcactggtgt gaatgcactg gtgctgtgca ctggtgctgt gcactggtgt aaatgtactg    8520
gtgctgtgca ctggtgctgt gcactggtgt aaatgcactg gtgctgtgca ctggtgctgt    8580
gcactggtgt gaatgcactg gtgctgtgca ctggtgtgaa tgcactggtg tgaatgcact    8640
ggtgctgtgc actggtgctg tgcactggtg tgaatgcact ggtgtgaatg cactggtgct    8700
gtgcactggt gtgaatgcac tggtgctgtg cactggtgct gtgcactggt gtgaatgcac    8760
tggtgctgtg cactggtgtg aatgcactgg tgtgaatgca ctggtgctgt gcactggtgc    8820
tgtgcactgg tgtgaatgca ctggtgtgaa tgcactggtg ctgtgcactg gtgtgaatgc    8880
actggtgctg tgcactggag ttgtgcactg gctgtggcac ttaggaaaac aaaggtcatc    8940
tatactcttt ctgtctcctc ctcctccatg tgtggtccaa ggagctgagt ctcacttctg    9000
tttcttaagt cccactagaa tttgtcttcc tcagtctccc tgaccctatg caggcctgca    9060
aatcattgct gaaggaagga caggtttggg gcgccctttc tccgctggac tgaaccagcc    9120
tactgatatt aaggggggtga gggccttttg gaagtttcac tggctacacc cctagaaatt   9180
aatgcccgag agggagggct tagaggaagt ggttgggccc ctagctcagt gtgcttccat    9240
ggtacgtggc tctgggatga cttgcctgac atctctgtcc ccatccaggc cacatgctct    9300
ctgcagtgac cacgtccaca cccacctctc ttctttttagg gtttccttgg ctttgggtaa    9360
```

```
agccatgaaa agagaattca acaagcctcg ttatcatggc ctgaagggat attcgtatgt   9420
ctacaggaca gggacactga gtaactcccc acaaccctat ccccttgta gtcctggcta    9480
gcctgaaact cactatgtag accaggatga cttgaactt gtgatcctct tgctccactt    9540
cagataaaaa cttggcccttt tatgaaactg gctggtttat taacatactc accctagct    9600
tccagcagct gctcctggaa atgctacaag gaaggtccag ccccggagcc cattgcgtcc    9660
tgcgggcctg tgaaggtatt ctgaaaagat atgaatgagc tgcccatgtt agtcagttag    9720
aagataggct gaggtaccat atgctcgccc tgaagcattg agctgggtgg gccttggggg    9780
atagagccag gacagacacc cactttcttg aaggacaggt gttgactgct caggctcctg    9840
gtgggataac agagtgtggc cttgtattaa agaacacgtt ctgtgtttgc acactctagt    9900
atccttcgat tgatgggagc tgaggcagtc tgttctgccc tgtgctgata aagcatagga    9960
gagaggctga tgtttgtcag tgagctgcag atctggaagt gaacccagat ctgtgttgta  10020
gccactctct cacctgctgt catagagcag ggctcttagt ggcagccatc acctctatat  10080
atgcagactt agactgatat cgaagtgcgg gcatgtctgg gtgttcattt ccttctctgt  10140
caaatggcag ctctgatacc tgctctcctg tgtcccttga gtcccaggag actccattaa  10200
ggagtgagac ctcagtctta gcattcaggt gacaaagata ggctgatctc taggtttgag  10260
gctggctttg tcttcccgca gtatgaccta tgcaaaatcg tgaactttat ataaaaaag    10320
gatttatttt attcatcttt tttgttttt gtttttgtt ctttgttttg ttttaggatc   10380
gctatgtata tagcctttac tagcctgaaa cttgctacat agaccaggct agtcttgaac  10440
tcacagatat ctacctgtct ctcgctccag agtgctggga ttaaagtgta ccaccacaca  10500
cagtgctttt tacattttta acttttttat ttacgagtat gctatgcatc tccgtgtgcg  10560
cacctccgat ggctgggggc atcagctccc caggggctgg agacaggcag ttataagctg  10620
cagaggcact aggagctgtg ctcactcctc tgaagagcct caggcactct tagcctccct  10680
ctagcctggt ccctgatgcc tgaaaacacc acacatccca tggaaagtga atttagaagg  10740
ttgactttgg atcttctcct ggggctaatg aggtgaagtg ccatcttcca tgtgagtctg  10800
ggtgacttca gcatgaccca caactgtgag gaggaccaga agcccttcac aggacattat  10860
gttgttaagg tgtgaaggtg tgacagacaa gcagtagatt gaatggactc cgtgcttttt  10920
cctttttttt ttcccactgc atggagactg gctatgagga ttattgacga acttgtgcaa  10980
gcagcagaca ttcttaagcc ctaagccatg tctccagccc cacctaacag cattttctac  11040
ctggaggtgg cctgtggcat gtgaccctg ccccacacat caaaacattt gtagatacag    11100
gttctagacg ccagtgtcag gactgcaccc gggcgggttt tctggtggtc agatctcagg  11160
ttgctgaggt gacaaacata gacaggatgt ttagaacagt ccctgaggat ttgggaacgt  11220
gtataggac agtggtatga ggagaagttc agttttcttg agctaacaga ttcatgccac    11280
ttcctggcag tcaagagttc aggctggcat cctgttctgg caagattgga cccatgtgct  11340
gtttcagaat ggatggggta gactgttagc cttgttaaag tgtatttcac gtcttattac  11400
aaatttttac atgttttgtt gttgttgttg ttgttgtttt ggtattgtga ggcagaggtg  11460
tgtgtgtgtg tgtgacctgt ggggaggtca gaggacagtt tgtgggactt ggttctcttc  11520
ctctcctgtg cgggtctctt gaagattgaa ctcagttgac ttggcagcaa gagccttctc  11580
ctgctgaatc atgttgctgg tcctcttgt tactttgttt tgcagttttt gagacagagt    11640
cttagatatg cttggtgagc ttgaactcac tatgtagttg aggacaatct gatcctcctg  11700
```

```
cctcccccctc ttgagtactg ggattacagg tctgtgccac caagcctgct ttagtggtgt   11760
tagagatgca gggtcattcg gacttacccc atgctagaca agcactctgt caactaagcc   11820
atgtccccag tcgtggctac ttcccttaga agtgtgtcct ctgctggctt ccccatgtgt   11880
cacatttctc tgattgccat ttcttaatga tgtgctgcag tcgcctaaat tggattttgc   11940
tttactttga acttttcttt actaagtagc tctagctggc ttagaactgg agatgtagac   12000
caggctggcc ccaaatgtac agcagtccct ctgcctgctc ggattacggg caagctccac   12060 cacaccggc ttttatttca ttattattgt tatcatttta aatggaggca gggtctctgt   12120
agcctcagct ggctttatgg ccacagagcc tttgcattcc tgattctgtt gtcttcagct   12180
cccaagtgct ggagctggaa cgattcggca tcctgtctag catgggtttt tacagtgtgt   12240
ggtaggcggg acttctcttg ttatttgggg ggaatgtaga ctgaattgaa aatagattaa   12300
aaaaaaaaaa gaaaatagat ggaaatctta cttttaccat ccaaaaacta accctgctta   12360
gcttctttta aaaatcagac catttaaaat ggtatggcca gggctggaga gatggctcag   12420
cggttaagag ccgactgctc ttccaaaggt cctgagttca attcctagca accacatggt   12480
ggctcacaac cacctgtaat gggatccaat gccctcttct ggtgtgtctg aagacagcaa   12540
actatgtact cacatatgta aaataaataa ataaatcttt tttaaaaaat taataataaa   12600
atagaatgat atggccatag accagaattt gttttctaac ctgatctgaa ctattgtgtt   12660
cagccaaaca gcacaaatgg cttatggtga tatgccatga tgtgggaaag tcacctaggg   12720
ctaaattaca taatgcaaat gaagactgtt caggcatgaa ttccaaattt aacctttcag   12780
ggtgagttcc tgtgacctct ccacctatac agtaagttaa caacaacaaa ttgaaatctg   12840
gtagccaatg tgacagtttc caaggtggag tctttcaagc agggtctagt gtcttggtct   12900
ggattcgttc ttagattgga ttaattctca taggtacagt gccttgggcc tgctttctct   12960
cctccacact cttccactct tgcccacgct ccaacccctc cagtgccttc tcccatccca   13020
ggacatagca taaggctctc accgagaagg agtgatcctg aactctccag tctctggagc   13080
tatgagaccc ataactctct ttataaagta cccaccttg gcaactctgt tacagcaact   13140
gtaaatctac taagacattc cttcaccttc ctcataccc aagccagccc acagaaggca   13200
caaggtgcaa aggtctcatt tctatttggg tatagcagtt gtactcagat ttttaagtct   13260 ctttttatt tttgatgtgt gcgcatttca catgtgtatg tagcccagag gccacaggca   13320
gtgtcatctg cagttactct tcggcttct ttttttttc tttgaaagga aggttacccc   13380
taccaagtct ttcttgttta ttttagattt gaagtgattt acagaactta gatataaggc   13440
tttgaaacct ttctttcatc ctagagaagc tcacatgtat ttgtcttttt aaaaatattt   13500
ttattaggta ttttcctcat ttacatttcc aatgctatcc caaaagtccc ccatacccctc   13560 cccccccac tcccctcccc acccactccc ccttttttggc cctggcattc ccctgtactg   13620
tggcatataa agtttgcaag tccaatgggc ctctctttcc agtgatggct gactaggcca   13680
tcttttgata catatgcagc tagagacatg agctctgggg tactggttag ttcataatgt   13740
tgttccacct ataggggttgc agatcacttt agctccttgg gtactttgtc tagctcctcc   13800 attggggtc ctgtgatcca tccaatagta ttttttttc tttgaaacag gagtgtgtgt   13860
gtgtgtgtgt gtgtgtgtgt gtgtgtaatg gccttggcta acgtggactt atttattgac   13920
caggctggcc tcgaactcac agagctccac ctgcctctgg ctcttgagtg gtatgctcga   13980
ccatgcccag cctctctaag ttacagccat ttctgtttag cggagcagag cgctcccaga   14040
agttagatcc cagcagcagc atctgtccag gggcaaggcc cagggttcat cagcctggtg   14100
```

```
ctgttccttg tgagggatgc ctgccatgtt cctggatgtc ctgcctagaa ttctgttaag   14160
gtgccacttc ctgtgggtaa cccttttctct caggatttcc agaggttgtt tactgctagt   14220
caagatggac agctggtgag ggattagagc tgcaggcaga gcctgtgtct gcctggcaat   14280
gaatgatgtg attctggtgg gcacctaggt cacactgata agagtcatta gccttggtcc   14340
gagtttgtag taatcaagtt ttcctgttgg ctaccatcta tcattttggc tacagcagtg   14400
acgtaagctg gtgtgtgttg caactgcagg aatcttttgc tagcctttgc tgtcacagct   14460
gctactgcac tttggaaggt aaggacatgc ccactggagc tgagcctgga cctgattcct   14520
gctttacagt tggctagcta tgaccttacg caagcgtttg acatctgagt cttgttttcc   14580
tcgtcagtga atggggacaa ccggggattc attaattaga gttgtagtta gaatttaaca   14640
agctgatgga tgagaaacaa attaataata ataataaaac cggcaggtgg cccatgccct   14700
taattccact tggtaagcag aaggtggaat ctgtgagtct caggccaggc agggcctccc   14760
tcatagaccc tgtcagaaga agaagagaaa aggcttggga tgaggatacg gttcggtgag   14820
ttatgtgctt gccgtgcaag catgaggagc tgagtacgga tcccagggcc cacataagaa   14880
gccgggagca gtggtgcata tctgtaatgc taaccctggg attagagaca gagaccggag   14940
gaaccctggg gctcgctggt tagccagcct ccccacatcg gcggtctctg ggctccgagg   15000 gagaccctttt ctcaaacaat aaggtaaaga gtgatggaca ccgatttgga cacaggcatt   15060
catgcacaaa atagggaggg cattgtttgg tttgtgccaa gcagttatta ggcaaaccccc   15120 acaccttctt ggccatgaaa acaagcctgc taaccatcca tgctagtata cggtgagtca   15180
cctgcttgcc tgttgtcttg tctaccgacc tatctggctc cccatctgtg ggctgcaggg   15240
ctgtgttgca atactccctg gggcccagaa tccatttgca taattcagtt actcagaagc   15300
ctgtcatccc tgggtaggtc ttattgtttg atttatatgg tggacacggt tttctcattg   15360
cagtttctct ggcatgtgcc agtttctggc ggtgtgctgg gcctctcctg aacttcgccc   15420
tccttcccta gctgactgcc tctcaactct gcagccctgg ggagctacag gaagagcaga   15480
gaggctgaga gggcctggtc gtggggtggc agcttggtgg catggccatc gttagggctc   15540
atgggctgac ctcagaggtg aaatggtttt gatgcaggcg gcttgactgt ggagaaagca   15600
agcccagtag ataagtccat cagccaagct cagaggactg gcgcttgaca ccaagccatg   15660
ttattaaaat gaagacagtc tcaagtcagc aagaagcctc agcagataaa gtgcttgctg   15720
cgcaagcttt gtgacctgag acaactccct gatcccacat acatgtagaa gataagagac   15780
tccacagagc tgtccactgc ctctgcacat gctcagtagc gtgtgtcccc accccacccc   15840
accccctcca tgcacaaaca ctagaacaat actaaagaca aattaaaaaa atgaagacag   15900
ttgtggcaga ggtaattgtg ctgcagcctg cagggttctc atgatttgat caagagcatt   15960
aagctttggg gtctttgaaa agctttcagc ttattggggg ggggtgatt agacacggct   16020 tggaaagggg gaatcctttg ccagagagca gaggtgagtg cttgagtgcc atcttgtgca   16080
tctctgtgct ttgggaatgt gaagtcagta gctgtccaaa accgggtcct gagggggcta   16140
actgtgatga aggtaagaac aggtatgacc cagtagggc taaggaaatg aacagacag    16200 tgaagtgctt gccttgcaag cgtggggacc caagaaggt caggtgtggc agtgcacagt    16260
tgcaacccca gctcaggaga ggtgaattca ggagaacctc tggggctcac caccagccaa   16320
accagcctcg ctgaattagc cagggagaga agcttggccc ttcaggaaca cacccagga    16380 ttgatctcag gtacacacac acacacacac acacacacac acacacacac accaagagca   16440
```

```
tagtgcaggc agagatacaa catagcaagc aggtgccagt taagcaccag acctaatatg    16500
tgtccttagt ttttggtgga ggtctcttgt tctgcattgc agtgagggc ttaggagact    16560 aaagtagccc tctttgggag ttcctccttg gcaagtgagg ttcgaggctg gtatgtaggc    16620
agggttgggc ctggaagcat ggggacacct gcgacaagga agttggcagg taggatttgg    16680
gagtgagcag tcacccacca cactaacact gccacttggg gcagagcaag agcacaggtc    16740
tccacgggag catctttgtg ttctctctga caccagaaac caagcctagt catacaccta    16800
acggaggttt taactctagg cttgtgggt gtattcctgt ccgtgtctaa ctctaggcct    16860
tgtgggtgca tccctggcca tgtcctcctg ggacctgggc tagggtagag gtttctgtca    16920
cagaaaccac ctgcagtttt gccctgagcc attgtgagga cacagggcaa gacactgtgt    16980
tgtgttagga acaatcccag agggggcctt cctgtgtacc tggccagact tgcttctggg    17040
ttgaagctgt ccgtgtgttt accctacagg gtgtgtccca tgtaacccttt ttcctctggt    17100 tttgatttct aatccaaagg ctaaagctag gtgtggtggt tatatatact gtaatcccaa    17160
tatgagggca gccacaaggt caaggccagt ctggtgtaga cactgagttg tccttgctga    17220
gcagcttggg agggacagtg agtggcgagag gcaggtcaa agcccttctc tctgtgccca    17280
tgtgtctcca tcatgcttct gtccagtgtg tgctcttgtg gccctctttg aacttgggtc    17340
ccaggtgcat gccctacagg tatagtccct gtggtcctgg tgctgtgatg gctcagcccc    17400
tgggggaata tacaaagcag agcttcatgg ggcacttggg acatcttgtg agcagtaata    17460
gaggtcgggg agttgggggg gggcactgaa aagccgagtc tatacccagg caaagaaggg    17520
tgcaggttga ggaggtgctg gtgggctaac acacctcctt cctctgtggg ttctgtgcct    17580
gggtgagtga agcagaggca gggagattat tttgggtaac tgatggttcc tgtgtgcccc    17640
actgaggcag gccaagtagg ggagaggtca ggtcgagagg gtgcagcttg agagatgggc    17700
tgatgtccag tctctgtagt ttgggtcttg gaaggtgggt ttgtaacatc tgatcacatg    17760
cacaggttgt agaggtctgg ttagggacag gggccctggc tagctcctag ggtaaagaga    17820
gccaaagaag ctcctattag tgcagacaga gatcggggct ggaggtctag cagacaatgt    17880
ggtgggcctg gcctgtgtaa tcgaggactg gttgtgggaa ggcagtgctt tagtgcccc     17940 tgcatggagc caccatggag gtctgccggg ccctccctgc aacagccttt ggaagggagg    18000
aagcagctgc ccaatgtcag tggtctgtat ccaggcacag ctggcttgcc agacagaatg    18060
gctgggacag ttggccccga gggccttcct tccaggacgt caggttccca gcttggtaga    18120
cacaagaatg cagccttgtg cccaggctgg gcagggtgtg atggcaggaa gggagagtgg    18180
gaagggagag tgggagtcag agcagtcagg gctcttactc tccggcctca ggtgccagct    18240
ggggaatgga ttggctttct attggcaagg gcacaccaaa gaagaatggg ggatacggca    18300
agatttgtgg accacatgca catacatgct tgcatgtaca aatgtgtaca ctcacacagg    18360
tagcccatgg ctgctcagaa gcccagggtt ccagggaaga ggtgtctgaa atgtctgcgt    18420
gtgtgtatca tgtgcattgc agtggccttg gagcctagaa aagacattg ggccctctgg     18480 agttggagtt caggcagcta ttgagcctca tagtgttggt gctgggaact gaacttgggt    18540
cctctgcatg aacagagtgt gttttttaact acctagccac ctctccagcc cgaggtgttc    18600
ttatttattt attttttactt tttattgatt ctttgtgagt ttcacactgt gcaccccagt    18660
cccactcatc ttcctgtccc ctcaggtcag cccttgtaac cccaaaataa cacacacaca    18720
atagaaaaaa catctcatca cataagctgt agtgtgttag tgtgtcccac agtatatccg    18780
tctgtccaca catattccct tgcaacaagg agtcattgga agtgtctggc ttctgtgaca    18840
```

```
ccatcaatac tgggtcctca ctgggtctcc tccaggttat gctgttgtta ccctgtgtcg   18900
tggaggttct gcacctttgg atcagtagta ccagcttttc catgcatccc agcgattgac   18960
agatgataca gattttgggg tgggccaatt cagtgccctg ggtctgggcc tgggcagtag   19020
ctgagctgat ggtcagcaca ctggctcttc ctcaccagca ccactagggc aagttctcca   19080
gcattgtttc agctaagcca tccaatgcca ccatcagcag gaggcagagc tatgccctca   19140
ggctggttca cccacaccca tgccttcaga gccagctcca ctgtgctgcc cagtcaaggt   19200
gcagggccca ctttccccag ggctgcaacc agtaaggggg cagggccagt tctcccgctc   19260
tcacactctt ggagctggct cccccttgcc tttgccatca gagccagctc cactgagttg   19320
cccaggcaag gtgcagggcc cactcttccg agtgctatag ccagtgaggg tgcagagcta   19380
ggtctcccac tctcatccct agggaccaac taactaccct aactgctgag atggtaaggg   19440
aaggagggaa ggcatcaccc ccgcatcctt gccatctccc agcagacaag tggcagagcc   19500
tgcctccccc ccttgctctt gtcctcaggg ttggagcacc cacacactct tgaccagggc   19560
cagcccttct gtgttgtcca ggtgaggggc aggaccagct catctgctct cacagccctg   19620
tggtcagctc tcccaactgc cacaggtggc aagagaggag ggaagtgcat cacggccaaa   19680
accacatcac ctcctggcaa cgtggggcca gctctccccc acccccaccc ccatccccac   19740
cccactccac tcttaccctc aggggaccag ctcacctgtg ctcccaccac cagggccagc   19800
tctgctgtgc tgtccagggg aggggcaggg cctgctctcc cgagggctgc agctggtgag   19860
ggacggggct agctctcgtg agtccactgc cagagtcaac tctcccccact ctcacaccat   19920 gagggccagc tctccagagt gctgtagcca atgaggggca gggccagttc tgcacagccc   19980
ttggtcagcc ttatggtccc ctatggctgt cccaactagg aacttgccca tgtcctctag   20040
tggtaatatg agtcaaggat agaaacaccg gcccctgcca ctgggtagcc attgactcag   20100
acttggccct taacagcagc aagctgggac ctgtaacaag ctcaggtggc agggctggcc   20160
actcacaaca ggcgactcct ctccaccctc gagtctccag tcccatctct tcataatact   20220
caagctgctg cgcttctccc tctcttccct ctgaccaccc attcctgcga attgtggtgg   20280
ctcctgctgc aggctggtca tgcagttggt ggccctggg tgacatcctc agtctgtaca   20340
acagagcagc agcctgtgct gtgtgccaga gggcagtcct gtgggtggca ttgtggtctg   20400
caggccttgt cttccttctc gttacactgc gtggtgacag gcggggctct gtgtgtctgt   20460
ggcctgcctg tgccacgggg cagctctggc caccaagcca ggcatcaaac taggatgaac   20520
aaatgactgc cctaacccta taaggttaga ctgctataag gacagcaagg tgtctcttcg   20580
cctttggctg ggggttgggg ggtgctgtat tattaattga agaggaccag attgccatag   20640
gtctgtgtca ccaacaggcc attgctggag caggtacaca ggtgaagttc tgtactgacc   20700
tgtatgtgtt gtgttttata actgagcatt tgaggaagtg ttcagttaag gccaagttca   20760
tggaggcttt gggggaactc ttgcaagctc cttggatttg tggcattttt gcttcctcca   20820
tgggactgtg tataccccag taccttctcc ccacacatcc agccggctct gccaggtgca   20880
ccaggcctcc aatcccacgc ttgagggtga actcgctttt ggtgctttgc agagagctac   20940
tcattctacc acagtggctt caaatggtag gtgagggga ccgagggtgt ctgacccgca   21000
gcctgtgggg cacatgcagc taaggctatg aaaacagccc agcacatgct ccatagcatt   21060
gagtagaggt tagaagacag ctttcagggg ttggttcgct tatcccaccc accgtatat   21120 tctgggaatt gactgtgagt gggcaggact tggcagcatg cacctgtccc cggtagcaat   21180
```

```
cttgctggcc caggatgttt ttccttttt ctttttcgta acttgattga ttgttgtaga    21240
taagtaatgt tctgttgaaa gtcaaaacgt gagacaccct gcctacggtt actttccctc    21300
gagggcctct gggatgctgg ctctgagtca gggatgaaga gagccttccc cacacgggcc    21360
tgggatcagg tttactaagc agaactgtgg tgactgggtt gggactctct gggactactg    21420
tttctggggt cacagagcct cccacaggga catctgtgcc cacctgaaaa ggagggagct    21480
gcaggtggca gtttctgcca ggtgtggggt gtggtctcca gggcaggaag agaatggcag    21540
gaccagcgtg catcccgacc agcaggtgtc attgggtctg gtcaaagtgg agagtggcgt    21600
atgtacacac atgaactcaa tccagatcag gccacaaaag cccaactggg caaaacagtg    21660
atttttggcg gggagaggta tttacgggaa tatagggag ggattcctta ctggagcaga    21720
aattactcaa agacagctgc cttcccaagg cacaccccag catgggtgac agcccacaaa    21780
gctgggaact tagagcacac tgcacacact gatggcccct cacacattgg agagagttct    21840
ttccaggagc ctcggttagt ctaaacctct atcagttagc ttggctggtt tctgcttctt    21900
ttaggcagct ggtctctaga ggcttctttg aagcttgtct tgtctttgtc ttagtagcag    21960
ctctgttgtt gggctagtct cagagggacc caccgctttt attgctttct ctgtcagtga    22020
gtgcctagtg gatctggtca gtttcaggga cttcctggag gtgtttaccc ttgttaagga    22080
gcctgcctgc atgatggggt gttttggagg aaatggatac acaagaagtg ggcatgggat    22140
gggagttggg agcttgggtt gctgcagctg ccttcccctc cctcctgact ccacttgcag    22200
gagtctgctg tgctgtacgt gggtggagca agtgcttact tcacagcaag catgggcacc    22260
cagttctgct tagcatccat gagagctctg gcttactgaa cagacagctg tgtgggtaca    22320
ttcagagctg tggggagacg atagacttga acagaggaag agctcagagg atgggcttc    22380
ctgtggtcac tgcccacctt tccgggctct cactgaagct tgcccactc ttcctcaccc    22440
aagccctagg tgccatggaa tccatgctgg gattcgtgtg ggtcagaggt cagccgtgat    22500
tgtcattcct tgcacagtct gccttgtttt tttgaggcag ggttgaagca ggctggctgg    22560
tgagcccaag ggatcctcct gtgtctgcct cccagtgttg ggattacatt gtgcctggct    22620
tttttttgtag attgagctca gatcttcatt ccgctcagca agggacgcgc ctaacagtct    22680
gagctgtctg cagatgcttt ggtatctgtc ctaccgcacc agggatccc tgaaaaatta    22740
cttagttctg gagggtgata tttgttctga atgaagcctt ggtgggaaca gtggtggggt    22800
ggcctgctag agccactcct tccacactga tggccgcaac tgtgtgacca gagatggatt    22860
tgatgcttaa gtgtaagtgt taagaagaca acatttgtgt tttgtgagag acatttcct    22920
ttttttcctt tctttcttca cagttttttc tttgtgaatg tgcagtatat tcatgtgtat    22980
gcgtgccttc atgtgtgtgc atgtggaggt cagaggtcaa ttgtcttagc agtggtcagt    23040
tttctttcca cttaaaaatt ttagtttagc actggggagg cagaggcagg aggatttctg    23100
agctcgaggc cagcctggtc tacagagtga gctccaggac agccagggct atacagagaa    23160
accctgtctc aaaaaacaaa aacaaacaa acaaacaaaa ttttagttta ctattactgt    23220
gtacatgatg tgtgtgagag agagtgggga tgcatgcacc ataatgtatg gagggcagag    23280
gacagctctg gaagtcagtc ctttcctttc aaatttttt cctttttaatt aaaagaaatt    23340
tggggggggg gtgtgcacgc gcatgtgtgc acatgagtgt aagtgtcctc agagagcagg    23400
attaggaccc aactcgggct gttttcttca ggtgcttcac aactgaacca cctccctgtt    23460
ctgttttttg tttctttgtt tgtttatttt ttaaagacag tttcttactt ctgtaggttt    23520
cacagcaaac ctcctgcctc aaccactcag agtctgggat tgcagatgtg aactaccatg    23580
```

```
cccagctgag acagggttgg ttttttttttt cccctaagtg atatgtttag cagggcgtgg   23640
tggtgcccac actttaatcc cagtactggg gagaaagagg cagaggggtc gctggaagtc   23700
caagaccatt ctggtttaca gagtaagttc caggataact agggctacat ataaagaccc   23760
tgactcaaac taccaagaca aaacaaaaaa gataagttta tgcatcaatt tttaaaattt   23820
atttttattt gattgattga ttggtttttc aagacagggt ttctctgtat agccctggct   23880
gtcctggaac tcactttgta gatcaggctg acctcgaact cagaaatcca cctgcctctg   23940
cctcttggtg ctgggattaa aggcgtgtgc caccatgccc ggcaaaattt atttattttt   24000
ctgtgtttgg atagtttgtc tgtatgcaca gctatgcacc atgtgagtgg agtgtctggt   24060
ggccagggag accagaggaa ggcatcacat cccctgggac aggggtcaca gatggttgtg   24120
agctaccata tgggtgctgg gaatctgacc caggtcactt agaagagcaa ccagtggctg   24180
ctgagccatc taggaagaga agctcaattt aaatttctct ttatttattt gtgtatgtaa   24240
cgcgcacgtg tgtgtgtgtg tgtgtgtgtg tgtatgtgtg tatgtgtgtg tgccacataa   24300
gtgcagtgcc catagaggcc agaagaaggc atcaaatatc ctggaactat aattacaggt   24360
ggttgtgagc tgcttgataa gggttctggg aactgaactc agatcttcgg gaagagcagt   24420
aagctctctt aatgactgag tctctgagac tatattttta aataacaacc tcaatgaggt   24480
gtgcctaagc tagtttttata tgaacttgac acagggtata gtcagtcatc tgagagggag   24540
gaggaaacct cagttgagaa aatgcctcta taagaccagg ctataaggga ttttcttaat   24600
tagtaattga tggggaggg cccagcccca gcctattgtg ggtggtacca tccctgggct   24660
gtaagaaagc agactgagta agccatgcag agcaagccag taaacaacat gcactgtggc   24720
ctctgcatca gctcctgcct ctaggtttgg agtgagttcc tatcccaact tcctttgatg   24780
atgtactgtg atacagacgc ttgtgccaaa taaacctttt cctccccagc ttgttttgtt   24840
catgtgtttc attgaagcag ccgaatccta agacggtgga gaattcacag aaggaattca   24900
cccatctaaa gtgtgtttg gtgatctttg atttattcac agcaacgtgc cactgtgtag   24960
cattgtaacc agttagggaa cattttatc aaccctccca aatactcctt cttagcctca   25020
tccagcctcc cctggtgtgt ccctggctgc tctggtctttt ccttctctgt aggtttgttc   25080
tgttctggac acgtcatgta aatggagtga cacattggct tccttggctt cctgccatgc   25140
tggtttggtt tgtcttggtt ttgtgagaca gggtctcctg tagctcaggc taacttctag   25200
ctaaggatga tttgaacatc tgatcctccc acctcctctc tcaagtgctc tgacctcagg   25260
agagtgccac catgctgtgt tcatgtgtcg ctgggatgga accctgcacc atgtatgtgt   25320
aaggtgaacc ctctgctgtg tccccagacc ctggtgccat gctatcatct gtgtcactgc   25380
gtgtgttggt gctgctgtcc ttcttaggat agagtcatgt tcctggtgtg tggctgcatc   25440 agtttacccca cgctcttcct ctgtggaagg ggctggctgt actttcctct cctgctgtaa   25500
ttttgtctgt catgagcatt tgaacgtgt gtgtgtgtgt gtgtgtgtgt gtgtgtgtag   25560
gttttcctga gaacttgttg gggttagctt agccaaggag aggttgctgg gttccatggg   25620
ttttagtttt gatttgttgt tgttgttgtt gttgagatga tggtcattta gtgtagccca   25680
ggctagcctg gaattagctt tatgcttagc cttttcaggaa aggacaggct gtcttccaga   25740
atgacctgaa cctgtcacat ttctttgaca gtggcgtagg taggggacag ggtggggtgg   25800
gggagagctc ctgatctctc tcctcccctct gacagcacct gtcactcatt gtttgcattc   25860
tagccattcc tgtgggtagt atgtgctgtg atttgattgt acttctggaa gcagtcagag   25920
```

```
aatttgaatt agtctgtgaa gccaacatgg aggctgtggc cgcctcatta gatctgtagg   25980
cctgagtttc tcaggctcat gttttctggc accagtgcct gcttaatgac ttgaagcagg   26040
gaggctgtga gggcagagtg cattgttcat gcatgcccac ggagcagcag gagtgcctgc   26100
tatcgggggc ctttattaag gcctttatta agtttaggca ggtcttttta gtctgttgga   26160
ggcagggttt tatgtagacc aggctggtct tgaattcact gtgtagccaa agataacctt   26220
gaagagcctc ttgcttctac atcgataatg ttaggtttat aggcttgtgc cgtcacacct   26280
ggtaggttcg ggtggttctg aacattagac tcaggtcatg tgacagggct atttcaccct   26340
ggaaaggaca ccataaatat tcccaggccc catgattgtc ctgagaccag gtttggtttc   26400
cgggcaaaca tggggttcat gactttggat agaattaatt gcaacactgt gtttaatcca   26460
ctgctgttaa caaccccctt gtgagctggg gagatgactc agtgggtaaa gtgcaggctg   26520
ggcttgaggg cctgagtttg agcctcagta tccatggaaa gtgctgagaa cagaagcgca   26580
ggtcagtttc cagtgctggg gttggtggtg ggagcaggag gttcctcggg ttcacggatc   26640
actcagccag tcagcgtgct ccaggtcctg tgagagacct tgcctccaaa cagtaaggtt   26700
ataagccaca gaagaatgca tctcgtgttg aactcaggcc tgcaggtatg cacacccacg   26760
aacgcatgtg cactcacata cacatacaga aaagtttgca tcgaaatagt tccccggtgt   26820
ttcaaaagtt cattaatgta tttattgagt tcgtttgttt ttgttcttgc tacaagatct   26880
gtctgtagtc cagcctggaa ttcactgttg agcccacagg ctggctttga acttgaaaca   26940
atactcctgc ctctgcctta taactagtgg gattacagag tatgagccat tgtgcctggc   27000
tcacccttga ggttgtataa aagattggcc aggtggccag ccacagagct ctgttgccaa   27060
gattgatgcc aaatgtagac attcaccatg gctaggcctt gttgccctct tcctgcctgt   27120
cacaggatgt agatacacag gaacttccct tgggctctaa attatcttca gtaccaggct   27180
gtctccacct caacctttct gaggtcagaa cagcactcaa aggccagttt ccaggtgtgc   27240
cacccacagg cattgtcctc ttcctcccac atccacctgt ccctagccgc cccacctagg   27300
tgtcctagat gacactgtgc catttccaac acagcaggcc cacaggtgca ttgtctgatg   27360
tctgctcctg ccaccccagg aatggctccg cagagcacaa tagttcaagg ctggagggtc   27420
cctttgatca gcttgtccag ctcacaggtc tcagacctgt tcattagggt ggcatcttca   27480
tcttcactag caccacactg gccagggct gtctgctctc cttttcagag tggcctgctg   27540
agctgtgtgg tgtcctgcct ggccctcttt ctctaactac tatgtaggca ttgcttgctc   27600
tttgcctctc agctctgcca caggagggca gaagggtcgt ttctgcgagg gtctagttcc   27660
tcacctcttg agttcacggg acgcagacag caagtatttg ttgaatggac aagtgattga   27720
cagttgatac catctcattc tgcagcttaa gctggtagat cactcaagct ggcctcaaac   27780
ttgtggcaat catcctcctg aggtgcatgt caccacacac agctagcttt ggttgatatc   27840
tttgagttgt attgatgtgt gtgtgtgtgt gtgtgtgtgt gtgtgtgtat   27900
tatttattta cttatttatt tataatttct tttgcagtgc tggggttaaa acccaggcct   27960
cacatacatt agcaaatgat ccaaccactg agctacatcc ccaattctgc ttgttgatat   28020
catgtagccc aggctggcct ctaactttcg atataaccaa ggataacact gaactcctga   28080
ttttcttgcc tccatctcct gagtgctgga attacaggca tgtactacca cacacaataa   28140
taagcatcac accgagggct cgtgcaagct aaacaggcat tcttctatct gagctacagc   28200
ctagaaccct gactgctgat tttctaaaaa ggcacatatt taaagttttt tttaaaatct   28260
gagtgttttg cctacatgca tataaatatg cagcatatat aagtcgtacc taggaaagac   28320
```

```
agaagacagt gtgtgatcct atggaactga agatacagat ggttgtgagc caccatttaa  28380
atgctgggaa ctaaagacag gtcctctgta agaccagtaa gtacttttaa aagctaaacc  28440
atctctctag tcctgatacc tattggtttt gacaggtttc tcagactatc tgggcctcag  28500
taggaaagtt actatctgat gagaacatac ccataaattt gattttatta ttgttctgca  28560
tagttttac cttgtatctt ttatatattt gtgtgtatac aaatacatat atgtatacac  28620
attttatatg tatatagtat atacaaagtg tgtgtatata tagatacaca cacacataca  28680
cacactttgg acacacactt tgtaacaaac agctttggaa aacagaggga ttgcacactt  28740
tcagaagagg ggatacctca ggcagtgctg gggagtgagg gaagccagga aggggtgata  28800
cgtctgctgt actgagtgtg aggggggttg gaagctgttg attctgaaga caacaggagt  28860
aaatgaagaa gagagggaaa gaatgcattg tagatccctc ttgttctatt ttttacctgt  28920
attagtgtac actgtgtgta tgtgcatgtg agtgtagtac ccacagaggc cagaagaggg  28980
catcagatct catggagctg gaggtataga tggcagtgag ctagctgctt gtcttgggtt  29040
ctgggaattg aactcaggtc ctctgcaaga gcaggaaaca ttgttcccag ccaagccatc  29100
tcttcagctc cagatcctct tattttgggg ggttggggat ctaacctggg cttcacacat  29160
gacaggtatt gagatagcac ctgtagattt ctaagattta ctgtattgag ttgggcaaag  29220
tacagaagag gccttgtttt gtgcagggat gacgaaggcc ccatacatgg gtgcttaaga  29280
ccagtttgac tttaggactg gcctcagagg atcaggacca gagggtgtct gtgcagtttg  29340
tagggtgcta gtggagtctt tttcattttt cttgttgggt tttgttttgt tttgtttttt  29400
aagttttttgt tggttttttt gagtcagggt ttttctatgt agtcctggct gtcttggaac  29460
ttccactgta aaccaggctg gcctcaaact cagaaatctg ccttcttctg cctcctaagt  29520
gctgggatta aaggcataca tcaccacaac cagtgttaaa agcattttta tttattacgt  29580
gggggtgggg cagggcatgc acaccacagt gttgttgtga aggtcaaagg acaactttgt  29640
ggagtcggtc ctctccttcc acctttcctg gattctggga tggagctcac atttgtcagt  29700
ctttggagga ctgagcttgt ccagccgagc tatctcacca ccccacttgg agtctttata  29760
gcaccatcca aagctggagg tgcagtggtc ctgtctgaag gccagggttc agggccactg  29820
ggggcgtgtt tgtggctact ccaggtgtct tcacaaaaac tgaaggggat gagctgcaag  29880
aagctgccat ctctgcagtt caggtcaatg catggccacc aatgtccttt gccatgctgg  29940
ctgagaatgc cagtggaggt gtggctctgt gggataggta gagagggttg gtgagcccac  30000
accatcaccc cgggtctcta aatggagcag gcctgttggg agctacacag tgaggtgtgt  30060
ggtgtgaggg gcaaaactgt atctattgag catgagtctg ttgggccaca gggttcactt  30120
cgagagtgtc ttctcctgct gcttcctggt gccaggcttc tcaaagccat ctcttgcccc  30180
tcctccaggt caccactcaa gatggcagag gctcaccaag ctgtggcctt ccagttcaca  30240
gtcacccctg atggcatcga tctccgcctg agccatgaag ccctcaaaca gatctgcctg  30300
tcagggctgc actcctggaa gaagaagttc atccgattca aggttagttg gttgatcgtc  30360
tctgcagcac ttgcttgcat gcacctccct gggtcccgct gaagaaggaa tgtgtcttag  30420
gtgggtctct gacagagcag tggtctcagt gctggctaag gcttgtggag gacacagata  30480
tataaaatgg cctcatcgct tcatagctcc ttcttattgt tgggttttgg gcttttgtt  30540
tgtttgcttc tgttttttaa gacacagtct ctctgcatcc ctcactctcc tggaactcac  30600
tcagtagacc agactggcct tgaactcaca gagatccgct tgtttctgcc tcccaagtgc  30660
```

```
tgggataaca agcctatgct accatgccct ggaaggcaac tggagctcat cagattaatg   30720
taaaacaggc caagcacctg atgccagagc aggggggccca cttatgggga gtcagtgtcc   30780
aaataggaac acaggcctgc cctctgcccc tcagctggat tccttgcacc ttactgaaga   30840
ggattatttt caaactttaa tgaatttgtg tcttatttgc ttaaagaaaa gttctcaggt   30900
agctcaggct agcctgaaat tctccatgta gctgaggatg gccttgtata tctggttctt   30960
ctgcctctgt cctccctggt gctgaaccac agacatgtct gttgggtttt attaggtttc   31020
ttagggtttg gttggcatca gggatgccag gggtttgctc aggctaggca gtcatacatg   31080
ttacatgtgt cacaaaaacg aaaggttctc agaggtcagt gtgatgtgac ctgtcatccc   31140
agcactttag aggctgaggc aggactgtct agcttggact acaatgagac cctatcttaa   31200
aaattgcttt taattatgta gatctctgtg tgtctgtgta tgggtaggtg cctgcagagg   31260
ccagaggcat gtgatcccct gaatctggca ttataggtgg tcaccagcta cctgacatgg   31320
gtgttaggaa ttcaactcgg gtctctacaa gagcaagtgc tcttaactac tgagccttct   31380
ctagccccaa gaatgtgtgt cttagttagg ttttactgc tgtgaacaga caccatgacc   31440
aaggcaagtc ttataaaaac aaaaacaaaa acatttaat tggggctggc ttacaggttc   31500
agaagttcag tccattatca tcaagatggg aacatgacag catccaggca ggcatggcgc   31560
aggcagagtt gagagttcta cgtcttcatc caaaggctgc tagtggaaga ctgactttca   31620
ggcaactagg atgagagtct taagcccaca cccacagtga cacacctatt ccaaccaggc   31680
cacacctcca gatgttgcca ctccctggtc cgaaaatata caaaccatca caatgtgttt   31740
ttagttgaaa ggtttttctt cttggttttg tttgcctgtg tttacaggag tgggggggaga   31800 gagagagtgt gtgagagtga gtgtgtgtga gcacacgagt gtgtttatgc atggaggccc   31860 aaccttaca gcagatgtct tcttctctag cttcatttat tgagatgagt ctctcacaga   31920
acctgagatc actgattctg gctagtctag agtctggcta gtctagagtc tggctagtct   31980
agttagccag cttgcctctg gagcactggg gttacataca ggtgaaagcc attcctgcct   32040
ggcttttaca ttgattctag agatccaaat gccaggcctt cccccagctt gtgtgctaag   32100
tgctttaccc actgagccat gtcccagcct agttttactt ttttgagacg gtgtctgacc   32160
ctagccaggc tcctctgtaa ctaaaggcag ttctccttttc ttagcctctc aagtgcttgg   32220
aggatgtgtg agcccccaca ccgtgcttgg acagttgttg ttattgttgt taatatcaat   32280
attattgagt taggatctca ctgtgtactc atggctgacc cggatctcac ggtggagacc   32340
agactgccct caaactcaca gagctccatc tgcctctgct tcccaagtgc tgaggtgaaa   32400
tgtgtgtatc cattaagaat ttattatgca gggctggaga gatggcttag cggttaagag   32460
cactgactgc tcttctgaag gtcctgagtt caaatcccag caaccacatg gtggctcaca   32520
accatctata atgagatctg actccctctt ctggagtgtc agaagacaac tgcagtgttc   32580
ttacatataa taaataaatc tcttttttaa aagaatttat tatgctgggt gtggtggcac   32640
acttctctaa tcgcagcatt caaaaaacaa aaccaaaaaa acaacaaaaa tagaattaac   32700
tttttgtaag actcaaacat ccaacaaagc agaaaaaaca gctctccctc cccattaccc   32760
tcctcctggt tccagagct ggcggagtct gggcagtgtt gagtcacgca agccttctct   32820
ccccaaacct cagttcttta gaccagtttt ttaatcgggt gggcaagatt gcagcccagc   32880
tgatgacctg agtttgaccc aaagttccac aaaataggag gagagatctg acctctgacc   32940
tccacctttg cgcctatgg tccttgcatg cacctacgta caataaataa atgtaacaac   33000
aaaaaattaa tgtaaacttt attttgctgg gttatttttgc agcaatggta tggggctcc   33060
```

```
tgtaaacaca tcttgactca ggaacagggc aagggtagtt tgggagctgg ggttcctgac   33120
tggcagatag tggcagtgta ggaatgggac ctcacagtgc ccaggctgcc agtcaccata   33180
tggagacctg tatggtaagt caggcctggc tgttttacca acctggagtc cctttcttgg   33240
agaatcttcc aagatgcatt tgggctcaga agtcagggga gagaatagac tgtgtaaaga   33300
aaggtaaggc agttgtgact ccaggcagag acacagctac tgggctttgg tctttggtgg   33360
cctgcatata tggcacccttc tccctgctgc ctgatgtccc aactgcctgt tgccacaggg   33420
ctgctgacag gtagtgatgg tgacctcggg gaggatgcag ctcacagctc acatgtcttt   33480
ccagaatgga atcatcactg gtgtgttccc cgcgagtccc tccagctggc ttatcgtggt   33540
ggtgggtgtg atatcatcca tgcataccaa agtggacccc tccctgggca tgattgcaaa   33600
gatcaatcgg accctagaca ccacgtgagt aacccacctc caccctctgc atcttgaaga   33660
agatggtggt acctctgttg actgtcctcg ctctgaaatg tctgagtaca actatgctat   33720
cgctgttttt ccgcatgctc tttgccctcc tgacctgcta ttgaaagtct gcagacactg   33780
ccacccttct tctgaagact aggctaagag tggcagaggc acggggacct gccttccagg   33840
tgtctgtctc ctgaggtcaa gatggagaca gtgatgacct cagagggcat ctctgcccca   33900
gaagatggct ccaagtgtgg ctgttgccct ggagttggtc catccagtga tctggtcctc   33960
tgaacttact gccggtcatt gcttagggac aactcagccc ttggccccctt cacagtggct   34020 tagatgcctg cagggaagtg cgttactcct tggctttgag ttttagttta ttctgggaac   34080 ttaaaaagt agatgtcatc ctgtctaggg acaaatcctg gccatcttct ggttttcttt   34140
tttcttttct tttcttttct tttcttttct tttcttttct cttctcttct cttctgttct   34200 cttttctttct ttcttccttt cttttcttct ttcttctttt cttctttct cccttccttt   34260 cttccttcct tccttccttc cttccttttt ttttttttga gacagggtct caccgtatag   34320
ctccagctgt tctggcctag aactcaggga tcttatctct gtctgtctct gtctgtctgt   34380
ctgtctctct ctctctctct ctctctctct ctctctctct cctggttgtt   34440
cagctgtaga tactgtatgc taggaaggat tgcacaagca aacagatgag agagtggccc   34500
cagggaacac tcacagctgg aggagttggt ttctgctgac tcagagcaac tagcagattt   34560
aacccagcag tgtggcatgt ttaagacagc ttgaataggt gctcgggaat cctggaggtc   34620
agtctttaat gggtctgcat gccctgcctt ctgattgaga cacccaggag tgactgagaa   34680
gccagccagc tcctcagcct ccagccctcc tggcagcatt ggtcattcct ttgtaagcaa   34740
ctgtaggaaa caagataaaa atgcctgtcc aggcatcctg ccaagggtcc tgtctgcctg   34800
gggcctggaa catcgagctg gggctaggtt ctcagaagca gctggcagag ctggtcacta   34860
aagactggac ctgtgctgtc ctgagaggtg aggaaagtcc tgtgaacgct caccctgctt   34920
ccctgagtgt tgagctggct gccaggccca aggcagctgt gaggccaaca gccaagcttt   34980
gctcttacat gggctgtgtg tctcaaagcc ggattgcaca cagccacgcc agctactaaa   35040
accttgctta atctcagtct ttatacgatt tgtttctttg tcccttagac tctattttcg   35100
taaactgggt catgtctggc tcaaatttag aaaggtcagg tgaaggctca gagacttgca   35160
gcctgagggg ctgttctgga agcatctttc cagtgtgggt ggagtgcctg tgtctcctag   35220
gctgctttgg ttttgtttgc tgagatctga aaggaaggcc atagaggtta tcagcacagc   35280
tgaaagtgaa attactttt tgtccttatt ggatttttt ttttttttt ggttttttga   35340 gacagggtct ctgtgtagcc ctggctgtcc tggaacttgc tatgttgcta tgttgaccaa   35400
```

```
ccttgtctca tgaactcata gagatctact tgcctctaca tgtgacacca tgcccagctt   35460
ggattttttc tttaaatttt attctgtgtg tatgtgtact atacgtgtgc ctggtgcctt   35520
cagaggtcag aagagggcat cagatcccct gagaccagag tttcagatga gtgtgagcca   35580
ctgtgtatct gttcccatca gctgcaggag gaagcatctt ccaatgacag ttgtgctagg   35640
cacccatcct gttcttctgg gaggcgaggc ctccagagca taggtctctc acatgatgtt   35700
aatgttttcc aatatcagag ctctgaaggt tagatatgct actactttga tcatttggga   35760
cctcttatgt tatgttttgc ttttagattt atttattttt atgtattatg tgttagtcac   35820
atattatgca tatatgtttt taagaattgt ctatttattt tagtacacta tagctgtcct   35880
cagacacacc tgaagagagc atcagattcc tttacagatg gttgtgagcc accatgtggt   35940
tgctgggaat tgaactcagg acctctggaa gagcagtcag tgctcttaac ctctgagcca   36000
tctctccagc ctcatattat gcatatatta tgtatgtatg tgtgtatgtg tgtatgtatg   36060
tatgtatgtg cctgcaggcc agaagagggc accagatctc attatagatc agccaccatt   36120
tggttgctgg gaattgaact taagataact ggaagagcag ccagtgtgct taacctctga   36180
gccagactcg atctctttta tttgttcctt gacaattgca tacacgtcaa caggatacct   36240
tgatttaacc catcccaact ctccactcaa acctttttaa aaacccgctg agttcccttc   36300
gcgccccctg ctggaggatc cctggtcggc cagctggctt ggtccacttc tcagtgagtc   36360
ttgtctgcag cagccatgtt gtgttcacat ctggctgcac cctttccacc ccttcttcca   36420
tgatgtcccc tgagccatga aggggaaggg ctagttttta tttttgtcac tatttttcct   36480
tttctaaaac aactgaaata acccctcaaa tagcagcact ttgttttgag ttttctttca   36540
tagtcggtga ctttgatttt taactattta aaaatctttt aagttttta aaagatttat   36600 ttatttttat ttatgtgggg atttttttggc tttgttttgt tctgttttg tgtttgagac   36660 aaggtcttat gtagaccatg ctagtcttga actcacagag gtctacctgc ctctgcctcc   36720
agcttgctgg gatatttgag tttcttataa ataaagacag catttaaggt tatatctgag   36780
gactggggat ataactcagg ggttgagccc ctgcctagaa agcatgaagc ccatagttca   36840
cccctgggca cagcaaaacc cagcaaatgc tagcaaagta tgtttgagag actggcaaag   36900
cattataatc tgaagaaaac gggccaggat ccctttgagc agcagttggc aggtcccacc   36960
cactgggagc agttgccatc gtgagcagct ctctgcccca caggagcctc tccaccattc   37020
ctccagagac tggaaaaact gtgtgttgtt caagactgct caggtcgctg gccggcctct   37080
tgattcttcc ttgggcctcc agagacaggc cactctgctg cacccagcca aggctggccc   37140
attttgagag gaatagagac tgccagggcg cttggagaac tggggtccct caggcttctt   37200
ctgcagcctg ctcactcctg tcgctgggag ggtgcttggt cagcccgctt tctggtagct   37260
gccattacca ccttccatgc tgacgtctta gctccttgtc tgctccatcc tcacagtggc   37320
cgcatgtcaa gccagacgaa gaacatcgtg agtggcgtcc tctttggcac agggctctgg   37380
gtggcgatca tcatgactat gcgctactcg ctgaaggtgc tgctctccta ccatggctgg   37440
atgtttgcag agcacggcaa aatgagccgc agcaccagaa tctggatggt aaccacccgt   37500
cacccaccag gggacccgct ccgagtcaga gcaggaccct tgcctcctta gacctttcct   37560
cctctgttcc ttggtgtgta acctgtcccc agcctctggc tatgggagag ctatggctca   37620
tgacacttgc atggatggag ccagggctgc ttttgctaat ggtttctggg agttctgcca   37680
tctctctgtt cacctctgtg tgacctgtgg ttcaggctgg atattgagca taagtaccac   37740
ccaggaggtc tttgtagcct tagggggccac tttgcaggca gacaccagac ggttttctga   37800
```

```
gttggtcaga tcacatgatt taccctaatc cgtcagtgtt ctctatttct tcgtgacctt    37860
aaggccaagg caccatgttt aagagagaga gagggttata ccatatacat gtgtgtttgt    37920
taaattataa ctggttgtga aggcttttgt tgttgtttag ttttggtttt tgagatgggg    37980
gctcatgtca ccctggctgg ccatttcctg actgtagcca atgatgacct tgagtttctg    38040
gttctcctgc accaccatgc ctgatgttta tgagatgcca gtgaccaaac ccagagcttc    38100
atgcctggct tacccagatg agccgtctgc ccagggaagg acatccaaag ccccaacgag    38160
ctgcttttat aagcttagct ctctggagta gggggaggag gatgacggat cactcctggg    38220
acctccctct ttggcactca gaccccagcc tttccttccc acacacacca ttgtatggct    38280
gtcacatatc ccccacccac ccacccacat attgtcaccc ctcttggctt ctgattttta    38340
taaagaaaag gtcattttct gcacccaagg tttgtaaagg atttcagtga atctggttct    38400
ggtaacattg cctttcaaat gcttgttact ggagctcctc ctttgtgcat gggaggagta    38460
ggtcagcttg gccttgactt gcgggccagt gtgcccccat gcccgcactt gtgaacgtct    38520
tcaaggtccc tttgctgccc accacgcact cctggcctcc atctttcaca aaccagcttc    38580
caccttatat attagttttt taatgtctag agtagcaaaa cttaaccaac aggcttaaca    38640
cagtgtcctc taggatggcc ctgtggctgc tgttgagctg agtcccagca cttcctgagc    38700
atcgcaaatg agaatcaccg actacacctt gaacccttag agatgcccta gctcctgcca    38760
gcaggaggca gctgccttcc atagctggcc tgcaaaatct tcctacaggc tgtgggggga    38820
gctcactctc taggctgctt gacctgatgg gcagggacac actgctgccc ctgggggtgg    38880
cttgagggtc aggcacctca gctgatccta ctccctatgt gcagagcggg caccagcctc    38940
aaatcaagga ccttccagga ggaggcagac agccctcctg cagaatcggg aaggacagta    39000
ggcagccaca ccagaagact tctctttttca gctgagctct cggtgggacc ggagcctgat    39060
ggtgtagacc agggatggct ctgtcataaa acactcagag agtcaaacgc agttgaaccc    39120
tggctttggt tctttaacac agcctcatct ttgaaaacgt aacttgtatc tccaggctat    39180
ggtcaaggtc ttctcgggtc gaaagcccat gttgtacagc ttccagacgt ctctgccgcg    39240
cctgcctgtc ccagctgtca aagataccgt gagcagggta ggtattatcc acactcctgc    39300
tgagatgcca gtgtccttgg gatccatgtt tctgcctaat tgtgactgta aattaaagtt    39360
cttaatcttt gttattgctc tgcagtctct cctgtagggt tattataaga atgttcccct    39420
gtctcccacc ccacagagtc cttgcactgg ctagacaagt gttctaccag tgagctacat    39480
ccacagccct ttgatatata tatatatatt ggatacaggt ctttctagtt agcacacact    39540
ggccttgaat cttttttttgt ttgcttgttt ggttggggct tttgtttttgt tttgtttttc    39600 tcgacagggt ttctccatgt agccttgact gtcctggact gactttgtac actgggctgt    39660
cctagaactc ccagagatcc tcctgcctct gcctcctaag cactggtatt aaaggcatgc    39720
gcaaccactt ctggtgaaca ttttaagatc tactcacctt ttgctttata tgtgggagtg    39780
tttgactttg tgtatgtatg tacaccatat gctcgcagtg cctgaggagg ccagaagagg    39840
gtgttggatt ccctgggact ggggttacag atgactgtga gcctccaagt gaatgttagc    39900
gacagagcct gggtcctctg caagagtagc cagtgttctt ccctaccatc catccctcag    39960
ccccatgacc ttgaactcct gatctcttgc tgtagcctcc tgatggtaga cgagtttcac    40020
tatccatggc ttgatactgt tttctctaga gcattattgc atctgcagtg tttaaagtgc    40080
tgtgtcccac ctattggggc atgatcactt ttttgtttgt ttgtttggtt ggttggtttt    40140
```

```
gttttgtttt tttgagacag ggtttctctg tattagccct ggctgtcctg gaactcactt   40200
tgtagaccag gctggcctca aactcagaaa tctgcctgcc tctgccttcc gagtgctggg   40260
attaaaggcg tgcaccacca ccacccggct gcatgattgc ttttaatgg tgttactgag    40320 atgcagttta ggactgtata gtgtccttga ttaatgtgca gagttcagtg atttgagttt   40380
gtatccatta ttttaaactg gaaaatacat acaaagacca catttattat ttttttttaag  40440 gctgggcatg gtggcactag ccaccttta atcttttaat cttagcaccc aaaaggcaaa    40500
ggaaggcaga tctcttgtga gttcagacca gccagggcta cacagtgaaa cactttccaa   40560
aaaaaagaaa aaaacagaag gaagaaaatg gttaaggaga tggctcagtc ggtaaaacgt   40620
ttgcctggca aacatgagag cctgcattct gcatttgatt tgtcagcacc catacatgat   40680
agcgacagat ttgcagcata cactggtaat cccagtactg gggagtggag caggggat     40740 gcctgtggct cactgcccag taagcctagc ctgactggtg aacttcaggc ggcttccagg   40800
gaggtggata gcctgtgtca ggctgactcc tgagtgccac cacacatggg ttcatctttt   40860
cgctctggct ctcgggcacg tgtgcacata cacagaattg ttttaactgt ttccaagtgt   40920
acgcccagca gtgcaactct ctgtgcttta gggtgtcaag gagttgtgac caccctggat   40980
tgtcaggctt ttttatagcc ttgggcagaa gccacaaaac tccctgccac aggcctgcca   41040
gcttctgttc cactttctgt ttctagttct gcctcgagag ggagtatggt aggaatggga   41100
ttatgtaatc tgtgacttt gtgaggggtt ccccctacta gcgtttattt ttctttgagt    41160
caggatctta accgaagcta gcctcagact tgtaatcctc ctgtctcagc ttcccaggca   41220
ggatgatttc aagcttcatc actgactttt gtttttgtt ttttgtttt ttttttttg     41280 ttttgctttt tgtttttgtt tttcaagacg ggtttctctg tatagccctg gcttcatccc   41340
tttcttaaca aagctatgct tcttcccctt ttgtggctga taacgctcct cgctcgtcgt   41400
gtgggtagac cagttatctg tccatctgat ggtgtgaatg tgggttgtgt tgtaagcagg   41460
gaagctggga atatctatgc atgttttta tctgggtact tgaccgcctc tggttgatag    41520
cagagtccat cacatcacag agtaagtagc agaggctggc tctgtcatga tcctgatctg   41580
ctgtaaaatg gcagcaccct agttctttcc agcttccaat gctggagggc acccatattg   41640
ttatgacttc tgccctcttc tcagaactgt aaatcaaaaa caccttggct tcaggtgttg   41700
gttcctggct tagggattta gtccttattg cccttggcaa gttcctttcc atctctcatc   41760
tcccagattg gggcacaaac gagactccca gccttggctt gggggtggtg cagccaccta   41820
cctgccccac tcttcttctt aaaacaggat ctcacattgc ccagactggt tttgaacttc   41880
ctagactccc tatatagctg agaacgacct agaacctcag gttcttcagt atctgccacc   41940
tgagtgctgg gtcacaggct ggcctattac actcagtttt atgcagtgct ggggatagaa   42000
tccagggcct tgtgtgtgct aggcaagtga tctgccagct tagccatgga gagtccaacc   42060
tttgttttat cagtttggag ttagccagac agttgcagct ggctctgacc cttcattgtg   42120
caaagctggc cctatgtagc ctctgttgcc ctggaatttt ccatgtagac caggctggac   42180
ttgaaccctc attggttcct gctacttcac ttcctaaatg ctgggattat aggtattgtc   42240
caccacaccc tgctcaaact tgtttcctg accaatcagg cttggcggca gttctgcttc    42300
ctggaactca ctcagtatag gtgggagctt tcagaatcct cagaaagagc cacacttagc   42360
caagcgtggt ggcacatgct gtcaccccaa cacttgggag ataaaggtag gaggaggatc   42420
aggagttcaa gaccagcctc agttatattg tgagtttgag tccaaaaaag ggggctggag   42480
agatggctca gcagttactc ttccagaggt cctgaattca atttccagca accacatggt   42540
```

```
ggctcacaac catctgtaat gggatctgat gccctcttt ggcatgcaag tgtgcatgaa   42600
ggtagagcac tcatatgcat aaatcttag gaaaaagaa gattgcgtgt gagatgttcc    42660
tgtatgtttt accccaagc ctgttcaagg tgtgtgtctg ccagtctgtg tgagctgagg   42720
atctagaccc taaacatggc ctgtgtcatg actgccttgt tgagcacctg cctggcctca   42780
ctgggctgtc agggttccca cccatctcac cacaccaacc caggtcatca ctgaagcaat   42840
ggctaggtgt cttggtacct ccatcaggaa gccgtgacct taattatcat ccacctgcag   42900
ccctgctcag ccctgcaggg gactgtcttg tccggtctat ctgcctatgt aaaagcagag   42960
aggacagact gacttaggga agcttttcta acctttcta caccgtctta cttttctgag    43020
gcatttgaag tgatgcacgg cttggagaag ggtgtttaac tctgcccgtg ttttctctct   43080
ccagtacctg gagtctgtga ggccactgat gaaggaggga gacttccaac gcatgacagc   43140
actggcccag gattttgctg tcaaccttgg acccaaattg cagtggtatt tgaagctaaa   43200
atcctggtgg gccacaaatt atgtaagtaa ttctgcatgt agtgctgtga aagttcttac   43260
ttgggtacca gggctcacag agttctagct gtggctgagg gcagccatac tttcccctga   43320
gagctgtgct cagagatgct agcatctctt ccctcctgca agctccttag cagcctttgc   43380
accctgctca gggcagggag ctgctttgga ccctctagtc ccgacctggc ataccacagg   43440
ctgttctctc ctgtggtggc ccagccaccc cacctccctt tgtggcatct tctccatcca   43500
agagtatcac ttctgagtgc tctggtcaga gttcagatgc tgttgacagt ggcagctgtc   43560
tgctgggagc cagctaagcg tctgtgtgtg tgttggggg tggggtagc aagtgggcac     43620 actgcaggat atgaagccaa gagggggaat tcaggtgtca tgaataactt gatggaaggg   43680
aagggattga aaataaccta tgggagccag acacatgcct ataggcaaga taggtacatg   43740
cctatagtcc cagcactcag aaggcagagg caggagaact gtgggctcaa actaaccagg   43800
gtcacacagg gataccagac cctatctcaa gaaaaactct taaatttaaa aaattattta   43860
cttattcatg tatatattg cctaggtgag tttatatgta ttacacaaat gcagatgaca    43920
tggaaactag agggcattgt atctcctaac agttgcaggt gattgtgtgc tgcccaacac   43980
aggtgctggg agccaaacta gggtcctctg taagagcagc acacactgag ccagctctgt   44040
agtccatcaa aaagaagtct caagagctgg gaatgaagct cagttggagt ctctgcctct   44100
ggtgcacaat gccctgggtt cagtctccag caccacacct gttctgtccc acacgcatgt   44160
atcccgaggg cttgagagat agaggcagaa agatcaaagt tcaaggttgt ctgtgcttct   44220
atagagttta aggtgagcct gaactgcttg agaccctgct ttaaaaataa aaccaggagc   44280
tggagagaag gctcagcagt taagagcatt tgccattctt gctgaagacc tgggtttggt   44340
tcccagcact cacaaggtgg ctcacaacta tctataactc cagggccagg ggatccaaca   44400
tccttttctg acttctatag gtgccatgca cacacatggt gcacatactt tatatgtaga   44460
caaaacacac acatgaaaga catcttagtg cacaccttta gtcccagcac tgggaaggca   44520
gagagaggca ggtgggtctc tgagttcaaa gccagggcta cacagagaaa ccctgacccc   44580
tggcccctca aaaagaaaa attattttaa aaacacaaat aataagtaga caaaaatcaa    44640
cagagaaagt agacaaaaag aaacaagaga agagccagca gatggtgcca gacccaggca   44700
ctgtgcccag cagggcagga ggccacagca cctgggtcat caggactggg tctaatccta   44760
agcagctggc ccgctgtgca tttagactct cgtgcaagcc ttttctcagg tgtgcgctcc   44820
agcacgatgc tcaaatcatc acaggttgta gatcagcagc ccctgggtgg ctagggcagc   44880
```

```
ttgctgggta acattgccat ggtcactctg gagaatcgag acagcacatg ctggcctcag    44940
gcttagttct gtggctgaga tgtaccaggc atcaggaaga tcgatctttg gggagatctg    45000 ggttatttttt tttttcctgc agtgctgggg atgggactgg gacccaaggc ctggtgaata    45060
tcagacaagc attcggcaca gcactttggc agtaaggggt ttttggaaat atggcccca     45120 ggctagcctt aaagttgcta catagcagtc ttgaacttgc tataaccttg aattcctgat    45180
cctcctgccc atgtgtgcac tgctatatag ttctatgcct agttttatac attccaacag    45240
ttgagctaaa acccagcccg actctttta tttatttatt taaacgcaat atgaaactat    45300
gctctatagt ctagccaggt ctcccttta gaccagtgtg tctctcaatt ccttatggcc    45360
tgtctgcttg agacaacttt gttttggagc ctgtcataca ctggaatttt ccagaaagat    45420
ttgcatacat ctgggcatga ctgctcagcg tgctgacttg tcgtgtttgt accataggtg    45480
agtgactggt gggaggaata catctacctg cggggccgag ggccgatcat ggttaacagc    45540
aactactacg ccatggtgag ttggtcttcc attcccactg cagccaagat gggtttgtcc    45600
tgctgggtgg cctgggaaag ctcctcttgc tcctgcttct tttgtccaag tcttcatgtt    45660
gctgtgaaga gcccacctgg ggcccatgtg ttagaccccc ctgtgtctta acgggcccct    45720
gccctccacc caacagtgca aatacatttt cattgcaaac aacacttgct atgtaagtgc    45780
aggctgacct tgaacctgtg gtagaacaac aggaagctgg cgttgtaata gagcaataac    45840
aaaattaggg cttgtggtgt ctcatgcctg ccaggcaagc actggggagg tggagacagg    45900
gggattagtt cagggtcatc cttggctaca taggtagttc aaggccctcc tagattgtat    45960
gagatactct ttcaaaaaag taagtctgag ccaggcgtgg gggcgcacgc ctttaatccc    46020
agcactcggg aggcagaggc aggcagattt ctgagtttga ggccagcctg gtctacagag    46080
tgagttccag gacagccagg gctacacaga aaaaccctgt ctcgaaaaac caaaaaaaaa    46140
aaaaaagtaa gtctggcgct agaaggatgg tttagcagtt taagagccct tactgctctt    46200
ccagaggacc tgagttcggt ttccagtaca cacctcaagt ggttcagaac catctgtaac    46260
tccagttgca ggaaatctga tgccctcttc tggccactct gggtacctgc acacacatat    46320
acacttaacc ccacacaatc acacacatac acatagagag aaaaaacata tccaatttgc    46380
cagaaaaaca aatggaccta aaacagtaac aaaagtgtcc aaagttgtaa agtcaggcat    46440
agtgacacat agctttaatc ctagcactca gggacctggg gtaggagaat tgcctgaaag    46500
ctacataacc tgctcccaac aacaacaaaa gccaaaagcc cacctaaaac aaatacaaaa    46560
ggcggctgta acttagcaca gctgtcaggg agcacccccc ccacacacac acacaccttg    46620
tatacagacc gccgtgtcac cccatgagcc ctcttttctg tctcatcctc acaggagatg    46680
ctctacatca ccccaaccca tattcaggca gcgagagctg gcaacaccat ccacgccata    46740
ctgctgtatc gtcgcacggt agaccgtgag gaactcaaac ctgtatgtca acttgccttt    46800
aaaaatatct cttgggaggc tagagaggcg gctcgattaa taaagtgctt gctttgagaa    46860
gagtgttcag acttggccca gaggtgccca gctagatgca gcagtgcacg gttgtaatcc    46920
cggcactggg gagccagagt cagacaacgc tggggcttcc cagtcagtga ggcccaggtg    46980
cagcgagggg cttgtcgagg cctggtgtgt tcaatcccggg aatccacatg gtgggctgag    47040
agaaccagct cctgcaagct gtcctctgac ccccacatgt actgatacac gggtaaactc    47100
ctcaggagaa cggtttcttc ataacatcag gtggcttaag tgtttatctg gaaggaactt    47160
cagtagcctg gccctgctcg gcaagtcccc caggtgctac cctagggatg ctgagtgatg    47220
tggtcagact gggcagtgtg cacaggaaac aaaccgcatt ttaatcagtt cattgcaaag    47280
```

```
ctttcctctg ggattttgcc tgttggttta aaacacattt ttactacaga ttcgtcttct   47340
gggatctaca attcccctct gctctgctca gtgggagcga ctcttcaata cttcccgcat   47400
ccctggggag gagacaggtg ggtagtgctt actgggtct ccgctgggag ccagcatttg    47460
ccattttgct gctcggaacc aggaatagtt ggggaacgtt gggaacagaa tggtctacag   47520
ggtctgtccc aagagcgtct gactctgatt gttcctcctc ttggaatcgc tttgtctttt   47580
gtcattgggg gtggtttggg aatgggatct cacatgttcc aggctggcct aaaataatat   47640
gcagctaagg atgaccctt tgcctcccag tggattctag acatgtgtca tcatgcccag    47700
agtatatatg ttgctcaaat tgaaactctt ggcttcatat atattagaca acccaactga   47760
accgaagttc agctctggcc tgaatttcct ttgtccacta ggcctgtaca acaggcccgt   47820
ttccagattt tagtgtttct tctgttgaga gtttctttcg ttgggcattt tcctcagacc   47880
tgctggaata ttttcacatg actccttggg caccttgttc tggcccatgc agggtttgct   47940
gtaagatacc cttgagaacc aatgtgcctg agaggctcga tggaggccca gctgctgctg   48000
ctggcagcct ggcctgggct gggctcatct catctgcttc taacctagga catccttgga   48060
aaaggatgga gggagggaga cggatgccag atggtgccat gcaggcctgc tggggtcaag   48120
tgtacagcat tggtcacttt taaacttggt gacaaataac gtgagcaaaa ccacttaggg   48180
aggaaagatt tattctacct cctggagcca gagcctggag cctattgttg ctgggctatg   48240
gaagggcaaa gcatcatggg tacaggacat gtgagggagc agagcattta cctctaacag   48300
gaaggacaca gctcaagaaa aaggactaga gtcaaaggtc cccttcaggc tgacaggtga   48360
ctcagcgcct gaatgagcct gtctgtaaac cgggtgcttg tacttgatgc caggctctct   48420
tgtggtaaaa ggagacaaca gactcccagg agctgtcctc tgccatctac acatgtatgg   48480
ggcatgcttg tcctcacaca tatttgagct cacacaagat aaataaataa attccattta   48540
tttattttat ccttgaggga gctggttttc ttcttgtcca ggccaggcag caagtgtctt   48600
tgccacctga gccatttcac tggctccagc atggtcttca atagtagtga tcacaaatat   48660
taactaaaat ctgggtaaca ctgggtatgg tggcatatgc ctttaatcct agcattcagg   48720
aggctgaaac aggtagattt cagtgagtgt gagcccagtc tggtctatac tatgtctaca   48780
tagtgagtta caggccagct aaagcttctt aatgaaccct tgccacaaag acaagttatc   48840
atttatgaaa atgtagtatg ctcggtgagg tcgtacagcg catgctagct gtcagaggcc   48900
tctcctgctc tgtggtgggc tctgattgtt tgcgtcttct gagacaggat ctcctgaaac   48960
cctggctctt ctgaattccc tagctagacc aagttaactc acagagatcc acctgcctct   49020
gcctcctcag tgctgggatt aaaggtgtgt gccaccacaa ccggccttt gctatcaatt    49080 ctctttaaga tttttcactg tgtttgtgtg taggaaggac acagccacac tatagcagtc   49140
atgtgcaggt cagatgacag tgccgtgagg ctgcagatca aacgagggcc attggcttac   49200
acggcaaggt ttaccacaa gtcatctccc aggtcctctt cccccccttt gagacagggt    49260
cttatgtagc ccagactagc ctctaatttg ttatgtagaa gctggctttg agctcctgat   49320
ccttccaagt ggtacaccat tgtgcctggc taaaacattc ctttttttt aagatttatt    49380 tttgcttttt attttatgt atgtgttgcc tctttatgtg tatatgcact gagcatatga    49440
agtgcccaca gaagccagaa gagggcacca gatccccgga gctggagatc cggaggctg    49500 taaaccacct gatgtgggta ctgggacctg aactctgcct gtgacttatg ggagagatcc   49560
cattcaatac tacgtgtgcc aaccttgttt catagatagg aaactgactt aggttatagg   49620
```

```
ggctggttaa gccaaaggga gtgactcagt atggagtcaa gggccacaca gcagtattcc  49680
cagaactcag gaggtggagg cagaagaatc gggagttcaa ggtcacccct ggctacatag  49740
acagtttaag accagcctgg gatacatgag atcctcacga agcaaaccgg tcaggtcaga  49800
tgagcccaag gctttctgac ttcttgtcac tccttcgtct cctcaccacc tcagacacca  49860
tccaacacgt caaggacagc aggcacattg tcgtgtacca cagaggccgt tacttcaagg  49920
tctggctcta ccatgacggg aggctgctga ggccccgtga gctggagcag cagatgcagc  49980
agatcctgga tgacacctca gagccgcagc ccggggaagc caagcttgcc gccctcactg  50040
ccgcagacag gtgcgtgtgt gcgtgcgtgc gtgcatggcc tcgcacaccc ttcccggtgt  50100
gtttgagggc ctcagtccaa tgccttaatc ctggggtcct ccgttcctcc acctcctata  50160
agcttggatc aaagtcctgt atcacggcat tcagttaact tccttcgttt cttttttctga  50220 ggtaagtgct ccaccactga gcagccaggg agactctgtg tgtgtgtgtg tgtgtgtgta  50280
atgtagtgta tgtgcatgtg tgtcaatgct gggtgtcttc atctgttcct ctccatctta  50340
tattatgcag acaaggtcac tcccaaagcc tggagctcac tgactggctt gtctggcaga  50400
ccagtgagtt ctaggggataa tcttgtctct gccttctcag tactaggata ataggtcagg  50460
gccccagatc ctcatgctta tgcagagagt actttaccca cactcccaa cacacaccaa  50520 aggagcatgc gtatctttaa gaccagcatt gtggggttgg actgtgggaa agagaaactg  50580
ccctgtgccc tgtgccctgt gcccgtgcc ctgtgccctg ctttgaacag ggtaagaaac  50640
aggtagagtg agttggtggg gagaggattt tgctctctgg ggccaaaagt atacagcact  50700
tcacaaaaga ccatctttca cagaaccctg agctgctcta agtctaact ctttaataaa  50760 gagttgctcc aggcactcag gagataacaa ggctgtgtgt tgtttggagc ctgggactga  50820
gaaggaaaac cagaaagcga ggaaggccat agtctatgct tcatctcctg ccttgagggc  50880
tggggtgcac tgggggcctg cggcatttgt gggtgttgat accaaaagtt gttgagagag  50940
gtgggtagtg gatgggaggc agcacagaag gcctgaggct gagaactgtg ggagggaccc  51000
aggatccata ggaggaagct acttcagggt agctctgaag agagaccaag gtgagcatca  51060
tggtgggcac atggaggtca ttgtgggagt gtcatgtgac cagtcctggt ctggggtcag  51120
gggccagatg gtgtcgttcc ttccctgccc caaagtagtt gtggcatgat ctctgtgcct  51180
caggtttcct catctgacaa atgggtctgt ggtgctgaag acatcagtgg actgattgat  51240
gcctgagaga ggctcaggtc agagcctggc tccagggcca ggtccttcgg catttgttat  51300
aacttctgct ggggatgtct ggggcagaga agggtgcttc tccctggctg ctgcagagac  51360
aggttggatt tcattctgag cagtgtgtgt gtgtgtgt gtgtgtgt gtgtgtgaat  51420 atgttgttcc tcgggtacta gctgtcgaca ctgatgttgg agacagggtc cctcactagc  51480
ctggagcata tccatttagg tgacctgtct ggctaacaag ccctggggat cctgattttg  51540
tctctcagac ctgagattag gagcacatac caccacacct ggctcctcta catgggctgt  51600
gggggtgaaa ttcaggttct cgggctgaca agcaagcact attgcctact gagccatctc  51660 cccacccctgg acaactgatt ttagatgcgt ttactccttg ccacagagtg ccctgggcga  51720
agtgtcggca gacctatttt gcacgaggaa aaaataagca atctctggat gcggtagaaa  51780
aggcagcatt cttcgtgacg ttggacgaat cggaacaggg atatagagag gaggaccctg  51840
aggcatctat tgacagctat gccaaatctc tgctgcatgg tagatgtttc gacaggtaac  51900
tcccattttt aatctctgag gttgatgggg ggttgtggga gatgtttctg ggggtacctg  51960
tgagcagcct ccccaaatct gaccccctgct atggggttgt actaggaagg aataagcatc  52020
```

```
caaccagaaa gctctgcttt cttccctcca cacaaactca gacacagttg taggcccggt    52080
agttttgagg tccccctcctt tgcttaccca ccacccttct taactgtggg ttacctggct    52140
cccagcagaa ctgtgggagg ggcccaggat acatggagga agcacatagg acagtcctgg    52200
gaaccatcac tggccttgtg cagttgctgt gaccctgccc tcctggatcc cctttctgta    52260
ggtgtaaagt gaggaggtac ctcccaggcc tggctggaga gggcatggcc ccagactcct    52320
tgttacagta gtctacacgc ctctggaccc agggctcaca cacatgctat attgtatctc    52380
tgatacaaga agctatgaat ggctctgtgt tctctgtgcc cccttgagtc accttcctag    52440
gatgtagaag cctggagaat tgtcagggtg gagagaagca acggtctctg cagaaagaag    52500
cacccatgta gcttttgggt tcccatgtcg atataaccct ggaagcccat gatcatgttg    52560
tctccctgta ggtggtttga caagtccatc acctttgttg tcttcaaaaa cagcaagata    52620
ggcataaacg cagagcattc ctgggcggac gcgcccatcg tgggccatct gtgggaggtg    52680
agccacacca ttgttacctg tctgaatgtg aaggtgctt tgggaaagaa acccaacgca    52740
ggcccacttg aactctgcag tatttgtcta attctgtatt ggttacattt ctctctccct    52800
gatgaaatac cttggagagg gaggagtgag tgtgtgtgag agtgagtatg agtgtgtgtg    52860
tgtgggggg gtgctaggga tggaacccag ggcctgcctc atacttgctg ggcagctgct    52920
ccacaccaag gctgtataac cttagccttt attttggaga caaggtctca ctagatagaa    52980
acatgctaga cttgaactca ctgtgttgcc cagactggcc tcagacctgg aatcctcctg    53040
cctcagcgtg ttgagtatca gagattacag gtatgtgcca ccgggcctgg gttagcatct    53100
tggcttataa aatggcagtg tcctggagcc agagagatgc tagtagggta gagtctgacg    53160
atctgagttc aaccctggc acccatgtga cagtagaagg gcagcacccc atgtgcaccc    53220
tcacttcaca caccccatgt gcaccctcac ctcacacacc ccatgtgcac cctcacctca    53280
cacacccat gtgcatcctc acctcacaca ccccatgtgc accctcacct cacacaccc    53340
atatgcaccc tcacacaccc catgtgcacc ctcacacacc tcatgtgcac cctcacctca    53400
cacacccat gtgcaccctc acacacctca tgtgcaccct cacacacccc atgtgcaccc    53460
tcacctcaca caccccatgt gcaccctcac ctcacacacc ccatgtgcat cctcacctca    53520
cacacccat gtgcaccctc acacacccca tgtgcaccct cacacacctc atgtgcaccc    53580
tcacacaccc catgtgcatc ctcacctcac acacccatg tgcaccctca cctcacacac    53640
cccatgtgca ccctcacaca cctcatgtgc accctcacac acccatgtg caccctcacc    53700
tcacacaccc catatgcacc ctcacacatc ccctatgcac cctcacacac ctcatgtgca    53760
ccctcacctc acacaccccca tttgcaccct cacacatccc ctatgcaccc tcacacacct    53820
catatgcacc ctcacctcac acccccatg tgcaccctca tacatcctaa tagttaaatc    53880
aaaaaaaatt aaggcaatgt atcttactga aaatatttca gttactaaaa tgaccaggtt    53940
acttaaagac caccaaatct ctgtccccct ttctcctaac ccagctttca aaaacacaga    54000
gttgggtgtg gtgacacatg tcaccctagt acaggagcct gaggcaggag gatcaggaac    54060
ttgaggccag cttggactat aaaacgaagt catttcaaaa cagagagagg caaagcaaaa    54120
gaaagggtca gacccagact gcagatctgg tgcctttgtg gacttctcag tcaaatagct    54180
gtattgcagg aatctgaaat ttattaaata ttgacgtaac tctcaacgaa gtttttaaatt    54240
tttgtaagat tttggacttc aggctaggga tgctctctct cttttccctcc cttcctctct    54300
cttccagggt ctcaccattt agcccaagcc aaatggcact gctcttgcct cagcctcggg    54360
```

```
agtgctgctg gtttcgggtt gcccggccac ccccagctaa gactttgcat cttagttttt    54420
ccttgcagtg ctgtgccagc gatttctttt cctgtggtgc agagtcaact gcagggtgca    54480
gattgtgtct gcttgtttgt gcgcatgctc tggcctccct ccctccctcg atcactcacc    54540
ctctcatccc ttgggtgctc ggacctctgc ttggggtctt ggcagagtcc cagctgctcg    54600
gcttcagcca gggaagagtt cctacacgag acagcctggg aaaggaagaa gcaggcagtc    54660
tggatctaag acaccagcgt gctccgctga gacaccaatt ccaatggcga agtgcaaggg    54720
ctcgtgtccc tgcgaggcag cccctgaact gatgccagca gcagcctcag tccagatgca    54780
gatacctcac ctccattagc tcccagaccc tgcggctcac acacagatct ctgggaagct    54840
ctgcaaagcc caacagtata ggcccatgag aatatcccag ggacttttca gataacacat    54900
gcacagctgc cgttgggtaa tgagggtctc tgaggcccag gcaacttgca gcatacacag    54960
caccgttctc aagggcagac atagagggca catagtggca catgcctata attccagcac    55020
tccagaggct gagatgggag aattactgaa aagcctgagg acaatcaggg ctacataata    55080
aaaaacaaaa ccaaacaaaa ggttgaaaag agatgaagaa gaaatttcag caagatatcc    55140
acaaggtctg gctgatgtta aggtttcttg tgtgtctaca tgtatgtgct catgagtgca    55200
gtacatgcag caaccaaagg ggggcgatag atcccttgga gctggggtta aaggtagttg    55260
tgagctggga cccaaacccc aaacttctgc tagagcagca ggcactttta acagctgagt    55320
tggctctcca gccctcgggc taatatttta agtaactga tcaagataag ctaaggagg    55380
ccaagatcaa gataaggcta aggccaaggc cacaagtaga atcagtattt agtttcctgt    55440
ctgcctggtg gaatgaggag gactcttgaa tggagcctag gttcccagga tagtgctggg    55500
cacccagctc tcatcttgga gggacagtgc cccagtaaca atgggctgat tctgagatgt    55560
gaaaccaggt ggggacaact tcgtagtagc atcctgtgtg ctgtgggtcc agcatcctga    55620
gaactgagga tcctcccatc agccctgatt caaggtttct ccgcttacct tctcttgaca    55680
gattcatctc ctagagcagc tctggctcgg ggagacgcct atgcttctct cttattacaa    55740
agggcgcaga aggctgtggc aggtgggctc cagagatgca gaggttcaga gccacggtgt    55800
taccctccct ggtttctaga aaccacccat cagttagctt tctggggcct tcctgctctt    55860
tgccctctgg tgtgtgtgtg tgtgtgtgtg tgtgtgtgtg tgtgagag agagagagag    55920
agagagagag agagagagtg tgacagagac tggagaaggt gcttggtgtg tggagattcc    55980
gcccttactc ccaggattgg tcccaggagt gtggagtgtc tgtcctgagc gcagtaggaa    56040
ggaaacactg ctcactcgtg gcttctactc catctctgct tctttgtctc agtatgtcat    56100
ggccaccgac gtcttccagc tgggctactc agaggatgga cactgtaaag gagacaagaa    56160
ccccaacatc cccaaaccca ccaggctaca gtgggacatt ccaggagaag taagtctggt    56220
gtcccagaga ccatcactca cctgggtggc aatcttgttc ctgagctctg gtgataggca    56280
agctctctac caaacagaaa gctgtttgcc cagagttggg gaaggggcct gggatgctga    56340
gagaaatggg acttccgttc tcagttgaga tttcagctga aaagtagctg gcttctgta    56400
aattccctgt aaacagggat aaaaacttaa atcctagtca ggcaatggtg gtacactccc    56460
gtaatcccag cactcaggag gcagtagcag gcagatcttt ttgagttcca ggccagcctg    56520
gtctacaaag ctagttccag gacaataagg actacataga aaaacctagt cttagagatt    56580
ttggggctgt gtaaagatgg cctgtttctg tcatcccaac ccctgtggct gaggccagag    56640
aattctgtga ccgtgtctca acaaccaaca acagattctg agattcagtc cactcaagta    56700
ggagccctga gaagagatgt tagggttgga accataactc cagcctgtct gatccaagtg    56760
```

```
tgagtttctg gggcctgaga agtactttt cgtgtggtaa agtccagcac tctgaggacc    56820
caggacagtg tgtgatccat agaggaacaa tacctctgtg gaggcctgac cttggggccg    56880
ggctgactgg accaccaggg ctcactggct ctcttcaaca cacctgtaat agagccatgc    56940
tgggttcatg gcagaatttt gagaaagatg caggtatttc ctggaaaccc acggtctgcc    57000
ccctcagcat cctcactagt ggtctgtcag gcctcctggc acatcccagg tttacacagc    57060
gtcgcctgga tgggattggg tgtgtagtgt cacgtgacta gtgcccagag tcagatggca    57120
gtgacattgc tataaacacc atggcctccg cctctcatcc agctccttcc tggcccctgg    57180
ccaccgtgga tccctgtgtt tgtccttta aaaacaatat tatttgtgct tctagaattg    57240
aacacatgta acaatgtgt cttgattata tccatggctt cctcctccag ccagctcccc    57300
taaggcccta gactagagac tgaagtgcag acttccagac tgttccgccc tgcttccttc    57360
tcctcctgct gtgcttcccc actaagcaga gctgccttct tcctctgcag tgccaggagg    57420
tcatagagac atccctaagc agtgccagtt ttttggcaaa tgatgtggac ctgcattcct    57480
tcccatttga caccttggc aaaggcttga tcaagaagtg ccggacgagt cccgatgcct    57540
tcatccagct ggcactgcag ctcgcacatt acaaggtaag aagggcactc actgtgggca    57600
ctctggagct gtttccctag tgggcagagg ctataaagcc cagcatggag ggcagctgac    57660
accaaacacc agccctgggg ctacctgcgg taccaaggtg tgaaatgcta gactgcagag    57720
cagatcaccc ttggttttgt gacatccctc tcaggctcct atcacagatg agagcttggg    57780
acataagcaa atgaacagtg taacctgac tggagagatg gcctggcggt tcagaccacg    57840
tgctacctct gcagaggacc ccattcggct cttggcacct tcacatagcg gctcacagcc    57900
acctgtaact gcagttccat gggatctggt gccactcttc tgccttctgt gaactacaca    57960
tagttacaca tatgcacaaa ggcaagcaca cacataaaat gttaaaatat aaatcttgta    58020
aaacaacccc ataataagct ctgactctta cagtattgtt aagaaatact taggacaaat    58080
tgcttaatgt gtctgacttt tgacaggcct ttccttaaag cagaagttat gagctcctca    58140
ttgctctagg ctgagtcaga tttctgtatc cacccaggac tgtgtgccaa ttctatcgtt    58200
tccctgagca gtgctaaagg gtggcagaag caatctgtac ctgtgtgagg atgtggaagg    58260
aactttagtt cttggtagag gtcagcctac tccagacaga agcattcagt tgctggcaat    58320
gcagaagtca ttgtggcacc agatctagaa gtgcacagtg ggagggtgga catcccaggg    58380
gctcagcttc aggtgccacc agctgtgtcc accacccttg cctccccagg agctcttcct    58440
gccccacccc taccctgttt ctcttcttgt tctctctggc acaactccca aggcctctgt    58500
aatcacttct aaccccagct tcctcgactc tctccctagc cacgccccct gaccactccc    58560
ctgctgcctt ttccccagcc ctagccacac tctcctccag ccaggagcct ctcatctctt    58620
cctgaagctc atcgccagct tctactctgc ttccagaaag gcagccttac ctgcagacac    58680 cttt gcttca agctaaggag tgctggctgc agtagccttc cacctgtgat acctcccatc    58740
ctgccttcca caggtggccc ttctgtccca tccagacaat aggcttttcc catctgcatc    58800
tgctcgctcc tcctggctac tgtcttgtcc atggccatag tgactgaact cctcctcatt    58860
ccctagtcct gccctcttgc ctgtccctcc cctgtgtctc tcagacctca gaccttgctg    58920
tgtgccttgt cctttctcct aaaaattcac atcagctgga gggctttctg gaggacattg    58980
tggccttagt catgtcttgg accagaaacc atgcaaagac aaactccagg aggctggaga    59040
gacggctcag cagttaagag caccgtctgc acttccaggg gatttgagtt caatttctag    59100
```

```
cactcacatg gcagctcaca gtcatctgta actccagtcc tcaggatcc agtgccctct    59160
tctggcctct ggacaccagg tttatccttg ttggtcagat gtatgtgccg gcaacacaca    59220
cacacacaca cacacacaca cacacagtgg gggaagcaga ctgccacctc ctctcagatc    59280
cattccaggt cccttctccc ttagacttag atggccactc ccacctgtta gcctgttagc    59340
cctaagctag ttttccttcc ttcccaggac atgggcaagt tctgcctcac gtatgaggct    59400
tccatgactc ggctcttccg agaggggagg acagagactg tacgctcctg cactacggag    59460
tcctgcaact ttgtgctggc catgatggac cccacaacaa cggtaagacc atggtggcag    59520
aacatggcat ggtgcatggt ttctggacga cactagaaca gtggttctca acttgtgggt    59580
cgtgacccca ttggggtcac atatcagata tcctacacat cagatactta cactgtaatt    59640
cataaagtag caaaattaca gttatgaagt agcaatgaaa taattgtatt cattatgagg    59700
aaccatgtta cacaacatga ggaactgtgt taaagggaga cagcaagagg aaggttgaaa    59760
gtcactgccc tggaagctga ccatgaagct ccatagcccc tccagctcca cccttcctcc    59820
ctcaacccct cctcccctg ctcctccacc cttaccctac ttctgcatcc cctcccccag    59880
ctccttatgc ataggaacag aaagcattta agaggacata cagaagagag tattgctcgc    59940
tgagctttgg gaatgagatt atatgtatcg agacccttca catgcgactg gacatggcac    60000
agacacagga aaccggacac ccatccctgg ggtcagagcc tgtctgacca atctaccaga    60060
tactacagag tactacagta tgttctgcct cttaggagcc ctgcagtggc cttgggaaaa    60120
tgaactcaga tgaatccaat gcattgctgg tcccagctgg cacatggcca cattcagagc    60180
tatgcctagg ttccccaagc cctgagacag gcgtttacca ccaacagaca acagactgca    60240
ttttttcttt ttttttttt ttactctaga gagaggaaaa aaaaaaagc aagcggctac    60300
ttctgtcact agaacttcca ggaggctcct atgaggctgg gtctgtcata ggaaggccag    60360
tgccttgaca tacctccatg tagaggccac gtgtctcagg tggtgttgta atgtccagaa    60420
gattccaaag cagcctatat gtctgtgttt gttatgtgtg aacacatgtg tatgtatgta    60480
cttgtgttat gttgtacatg tgtatacaca tgtgtagtga ggccggaaat gtgcgctgtt    60540
gtcttcatcc attacgctcc accctgtact ttgagccagg gtctctcccc gaatgtagag    60600
ctgctactta ggctagactg gctgctcagc aagcctcccc cttgggtcat aaggaagccc    60660
tcacatttta gcagagtagc caaggagggt tagcgttcat ccctgtgaca aaataaactt    60720
ggggtcagag ctgggataga gctccaggtt tggcaagaac tcttaacagc ttgagtggtc    60780
cacatttggc tctctgtgta catagcacac acaccgtcac agggtgcctc tccatcaacc    60840
tacctactgc ccagcagccc ttctgaggca agaatctgga aagggatcgt gggctggtgg    60900
ggctctgtca agtatattgg tcacagcacc ctgccttta cagaccactg aagagaaagt    60960
ggcccgacgc acaacctgaa ccatgcaaag catgtccttc tcctgttgac ccttaggcag    61020
agcagaggtt caagctgttc aagatagctt gtgaaaagca ccagcacctg taccgcctcg    61080
ccatgacggg cgctggcatc gaccgccacc tcttctgcct ctatgtggtg tccaagtatc    61140
tggcagtcga ctcacctttc ctgaaggagg taagtgcttg gactgtgtgt gtccagcctg    61200
gcttttctgt gttgagacag gatcttactc tgtagcctag ctagccttaa atagcaatc    61260
ctcctgcttc agcctcctga atgctgggac tacaggcatg catcagcata ctggctttta    61320
acagtggctg catagaatga gctagaaaag cccttgagaa cctagaggtg ggtttgtaga    61380
ggctacctta gaccccacgg gctgtcctct gccttccctg tgagaggcag tttggtcaag    61440
gggaggggct cagatacttt aaccttagtg tggccctgag gggcttggag aaatagtctc    61500
```

```
tgaccacgca gttttccctt gcctccctct tagggatcc tcagacaaaa aggaggtatt    61560
ctgcattgct ctctgcattg ctctctgcat tgctctctgc attgctctct gcattgctct    61620
ctgcattgct ctctgcattg ctctctgcat tgctctctgc attgctctct gcattgctct    61680
ctgcattgct ctctgctgct gtataaagca ctctgaccac ttgcccttg gaagtcaggg    61740 caggaactta agcaggaaca gagtcagaag ctgtggagga aggcttcttg ccggcctgtg    61800
cacgggctca catttggtta actttcttta caaatataat tttacatgtg tgctttgcct    61860
tcatgtgtag gtgtatgttt ggtgtgtgtg cagtgcctag agggatgtct aggaactaga    61920
gttacaggtc cactatgtgg gtgctagcaa tcaaagctgg gtgctcttag ccactgagcc    61980
ctctctctag tcctctccag ctagatggac acctgtccag ggacagaacc cacctaccct    62040
gagctggacc ttcctgcagc aagacaattt cccacagaca tgtctgtctt aatgagtgtt    62100
ttgggcagaa agtgtttatt cagcttacat gtccatatca tagtccatta ctgaaggaag    62160
tcaggataga aacccaagca gaggtggacc tgtgaggtgg gacctggcgc ataggccatg    62220 gagggggtgct gcttgctggc ttgctgcccc tggttcactc agccttccct atagaactca    62280
gcatcaccag cccagggatg atcccatcca gaatgggctg ggcctcccta aattgatgga    62340
taattgagaa aatgccttac atctggatct cactgaggca gttcctcaac tgaagttcct    62400
tcctctatga tgactctagc ttgtgtcaac ctgacacata aaacaagcca ggacagtgtc    62460
cacaaatcag tgtgatggca gatagtcact cagttgagaa tgtcttgtgg ttcctcccag    62520
gtgattgtca gcagtgtcag gttgacagtc ggtgctcact aggagaagcg agtagggaag    62580
tcatgtggac atttttgct ttgtcgcagg tactgtctga gccatggagg ttgtccacga    62640
gccagactcc tcagcagcag gtggaactgt ttgactttga gaaataccct gactatgtgt    62700
cctgtggcgg gggctttggg ccggtaagtg cagccaggcc cacccactaa cttcaagccc    62760
atcccattgt ccccaggctg gcctcaaact cactcactgt aaagtccagg ctggccatca    62820
ccatcctcct gcctcagcct cttcagtgcc cagacttaca ttgagaacag gaagtcgccg    62880
tccacgttat ctcatttcct agtgataaaa ctgcccttc tctctctgca ggttgctgat    62940
gacggctatg gtgtttccta cattattgtg ggagagaatt tcatccactt ccatatttct    63000
tccaagttct ctagccctga gacagtgagt atattgggca ctacttttc tagacatgag    63060 gtaaatttct ttttggaggg agcacatctt taaccaaaac attcatttca ggtgtcatcc    63120 ttttttagc ttagtttcac atcgatgaat ttcacccatt tgaaagacat atatttattt    63180
catttacctg cctttgatgg tagcagtggt cttaagtctc aatgtgtctg tgtttctgtc    63240
attctttcta ctctaaacaa ctccgtgagc aggttctggc cttccgtagg gagtaagtct    63300
ctgagggagc ctcttgggaa cctctaatgg tggccctccg cagtatcagc ctagccagtg    63360
ctacaaaatc ttccaggctg cccactccca cccacagacc ccgagtcctc aggaagctag    63420
gcatgagtta cacacctcta atcctagcat tatttaggaa gctgaggcag gaactgagag    63480
ttcagggata gcctggggtg tagtacagag tgacagggag gcctcagatc tgacccatcc    63540
atgcatatat caagccacct atggctgtcc cccactgagt gctcagggtg ctttttattgc    63600 tcctccacta attccctcag agcttggaga gtggaagac aggaggttgg cctaacccag    63660
ggacagatga taatgggcaa ttccaaaagt gagacttgct gcgtgccaga gcttttcctt    63720
ctctgtgtct ctgtctctgt ctctctctgt ctctctctct ctctctctcc ctctctctct    63780
ctctctctct ctctctctct ctctctctgt gtgtgtgtgt gtgtgtgtgt gtgtgtgtgt    63840
```

| | |
|---|---|
| gtgtgcttgc acaagcactt tatccactga gccatctccc caactcctct catttggttc | 63900 |
| ttttttttt ttttccattt tttattaggt atttagctca tttggttctt ttttttccat | 63960 |
| tttttattag gtatttagct catttacatt tccaatgcta taccaaaagt cccccatacc | 64020 |
| cacccacccc cactccccta cccacccact cccccttttt ggccctggcg ttcccctgta | 64080 |
| ctggggcata taaagtttgc gtgtcctatg ggcctctctt tccagtgatg gccgactagg | 64140 |
| ccatcttttg atacatatgc agctagagtc aagagctccg gggtactggt tagttcataa | 64200 |
| tgttgttcca cctatagggt tgcagatccc tttagctcct tggctacttt ctctagctcc | 64260 |
| tccattggga gccctatgat ccatccatta gctgactgtg agcatccact tctgtgtttg | 64320 |
| ctaggccccg gcatagtctc acaagagaca gctacatctg gatcctttcg ataatatctt | 64380 |
| gctagtgtat gcaatggtgt cagcgtttgg atgctgatta tggggtggat ccctggatat | 64440 |
| gggtctctac atggtccatc ctttcatctc agctccaaac tttgtctctg taactccttc | 64500 |
| cctgggtgtt ttgttcccaa ttctaaggag gggcatagtg tccacacttc agtcttcatt | 64560 |
| cttcttgagt ttcatgtgtt tagcaaattg tatcttatat ctttgggtatt ctcatttggt | 64620 |
| tcttgaagac agagtcttgc tatatagccc aggctgggtt tgaacttgct gcagttgatg | 64680 |
| ctcctgcctc agttttcagg cgctgggatt tatttgcccg gctgctgatg tgctgttcgg | 64740 |
| cttctttctt ttaggactca caccgctttg ggaagcactt gagacaagcc atgatggaca | 64800 |
| ttatcacctt gttttggcctc accgccaatt ccaaaaagta actgtcggag ccgcacggaa | 64860 |
| ggaaaatgga ctctagtgat acaaaccaaa tgaataggtg ttgctcctga ccataggaca | 64920 |
| ggcagaaaat tgttcttata aaactcagtt ttccttccag aaggtttacc gtcggtctcc | 64980 |
| ctagaacaac cgtaggctcc accgtttgac ttgtgaccct actacatcca gagatgcctt | 65040 |
| ggctccagga atattgggca cagtcccccg aagtcttttg aatcggctcc taatggataa | 65100 |
| agggatttaa atgctggtga atccctggat tttgggggtt gtatcaatat gtgttggagg | 65160 |
| tgacagactt cctcagtggt gaccctgtgg atacttggga cttgacttca cccaggcagt | 65220 |
| gagagcatca ccttgtggaa agagaaagtg gcttcagagc cagtggaggt aacagctcta | 65280 |
| gctaacacac ctgtaacaca ctaatggaat ggttaggcct ggggattaag ttctgctat | 65340 |
| gaatgacagc caccatcgct ttgggagtcc acatttgact ccacatttcc tggaagcagg | 65400 |
| ataccacctc ctcagtgcca ccttcgaaac ccagtgcctt aacgatggga gcccattggc | 65460 |
| aagtgggggcc atagagaagg cttagcatgt gaagcctttg ggtggatatg tgagggtgct | 65520 |
| gcttcccctc acaagttcct gcatagagat gtccctaagt aagcacttcc cccaccctag | 65580 |
| aagatgaggt ccctggtgga gggagcgatg cagaatctca ttggccacca gttccattaa | 65640 |
| gcaacaaaat aacagatgtg tccacagagg gaagtgaggg gcttggtagt caaaggctac | 65700 |
| caagttggac accagctgga gagtgtggca gccattggca aggagagtga gaccctggtc | 65760 |
| actgagtcag gcatactgac acaggcagcc aaagccttgt catggcagcc aggagataga | 65820 |
| gatcctggca gatacaccaa cgggctcatc ttctaatccc acccagtcag attccaacca | 65880 |
| gagcaaattc gatagaaggc taggtcattt tggtgacaga ctcggggggtc tcaagtaatg | 65940 |
| ggtgctttgt acccaaatac catccctctg tgagagtgcc tttcttgaca acatccaata | 66000 |
| gactgtaaag caactccgtt tggtattcca tgtaaacata gcataatgga gtggcctccc | 66060 |
| ctacctgtta ccatcctgtc ctgacaagtt tagctcttcg tgtttttaaat catgtatta | 66120 |
| ttttccagtg ccccttttggc cttgcttgat tcctactcgt gtgctagctg taacagaagt | 66180 |
| gagggtgggg tggccagaag tacagagagg tgctggctga acagctcatg cgtgttttat | 66240 |

```
aagtatccat gaatacaaaa aaaagaatca cacctacaag ggccaaagtt ttttctcctac  66300 taaaaacaag aaaacaaaag gcaacataaa tatatagcag agacaactgt aagtcaaagc  66360
cgcctgaccg cgctcttagg actacttgct aacctctgtt actcggagta ttcctgctag  66420
tacccaagtg tgacattcct ctctcaggtc tccagtgtcc ttccttgctg ctcctgagca  66480
gttaccaatg caatttttta ctccttccaa ggcagaagag tgggctttca ctgtaagtgt  66540
tcaaaggagg aggtaagact actatgtatt taatgtggaa caaaacatag tcttaccgca  66600
gccaaggttc gaatttggtt ttctaatctg tccattgcat gtaaataccca tatgctgttt  66660 ggatataaat cttagaaatg catgtgtgaa cgaatatagc tgaccattaa taaaacatta  66720
atcccgccta ctacatcatc tgtccctgtc tcccttgtca tactaatcag ggttatacta  66780
tcaggtactg gctgtgagcc tgcagtgtgc agggcaccac tgtcatgtac ttgaccaagg  66840
agcagcacac agtggagcta tcctccattc ctgtgtgggt gcctggcacc acagaggtgc  66900
tatagtgcat gttcagtgaa tgataacact tccttttag aaacatgtaa tgtgtgtgcc  66960
tgtgtggcat atgcacattg gcatacggct gcaggtacat gaagaggcca gaggagttgt  67020
ccggcattct tcacccccctt tctttgagac agggtctgta tctaaacctg gagcttatat  67080 tttttttggca atgccagtgg ccagcaagcc ccaggagtgc tgactcggtc ccacttcagt  67140
gatgggtttt aggcatgtgt acaagcacac ctaccatgtt aagggatgaa ctctggtatc  67200
tgaactctgg tcctcatgtc atctgtgtct taactgctga gccatctctc cagaccagca  67260
ctgagtttct tcatcaggct cttccaagca tctgctctag gcacgagaa taaagaacta  67320 gctccctgcc tctagttctg gatgttagct ccagttccaa gacagccaac tgaaggaagg  67380
atcctaagta ttgcaactcg agtgaggtct gggcacgatg tcatggacct cgaatcccag  67440
tactaggaag gtgaaggtag aagatcatg actatgaggc caacctaggc tacatagaga  67500
gttccagact aacctgatct atatagtgaa accctgtctc atagaatgaa acaacatgaa  67560
actggacata gcaattaaga acacttgttg ctcttccaga ggacctgggg tcaatgccca  67620
gcactcatgg taacttgcaa ccacctgtaa ctccagttca gagcatctga caccctcttc  67680
tgacctccaa cacaggcatg cacatggtgc acatacagac agacaaaaca tccattcaca  67740 taaaatttttt ttttttttt ggttttttcga cacagggtt ctctgtatag tcctggctgt  67800
cctggaactc actctgtaga ccaagctggc ctctaattca gaaatctgcc tgcttctgcc  67860
tcccgagtgc tgggattaaa ggggtgcgcc accaccacct ggcaaaaata aatctttaaa  67920
aaatgtaaaa ataaacaaga gccccaagag ccagatgtag gaagtggaag ctggcacaag  67980
gaagtgccca gctgggcatg ggttagaact gtgaccaaca agaataacaa gacagaggca  68040
gctttagcca acctactggg acagcagcag tcatggaggt gccaggcttc attctgacca  68100
gcttggtgac ataccagtgt ctgtgtttat ctggtggata ggtgtctgag actccttacc  68160
attctttctt ggcaatttt gattgaatgc actaggattc tcaggctagc ccttaatgca  68220
gtgtgcttat tacagctgtg gaacatgtgt gcacagaccc aggagagcat agggagatac  68280
gagccattgt gacagtctgg tgcacgacaa gatgtcagcc tcaccttcca tttaaacagt  68340
tggtgagaga ctttcatagt atgtaactga gtcgggggctc gcctcatttt aactggaaga  68400
agccgccaga gcactgtata gaatccttct caacgatatg ggaatgcaag gtgcaaagga  68460
attcttgctg ccgactgtgg gatgtggatt agcttacaga gtgcttgcct ggcatgcaag  68520
aagccctggg tttaattccc atactaaata agctgatgat agtggtgcat acctattatc  68580
```

```
ctagcactca gtaggcagag gcaggaaaat gagaagttca agattgcctt tgattacata    68640
gtaaattcaa ggaagtctgg gccacatgag accttacctt taaaagatat aagtaaaaca    68700
tgagttggaa gccaacctgg actaaatagt gatcaccagg tcaactagag tcacgcaaca    68760
agaccctgtc tcaaacagac taacaagaaa ctaaaatggc tgatgaggta gcttagtggg    68820
taaaggtgtg tgctgccaag tctgacaacc tgagtttgat cccagaagcc gcacagggaa    68880
ggagagacaa ctctcgactc tggaacgttt tcctttcctt cagattaatg ccatggtgtg    68940
tccacaaatg tatatgcaaa tacgcattaa gtgtaaataa acaaaaccct gaaagcaaaa    69000
cctgatggca caggatttta attgcaacta ctgagactga gacaaggtaa cacgttcaag    69060
ggcagagttc ccagcatgta ggaggcccta gattcaatct ccagtactgc ctgagcaata    69120
atagataaat gtactggaag tgactcacag gttaatagca cttttttttcg ctgaggaccc    69180 aaactcactt cccagcacct attaactcag tttcgtaatg ccccccccccc ccccaggttg    69240 gaccgttagg gaaggggggcg gggccatctc tgcctggaca gggcgggcct taacaggggt    69300
gggtggggcc tcccacctag cactgcttca aatttcctgg agtattagtc atgttttttaa    69360 ccccaatttt tgggaggcag aggcaggtgg agctctgtga gttccaggcc agcttggtct    69420
acgtaaagag ttctaagcca gccaagtcta cctactaaga ttctgactta aaaacaaaaa    69480
cagatgaaaa ggaggggtga aaatgatgta aatacagtac tcaccaatga aatttttcaaa    69540 gtttaaaaaa agagagaaag aaccaccacc tgggagcctc agtttccccc actaggtgca    69600
ggagaggttg gctgataccc agtccctcca gcctccatcc aagcataccg aaaggctgcc    69660
ttgtgggcca accacagccc aggtcccatc catcatgctc aggccccgcc caccaagagc    69720
caaagcccaa cctccatggc aaggccccgc ccaccataga cacccaccta ccacaaccca    69780
ggctcctgtc atcttggcag aggcccccacc caccgcagcc caggctccgc cccgttcagt    69840
cagagacggg ccccgcccct ttccctaacg gtcaacggtc gtccagcctc tcagaagcaa    69900
ggcgagctgg acgccgcgt cgtgtcgctg ttctcgggtc ccagtggcca tggaggacgc    69960
gctgctcggc gccatgactg gccccgaaga cgagctgggc                         70000
```

<210> SEQ ID NO 7

<400> SEQUENCE: 7

000

<210> SEQ ID NO 8

<400> SEQUENCE: 8

000

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
ccagagccaa cgtcaagcat                                                   20

<210> SEQ ID NO 10
<211> LENGTH: 20
<212> TYPE: DNA
<213> ORGANISM: Artificial sequence

```
<220> FEATURE:
<223> OTHER INFORMATION: Primer

<400> SEQUENCE: 10
cagccgtgca acaatctgaa                                                20

<210> SEQ ID NO 11
<211> LENGTH: 29
<212> TYPE: DNA
<213> ORGANISM: Artificial sequence
<220> FEATURE:
<223> OTHER INFORMATION: Probe

<400> SEQUENCE: 11
tgaaaatcct caacactcca aactgtgcc                                      29

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
gccctcagaa agctctggaa                                                20

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
tagggtcgag gctctgcttg t                                              21

<210> SEQ ID NO 14
<211> LENGTH: 30
<212> TYPE: DNA
<213> ORGANISM: Artificial sequence
<220> FEATURE:
<223> OTHER INFORMATION: Probe

<400> SEQUENCE: 14
ccatcggtgc aaacctacag aagcagtatg                                     30

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
tgatggtgtt gaggaagctt ttt                                            23

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
tccctcaagt ctcctgttcc a                                              21
```

```
<210> SEQ ID NO 17
<211> LENGTH: 26
<212> TYPE: DNA
<213> ORGANISM: Artificial sequence
<220> FEATURE:
<223> OTHER INFORMATION: Probe

<400> SEQUENCE: 17
acaacagatc gcgtgatgac cgtctc                                          26

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
gcatgttctc acatta                                                     16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 19
gcaugttctc acatta                                                     16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA
```

<400> SEQUENCE: 20
gcatgtuctc acatta                                                                16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 21
gcatgtuctc acatta                                                                16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gtctgtgcat ctctcc                                                                16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)
<223> OTHER INFORMATION: bases at these positions are RNA
<220> FEATURE:
<221> NAME/KEY: misc_feature
<222> LOCATION: (5)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)

<223> OTHER INFORMATION: bases at these positions are RNA

<400> SEQUENCE: 23
gtctgugcat ctctcc                                                          16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
atcatggctg cagctt                                                          16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(14)
<223> OTHER INFORMATION: bases at these positions are RNA

<400> SEQUENCE: 25
atcauggctg cagctt                                                          16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
tgaggtcctg cactgg                                                          16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(8)
<223> OTHER INFORMATION: bases at these postitions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these postitions are RNA

<400> SEQUENCE: 27
tgaggucctg cactgg                                                          16

```
<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ttcagtcatg acttcc                                                           16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 29
ttcagucatg acttcc                                                           16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t

<400> SEQUENCE: 30
gcatnttctc acatta                                                           16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
gcatattctc acatta                                                           16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
gcatgatctc acatta                                                           16
```

```
<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 33
gcatuttctc acatta                                                    16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: p

<400> SEQUENCE: 34
gcatgutctc acatta                                                    16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: p

<400> SEQUENCE: 35
gcaugttctc acatta                                                    16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 36
gcatuttctc acatta                                                    16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: p

<400> SEQUENCE: 37
gcatgutctc acatta                                                    16
```

```
<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: p

<400> SEQUENCE: 38
gcatgtuctc acatta                                               16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 39
gcatgttcuc acatta                                               16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<220> FEATURE:
<221> NAME/KEY: misc_feature
<222> LOCATION: (5)..(5)
<223> OTHER INFORMATION: n is a, c, g, or t

<400> SEQUENCE: 40
gtctntgcat ctctcc                                               16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
gaggatggca agcaca                                               16

<210> SEQ ID NO 42
<211> LENGTH: 16
```

```
<212> TYPE: DNA
<213> ORGANISM: Artificial sequence
<220> FEATURE:
<223> OTHER INFORMATION: Synthetic oligonucleotide

<400> SEQUENCE: 42
cacctgcggg aagctc                                                   16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
tgtgccccag cccatt                                                   16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
cttccacagt atatct                                                   16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
tactggtagt gttgct                                                   16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ttgacacaaa gggagt                                                   16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
gaatctcctt ttccag                                                   16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
```
tttacacgct tccgcc                                                        16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
agactctcgg ttccga                                                        16

<210> SEQ ID NO 50

<400> SEQUENCE: 50

000

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
cttttctatc agtctc                                                        16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cttcttgatg tctttc                                                        16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
aagtgtcact aaaacc                                                        16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
ggactgaaat agcaga                                                        16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
aggctggccc ccactg                                                    16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ggtttttgat tcttcc                                                    16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
gcatgccgcc ccgtcc                                                    16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
tcttcataca atagca                                                    16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
cgttcaaatt ccgtct                                                    16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
tccggctgcg gctcag                                                    16

<210> SEQ ID NO 61
<211> LENGTH: 18
<212> TYPE: DNA
<213> ORGANISM: Artificial sequence
<220> FEATURE:
<223> OTHER INFORMATION: Primer

<400> SEQUENCE: 61
agaggagacc gagcgaat                                                  18

<210> SEQ ID NO 62
<211> LENGTH: 23
<212> TYPE: DNA
<213> ORGANISM: Artificial sequence

```
<220> FEATURE:
<223> OTHER INFORMATION: Primer

<400> SEQUENCE: 62
catggtttgt gttgatgtac gac                                    23

<210> SEQ ID NO 63
<211> LENGTH: 24
<212> TYPE: DNA
<213> ORGANISM: Artificial sequence
<220> FEATURE:
<223> OTHER INFORMATION: Probe

<400> SEQUENCE: 63
cctacatcag ggagcgagaa ggga                                   24

<210> SEQ ID NO 64
<211> LENGTH: 21
<212> TYPE: DNA
<213> ORGANISM: Artificial sequence
<220> FEATURE:
<223> OTHER INFORMATION: Primer

<400> SEQUENCE: 64
gtcaagacta caacacacag c                                      21

<210> SEQ ID NO 65
<211> LENGTH: 23
<212> TYPE: DNA
<213> ORGANISM: Artificial sequence
<220> FEATURE:
<223> OTHER INFORMATION: Primer

<400> SEQUENCE: 65
aaaactataa ggagggtga agg                                     23

<210> SEQ ID NO 66
<211> LENGTH: 33
<212> TYPE: DNA
<213> ORGANISM: Artificial sequence
<220> FEATURE:
<223> OTHER INFORMATION: Probe

<400> SEQUENCE: 66
ctgaaggact tttaaatgta gcctgctcac taa                         33

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
tgcagggagc cactctgagt                                        20

<210> SEQ ID NO 68
<211> LENGTH: 24
<212> TYPE: DNA
<213> ORGANISM: Artificial sequence
<220> FEATURE:
<223> OTHER INFORMATION: Primer

<400> SEQUENCE: 68 agaacccca ctgacttatc tgaa                                    24
```

```
<210> SEQ ID NO 69
<211> LENGTH: 26
<212> TYPE: DNA
<213> ORGANISM: Artificial sequence
<220> FEATURE:
<223> OTHER INFORMATION: Probe

<400> SEQUENCE: 69
cacagagcct aagatgtgca cgcctg                                              26

<210> SEQ ID NO 70
<211> LENGTH: 20
<212> TYPE: DNA
<213> ORGANISM: Artificial sequence
<220> FEATURE:
<223> OTHER INFORMATION: Primer

<400> SEQUENCE: 70
ccggagctag aagcgatcaa                                                     20

<210> SEQ ID NO 71
<211> LENGTH: 24
<212> TYPE: DNA
<213> ORGANISM: Artificial sequence
<220> FEATURE:
<223> OTHER INFORMATION: Primer

<400> SEQUENCE: 71
cctttagctt ctcagcctct tcct                                                24

<210> SEQ ID NO 72
<211> LENGTH: 17
<212> TYPE: DNA
<213> ORGANISM: Artificial sequence
<220> FEATURE:
<223> OTHER INFORMATION: Probe

<400> SEQUENCE: 72
ctcgagtcag ggagatg                                                        17

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
aatgtgcctg ctgtccttga                                                     20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(8)
<223> OTHER INFORMATION: bases at these positions are RNA
<220> FEATURE:
<221> NAME/KEY: misc_feature
<222> LOCATION: (10)..(11)
<223> OTHER INFORMATION: bases at these positions are RNA
```

```
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA
<220> FEATURE:
<221> NAME/KEY: misc_feature
<222> LOCATION: (19)..(20)
<223> OTHER INFORMATION: bases at these positions are RNA

<400> SEQUENCE: 74
aatgugcctg ctgtccttga                                              20

<210> SEQ ID NO 75
<211> LENGTH: 21
<212> TYPE: DNA
<213> ORGANISM: Artificial sequence
<220> FEATURE:
<223> OTHER INFORMATION: Primer

<400> SEQUENCE: 75
agatcaatcg gaccctagac a                                            21

<210> SEQ ID NO 76
<211> LENGTH: 18
<212> TYPE: DNA
<213> ORGANISM: Artificial sequence
<220> FEATURE:
<223> OTHER INFORMATION: Primer

<400> SEQUENCE: 76
cagcaccttc agcgagta                                                18

<210> SEQ ID NO 77
<211> LENGTH: 24
<212> TYPE: DNA
<213> ORGANISM: Artificial sequence
<220> FEATURE:
<223> OTHER INFORMATION: Probe

<400> SEQUENCE: 77
aagaggacgc cactcacgat gttc                                         24

<210> SEQ ID NO 78
<211> LENGTH: 20
<212> TYPE: DNA
<213> ORGANISM: Artificial sequence
<220> FEATURE:
<223> OTHER INFORMATION: Primer

<400> SEQUENCE: 78
acatgacagg cgcgatctct                                              20

<210> SEQ ID NO 79
<211> LENGTH: 25
<212> TYPE: DNA
<213> ORGANISM: Artificial sequence
<220> FEATURE:
<223> OTHER INFORMATION: Primer

<400> SEQUENCE: 79
tctaggttca cgtacacatc tttgc                                        25

<210> SEQ ID NO 80
```

```
<211> LENGTH: 26
<212> TYPE: DNA
<213> ORGANISM: Artificial sequence
<220> FEATURE:
<223> OTHER INFORMATION: Probe

<400> SEQUENCE: 80
ttccttcaag caatgccctc agcaat                                            26

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gttattgtgg ttggcg                                                       16

<210> SEQ ID NO 82
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 82
attctgtgtg cactgc                                                       16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tcttgtctga cattct                                                       16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
ttttgtgtct tctgta                                                       16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ctgtttgagt tttctc                                                       16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
```
caaagtgata ccagtt 16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
aatcttccag ggccac 16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
tcatttctat ggaata 16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gtcagtatcc cagtgt 16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ggttacagtg gaagag 16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
tctgggtgtt cttacg 16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
tttccttgag tagtag 16

<210> SEQ ID NO 93
<211> LENGTH: 16
<212> TYPE: DNA

```
<213> ORGANISM: Artificial sequence
<220> FEATURE:
<223> OTHER INFORMATION: Synthetic oligonucleotide

<400> SEQUENCE: 93
tctccttgct gtattt                                                   16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ttgccaatat caccat                                                   16

<210> SEQ ID NO 95
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 95
caactgaacc acccgt                                                   16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gcacaatatc attaac                                                   16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gactctctga tgatac                                                   16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
ctataccatc tctcat                                                   16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
catcatctat accatc                                                   16
```

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
acacatttag catgac                                                     16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
attatatggc aactca                                                     16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
gactaatatg cagttt                                                     16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
gtcaaattca agggtt                                                     16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
cataaagcat ggtgga                                                     16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
tagtctctgt cagtta                                                     16

<210> SEQ ID NO 106
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 106
gtacctatag tctctg                                                      16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
tcatgtacct atagtc                                                      16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
tcttaatttc atgtac                                                      16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
accctcaagt ctcctg                                                      16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
cagatatagg actgga                                                      16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
gacgcgcctg aaggtt                                                      16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
ggacacattg gccaca                                                      16

```
<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
ggccaccacg ctgtca                                                    16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
tgccaccgta gacacg                                                    16

<210> SEQ ID NO 115
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 115
gctagcctct ggattt                                                    16

<210> SEQ ID NO 116
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 116
gauaauguga gaacaugccu                                                20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
aggcatgttc tcacattatc                                                20

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ggctactacg ccgtca                                                    16

<210> SEQ ID NO 119
<211> LENGTH: 19
<212> TYPE: DNA
<213> ORGANISM: Artificial sequence
<220> FEATURE:
<223> OTHER INFORMATION: Primer
```

```
<400> SEQUENCE: 119 tttttttgcgc ggtcctttc                                              19

<210> SEQ ID NO 120
<211> LENGTH: 22
<212> TYPE: DNA
<213> ORGANISM: Artificial sequence
<220> FEATURE:
<223> OTHER INFORMATION: Primer

<400> SEQUENCE: 120
gagggaccag agagagcaag ac                                           22

<210> SEQ ID NO 121
<211> LENGTH: 19
<212> TYPE: DNA
<213> ORGANISM: Artificial sequence
<220> FEATURE:
<223> OTHER INFORMATION: Probe

<400> SEQUENCE: 121
cgccttccgt ccgtcggct                                               19

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
tggagactct cagggtcgaa a                                            21

<210> SEQ ID NO 123
<211> LENGTH: 22
<212> TYPE: DNA
<213> ORGANISM: Artificial Sequence
<220> FEATURE:
<223> OTHER INFORMATION: Primer

<400> SEQUENCE: 123
ggcgtttgga gtggtagaaa tc                                           22

<210> SEQ ID NO 124
<211> LENGTH: 20
<212> TYPE: DNA
<213> ORGANISM: Artificial Sequence
<220> FEATURE:
<223> OTHER INFORMATION: Probe

<400> SEQUENCE: 124
cggcggcaga ccagcatgac                                              20

<210> SEQ ID NO 125
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 125
gcatgttctc acattat                                                 17

<210> SEQ ID NO 126
<211> LENGTH: 16
```

```
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 126
caccugcggg aagctc                                                     16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: bases at these positions are RNA
<220> FEATURE:
<221> NAME/KEY: misc_feature
<222> LOCATION: (8)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 127
agacuctcgg ttccga                                                     16

<210> SEQ ID NO 128
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 128
ctttuctatc agtctc                                                     16

<210> SEQ ID NO 129
```

```
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(10)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 129
cttcutgatg tctttc                                                 16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(16)
<223> OTHER INFORMATION: bases at these positions are RNA

<400> SEQUENCE: 130
ggacugaaat agcaga                                                 16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonuclotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 131
aggcuggccc ccactg                                                 16

<210> SEQ ID NO 132
<211> LENGTH: 16
<212> TYPE: DNA
<213> ORGANISM: Artificial sequence
```

<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(9)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 132
ggttuttgat tcttcc                                                        16

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 133
gttautgtgg ttggcg                                                        16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:

```
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 134
attcugtgtg cactgc                                                        16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 135
ctgtutgagt tttctc                                                        16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(16)
<223> OTHER INFORMATION: bases at these positions are RNA

<400> SEQUENCE: 136
aatcutccag ggccac                                                        16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide
```

```
<220> FEATURE:
<221> NAME/KEY: misc_feature
<222> LOCATION: (2)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 137
tcatutctat ggaata                                                    16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA

<400> SEQUENCE: 138
caacugaacc acccgt                                                    16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 139
attauatggc aactca                                                    16

<210> SEQ ID NO 140
<211> LENGTH: 16
<212> TYPE: DNA
<213> ORGANISM: Artificial sequence
<220> FEATURE:
```

<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 140
acccucaagt ctcctg                                                   16

<210> SEQ ID NO 141
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 141
ggcatgttct cacatta                                                  17

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ggactgaaat tgcaga                                                   16

<210> SEQ ID NO 143
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 143
gtcugtgcat ctctcc                                                                16

<210> SEQ ID NO 144
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 144
acatcttcag atcatt                                                                16

<210> SEQ ID NO 145
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (2)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 145
taguctctgt cagtta                                                                16

<210> SEQ ID NO 146
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 146
gcatgutctc acattat                                                               17

<210> SEQ ID NO 147
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 147
acaaggacac caagat                                                    16

<210> SEQ ID NO 148
<211> LENGTH: 25
<212> TYPE: DNA
<213> ORGANISM: Artificial sequence
<220> FEATURE:
<223> OTHER INFORMATION: Primer

<400> SEQUENCE: 148
gggattacag agatcgtgac tgatt                                          25

<210> SEQ ID NO 149
<211> LENGTH: 20
<212> TYPE: DNA
<213> ORGANISM: Artificial sequence
<220> FEATURE:
<223> OTHER INFORMATION: Primer

<400> SEQUENCE: 149
tgcagctgga agaaccaaaa                                                20

<210> SEQ ID NO 150
<211> LENGTH: 30
<212> TYPE: DNA
<213> ORGANISM: Artificial sequence
<220> FEATURE:
<223> OTHER INFORMATION: Probe

<400> SEQUENCE: 150
cagagtaaaa tacccattcc agctcctggg                                     30

<210> SEQ ID NO 151
<211> LENGTH: 21
<212> TYPE: DNA
<213> ORGANISM: Artificial sequence
<220> FEATURE:
<223> OTHER INFORMATION: Primer

<400> SEQUENCE: 151
gattcgtcag ctttgccaag t                                              21

<210> SEQ ID NO 152
<211> LENGTH: 22
<212> TYPE: DNA
<213> ORGANISM: Artificial sequence
<220> FEATURE:
<223> OTHER INFORMATION: Primer

<400> SEQUENCE: 152
cgtctgttca gttgtcaatg ca                                             22

<210> SEQ ID NO 153
<211> LENGTH: 29
<212> TYPE: DNA
<213> ORGANISM: Artificial sequence
<220> FEATURE:
<223> OTHER INFORMATION: Probe

<400> SEQUENCE: 153
tctgggcctc aaggataaca acatcgttt                                              29

<210> SEQ ID NO 154
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(4)
<223> OTHER INFORMATION: bases at these positions are RNA
<220> FEATURE:
<221> NAME/KEY: misc_feature
<222> LOCATION: (6)..(7)
<223> OTHER INFORMATION: bases at these positions are RNA
<220> FEATURE:
<221> NAME/KEY: misc_feature
<222> LOCATION: (7)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 154
gttatugtgg ttggcg                                                            16

MODIFIED COMPOUNDS AND USES THEREOF

SEQUENCE LISTING

The present application is being filed along with a Sequence Listing in electronic format. The Sequence Listing is provided as a file entitled CORE0148USASEQ_ST25.txt created Aug. 4, 2020, which is 368 kb in size. The information in the electronic format of the sequence listing is incorporated herein by reference in its entirety.

FIELD

The present disclosure provides oligomeric compounds comprising a modified oligonucleotide having a central region comprising one or more modifications. In certain embodiments, the present disclosure provides oligomeric compounds having an improved therapeutic index or an increased maximum tolerated dose.

BACKGROUND

The principle behind antisense technology is that an antisense compound hybridizes to a target nucleic acid and modulates the amount, activity, and/or function of the target nucleic acid. For example, in certain instances, antisense compounds result in altered transcription or translation of a target. Such modulation of expression can be achieved by, for example, target RNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics, or affinity for a target nucleic acid.

SUMMARY

The present disclosure provides oligomeric compounds and methods of using oligomeric compounds that comprise a modified oligonucleotide consisting of 14-23 linked nucleosides, wherein the modified oligonucleotide comprises a gapmer consisting of a 5'-region, a central region, and a 3'-region wherein:
  the 5'-region consists of 2-5 linked modified nucleosides, wherein each nucleoside of the 5'-region comprises a 2'-modified furanosyl sugar moiety;
  the 3'-region consists of 1-5 linked modified nucleosides, wherein each nucleoside of the 3'-region comprises a 2'-modified furanosyl sugar moiety;
  the central region consists of 7-10 linked nucleosides, where each nucleoside of the central region comprises a sugar moiety selected from an unmodified 2'-β-D-deoxyribosyl sugar moiety and a modified sugar moiety; wherein
  the 3'- and 5'-most nucleosides of the central region each comprise a sugar moiety independently selected from a 2'-deoxyfuranosyl sugar moiety or a sugar surrogate; and wherein
  the central region comprises:
    at least one altered nucleotide, comprising a modified internucleoside linkage other than phosphorothioate and/or a modified nucleobase other than 5-methylcytosine and/or a modified sugar moiety; and
    at least 6 nucleosides each comprising an unmodified 2'-β-D-deoxyribosyl sugar moiety.

In certain embodiments, oligomeric compounds are provided comprising a single conjugate group linked to the 5'-end. In certain embodiments, oligomeric compounds are provided comprising a single conjugate group linked to the 3'-end.

In certain embodiments, the oligomeric compounds provided herein have an increased maximum tolerated dose when administered to an animal compared to an otherwise identical oligomeric compound except that the otherwise identical oligomeric compound lacks the altered nucleotide in the central region.

In certain embodiments, the oligomeric compounds provided herein have an increased therapeutic index compared to an otherwise identical oligomeric compound except that the otherwise identical oligomeric compound lacks the altered nucleotide in the central region.

In certain embodiments, methods of inhibiting target RNA are provided comprising contacting one or more cells, a tissue or an animal with an oligomeric compound as provided herein wherein said oligomeric compound is complementary to a target RNA.

In certain embodiments, the cells are in a human. In certain embodiments, the target RNA is human RNA. In certain embodiments, the target is human mRNA. In certain embodiments, the target RNA is cleaved, thereby inhibiting its function.

In certain embodiments, in vitro methods of inhibiting gene expression are provided comprising contacting one or more cells or a tissue with an oligomeric compound as provided herein.

In certain embodiments, oligomeric compounds are provided for use in an in vivo method of inhibiting gene expression wherein the method comprises contacting one or more cells, a tissue or an animal with an oligomeric compound as provided herein.

In certain embodiments, oligomeric compounds are provided for use in medical therapy.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH(H) sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein mC indicates a cytosine base comprising a methyl group at the 5-position.

As used herein, "2'-deoxyfuranosyl sugar moiety" or "2'-deoxyfuranosyl sugar" means a furanosyl sugar moiety having two hydrogens at the 2'-position. 2'-deoxyfuranosyl sugar moieties may be unmodified or modified and may be substituted at positions other than the 2'-position or unsubstituted. A β-D-2'-deoxyribosyl sugar moiety or 2'-β-D-deoxyribosyl sugar moiety in the context of an oligonucleotide is an unsubstituted, unmodified 2'-deoxyfuranosyl and is found in naturally occurring deoxyribonucleic acids (DNA).

As used herein, "2'-modified" in reference to a furanosyl sugar moiety or nucleoside comprising a furanosyl sugar moiety means the furanosyl sugar moiety comprises a substituent other than H or OH at the 2'-position of the furanosyl sugar moiety. 2'-modified furanosyl sugar moieties include non-bicyclic and bicyclic sugar moieties and may comprise, but are not required to comprise, additional substituents at other positions of the furanosyl sugar moiety.

As used herein, "2'-ribo-F" indicates a 2'-fluororibose.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "4'-modified" in reference to a furanosyl sugar moiety or nucleoside comprising a furanosyl sugar moiety means the furanosyl sugar moiety comprises a substituent other than H at the 4'-position of the furanosyl sugar moiety. 4'-modified furanosyl sugar moieties include non-bicyclic and bicyclic sugar moieties and may but are not required to comprise additional substituents at other positions of the furanosyl sugar moiety.

As used herein, "4'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 4'-position and is a non-bicyclic furanosyl sugar moiety. 4'-substituted furanosyl sugar moieties do not comprise additional substituents at other positions of the furanosyl sugar moiety other than a nucleobase and/or internucleoside linkage(s) when in the context of an oligonucleotide.

As used herein, "5'-modified" in reference to a furanosyl sugar moiety or nucleoside comprising a furanosyl sugar moiety means the furanosyl sugar moiety comprises a substituent other than H at the 5'-position of the furanosyl sugar moiety. 5'-modified furanosyl sugar moieties may but are not required to comprise additional substituents at other positions of the furanosyl sugar moiety.

As used herein, "5'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 5'-position and is a non-bicyclic furanosyl sugar moiety. 5'-substituted furanosyl sugar moieties do not comprise additional substituents at other positions of the furanosyl sugar moiety other than a nucleobase and/or internucleoside linkage(s) when in the context of an oligonucleotide.

As used herein, "administration" or "administering" refers to routes of introducing a compound or composition provided herein to a subject to perform its intended function. Examples of routes of administration that can be used include, but are not limited to, administration by inhalation, subcutaneous injection, intrathecal injection, and oral administration.

As used herein, "administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel, sequentially, separate, or simultaneous administration.

As used herein, "ALT" means alanine aminotransferase. As used herein, "AST" means aspartate transaminase. In certain embodiments, plasma levels of ALT and AST in a subject are measured in units per liter. As used herein, "units per liter" in the context of plasma ALT or plasma AST levels means international units per liter, the standard units for measurement of plasma ALT or plasma AST levels used by those of ordinary skill in the medical arts.

As used herein, "animal" refers to a human or non-human animal, including, but not limited to, mice, rats, rabbits, dogs, cats, pigs, and non-human primates, including, but not limited to, monkeys and chimpanzees.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified furanosyl sugar moiety. In certain embodiments, the bicyclic sugar moiety does not comprise a furanosyl moiety.

As used herein, a "central nervous system target" is a target RNA that is expressed in the central nervous system.

As used herein, "cEt" or "constrained ethyl" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-CH($CH_3$)—O-2', and the methyl group of the bridge is in the S configuration. A cEt bicyclic sugar moiety is in the β-D configuration.

As used herein, a "cEt nucleoside" or "cEt nucleotide" is a nucleoside or nucleotide comprising a cEt.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups may comprise a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" or "adjacent" in the context of an oligonucleotide refers to nucleosides, nucleobases, sugar moieties, or internucleoside linkages that are immediately adjacent to each other independent of the other moieties of the oligonucleotide. For example, "contiguous nucleobases" means nucleobases that are immediately adjacent to each other in a sequence. Moieties that are "directly linked" are immediately adjacent to each other and not separated by any other type of moiety.

As used herein, "cytotoxic" or "cytotoxicity" in the context of an effect of an oligomeric compound or a parent oligomeric compound on cultured cells means an at least 2-fold increase in caspase activation following administration of 10 μM or less of the oligomeric compound or parent oligomeric compound to the cultured cells relative to cells cultured under the same conditions but that are not administered the oligomeric compound or parent oligomeric compound. In certain embodiments, cytotoxicity is measured using a standard in vitro cytotoxicity assay.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "effective amount" means the amount of compound sufficient to effectuate a desired physiological outcome in a subject in need of the compound. The effective amount may vary among subjects depending on the health and physical condition of the subject to be treated, the taxonomic group of the subjects to be treated, the formulation of the composition, assessment of the subject's medical condition, and other relevant factors.

As used herein, "efficacy" means the ability to produce a desired effect.

As used herein, "expression" includes all the functions by which a gene's coded information is converted into structures present and operating in a cell. Such structures include, but are not limited to, the products of transcription and translation. As used herein, "modulation of expression" means any change in amount or activity of a product of transcription or translation of a gene. Such a change may be an increase or a reduction of any amount relative to the expression level prior to the modulation.

As used herein, "gapmer" means an oligonucleotide having a central region comprising a plurality of nucleosides that support RNase H cleavage positioned between a 5'-region and a 3'-region. Herein, the nucleosides of the 5'-region and 3'-region each comprise a 2'-modified furanosyl sugar moiety, and the 3'- and 5'-most nucleosides of the central region each comprise a sugar moiety independently selected from a 2'-deoxyfuranosyl sugar moiety or a sugar surrogate. The positions of the central region refer to the order of the nucleosides of the central region and are counted starting from the 5'-end of the central region. Thus, the 5'-most nucleoside of the central region is at position 1 of the central region. The "central region" may be referred to as a "gap", and the "5'-region" and "3'-region" may be referred to as "wings".

As used herein, "hepatotoxic" in the context of a mouse means a plasma ALT level that is above 300 units per liter. Hepatotoxicity of an oligomeric compound or parent oligoage" means a modified internucleoside linkage in which one of the non-bridging oxygen atoms of a phosphodiester is replaced with a sulfur atom. Modified internucleoside linkages may or may not contain a phosphorus atom. A "neutral internucleoside linkage" is a modified internucleoside linkage that does not have a negatively charged phosphate in a buffered aqueous solution at pH=7.0.

As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "LICA-1" is a conjugate group that is represented by the formula:

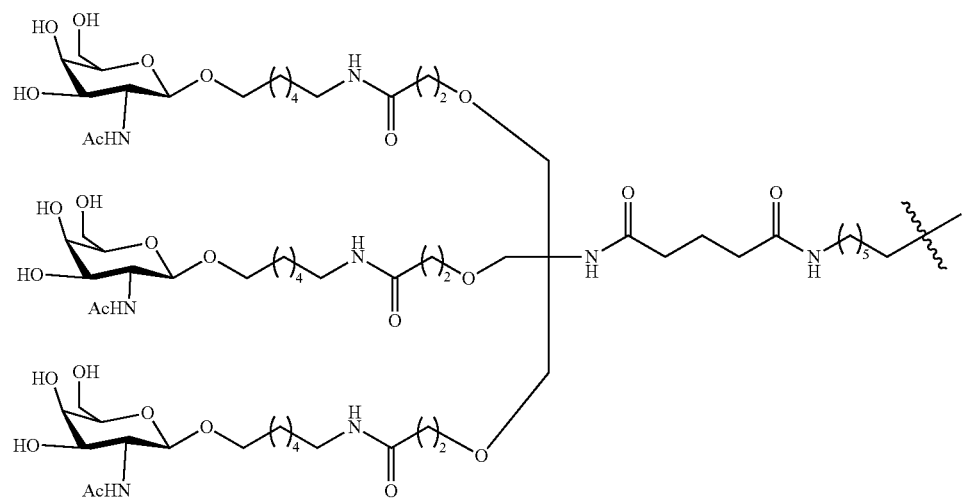

meric compound that is administered to a mouse is determined by measuring the plasma ALT level of the mouse 24 hours to 2 weeks following at least one dose of 1-150 mg/kg of the compound.

As used herein, "hepatotoxic" in the context of a human means a plasma ALT level that is above 150 units per liter. Hepatotoxicity of an oligomeric compound or parent oligomeric compound that is administered to a human is determined by measuring the plasma ALT level of the human 24 hours to 2 weeks following at least one dose of 10-300 mg of the compound.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample and does not necessarily indicate a total elimination of expression or activity.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphodiester internucleoside linkage. "Phosphorothioate link- As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic sugar" or "non-bicyclic sugar moiety" means a sugar moiety that comprises fewer than 2 rings. Substituents of modified, non-bicyclic sugar moieties do not form a bridge between two atoms of the sugar moiety to form a second ring.

As used herein, "linked nucleosides" are nucleosides that are connected in a continuous sequence (i.e. no additional nucleosides are present between those that are linked).

As used herein, "liver target" is a target RNA expressed in the liver wherein modulation of the expression of the target RNA in the liver is desired for therapeutic benefit. In certain embodiments, a liver target is expressed in tissues other than the liver as well as in the liver. As used herein, modulation of the expression of a target RNA that is "not a liver target" is desired in a tissue that is not the liver for therapeutic benefit. In certain embodiments, a target RNA that is not a liver target is expressed in the liver and is modulated by an oligomeric compound in therapy.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism.

As used herein, "MOE" means methoxyethyl. "2'-MOE" or "2'-O-methoxyethyl" means a 2'-OCH$_2$CH$_2$OCH$_3$ group at the 2'-position of a furanosyl ring. In certain embodiments, the 2'-OCH$_2$CH$_2$OCH$_3$ group is in place of the 2'-OH group of a ribosyl ring or in place of a 2'-H in a 2'-deoxyribosyl ring.

As used herein, "MOP" or "methoxypropyl internucleoside linkage" means the alkyl phosphonate internucleoside bond shown below:

MOP (alkyl phosphonate)

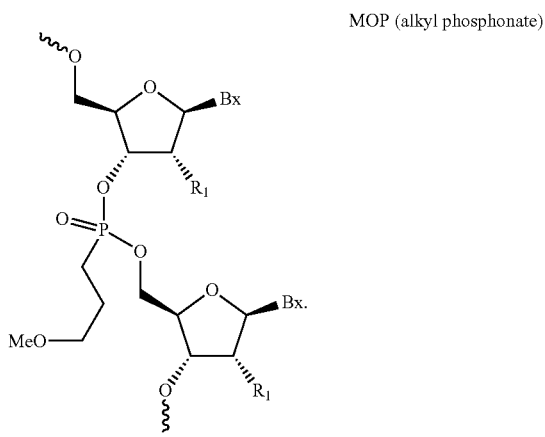

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a nucleobase that can pair with any one of the five unmodified nucleobases. 5-methylcytosine (NC) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "parent oligomeric compound" in the context of an oligomeric compound comprising at least one modification in the central region other than phosphorothioate or 5-methylcytosine means an oligomeric compound that is identical to the oligomeric compound comprising the at least one modification in the central region except that the parent oligomeric compound does not comprise at least one modified internucleoside linkage other than phosphorothioate and/or at least one modified nucleoside comprising a modified nucleobase other than 5-methylcytosine and/or a modified sugar moiety. A parent oligomeric compound and its counterpart oligomeric compound comprising at least one modification in the central region have identical nucleobase sequences or differ in nucleobase sequence only due to inclusion of a modified nucleobase other than 5-methylcytosine in the oligomeric compound comprising at least one modification in the central region.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "standard cell assay" means any of the assays described in Examples 1-9, and reasonable variations thereof.

As used herein, "standard in vitro activity assay" means a procedure, as described in Example 1 herein, wherein expression is measured by RT-PCR in cultured cells expressing the target RNA following administration of an oligomeric compound to the cultured cells.

As used herein, "standard in vitro cytotoxicity assay" means a procedure, as described in Example 8 herein, wherein activation of caspases 3 and 7 is measured in cultured 3T3-L1 cells following administration of an oligomeric compound to the cells.

As used herein, "standard in vivo experiment" means the procedure described in Example 10 and reasonable variations thereof.

As used herein, "stereorandom" in the context of a compound or moiety comprising a chiral center means the chiral center has a random stereochemical configuration. For example, in a population of molecules of identical formula comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration.

As used herein, "subject" means a human or non-human animal selected for treatment or therapy.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not have a stereoconfiguration other than β-D-ribosyl. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "susceptible" in the context of a disease, disorder, condition, or symptom such as degeneration, damage, or elevated apoptosis means that a subject has a higher risk than the average risk for the general population for the disease, disorder, condition, or symptom.

As used herein, "target nucleic acid," "target RNA," "target RNA transcript" and "nucleic acid target" mean a nucleic acid that an oligomeric compound, such as an antisense compound, is designed to affect. In certain embodiments, an oligomeric compound comprises an oligonucleotide having a nucleobase sequence that is complementary to more than one RNA, only one of which is the target RNA of the oligomeric compound. In certain embodiments, the target RNA is an RNA present in the species to which an oligomeric compound is administered. As used herein, a "liver target" is a target RNA that is expressed in the liver, and modulation of expression of the target RNA in the liver provides a therapeutic effect. As used herein a "central nervous system target" is a target RNA that is expressed in the central nervous system, and modulation of expression of the target RNA in the central nervous system provides a therapeutic effect.

The present disclosure provides certain individual cellular, tissue, or organ targets. For example, a "macrophage target" or a "liver target." For each such individual target, modulation of the expression of the target RNA in the individual cellular, tissue, or organ target is desired for therapeutic benefit. In certain embodiments, modulation of the target RNA in an individual cellular, tissue, or organ target provides a therapeutic effect. In certain embodiments, a cellular, tissue, or organ target is expressed in tissues other than in a particular type of cell, tissue, or organ as well as being expressed in a particular type of cell, tissue, or organ. For example, certain target RNAs may be expressed in both a macrophage and a hepatocyte.

As used herein, "therapeutically effective amount" means an amount of a compound, pharmaceutical agent, or composition that provides a therapeutic benefit to a subject.

As used herein, "treat" refers to administering a compound or pharmaceutical composition to an animal in order to effect an alteration or improvement of a disease, disorder, or condition in the animal.

As used herein, "maximum tolerated dose" means the highest dose of a compound that does not cause unacceptable side effects. In certain embodiments, the maximum tolerated dose is the highest dose of a modified oligonucleotide that does not cause an ALT elevation of three times the upper limit of normal as measured by a standard assay, e.g. the assay of Example 12 or Example 1. In certain embodiments, the maximum tolerated dose is the highest dose of a modified oligonucleotide that does not cause caspase elevation of greater than 30,000 RLU as measured by a standard assay, e.g. the assay of Example 13, Example 8, or Example 4.

As used herein, "DNA isomer" means a nucleoside that comprises a modified sugar moiety that is a stereoisomer of β-D-2'-deoxyribosyl. As used herein, a "DNA isomer" does not include β-D-2'-deoxyribosyl nucleosides. Seven such isomers of 2'-β-D-deoxyribosyl exist: 2'-β-D-deoxyxylosyl (β-D-XNA), 2'-α-D-deoxyribosyl (α-D-DNA), 2'-α-L-deoxyribosyl (α-L-DNA), 2'-β-L-deoxyribosyl ((3-L-DNA), 2'-α-D-deoxyxylosyl (α-LANA), 1, 2'-α-L-deoxyxylosyl (α-LANA), 2'-β-L-deoxyxylosyl (β-L-XNA). In certain embodiments, a DNA isomer is 2'-α-D-deoxyribosyl, 2'-α-L-deoxyribosyl, 2'-β-L-deoxyribosyl, or 2'-β-D-deoxyxylosyl sugar moiety. As used herein, "DNA isomer" does not include any nonfuranosyl sugar moieties.

As used herein, "DNA nucleoside" means a nucleoside comprising a 2'-H(H) β-D-2'-deoxyribosyl sugar moiety, as found in naturally-occurring DNA. A "DNA nucleoside" may comprise a modified nucleobase or a uracil nucleobase. A DNA nucleoside may be linked to adjacent nucleosides through unmodified phosphodiester internucleoside linkages or through modified internucleoside linkages.

As used herein, a "2'-modified DNA isomer" means a nucleoside that comprises a modified sugar moiety that is selected from 2'-β-D-deoxyxylosyl (β-D-XNA), 2'-α-D-deoxyribosyl (α-D-DNA), 2'-α-L-deoxyribosyl (α-L-DNA), 2'-β-L-deoxyribosyl (β-L-DNA), 2'-α-D-deoxyxylosyl (α-LANA), 1, 2'-α-L-deoxyxylosyl (α-LANA), 2'-β-L-deoxyxylosyl (β-L-XNA), and that further comprises a 2'-substituent. In certain embodiments, the 2'-substituent is fluoro, alkoxy, or $C_1$-$C_{10}$ alkyl.

As used herein, "DNA mimic" means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms. In certain embodiments, a DNA mimic comprises a structure represented by the formula:

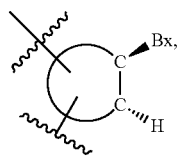

wherein Bx is a heterocylic base moiety, the ring contains 5-7 members, and the ring is attached at two positions to a hydroxyl, a phosphate, an internucleoside linking group, or a conjugate linker.

As used herein, a "standard RNase H cleavage assay" is an assay wherein a heteroduplex of the modified oligonucleotide and a complementary strand of unmodified RNA are incubated with each other to form a heteroduplex, and are then incubated with RNase H1 for specified time points before being analyzed on a polyacrylamide gel.

As used herein, a modified nucleoside "supports RNase H cleavage" when incorporated into an oligonucleotide if RNase H cleavage of the complementary RNA is observed within two nucleobases of the modified nucleoside in a standard RNase H cleavage assay.

As used herein, "therapeutic index" means a comparison of the amount of a compound that causes a therapeutic effect to the amount that causes toxicity. Compounds having a high therapeutic index have strong efficacy and low toxicity. In certain embodiments, increasing the therapeutic index of a compound increases the amount of the compound that can be safely administered. In certain embodiments, therapeutic index is the ratio of the amount of modulation of a target nucleic acid by a modified oligonucleotide compared to ALT elevation, wherein the ALT elevation is measured by a standard assay, e.g. the assay of Example 12 or Example 1. In certain embodiments, therapeutic index is the ratio of the amount of modulation of a target nucleic acid by a modified oligonucleotide compared to caspase elevation, wherein the caspase elevation is measured by a standard assay, e.g. the assay of Example 13, Example 8, or Example 4.

As used herein, an "altered nucleotide" is a nucleotide that comprises one or more modifications relative to a nucleotide comprising a 2'-β-D-deoxyribosyl sugar moiety, a nucleobase selected from adenine (A), thymine (T), cytosine (C), 5-methyl cytosine (mC), uracil (U), or guanine (G), and a 5' to 3' internucleoside linkage selected from phosphodiester or stereorandom phosphorothioate. In certain embodiments, the altered nucleotide is an altered nucleoside attached to a phosphorothioate or phosphodiester internucleoside linkage. In certain embodiments, the altered nucleotide comprises a 2'-modified sugar moiety, or is a "2'-altered nucleotide". In certain embodiments, the altered nucleotide comprises a modified internucleoside linking group, and is a "linkage-altered nucleotide". Herein, a linkage-altered nucleotide comprises an internucleoside linking group other than phosphodiester or phosphorothioate attached to the 3' carbon of the sugar moiety, or the equivalent position for a sugar surrogate. The nucleotide on the 5'-end of an internucleoside linking group other than phosphodiester or phosphorothioate is not an "altered nucleotide", as used herein.

Certain embodiments are described in the numbered embodiments below:

1. An oligomeric compound comprising a modified oligonucleotide consisting of 14-23 linked nucleosides, wherein the modified oligonucleotide comprises a gapmer consisting of a 5'-region, a central region, and a 3'-region wherein:
   the 5'-region consists of 2-5 linked modified nucleosides, wherein each nucleoside of the 5'-region comprises a 2'-modified furanosyl sugar moiety;
   the 3'-region consists of 1-5 linked modified nucleosides, wherein each nucleoside of the 3'-region comprises a 2'-modified furanosyl sugar moiety;
   the central region consists of 7-10 linked nucleosides, where each nucleoside of the central region comprises a sugar moiety selected from an unmodified 2'-β-D-deoxyribosyl sugar moiety and a modified sugar moiety; wherein
   the 3'- and 5'-most nucleosides of the central region each comprise a sugar moiety independently selected from a 2'-deoxyfuranosyl sugar moiety or a sugar surrogate; and wherein the central region comprises:
   at least one modified internucleoside linkage other than phosphorothioate and/or at least one modified nucleoside comprising a modified nucleobase other than 5-methylcytosine and/or a modified sugar moiety; and at least 6 nucleosides each comprising an unmodified 2'-β-D-deoxyribosyl sugar moiety.
2. The oligomeric compound of embodiment 1, wherein the 5'-region consists of 2-4 linked nucleosides.
3. The oligomeric compound of embodiment 1, wherein the 5'-region consists of 2 linked nucleosides.
4. The oligomeric compound of embodiment 1, wherein the 5'-region consists of 3 linked nucleosides.
5. The oligomeric compound of embodiment 1, wherein the 5'-region consists of 4 linked nucleosides.
6. The oligomeric compound of embodiment 1, wherein the 5'-region consists of 5 linked nucleosides.
7. The oligomeric compound of any of embodiments 1-6, wherein each nucleoside of the 5'-region comprises a 2'-modified ribosyl sugar moiety.
8. The oligomeric compound of any of embodiments 1-7, wherein at least one nucleoside of the 5'-region comprises a bicyclic furanosyl sugar moiety.
9. The oligomeric compound of any of embodiments 1-8, wherein each nucleoside of the 5'-region comprises a bicyclic furanosyl sugar moiety.
10. The oligomeric compound of any of embodiments 1-8, wherein at least one nucleoside of the 5'-region comprises a non-bicyclic sugar moiety.
11. The oligomeric compound of embodiment 10, wherein the non-bicyclic sugar moiety of the at least one nucleoside of the 5'-region is a 2'-substituted ribosyl sugar moiety.
12. The oligomeric compound of any of embodiments 1-7 or 10-11, wherein each nucleoside of the 5'-region comprises a non-bicyclic sugar moiety.
13. The oligomeric compound of embodiment 12, wherein each nucleoside of the 5'-region comprises a 2'-substituted ribosyl sugar moiety.
14. The oligomeric compound of any of embodiments 1-7, wherein each nucleoside of the 5'-region comprises a 2'-modified furanosyl sugar moiety independently selected from a bicyclic sugar moiety and a non-bicyclic sugar moiety, 2'-substituted ribosyl sugar moiety.

15. The oligomeric compound of any of embodiments 8-11 or 14, wherein each bicyclic sugar moiety of the 5'-region is selected from among cEt, LNA, and ENA.
16. The oligomeric compound of any of embodiments 10-14, wherein each nonbicyclic sugar moiety of the 5'-region has a 2'-substituent selected from among 2'-MOE, 2'-OMe, and 2'-NMA.
17. The oligomeric compound of any of embodiments 1-16, wherein none of the nucleosides of the 5'-region comprise a sugar moiety having a 2'-F substituent.
18. The oligomeric compound of any of embodiments 1-17, wherein each nucleobase of the 5'-region is independently selected from among thymine, uracil, guanine, cytosine, 5-methylcytosine, and adenine.
19. The oligomeric compound of any of embodiments 1-18, wherein each internucleoside linkage of the 5'-region is selected from among phosphodiester and phosophorothioate internucleoside linkages.
20. The oligomeric compound of any of embodiments 1-19, wherein the 3'-region consists of 2-4 linked nucleosides.
21. The oligomeric compound of any of embodiments 1-19, wherein the 3'-region consists of 1 nucleoside.
22. The oligomeric compound of any of embodiments 1-19, wherein the 3'-region consists of 2 linked nucleosides.
23. The oligomeric compound of any of embodiments 1-19, wherein the 3'-region consists of 3 linked nucleosides.
24. The oligomeric compound of any of embodiments 1-19, wherein the 3'-region consists of 4 linked nucleosides.
25. The oligomeric compound of any of embodiments 1-19, wherein the 3'-region consists of 5 linked nucleosides.
26. The oligomeric compound of any of embodiments 1-25, wherein each nucleoside of the 3'-region comprises a 2'-modified ribosyl sugar moiety.
27. The oligomeric compound of any of embodiments 1-26, wherein at least one nucleoside of the 3'-region comprises a bicyclic furanosyl sugar moiety.
28. The oligomeric compound of any of embodiments 1-27, wherein each nucleoside of the 3'-region comprises a bicyclic furanosyl sugar moiety.
29. The oligomeric compound of any of embodiments 1-27, wherein at least one nucleoside of the 3'-region comprises a non-bicyclic sugar moiety.
30. The oligomeric compound of embodiment 29, wherein the non-bicyclic sugar moiety of the at least one nucleoside of the 3'-region is a 2'-substituted ribosyl sugar moiety.
31. The oligomeric compound of any of embodiments 1-26 or 29-30, wherein each nucleoside of the 3'-region comprises a non-bicyclic sugar moiety.
32. The oligomeric compound of embodiment 31, wherein each nucleoside of the 3'-region comprises a 2'-substituted ribosyl sugar moiety.
33. The oligomeric compound of any of embodiments 1-26, wherein each nucleoside of the 3'-region comprises a 2'-modified furanosyl sugar moiety independently selected from a bicyclic sugar moiety and a non-bicyclic sugar moiety, 2'-substituted ribosyl sugar moiety.
34. The oligomeric compound of any of embodiments 27-30 or 33, wherein each bicyclic sugar moiety of the 3'-region is selected from among cEt, LNA, and ENA.
35. The oligomeric compound of any of embodiments 29-33, wherein each nonbicyclic sugar moiety of the 3'-region has a 2'-substituent selected from among 2'-MOE, 2'-OMe, and 2'-NMA.
36. The oligomeric compound of any of embodiments 1-35, wherein none of the nucleosides of the 3'-region comprise a sugar moiety having a 2'-F substituent.
37. The oligomeric compound of any of embodiments 1-36, wherein each nucleobase of the 3'-region is independently selected from among thymine, uracil, guanine, cytosine, 5-methylcytosine, and adenine.
38. The oligomeric compound of any of embodiments 1-37, wherein each internucleoside linkage of the 3'-region is selected from among phosphodiester and phosophorothioate internucleoside linkages.
39. The oligomeric compound of any of embodiments 1-38, wherein the central region consists of 7 linked nucleosides.
40. The oligomeric compound of any of embodiments 1-38, wherein the central region consists of 8 linked nucleosides.
41. The oligomeric compound of any of embodiments 1-38, wherein the central region consists of 9 linked nucleosides.
42. The oligomeric compound of any of embodiments 1-38, wherein the central region consists of 10 linked nucleosides.
43. The oligomeric compound of any of embodiments 1-42, wherein each of the two internucleoside linkages connecting the central region to the 5'-region and 3'-region are independently selected from among phosphosdiester and phosphorothioate internucleoside linkages.
44. The oligomeric compound of any of embodiments 1-43, wherein the modified oligonucleotide consists of the gapmer.
45. The oligomeric compound of any of embodiments 1-43, comprising a conjugate group.
46. The oligomeric compound of any of embodiments 1-43 or 45, wherein the modified oligonucleotide comprises 1-3 linker nucleosides.
47. The oligomeric compound of embodiment 46, wherein the linker nucleosides are linked to the 5'-end or the 3'-end of the gapmer.
48. The oligomeric compound of any of embodiments 45-47, wherein the conjugate group comprises GalNAc.
49. The oligomeric compound of any of embodiments 45-47, comprising LICA-1.
50. The oligomeric compound of any of embodiments 1-49, wherein the central region comprises one, and no more than one, modified sugar moiety.
51. The oligomeric compound of embodiment 50, wherein the each internucleoside linkage within the central region is selected from among phosphodiester and phosophorothioate internucleoside linkages.
52. The oligomeric compound of any of embodiments 50-51, wherein each nucleobase of the central region is independently selected from among thymine, uracil, guanine, cytosine, 5-methylcytosine, and adenine.
53. The oligomeric compound of any of embodiments 1-50 or 52, wherein the central region comprises one, and no more than one, modified internucleoside linkage other than phosphorothioate.
54. The oligomeric compound of embodiment 53, wherein the modified internucleoside linkage other than phosphorothioate contains phosphorus.
55. The oligomeric compound of any of embodiments 53-54, wherein the modified internucleoside linkage other than phosphorothioate is a neutral internucleoside linkage.
56. The oligomeric compound of any of embodiments 1-50 or 52, wherein the central region comprises two, and no more than two, modified internucleoside linkages other than phosphorothioate.

57. The oligomeric compound of embodiment 56, wherein the two modified internucleoside linkages other than phosphorothioate each contain phosphorus.
58. The oligomeric compound of any of embodiments 56-57, wherein at least one of the modified internucleoside linkages other than phosphorothioate is a neutral internucleoside linkage.
59. The oligomeric compound of any of embodiments 56-57, wherein the two modified internucleoside linkages other than phosphorothioate are neutral internucleoside linkages.
60. The oligomeric compound of any of embodiments 1-51 or 53-59, wherein the central region comprises one, and no more than one, modified nucleobase other than 5-methylcytosine.
61. The oligomeric compound of any of embodiments 1-60, wherein each of the unmodified sugar moieties of the central region are 2'-β-D-deoxyribosyl sugar moieties.
62. The oligomeric compound of any of embodiments 50-61, wherein the one modified sugar moiety of the central region is at one of positions 2-9 of the central region.
63. The oligomeric compound of any of embodiments 50-61, wherein the one modified sugar moiety of the central region is at one of positions 1-6 of the central region.
64. The oligomeric compound of any of embodiments 50-61, wherein the one modified sugar moiety of the central region is at one of positions 1-4 of the central region.
65. The oligomeric compound of any of embodiments 50-61, wherein the one modified sugar moiety of the central region is at one of positions 2-4 of the central region.
66. The oligomeric compound of any of embodiments 50-61, wherein the one modified sugar moiety of the central region is at one of positions 3-4 of the central region.
67. The oligomeric compound of any of embodiments 50-66, wherein the one modified sugar moiety of the central region is a sugar surrogate, a bicyclic furanosyl sugar moiety, a non-bicyclic 2'-modified furanosyl sugar moiety, a non-bicyclic 4'-modified furanosyl sugar moiety, a non-bicyclic 5'-modified furanosyl sugar moiety, or a modified 2'-deoxyfuranosyl sugar moiety.
68. The oligomeric compound of embodiment 67, wherein the one modified sugar moiety of the central region is a bicyclic ribosyl sugar moiety, a non-bicyclic 2'-modified ribosyl sugar moiety, a non-bicyclic 4'-modified 2'-deoxyribosyl sugar moiety, a non-bicyclic 5'-modified 2'-deoxyribosyl sugar moiety, or a modified 2'-deoxyfuranosyl sugar moiety.
69. The oligomeric compound of embodiment 68, wherein the one modified sugar moiety of the central region is a bicyclic ribosyl sugar moiety, a non-bicyclic 2'-substituted ribosyl sugar moiety, a non-bicyclic 4'-substituted 2'-deoxyribosyl sugar moiety, a non-bicyclic 5'-substituted 2'-deoxyribosyl sugar moiety, or a modified, unsubstituted 2'-deoxyfuranosyl sugar moiety.
70. The oligomeric compound of any of embodiments 67-69, wherein the one modified sugar moiety of the central region is a 2'-substituted ribosyl sugar moiety.
71. The oligomeric compound of embodiment 70, wherein the 2'-substituted ribosyl sugar moiety is a 2'-F, 2'-MOE, or 2'-O-methyl substituted sugar moiety.
72. The oligomeric compound of any of embodiments 67-69, wherein the one modified sugar moiety of the central region is a 4'-alkyl substituted 2'-deoxyribosyl sugar moiety.
73. The oligomeric compound of embodiment 72, wherein the 4'-alkyl substituted ribosyl sugar moiety is a 4'-methyl substituted 2'-deoxyribosyl sugar moiety.
74. The oligomeric compound of any of embodiments 67-69, wherein the one modified sugar moiety of the central region is a 5'-alkyl substituted 2'-deoxyribosyl sugar moiety.
75. The oligomeric compound of embodiment 74, wherein the 5'-alkyl substituted ribosyl sugar moiety is a 5'-methyl, 5'-ethyl, or 5'-allyl substituted 2'-deoxyribosyl sugar moiety.
76. The oligomeric compound of any of embodiments 67-69, wherein the one modified sugar moiety of the central region is a modified, unsubstituted 2'-deoxyfuranosyl sugar moiety.
77. The oligomeric compound of embodiment 76, wherein the modified, unsubstituted 2'-deoxyfuranosyl sugar moiety is an unsubstituted α-D-2'-deoxyribosyl, α-L-2'-deoxyribosyl, β-L-2'-deoxyribosyl, or β-D-2'-deoxyxylosyl sugar moiety.
78. The oligomeric compound of any of embodiments 67-69, wherein the one modified sugar moiety of the central region is a bicyclic ribosyl sugar moiety.
79. The oligomeric compound of embodiment 78, wherein the bicyclic ribosyl sugar moiety is cEt, LNA, or ENA.
80. The oligomeric compound of any of embodiments 67-69, wherein the one modified sugar moiety of the central region is a morpholino, cEt, 2'-F, 2'-MOE, 4'-Methyl, 5'-Methyl, 5'-allyl, 5'-ethyl, β-L-2'-deoxyribosyl, α-D-2'-deoxyribosyl, β-D-2'-deoxyxylosyl, or α-L-2'-deoxyribosyl sugar moiety.
81. The oligomeric compound of embodiment 62, wherein the one modified sugar moiety of the central region is a 2'-O-Methyl substituted ribosyl, unsubstituted α-D-2'-deoxyribosyl, unsubstituted α-L-2'-deoxyribosyl, or unsubstituted β-L-2'-deoxyribosyl sugar moiety.
82. The oligomeric compound of embodiment 81, wherein the one modified sugar moiety of the central region is a 2'-O-Methyl substituted ribosyl or unsubstituted β-L-2'-deoxyribosyl sugar moiety.
83. The oligomeric compound of embodiment 63, wherein the one modified sugar moiety of the central region is a morpholino, 2'-O-Methyl substituted ribosyl, unsubstituted α-D-2'-deoxyribosyl, or unsubstituted (3-L-2'-deoxyribosyl sugar moiety sugar moiety.
84. The oligomeric compound of embodiment 64, wherein the one modified sugar moiety of the central region is a morpholino, unsubstituted α-D-2'-deoxyribosyl, or unsubstituted β-L-2'-deoxyribosyl sugar moiety sugar moiety.
85. The oligomeric compound of embodiment 65, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-allyl substituted 2'-deoxyribosyl, unsubstituted α-D-2'-deoxyribosyl, or cEt bicyclic sugar moiety.
86. The oligomeric compound of embodiment 85, wherein the one modified sugar moiety of the central region is a 2'-MOE substituted ribosyl, 2'-O-Methyl substituted ribosyl, or 5'-allyl substituted 2'-deoxyribosyl sugar moiety.

87. The oligomeric compound of embodiment 85 or 86, wherein the 5'-allyl substituted ribosyl sugar moiety is stereorandom at the 5'-position of the modified sugar moiety.

88. The oligomeric compound of embodiment 66, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(S)-Methyl substituted 2'-deoxyribosyl, 5'-(R)-Methyl substituted 2'-deoxyribosyl, 5'-stereorandom Methyl substituted 2'-deoxyribosyl, 5'-(S)-Ethyl substituted 2'-deoxyribosyl, 5'-(R)-Ethyl substituted 2'-deoxyribosyl, 5'-stereorandom Ethyl 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted α-D-2'-deoxyribosyl, unsubstituted α-L-2'-deoxyribosyl, unsubstituted β-L-2'-deoxyribosyl, cEt, or morpholino sugar moiety.

89. The oligomeric compound of embodiment 88, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, cEt, or morpholino sugar moiety.

90. The oligomeric compound of any of embodiments 50-61 or 67-69, wherein the one modified sugar moiety of the central region is at position 1 of the central region.

91. The oligomeric compound of embodiment 90, wherein the one modified sugar moiety of the central region is a morpholino, unsubstituted β-L-2'-deoxyribosyl, or unsubstituted α-D-2'-deoxyribosyl sugar moiety.

92. The oligomeric compound of embodiment 90, wherein the one modified sugar moiety of the central region is a morpholino or unsubstituted α-D-2'-deoxyribosyl sugar moiety.

93. The oligomeric compound of any of embodiments 50-61 or 67-69, wherein the one modified sugar moiety of the central region is at position 2 of the central region.

94. The oligomeric compound of embodiment 93, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-Allyl substituted 2'-deoxyribosyl, unsubstituted α-D-2'-deoxyribosyl, or cEt sugar moiety.

95. The oligomeric compound of embodiment 93, wherein the one modified sugar moiety of the central region is a 2'-MOE substituted ribosyl, 2'-O-Methyl substituted ribosyl, 5'-(S)-Methyl substituted 2'-deoxyribosyl, 5'-Allyl substituted 2'-deoxyribosyl, or unsubstituted α-D-2'-deoxyribosyl sugar moiety.

96. The oligomeric compound of embodiment 94 or 95, wherein the 5'-allyl substituted 2'-deoxyribosyl sugar moiety is stereorandom at the 5'-position of the modified sugar moiety.

97. The oligomeric compound of any of embodiments 50-61 or 67-69, wherein the one modified sugar moiety of the central region is at position 3 of the central region.

98. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, unsubstituted α-L-2'-deoxyribosyl, unsubstituted α-D-2'-deoxyribosyl, cEt, or morpholino sugar moiety.

99. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, cEt, or morpholino sugar moiety.

100. The oligomeric compound of any of embodiments 50-61 or 67-69, wherein the one modified sugar moiety of the central region is at position 4 of the central region.

101. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted α-L-2'-deoxyribosyl, unsubstituted α-D-2'-deoxyribosyl, cEt, or morpholino sugar moiety.

102. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted L-2'-deoxyribosyl, unsubstituted α-L-2'-deoxyribosyl, unsubstituted α-D-2'-deoxyribosyl, cEt, or morpholino sugar moiety.

103. The oligomeric compound of any of embodiments 50-61 or 67-69, wherein the one modified sugar moiety of the central region is at position 5 of the central region.

104. The oligomeric compound of embodiment 103, wherein the one modified sugar moiety of the central region is a 2'-O-Methyl substituted ribosyl or unsubstituted β-L-2'-deoxyribosyl sugar moiety.

105. The oligomeric compound of embodiment 103, wherein the one modified sugar moiety of the central region is an unsubstituted β-L-2'-deoxyribosyl sugar moiety.

106. The oligomeric compound of any of embodiments 50-61 or 67-69, wherein the one modified sugar moiety of the central region is at position 6 of the central region.

107. The oligomeric compound of embodiment 106, wherein the one modified sugar moiety of the central region is a 2'-O-Methyl substituted ribosyl, unsubstituted β-L-2'-deoxyribosyl, unsubstituted α-D-2'-deoxyribosyl, or morpholino sugar moiety.

108. The oligomeric compound of any of embodiments 50-61 or 67-69, wherein the one modified sugar moiety of the central region is at position 7 of the central region.

109. The oligomeric compound of embodiment 108, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

110. The oligomeric compound of any of embodiments 50-61 or 67-69, wherein the one modified sugar moiety of the central region is at position 8 of the central region.

111. The oligomeric compound of embodiment 110, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

112. The oligomeric compound of any of embodiments 50-61 or 67-69, wherein the one modified sugar moiety of the central region is at position 9 of the central region.

113. The oligomeric compound of embodiment 112, wherein the one modified sugar moiety of the central region is a 2'-O-Methyl substituted ribosyl or unsubstituted β-L-2'-deoxyribosyl sugar moiety.

114. The oligomeric compound of any of embodiments 50-61 or 67-69, wherein the one modified sugar moiety of the central region is at position 10 of the central region.

115. The oligomeric compound of any of embodiments 50-61 or 67-69, wherein the one modified sugar moiety of the central region is a morpholino modified sugar moiety at position 1 of the central region.

116. The oligomeric compound of any of embodiments 50-61 or 67-69, wherein the one modified sugar moiety of the central region is a modified, unsubstituted 2'-deoxyfuranosyl sugar moiety at position 1 of the central region.

117. The oligomeric compound of embodiment 116, wherein the one modified sugar moiety of the central region is an unsubstituted β-L-2'-deoxyribosyl sugar moiety at position 1 of the central region.

118. The oligomeric compound of embodiment 116, wherein the one modified sugar moiety of the central region is an unsubstituted α-D-2'-deoxyribosyl sugar moiety 119. The oligomeric compound of any of embodiments 50-61 or 67-69, wherein the one modified sugar moiety of the central region is a 2'-substituted ribosyl sugar moiety at position 2 of the central region.

120. The oligomeric compound of embodiment 119, wherein the 2'-substituted ribosyl sugar moiety at position 2 of the central region is a 2'-F ribosyl sugar moiety.

121. The oligomeric compound of embodiment 119, wherein the 2'-substituted ribosyl sugar moiety at position 2 of the central region is a 2'-MOE ribosyl sugar moiety.

122. The oligomeric compound of embodiment 119, wherein the 2'-substituted ribosyl sugar moiety at position 2 of the central region is a 2'-O-methyl ribosyl sugar moiety.

123. The oligomeric compound of any of embodiments 50-61 or 67-69, wherein the one modified sugar moiety of the central region is a 5'-alkyl substituted 2'-deoxyribosyl sugar moiety at position 2 of the central region.

124. The oligomeric compound of embodiment 123, wherein the 5'-alkyl substituted 2'-deoxyribosyl sugar moiety at position 2 of the central region is a 5'-(S)Me 2'-deoxyribosyl sugar moiety.

125. The oligomeric compound of embodiment 123, wherein the 5'-alkyl substituted 2'-deoxyribosyl sugar moiety at position 2 of the central region is a 5'-allyl 2'-deoxyribosyl sugar moiety.

126. The oligomeric compound of embodiment 125, wherein the 5'-allyl 2'-deoxyribosyl sugar moiety is stereorandom at the 5'-position of the 5'-allyl 2'-deoxyribosyl sugar moiety.

127. The oligomeric compound of any of embodiments 50-61 or 67-69, wherein the one modified sugar moiety of the central region is a modified, unsubstituted 2'-deoxyfuranosyl sugar moiety at position 2 of the central region.

128. The oligomeric compound of embodiment 127, wherein the modified, unsubstituted 2'-deoxyfuranosyl sugar moiety at position 2 of the central region is a α-D-2'-deoxyribosyl modified sugar moiety.

129. The oligomeric compound of any of embodiments 50-61 or 67-69, wherein the one modified sugar moiety of the central region is a cEt or LNA sugar moiety at position 2 of the central region.

130. The oligomeric compound of any of embodiments 50-61 or 67-69, wherein the one modified sugar moiety of the central region is a 2'-substituted ribosyl sugar moiety at position 3 of the central region.

131. The oligomeric compound of embodiment 130, wherein the 2'-substituted ribosyl sugar moiety at position 3 of the central region is a 2'-F ribosyl sugar moiety.

132. The oligomeric compound of embodiment 130, wherein the 2'-substituted ribosyl sugar moiety at position 3 of the central region is a 2'-MOE ribosyl sugar moiety.

133. The oligomeric compound of embodiment 130, wherein the 2'-substituted ribosyl sugar moiety at position 3 of the central region is a 2'-O-methyl ribosyl sugar moiety.

134. The oligomeric compound of any of embodiments 50-61 or 67-69, wherein the one modified sugar moiety of the central region is a 4'-alkyl substituted 2'-deoxyribosyl sugar moiety at position 3 of the central region.

135. The oligomeric compound of embodiment 134, wherein the 4'-substituted 2'-deoxyribosyl sugar moiety at position 3 of the central region is a 4'-methyl 2'-deoxyribosyl sugar moiety.

136. The oligomeric compound of any of embodiments 50-61 or 67-69, wherein the one modified sugar moiety of the central region is a 5'-alkyl substituted 2'-deoxyribosyl sugar moiety at position 3 of the central region.

137. The oligomeric compound of embodiment 136, wherein the 5'-alkyl substituted 2'-deoxyribosyl sugar moiety at position 3 of the central region is a 5'-(R)-methyl 2'-deoxyribosyl sugar moiety.

138. The oligomeric compound of embodiment 136, wherein the 5'-alkyl substituted 2'-deoxyribosyl sugar moiety at position 3 of the central region is a 5'-(S)-methyl 2'-deoxyribosyl sugar moiety.

139. The oligomeric compound of embodiment 136, wherein the 5'-alkyl substituted 2'-deoxyribosyl sugar moiety at position 3 of the central region is a 5'-stereorandom methyl 2'-deoxyribosyl sugar moiety.

140. The oligomeric compound of embodiment 136, wherein the 5'-alkyl substituted 2'-deoxyribosyl sugar moiety at position 3 of the central region is a 5'-(R)-ethyl 2'-deoxyribosyl sugar moiety.

141. The oligomeric compound of embodiment 136, wherein the 5'-alkyl substituted 2'-deoxyribosyl sugar moiety at position 3 of the central region is a 5'-(S)-ethyl 2'-deoxyribosyl sugar moiety.

142. The oligomeric compound of embodiment 136, wherein the 5'-alkyl substituted 2'-deoxyribosyl sugar moiety at position 3 of the central region is a 5'-stereorandom ethyl 2'-deoxyribosyl sugar moiety.
143. The oligomeric compound of embodiment 136, wherein the 5'-alkyl substituted 2'-deoxyribosyl sugar moiety at position 3 of the central region is a 5'-(R)-allyl 2'-deoxyribosyl sugar moiety.
144. The oligomeric compound of embodiment 136, wherein the 5'-alkyl substituted 2'-deoxyribosyl sugar moiety at position 3 of the central region is a 5'-(S)-allyl 2'-deoxyribosyl sugar moiety.
145. The oligomeric compound of embodiment 136, wherein the 5'-alkyl substituted 2'-deoxyribosyl sugar moiety at position 3 of the central region is a 5'-stereorandom allyl 2'-deoxyribosyl sugar moiety.
146. The oligomeric compound of any of embodiments 50-61 or 67-69, wherein the one modified sugar moiety of the central region is a modified, unsubstituted 2'-deoxyfuranosyl sugar moiety at position 3 of the central region.
147. The oligomeric compound of embodiment 146, wherein the modified, unsubstituted 2'-deoxyfuranosyl sugar moiety at position 3 of the central region is an α-D-2'-deoxyribosyl modified sugar moiety.
148. The oligomeric compound of embodiment 146, wherein the modified, unsubstituted 2'-deoxyfuranosyl sugar moiety at position 3 of the central region is an α-L-2'-deoxyribosyl modified sugar moiety.
149. The oligomeric compound of embodiment 146, wherein the modified, unsubstituted 2'-deoxyfuranosyl sugar moiety at position 3 of the central region is an β-L-2'-deoxyribosyl modified sugar moiety.
150. The oligomeric compound of embodiment 146, wherein the modified, unsubstituted 2'-deoxyfuranosyl sugar moiety at position 3 of the central region is an β-D-2'-deoxyxylosyl modified sugar moiety.
151. The oligomeric compound of any of embodiments 50-61 or 67-69, wherein the one modified sugar moiety of the central region is a bicyclic ribosyl sugar moiety at position 3 of the central region.
152. The oligomeric compound of embodiment 151, wherein the bicyclic ribosyl sugar moiety at position 3 of the central region is a cEt or LNA sugar moiety.
153. The oligomeric compound of embodiment 151, wherein the bicyclic ribosyl sugar moiety at position 3 of the central region is a cEt sugar moiety.
154. The oligomeric compound of embodiment 151, wherein the bicyclic ribosyl sugar moiety at position 3 of the central region is a LNA sugar moiety.
155. The oligomeric compound of any of embodiments 50-61 or 67-69, wherein the one modified sugar moiety of the central region is a morpholino sugar moiety at position 3 of the central region.
156. The oligomeric compound of any of embodiments 50-61 or 67-69, wherein the one modified sugar moiety of the central region is a 2'-substituted ribosyl sugar moiety at position 4 of the central region.
157. The oligomeric compound of embodiment 156, wherein the 2'-substituted ribosyl sugar moiety at position 4 of the central region is a 2'-F ribosyl sugar moiety.
158. The oligomeric compound of embodiment 156, wherein the 2'-substituted ribosyl sugar moiety at position 4 of the central region is a 2'-MOE ribosyl sugar moiety.
159. The oligomeric compound of embodiment 156, wherein the 2'-substituted ribosyl sugar moiety at position 4 of the central region is a 2'-O-methyl ribosyl sugar moiety.
160. The oligomeric compound of any of embodiments 50-61 or 67-69, wherein the one modified sugar moiety of the central region is a 4'-alkyl substituted 2'-deoxyribosyl sugar moiety at position 4 of the central region.
161. The oligomeric compound of embodiment 160, wherein the 4'-substituted 2'-deoxyribosyl sugar moiety at position 4 of the central region is a 4'-methyl 2'-deoxyribosyl sugar moiety.
162. The oligomeric compound of any of embodiments 50-61 or 67-69, wherein the one modified sugar moiety of the central region is a 5'-alkyl substituted 2'-deoxyribosyl sugar moiety at position 4 of the central region.
163. The oligomeric compound of embodiment 162, wherein the 5'-alkyl substituted 2'-deoxyribosyl sugar moiety at position 4 of the central region is a 5'-(R)-methyl 2'-deoxyribosyl sugar moiety.
164. The oligomeric compound of embodiment 162, wherein the 5'-alkyl substituted 2'-deoxyribosyl sugar moiety at position 4 of the central region is a 5'-(S)-methyl 2'-deoxyribosyl sugar moiety.
165. The oligomeric compound of embodiment 162, wherein the 5'-alkyl substituted 2'-deoxyribosyl sugar moiety at position 4 of the central region is a 5'-stereorandom methyl 2'-deoxyribosyl sugar moiety.
166. The oligomeric compound of embodiment 162, wherein the 5'-alkyl substituted 2'-deoxyribosyl sugar moiety at position 4 of the central region is a 5'-(R)-ethyl 2'-deoxyribosyl sugar moiety.
167. The oligomeric compound of embodiment 162, wherein the 5'-alkyl substituted 2'-deoxyribosyl sugar moiety at position 4 of the central region is a 5'-(S)-ethyl 2'-deoxyribosyl sugar moiety.
168. The oligomeric compound of embodiment 162, wherein the 5'-alkyl substituted 2'-deoxyribosyl sugar moiety at position 4 of the central region is a 5'-stereorandom ethyl 2'-deoxyribosyl sugar moiety.
169. The oligomeric compound of embodiment 162, wherein the 5'-alkyl substituted 2'-deoxyribosyl sugar moiety at position 4 of the central region is a 5'-(R)-allyl 2'-deoxyribosyl sugar moiety.
170. The oligomeric compound of embodiment 162, wherein the 5'-alkyl substituted 2'-deoxyribosyl sugar moiety at position 4 of the central region is a 5'-(S)-allyl 2'-deoxyribosyl sugar moiety.
171. The oligomeric compound of embodiment 162, wherein the 5'-alkyl substituted 2'-deoxyribosyl sugar moiety at position 4 of the central region is a 5'-stereorandom allyl 2'-deoxyribosyl sugar moiety.
172. The oligomeric compound of any of embodiments 50-61 or 67-69, wherein the one modified sugar moiety of the central region is a modified, unsubstituted 2'-deoxyfuranosyl sugar moiety at position 4 of the central region.
173. The oligomeric compound of embodiment 172, wherein the modified, unsubstituted 2'-deoxyfuranosyl sugar moiety at position 4 of the central region is an α-D-2'-deoxyribosyl modified sugar moiety.
174. The oligomeric compound of embodiment 172, wherein the modified, unsubstituted 2'-deoxyfuranosyl sugar moiety at position 4 of the central region is an α-L-2'-deoxyribosyl modified sugar moiety.
175. The oligomeric compound of embodiment 172, wherein the modified, unsubstituted 2'-deoxyfuranosyl sugar moiety at position 4 of the central region is an β-L-2'-deoxyribosyl modified sugar moiety.
176. The oligomeric compound of any of embodiments 50-61 or 67-69, wherein the one modified sugar moiety of the central region is a bicyclic ribosyl sugar moiety at position 4 of the central region.
177. The oligomeric compound of embodiment 176, wherein the bicyclic ribosyl sugar moiety at position 4 of the central region is a cEt or LNA sugar moiety.
178. The oligomeric compound of embodiment 176, wherein the bicyclic ribosyl sugar moiety at position 4 of the central region is a cEt sugar moiety.
179. The oligomeric compound of embodiment 176, wherein the bicyclic ribosyl sugar moiety at position 4 of the central region is a LNA sugar moiety.
180. The oligomeric compound of any of embodiments 50-61 or 67-69, wherein the one modified sugar moiety of the central region is a morpholino sugar moiety at position 4 of the central region.
181. The oligomeric compound of any of embodiments 50-61 or 67-69, wherein the one modified sugar moiety of the central region is a 2'-O-methyl substituted ribosyl sugar moiety at position 5 of the central region.
182. The oligomeric compound of any of embodiments 50-61 or 67-69, wherein the one modified sugar moiety of the central region is a modified, unsubstituted 2'-deoxyfuranosyl sugar moiety at position 5 of the central region.
183. The oligomeric compound of embodiment 182, wherein the modified, unsubstituted 2'-deoxyfuranosyl sugar moiety at position 5 of the central region is a β-L-2'-deoxyribosyl sugar moiety.
184. The oligomeric compound of any of embodiments 50-61 or 67-69, wherein the one modified sugar moiety of the central region is a morpholino sugar moiety at position 6 of the central region.
185. The oligomeric compound of any of embodiments 50-61 or 67-69, wherein the one modified sugar moiety of the central region is a 2'-O-methyl substituted ribosyl sugar moiety at position 6 of the central region.
186. The oligomeric compound of any of embodiments 50-61 or 67-69, wherein the one modified sugar moiety of the central region is a modified, unsubstituted 2'-deoxyfuranosyl sugar moiety at position 6 of the central region.
187. The oligomeric compound of embodiment 186, wherein the modified, unsubstituted 2'-deoxyfuranosyl sugar moiety at position 6 of the central region is a β-L-2'-deoxyribosyl sugar moiety.
188. The oligomeric compound of embodiment 186, wherein the modified, unsubstituted 2'-deoxyfuranosyl sugar moiety at position 6 of the central region is an α-D-2'-deoxyribosyl sugar moiety.
189. The oligomeric compound of any of embodiments 50-61 or 67-69, wherein the one modified sugar moiety of the central region is a 2'-O-methyl substituted ribosyl sugar moiety at position 7 of the central region.
190. The oligomeric compound of any of embodiments 50-61 or 67-69, wherein the one modified sugar moiety of the central region is a modified, unsubstituted 2'-deoxyfuranosyl sugar moiety at position 7 of the central region.
191. The oligomeric compound of embodiment 190, wherein the modified, unsubstituted 2'-deoxyfuranosyl sugar moiety at position 7 of the central region is a β-L-2'-deoxyribosyl sugar moiety.
192. The oligomeric compound of embodiment 190, wherein the modified, unsubstituted 2'-deoxyfuranosyl sugar moiety at position 7 of the central region is an α-D-2'-deoxyribosyl sugar moiety.
193. The oligomeric compound of any of embodiments 50-61 or 67-69, wherein the one modified sugar moiety of the central region is a 2'-O-methyl substituted ribosyl sugar moiety at position 8 of the central region.
194. The oligomeric compound of any of embodiments 50-61 or 67-69, wherein the one modified sugar moiety of the central region is a modified, unsubstituted 2'-deoxyfuranosyl sugar moiety at position 8 of the central region.
195. The oligomeric compound of embodiment 194, wherein the modified, unsubstituted 2'-deoxyfuranosyl sugar moiety at position 8 of the central region is a β-L-2'-deoxyribosyl sugar moiety.
196. The oligomeric compound of embodiment 194, wherein the modified, unsubstituted 2'-deoxyfuranosyl sugar moiety at position 8 of the central region is an α-D-2'-deoxyribosyl sugar moiety.
197. The oligomeric compound of any of embodiments 50-61 or 67-69, wherein the one modified sugar moiety of the central region is a 2'-O-methyl substituted ribosyl sugar moiety at position 9 of the central region.
198. The oligomeric compound of any of embodiments 50-61 or 67-69, wherein the one modified sugar moiety of the central region is a modified, unsubstituted 2'-deoxyfuranosyl sugar moiety at position 9 of the central region.
199. The oligomeric compound of embodiment 198, wherein the modified, unsubstituted 2'-deoxyfuranosyl sugar moiety at position 9 of the central region is a β-L-2'-deoxyribosyl sugar moiety.
200. The oligomeric compound of any of embodiments 50-61 or 67-69, wherein the one modified sugar moiety of the central region is a 2'-O-methyl substituted ribosyl sugar moiety at position 2, 3, 4, 5, 6, 7, 8, or 9 of the central region.
201. The oligomeric compound of any of embodiments 50-61 or 67-69, wherein the one modified sugar moiety of the central region is a 2'-O-methyl substituted ribosyl sugar moiety at position 2, 3, 4, 8, or 9 of the central region.
202. The oligomeric compound of any of embodiments 50-61 or 67-69, wherein the one modified sugar moiety of the central region is a 2'-F substituted ribosyl sugar moiety at position 2, 3, or 4 of the central region.
203. The oligomeric compound of any of embodiments 50-61 or 67-69, wherein the one modified sugar moiety of the central region is a 2'-F substituted ribosyl sugar moiety at position 3 or 4 of the central region.
204. The oligomeric compound of any of embodiments 50-61 or 67-69, wherein the one modified sugar moiety of the central region is a 2'-MOE substituted ribosyl sugar moiety at position 2, 3, or 4 of the central region.
205. The oligomeric compound of any of embodiments 50-61 or 67-69, wherein the one modified sugar moiety of the central region is a 4'-methyl substituted 2'-deoxyribosyl sugar moiety at position 3 or 4 of the central region.
206. The oligomeric compound of any of embodiments 50-61 or 67-69, wherein the one modified sugar moiety of the central region is a 5'-(R)-methyl substituted 2'-deoxyribosyl sugar moiety at position 3 or 4 of the central region.
207. The oligomeric compound of any of embodiments 50-61 or 67-69, wherein the one modified sugar moiety of the central region is a 5'-(S)-methyl substituted 2'-deoxyribosyl sugar moiety at position 2, 3, or 4 of the central region.

208. The oligomeric compound of any of embodiments 50-61 or 67-69, wherein the one modified sugar moiety of the central region is a 5'-(R)-ethyl substituted 2'-deoxyribosyl sugar moiety at position 3 or 4 of the central region.
209. The oligomeric compound of any of embodiments 50-61 or 67-69, wherein the one modified sugar moiety of the central region is a 5'-(S)-ethyl substituted 2'-deoxyribosyl sugar moiety at position 3 or 4 of the central region.
210. The oligomeric compound of any of embodiments 50-61 or 67-69, wherein the one modified sugar moiety of the central region is a 5'-(R)-allyl substituted 2'-deoxyribosyl sugar moiety at position 3 or 4 of the central region.
211. The oligomeric compound of any of embodiments 50-61 or 67-69, wherein the one modified sugar moiety of the central region is a 5'-(S)-allyl substituted 2'-deoxyribosyl sugar moiety at position 3 or 4 of the central region.
212. The oligomeric compound of any of embodiments 50-61 or 67-69, wherein the one modified sugar moiety of the central region is a 5'-stereorandom allyl substituted 2'-deoxyribosyl sugar moiety at position 2, 3, or 4 of the central region.
213. The oligomeric compound of any of embodiments 50-61 or 67-69, wherein the one modified sugar moiety of the central region is a cEt ribosyl sugar moiety at position 2, 3, or 4 of the central region.
214. The oligomeric compound of any of embodiments 50-61 or 67-69, wherein the one modified sugar moiety of the central region is a cEt ribosyl sugar moiety at position 3 or 4 of the central region.
215. The oligomeric compound of any of embodiments 50-61 or 67-69, wherein the one modified sugar moiety of the central region is a LNA ribosyl sugar moiety at position 2, 3, or 4 of the central region.
216. The oligomeric compound of any of embodiments 50-61 or 67-69, wherein the one modified sugar moiety of the central region is a LNA ribosyl sugar moiety at position 3 or 4 of the central region.
217. The oligomeric compound of any of embodiments 50-61 or 67-69, wherein the one modified sugar moiety of the central region is a morpholino sugar moiety at position 1, 3, 4, or 6 of the central region.
218. The oligomeric compound of any of embodiments 50-61 or 67-69, wherein the one modified sugar moiety of the central region is a morpholino sugar moiety at position 1, 3, or 4 of the central region.
219. The oligomeric compound of any of embodiments 50-61 or 67-69, wherein the one modified sugar moiety of the central region is a modified, unsubstituted 2'-deoxyfuranosyl sugar moiety.
220. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, 6, 7, 8, or 9 of the central region.
221. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, or 9 of the central region.
222. The oligomeric compound of any of embodiments 50-61 or 67-69, wherein the one modified sugar moiety of the central region is an unsubstituted α-D-2'-deoxyribosyl sugar moiety.
223. The oligomeric compound of any of embodiments 50-61 or 67-69, wherein the one modified sugar moiety of the central region is an unsubstituted α-D-2'-deoxyribosyl sugar moiety at position 1, 2, 3, 4, 6, or 8 of the central region.
224. The oligomeric compound of any of embodiments 50-61 or 67-69, wherein the one modified sugar moiety of the central region is an unsubstituted α-D-2'-deoxyribosyl sugar moiety at position 1, 2, or 4 of the central region.
225. The oligomeric compound of any of embodiments 50-61 or 67-69, wherein the one modified sugar moiety of the central region is an unsubstituted α-L-2'-deoxyribosyl sugar moiety.
226. The oligomeric compound of any of embodiments 50-61 or 67-69, wherein the one modified sugar moiety of the central region is an unsubstituted α-L-2'-deoxyribosyl sugar moiety at position 3, 4, or 7 of the central region.
227. The oligomeric compound of any of embodiments 50-61 or 67-69, wherein the one modified sugar moiety of the central region is an unsubstituted β-L-2'-deoxyribosyl sugar moiety.
228. The oligomeric compound of any of embodiments 50-61 or 67-69, wherein the one modified sugar moiety of the central region is an unsubstituted β-L-2'-deoxyribosyl sugar moiety at position 1, 3, 4, 5, 6, 7, 8, or 9 of the central region.
229. The oligomeric compound of any of embodiments 50-61 or 67-69, wherein the one modified sugar moiety of the central region is an unsubstituted β-L-2'-deoxyribosyl sugar moiety at position 3, 4, 5, or 9 of the central region.
230. The oligomeric compound of any of embodiments 50-61 or 67-69, wherein the one modified sugar moiety of the central region is an unsubstituted β-D-2'-deoxyxylosyl sugar moiety.
231. The oligomeric compound of any of embodiments 53-55 or 60-230, wherein the one modified internucleoside linkage of the central region other than phosphorothioate is a phosphonate or phosphotriester internucleoside linkage.
232. The oligomeric compound of embodiment 231, wherein the one modified internucleoside linkage of the central region other than phosphorothioate is an alkyl phosphonate or alkoxy phosphonate internucleoside linkage.
233. The oligomeric compound of embodiment 232, wherein the one modified internucleoside linkage of the central region other than phosphorothioate is a methoxypropyl internucleoside linkage.
234. The oligomeric compound of embodiment 232, wherein the one modified internucleoside linkage of the central region other than phosphorothioate is a methyl phosphonate internucleoside linkage.
235. The oligomeric compound of embodiment 232, wherein the one modified internucleoside linkage of the central region other than phosphorothioate is an isopropyl phosphonate internucleoside linkage.
236. The oligomeric compound of embodiment 232, wherein the one modified internucleoside linkage of the central region other than phosphorothioate is an isobutyl phosphonate internucleoside linkage.
237. The oligomeric compound of embodiment 231, wherein the one modified internucleoside linkage of the central region other than phosphorothioate is a phosphonoacetate internucleoside linkage.
238. The oligomeric compound of embodiment 231, wherein the one modified internucleoside linkage of the central region other than phosphorothioate is an isopropyl phosphotriester internucleoside linkage.

239. The oligomeric compound of embodiment 231, wherein the one modified internucleoside linkage of the central region other than phosphorothioate is a tetrahydropyran phosphotriester internucleoside linkage.
240. The oligomeric compound of any of embodiments 53, 55, or 60-230, wherein the one modified internucleoside linkage of the central region other than phosphorothioate is a formacetal internucleoside linkage.
241. The oligomeric compound of any of embodiments 53, 55, or 60-230, wherein the one modified internucleoside linkage of the central region other than phosphorothioate is an acetamide internucleoside linkage.
242. The oligomeric compound of any of embodiments 53, 55, or 60-230, wherein the one modified internucleoside linkage of the central region other than phosphorothioate is a thioacetamide internucleoside linkage.
243. The oligomeric compound of any of embodiments 231-242, wherein the one modified internucleoside linkage of the central region other than phosphorothioate is between the nucleosides at positions 1 and 2 of the central region.
244. The oligomeric compound of any of embodiments 231-242, wherein the one modified internucleoside linkage of the central region other than phosphorothioate is between the nucleosides at positions 2 and 3 of the central region.
245. The oligomeric compound of any of embodiments 231-242, wherein the one modified internucleoside linkage of the central region other than phosphorothioate is between the nucleosides at positions 3 and 4 of the central region.
246. The oligomeric compound of any of embodiments 231-242, wherein the one modified internucleoside linkage of the central region other than phosphorothioate is between the nucleosides at positions 4 and 5 of the central region.
247. The oligomeric compound of any of embodiments 231-246, wherein the one modified internucleoside linkage of the central region other than phosphorothioate is directly linked to a nucleoside comprising a modified sugar moiety.
248. The oligomeric compound of any of embodiments 56-230, wherein the two neutral internucleoside linkages of the central region are independently selected from a phosphonate internucleoside linkage, phosphotriester internucleoside linkage, and a neutral internucleoside linkage that does not contain phosphorus.
249. The oligomeric compound of embodiment 248, wherein at least one of the modified internucleoside linkages of the central region other than phosphorothioate is an alkyl phosphonate or alkoxy phosphonate internucleoside linkage.
250. The oligomeric compound of embodiment 248, wherein at least one of the modified internucleoside linkages of the central region other than phosphorothioate is a methoxypropyl internucleoside linkage.
251. The oligomeric compound of embodiment 248, wherein at least one of the modified internucleoside linkages of the central region other than phosphorothioate is a methyl phosphonate internucleoside linkage.
252. The oligomeric compound of embodiment 248, wherein at least one of the modified internucleoside linkages of the central region other than phosphorothioate is an isopropyl phosphonate internucleoside linkage.
253. The oligomeric compound of embodiment 248, wherein at least one of the modified internucleoside linkages of the central region other than phosphorothioate is an isobutyl phosphonate internucleoside linkage.
254. The oligomeric compound of embodiment 248, wherein at least one of the modified internucleoside linkages of the central region other than phosphorothioate is a phosphonoacetate internucleoside linkage.
255. The oligomeric compound of embodiment 248, wherein at least one of the modified internucleoside linkages of the central region other than phosphorothioate is an isopropyl phosphotriester internucleoside linkage.
256. The oligomeric compound of embodiment 248, wherein at least one of the modified internucleoside linkages of the central region other than phosphorothioate is a tetrahydropyran phosphotriester internucleoside linkage.
257. The oligomeric compound of embodiment 248, wherein at least one of the modified internucleoside linkages of the central region other than phosphorothioate is a formacetal internucleoside linkage.
258. The oligomeric compound of embodiment 248, wherein at least one of the modified internucleoside linkages of the central region other than phosphorothioate is an acetamide internucleoside linkage.
259. The oligomeric compound of embodiment 248, wherein at least one of the modified internucleoside linkages of the central region other than phosphorothioate is a thioacetamide internucleoside linkage.
260. The oligomeric compound of any of embodiments 248-259, wherein the two modified internucleoside linkages other than phosphorothioate of the central region are adjacent to each other.
261. The oligomeric compound of any of claims 248-260, wherein the two modified internucleoside linkages other than phosphorothioate of the central region are the same as one another.
262. The oligomeric compound of any of embodiments 248-261, wherein one of the modified internucleoside linkages of the central region other than phosphorothioate is between the nucleosides at positions 1 and 2 of the central region.
263. The oligomeric compound of any of embodiments 248-261, wherein one of the modified internucleoside linkages of the central region other than phosphorothioate is between the nucleosides at positions 2 and 3 of the central region.
264. The oligomeric compound of any of embodiments 248-261, wherein one of the modified internucleoside linkages of the central region other than phosphorothioate is between the nucleosides at positions 3 and 4 of the central region.
265. The oligomeric compound of any of embodiments 248-261, wherein one of the modified internucleoside linkages of the central region other than phosphorothioate is between the nucleosides at positions 4 and 5 of the central region.
266. The oligomeric compound of any of embodiments 248-261, wherein one of the modified internucleoside linkages of the central region other than phosphorothioate is directly linked to a nucleoside comprising a modified sugar moiety.
267. The oligomeric compound of any of embodiments 60-266, wherein the one modified nucleobase other than 5-methylcytosine of the central region is 2-thiothymine, 6-methyladenine, inosine, or pseudouracil.
268. The oligomeric compound of embodiment 267, wherein the one modified nucleobase other than 5-methylcytosine is at position 1, 2, 3, or 4 of the central region.

269. The oligomeric compound of embodiment 267, wherein the one modified nucleobase other than 5-methylcytosine is at position 2, 3, or 4 of the central region.
270. The oligomeric compound of embodiment 267, wherein the one modified nucleobase other than 5-methylcytosine is at position 1 of the central region.
271. The oligomeric compound of embodiment 267, wherein the one modified nucleobase other than 5-methylcytosine is at position 2 of the central region.
272. The oligomeric compound of embodiment 267, wherein the one modified nucleobase other than 5-methylcytosine is at position 3 of the central region.
273. The oligomeric compound of embodiment 267, wherein the one modified nucleobase other than 5-methylcytosine is at position 4 of the central region.
274. The oligomeric compound of any of embodiments 267 or 270, wherein the one modified nucleobase other than 5-methylcytosine is 2-thiothymine.
275. The oligomeric compound of any of embodiments 267 or 271, wherein the one modified nucleobase other than 5-methylcytosine is 6-methyladenine.
276. The oligomeric compound of any of embodiments 267 or 271, wherein the one modified nucleobase other than 5-methylcytosine is inosine.
277. The oligomeric compound of any of embodiments 267-273, wherein the one modified nucleobase other than 5-methylcytosine is pseudouracil.
278. The oligomeric compound of embodiment 277, wherein the nucleoside comprising the pseudouracil nucleobase comprises an unmodified ribosyl sugar moiety.
279. The oligomeric compound of any of embodiments 1-52, 60-230, or 267-278, wherein each internucleoside linkage of the central region is independently selected from among a phosphodiester or a phosphorothioate internucleoside linkage.
280. The oligomeric compound of embodiment 279, wherein each internucleoside of the central region is a phosphorothioate internucleoside linkage.
281. The oligomeric compound of any of embodiments 1-279, wherein the central region does not comprise any phosphodiester internucleoside linkages.
282. The oligomeric compound of any of embodiments 1-281, wherein each phosphorothioate internucleoside linkage of the oligomeric compound is strereorandom.
283. The oligomeric compound of any of embodiments 1-281, wherein at least one phosphorothioate internucleoside linkage of the oligomeric compound is in the Rp configuration.
284. The oligomeric compound of any of embodiments 1-281, wherein at least one phosphorothioate internucleoside linkage of the oligomeric compound is in the Sp configuration.
285. The oligomeric compound of any of embodiments 1-284, wherein the nucleobase sequence of the modified oligonucleotide is complementary to a target RNA.
286. The oligomeric compound of embodiment 285, wherein the nucleobase sequence of the modified oligonucleotide is at least 75% complementary to the target RNA.
287. The oligomeric compound of embodiment 285, wherein the nucleobase sequence of the modified oligonucleotide is at least 80% complementary to the target RNA.
288. The oligomeric compound of embodiment 285, wherein the nucleobase sequence of the modified oligonucleotide is at least 85% complementary to the target RNA.
289. The oligomeric compound of embodiment 285, wherein the nucleobase sequence of the modified oligonucleotide is at least 90% complementary to the target RNA.
290. The oligomeric compound of embodiment 285, wherein the nucleobase sequence of the modified oligonucleotide is at least 95% complementary to the target RNA.
291. The oligomeric compound of embodiment 285, wherein the nucleobase sequence of the modified oligonucleotide is 100% complementary to the target RNA.
292. The oligomeric compound of any of embodiments 285-291, wherein the target RNA is a target mRNA or a target pre-mRNA.
293. The oligomeric compound of embodiment 292, wherein the target mRNA or target pre-mRNA is not a mouse, rat, monkey, or human PTEN RNA.
294. The oligomeric compound of embodiment 292 or 293, wherein the target mRNA or target pre-mRNA is not a mouse, rat, monkey, or human SRB-1 RNA.
295. The oligomeric compound of any of embodiments 292-294, wherein the target mRNA or target pre-mRNA is not a mouse, rat, monkey, or human MYD88 RNA.
296. The oligomeric compound of any of embodiments 292-295, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.
297. The oligomeric compound of any of embodiments 285-296, wherein the target RNA is a human RNA.
298. The oligomeric compound of any of embodiments 285-297, wherein the target RNA is expressed in the liver.
299. The oligomeric compound of any of embodiments 285-298, wherein the target RNA is a liver target.
300. The oligomeric compound of any of embodiments 285-297, wherein the target RNA is not expressed in the liver.
301. The oligomeric compound of any of embodiments 285-298 or 300, wherein the target RNA is not a liver target.
302. The oligomeric compound of any of embodiments 285-299, wherein modulation of the expression of the target RNA in the liver is associated with treating a disorder or condition.
303. The oligomeric compound of embodiment 302, wherein the disorder or condition is a liver disorder or condition.
304. The oligomeric compound of any of embodiments 285-303, wherein the target RNA is expressed in the central nervous system.
305. The oligomeric compound of any of embodiments 285-303, wherein the target RNA is not expressed in the central nervous system.
306. The oligomeric compound of any of embodiments 285-298, 300, 301, or 304, wherein the target RNA is a central nervous system target.
307. The oligomeric compound of any of embodiments 285-305, wherein the target RNA is not a central nervous system target.
308. The oligomeric compound of any of embodiments 285-298, 300-301, 304, or 306, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

309. The oligomeric compound of any of embodiments 285-297, 300-301, 304, or 306, wherein the target RNA is a HTT RNA.

310. The oligomeric compound of embodiment 308, wherein the target RNA is a MeCP2 RNA.

311. The oligomeric compound of embodiment 308, wherein the target RNA is a DUX4 RNA.

312. The oligomeric compound of embodiment 308, wherein the target RNA is a HDAC2 RNA.

313. The oligomeric compound of embodiment 308, wherein the target RNA is a Ataxin 1 RNA.

314. The oligomeric compound of embodiment 308, wherein the target RNA is a Ataxin 2 RNA.

315. The oligomeric compound of embodiment 308, wherein the target RNA is a Ataxin 3 RNA.

316. The oligomeric compound of embodiment 308, wherein the target RNA is a Ataxin 6 RNA.

317. The oligomeric compound of embodiment 308, wherein the target RNA is a Ataxin 7 RNA.

318. The oligomeric compound of embodiment 308, wherein the target RNA is a C9ORF72 RNA.

319. The oligomeric compound of embodiment 285-297, 300-301, 304, or 306, wherein the target RNA is an alpha-synuclein RNA.

320. The oligomeric compound of embodiment 308, wherein the target RNA is an UBE3A RNA.

321. The oligomeric compound of embodiment 285-297, 300-301, 304, or 306, wherein the target RNA is a SOD1 RNA.

322. The oligomeric compound of embodiment 308, wherein the target RNA is a Prion RNA.

323. The oligomeric compound of embodiment 308, wherein the target RNA is a PMP22 RNA.

324. The oligomeric compound of embodiment 308, wherein the target RNA is a Tau RNA.

325. The oligomeric compound of embodiment 308, wherein the target RNA is a LRRK2 RNA.

326. The oligomeric compound of embodiment 308, wherein the target RNA is an APP RNA.

327. The oligomeric compound of embodiment 308, wherein the target RNA is a LINGO2 RNA.

328. The oligomeric compound of embodiment 308, wherein the target RNA is a GYS1 RNA.

329. The oligomeric compound of embodiment 308, wherein the target RNA is a KCNT1 RNA.

330. The oligomeric compound of embodiment 308, wherein the target RNA is a IRF8 RNA.

331. The oligomeric compound of embodiment 308, wherein the target RNA is a Progranulin RNA.

332. The oligomeric compound of embodiment 308, wherein the target RNA is a GFAP RNA.

333. The oligomeric compound of any of embodiments 304, 306, or 308-332, wherein modulation of the expression of the target RNA in the central nervous system is associated with treating a disorder or condition.

334. The oligomeric compound of embodiment 333, wherein the disorder or condition is a neurological disorder or condition.

335. The oligomeric compound of embodiment 333 or 334, wherein the disorder or condition alters the function of sensory or motor neurons.

336. The oligomeric compound of any of embodiments 333-335, wherein the disorder or condition alters the function of sensory neurons.

337. The oligomeric compound of any of embodiments 333-336, wherein the disorder or condition alters the function of motor neurons.

338. The oligomeric compound of any of embodiments 333-337, wherein the disorder or condition alters the function of glial cells.

339. The oligomeric compound of embodiment 338, wherein the disorder or condition alters the function of astrocytes.

340. The oligomeric compound of embodiment 338, wherein the disorder or condition alters the function of oligodendrocytes.

341. The oligomeric compound of embodiment 338, wherein the disorder or condition alters the function of microglia.

342. The oligomeric compound of embodiment 338, wherein the disorder or condition alters the function of ependymal cells.

343. The oligomeric compound of any of embodiments 333-342, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

344. The oligomeric compound of embodiment 343, wherein the disorder or condition is Alzheimer's Disease.

345. The oligomeric compound of embodiment 343, wherein the disorder or condition is Amyotrophic Lateral Sclerosis.

346. The oligomeric compound of embodiment 343, wherein the disorder or condition is Parkinson's Disease.

347. The oligomeric compound of embodiment 343, wherein the disorder or condition is a Spinocerebellar ataxia.

348. The oligomeric compound of embodiment 343, wherein the disorder or condition is Angelman Syndrome.

349. The oligomeric compound of embodiment 343, wherein the disorder or condition is Alexander's Disease.

350. The oligomeric compound of embodiment 343, wherein the disorder or condition is Lafora Disease.

351. The oligomeric compound of embodiment 343, wherein the disorder or condition is Charcot-Marie Tooth Disease.

352. The oligomeric compound of embodiment 343, wherein the disorder or condition is Prion Disease.

353. The oligomeric compound of embodiment 343, wherein the disorder or condition is a dementia.

354. The oligomeric compound of embodiment 343, wherein the disorder or condition is neurodegeneration.

355. The oligomeric compound of embodiment 343, wherein the disorder or condition is MeCP2 Duplication Syndrome.

356. The oligomeric compound of embodiment 343, wherein the disorder or condition is encephalopathy.

357. The oligomeric compound of embodiment 343, wherein the disorder or condition is neuroinflammation.

358. The oligomeric compound of embodiment 343, wherein the disorder or condition is multiple sclerosis.

359. The oligomeric compound of any of embodiments 1-358, wherein the parent oligomeric compound of the oligomeric compound of any of embodiments 1-358 is cytotoxic in vitro.

360. The oligomeric compound of embodiment 359, wherein the parent oligomeric compound is cytotoxic in a standard in vitro cytotoxicity assay.

361. The oligomeric compound of any of embodiments 1-360, wherein administration to a mouse of the parent oligomeric compound of the oligomeric compound of any of embodiments 1-360 is hepatotoxic to the mouse.

362. The oligomeric compound of embodiment 361, wherein the administration of the parent oligomeric compound to the mouse is systemic administration.

363. The oligomeric compound of embodiment 362, wherein the systemic administration is subcutaneous administration.

364. The oligomeric compound of any of embodiments 361-363, wherein the mouse is a CD-1 mouse.

365. The oligomeric compound of any of embodiments 361-363, wherein the mouse is a C57BL/6 mouse.

366. The oligomeric compound of any of embodiments 361-363, wherein the mouse is a BALB/c mouse.

367. The oligomeric compound of any of embodiments 361-366, wherein the plasma ALT level in the mouse is higher than 500 units per liter following the administration of the parent oligomeric compound.

368. The oligomeric compound of any of embodiments 361-366, wherein the plasma AST level in the mouse is higher than 500 units per liter following the administration of the parent oligomeric compound.

369. The oligomeric compound of any of embodiments 361-366, wherein the plasma ALT level in the mouse is higher than 1000 units per liter following the administration of the parent oligomeric compound.

370. The oligomeric compound of any of embodiments 361-366, wherein the plasma AST level in the mouse is higher than 1000 units per liter following the administration of the parent oligomeric compound.

371. The oligomeric compound of any of embodiments 361-370, wherein the hepatotoxicity is measured 24-48 hours following the administration of the parent oligomeric compound.

372. The oligomeric compound of any of embodiments 361-370, wherein the hepatotoxicity is measured 72 hours following the administration of the parent oligomeric compound.

373. The oligomeric compound of any of embodiments 361-370, wherein the hepatotoxicity is measured 3 days following the administration of the parent oligomeric compound.

374. The oligomeric compound of any of embodiments 361-370, wherein the hepatotoxicity is measured 5 days following the administration of the parent oligomeric compound.

375. The oligomeric compound of any of embodiments 361-370, wherein the hepatotoxicity is measured 7 days following the administration of the parent oligomeric compound.

376. The oligomeric compound of any of embodiments 361-370, wherein the hepatotoxicity is measured 10 days following the administration of the parent oligomeric compound.

377. The oligomeric compound of any of embodiments 361-370, wherein the hepatotoxicity is measured 14 days following the administration of the parent oligomeric compound.

378. The oligomeric compound of any of embodiments 361-377, wherein 1-10 mg/kg of the parent oligomeric compound is administered to the mouse.

379. The oligomeric compound of any of embodiments 361-377, wherein 10-25 mg/kg of the parent oligomeric compound is administered to the mouse.

380. The oligomeric compound of any of embodiments 361-377, wherein 25-50 mg/kg of the parent oligomeric compound is administered to the mouse.

381. The oligomeric compound of any of embodiments 361-377, wherein 50-100 mg/kg of the parent oligomeric compound is administered to the mouse.

382. The oligomeric compound of any of embodiments 361-377, wherein 100-150 mg/kg of the parent oligomeric compound is administered to the mouse.

383. The oligomeric compound of any of embodiments 361-363, 366-370, 372, or 382, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

384. The oligomeric compound of any of embodiments 1-383, wherein administration of 50 mg/kg of the oligomeric compound of any of embodiments 1-383 to a mouse is not hepatotoxic to the mouse.

385. The oligomeric compound of embodiment 384, wherein plasma ALT level in the mouse is lower than 100 units per liter following the administration of the oligomeric compound of embodiment 384.

386. The oligomeric compound of embodiment 384 or 385, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.

387. The oligomeric compound of embodiment 386, wherein the plasma ALT level in the mouse is at least 100-fold lower than the plasma ALT level in the mouse administered the parent oligomeric compound.

388. The oligomeric compound of embodiment 386, wherein the plasma ALT level in the mouse is at least 500-fold lower than the plasma ALT level in the mouse administered the parent oligomeric compound.

389. The oligomeric compound of any of embodiments 359-388, wherein the therapeutic index in a mouse of the oligomeric compound of any of embodiments 359-388 is increased relative to the therapeutic index of the parent oligomeric compound.

390. The oligomeric compound of embodiment 389, wherein the therapeutic index in a mouse of the oligomeric compound of embodiment 365 is at least two-fold greater than the therapeutic index of the parent oligomeric compound.

391. The oligomeric compound of any of embodiments 1-390, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

392. The oligomeric compound of embodiment 391, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.
393. The oligomeric compound of embodiment 392, wherein the 2'-O-methyl modified sugar moiety is at position 2 of the central region.
394. The oligomeric compound of embodiment 392 or 393, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.
395. The oligomeric compound of any of embodiments 391-394, wherein the nucleobase sequence of the otherwise identical oligomeric compound is 100% complementary to the target RNA.
396. The oligomeric compound of any of embodiments 391-395, wherein the otherwise identical oligomeric compound is a parent oligomeric compound of the oligomeric compound of any of embodiments 391-395.
397. The oligomeric compound of any of embodiments 285-396, wherein the oligomeric compound inhibits the target RNA with an $IC_{50}$ lower than 100 nM in a standard in vitro activity assay.
398. The oligomeric compound of any of embodiments 285-397, wherein the parent oligomeric compound of the oligomeric compound of any of embodiments 285-397 inhibits the target RNA with an $IC_{50}$ lower than 100 nM in a standard in vitro activity assay.
399. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 4-fold.
400. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 3-fold.
401. The oligomeric compound of any of embodiments 285-398, wherein the difference between the $IC_{50}$ of the parent oligomeric compound measured in a standard in vitro activity assay and the $IC_{50}$ of the oligomeric compound of any of embodiments 285-398 measured in a standard in vitro activity assay is less than 2-fold.
402. The oligomeric compound of any of embodiments 359-390 or 396-401, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.
403. The oligomeric compound of any of embodiments 359-390 or 396-402, wherein the nucleobase sequence of the parent oligomeric compound is 100% complementary to the target RNA.
404. The oligomeric compound of any of embodiments 1-403, wherein administration of 10-50 mg of the oligomeric compound to a human is not hepatotoxic to the human.
405. The oligomeric compound of any of embodiments 1-403, wherein administration of 50-100 mg of the oligomeric compound to a human is not hepatotoxic to the human.
406. The oligomeric compound of any of embodiments 1-403, wherein administration of 100-300 mg of the oligomeric compound to a human is not hepatotoxic to the human.
407. The oligomeric compound of any of embodiments 404-406, wherein the administration is systemic administration.
408. A composition comprising the oligomeric compound of any of embodiments 1-407 and a second oligomeric compound, wherein the second oligomeric compound is complementary to the oligomeric compound of any of embodiments 1-407.
409. The composition of embodiment 408, wherein the second oligomeric compound comprises at least 14 contiguous linked nucleosides that are at least 90% complementary to the oligomeric compound of any of embodiments 1-407.
410. The composition of embodiment 408, wherein the second oligomeric compound comprises at least 14 contiguous linked nucleosides that are 100% complementary to the oligomeric compound of any of embodiments 1-407. 411. A pharmaceutical composition comprising the oligomeric compound of any of embodiments 1-407 or the composition of any of embodiments 408-410, comprising a pharmaceutically acceptable carrier or diluent.
412. A method comprising administering the oligomeric compound or composition of any of embodiments 1-411 to a human subject.
413. A method of treating a disease or disorder comprising administering the oligomeric compound or composition of any of embodiments 1-411 to a human subject.
414. A method of modulating the amount or activity of a target RNA in a human subject comprising administering the oligomeric compound or composition of any of embodiments 1-411 to the human subject; and thereby modulating the amount or activity of the target RNA in the human subject.
415. A method of treating a disease or disorder in a human subject comprising administering the oligomeric compound or composition of any of embodiments 1-411 to the human subject having the disease or disorder; and thereby treating the disease or disorder in the human subject.
416. The method of embodiment 413 or 415, wherein the disease or disorder is a liver disease, and wherein the oligomeric compound modulates the amount or activity of a liver target RNA.
417. The method of embodiment 413 or 415, wherein the disease or disorder is a central nervous system disease, and wherein the oligomeric compound modulates the amount or activity of a central nervous system target RNA.
418. The method of any of embodiments 413 or 415-417, wherein the disease or disorder is a cancer, a neurodegenerative disease, a cardiovascular disease, an immunological disease, a hereditary disease, a repeat expansion disease, a muscle-wasting disease, or a metabolic disease.
419. The method of any of embodiments 412-418, wherein the plasma ALT level of the human subject after the administration is not more than three times higher than it was prior to the administration.
420. The method of any of embodiments 412-418, wherein the plasma ALT level of the human subject after the administration is not more than 150 units per liter.
421. The method of any of embodiments 412-416 or 418-420, wherein the human subject is susceptible to liver damage.

422. The method of any of embodiments 412-416 or 418-420, wherein the human subject is susceptible to liver degeneration.
423. The method of any of embodiments 412-416 or 418-420, wherein the human subject is susceptible to elevated apoptosis in the liver.
424. The method of any of embodiments 412-416 or 418-423, wherein the human subject has a liver disease.
425. The method of any of embodiments 412-424, comprising administering the parent oligomeric compound of the oligomeric compound of any of embodiments 1-407 to a mouse.
426. The method of any of embodiments 412-424, comprising contacting a cell with the parent oligomeric compound of the oligomeric compound of any of embodiments 1-407.
427. The method of embodiment 425 or 426, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.
428. A method of designing an oligomeric compound comprising starting with a parent oligomeric compound and changing the design of that compound in order to arrive at an oligomeric compound of any one of embodiments 1-407.
429. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1-407.
430. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1-407.
431. The method of embodiment 428, wherein the method designs an oligomeric compound with improved therapeutic index relative to the parent oligomeric compound.
432. The method of embodiment 428 or 431, wherein the method designs an oligomeric compound with lower hepatotoxicity relative to the parent oligomeric compound.
433. The method of embodiment 429, wherein the second oligomeric compound has an improved therapeutic index relative to the parent oligomeric compound.
434. The method of embodiment 429 or 433, wherein the second oligomeric compound has reduced hepatotoxicity in a mouse relative to the parent oligomeric compound.
435. The method of embodiment 430, wherein the oligomeric compound according to any one of embodiments 1-407 has reduced hepatotoxicity relative to the parent oligomeric compound.
436. A method comprising administering an oligomeric compound of any of embodiments 1-407 to a mouse and separately administering the parent oligomeric compound of the oligomeric compound of any of embodiments 1-407 to a second mouse, wherein the therapeutic index of the oligomeric compound of any of embodiments 1-407 is improved relative to the therapeutic index of the parent oligomeric compound.
437. The method of any of embodiments 412-436, wherein the level of p21 RNA is measured in the mouse, the cell, and/or the human subject.
438. A method comprising administering an oligomeric compound to a subject and measuring the level of p21 RNA in the subject.
439. A method comprising administering an oligomeric compound of any of embodiments 1-407 to a subject and measuring the level of p21 RNA in the subject.
440. The method of embodiment 438 or 439, wherein the subject is a mouse.
441. The method of embodiment 438 or 439, wherein the subject is a human.
442. The method of any of embodiments 437-441, wherein the p21 RNA level is measured within 24 hours of the administration.
443. The method of any of embodiments 437-441, wherein the p21 RNA level is measured 24-48 hours following the administration.
444. An oligomeric compound or composition of any one of embodiments 1-411, for use in medical therapy.
445. A method comprising contacting a cell with an oligomeric compound and detecting the cellular localization of p54nrb protein in the cell.
446. The method of embodiment 445, comprising determining the relative amount of p54nrb protein in the nucleolus relative to other cells contacted with different oligomeric compounds.
447. The method of embodiment 445 or 446, comprising determining the relative amount of p54nrb in the nucleolus relative to the amount of p54nrb in the rest of the cell.
448. The method of any of embodiments 445-447, wherein the cell is in a plate containing at least 96 wells.
449. The method of any of embodiments 445-448, wherein the detection of the cellular localization of p54nrb comprises contacting the cell with a p54nrb antibody.
450. A method of screening for a tolerable oligomeric compound comprising any of the methods of embodiments 445-449.
451. The method of any of embodiments 445-450, wherein the oligomeric compound is the oligomeric compound of any of embodiments 1-407.
452. An oligomeric compound comprising a modified oligonucleotide consisting of 12-23 linked nucleosides, wherein the modified oligonucleotide comprises a 5'-region, a central region, and a 3'-region wherein:
the 5'-region consists of 1-5 linked modified nucleosides;
the 3'-region consists of 1-5 linked modified nucleosides; and the central region consists of 7-11 linked nucleosides and has the formula:

$(N_{d1})(N_x)(N_y)(N_z)(N_d)_q$ wherein one of $N_x$, $N_y$, and $N_z$, is a safety enhancing nucleoside;
the other two of $N_x$, $N_y$, and $N_z$ are independently selected from an unmodified 2'-β-D-deoxyribosyl, a DNA isomer, and a DNA mimic;
$N_{d1}$ and each $N_d$ is independently selected from an unmodified 2'-β-D-deoxyribosyl, a DNA isomer, and a DNA mimic; and wherein
q is 2-7.
453. The oligomeric compound of embodiment 1, wherein the safety enhancing nucleoside is $N_x$ or $N_y$.
454. The oligomeric compound of embodiment 1, wherein the safety enhancing nucleoside is $N_x$.
455. The oligomeric compound of embodiment 1, wherein the safety enhancing nucleoside is $N_y$.
456. The oligomeric compound of embodiment 1, wherein the safety enhancing nucleoside is $N_z$.

457. The oligomeric compound of any of embodiments 452-456, wherein the safety enhancing nucleoside has a sugar moiety selected from among a sugar surrogate, a bicyclic furanosyl sugar moiety, a non-bicyclic 2'-modified furanosyl sugar moiety, a non-bicyclic 4'-modified furanosyl sugar moiety, or a non-bicyclic 5'-modified furanosyl sugar moiety.

458. The oligomeric compound of any of embodiments 452-457, wherein the safety-enhancing nucleoside has a sugar moiety selected from among a morpholino, a 2'-O-methyl-2'-β-D-deoxyribosy sugar moiety, a cEt bicyclic sugar moiety, a LNA sugar moiety, an ENA sugar moiety, a 5'-methyl substituted 2'-deoxyribosyl sugar moiety, 5'-ethyl substituted 2'-deoxyribosyl sugar moiety, a 5'-allyl substituted 2'-deoxyribosyl sugar moiety and a 2'-β-L-deoxyxylosyl sugar moiety.

459. The oligomeric compound of any of embodiments 452-458, wherein the safety-enhancing nucleoside has a sugar moiety selected from among a 2'-O-methyl-modified sugar moiety and a 5'-modified sugar moiety.

460. The oligomeric compound of embodiment 459, wherein the safety-enhancing nucleoside has a 2'-O-methyl substituted ribosyl sugar moiety.

461. The oligomeric compound of any of embodiments 452-457, wherein the safety-enhancing nucleoside is a sugar surrogate.

462. The oligomeric compound of embodiment 461, wherein the sugar surrogate is selected from among a morpholino, a modified morpholino, and F-HNA.

463. The oligomeric compound of any of embodiments 452-462, wherein $N_{d1}$ is an unmodified 2'-β-D-deoxyribosyl sugar moiety.

464. The oligomeric compound of any of embodiments 452-462, wherein $N_{d1}$ is a DNA isomer.

465. The oligomeric compound of any of embodiments 452-462, wherein $N_{d1}$ is a DNA mimic.

466. The oligomeric compound of any of embodiments 452-465, wherein no more than 3 of the central region nucleosides comprise a sugar moiety other than 2'-β-D-deoxyribosyl.

467. The oligomeric compound of any of embodiments 452-466, wherein each DNA isomer has a sugar moiety independently selected from among 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl.

468. The oligomeric compound of any of embodiments 452-467, wherein each DNA mimic has a sugar moiety is independently selected from among 5'-methyl-2'-β-D-deoxyribosyl and 5'-ethyl-2'-β-D-deoxyribosyl.

469. The oligomeric compound of any of embodiments 452-463, wherein each nucleoside of the central region other than the safety-enhancing nucleoside has a 2'-β-D-deoxyribosyl sugar moiety.

470. The oligomeric compound of any of 452-469, wherein at least one internucleoside linkage is a phosphorothioate linkage.

471. The oligomeric compound of any of embodiments 452-470, wherein at least 4 internucleoside linkages are phosphorothioate linkages.

472. The oligomeric compound of any of embodiments 452-471, wherein at least one internucleoside linkage is a neutral internucleoside linkage.

473. The oligomeric compound of any of embodiments 452-472, wherein at least one neutral internucleoside linkage is a phosphonate internucleoside linkage.

474. The oligomeric compound of any of embodiments 452-474, wherein at least one neutral internucleoside linkage is a methoxypropyl internucleoside linkage.

475. The oligomeric compound of any of embodiments 452-475, wherein at least one internucleoside linkage of the central region selected from among: the internucleoside Nd1 to Nx, Nx to Ny, Ny to Nz, or Nz to the adjacent Nd is a neutral internucleoside linkage.

476. The oligomeric compound of embodiment 475, wherein the modified oligonucleotide comprises one neutral linkage and the other internucleoside linkages are each independently selected from phosphodiester and phosphorothioate.

477. The oligomeric compound of any of embodiments 542-454 or embodiments 457-476, wherein the safety enhancing nucleoside is $N_x$ and is a 2'O-methyl-substituted nucleoside.

478. The oligomeric compound of any of embodiments 2-453, 455, or embodiments 457-476, wherein the safety enhancing nucleoside is $N_y$ and is a 2'O-methyl-substituted nucleoside.

479. The oligomeric compound of any of embodiments 452-453, 455, or embodiments 457-476, wherein the safety enhancing nucleoside is $N_y$ and has a 5'-substituted 2'-deoxyribosyl sugar moiety.

480. The oligomeric compound of any of embodiments 452 or embodiments 457-476, wherein the safety enhancing nucleoside is $N_z$ and has a 5'-substituted 2'-deoxyribosyl sugar moiety.

481. The oligomeric compound of embodiments 479 or 480, wherein the 5'-substituted ribosyl sugar moiety is a 5'-methyl, 5'-ethyl, or 5'-allyl substituted 2'-deoxyribosyl sugar moiety.

482. The oligomeric compound of embodiments 477-481, wherein at least one nucleoside of the 5'-region comprises a bicyclic furanosyl sugar moiety.

483. The oligomeric compound of any of embodiments 477-482, wherein each nucleoside of the 5'-region comprises a bicyclic furanosyl sugar moiety.

484. The oligomeric compound of any of embodiments 482 or 483, wherein each bicyclic sugar moiety of the 5'-region is selected from among cEt, LNA, and ENA.

485. The oligomeric compound of any of embodiments 452-482 or 484, wherein at least one nucleoside of the 5'-region comprises a non-bicyclic sugar moiety.

486. The oligomeric compound of embodiment 485, wherein the non-bicyclic sugar moiety of the at least one nucleoside of the 5'-region is a 2'-substituted ribosyl sugar moiety.

487. The oligomeric compound of any of embodiments 485-487, wherein each non-bicyclic sugar moiety of the 5'-region has a 2'-substituent selected from among 2'-MOE, 2'-OMe, and 2'-NMA.

488. The oligomeric compound of any of embodiments 477-480, wherein the 5'-region comprises a 2'-MOE modified nucleoside and an LNA modified nucleoside.

489. The oligomeric compound of any of embodiments 477-480, wherein the 5'-region comprises a 2'-MOE modified nucleoside and a cEt modified nucleoside.

490. The oligomeric compound of embodiments 477-489, wherein at least one nucleoside of the 3'-region comprises a bicyclic furanosyl sugar moiety.

491. The oligomeric compound of any of embodiments 477-490, wherein each nucleoside of the 3'-region comprises a bicyclic furanosyl sugar moiety.

492. The oligomeric compound of any of embodiments 490 or 491, wherein each bicyclic sugar moiety of the 3'-region is selected from among cEt, LNA, and ENA.

493. The oligomeric compound of any of embodiments 490 or 492, wherein at least one nucleoside of the 3'-region comprises a non-bicyclic sugar moiety.

494. The oligomeric compound of embodiment 493, wherein the non-bicyclic sugar moiety of the at least one nucleoside of the 3'-region is a 2'-substituted ribosyl sugar moiety.

495. The oligomeric compound of any of embodiments 490 or 492-494, wherein each non-bicyclic sugar moiety of the 3'-region has a 2'-substituent selected from among 2'-MOE, 2'-OMe, and 2'-NMA.

496. The oligomeric compound of any of embodiments 477-490 or 492-495, wherein the 3'-region comprises a 2'-MOE modified nucleoside and an LNA modified nucleoside.

497. The oligomeric compound of any of embodiments 477-490 or 492-495, wherein the 3'-region comprises a 2'-MOE modified nucleoside and a cEt modified nucleoside.

498. The oligomeric compound of any of embodiments 477-480, wherein each nucleoside of the 5'-region comprises a bicyclic furanosyl sugar moiety and each nucleoside of the 3'-region comprises a non-bicyclic sugar moiety.

499. The oligomeric compound of any of embodiments 477-480, wherein each nucleoside of the 5'-region comprises an LNA sugar moiety and each nucleoside of the 3'-region comprises a 2'MOE sugar moiety.

500. The oligomeric compound of any of embodiments 477-480, wherein each nucleoside of the 5'-region comprises cEt sugar moiety and each nucleoside of the 3'-region comprises a 2'MOE sugar moiety.

501. The oligomeric compound of any of embodiments 452-500, wherein the modified oligonucleotide has a nucleobase sequence complementary to a target RNA; wherein the target RNA is a mRNA or pre-mRNA.

502. The oligomeric compound of embodiment 501, wherein the target RNA encodes a protein that is expressed in the liver.

503. The oligomeric compound of embodiment 502, wherein the target RNA encodes a protein that is expressed in the CNS.

504. The oligomeric compound of any of embodiments 452-503, wherein the oligomeric compound is not toxic.

505. The oligomeric compound of any of embodiment 452-504, wherein a comparator compound is toxic; wherein the comparator compound is identical to the oligomeric compound except that each nucleoside of the central region of the comparator compound is a nucleoside comprising 2'-β-D-deoxyribosyl sugar moiety.

506. The oligomeric compound of embodiment 505, wherein administering a dose of the oligomeric compound to an animal results in a circulating ALT level that is at least 3-fold lower than the ALT level that results from administering the same dose of the comparator compound to an animal for at least one matched dose.

507. The oligomeric compound of embodiment 505 or 506, wherein the lowest dose of the oligomeric compound that raises circulating ALT to over 300 units per liter is at least three-fold higher than the lowest dose of the comparator compound that raises circulating ALT to over 300 units per liter.

508. The oligomeric compound of any of embodiments 502-507, wherein the oligomeric compound is capable of reducing the target RNA in a cell.

509. The oligomeric compound of embodiment 508, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

510. The oligomeric compound of embodiment 509 having RNA-reducing activity that is no more than 2-fold worse than the RNA-reducing activity of the comparator compound.

511. An oligomeric compound comprising a modified oligonucleotide consisting of 12-23 linked nucleosides, wherein the modified oligonucleotide comprises a 5'-region, a central region, and a 3'-region wherein:
the 5'-region consists of 1-5 linked nucleosides; wherein at least one 5'-region nucleoside is modified;
the 3'-region consists of 1-5 linked nucleosides; wherein at least one 3'-region nucleoside is modified; and the central region consists of 7-11 linked nucleosides, and has the formula:

$$(N_{d1})_{L1}(N_{d2})_{L2}(N_{d3})_{L3}(N_{d4})_{L4}(N_d)_q;$$

wherein $N_{d1}$, $N_{d2}$, $N_{d3}$, $N_{d4}$, and each $N_d$ are independently selected from among a nucleoside comprising an unmodified 2'-β-D-deoxyribosyl sugar moiety, a DNA isomer sugar moiety, or a DNA mimic sugar moiety;
wherein each L1, L2, L3, and L4 is an internucleoside linkage; and wherein at least one of L1, L2, L3, and L4 is a neutral internucleoside linkage.

512. The oligomeric compound of embodiment 511, wherein L1 is a neutral internucleoside linkage.

513. The oligomeric compound of embodiment 511, wherein L2 is a neutral internucleoside linkage.

514. The oligomeric compound of embodiment 511, wherein L3 is a neutral internucleoside linkage.

515. The oligomeric compound of any of embodiments 511-514, wherein the neutral linkage is a phosphonate internucleoside linkage.

516. The oligomeric compound of any of embodiments 511-515, wherein the neutral linkage is a methoxypropyl internucleoside linkage.

517. The oligomeric compound of any of embodiments 511-516, wherein each remaining internucleoside linkage is a phosphodiester or phosphorothioate internucleoside linkage.

518. A method comprising administering the oligomeric compound or composition of any of embodiments 452-517 to a human subject.

519. A method of treating a disease or disorder comprising administering the oligomeric compound or composition of any of embodiments 452-517 to a human subject.

520. A method of modulating the amount or activity of a target RNA in a human subject comprising administering the oligomeric compound or composition of any of embodiments 452-517 to the human subject; and thereby modulating the amount or activity of the target RNA in the human subject.

521. A method of treating a disease or disorder in a human subject comprising administering the oligomeric compound or composition of any of embodiments 452-517 to the human subject having the disease or disorder; and thereby treating the disease or disorder in the human subject.

522. The method of embodiment 520 or 521, wherein the disease or disorder is a liver disease, and wherein the oligomeric compound modulates the amount or activity of a liver target RNA.

523. The method of embodiment 520 or 521, wherein the disease or disorder is a central nervous system disease, and wherein the oligomeric compound modulates the amount or activity of a central nervous system target RNA.

524. The method of any of embodiments 519-523, wherein the disease or disorder is a cancer, a neurodegenerative disease, a cardiovascular disease, an immunological disease, a hereditary disease, a repeat expansion disease, a muscle-wasting disease, or a metabolic disease.

525. The method of any of embodiments 518-524, wherein the plasma ALT level of the human subject after the administration is not more than three times higher than it was prior to the administration.

526. The method of any of embodiments 518-525, wherein the plasma ALT level of the human subject after the administration is not more than 150 units per liter.

527. The method of any of embodiments 518-526, wherein the human subject is susceptible to liver damage.

528. The method of any of embodiments 518-527, wherein the human subject is susceptible to liver degeneration.

529. The method of any of embodiments 518-528, wherein the human subject is susceptible to elevated apoptosis in the liver.

530. The method of any of embodiments 518-529, wherein the human subject has a liver disease.

531. The method of any of embodiments 518-530, comprising administering the parent oligomeric compound of the oligomeric compound of any of embodiments 452-517 to a mouse.

532. The method of any of embodiments 518-531, comprising contacting a cell with the parent oligomeric compound of the oligomeric compound of any of embodiments 452-517.

533. The method of embodiment 518-532, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

534. A method of designing an oligomeric compound comprising starting with a parent oligomeric compound and changing the design of that compound in order to arrive at an oligomeric compound of any one of embodiments 452-517.

535. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 452-517.

536. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 452-517.

537. The method of embodiment 536, wherein the method designs an oligomeric compound with improved therapeutic index relative to the parent oligomeric compound.

538. The method of embodiment 534-537, wherein the method designs an oligomeric compound with lower hepatotoxicity relative to the parent oligomeric compound.

539. The method of embodiment 535-538, wherein the second oligomeric compound has an improved therapeutic index relative to the parent oligomeric compound.

540. The method of embodiment 535-539, wherein the second oligomeric compound has reduced hepatotoxicity in a mouse relative to the parent oligomeric compound.

541. The method of embodiment 540, wherein the oligomeric compound according to any one of embodiments 452-517 has reduced hepatotoxicity relative to the parent oligomeric compound.

542. A method comprising administering an oligomeric compound of any of embodiments 452-517 to a mouse and separately administering the parent oligomeric compound of the oligomeric compound of any of embodiments 452-517 to a second mouse, wherein the therapeutic index of the oligomeric compound of any of embodiments 452-517 is improved relative to the therapeutic index of the parent oligomeric compound.

543. The method of any of embodiments 518-542, wherein the level of p21 RNA is measured in the mouse, the cell, and/or the human subject.

544. A method comprising administering an oligomeric compound of any of embodiments 452-517 to a subject and measuring the level of p21 RNA in the subject.

545. The method of embodiment 543 or 544, wherein the subject is a mouse.

546. The method of embodiment 543 or 544, wherein the subject is a human.

547. The method of any of embodiments 543-546, wherein the p21 RNA level is measured within 24 hours of the administration.

548. The method of any of embodiments 437-441, wherein the p21 RNA level is measured 24-48 hours following the administration.

549. An oligomeric compound or composition of any one of embodiments 452-517, for use in medical therapy.

550. The method of any of embodiments 445-449, wherein the oligomeric compound is the oligomeric compound of any of embodiments 452-517.

551. An oligomeric compound comprising a modified oligonucleotide consisting of 12-21 linked nucleosides, wherein the modified oligonucleotide has the formula A-B-C, wherein A is a 5'-region,
B is a central region, and C is a 3'-region; wherein:
the 5'-region consists of 1-5 linked nucleosides, wherein at least one nucleoside of the 5'-region is a modified nucleoside comprising a modified sugar;
the 3'-region consists of 1-5 linked nucleosides wherein at least one nucleoside of the 3'-region is a modified nucleoside comprising a modified sugar; and
the central region consists of 7-11 linked nucleosides, wherein
the 5'-most portion of the central region has the following formula:

$$(N_{da})(N_x)(N_y)(N_z)(N_{db})$$

wherein one of $N_x$, $N_y$, and $N_z$, is a safety-enhancing nucleoside;
the other two of $N_x$, $N_y$, and $N_z$ are independently selected from a DNA nucleoside, a DNA isomer, a modified DNA isomer, and a DNA mimic; and $N_{da}$ and $N_{db}$ are each independently selected from a DNA nucleoside, a DNA isomer, a modified DNA isomer, and a DNA mimic.

552. The oligomeric compound of embodiment 551, wherein the 5'-region consists of one nucleoside.
553. The oligomeric compound of embodiment 551, wherein the 5'-region consists of 2-5 linked nucleosides.
554. The oligomeric compound of embodiment 551, wherein the 5'-region consists of 2-4 linked nucleosides.
555. The oligomeric compound of embodiment 551, wherein the 5'-region consists of 2 linked nucleosides.
556. The oligomeric compound of embodiment 551, wherein the 5'-region consists of 3 linked nucleosides.
557. The oligomeric compound of embodiment 551, wherein the 5'-region consists of 4 linked nucleosides.
558. The oligomeric compound of embodiment 551, wherein the 5'-region consists of 5 linked nucleosides.
559. The oligomeric compound of any of embodiments 551-558, wherein each nucleoside of the 5'-region is a modified nucleoside.
560. The oligomeric compound of any of embodiments 551-559, wherein each nucleoside of the 5'-region is a modified nucleoside comprising a modified sugar.
561. The oligomeric compound of any of embodiments 551-560, wherein each modified nucleoside of the 5'-region has the same modification.
562. The oligomeric compound of and of embodiments 551-560, wherein at least two nucleosides of the 5'-region are modified nucleosides having different modifications.
563. The oligomeric compound of any of embodiments 551-562, wherein each nucleoside of the 5'-region comprises a 2'-modified ribosyl sugar moiety.
564. The oligomeric compound of any of embodiments 551-563, wherein at least one nucleoside of the 5'-region comprises a bicyclic furanosyl sugar moiety.
565. The oligomeric compound of any of embodiments 551-564, wherein each nucleoside of the 5'-region comprises a bicyclic furanosyl sugar moiety.
566. The oligomeric compound of any of embodiments 551-565, wherein at least one nucleoside of the 5'-region comprises a non-bicyclic sugar moiety.
567. The oligomeric compound of embodiment 566, wherein the non-bicyclic sugar moiety of the at least one nucleoside of the 5'-region is a 2'-substituted ribosyl sugar moiety.
568. The oligomeric compound of any of embodiments 551-567, wherein each nucleoside of the 5'-region comprises a non-bicyclic sugar moiety.
569. The oligomeric compound of embodiment 568, wherein each nucleoside of the 5'-region comprises a 2'-substituted furanosyl sugar moiety.
570. The oligomeric compound of any of embodiments 551-569, wherein each nucleoside of the 5'-region comprises a 2'-modified furanosyl sugar moiety independently selected from a bicyclic sugar moiety and a non-bicyclic 2'-substituted ribosyl sugar moiety.
571. The oligomeric compound of any of embodiments 551-570, wherein each nucleoside of the 5'-region comprises a bicyclic sugar moiety.
572. The oligomeric compound of any of embodiments 551-571, wherein each nucleoside of the 5'-region comprises a non-bicyclic 2'-substituted ribosyl sugar moiety.
573. The oligomeric compound of any of embodiments 551-572, wherein each bicyclic sugar moiety of the 5'-region is selected from among cEt, LNA, and ENA.
574. The oligomeric compound of any of embodiments 551-573, wherein each bicyclic sugar moiety of the 5'-region is a cEt sugar moiety.
575. The oligomeric compound of any of embodiments 551-574, wherein each bicyclic sugar moiety of the 5'-region is an LNA sugar moiety.
576. The oligomeric compound of any of embodiments 551-575, wherein each non-bicyclic sugar moiety of the 5'-region has a 2'-substituent selected from among 2'-MOE, 2'-OMe, and 2'-NMA.
577. The oligomeric compound of any of embodiments 551-576, wherein none of the nucleosides of the 5'-region comprise a sugar moiety having a 2'-F substituent.
578. The oligomeric compound of any of embodiments 551-577, wherein none of the nucleosides of the 5'-region comprise a sugar moiety having a 2'-MOE substituent.
579. The oligomeric compound of any of embodiments 551-578, wherein none of the nucleosides of the 5'-region comprise a sugar moiety having a 2'-OMe substituent.
580. The oligomeric compound of any of embodiments 551-579, wherein none of the nucleosides of the 5'-region comprise a cEt sugar moiety.
581. The oligomeric compound of any of embodiments 551-580, wherein none of the nucleosides of the 5'-region comprise a LNA sugar moiety.
582. The oligomeric compound of any of embodiments 551-581, wherein each nucleobase of the 5'-region is independently selected from among thymine, uracil, guanine, cytosine, 5-methylcytosine, and adenine.
583. The oligomeric compound of any of embodiments 551-582, wherein each internucleoside linkage of the 5'-region is selected from among phosphodiester and phosphorothioate internucleoside linkages.
584. The oligomeric compound of any of embodiments 551-583, wherein the 3'-region consists of one nucleoside.
585. The oligomeric compound of any of embodiments 551-583, wherein the 3'-region consists of 2-5 linked nucleosides.
586. The oligomeric compound of any of embodiments 551-583, wherein the 3'-region consists of 2-4 linked nucleosides.
587. The oligomeric compound of any of embodiments 551-583, wherein the 3'-region consists of 2 linked nucleosides.
588. The oligomeric compound of any of embodiments 551-583, wherein the 3'-region consists of 3 linked nucleosides.
589. The oligomeric compound of any of embodiments 551-583, wherein the 3'-region consists of 4 linked nucleosides.
590. The oligomeric compound of any of embodiments 551-583, wherein the 3'-region consists of 5 linked nucleosides.
591. The oligomeric compound of any of embodiments 551-590, wherein each nucleoside of the 3'-region is a modified nucleoside.
592. The oligomeric compound of any of embodiments 551-591, wherein each nucleoside of the 3'-region is a modified nucleoside comprising a modified sugar moiety.
593. The oligomeric compound of any of embodiments 551-592, wherein each modified nucleoside of the 3'-region has the same modification.
594. The oligomeric compound of and of embodiments 551-592, wherein at least two nucleosides of the 3'-region are modified nucleosides having different modifications.

595. The oligomeric compound of any of embodiments 551-594, wherein each nucleoside of the 3'-region comprises a 2'-modified ribosyl sugar moiety.

596. The oligomeric compound of any of embodiments 551-595, wherein at least one nucleoside of the 3'-region comprises a bicyclic furanosyl sugar moiety.

597. The oligomeric compound of any of embodiments 551-596, wherein each nucleoside of the 3'-region comprises a bicyclic furanosyl sugar moiety.

598. The oligomeric compound of any of embodiments 551-597, wherein at least one nucleoside of the 3'-region comprises a non-bicyclic sugar moiety.

599. The oligomeric compound of embodiment 598, wherein the non-bicyclic sugar moiety of the at least one nucleoside of the 3'-region is a 2'-substituted ribosyl sugar moiety.

600. The oligomeric compound of any of embodiments 551-599, wherein each nucleoside of the 3'-region comprises a non-bicyclic sugar moiety.

601. The oligomeric compound of embodiment 600, wherein each nucleoside of the 3'-region comprises a 2'-substituted furanosyl sugar moiety.

602. The oligomeric compound of any of embodiments 551-601, wherein each nucleoside of the 3'-region comprises a 2'-modified furanosyl sugar moiety independently selected from a bicyclic sugar moiety and a non-bicyclic 2'-substituted ribosyl sugar moiety.

603. The oligomeric compound of any of embodiments 551-602, wherein each nucleoside of the 3'-region comprises a bicyclic sugar moiety.

604. The oligomeric compound of any of embodiments 551-602, wherein each nucleoside of the 3'-region comprises a non-bicyclic 2'-substituted ribosyl sugar moiety.

605. The oligomeric compound of any of embodiments 551-603, wherein each bicyclic sugar moiety of the 3'-region is selected from among cEt, LNA, and ENA.

606. The oligomeric compound of any of embodiments 551-605, wherein each bicyclic sugar moiety of the 3'-region is a cEt sugar moiety.

607. The oligomeric compound of any of embodiments 551-606, wherein each bicyclic sugar moiety of the 3'-region is an LNA sugar moiety.

608. The oligomeric compound of any of embodiments 551-607, wherein each non-bicyclic sugar moiety of the 3'-region has a 2'-substituent selected from among 2'-MOE, 2'-OMe, and 2'-NMA.

609. The oligomeric compound of any of embodiments 551-608, wherein none of the nucleosides of the 3'-region comprise a sugar moiety having a 2'-F substituent.

610. The oligomeric compound of any of embodiments 551-609, wherein none of the nucleosides of the 3'-region comprise a sugar moiety having a 2'-MOE substituent.

611. The oligomeric compound of any of embodiments 551-610, wherein none of the nucleosides of the 3'-region comprise a sugar moiety having a 2'-OMe substituent.

612. The oligomeric compound of any of embodiments 551-611, wherein none of the nucleosides of the 3'-region comprise a cEt sugar moiety.

613. The oligomeric compound of any of embodiments 551-612, wherein none of the nucleosides of the 3'-region comprise a LNA sugar moiety.

614. The oligomeric compound of any of embodiments 551-613, wherein each nucleobase of the 3'-region is independently selected from among thymine, uracil, guanine, cytosine, 5-methylcytosine, and adenine.

615. The oligomeric compound of any of embodiments 551-614, wherein each internucleoside linkage of the 3'-region is selected from among phosphodiester and phosphorothioate internucleoside linkages.

616. The oligomeric compound of any of embodiments 551-615, wherein the modified nucleosides of the 5'-region have the same modifications as the modifications of the modified nucleosides of the 3'-region.

617. The oligomeric compound of any of embodiments 551-615, wherein at least one modified nucleoside of the 5'-region and one modified nucleoside of the 3'-region comprise modifications that differ from one another.

618. The oligomeric compound of any of embodiments 551-617, wherein the 5'-region and the 3'-region together include at least one non-bicyclic 2'-substituted modified nucleoside and at least one bicyclic nucleoside.

619. The oligomeric compound of any of embodiment 618, where the bicyclic nucleoside is a cEt nucleoside.

620. The oligomeric compound of embodiment 618, where the bicyclic nucleoside is an LNA nucleoside.

621. The oligomeric compound of any of embodiments 618-620, wherein the non-bicyclic 2'-modified nucleoside is a 2'-MOE nucleoside.

622. The oligomeric compound of any of embodiments 618-620, wherein the non-bicyclic 2'-modified nucleoside is a 2'-OMe nucleoside.

623. The oligomeric compound of any of embodiments 618-622, wherein at least one nucleoside of the 5'-region or the 3'-region is an unmodified DNA nucleoside.

624. The oligomeric compound of any of embodiments 551-623, wherein the central region has the formula:

$(N_{da})(N_x)(N_y)(N_z)(N_{db})(N_{dc})_q$ wherein each $N_{dc}$ is independently selected from an unmodified DNA nucleoside, a DNA isomer, a 2'-modified DNA isomer, and a DNA mimic; and q is 2-6.

625. The oligomeric compound of any of embodiments 551-624, wherein the central region consists of 7 linked nucleosides.

626. The oligomeric compound of any of embodiments 551-624, wherein the central region consists of 8 linked nucleosides.

627. The oligomeric compound of any of embodiments 551-624, wherein the central region consists of 9 linked nucleosides.

628. The oligomeric compound of any of embodiments 551-624, wherein the central region consists of 10 linked nucleosides.

629. The oligomeric compound of any of embodiments 551-624, wherein the central region consists of 11 linked nucleosides.

630. The oligomeric compound of any of embodiments 551-629, wherein Nx is the safety-enhancing nucleoside.

631. The oligomeric compound of any of embodiments 551-629, wherein Ny is the safety-enhancing nucleoside.

632. The oligomeric compound of any of embodiments 551-629, wherein Nz is the safety-enhancing nucleoside.

633. The oligomeric compound of any of embodiments 551-632, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

634. The oligomeric compound of any of embodiments 551-33, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a nonbicyclic, 4'-modified furanosyl sugar moiety, or a non-bicyclic 5'-modified furanosyl sugar moiety.

635. The oligomeric compound of any of embodiments 551-634, wherein the safety enhancing nucleoside comprises a sugar surrogate selected from a morpholino, a modified morpholino, a modified cyclohexenyl, or a modified tetrahydropyran.

636. The oligomeric compound of any of embodiments 551-634, wherein the safety enhancing nucleoside comprises a sugar surrogate selected from a morpholino, a modified morpholino, CeNA, F-CeNA, HNA, OMe-HNA or F-HNA.

637. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

638. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, and 2'-O-L-deoxyribosyl.

639. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

640. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

641. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

642. The oligomeric compound of any of embodiments 551-634, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

643. The oligomeric compound of any of embodiments 551-634, wherein the safety enhancing nucleoside is a modified nucleoside comprising a bicyclic furanosyl sugar moiety 644. The oligomeric compound of any of embodiments 551-634, wherein the safety enhancing nucleoside is selected from among cEt, LNA, α-L-LNA, and ENA.

645. The oligomeric compound of any of embodiments 551-634, wherein the safety enhancing nucleoside comprises a 2'-substituted furanosyl sugar moiety.

646. The oligomeric compound of embodiment 645, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$S$CH_3$, O($CH_2$)$_2$ON($R_m$)($R_n$) or O$CH_2$C(=O)—N($R_m$)($R_n$), where each $R_m$ and $R_n$ is, independently, H, an amino protecting group, or substituted or unsubstituted $C_1$-$C_{10}$ alkyl.

647. The oligomeric compound of embodiment 645, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O($CH_2$)$_2$ON($R_m$)($R_n$) or O$CH_2$C(=O)—N($R_m$)($R_n$), where each $R_m$ and $R_n$ is, independently, H, an amino protecting group, or substituted or unsubstituted $C_1$-$C_{10}$ alkyl.

648. The oligomeric compound of embodiment 645, wherein the 2'-substituted furanosyl sugar moiety of the safety enhancing nucleoside has a 2' substituent selected from: fluoro, OMe, MOE, NMA.

649. The oligomeric compound of any of embodiments 551-648, wherein the safety enhancing nucleoside comprises a 2'-substituted furanosyl sugar moiety comprising a 2'-OMe or 2'-MOE.

650. The oligomeric compound of any of embodiments 551-649, wherein the safety enhancing nucleoside comprises a 2'-substituted furanosyl sugar moiety comprising a 2'-OMe.

651. The oligomeric compound of any of embodiments 551-650, wherein the safety enhancing nucleoside comprises a 2'-OMe modified 2'-β-D-deoxyribosyl sugar moiety.

652. The oligomeric compound of any of embodiments 551-634, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

653. The oligomeric compound of any of embodiments 551-634 or embodiment 652, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

654. The oligomeric compound of any of embodiments 551-634 or 652-653, wherein the safety enhancing nucleoside comprises a 3'-methyl furanosyl sugar moiety.

655. The oligomeric compound of any of embodiments 551-634, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$S$CH_3$, O($CH_2$)$_2$ON($R_m$)($R_n$) or O$CH_2$C(=O)—N($R_m$)($R_n$), where each $R_m$ and $R_n$ is, independently, H, an amino protecting group, or substituted or unsubstituted $C_1$-$C_{10}$ alkyl.

656. The oligomeric compound of any of embodiments 551-634 or 655, wherein the safety enhancing nucleoside comprises a 4'-modified furanosyl sugar moiety having a 4'-methyl.

657. The oligomeric compound of any of embodiments 551-634, wherein the safety enhancing nucleoside has the structure shown below, wherein R represents an optional 2' substituent group and Bx is a heterocyclic base moiety:

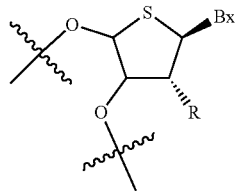

658. The oligomeric compound of embodiment 657, wherein in R is selected from among H, OH, OMe, F, or MOE.
659. The oligomeric compound of any of embodiments 551-634, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.
660. The oligomeric compound of any of embodiments 551-634 or 659, wherein the safety enhancing nucleoside comprises a 5'-modified furanosyl sugar moiety with a 5' substituent selected from: 5'-methyl, 5'-ethyl or a 5'-allyl.
661. The oligomeric compound of any of embodiments 551-634 or 659-660, wherein the safety enhancing nucleoside comprises a 5'-modified furanosyl sugar moiety with a 5' substituent selected from: 5'-(R)-methyl- or 5'-(R)-ethyl.
662. The oligomeric compound of any of embodiments 551-634 or 659-661, wherein the safety enhancing nucleoside comprises a 5'-(R)-methyl-2'-β-D-deoxyribosyl sugar moiety.
663. The oligomeric compound of any of embodiments 551-634 or 659-662, wherein the safety enhancing nucleoside comprises a 5'-(R)-ethyl-2'-β-D-deoxyribosyl sugar moiety.
664. The oligomeric compound of any of embodiments 551-663, wherein the safety enhancing nucleoside does not comprise a 2'-F modified sugar moiety.
665. The oligomeric compound of any of embodiments 551-664, wherein the safety enhancing nucleoside does not comprise a cEt modified sugar moiety.
666. The oligomeric compound of any of embodiments 551-665, wherein the safety enhancing nucleoside does not comprise a 2'-MOE modified sugar moiety.
667. The oligomeric compound of any of embodiments 551-666, wherein the safety enhancing nucleoside comprises a hypoxanthine nucleobase.
668. The oligomeric compound of any of embodiments 551-667, wherein the safety enhancing nucleoside comprises a nucleobase selected from among A, T, G, C, mC, and U.
669. The oligomeric compound of any of embodiments 551-668, wherein the safety enhancing nucleoside is a modified nucleoside other than cEt, MOE, LNA, or FANA.
670. The oligomeric compound of any of embodiments 551-669, wherein each Nd is independently selected from among a DNA nucleoside, a DNA isomer, a modified DNA isomer, and a DNA mimic.
671. The oligomeric compound of embodiment 670, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.
672. The oligomeric compound of embodiment 671, wherein each DNA isomer comprises a sugar moiety selected from among 2'-β-D-deoxyxylosyl, 2'-α-L-deoxyribosyl, and 2'-β-L-deoxyribosyl.
673. The oligomeric compound of embodiment 670, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.
674. The oligomeric compound of embodiment 673, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.
675. The oligomeric compound of embodiment 674, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.
676. The oligomeric compound of embodiment 675, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.
677. The oligomeric compound of embodiment 670, wherein each DNA mimic comprises a structure represented by one of the formulas below:

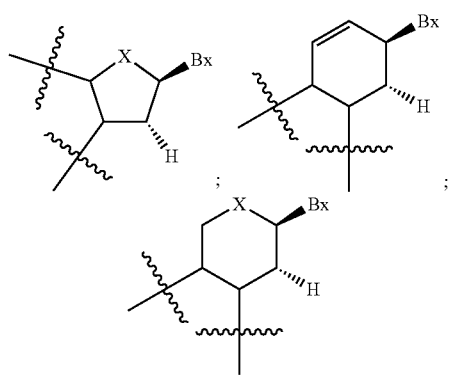

wherein X is O or S and Bx represents a heterocylic base moiety.

678. The oligomeric compound of embodiment 670, wherein each DNA mimic comprises a structure represented by one of the formulas below:

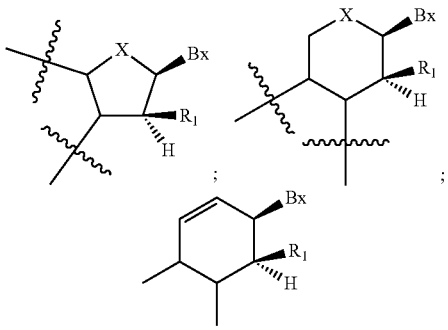

wherein X is O or S, Bx represents a heterocyclic base moiety, and R1 is selected from among H, OH, halo, allyl, amino, azido, SH, CN, OCN, CF$_3$, OCF$_3$, O—C$_1$-C$_{10}$ alkoxy, O—C$_1$-C$_{10}$ substituted alkoxy, C$_1$-C$_{10}$ alkyl, C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl.

679. The oligomeric compound of embodiment 678, wherein R1 is H, OH, OMe, or F.

680. The oligomeric compound of embodiment 678, wherein R1 is not F.

681. The oligomeric compound of embodiment 670, wherein each DNA mimic comprises a structure represented by the formula below:

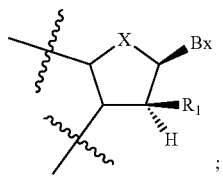

wherein X is O, Bx represents a heterocyclic base moiety, and R1 is H.

682. The oligomeric compound of embodiment 670, wherein DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

683. The oligomeric compound of embodiment 670, wherein DNA mimic comprises a 2'-fluoro-β-D-arabinofuranosyl sugar moiety 684. The oligomeric compound of embodiment 670, wherein the DNA mimic does not comprise a 2'-fluoro-β-D-arabinofuranosyl sugar moiety.

685. The oligomeric compound of any of embodiments 551-684, wherein each Nd is a DNA nucleoside.

686. The oligomeric compound of any of embodiments 551-685, wherein the central region comprises no more than four nucleosides selected from among DNA isomers, modified DNA isomers, and DNA mimics.

687. The oligomeric compound of any of embodiments 551-685, wherein the central region comprises no more than three nucleosides selected from among DNA isomers, modified DNA isomers, and DNA mimics.

688. The oligomeric compound of any of embodiments 551-685, wherein the central region comprises no more than two nucleosides selected from among DNA isomers, modified DNA isomers, and DNA mimics.

689. The oligomeric compound of any of embodiments 551-685, wherein the central region comprises no more than one nucleoside selected from among DNA isomers, modified DNA isomers, and DNA mimics.

690. The oligomeric compound of any of embodiments 551-689, wherein the central region contains exactly one safety enhancing nucleoside and the remainder of nucleosides in the central region are DNA nucleosides.

691. The oligomeric compound of any of embodiments 551-690, wherein at least one internucleoside linkage of the central region selected from among: the internucleoside Nda to Nx, Nx to Ny, Ny to Nz, or Nz to the adjacent Ndb is a neutral internucleoside linkage.

692. The oligomeric compound of embodiments 691, wherein the neutral linkage is a phosphonate internucleoside linkage.

693. The oligomeric compound of embodiments 691, wherein the neutral linkage is a methoxypropyl internucleoside linkage.

694. The oligomeric compound of embodiments 691, wherein each remaining internucleoside linkage is a phosphodiester or phosphorothioate internucleoside linkage.

695. A chirally enriched population of modified oligonucleotides of any of embodiments 551-690, wherein the central region has at least one particular phorphorothioate internucleoside linkage having a particular stereochemical configuration.

696. The chirally enriched population of embodiment 695, wherein the central region has at least one phorphorothioate internucleoside linkage having the (Sp) configuration.

697. The chirally enriched population of embodiment 695, wherein central region has at least one phorphorothioate internucleoside linkage having the (Rp) configuration.

698. The chirally enriched population of embodiment 695, wherein the central region has a particular, independently selected stereochemical configuration at each phosphorothioate internucleoside linkage.

699. The chirally enriched population of embodiment 698, wherein the each phosphorothioate internucleoside linkage of the central region has the (Sp) configuration.

700. The chirally enriched population of embodiment 698, wherein the central region has one phosphorothioate internucleoside linkage having the (Rp) configuration and wherein each remaining central region phosphorothioate internucleoside linkage has the (Sp) configuration.

701. The chirally enriched population of embodiment 695, wherein the central region has an (Rp) phosphorothioate internucleoside linkage adjacent to an (Sp) phosphorothioate internucleoside linkage.

702. The chirally enriched population of embodiment 695, wherein the central region has an (Rp) phosphorothioate internucleoside linkage adjacent to a second (Rp) phosphorothioate internucleoside linkage.

703. The chirally enriched population of embodiment 695, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

704. The chirally enriched population of any of embodiments 696, 697, 701, or 702 wherein each phosphorothioate internucleoside linkage that does not have the (Rp) or (Sp) configuration is stereorandom.
705. The oligomeric compound of any of embodiments 551-704 comprising a conjugate group.
706. The oligomeric compound of embodiment 705, wherein the conjugate group comprises a linking group attaching the remainder of the conjugate group to the modified oligonucleotide, wherein the linking group comprises 1-5 nucleosides.
707. The oligomeric compound of any of embodiments 1-705, wherein the oligomeric compound does not comprise additional nucleosides beyond those of the modified oligonucleotide.
708. The oligomeric compound of any of embodiments 551-707, wherein the nucleobase sequence of the modified oligonucleotide is complementary to a target RNA.
709. The oligomeric compound of embodiment 708, wherein the nucleobase sequence of the modified oligonucleotide is at least 85% complementary to the target RNA.
710. The oligomeric compound of embodiment 708, wherein the nucleobase sequence of the modified oligonucleotide is at least 90% complementary to the target RNA.
711. The oligomeric compound of embodiment 708, wherein the nucleobase sequence of the modified oligonucleotide is at least 95% complementary to the target RNA.
712. The oligomeric compound of embodiment 711, wherein the nucleobase sequence of the modified oligonucleotide is 100% complementary to the target RNA.
713. The oligomeric compound of any of embodiments 708-712, wherein the target RNA is a target mRNA or a target pre-mRNA.
714. The oligomeric compound of embodiment 713, wherein the target mRNA or target pre-mRNA is not a mouse, rat, monkey, or human PTEN RNA.
715. The oligomeric compound of embodiment 713 or 714, wherein the target mRNA or target pre-mRNA is not a mouse, rat, monkey, or human SRB-1 RNA.
716. The oligomeric compound of any of embodiments 713-715, wherein the target mRNA or target pre-mRNA is not a mouse, rat, monkey, or human MYD88 RNA.
717. The oligomeric compound of any of embodiments 713-716, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.
718. The oligomeric compound of any of embodiments 708-717, wherein the target RNA is a human RNA.
719. The oligomeric compound of any of embodiments 708-718, wherein the target RNA is expressed in the liver.
720. The oligomeric compound of any of embodiments 708-719, wherein the target RNA is a liver target.
721. The oligomeric compound of any of embodiments 708-718, wherein the target RNA is not expressed in the liver.
722. The oligomeric compound of any of embodiments 708-718 or 721, wherein the target RNA is not a liver target.
723. The oligomeric compound of any of embodiments 708-722, wherein modulation of the expression of the target RNA in the liver is associated with treating a disorder or condition.
724. The oligomeric compound of embodiment 723, wherein the disorder or condition is a liver disorder or condition.
725. The oligomeric compound of any of embodiments 708-724, wherein the target RNA is expressed in the central nervous system.
726. The oligomeric compound of any of embodiments 708-724, wherein the target RNA is not expressed in the central nervous system.
727. The oligomeric compound of any of embodiments 708-725, wherein the target RNA is a central nervous system target.
728. The oligomeric compound of any of embodiments 708-726, wherein the target RNA is not a central nervous system target.
729. The oligomeric compound of any of embodiments 708-727, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.
730. The oligomeric compound of any of embodiments 708-729, wherein the target RNA is a HTT RNA.
731. The oligomeric compound of embodiment 729, wherein the target RNA is a MeCP2 RNA.
732. The oligomeric compound of embodiment 729, wherein the target RNA is a DUX4 RNA.
733. The oligomeric compound of embodiment 729, wherein the target RNA is a HDAC2 RNA.
734. The oligomeric compound of embodiment 729, wherein the target RNA is a Ataxin 1 RNA.
735. The oligomeric compound of embodiment 729, wherein the target RNA is a Ataxin 2 RNA.
736. The oligomeric compound of embodiment 729, wherein the target RNA is a Ataxin 3 RNA.
737. The oligomeric compound of embodiment 729, wherein the target RNA is a Ataxin 6 RNA.
738. The oligomeric compound of embodiment 729, wherein the target RNA is a Ataxin 7 RNA.
739. The oligomeric compound of embodiment 729, wherein the target RNA is a C9ORF72 RNA.
740. The oligomeric compound of embodiment 708-727, wherein the target RNA is an alpha-synuclein RNA.
741. The oligomeric compound of embodiment 729, wherein the target RNA is an UBE3A RNA.
742. The oligomeric compound of any of embodiments 708-727, wherein the target RNA is a SOD1 RNA.
743. The oligomeric compound of any of embodiments 708-727, wherein the target RNA is a Prion RNA.
744. The oligomeric compound of any of embodiments 708-727, wherein the target RNA is a PMP22 RNA.
745. The oligomeric compound of any of embodiments 708-727, wherein the target RNA is a Tau RNA.
746. The oligomeric compound of any of embodiments 708-727, wherein the target RNA is a LRRK2 RNA.
747. The oligomeric compound of any of embodiments 708-727, wherein the target RNA is an APP RNA.
748. The oligomeric compound of any of embodiments 708-727, wherein the target RNA is a LINGO2 RNA.
749. The oligomeric compound of any of embodiments 708-727, wherein the target RNA is a GYS1 RNA.
750. The oligomeric compound of any of embodiments 708-727, wherein the target RNA is a KCNT1 RNA.
751. The oligomeric compound of any of embodiments 708-727, wherein the target RNA is a IRF8 RNA.
752. The oligomeric compound of any of embodiments 708-727, wherein the target RNA is a Progranulin RNA.

753. The oligomeric compound of any of embodiments 708-727, wherein the target RNA is a GFAP RNA.
754. The oligomeric compound of any of embodiments 725-753, wherein modulation of the expression of the target RNA in the central nervous system is associated with treating a disorder or condition.
755. The oligomeric compound of embodiment 754, wherein the disorder or condition is a neurological disorder or condition.
756. The oligomeric compound of embodiment 754-755, wherein the disorder or condition alters the function of sensory or motor neurons.
757. The oligomeric compound of any of embodiments 754-756, wherein the disorder or condition alters the function of sensory neurons.
758. The oligomeric compound of any of embodiments 754-757, wherein the disorder or condition alters the function of motor neurons.
759. The oligomeric compound of any of embodiments 754-758, wherein the disorder or condition alters the function of glial cells.
760. The oligomeric compound of any of embodiments 754-759, wherein the disorder or condition alters the function of astrocytes.
761. The oligomeric compound of any of embodiments 754-760, wherein the disorder or condition alters the function of oligodendrocytes.
762. The oligomeric compound of any of embodiments 754-761, wherein the disorder or condition alters the function of microglia.
763. The oligomeric compound of any of embodiments 754-762, wherein the disorder or condition alters the function of ependymal cells.
764. The oligomeric compound of any of embodiments 754-763, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.
765. The oligomeric compound of embodiment 764, wherein the disorder or condition is Alzheimer's Disease.
766. The oligomeric compound of embodiment 764, wherein the disorder or condition is Amyotrophic Lateral Sclerosis.
767. The oligomeric compound of embodiment 764, wherein the disorder or condition is Parkinson's Disease.
768. The oligomeric compound of embodiment 764, wherein the disorder or condition is a Spinocerebellar ataxia.
769. The oligomeric compound of embodiment 764, wherein the disorder or condition is Angelman Syndrome.
770. The oligomeric compound of embodiment 764, wherein the disorder or condition is Alexander's Disease.
771. The oligomeric compound of embodiment 764, wherein the disorder or condition is Lafora Disease.
772. The oligomeric compound of embodiment 764, wherein the disorder or condition is Charcot-Marie Tooth Disease.
773. The oligomeric compound of embodiment 764, wherein the disorder or condition is Prion Disease.
774. The oligomeric compound of embodiment 764, wherein the disorder or condition is a dementia.
775. The oligomeric compound of embodiment 764, wherein the disorder or condition is neurodegeneration.
776. The oligomeric compound of embodiment 764, wherein the disorder or condition is MeCP2 Duplication Syndrome.
777. The oligomeric compound of embodiment 764, wherein the disorder or condition is encephalopathy.
778. The oligomeric compound of embodiment 764, wherein the disorder or condition is neuroinflammation.
779. The oligomeric compound of embodiment 764, wherein the disorder or condition is multiple sclerosis.
780. The oligomeric compound of any of embodiments 551-779, wherein the parent oligomeric compound of the oligomeric compound of any of embodiments 551-779 is cytotoxic in vitro.
781. The oligomeric compound of embodiment 780, wherein the parent oligomeric compound is cytotoxic in a standard in vitro cytotoxicity assay.
782. The oligomeric compound of any of embodiments 551-781 wherein administration to a mouse of the parent oligomeric compound of the oligomeric compound of any of embodiments 551-781 is hepatotoxic to the mouse.
783. The oligomeric compound of embodiment 782, wherein the administration of the parent oligomeric compound to the mouse is systemic administration.
784. The oligomeric compound of embodiment 783, wherein the systemic administration is subcutaneous administration.
785. The oligomeric compound of any of embodiments 782-784, wherein the mouse is a CD-1 mouse.
786. The oligomeric compound of any of embodiments 782-784, wherein the mouse is a C57BL/6 mouse.
787. The oligomeric compound of any of embodiments 782-784, wherein the mouse is a BALB/c mouse.
788. The oligomeric compound of any of embodiments 782-784, wherein the plasma ALT level in the mouse is higher than 500 units per liter following the administration of the parent oligomeric compound.
789. The oligomeric compound of any of embodiments 782-788, wherein the plasma AST level in the mouse is higher than 500 units per liter following the administration of the parent oligomeric compound.
790. The oligomeric compound of any of embodiments 782-789, wherein the plasma ALT level in the mouse is higher than 1000 units per liter following the administration of the parent oligomeric compound.
791. The oligomeric compound of any of embodiments 782-790, wherein the plasma AST level in the mouse is higher than 1000 units per liter following the administration of the parent oligomeric compound.
792. The oligomeric compound of any of embodiments 782-791, wherein the hepatotoxicity is measured 24-48 hours following the administration of the parent oligomeric compound.
793. The oligomeric compound of any of embodiments 782-791, wherein the hepatotoxicity is measured 72 hours following the administration of the parent oligomeric compound.
794. The oligomeric compound of any of embodiments 782-791, wherein the hepatotoxicity is measured 3 days following the administration of the parent oligomeric compound.
795. The oligomeric compound of any of embodiments 782-791, wherein the hepatotoxicity is measured 5 days following the administration of the parent oligomeric compound.

796. The oligomeric compound of any of embodiments 782-791, wherein the hepatotoxicity is measured 7 days following the administration of the parent oligomeric compound.

797. The oligomeric compound of any of embodiments 782-791, wherein the hepatotoxicity is measured 10 days following the administration of the parent oligomeric compound.

798. The oligomeric compound of any of embodiments 782-791, wherein the hepatotoxicity is measured 14 days following the administration of the parent oligomeric compound.

799. The oligomeric compound of any of embodiments 782-791, wherein 1-10 mg/kg of the parent oligomeric compound is administered to the mouse.

800. The oligomeric compound of any of embodiments 782-791, wherein 10-25 mg/kg of the parent oligomeric compound is administered to the mouse.

801. The oligomeric compound of any of embodiments 782-791, wherein 25-50 mg/kg of the parent oligomeric compound is administered to the mouse.

802. The oligomeric compound of any of embodiments 782-791, wherein 50-100 mg/kg of the parent oligomeric compound is administered to the mouse.

803. The oligomeric compound of any of embodiments 782-791, wherein 100-150 mg/kg of the parent oligomeric compound is administered to the mouse.

804. The oligomeric compound of any of embodiments 782-791, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

805. The oligomeric compound of any of embodiments 551-804, wherein administration of 50 mg/kg of the oligomeric compound of any of embodiments 551-804 to a mouse is not hepatotoxic to the mouse.

806. The oligomeric compound of embodiment 805, wherein plasma ALT level in the mouse is lower than 100 units per liter following the administration of the oligomeric compound of embodiment 805.

807. The oligomeric compound of embodiment 805 or 806, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.

808. The oligomeric compound of embodiment 807, wherein the plasma ALT level in the mouse is at least 100-fold lower than the plasma ALT level in the mouse administered the parent oligomeric compound.

809. The oligomeric compound of embodiment 807, wherein the plasma ALT level in the mouse is at least 500-fold lower than the plasma ALT level in the mouse administered the parent oligomeric compound.

810. The oligomeric compound of any of embodiments 782-809, wherein the therapeutic index in a mouse of the oligomeric compound of any of embodiments 782-809 is increased relative to the therapeutic index of the parent oligomeric compound.

811. The oligomeric compound of embodiment 810, wherein the therapeutic index in a mouse of the oligomeric compound of embodiment 365 is at least two-fold greater than the therapeutic index of the parent oligomeric compound.

812. The oligomeric compound of any of embodiments 551-811, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

813. The oligomeric compound of embodiment 812, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

814. The oligomeric compound of embodiment 813, wherein the 2'-O-methyl modified sugar moiety is at position 2 of the central region.

815. The oligomeric compound of embodiment 812-814, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

816. The oligomeric compound of any of embodiments 812-815, wherein the nucleobase sequence of the otherwise identical oligomeric compound is 100% complementary to the target RNA.

817. The oligomeric compound of any of embodiments 812-816, wherein the otherwise identical oligomeric compound is a parent oligomeric compound of the oligomeric compound of any of embodiments 812-816.

818. The oligomeric compound of any of embodiments 708-817, wherein the oligomeric compound inhibits the target RNA with an $IC_{50}$ lower than 100 nM in a standard in vitro activity assay.

819. The oligomeric compound of any of embodiments 708-818, wherein the parent oligomeric compound of the oligomeric compound of any of embodiments 708-818 inhibits the target RNA with an $IC_{50}$ lower than 100 nM in a standard in vitro activity assay.

820. The oligomeric compound of any of embodiments 708-819, wherein the difference between the $IC_{50}$ of the parent oligomeric compound measured in a standard in vitro activity assay and the $IC_{50}$ of the oligomeric compound of any of embodiments 708-819 measured in a standard in vitro activity assay is less than 4-fold.

821. The oligomeric compound of any of embodiments 708-820, wherein the difference between the $IC_{50}$ of the parent oligomeric compound measured in a standard in vitro activity assay and the $IC_{50}$ of the oligomeric compound of any of embodiments 708-820 measured in a standard in vitro activity assay is less than 3-fold.

822. The oligomeric compound of any of embodiments 708-821, wherein the difference between the $IC_{50}$ of the parent oligomeric compound measured in a standard in vitro activity assay and the $IC_{50}$ of the oligomeric compound of any of embodiments 708-821 measured in a standard in vitro activity assay is less than 2-fold.

823. The oligomeric compound of any of embodiments 708-822, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

824. The oligomeric compound of any of embodiments 708-823, wherein the nucleobase sequence of the parent oligomeric compound is 100% complementary to the target RNA.

825. The oligomeric compound of any of embodiments 551-824, wherein administration of 10-50 mg of the oligomeric compound to a human is not hepatotoxic to the human.

826. The oligomeric compound of any of embodiments 551-824, wherein administration of 50-100 mg of the oligomeric compound to a human is not hepatotoxic to the human.

827. The oligomeric compound of any of embodiments 551-824, wherein administration of 100-300 mg of the oligomeric compound to a human is not hepatotoxic to the human.

828. The oligomeric compound of any of embodiments 825-827, wherein the administration is systemic administration.

829. A composition comprising the oligomeric compound of any of embodiments 551-828 and a second oligomeric compound, wherein the second oligomeric compound is complementary to the oligomeric compound of any of embodiments 551-828.

830. The composition of embodiment 829, wherein the second oligomeric compound comprises at least 14 contiguous linked nucleosides that are at least 90% complementary to the oligomeric compound of any of embodiments 551-828.

831. The composition of embodiment 830, wherein the second oligomeric compound comprises at least 14 contiguous linked nucleosides that are 100% complementary to the oligomeric compound of any of embodiments 551-828.

832. A pharmaceutical composition comprising the oligomeric compound of any of embodiments 551-828 or the composition of any of embodiments 829-831, comprising a pharmaceutically acceptable carrier or diluent.

833. A method comprising administering the oligomeric compound or composition of any of embodiments 551-832 to a human subject.

834. A method of treating a disease or disorder comprising administering the oligomeric compound or composition of any of embodiments 551-832 to a human subject.

835. A method of modulating the amount or activity of a target RNA in a human subject comprising administering the oligomeric compound or composition of any of embodiments 551-832 to the human subject; and thereby modulating the amount or activity of the target RNA in the human subject.

836. A method of treating a disease or disorder in a human subject comprising administering the oligomeric compound or composition of any of embodiments 551-832 to the human subject having the disease or disorder; and thereby treating the disease or disorder in the human subject.

837. The method of embodiment 835-836, wherein the disease or disorder is a liver disease, and wherein the oligomeric compound modulates the amount or activity of a liver target RNA.

838. The method of embodiment 835-837, wherein the disease or disorder is a central nervous system disease, and wherein the oligomeric compound modulates the amount or activity of a central nervous system target RNA.

839. The method of any of embodiments 834-838, wherein the disease or disorder is a cancer, a neurodegenerative disease, a cardiovascular disease, an immunological disease, a hereditary disease, a repeat expansion disease, a muscle-wasting disease, or a metabolic disease.

840. The method of any of embodiments 834-839, wherein the plasma ALT level of the human subject after the administration is not more than three times higher than it was prior to the administration.

841. The method of any of embodiments 834-840, wherein the plasma ALT level of the human subject after the administration is not more than 150 units per liter.

842. The method of any of embodiments 834-841, wherein the human subject is susceptible to liver damage.

843. The method of any of embodiments 834-842, wherein the human subject is susceptible to liver degeneration.

844. The method of any of embodiments 834-843, wherein the human subject is susceptible to elevated apoptosis in the liver.

845. The method of any of embodiments 834-844, wherein the human subject has a liver disease.

846. The method of any of embodiments 834-841, comprising administering the parent oligomeric compound of the oligomeric compound of any of embodiments 551-832 to a mouse.

847. The method of any of embodiments 833-846, comprising contacting a cell with the parent oligomeric compound of the oligomeric compound of any of embodiments 551-832.

848. The method of embodiment 846-847, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

849. A method of designing an oligomeric compound comprising starting with a parent oligomeric compound and changing the design of that compound in order to arrive at an oligomeric compound of any one of embodiments 551-833.

850. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 551-833.

851. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 551-833.

852. The method of embodiment 851, wherein the method designs an oligomeric compound with improved therapeutic index relative to the parent oligomeric compound.

853. The method of embodiment 851-852, wherein the method designs an oligomeric compound with lower hepatotoxicity relative to the parent oligomeric compound.

854. The method of embodiment 853, wherein the second oligomeric compound has an improved therapeutic index relative to the parent oligomeric compound.

855. The method of embodiment 851-852, wherein the second oligomeric compound has reduced hepatotoxicity in a mouse relative to the parent oligomeric compound.

856. The method of embodiment 855, wherein the oligomeric compound according to any one of embodiments 551-833 has reduced hepatotoxicity relative to the parent oligomeric compound.

857. A method comprising administering an oligomeric compound of any of embodiments 551-833 to a mouse and separately administering the parent oligomeric compound of the oligomeric compound of any of embodiments 551-833 to a second mouse, wherein the therapeutic index of the oligomeric compound of any of embodiments 551-833 is improved relative to the therapeutic index of the parent oligomeric compound.

858. The method of any of embodiments 833-857, wherein the level of p21 RNA is measured in the mouse, the cell, and/or the human subject.

859. A method comprising administering an oligomeric compound of any of embodiments 551-833 to a subject and measuring the level of p21 RNA in the subject.

860. The method of embodiment 858 or 859, wherein the subject is a mouse.

861. The method of embodiment 858 or 859, wherein the subject is a human.

862. The method of any of embodiments 858-861, wherein the p21 RNA level is measured within 24 hours of the administration.

863. The method of any of embodiments 858-862, wherein the p21 RNA level is measured 24-48 hours following the administration.

864. An oligomeric compound or composition of any one of embodiments 551-832, for use in medical therapy.

865. The oligomeric compound of any of embodiments 551-832, wherein the oligomeric compound is not toxic.

866. The oligomeric compound of any of embodiment 551-832, wherein a comparator compound is toxic; wherein the comparator compound is identical to the oligomeric compound except that each nucleoside of the central region of the comparator compound is a nucleoside comprising 2'-β-D-deoxyribyl sugar moiety.

867. The oligomeric compound of embodiment 866, wherein administering a dose of the oligomeric compound to an animal results in a circulating ALT level that is at least 3-fold lower than the ALT level that results from administering the same dose of the comparator compound to an animal for at least one matched dose.

868. The oligomeric compound of embodiment 866 or 867, wherein the lowest dose of the oligomeric compound that raises circulating ALT to over 300 units per liter is at least three-fold higher than the lowest dose of the comparator compound that raises circulating ALT to over 300 units per liter.

869. The oligomeric compound of any of embodiments 865-868, wherein the oligomeric compound is capable of reducing the target RNA in a cell.

870. The oligomeric compound of embodiment 869, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

871. The oligomeric compound of embodiment 870 having RNA-reducing activity that is no more than 2-fold worse than the RNA-reducing activity of the comparator compound.

872. A method of modulating the amount or activity of a target RNA in a human subject comprising administering the oligomeric compound or composition of any of embodiments 551-832 to the human subject; and thereby modulating the amount or activity of the target RNA in the human subject.

873. A method of treating a disease or disorder in a human subject comprising administering the oligomeric compound or composition of any of embodiments 551-832 to the human subject having the disease or disorder; and thereby treating the disease or disorder in the human subject.

874. The method of embodiment 872-873, wherein the disease or disorder is a liver disease, and wherein the oligomeric compound modulates the amount or activity of a liver target RNA.

875. The method of embodiment 872-873, wherein the disease or disorder is a central nervous system disease, and wherein the oligomeric compound modulates the amount or activity of a central nervous system target RNA.

876. The method of any of embodiments 872-874, wherein the disease or disorder is a cancer, a neurodegenerative disease, a cardiovascular disease, an immunological disease, a hereditary disease, a repeat expansion disease, a muscle-wasting disease, or a metabolic disease.

877. The method of any of embodiments 872-876, wherein the plasma ALT level of the human subject after the administration is not more than three times higher than it was prior to the administration.

878. The method of any of embodiments 872-877, wherein the plasma ALT level of the human subject after the administration is not more than 150 units per liter.

879. A method of treating a disease or disorder in a human subject comprising administering the oligomeric compound or composition of any of embodiments 1-410, 452-518, 551-828, or 864-871 to the human subject having the disease or disorder; and thereby treating the disease or disorder in the human subject.

880. The method of embodiment 879, wherein the disease or disorder is not a CNS disease or disorder.

881. The method of embodiment 879, wherein the disease or disorder is a disease or disorder of the muscle.

882. The method of embodiment 879, wherein the disease or disorder is a disease or disorder of the lung.

883. The method of embodiment 879, wherein the disease or disorder is a disease or disorder of the kidney.

884. The method of embodiment 879, wherein the disease or disorder is a disease or disorder of the eye.

885. The method of embodiment 879, wherein the disease or disorder is a disease or disorder of the pancreas.

886. A method of screening a library of oligomeric compounds for activity against a target RNA, wherein the library of oligomeric compounds comprises a plurality of oligomeric compounds of any of embodiments 1-410, 452-218, 551-831, or 864-871.

887. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:
the 5'-region consists of 1-5 linked nucleosides, wherein at least one nucleoside of the 5'-region is a modified nucleoside comprising a modified sugar;
the 3'-region consists of 1-5 linked nucleosides wherein at least one nucleoside of the 3'-region is a modified nucleoside comprising a modified sugar; and the central region consists of 7-11 linked nucleosides, wherein the 5'-most portion of the central region has the following formula:

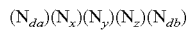

wherein one of $N_x$, $N_y$, and $N_z$, is a safety-enhancing nucleoside;

the other two of $N_x$, $N_y$, and $N_z$ are independently selected from a DNA nucleoside, a DNA isomer, a modified DNA isomer, and a DNA mimic; and $N_{da}$ and $N_{db}$ are each independently selected from a DNA nucleoside, a DNA isomer, a modified DNA isomer, and a DNA mimic.

888. The oligomeric compound of embodiment 887, wherein the 5'-region consists of one nucleoside.
889. The oligomeric compound of embodiment 887, wherein the 5'-region consists of 2-5 linked nucleosides.
890. The oligomeric compound of embodiment 887, wherein the 5'-region consists of 2-4 linked nucleosides.
891. The oligomeric compound of embodiment 887, wherein the 5'-region consists of 2 linked nucleosides.
892. The oligomeric compound of embodiment 887, wherein the 5'-region consists of 3 linked nucleosides.
893. The oligomeric compound of embodiment 887, wherein the 5'-region consists of 4 linked nucleosides.
894. The oligomeric compound of embodiment 887, wherein the 5'-region consists of 5 linked nucleosides.
895. The oligomeric compound of any of embodiments 887-894, wherein each nucleoside of the 5'-region is a modified nucleoside.
896. The oligomeric compound of any of embodiments 887-895, wherein each nucleoside of the 5'-region is a modified nucleoside comprising a modified sugar.
897. The oligomeric compound of any of embodiments 887-896, wherein each modified nucleoside of the 5'-region has the same modification.
898. The oligomeric compound of any of embodiments 887-896, wherein at least two nucleosides of the 5'-region are modified nucleosides having different modifications.
899. The oligomeric compound of any of embodiments 887-898, wherein each nucleoside of the 5'-region comprises a 2'-modified ribosyl sugar moiety.
900. The oligomeric compound of any of embodiments 887-899, wherein at least one nucleoside of the 5'-region comprises a bicyclic furanosyl sugar moiety.
901. The oligomeric compound of any of embodiments 887-900, wherein each nucleoside of the 5'-region comprises a bicyclic furanosyl sugar moiety.
902. The oligomeric compound of any of embodiments 887-900, wherein at least one nucleoside of the 5'-region comprises a non-bicyclic sugar moiety.
903. The oligomeric compound of embodiment 902, wherein the non-bicyclic sugar moiety of the at least one nucleoside of the 5'-region is a 2'-substituted ribosyl sugar moiety.
904. The oligomeric compound of any of embodiments 887-889 or 902-903, wherein each nucleoside of the 5'-region comprises a non-bicyclic sugar moiety.
905. The oligomeric compound of embodiment 904, wherein each nucleoside of the 5'-region comprises a 2'-substituted furanosyl sugar moiety.
906. The oligomeric compound of any of embodiments 887-905, wherein each nucleoside of the 5'-region comprises a 2'-modified furanosyl sugar moiety independently selected from a bicyclic sugar moiety and a non-bicyclic 2'-substituted ribosyl sugar moiety.
907. The oligomeric compound of any of embodiments 887-901 or 906, wherein each nucleoside of the 5'-region comprises a bicyclic sugar moiety.
908. The oligomeric compound of any of embodiments 887-889 or 902-906, wherein each nucleoside of the 5'-region comprises a non-bicyclic 2'-substituted ribosyl sugar moiety.
909. The oligomeric compound of any of embodiments 887-903 or 906-907, wherein each bicyclic sugar moiety of the 5'-region is selected from among cEt, LNA, and ENA.
910. The oligomeric compound of any of embodiments 887-903 or 906-909, wherein each bicyclic sugar moiety of the 5'-region is a cEt sugar moiety.
911. The oligomeric compound of any of embodiments 887-903, or 906-907 or 909 wherein each bicyclic sugar moiety of the 5'-region is an LNA sugar moiety.
912. The oligomeric compound of any of embodiments 887-900, 902-906, or 908-911, wherein each non-bicyclic sugar moiety of the 5'-region has a 2'-substituent selected from among 2'-MOE, 2'-OMe, and 2'-NMA.
913. The oligomeric compound of any of embodiments 887-912, wherein none of the nucleosides of the 5'-region comprise a sugar moiety having a 2'-F substituent.
914. The oligomeric compound of any of embodiments 887-913, wherein none of the nucleosides of the 5'-region comprise a sugar moiety having a 2'-MOE substituent.
915. The oligomeric compound of any of embodiments 887-914, wherein none of the nucleosides of the 5'-region comprise a sugar moiety having a 2'-OMe substituent.
916. The oligomeric compound of any of embodiments 887-915, wherein none of the nucleosides of the 5'-region comprise a cEt sugar moiety.
917. The oligomeric compound of any of embodiments 887-916, wherein none of the nucleosides of the 5'-region comprise a LNA sugar moiety.
918. The oligomeric compound of any of embodiments 887-917, wherein each nucleobase of the 5'-region is independently selected from among thymine, uracil, guanine, cytosine, 5-methylcytosine, and adenine.
919. The oligomeric compound of any of embodiments 887-918, wherein each internucleoside linkage of the 5'-region is independently selected from among phosphodiester and phosphorothioate internucleoside linkages.
920. The oligomeric compound of any of embodiments 887-919, wherein the 3'-region consists of one nucleoside.
921. The oligomeric compound of any of embodiments 887-919, wherein the 3'-region consists of 2-5 linked nucleosides.
922. The oligomeric compound of any of embodiments 887-919, wherein the 3'-region consists of 2-4 linked nucleosides.
923. The oligomeric compound of any of embodiments 887-919, wherein the 3'-region consists of 2 linked nucleosides.
924. The oligomeric compound of any of embodiments 887-919, wherein the 3'-region consists of 3 linked nucleosides.
925. The oligomeric compound of any of embodiments 887-919, wherein the 3'-region consists of 4 linked nucleosides.
926. The oligomeric compound of any of embodiments 887-919, wherein the 3'-region consists of 5 linked nucleosides.

927. The oligomeric compound of any of embodiments 887-926, wherein each nucleoside of the 3'-region is a modified nucleoside.

928. The oligomeric compound of any of embodiments 887-927, wherein each nucleoside of the 3'-region is a modified nucleoside comprising a modified sugar moiety.

929. The oligomeric compound of any of embodiments 887-928, wherein each modified nucleoside of the 3'-region has the same modification.

930. The oligomeric compound of and of embodiments 887-928, wherein at least two nucleosides of the 3'-region are modified nucleosides having different modifications.

931. The oligomeric compound of any of embodiments 887-930, wherein each nucleoside of the 3'-region comprises a 2'-modified ribosyl sugar moiety.

932. The oligomeric compound of any of embodiments 887-931, wherein at least one nucleoside of the 3'-region comprises a bicyclic furanosyl sugar moiety.

933. The oligomeric compound of any of embodiments 887-932, wherein each nucleoside of the 3'-region comprises a bicyclic furanosyl sugar moiety.

934. The oligomeric compound of any of embodiments 887-933, wherein at least one nucleoside of the 3'-region comprises a non-bicyclic sugar moiety.

935. The oligomeric compound of embodiment 934, wherein the non-bicyclic sugar moiety of the at least one nucleoside of the 3'-region is a 2'-substituted ribosyl sugar moiety.

936. The oligomeric compound of any of embodiments 887-935, wherein each nucleoside of the 3'-region comprises a non-bicyclic sugar moiety.

937. The oligomeric compound of embodiment 936, wherein each nucleoside of the 3'-region comprises a 2'-substituted furanosyl sugar moiety.

938. The oligomeric compound of any of embodiments 887-937, wherein each nucleoside of the 3'-region comprises a 2'-modified furanosyl sugar moiety independently selected from a bicyclic sugar moiety and a non-bicyclic 2'-substituted ribosyl sugar moiety.

939. The oligomeric compound of any of embodiments 887-935, or 938 wherein each nucleoside of the 3'-region comprises a bicyclic sugar moiety.

940. The oligomeric compound of any of embodiments 887-932 or 934-938, wherein each nucleoside of the 3'-region comprises a non-bicyclic 2'-substituted ribosyl sugar moiety.

941. The oligomeric compound of any of embodiments 887-935 or 938-939, wherein each bicyclic sugar moiety of the 3'-region is selected from among cEt, LNA, and ENA.

942. The oligomeric compound of any of embodiments 887-935, 938-939, or 941, wherein each bicyclic sugar moiety of the 3'-region is a cEt sugar moiety.

943. The oligomeric compound of any of embodiments 887-935, 938-939, or 941, wherein each bicyclic sugar moiety of the 3'-region is an LNA sugar moiety.

944. The oligomeric compound of any of embodiments 887-932, 934-938 or 940, wherein each non-bicyclic sugar moiety of the 3'-region has a 2'-substituent selected from among 2'-MOE, 2'-OMe, and 2'-NMA.

945. The oligomeric compound of any of embodiments 887-944, wherein none of the nucleosides of the 3'-region comprise a sugar moiety having a 2'-F substituent.

946. The oligomeric compound of any of embodiments 887-945, wherein none of the nucleosides of the 3'-region comprise a sugar moiety having a 2'-MOE substituent.

947. The oligomeric compound of any of embodiments 887-946, wherein none of the nucleosides of the 3'-region comprise a sugar moiety having a 2'-OMe substituent.

948. The oligomeric compound of any of embodiments 887-947, wherein none of the nucleosides of the 3'-region comprise a cEt sugar moiety.

949. The oligomeric compound of any of embodiments 887-948, wherein none of the nucleosides of the 3'-region comprise a LNA sugar moiety.

950. The oligomeric compound of any of embodiments 887-949, wherein each nucleobase of the 3'-region is independently selected from among thymine, uracil, guanine, cytosine, 5-methylcytosine, and adenine.

951. The oligomeric compound of any of embodiments 887-950, wherein each internucleoside linkage of the 3'-region is independently selected from among phosphodiester and phosphorothioate internucleoside linkages.

952. The oligomeric compound of any of embodiments 887-951, wherein the modified nucleosides of the 5'-region have the same modifications as the modifications of the modified nucleosides of the 3'-region.

953. The oligomeric compound of any of embodiments 887-951, wherein at least one modified nucleoside of the 5'-region and one modified nucleoside of the 3'-region comprise modifications that differ from one another.

954. The oligomeric compound of any of embodiments 887-898, 900, 902-903, 906, 909-932, 934-935, 938, 941-953, wherein the 5'-region and the 3'-region together include at least one non-bicyclic 2'-substituted modified nucleoside and at least one bicyclic nucleoside.

955. The oligomeric compound of embodiment 954, where the bicyclic nucleoside is a cEt nucleoside.

956. The oligomeric compound of embodiment 954, where the bicyclic nucleoside is an LNA nucleoside.

957. The oligomeric compound of any of embodiments 954-956, wherein the non-bicyclic 2'-modified nucleoside is a 2'-MOE nucleoside.

958. The oligomeric compound of any of embodiments 954-956, wherein the non-bicyclic 2'-modified nucleoside is a 2'-OMe nucleoside.

959. The oligomeric compound of any of embodiments 954-958, wherein at least one nucleoside of the 5'-region or the 3'-region is an unmodified DNA nucleoside.

960. The oligomeric compound of any of embodiments 887-959, wherein the central region has the formula:

$$(N_{da})(N_x)(N_y)(N_z)(N_{db})(N_{dc})_q$$

wherein each $N_{dc}$ is independently selected from an unmodified DNA nucleoside, a DNA isomer, a modified DNA isomer, and a DNA mimic; and q is 2-6.

961. The oligomeric compound of any of embodiments 887-960, wherein the central region consists of 7 linked nucleosides.

962. The oligomeric compound of any of embodiments 887-960, wherein the central region consists of 8 linked nucleosides.

963. The oligomeric compound of any of embodiments 887-960, wherein the central region consists of 9 linked nucleosides.

964. The oligomeric compound of any of embodiments 887-960, wherein the central region consists of 10 linked nucleosides.

965. The oligomeric compound of any of embodiments 887-960, wherein the central region consists of 11 linked nucleosides.

966. The oligomeric compound of any of embodiments 887-965, wherein Nx is the safety-enhancing nucleoside.

967. The oligomeric compound of any of embodiments 887-965, wherein Ny is the safety-enhancing nucleoside.

968. The oligomeric compound of any of embodiments 887-965, wherein Nz is the safety-enhancing nucleoside.

969. The oligomeric compound of any of embodiments 887-968, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

970. The oligomeric compound of any of embodiments 887-969, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.

971. The oligomeric compound of any of embodiments 887-970, wherein the safety enhancing nucleoside comprises a sugar surrogate selected from a morpholino, a modified morpholino, a modified cyclohexenyl, or a modified tetrahydropyran.

972. The oligomeric compound of any of embodiments 887-970, wherein the safety enhancing nucleoside comprises a sugar surrogate selected from a morpholino, a modified morpholino, CeNA, F-CeNA, HNA, OMe-HNA or F-HNA.

973. The oligomeric compound of any of embodiments 887-970, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-O-L-deoxyxylosyl.

974. The oligomeric compound of any of embodiments 887-970 or 973, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

975. The oligomeric compound of any of embodiments 887-970, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

976. The oligomeric compound of any of embodiments 887-970 or 975, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

977. The oligomeric compound of any of embodiments 887-970 or 975-976, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

978. The oligomeric compound of any of embodiments 887-970 or 975-977, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

979. The oligomeric compound of any of embodiments 887-970, wherein the safety enhancing nucleoside is a modified nucleoside comprising a bicyclic furanosyl sugar moiety.

980. The oligomeric compound of any of embodiments 887-970, wherein the safety enhancing nucleoside is selected from among cEt, LNA, α-L-LNA, and ENA.

981. The oligomeric compound of any of embodiments 887-970, wherein the safety enhancing nucleoside comprises a 2'-substituted furanosyl sugar moiety.

982. The oligomeric compound of embodiment 981, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

983. The oligomeric compound of embodiment 981, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.

984. The oligomeric compound of embodiment 981, wherein the 2'-substituted furanosyl sugar moiety of the safety enhancing nucleoside has a 2' substituent selected from: fluoro, OMe, MOE, NMA.

985. The oligomeric compound of any of embodiments 887-978 or 981-984, wherein the safety enhancing nucleoside comprises a 2'-substituted furanosyl sugar moiety comprising a 2'-OMe or 2'-MOE.

986. The oligomeric compound of any of embodiments 887-978 or 981-986, wherein the safety enhancing nucleoside comprises a 2'-substituted furanosyl sugar moiety comprising a 2'-OMe.

987. The oligomeric compound of any of embodiments 887-978 or 981-986, wherein the safety enhancing nucleoside comprises a 2'-OMe modified 2'-β-D-deoxyribosyl sugar moiety.

988. The oligomeric compound of any of embodiments 887-970, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

989. The oligomeric compound of any of embodiments 887-970 or embodiment 988, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

990. The oligomeric compound of any of embodiments 887-970 or 988-989, wherein the safety enhancing nucleoside comprises a 3'-methyl furanosyl sugar moiety.
991. The oligomeric compound of any of embodiments 887-970, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.
992. The oligomeric compound of any of embodiments 887-970 or 991, wherein the safety enhancing nucleoside comprises a 4'-modified furanosyl sugar moiety having a 4'-methyl.
993. The oligomeric compound of any of embodiments 887-970, wherein the safety enhancing nucleoside has the structure shown below, wherein R represents an optional 2' substituent group and Bx is a heterocyclic base moiety:

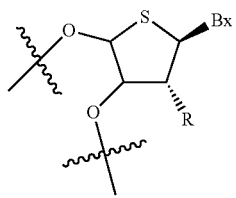

994. The oligomeric compound of embodiment 993, wherein in R is selected from among H, OH, OMe, F, or MOE.
995. The oligomeric compound of any of embodiments 887-970, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, O($CH_2$)$_2$$SCH_3$, O($CH_2$)$_2$ON($R_m$)($R_n$) or $OCH_2$C(=O)—N($R_m$)($R_n$), where each $R_m$ and $R_n$ is, independently, H, an amino protecting group, or substituted or unsubstituted $C_1$-$C_{10}$ alkyl.
996. The oligomeric compound of any of embodiments 887-970 or 995, wherein the safety enhancing nucleoside comprises a 5'-modified furanosyl sugar moiety with a 5' substituent selected from: 5'-methyl, 5'-ethyl or a 5'-allyl.
997. The oligomeric compound of any of embodiments 887-970 or 995-996, wherein the safety enhancing nucleoside comprises a 5'-modified furanosyl sugar moiety with a 5' substituent selected from: 5'-(R)-methyl- or 5'-(R)-ethyl.
998. The oligomeric compound of any of embodiments 887-970 or 995-997, wherein the safety enhancing nucleoside comprises a 5'-(R)-methyl-2'-β-D-deoxyribosyl sugar moiety.
999. The oligomeric compound of any of embodiments 887-970 or 995-998, wherein the safety enhancing nucleoside comprises a 5'-(R)-ethyl-2'-β-D-deoxyribosyl sugar moiety.

1000. The oligomeric compound of any of embodiments 887-999, wherein the safety enhancing nucleoside does not comprise a 2'-F modified sugar moiety.
1001. The oligomeric compound of any of embodiments 887-1000, wherein the safety enhancing nucleoside does not comprise a cEt modified sugar moiety.
1002. The oligomeric compound of any of embodiments 887-1001, wherein the safety enhancing nucleoside does not comprise a 2'-MOE modified sugar moiety.
1003. The oligomeric compound of any of embodiments 887-1002, wherein the safety enhancing nucleoside comprises a hypoxanthine nucleobase.
1004. The oligomeric compound of any of embodiments 887-1003, wherein the safety enhancing nucleoside comprises a nucleobase selected from among thymine, uracil, guanine, cytosine, 5-methylcytosine, and adenine.
1005. The oligomeric compound of any of embodiments 887-1004, wherein the safety enhancing nucleoside is a modified nucleoside other than cEt, MOE, LNA, or FANA.
1006. The oligomeric compound of any of embodiments 887-1005, wherein each Nd is independently selected from among a DNA nucleoside, a DNA isomer, a 2'-modified DNA isomer, and a DNA mimic.
1007. The oligomeric compound of embodiment 1006, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.
1008. The oligomeric compound of embodiment 1007, wherein each DNA isomer comprises a sugar moiety selected from among 2'-β-D-deoxyxylosyl, 2'-α-L-deoxyribosyl, and 2'-β-L-deoxyribosyl.
1009. The oligomeric compound of embodiment 1006, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.
1010. The oligomeric compound of embodiment 1009, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.
1011. The oligomeric compound of embodiment 1010, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.
1012. The oligomeric compound of embodiment 1011, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.
1013. The oligomeric compound of embodiment 1006, wherein each DNA mimic comprises a structure represented by one of the formulas below:

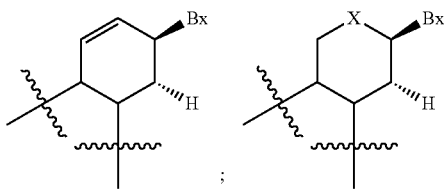

wherein X is O or S and Bx represents a heterocylic base moiety.

1014. The oligomeric compound of embodiment 1006, wherein each DNA mimic comprises a structure represented by one of the formulas below:

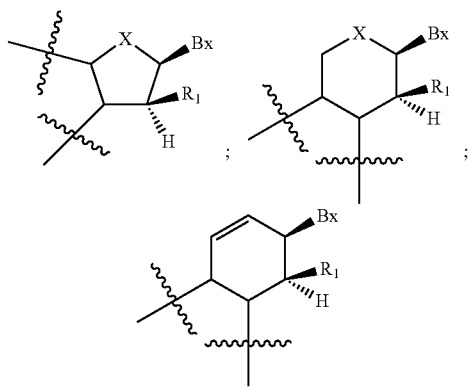

wherein X is O or S;

Bx represents a heterocyclic base moiety; and $R_1$ is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)-N(R_m)(R_n)$, where each $R_m$ and $R_n$ is, independently, H, an amino protecting group, or substituted or unsubstituted $C_1$-$C_{10}$ alkyl;

wherein if the DNA mimic comprises the structure:

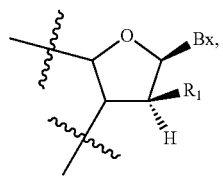

$R_1$ is other than H.

1015. The oligomeric compound of embodiment 1014, wherein R1 is H, OH, OMe, or F.

1016. The oligomeric compound of embodiment 1014, wherein $R_1$ is not F.

1017. The oligomeric compound of embodiment 1006, wherein each DNA mimic comprises a structure represented by the formula below:

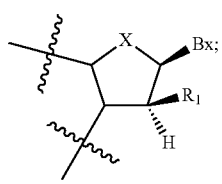

wherein X is S, Bx represents a heterocyclic base moiety, and $R_1$ is H.

1018. The oligomeric compound of embodiment 1006, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1019. The oligomeric compound of embodiment 1006, wherein the DNA mimic comprises a 2'-fluoro-β-D-arabinofuranosyl sugar moiety.

1020. The oligomeric compound of embodiment 1006, wherein the DNA mimic does not comprise a 2'-fluoro-β-D-arabinofuranosyl sugar moiety.

1021. The oligomeric compound of any of embodiments 887-1020, wherein each $N_d$ is a DNA nucleoside.

1022. The oligomeric compound of any of embodiments 887-1021, wherein the central region comprises no more than four nucleosides selected from among DNA isomers, modified DNA isomers, and DNA mimics.

1023. The oligomeric compound of any of embodiments 887-1021, wherein the central region comprises no more than three nucleosides selected from among DNA isomers, modified DNA isomers, and DNA mimics.

1024. The oligomeric compound of any of embodiments 887-1021, wherein the central region comprises no more than two nucleosides selected from among DNA isomers, modified DNA isomers, and DNA mimics.

1025. The oligomeric compound of any of embodiments 887-1021, wherein the central region comprises no more than one nucleoside selected from among DNA isomers, modified DNA isomers, and DNA mimics.

1026. The oligomeric compound of any of embodiments 887-1025, wherein the central region contains exactly one safety enhancing nucleoside and the remainder of nucleosides in the central region are DNA nucleosides.

1027. The oligomeric compound of any of embodiments 887-1026, wherein at least one internucleoside linkage of the central region selected from among: the internucleoside Nda to Nx, Nx to Ny, Ny to Nz, or Nz to the adjacent Ndb is a neutral internucleoside linkage.

1028. The oligomeric compound of embodiments 1027, wherein the neutral linkage is a phosphonate internucleoside linkage.

1029. The oligomeric compound of embodiments 1027, wherein the neutral linkage is a methoxypropyl internucleoside linkage.

1030. The oligomeric compound of embodiments 1027, wherein each remaining internucleoside linkage is a phosphodiester or phosphorothioate internucleoside linkage.

1031. A chirally enriched population of modified oligonucleotides of any of embodiments 887-1026, wherein the central region has at least one particular phorphorothioate internucleoside linkage having a particular stereochemical configuration.

1032. The chirally enriched population of embodiment 1031, wherein the central region has at least one phorphorothioate internucleoside linkage having the (Sp) configuration.

1033. The chirally enriched population of embodiment 1031, wherein central region has at least one phorphorothioate internucleoside linkage having the (Rp) configuration.
1034. The chirally enriched population of embodiment 1031, wherein the central region has a particular, independently selected stereochemical configuration at each phosphorothioate internucleoside linkage.
1035. The chirally enriched population of embodiment 1034, wherein the each phosphorothioate internucleoside linkage of the central region has the (Sp) configuration.
1036. The chirally enriched population of embodiment 1034, wherein the central region has one phosphorothioate internucleoside linkage having the (Rp) configuration and wherein each remaining central region phosphorothioate internucleoside linkage has the (Sp) configuration.
1037. The chirally enriched population of embodiment 1031, wherein the central region has an (Rp) phosphorothioate internucleoside linkage adjacent to an (Sp) phosphorothioate internucleoside linkage.
1038. The chirally enriched population of embodiment 1031, wherein the central region has an (Rp) phosphorothioate internucleoside linkage adjacent to a second (Rp) phosphorothioate internucleoside linkage.
1039. The chirally enriched population of embodiment 1031, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.
1040. The chirally enriched population of any of embodiments 1032, 1033, 1037, or 1038 wherein each phosphorothioate internucleoside linkage that does not have the (Rp) or (Sp) configuration is stereorandom.
1041. The oligomeric compound of any of embodiments 887-1040 comprising a conjugate group.
1042. The oligomeric compound of embodiment 1041, wherein the conjugate group comprises a linking group attaching the remainder of the conjugate group to the modified oligonucleotide, wherein the linking group comprises 1-5 nucleosides.
1043. The oligomeric compound of any of embodiments 887-1041, wherein the oligomeric compound does not comprise additional nucleosides beyond those of the modified oligonucleotide.
1044. The oligomeric compound of any of embodiments 887-1043, wherein the nucleobase sequence of the modified oligonucleotide is complementary to a target RNA.
1045. The oligomeric compound of embodiment 1044, wherein the nucleobase sequence of the modified oligonucleotide is at least 85% complementary to the target RNA.
1046. The oligomeric compound of embodiment 1044, wherein the nucleobase sequence of the modified oligonucleotide is at least 90% complementary to the target RNA.
1047. The oligomeric compound of embodiment 1044, wherein the nucleobase sequence of the modified oligonucleotide is at least 95% complementary to the target RNA.
1048. The oligomeric compound of embodiment 1047, wherein the nucleobase sequence of the modified oligonucleotide is 100% complementary to the target RNA.
1049. The oligomeric compound of any of embodiments 1044-1048, wherein the target RNA is a target mRNA or a target pre-mRNA.
1050. The oligomeric compound of embodiment 1049, wherein the target mRNA or target pre-mRNA is not a mouse, rat, monkey, or human PTEN RNA.
1051. The oligomeric compound of embodiment 1049 or 1050, wherein the target mRNA or target pre-mRNA is not a mouse, rat, monkey, or human SRB-1 RNA.
1052. The oligomeric compound of any of embodiments 1049-1051, wherein the target mRNA or target pre-mRNA is not a mouse, rat, monkey, or human MYD88 RNA.
1053. The oligomeric compound of any of embodiments 1049-1052, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.
1054. The oligomeric compound of any of embodiments 1044-1053, wherein the target RNA is a human RNA.
1055. The oligomeric compound of any of embodiments 1044-1054, wherein the target RNA is expressed in the liver.
1056. The oligomeric compound of any of embodiments 1044-1055, wherein the target RNA is a liver target.
1057. The oligomeric compound of any of embodiments 1044-1054, wherein the target RNA is not expressed in the liver.
1058. The oligomeric compound of any of embodiments 1044-1054 or 1057, wherein the target RNA is not a liver target.
1059. The oligomeric compound of any of embodiments 1044-1056, wherein modulation of the expression of the target RNA in the liver is associated with treating a disorder or condition.
1060. The oligomeric compound of embodiment 1059, wherein the disorder or condition is a liver disorder or condition.
1061. The oligomeric compound of any of embodiments 1044-1060, wherein the target RNA is expressed in the central nervous system.
1062. The oligomeric compound of any of embodiments 1044-1060, wherein the target RNA is not expressed in the central nervous system.
1063. The oligomeric compound of any of embodiments 1044-1061, wherein the target RNA is a central nervous system target.
1064. The oligomeric compound of any of embodiments 1044-1062, wherein the target RNA is not a central nervous system target.
1065. The oligomeric compound of any of embodiments 1044-1064, wherein the target RNA is expressed in white fat cells.
1066. The oligomeric compound of any of embodiments 1044-1064, wherein the target RNA is expressed in brown fat cells.
1067. The oligomeric compound of any of embodiments 1044-1064, wherein the target RNA is expressed in adipocytes.
1068. The oligomeric compound of any of embodiments 1044-1064, wherein the target RNA is expressed in macrophages.
1069. The oligomeric compound of any of embodiments 1044-1064, wherein the target RNA is expressed in cancer cells.
1070. The oligomeric compound of any of embodiments 1044-1064, wherein the target RNA is expressed in tumor cells.

1071. The oligomeric compound of any of embodiments 1044-1064, wherein the target RNA is expressed in smooth muscle cells.
1072. The oligomeric compound of any of embodiments 1044-1064, wherein the target RNA is expressed in lymphocytes.
1073. The oligomeric compound of any of embodiments 1044-1064, wherein the target RNA is expressed in pulmonary cells.
1074. The oligomeric compound of any of embodiments 1044-1064, wherein the target RNA is expressed in heart muscle cells.
1075. The oligomeric compound of any of embodiments 1044-1064, wherein the target RNA is expressed in cardiomyocytes.
1076. The oligomeric compound of any of embodiments 1044-1064, wherein the target RNA is expressed in endothelial cells.
1077. The oligomeric compound of any of embodiments 1044-1064, wherein the target RNA is expressed in fibroblasts.
1078. The oligomeric compound of any of embodiments 1044-1064, wherein the target RNA is expressed in glial cells.
1079. The oligomeric compound of any of embodiments 1044-1064, wherein the target RNA is expressed in Schwann cells.
1080. The oligomeric compound of any of embodiments 1044-1064, wherein the target RNA is expressed in pancreatic cells.
1081. The oligomeric compound of any of embodiments 1044-1064, wherein the target RNA is expressed in kidney cells.
1082. The oligomeric compound of any of embodiments 1044-1064, wherein the target RNA is expressed in beta cells.
1083. The oligomeric compound of any of embodiments 1044-1064, wherein the target RNA is expressed in non-parenchymal cells.
1084. The oligomeric compound of any of embodiments 1044-1064, wherein the target RNA is expressed in hepatocytes.
1085. The oligomeric compound of any of embodiments 1044-1064, wherein the target RNA is expressed in oligodendrocytes.
1086. The oligomeric compound of any of embodiments 1044-1064, wherein the target RNA is expressed in astrocytes.
1087. The oligomeric compound of any of embodiments 1044-1064, wherein the target RNA is expressed in microglia.
1088. The oligomeric compound of any of embodiments 1044-1064, wherein the target RNA is expressed in ependymal cells.
1089. The oligomeric compound of any of embodiments 1044-1064, wherein the target RNA is expressed in sensory neurons.
1090. The oligomeric compound of any of embodiments 1044-1064, wherein the target RNA is expressed in motor neurons.
1091. The oligomeric compound of any of embodiments 1044-1064, wherein the target RNA is expressed in skeletal muscle.
1092. The oligomeric compound of any of embodiments 1044-1064, wherein the target RNA is expressed in cardiac muscle.
1093. The oligomeric compound of any of embodiments 1044-1064, wherein the target RNA is expressed in smooth muscle.
1094. The oligomeric compound of any of embodiments 1044-1064, wherein the target RNA is expressed in adipose tissue.
1095. The oligomeric compound of any of embodiments 1044-1064, wherein the target RNA is expressed in white adipose tissue.
1096. The oligomeric compound of any of embodiments 1044-1064, wherein the target RNA is expressed in the spleen.
1097. The oligomeric compound of any of embodiments 1044-1064, wherein the target RNA is expressed in the bone.
1098. The oligomeric compound of any of embodiments 1044-1064, wherein the target RNA is expressed in the bone marrow.
1099. The oligomeric compound of any of embodiments 1044-1064, wherein the target RNA is expressed in the intestine.
1100. The oligomeric compound of any of embodiments 1044-1064, wherein the target RNA is expressed in the adrenal glands.
1101. The oligomeric compound of any of embodiments 1044-1064, wherein the target RNA is expressed in the testes.
1102. The oligomeric compound of any of embodiments 1044-1064, wherein the target RNA is expressed in the ovaries.
1103. The oligomeric compound of any of embodiments 1044-1064, wherein the target RNA is expressed in the pancreas.
1104. The oligomeric compound of any of embodiments 1044-1064, wherein the target RNA is expressed in the pituitary gland.
1105. The oligomeric compound of any of embodiments 1044-1064, wherein the target RNA is expressed in the prostate gland.
1106. The oligomeric compound of any of embodiments 1044-1064, wherein the target RNA is expressed in the skin.
1107. The oligomeric compound of any of embodiments 1044-1064, wherein the target RNA is expressed in the epidermis.
1108. The oligomeric compound of any of embodiments 1044-1064, wherein the target RNA is expressed in the uterus.
1109. The oligomeric compound of any of embodiments 1044-1064, wherein the target RNA is expressed in the bladder.
1110. The oligomeric compound of any of embodiments 1044-1064, wherein the target RNA is expressed in the brain.
1111. The oligomeric compound of any of embodiments 1044-1064, wherein the target RNA is expressed in the glomerulus.
1112. The oligomeric compound of any of embodiments 1044-1064, wherein the target RNA is expressed in the distal tubular epithelium.
1113. The oligomeric compound of any of embodiments 1044-1064, wherein the target RNA is expressed in breast tissue.
1114. The oligomeric compound of any of embodiments 1044-1064, wherein the target RNA is expressed in the lung.

1115. The oligomeric compound of any of embodiments 1044-1064, wherein the target RNA is expressed in the heart.
1116. The oligomeric compound of any of embodiments 1044-1064, wherein the target RNA is expressed in the kidney.
1117. The oligomeric compound of any of embodiments 1044-1064, wherein the target RNA is expressed in the ganglion.
1118. The oligomeric compound of any of embodiments 1044-1064, wherein the target RNA is expressed in the frontal cortex.
1119. The oligomeric compound of any of embodiments 1044-1064, wherein the target RNA is expressed in the spinal cord.
1120. The oligomeric compound of any of embodiments 1044-1064, wherein the target RNA is expressed in the trigeminal ganglion.
1121. The oligomeric compound of any of embodiments 1044-1064, wherein the target RNA is expressed in the sciatic nerve.
1122. The oligomeric compound of any of embodiments 1044-1064, wherein the target RNA is expressed in the dorsal root ganglion.
1123. The oligomeric compound of any of embodiments 1044-1064, wherein the target RNA is expressed in the epidymal fat.
1124. The oligomeric compound of any of embodiments 1044-1064, wherein the target RNA is expressed in the diaphragm.
1125. The oligomeric compound of any of embodiments 1044-1064, wherein the target RNA is expressed in the colon.
1126. The oligomeric compound of any of embodiments 1044-1064, wherein the target RNA is a white fat cell target.
1127. The oligomeric compound of any of embodiments 1044-1064, wherein the target RNA is a brown fat cell target.
1128. The oligomeric compound of any of embodiments 1044-1064, wherein the target RNA is an adipocyte target.
1129. The oligomeric compound of any of embodiments 1044-1064, wherein the target RNA is a macrophage target.
1130. The oligomeric compound of any of embodiments 1044-1064, wherein the target RNA is a cancer cell target.
1131. The oligomeric compound of any of embodiments 1044-1064, wherein the target RNA is a tumor cell target.
1132. The oligomeric compound of any of embodiments 158-178, wherein the target RNA is a smooth muscle cell target.
1133. The oligomeric compound of any of embodiments 1044-1064, wherein the target RNA is a lymphocyte target.
1134. The oligomeric compound of any of embodiments 1044-1064, wherein the target RNA is a pulmonary cell target.
1135. The oligomeric compound of any of embodiments 1044-1064, wherein the target RNA is a heart muscle cell target.
1136. The oligomeric compound of any of embodiments 1044-1064, wherein the target RNA is a cardiomyocyte target.
1137. The oligomeric compound of any of embodiments 1044-1064, wherein the target RNA is a endothelial cell target.
1138. The oligomeric compound of any of embodiments 1044-1064, wherein the target RNA is a fibroblast target.
1139. The oligomeric compound of any of embodiments 1044-1064, wherein the target RNA is a glial cell target.
1140. The oligomeric compound of any of embodiments 1044-1064, wherein the target RNA is a Schwann cell target.
1141. The oligomeric compound of any of embodiments 1044-1064, wherein the target RNA is a pancreatic cell target.
1142. The oligomeric compound of any of embodiments 1044-1064, wherein the target RNA is a kidney cell target.
1143. The oligomeric compound of any of embodiments 1044-1064, wherein the target RNA is a beta cell target.
1144. The oligomeric compound of any of embodiments 1044-1064, wherein the target RNA is a non-parenchymal cell target.
1145. The oligomeric compound of any of embodiments 1044-1064, wherein the target RNA is a hepatocyte target.
1146. The oligomeric compound of any of embodiments 1044-1064, wherein the target RNA a oligodendrocyte target.
1147. The oligomeric compound of any of embodiments 1044-1064, wherein the target RNA is a astrocyte target.
1148. The oligomeric compound of any of embodiments 1044-1064, wherein the target RNA is a microglia target.
1149. The oligomeric compound of any of embodiments 1044-1064, wherein the target RNA is a ependymal cell target.
1150. The oligomeric compound of any of embodiments 1044-1064, wherein the target RNA is a sensory neuron target.
1151. The oligomeric compound of any of embodiments 1044-1064, wherein the target RNA is a motor neuron target.
1152. The oligomeric compound of any of embodiments 1044-1064, wherein the target RNA is a skeletal muscle target.
1153. The oligomeric compound of any of embodiments 1044-1064, wherein the target RNA is a cardiac muscle target.
1154. The oligomeric compound of any of embodiments 1044-1064, wherein the target RNA is a smooth muscle target.
1155. The oligomeric compound of any of embodiments 1044-1064, wherein the target RNA is a adipose tissue target.
1156. The oligomeric compound of any of embodiments 1044-1064, wherein the target RNA is a white adipose tissue target.
1157. The oligomeric compound of any of embodiments 1044-1064, wherein the target RNA is a spleen target.
1158. The oligomeric compound of any of embodiments 1044-1064, wherein the target RNA is a bone target.
1159. The oligomeric compound of any of embodiments 1044-1064, wherein the target RNA is a bone marrow target.
1160. The oligomeric compound of any of embodiments 1044-1064, wherein the target RNA is an intestinal target.
1161. The oligomeric compound of any of embodiments 1044-1064, wherein the target RNA is an adrenal gland target.
1162. The oligomeric compound of any of embodiments 1044-1064, wherein the target RNA is a testicular target.
1163. The oligomeric compound of any of embodiments 1044-1064, wherein the target RNA is an ovarian target.

1164. The oligomeric compound of any of embodiments 1044-1064, wherein the target RNA is a pancreatic target.
1165. The oligomeric compound of any of embodiments 1044-1064, wherein the target RNA is a pituitary gland target.
1166. The oligomeric compound of any of embodiments 1044-1064, wherein the target RNA is a prostate gland target.
1167. The oligomeric compound of any of embodiments 1044-1064, wherein the target RNA is a skin target.
1168. The oligomeric compound of any of embodiments 1044-1064, wherein the target RNA is an epidermal target.
1169. The oligomeric compound of any of embodiments 1044-1064, wherein the target RNA is a uterine target.
1170. The oligomeric compound of any of embodiments 1044-1064, wherein the target RNA is a bladder target.
1171. The oligomeric compound of any of embodiments 1044-1064, wherein the target RNA is a brain target.
1172. The oligomeric compound of any of embodiments 1044-1064, wherein the target RNA is a glomerulus target.
1173. The oligomeric compound of any of embodiments 1044-1064, wherein the target RNA is a distal tubular epithelium target.
1174. The oligomeric compound of any of embodiments 1044-1064, wherein the target RNA is a breast tissue target.
1175. The oligomeric compound of any of embodiments 1044-1064, wherein the target RNA is a lung target.
1176. The oligomeric compound of any of embodiments 1044-1064, wherein the target RNA is a heart target.
1177. The oligomeric compound of any of embodiments 1044-1064, wherein the target RNA is a kidney target.
1178. The oligomeric compound of any of embodiments 1044-1064, wherein the target RNA is a ganglion target.
1179. The oligomeric compound of any of embodiments 1044-1064, wherein the target RNA is a frontal cortex target.
1180. The oligomeric compound of any of embodiments 1044-1064, wherein the target RNA is a spinal cord target.
1181. The oligomeric compound of any of embodiments 1044-1064, wherein the target RNA is a trigeminal ganglion target.
1182. The oligomeric compound of any of embodiments 1044-1064, wherein the target RNA is a sciatic nerve target.
1183. The oligomeric compound of any of embodiments 1044-1064, wherein the target RNA is a dorsal root ganglion target.
1184. The oligomeric compound of any of embodiments 1044-1064, wherein the target RNA is a epidymal fat target.
1185. The oligomeric compound of any of embodiments 1044-1064, wherein the target RNA is a diaphragm target.
1186. The oligomeric compound of any of embodiments 1044-1064, wherein the target RNA is a colon target.
1187. The oligomeric compound of any of embodiments 1044-1186, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.
1188. The oligomeric compound of any of embodiments 1044-1186, wherein the target RNA is a HTT RNA.
1189. The oligomeric compound of embodiment 1187, wherein the target RNA is a MeCP2 RNA.
1190. The oligomeric compound of embodiment 1187, wherein the target RNA is a DUX4 RNA.
1191. The oligomeric compound of embodiment 1187, wherein the target RNA is a HDAC2 RNA.
1192. The oligomeric compound of embodiment 1187, wherein the target RNA is a Ataxin 1 RNA.
1193. The oligomeric compound of embodiment 1187, wherein the target RNA is a Ataxin 2 RNA.
1194. The oligomeric compound of embodiment 1187, wherein the target RNA is a Ataxin 3 RNA.
1195. The oligomeric compound of embodiment 1187, wherein the target RNA is a Ataxin 6 RNA.
1196. The oligomeric compound of embodiment 1187, wherein the target RNA is a Ataxin 7 RNA.
1197. The oligomeric compound of embodiment 1187, wherein the target RNA is a C9ORF72 RNA.
1198. The oligomeric compound of embodiment 1044-1186, wherein the target RNA is an alpha-synuclein RNA.
1199. The oligomeric compound of embodiment 1187, wherein the target RNA is an UBE3A RNA.
1200. The oligomeric compound of any of embodiments 1044-1186, wherein the target RNA is a SOD1 RNA.
1201. The oligomeric compound of embodiment 1187, wherein the target RNA is a Prion RNA.
1202. The oligomeric compound of embodiment 1187, wherein the target RNA is a PMP22 RNA.
1203. The oligomeric compound of any of embodiments 1044-1187, wherein the target RNA is a Tau RNA.
1204. The oligomeric compound of embodiment 1187, wherein the target RNA is a LRRK2 RNA.
1205. The oligomeric compound of embodiment 1187, wherein the target RNA is an APP RNA.
1206. The oligomeric compound of 1187, wherein the target RNA is a LINGO2 RNA.
1207. The oligomeric compound of any of embodiments 1187, wherein the target RNA is a GYS1 RNA.
1208. The oligomeric compound of any of embodiments 1187, wherein the target RNA is a KCNT1 RNA.
1209. The oligomeric compound of any of embodiments 1187, wherein the target RNA is a IRF8 RNA.
1210. The oligomeric compound of any of embodiments 1187, wherein the target RNA is a Progranulin RNA.
1211. The oligomeric compound of any of embodiments 1187, wherein the target RNA is a GFAP RNA.
1212. The oligomeric compound of any of embodiments 1044-1211, wherein modulation of the expression of the target RNA is associated with treating a disorder or condition.
1213. The oligomeric compound of any of embodiments 1212, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.
1214. The oligomeric compound of embodiment 1212, wherein the disorder or condition is Alzheimer's Disease.
1215. The oligomeric compound of embodiment 1212, wherein the disorder or condition is Amyotrophic Lateral Sclerosis.
1216. The oligomeric compound of embodiment 1212, wherein the disorder or condition is Parkinson's Disease.
1217. The oligomeric compound of embodiment 1212, wherein the disorder or condition is a Spinocerebellar ataxia.

1218. The oligomeric compound of embodiment 1212, wherein the disorder or condition is Angelman Syndrome.
1219. The oligomeric compound of embodiment 1212, wherein the disorder or condition is Alexander's Disease.
1220. The oligomeric compound of embodiment 1212, wherein the disorder or condition is Lafora Disease.
1221. The oligomeric compound of embodiment 1212, wherein the disorder or condition is Charcot-Marie Tooth Disease.
1222. The oligomeric compound of embodiment 1212, wherein the disorder or condition is Prion Disease.
1223. The oligomeric compound of embodiment 1212, wherein the disorder or condition is a dementia.
1224. The oligomeric compound of embodiment 1212, wherein the disorder or condition is neurodegeneration.
1225. The oligomeric compound of embodiment 1212, wherein the disorder or condition is MeCP2 Duplication Syndrome.
1226. The oligomeric compound of embodiment 1212, wherein the disorder or condition is encephalopathy.
1227. The oligomeric compound of embodiment 1212, wherein the disorder or condition is neuroinflammation.
1228. The oligomeric compound of embodiment 1212, wherein the disorder or condition is multiple sclerosis.
1229. The oligomeric compound of any of embodiments 887-1228, wherein the parent oligomeric compound of the oligomeric compound of any of embodiments 887-1228 is cytotoxic in vitro.
1230. The oligomeric compound of embodiment 1228, wherein the parent oligomeric compound is cytotoxic in a standard in vitro cytotoxicity assay.
1231. The oligomeric compound of any of embodiments 887-1229 wherein administration to a mouse of the parent oligomeric compound of the oligomeric compound of any of embodiments 887-1229 is hepatotoxic to the mouse.
1232. The oligomeric compound of embodiment 1230, wherein the administration of the parent oligomeric compound to the mouse is systemic administration.
1233. The oligomeric compound of embodiment 1230, wherein the systemic administration is subcutaneous administration.
1234. The oligomeric compound of any of embodiments 1230-1232, wherein the mouse is a CD-1 mouse.
1235. The oligomeric compound of any of embodiments 1230-1232, wherein the mouse is a C57BL/6 mouse.
1236. The oligomeric compound of any of embodiments 1230-1232, wherein the mouse is a BALB/c mouse.
1237. The oligomeric compound of any of embodiments 1230-1236, wherein the plasma ALT level in the mouse is higher than 500 units per liter following the administration of the parent oligomeric compound.
1238. The oligomeric compound of any of embodiments 1230-1237, wherein the plasma AST level in the mouse is higher than 500 units per liter following the administration of the parent oligomeric compound.
1239. The oligomeric compound of any of embodiments 1230-1238, wherein the plasma ALT level in the mouse is higher than 1000 units per liter following the administration of the parent oligomeric compound.
1240. The oligomeric compound of any of embodiments 1230-1239, wherein the plasma AST level in the mouse is higher than 1000 units per liter following the administration of the parent oligomeric compound.
1241. The oligomeric compound of any of embodiments 1230-1240, wherein the hepatotoxicity is measured 24-48 hours following the administration of the parent oligomeric compound.
1242. The oligomeric compound of any of embodiments 1230-1241, wherein the hepatotoxicity is measured 72 hours following the administration of the parent oligomeric compound.
1243. The oligomeric compound of any of embodiments 1230-1241, wherein the hepatotoxicity is measured 3 days following the administration of the parent oligomeric compound.
1244. The oligomeric compound of any of embodiments 1230-1241, wherein the hepatotoxicity is measured 5 days following the administration of the parent oligomeric compound.
1245. The oligomeric compound of any of embodiments 1230-1241, wherein the hepatotoxicity is measured 7 days following the administration of the parent oligomeric compound.
1246. The oligomeric compound of any of embodiments 1230-1241, wherein the hepatotoxicity is measured 10 days following the administration of the parent oligomeric compound.
1247. The oligomeric compound of any of embodiments 1230-1241, wherein the hepatotoxicity is measured 14 days following the administration of the parent oligomeric compound.
1248. The oligomeric compound of any of embodiments 1230-1241, wherein 1-10 mg/kg of the parent oligomeric compound is administered to the mouse.
1249. The oligomeric compound of any of embodiments 1230-1241, wherein 10-25 mg/kg of the parent oligomeric compound is administered to the mouse.
1250. The oligomeric compound of any of embodiments 1230-1241, wherein 25-50 mg/kg of the parent oligomeric compound is administered to the mouse.
1251. The oligomeric compound of any of embodiments 1230-1241, wherein 50-100 mg/kg of the parent oligomeric compound is administered to the mouse.
1252. The oligomeric compound of any of embodiments 1230-1241, wherein 100-150 mg/kg of the parent oligomeric compound is administered to the mouse.
1253. The oligomeric compound of any of embodiments 1230-1241, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.
1254. The oligomeric compound of any of embodiments 887-1253, wherein administration of 50 mg/kg of the oligomeric compound of any of embodiments 887-1253 to a mouse is not hepatotoxic to the mouse.
1255. The oligomeric compound of embodiment 1254, wherein plasma ALT level in the mouse is lower than 100 units per liter following the administration of the oligomeric compound of embodiment 1254.
1256. The oligomeric compound of embodiment 1254 or 1255, wherein plasma ALT level in the mouse is at least 10-fold lower than plasma ALT level in a mouse administered the parent oligomeric compound of the oligomeric compound of embodiment 1254 or 1255, wherein the administrations and plasma ALT measurements of both the oligomeric compound of embodiment 1254 or 1255 and the parent oligomeric compound are completed in the same way.
1257. The oligomeric compound of embodiment 1256, wherein the plasma ALT level in the mouse is at least 100-fold lower than the plasma ALT level in the mouse administered the parent oligomeric compound.

1258. The oligomeric compound of embodiment 1256, wherein the plasma ALT level in the mouse is at least 500-fold lower than the plasma ALT level in the mouse administered the parent oligomeric compound.

1259. The oligomeric compound of any of embodiments 1230-1258, wherein the therapeutic index in a mouse of the oligomeric compound of any of embodiments 1230-1258 is increased relative to the therapeutic index of the parent oligomeric compound.

1260. The oligomeric compound of embodiment 1259, wherein the therapeutic index in a mouse of the oligomeric compound of embodiment 1259 is at least two-fold greater than the therapeutic index of the parent oligomeric compound.

1261. The oligomeric compound of any of embodiments 887-1229, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;
and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

1262. The oligomeric compound of embodiment 1261, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

1263. The oligomeric compound of embodiment 1262, wherein the 2'-O-methyl modified sugar moiety is at position 2 of the central region.

1264. The oligomeric compound of embodiment 1261-1263, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

1265. The oligomeric compound of any of embodiments 1261-1264, wherein the nucleobase sequence of the otherwise identical oligomeric compound is 100% complementary to the target RNA.

1266. The oligomeric compound of any of embodiments 1261-1265, wherein the otherwise identical oligomeric compound is a parent oligomeric compound of the oligomeric compound of any of embodiments 1202-1206.

1267. The oligomeric compound of any of embodiments 1044-1266, wherein the oligomeric compound inhibits the target RNA with an $IC_{50}$ lower than 100 nM in a standard in vitro activity assay.

1268. The oligomeric compound of any of embodiments 1044-1266, wherein the parent oligomeric compound of the oligomeric compound of any of embodiments 1044-1266 inhibits the target RNA with an $IC_{50}$ lower than 100 nM in a standard in vitro activity assay.

1269. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 4-fold.

1270. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 3-fold.

1271. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 2-fold.

1272. The oligomeric compound of any of embodiments 1044-1271, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1273. The oligomeric compound of any of embodiments 1044-1272, wherein the nucleobase sequence of the parent oligomeric compound is 100% complementary to the target RNA.

1274. The oligomeric compound of any of embodiments 887-1273, wherein administration of 10-50 mg of the oligomeric compound to a human is not hepatotoxic to the human.

1275. The oligomeric compound of any of embodiments 887-1273, wherein administration of 50-100 mg of the oligomeric compound to a human is not hepatotoxic to the human.

1276. The oligomeric compound of any of embodiments 887-1273, wherein administration of 100-300 mg of the oligomeric compound to a human is not hepatotoxic to the human.

1277. The oligomeric compound of any of embodiments 1274-1276, wherein the administration is systemic administration.

1278. A composition comprising the oligomeric compound of any of embodiments 887-1277, and a second oligomeric compound, wherein the second oligomeric compound is complementary to the oligomeric compound of any of embodiments 887-1277.

1279. The composition of embodiment 1278, wherein the second oligomeric compound comprises at least 14 contiguous linked nucleosides that are at least 90% complementary to the oligomeric compound of any of embodiments 887-1277.

1280. The composition of embodiment 1278, wherein the second oligomeric compound comprises at least 14 contiguous linked nucleosides that are 100% complementary to the oligomeric compound of any of embodiments 887-1277.

1281. A pharmaceutical composition comprising the oligomeric compound of any of embodiments 887-1277 or the composition of any of embodiments 1278-1280, comprising a pharmaceutically acceptable carrier or diluent.

1282. A method comprising administering the oligomeric compound or composition of any of embodiments 887-1281 to a human subject.

1283. A method of treating a disease or disorder comprising administering the oligomeric compound or composition of any of embodiments 887-1281 to a human subject.

1284. A method of modulating the amount or activity of a target RNA in a human subject comprising administering the oligomeric compound or composition of any of embodiments 887-1281 to the human subject; and thereby modulating the amount or activity of the target RNA in the human subject.

1285. A method of treating a disease or disorder in a human subject comprising administering the oligomeric compound or composition of any of embodiments 887-1281 to the human subject having the disease or disorder; and thereby treating the disease or disorder in the human subject.

1286. The method of embodiment 1284 or 1285, wherein the disease or disorder is a liver disease, and wherein the oligomeric compound modulates the amount or activity of a liver target RNA.

1287. The method of embodiment 1284 or 1285, wherein the disease or disorder is a central nervous system disease, and wherein the oligomeric compound modulates the amount or activity of a central nervous system target RNA.

1288. The method of any of embodiments 1284-1287, wherein the disease or disorder is a cancer, a neurodegenerative disease, a cardiovascular disease, an immunological disease, a hereditary disease, a repeat expansion disease, a muscle-wasting disease, or a metabolic disease.

1289. The method of embodiment 1284 or 1285, wherein the oligomeric compound modulates the amount or activity of a white fat cell target.

1290. The method of embodiment 1284 or 1285, wherein the oligomeric compound modulates the amount or activity of a brown fat cell target.

1291. The method of embodiment 1284 or 1285, wherein the oligomeric compound modulates the amount or activity of an adipocyte target.

1292. The method of embodiment 1284 or 1285, wherein the oligomeric compound modulates the amount or activity of a macrophage target.

1293. The method of embodiment 1284 or 1285, wherein the oligomeric compound modulates the amount or activity of a cancer cell target.

1294. The method of embodiment 1284 or 1285, wherein the oligomeric compound modulates the amount or activity of a tumor cell target.

1295. The method of embodiment 1284 or 1285, wherein the oligomeric compound modulates the amount or activity of a smooth muscle cell target.

1296. The method of embodiment 1284 or 1285, wherein the oligomeric compound modulates the amount or activity of a lymphocyte target.

1297. The method of embodiment 1284 or 1285, wherein the oligomeric compound modulates the amount or activity of a pulmonary cell target.

1298. The method of embodiment 1284 or 1285, wherein the oligomeric compound modulates the amount or activity of a heart muscle cell target.

1299. The method of embodiment 1284 or 1285, wherein the oligomeric compound modulates the amount or activity of a cardiomyocyte target.

1300. The method of embodiment 1284 or 1285, wherein the oligomeric compound modulates the amount or activity of a endothelial cell target.

1301. The method of embodiment 1284 or 1285, wherein the oligomeric compound modulates the amount or activity of a fibroblast target.

1302. The method of embodiment 1284 or 1285, wherein the oligomeric compound modulates the amount or activity of a glial cell target.

1303. The method of embodiment 1284 or 1285, wherein the oligomeric compound modulates the amount or activity of a Schwann cell target.

1304. The method of embodiment 1284 or 1285, wherein the oligomeric compound modulates the amount or activity of a pancreatic cell target.

1305. The method of embodiment 1284 or 1285, wherein the oligomeric compound modulates the amount or activity of a kidney cell target.

1306. The method of embodiment 1284 or 1285, wherein the oligomeric compound modulates the amount or activity of a beta cell target.

1307. The method of embodiment 1284 or 1285, wherein the oligomeric compound modulates the amount or activity of a non-parenchymal cell target.

1308. The method of embodiment 1284 or 1285, wherein the oligomeric compound modulates the amount or activity of a hepatocyte target.

1309. The method of embodiment 1284 or 1285, wherein the oligomeric compound modulates the amount or activity of a oligodendrocyte target.

1310. The method of embodiment 1284 or 1285, wherein the oligomeric compound modulates the amount or activity of a astrocyte target.

1311. The method of embodiment 1284 or 1285, wherein the oligomeric compound modulates the amount or activity of a microglia target.

1312. The method of embodiment 1284 or 1285, wherein the oligomeric compound modulates the amount or activity of a ependymal cell target.

1313. The method of embodiment 1284 or 1285, wherein the oligomeric compound modulates the amount or activity of a sensory neuron target.

1314. The method of embodiment 1284 or 1285, wherein the oligomeric compound modulates the amount or activity of a motor neuron target.

1315. The method of embodiment 1284 or 1285, wherein the oligomeric compound modulates the amount or activity of a skeletal muscle target.

1316. The method of embodiment 1284 or 1285, wherein the oligomeric compound modulates the amount or activity of a cardiac muscle target.

1317. The method of embodiment 1284 or 1285, wherein the oligomeric compound modulates the amount or activity of a smooth muscle target.

1318. The method of embodiment 1284 or 1285, wherein the oligomeric compound modulates the amount or activity of a adipose tissue target.

1319. The method of embodiment 1284 or 1285, wherein the oligomeric compound modulates the amount or activity of a white adipose tissue target.

1320. The method of embodiment 1284 or 1285, wherein the oligomeric compound modulates the amount or activity of a spleen target.

1321. The method of embodiment 1284 or 1285, wherein the oligomeric compound modulates the amount or activity of a bone target.

1322. The method of embodiment 1284 or 1285, wherein the oligomeric compound modulates the amount or activity of a bone marrow target.

1323. The method of embodiment 1284 or 1285, wherein the oligomeric compound modulates the amount or activity of an intestinal target.

1324. The method of embodiment 1284 or 1285, wherein the oligomeric compound modulates the amount or activity of an adrenal gland target.

1325. The method of embodiment 1284 or 1285, wherein the oligomeric compound modulates the amount or activity of a testicular target.
1326. The method of embodiment 1284 or 1285, wherein the oligomeric compound modulates the amount or activity of an ovarian target.
1327. The method of embodiment 1284 or 1285, wherein the oligomeric compound modulates the amount or activity of a pancreatic target.
1328. The method of embodiment 1284 or 1285, wherein the oligomeric compound modulates the amount or activity of a pituitary gland target.
1329. The method of embodiment 1284 or 1285, wherein the oligomeric compound modulates the amount or activity of a prostate gland target.
1330. The method of embodiment 1284 or 1285, wherein the oligomeric compound modulates the amount or activity of a skin target.
1331. The method of embodiment 1284 or 1285, wherein the oligomeric compound modulates the amount or activity of an epidermal target.
1332. The method of embodiment 1284 or 1285, wherein the oligomeric compound modulates the amount or activity of a uterine target.
1333. The method of embodiment 1284 or 1285, wherein the oligomeric compound modulates the amount or activity of a bladder target.
1334. The method of embodiment 1284 or 1285, wherein the oligomeric compound modulates the amount or activity of a brain target.
1335. The method of embodiment 1284 or 1285, wherein the oligomeric compound modulates the amount or activity of a glomerulus target.
1336. The method of embodiment 1284 or 1285, wherein the oligomeric compound modulates the amount or activity of a distal tubular epithelium target.
1337. The method of embodiment 1284 or 1285, wherein the oligomeric compound modulates the amount or activity of a breast tissue target.
1338. The method of embodiment 1284 or 1285, wherein the oligomeric compound modulates the amount or activity of a lung target.
1339. The method of embodiment 1284 or 1285, wherein the oligomeric compound modulates the amount or activity of a heart target.
1340. The method of embodiment 1284 or 1285, wherein the oligomeric compound modulates the amount or activity of a kidney target.
1341. The method of embodiment 1284 or 1285, wherein the oligomeric compound modulates the amount or activity of a ganglion target.
1342. The method of embodiment 1284 or 1285, wherein the oligomeric compound modulates the amount or activity of a frontal cortex target.
1343. The method of embodiment 1284 or 1285, wherein the oligomeric compound modulates the amount or activity of a spinal cord target.
1344. The method of embodiment 1284 or 1285, wherein the oligomeric compound modulates the amount or activity of a trigeminal ganglion target.
1345. The method of embodiment 1284 or 1285, wherein the oligomeric compound modulates the amount or activity of a sciatic nerve target.
1346. The method of embodiment 1284 or 1285, wherein the oligomeric compound modulates the amount or activity of a dorsal root ganglion target.
1347. The method of embodiment 1284 or 1285, wherein the oligomeric compound modulates the amount or activity of a epidymal fat target.
1348. The method of embodiment 1284 or 1285, wherein the oligomeric compound modulates the amount or activity of a diaphragm target.
1349. The method of embodiment 1284 or 1285, wherein the oligomeric compound modulates the amount or activity of a colon target.
1350. The method of any of embodiments 1282-1349, wherein the plasma ALT level of the human subject after the administration is not more than three times higher than it was prior to the administration.
1351. The method of any of embodiments 1282-1350, wherein the plasma ALT level of the human subject after the administration is not more than 150 units per liter.
1352. The method of any of embodiments 1282-1351, wherein the human subject is susceptible to liver damage.
1353. The method of any of embodiments 1282-1352, wherein the human subject is susceptible to liver degeneration.
1354. The method of any of embodiments 1282-1353, wherein the human subject is susceptible to elevated apoptosis in the liver.
1355. The method of any of embodiments 1282-1354, wherein the human subject has a liver disease.
1356. The method of any of embodiments 1282-1355, wherein the human subject has kidney disease.
1357. The method of any of embodiments 1282-1356, wherein the human subject is susceptible to kidney damage.
1358. The method of any of embodiments 1282-1357, wherein the human subject has heart disease.
1359. The method of any of embodiments 1282-1358, wherein the human subject is susceptible to heart damage.
1360. The method of any of embodiments 1282-1359, wherein the human subject has pancreatitis.
1361. The method of any of embodiments 1282-1360, wherein the human subject is susceptible to pancreatic damage.
1362. The method of any of embodiments 1282-1361, wherein the human subject has a neurological disease.
1363. The method of any of embodiments 1282-1362, wherein the human subject is susceptible to neurological damage.
1364. The method of any of embodiments 1282-1363, comprising administering the parent oligomeric compound of the oligomeric compound of any of embodiments 887-1281 to a mouse.
1365. The method of any of embodiments 1282-1363, comprising contacting a cell with the parent oligomeric compound of the oligomeric compound of any of embodiments 887-1281.
1366. The method of embodiment 1364 or 1365, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.
1367. A method of designing an oligomeric compound comprising starting with a parent oligomeric compound and changing the design of that compound in order to arrive at an oligomeric compound of any one of embodiments 887-1281.
1368. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 887-1281.
1369. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 887-1281.
1370. The method of embodiment 1368 or 1369, wherein the method designs an oligomeric compound with improved therapeutic index relative to the parent oligomeric compound.
1371. The method of embodiment 1368 or 1369, wherein the method designs an oligomeric compound with lower hepatotoxicity relative to the parent oligomeric compound.
1372. The method of embodiment 1368, wherein the second oligomeric compound has an improved therapeutic index relative to the parent oligomeric compound.
1373. The method of embodiment 1368 or 1369, wherein the second oligomeric compound has reduced hepatotoxicity in a mouse relative to the parent oligomeric compound.
1374. The method of embodiment 1368, wherein the oligomeric compound according to any one of embodiments 887-1281 has reduced hepatotoxicity relative to the parent oligomeric compound.
1375. A method comprising administering an oligomeric compound of any of embodiments 887-1281 to a mouse and separately administering the parent oligomeric compound of the oligomeric compound of any of embodiments 887-1281 to a second mouse, wherein the therapeutic index of the oligomeric compound of any of embodiments 887-1281 is improved relative to the therapeutic index of the parent oligomeric compound.
1376. The method of any of embodiments 1282-1375, wherein the level of p21 RNA is measured in the mouse, the cell, and/or the human subject.
1377. A method comprising administering an oligomeric compound of any of embodiments 887-1281 to a subject and measuring the level of p21 RNA in the subject.
1378. The method of embodiment 1377, wherein the subject is a mouse.
1379. The method of embodiment 1377, wherein the subject is a human.
1380. The method of any of embodiments 1377-1379, wherein the p21 RNA level is measured within 24 hours of the administration.
1381. The method of any of embodiments 1377-1380, wherein the p21 RNA level is measured 24-48 hours following the administration.
1382. An oligomeric compound or composition of any one of embodiments 887-1281, for use in medical therapy.
1383. The oligomeric compound of any of embodiments 887-1281, wherein the oligomeric compound is not toxic.
1384. The oligomeric compound of any of embodiment 887-1281, wherein a comparator compound is toxic; wherein the comparator compound is identical to the oligomeric compound except that each nucleoside of the central region of the comparator compound is a nucleoside comprising 2'-β-D-deoxyribosyl sugar moiety.
1385. The oligomeric compound of embodiment 1384, wherein administering a dose of the oligomeric compound to an animal results in a circulating ALT level that is at least 3-fold lower than the ALT level that results from administering the same dose of the comparator compound to an animal for at least one matched dose.
1386. The oligomeric compound of embodiment 1384 or 1385, wherein the lowest dose of the oligomeric compound that raises circulating ALT to over 300 units per liter is at least three-fold higher than the lowest dose of the comparator compound that raises circulating ALT to over 300 units per liter.
1387. The oligomeric compound of any of embodiments 1384-1386, wherein the oligomeric compound is capable of reducing the target RNA in a cell.
1388. The oligomeric compound of embodiment 1387, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.
1389. The oligomeric compound of embodiment 1388 having RNA-reducing activity that is no more than 2-fold worse than the RNA-reducing activity of the comparator compound.
1390. A method of modulating the amount or activity of a target RNA in a human subject comprising administering the oligomeric compound or composition of any of embodiments 887-1281 to the human subject; and thereby modulating the amount or activity of the target RNA in the human subject.
1391. A method of treating a disease or disorder in a human subject comprising administering the oligomeric compound or composition of any of embodiments 887-1281 to the human subject having the disease or disorder; and thereby treating the disease or disorder in the human subject.
1392. The method of embodiment 1390 or 1391, wherein the disease or disorder is a liver disease, and wherein the oligomeric compound modulates the amount or activity of a liver target RNA.
1393. The method of embodiment 1390 or 1391, wherein the disease or disorder is a central nervous system disease, and wherein the oligomeric compound modulates the amount or activity of a central nervous system target RNA.
1394. The method of any of embodiments 1390-1393, wherein the disease or disorder is a cancer, a neurodegenerative disease, a cardiovascular disease, an immunological disease, a hereditary disease, a repeat expansion disease, a muscle-wasting disease, or a metabolic disease.
1395. The method of any of embodiments 1390-1394, wherein the plasma ALT level of the human subject after the administration is not more than three times higher than it was prior to the administration.
1396. The method of any of embodiments 1390-1395, wherein the plasma ALT level of the human subject after the administration is not more than 150 units per liter.
1397. A method of treating a disease or disorder in a human subject comprising administering the oligomeric compound or composition of any of embodiments 887-1281 to the human subject having the disease or disorder; and thereby treating the disease or disorder in the human subject.
1398. The method of embodiment 1397, wherein the disease or disorder is not a CNS disease or disorder.
1399. The method of embodiment 1397, wherein the disease or disorder is a disease or disorder of the white fat cells.
1400. The method of embodiment 1397, wherein the disease or disorder is a disease or disorder of the brown fat cells.
1401. The method of embodiment 1397, wherein the disease or disorder is a disease or disorder of the adipocytes.

1402. The method of embodiment 1397, wherein the disease or disorder is a disease or disorder of the macrophages.
1403. The method of embodiment 1397, wherein the disease or disorder is a disease or disorder of the cancer cells.
1404. The method of embodiment 1397, wherein the disease or disorder is a disease or disorder of the tumor cells.
1405. The method of embodiment 1397, wherein the disease or disorder is a disease or disorder of the smooth muscle cells.
1406. The method of embodiment 1397, wherein the disease or disorder is a disease or disorder of the lymphocytes.
1407. The method of embodiment 1397, wherein the disease or disorder is a disease or disorder of the pulmonary cells.
1408. The method of embodiment 1397, wherein the disease or disorder is a disease or disorder of the heart muscle cells.
1409. The method of embodiment 1397, wherein the disease or disorder is a disease or disorder of the cardiomyocytes.
1410. The method of embodiment 1397, wherein the disease or disorder is a disease or disorder of the endothelial cells.
1411. The method of embodiment 1397, wherein the disease or disorder is a disease or disorder of the fibroblasts.
1412. The method of embodiment 1397, wherein the disease or disorder is a disease or disorder of the glial cells.
1413. The method of embodiment 1397, wherein the disease or disorder is a disease or disorder of the Schwann cells.
1414. The method of embodiment 1397, wherein the disease or disorder is a disease or disorder of the pancreatic cells.
1415. The method of embodiment 1397, wherein the disease or disorder is a disease or disorder of the kidney cells.
1416. The method of embodiment 1397, wherein the disease or disorder is a disease or disorder of the beta cells.
1417. The method of embodiment 1397, wherein the disease or disorder is a disease or disorder of the non-parenchymal cells.
1418. The method of embodiment 1397, wherein the disease or disorder is a disease or disorder of the hepatocytes.
1419. The method of embodiment 1397, wherein the disease or disorder is a disease or disorder of the oligodendrocytes.
1420. The method of embodiment 1397, wherein the disease or disorder is a disease or disorder of the astrocytes.
1421. The method of embodiment 1397, wherein the disease or disorder is a disease or disorder of the microglia.
1422. The method of embodiment 1397, wherein the disease or disorder is a disease or disorder of the ependymal cells.
1423. The method of embodiment 1397, wherein the disease or disorder is a disease or disorder of the sensory neurons.
1424. The method of embodiment 1397, wherein the disease or disorder is a disease or disorder of the motor neurons.
1425. The method of embodiment 1397, wherein the disease or disorder is a disease or disorder of the skeletal muscle.
1426. The method of embodiment 1397, wherein the disease or disorder is a disease or disorder of the cardiac muscle.
1427. The method of embodiment 1397, wherein the disease or disorder is a disease or disorder of the smooth muscle.
1428. The method of embodiment 1397, wherein the disease or disorder is a disease or disorder of the adipose tissue.
1429. The method of embodiment 1397, wherein the disease or disorder is a disease or disorder of the white adipose tissue.
1430. The method of embodiment 1397, wherein the disease or disorder is a disease or disorder of the spleen.
1431. The method of embodiment 1397, wherein the disease or disorder is a disease or disorder of the bone.
1432. The method of embodiment 1397, wherein the disease or disorder is a disease or disorder of the bone marrow.
1433. The method of embodiment 1397, wherein the disease or disorder is a disease or disorder of the intestine.
1434. The method of embodiment 1397, wherein the disease or disorder is a disease or disorder of the adrenal glands.
1435. The method of embodiment 1397, wherein the disease or disorder is a disease or disorder of the testes.
1436. The method of embodiment 1397, wherein the disease or disorder is a disease or disorder of the ovaries.
1437. The method of embodiment 1397, wherein the disease or disorder is a disease or disorder of the pancreas.
1438. The method of embodiment 1397, wherein the disease or disorder is a disease or disorder of the pituitary gland.
1439. The method of embodiment 1397, wherein the disease or disorder is a disease or disorder of the prostate gland.
1440. The method of embodiment 1397, wherein the disease or disorder is a disease or disorder of the skin.
1441. The method of embodiment 1397, wherein the disease or disorder is a disease or disorder of the epidermis.
1442. The method of embodiment 1397, wherein the disease or disorder is a disease or disorder of the uterus.
1443. The method of embodiment 1397, wherein the disease or disorder is a disease or disorder of the bladder.
1444. The method of embodiment 1397, wherein the disease or disorder is a disease or disorder of the brain.
1445. The method of embodiment 1397, wherein the disease or disorder is a disease or disorder of the glomerulus.
1446. The method of embodiment 1397, wherein the disease or disorder is a disease or disorder of the distal tubular epithelium.
1447. The method of embodiment 1397, wherein the disease or disorder is a disease or disorder of the breast tissue.
1448. The method of embodiment 1397, wherein the disease or disorder is a disease or disorder of the lung.
1449. The method of embodiment 1397, wherein the disease or disorder is a disease or disorder of the heart.
1450. The method of embodiment 1397, wherein the disease or disorder is a disease or disorder of the kidney.
1451. The method of embodiment 1397, wherein the disease or disorder is a disease or disorder of the ganglion.
1452. The method of embodiment 1397, wherein the disease or disorder is a disease or disorder of the frontal cortex.
1453. The method of embodiment 1397, wherein the disease or disorder is a disease or disorder of the spinal cord.
1454. The method of embodiment 1397, wherein the disease or disorder is a disease or disorder of the trigeminal ganglion.
1455. The method of embodiment 1397, wherein the disease or disorder is a disease or disorder of the sciatic nerve.
1456. The method of embodiment 1397, wherein the disease or disorder is a disease or disorder of the dorsal root ganglion.
1457. The method of embodiment 1397, wherein the disease or disorder is a disease or disorder of the epidymal fat.
1458. The method of embodiment 1397, wherein the disease or disorder is a disease or disorder of the diaphragm.
1459. The method of embodiment 1397, wherein the disease or disorder is a disease or disorder of the colon.
1460. A method of screening a library of oligomeric compounds for activity against a target RNA, wherein the library of oligomeric compounds comprises a plurality of oligomeric compounds of any of embodiments 887-1281.
1461. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:

the 5'-region consists of 1-5 linked nucleosides, wherein at least one nucleoside of the 5'-region is a modified nucleoside comprising a modified sugar;

the 3'-region consists of 1-5 linked nucleosides wherein at least one nucleoside of the 3'-region is a modified nucleoside comprising a modified sugar; and the central region consists of 7-11 linked nucleosides, wherein the 5'-most portion of the central region has the following formula:

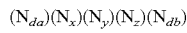

$(N_{da})(N_x)(N_y)(N_z)(N_{db})$ wherein one of $N_x$, $N_y$, and $N_z$, is a safety-enhancing nucleoside;

the other two of $N_x$, $N_y$, and $N_z$ are independently selected from an unmodified 2'-β-D-deoxyribosyl sugar moiety, a DNA isomer, a modified DNA isomer, and a DNA mimic; and $N_{da}$ and $N_{db}$ are each independently selected from an unmodified 2'-β-D-deoxyribosyl sugar moiety, a DNA isomer, a modified DNA isomer, and a DNA mimic.

1462. The oligomeric compound of embodiment 1461, wherein the 5'-region consists of one nucleoside.

1463. The oligomeric compound of embodiment 1461, wherein the 5'-region consists of 2-5 linked nucleosides.

1464. The oligomeric compound of embodiment 1461, wherein the 5'-region consists of 2-4 linked nucleosides.

1465. The oligomeric compound of embodiment 1461, wherein the 5'-region consists of 2 linked nucleosides.

1466. The oligomeric compound of embodiment 1461, wherein the 5'-region consists of 3 linked nucleosides.

1467. The oligomeric compound of embodiment 1461, wherein the 5'-region consists of 4 linked nucleosides.

1468. The oligomeric compound of embodiment 1461, wherein the 5'-region consists of 5 linked nucleosides.

1469. The oligomeric compound of any of embodiments 1461-1468, wherein each nucleoside of the 5'-region is a modified nucleoside.

1470. The oligomeric compound of any of embodiments 1461-1469, wherein each nucleoside of the 5'-region is a modified nucleoside comprising a modified sugar.

1471. The oligomeric compound of any of embodiments 1461-1470, wherein each modified nucleoside of the 5'-region has the same modification.

1472. The oligomeric compound of and of embodiments 1461-1470, wherein at least two nucleosides of the 5'-region are modified nucleosides having different modifications.

1473. The oligomeric compound of any of embodiments 1461-1472, wherein each nucleoside of the 5'-region comprises a 2'-modified ribosyl sugar moiety.

1474. The oligomeric compound of any of embodiments 1461-1473, wherein at least one nucleoside of the 5'-region comprises a bicyclic furanosyl sugar moiety.

1475. The oligomeric compound of any of embodiments 1461-1474, wherein each nucleoside of the 5'-region comprises a bicyclic furanosyl sugar moiety.

1476. The oligomeric compound of any of embodiments 1461-1474, wherein at least one nucleoside of the 5'-region comprises a non-bicyclic sugar moiety.

1477. The oligomeric compound of embodiment 1476, wherein the non-bicyclic sugar moiety of the at least one nucleoside of the 5'-region is a 2'-substituted ribosyl sugar moiety.

1478. The oligomeric compound of any of embodiments 1461-1474 or 1476-1477, wherein each nucleoside of the 5'-region comprises a non-bicyclic sugar moiety.

1479. The oligomeric compound of embodiment 1478, wherein each nucleoside of the 5'-region comprises a 2'-substituted furanosyl sugar moiety.

1480. The oligomeric compound of any of embodiments 1461-1474 or 1476-1477, wherein each nucleoside of the 5'-region comprises a 2'-modified furanosyl sugar moiety independently selected from a bicyclic sugar moiety and a non-bicyclic 2'-substituted ribosyl sugar moiety.

1481. The oligomeric compound of any of embodiments 1461-1477 or 1480, wherein each nucleoside of the 5'-region comprises a bicyclic sugar moiety.

1482. The oligomeric compound of any of embodiments 1461-1474 or 1476-1480, wherein each nucleoside of the 5'-region comprises a non-bicyclic 2'-substituted ribosyl sugar moiety.

1483. The oligomeric compound of any of embodiments 1461-1477 or 1480-1481, wherein each bicyclic sugar moiety of the 5'-region is selected from among cEt, LNA, and ENA.

1484. The oligomeric compound of any of embodiments 1461-1477 or 1480-1481, wherein each bicyclic sugar moiety of the 5'-region is a cEt sugar moiety.

1485. The oligomeric compound of any of embodiments 1461-1477 or 1480-1481, wherein each bicyclic sugar moiety of the 5'-region is an LNA sugar moiety.

1486. The oligomeric compound of any of embodiments 1461-1474, 1476-1480, or 1482-1485, wherein each non-bicyclic sugar moiety of the 5'-region has a 2'-substituent selected from among 2'-MOE, 2'-OMe, and 2'-NMA.

1487. The oligomeric compound of any of embodiments 1461-1486, wherein none of the nucleosides of the 5'-region comprise a sugar moiety having a 2'-F substituent.

1488. The oligomeric compound of any of embodiments 1461-1487, wherein none of the nucleosides of the 5'-region comprise a sugar moiety having a 2'-MOE substituent.

1489. The oligomeric compound of any of embodiments 1461-1488, wherein none of the nucleosides of the 5'-region comprise a sugar moiety having a 2'-OMe substituent.

1490. The oligomeric compound of any of embodiments 1461-1489, wherein none of the nucleosides of the 5'-region comprise a cEt sugar moiety.

1491. The oligomeric compound of any of embodiments 1461-1490, wherein none of the nucleosides of the 5'-region comprise a LNA sugar moiety.

1492. The oligomeric compound of any of embodiments 1461-1491, wherein each nucleobase of the 5'-region is independently selected from among thymine, uracil, guanine, cytosine, 5-methylcytosine, and adenine.

1493. The oligomeric compound of any of embodiments 1461-1492, wherein each internucleoside linkage of the 5'-region is independently selected from among phosphodiester and phosphorothioate internucleoside linkages.

1494. The oligomeric compound of any of embodiments 1461-1493, wherein the 3'-region consists of one nucleoside.

1495. The oligomeric compound of any of embodiments 1461-1493, wherein the 3'-region consists of 2-5 linked nucleosides.

1496. The oligomeric compound of any of embodiments 1461-1493, wherein the 3'-region consists of 2-4 linked nucleosides.

1497. The oligomeric compound of any of embodiments 1461-1493, wherein the 3'-region consists of 2 linked nucleosides.
1498. The oligomeric compound of any of embodiments 1461-1493, wherein the 3'-region consists of 3 linked nucleosides.
1499. The oligomeric compound of any of embodiments 1461-1493, wherein the 3'-region consists of 4 linked nucleosides.
1500. The oligomeric compound of any of embodiments 1461-1493, wherein the 3'-region consists of 5 linked nucleosides.
1501. The oligomeric compound of any of embodiments 1461-1500, wherein each nucleoside of the 3'-region is a modified nucleoside.
1502. The oligomeric compound of any of embodiments 1461-1501, wherein each nucleoside of the 3'-region is a modified nucleoside comprising a modified sugar moiety.
1503. The oligomeric compound of any of embodiments 1461-1502, wherein each modified nucleoside of the 3'-region has the same modification.
1504. The oligomeric compound of and of embodiments 1461-1502, wherein at least two nucleosides of the 3'-region are modified nucleosides having different modifications.
1505. The oligomeric compound of any of embodiments 1461-1504, wherein each nucleoside of the 3'-region comprises a 2'-modified ribosyl sugar moiety.
1506. The oligomeric compound of any of embodiments 1461-1505, wherein at least one nucleoside of the 3'-region comprises a bicyclic furanosyl sugar moiety.
1507. The oligomeric compound of any of embodiments 1461-1506, wherein each nucleoside of the 3'-region comprises a bicyclic furanosyl sugar moiety.
1508. The oligomeric compound of any of embodiments 1461-1506, wherein at least one nucleoside of the 3'-region comprises a non-bicyclic sugar moiety.
1509. The oligomeric compound of embodiment 1508, wherein the non-bicyclic sugar moiety of the at least one nucleoside of the 3'-region is a 2'-substituted ribosyl sugar moiety.
1510. The oligomeric compound of any of embodiments 1461-1509, wherein each nucleoside of the 3'-region comprises a non-bicyclic sugar moiety.
1511. The oligomeric compound of embodiment 1510, wherein each nucleoside of the 3'-region comprises a 2'-substituted furanosyl sugar moiety.
1512. The oligomeric compound of any of embodiments 1461-1511, wherein each nucleoside of the 3'-region comprises a 2'-modified furanosyl sugar moiety independently selected from a bicyclic sugar moiety and a non-bicyclic 2'-substituted ribosyl sugar moiety.
1513. The oligomeric compound of any of embodiments 1461-1512, wherein each nucleoside of the 3'-region comprises a bicyclic sugar moiety.
1514. The oligomeric compound of any of embodiments 1461-1512, wherein each nucleoside of the 3'-region comprises a non-bicyclic 2'-substituted ribosyl sugar moiety.
1515. The oligomeric compound of any of embodiments 1461-1509 or 1512-1513, wherein each bicyclic sugar moiety of the 3'-region is selected from among cEt, LNA, and ENA.
1516. The oligomeric compound of any of embodiments 1461-1509, 1512-1513, or 1515, wherein each bicyclic sugar moiety of the 3'-region is a cEt sugar moiety.
1517. The oligomeric compound of any of embodiments 1461-1509, 1512-1513, or 1515, wherein each bicyclic sugar moiety of the 3'-region is an LNA sugar moiety.
1518. The oligomeric compound of any of embodiments 1461-1506, 1508-1512 or 1514, wherein each non-bicyclic sugar moiety of the 3'-region has a 2'-substituent selected from among 2'-MOE, 2'-OMe, and 2'-NMA.
1519. The oligomeric compound of any of embodiments 1461-1518, wherein none of the nucleosides of the 3'-region comprise a sugar moiety having a 2'-F substituent.
1520. The oligomeric compound of any of embodiments 1461-1519, wherein none of the nucleosides of the 3'-region comprise a sugar moiety having a 2'-MOE substituent.
1521. The oligomeric compound of any of embodiments 1461-1520, wherein none of the nucleosides of the 3'-region comprise a sugar moiety having a 2'-OMe substituent.
1522. The oligomeric compound of any of embodiments 1461-1521, wherein none of the nucleosides of the 3'-region comprise a cEt sugar moiety.
1523. The oligomeric compound of any of embodiments 1461-1522, wherein none of the nucleosides of the 3'-region comprise a LNA sugar moiety.
1524. The oligomeric compound of any of embodiments 1461-1523, wherein each nucleobase of the 3'-region is independently selected from among thymine, uracil, guanine, cytosine, 5-methylcytosine, and adenine.
1525. The oligomeric compound of any of embodiments 1461-1524, wherein each internucleoside linkage of the 3'-region is independently selected from among phosphodiester and phosphorothioate internucleoside linkages.
1526. The oligomeric compound of any of embodiments 1461-1525, wherein the modified nucleosides of the 5'-region have the same modifications as the modifications of the modified nucleosides of the 3'-region.
1527. The oligomeric compound of any of embodiments 1461-1525, wherein at least one modified nucleoside of the 5'-region and one modified nucleoside of the 3'-region comprise modifications that differ from one another.
1528. The oligomeric compound of any of embodiments 1461-1474, 1476-1477, 1480, 1483-1506, 1508-1509, 1512, 1515-1527, wherein the 5'-region and the 3'-region together include at least one non-bicyclic 2'-substituted modified nucleoside and at least one bicyclic nucleoside.
1529. The oligomeric compound of any of embodiment 1528, where the bicyclic nucleoside is a cEt nucleoside.
1530. The oligomeric compound of embodiment 1528, where the bicyclic nucleoside is an LNA nucleoside.
1531. The oligomeric compound of any of embodiments 1528-1530, wherein the non-bicyclic 2'-modified nucleoside is a 2'-MOE nucleoside.
1532. The oligomeric compound of any of embodiments 1528-1530, wherein the non-bicyclic 2'-modified nucleoside is a 2'-OMe nucleoside.
1533. The oligomeric compound of any of embodiments 1528-1532, wherein at least one nucleoside of the 5'-region or the 3'-region is an unmodified 2'-β-D-deoxyribosyl sugar moiety.
1534. The oligomeric compound of any of embodiments 1461-1533, wherein the central region has the formula:

$$(N_{da})(N_x)(N_y)(N_z)(N_{db})(N_{db})_q$$

wherein each $N_{dc}$ is independently selected from an unmodified 2'-β-D-deoxyribosyl sugar moiety, a DNA isomer, a modified DNA isomer, and a DNA mimic; and q is 2-6.

1535. The oligomeric compound of any of embodiments 1461-1534, wherein the central region consists of 7 linked nucleosides.
1536. The oligomeric compound of any of embodiments 1461-1534, wherein the central region consists of 8 linked nucleosides.
1537. The oligomeric compound of any of embodiments 1461-1534, wherein the central region consists of 9 linked nucleosides.
1538. The oligomeric compound of any of embodiments 1461-1534, wherein the central region consists of 10 linked nucleosides.
1539. The oligomeric compound of any of embodiments 1461-1534, wherein the central region consists of 11 linked nucleosides.
1540. The oligomeric compound of any of embodiments 1461-1539, wherein Nx is the safety-enhancing nucleoside.
1541. The oligomeric compound of any of embodiments 1461-1539, wherein Ny is the safety-enhancing nucleoside.
1542. The oligomeric compound of any of embodiments 1461-1539, wherein Nz is the safety-enhancing nucleoside.
1543. The oligomeric compound of any of embodiments 1461-1542, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.
1544. The oligomeric compound of any of embodiments 1461-1543, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.
1545. The oligomeric compound of any of embodiments 1461-1544, wherein the safety enhancing nucleoside comprises a sugar surrogate selected from a morpholino, a modified morpholino, a modified cyclohexenyl, or a modified tetrahydropyran.
1546. The oligomeric compound of any of embodiments 1461-1544, wherein the safety enhancing nucleoside comprises a sugar surrogate selected from a morpholino, a modified morpholino, 2'-fluoroarabinose, 2'-fluororibose, CeNA, F-CeNA, HNA, OMe-HNA or F-HNA.
1547. The oligomeric compound of any of embodiments 1461-1544, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-O-L-deoxyxylosyl.
1548. The oligomeric compound of any of embodiments 1461-1544 or 1547, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.
1549. The oligomeric compound of any of embodiments 1461-1544, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.
1550. The oligomeric compound of any of embodiments 1461-1544 or 1549, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.
1551. The oligomeric compound of any of embodiments 1461-1544 or 1549-1550, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.
1552. The oligomeric compound of any of embodiments 1461-1544 or 1549-1551, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.
1553. The oligomeric compound of any of embodiments 1461-1544, wherein the safety enhancing nucleoside is a modified nucleoside comprising a bicyclic furanosyl sugar moiety.
1554. The oligomeric compound of any of embodiments 1461-1544, wherein the safety enhancing nucleoside is selected from among cEt, LNA, α-L-LNA, and ENA.
1555. The oligomeric compound of any of embodiments 1461-1544, wherein the safety enhancing nucleoside comprises a 2'-substituted furanosyl sugar moiety.
1556. The oligomeric compound of embodiment 1555, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.
1557. The oligomeric compound of embodiment 1555, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.
1558. The oligomeric compound of embodiment 1555, wherein the 2'-substituted furanosyl sugar moiety of the safety enhancing nucleoside has a 2' substituent selected from: fluoro, OMe, MOE, NMA.

1559. The oligomeric compound of any of embodiments 1461-1558, wherein the safety enhancing nucleoside comprises a 2'-substituted furanosyl sugar moiety comprising a 2'-OMe or 2'-MOE.

1560. The oligomeric compound of any of embodiments 1461-1559, wherein the safety enhancing nucleoside comprises a 2'-substituted furanosyl sugar moiety comprising a 2'-OMe.

1561. The oligomeric compound of any of embodiments 1461-1560, wherein the safety enhancing nucleoside comprises a 2'-OMe modified 2'-β-D-deoxyribosyl sugar moiety.

1562. The oligomeric compound of any of embodiments 1461-1544, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

1563. The oligomeric compound of any of embodiments 1461-1544 or embodiment 1562, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

1564. The oligomeric compound of any of embodiments 1461-1544 or 1562-1563, wherein the safety enhancing nucleoside comprises a 3'-methyl furanosyl sugar moiety.

1565. The oligomeric compound of any of embodiments 1461-1544, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

1566. The oligomeric compound of any of embodiments 1461-1544 or 1565, wherein the safety enhancing nucleoside comprises a 4'-modified furanosyl sugar moiety having a 4'-methyl.

1567. The oligomeric compound of any of embodiments 1461-1544, wherein the safety enhancing nucleoside has the structure shown below, wherein R represents an optional 2' substituent group and Bx is a heterocyclic base moiety:

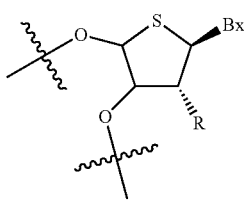

1568. The oligomeric compound of embodiment 1567, wherein in R is selected from among H, OH, OMe, F, or MOE.

1569. The oligomeric compound of any of embodiments 1461-1544, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—N($R_m$)($R_n$), where each $R_m$ and $R_n$ is, independently, H, an amino protecting group, or substituted or unsubstituted $C_1$-$C_{10}$ alkyl.

1570. The oligomeric compound of any of embodiments 1461-1544 or 1569, wherein the safety enhancing nucleoside comprises a 5'-modified furanosyl sugar moiety with a 5' substituent selected from: 5'-methyl, 5'-ethyl or a 5'-allyl.

1571. The oligomeric compound of any of embodiments 1461-1544 or 1569-1570, wherein the safety enhancing nucleoside comprises a 5'-modified furanosyl sugar moiety with a 5' substituent selected from: 5'-(R)-methyl- or 5'-(R)-ethyl.

1572. The oligomeric compound of any of embodiments 1461-1544 or 1569-1571, wherein the safety enhancing nucleoside comprises a 5'-(R)-methyl-2'-β-D-deoxyribosyl sugar moiety.

1573. The oligomeric compound of any of embodiments 1461-154 or 1569-1572, wherein the safety enhancing nucleoside comprises a 5'-(R)-ethyl-2'-β-D-deoxyribosyl sugar moiety.

1574. The oligomeric compound of any of embodiments 1461-1573, wherein the safety enhancing nucleoside does not comprise a 2'-F modified sugar moiety.

1575. The oligomeric compound of any of embodiments 1461-1574, wherein the safety enhancing nucleoside does not comprise a cEt modified sugar moiety.

1576. The oligomeric compound of any of embodiments 1461-1575, wherein the safety enhancing nucleoside does not comprise a 2'-MOE modified sugar moiety.

1577. The oligomeric compound of any of embodiments 1461-1576, wherein the safety enhancing nucleoside comprises a hypoxanthine nucleobase.

1578. The oligomeric compound of any of embodiments 1461-1577, wherein the safety enhancing nucleoside comprises a nucleobase selected from among thymine, uracil, guanine, cytosine, 5-methylcytosine, and adenine.

1579. The oligomeric compound of any of embodiments 1461-1578, wherein the safety enhancing nucleoside is a modified nucleoside other than cEt, MOE, LNA, or FANA.

1580. The oligomeric compound of any of embodiments 1461-1579, wherein each Nd is independently selected from among an unmodified 2'-β-D-deoxyribosyl sugar moiety, a DNA isomer, a 2'-modified DNA isomer, and a DNA mimic.

1581. The oligomeric compound of embodiment 1580, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1582. The oligomeric compound of embodiment 1581, wherein each DNA isomer comprises a sugar moiety selected from among 2'-β-D-deoxyxylosyl, 2'-α-L-deoxyribosyl, and 2'-β-L-deoxyribosyl.

1583. The oligomeric compound of embodiment 1580, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—C$_1$-C$_{10}$ alkoxy substituent.

1584. The oligomeric compound of embodiment 1583, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1585. The oligomeric compound of embodiment 1584, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1586. The oligomeric compound of embodiment 1585, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1587. The oligomeric compound of embodiment 1580, wherein each DNA mimic comprises a structure represented by one of the formulas below:

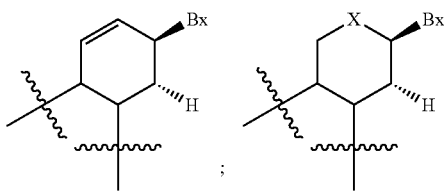

wherein X is O or S and Bx represents a heterocylic base moiety.

1588. The oligomeric compound of embodiment 1580, wherein each DNA mimic comprises a structure represented by one of the formulas below:

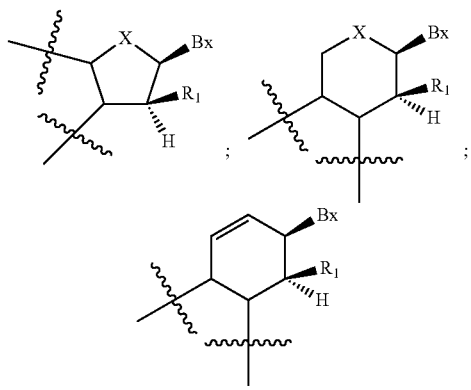

wherein X is O or S;
Bx represents a heterocyclic base moiety; and
R$_1$ is selected from among H, OH, halo, allyl, amino, azido, SH, CN, OCN, CF$_3$, OCF$_3$, O—C$_1$-C$_{10}$ alkoxy, O—C$_1$-C$_{10}$ substituted alkoxy, C$_1$-C$_{10}$ alkyl, C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl;
wherein if the DNA mimic comprises the structure:

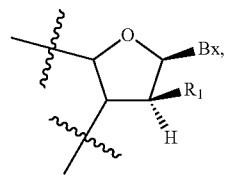

R$_1$ is other than H.

1589. The oligomeric compound of embodiment 1588, wherein R$_1$ is H, OH, OMe, or F.

1590. The oligomeric compound of embodiment 1588, wherein R$_1$ is not F.

1591. The oligomeric compound of embodiment 1580, wherein each DNA mimic comprises a structure represented by the formula below:

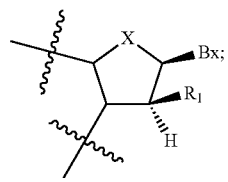

wherein X is S, Bx represents a heterocyclic base moiety, and R$_1$ is H.

1592. The oligomeric compound of embodiment 1580, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1593. The oligomeric compound of embodiment 1580, wherein the DNA mimic comprises a 2'-fluoro-β-D-arabinofuranosyl sugar moiety.

1594. The oligomeric compound of embodiment 1580, wherein the DNA mimic does not comprise a 2'-fluoro-β-D-arabinofuranosyl sugar moiety.

1595. The oligomeric compound of any of embodiments 1461-1594, wherein each N$_d$ is an unmodified 2'-β-D-deoxyribosyl sugar moiety.

1596. The oligomeric compound of any of embodiments 1461-1595, wherein the central region comprises no more than four nucleosides selected from among DNA isomers, modified DNA isomers, and DNA mimics.

1597. The oligomeric compound of any of embodiments 1461-1595, wherein the central region comprises no more than three nucleosides selected from among DNA isomers, modified DNA isomers, and DNA mimics.

1598. The oligomeric compound of any of embodiments 1461-1595, wherein the central region comprises no more than two nucleosides selected from among DNA isomers, modified DNA isomers, and DNA mimics.

1599. The oligomeric compound of any of embodiments 1461-1595, wherein the central region comprises no more than one nucleoside selected from among DNA isomers, modified DNA isomers, and DNA mimics.

1600. The oligomeric compound of any of embodiments 1461-1599, wherein the central region contains exactly one safety enhancing nucleoside and the remainder of nucleosides in the central region are unmodified 2'-β-D-deoxyribosyl sugar moieties.

1601. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a neutral internucleoside linkage.

1602. The oligomeric compound of embodiment 1601, wherein the neutral linkage is a phosphonate internucleoside linkage.

1603. The oligomeric compound of embodiment 1601, wherein the neutral linkage is a methoxypropyl internucleoside linkage.

1604. The oligomeric compound of embodiment 1601, wherein each remaining internucleoside linkage is a phosphodiester or phosphorothioate internucleoside linkage.

1605. The oligomeric compound of any of embodiments 1461-1600, wherein at least one internucleoside linkage of the central region is a 2'-5' internucleoside linkage.

1606. The oligomeric compound of any of embodiments 1461-1600, wherein exactly one internucleoside linkage of the central region is a 2'-5' internucleoside linkage.

1607. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a 2'-5' internucleoside linkage.

1608. A chirally enriched population of modified oligonucleotides of any of embodiments 1461-1607, wherein the central region has at least one particular phorphorothioate internucleoside linkage having a particular stereochemical configuration.

1609. The chirally enriched population of embodiment 1608, wherein the central region has at least one phorphorothioate internucleoside linkage having the (Sp) configuration.

1610. The chirally enriched population of embodiment 1608, wherein central region has at least one phorphorothioate internucleoside linkage having the (Rp) configuration.

1611. The chirally enriched population of embodiment 1608, wherein the central region has a particular, independently selected stereochemical configuration at each phosphorothioate internucleoside linkage.

1612. The chirally enriched population of embodiment 1608, wherein the each phosphorothioate internucleoside linkage of the central region has the (Sp) configuration.

1613. The chirally enriched population of embodiment 1608, wherein the central region has one phosphorothioate internucleoside linkage having the (Rp) configuration and wherein each remaining central region phosphorothioate internucleoside linkage has the (Sp) configuration.

1614. The chirally enriched population of embodiment 1608, wherein the central region has an (Rp) phosphorothioate internucleoside linkage adjacent to an (Sp) phosphorothioate internucleoside linkage.

1615. The chirally enriched population of embodiment 1608, wherein the central region has an (Rp) phosphorothioate internucleoside linkage adjacent to a second (Rp) phosphorothioate internucleoside linkage.

1616. The chirally enriched population of embodiment 1608, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

1617. The chirally enriched population of any of embodiments 1609, 1610, 1614, or 1615 wherein each phosphorothioate internucleoside linkage that does not have the (Rp) or (Sp) configuration is stereorandom.

1618. The oligomeric compound of any of embodiments 1461-1617 comprising a conjugate group.

1619. The oligomeric compound of embodiment 1618, wherein the conjugate group comprises a linking group attaching the remainder of the conjugate group to the modified oligonucleotide, wherein the linking group comprises 1-5 nucleosides.

1620. The oligomeric compound of any of embodiments 1461-1618, wherein the oligomeric compound does not comprise additional nucleosides beyond those of the modified oligonucleotide.

1621. The oligomeric compound of any of embodiments 1461-1620, wherein the nucleobase sequence of the modified oligonucleotide is complementary to a target RNA.

1622. The oligomeric compound of embodiment 1621, wherein the nucleobase sequence of the modified oligonucleotide is at least 85% complementary to the target RNA.

1623. The oligomeric compound of embodiment 1621, wherein the nucleobase sequence of the modified oligonucleotide is at least 90% complementary to the target RNA.

1624. The oligomeric compound of embodiment 1621, wherein the nucleobase sequence of the modified oligonucleotide is at least 95% complementary to the target RNA.

1625. The oligomeric compound of embodiment 1621, wherein the nucleobase sequence of the modified oligonucleotide is 100% complementary to the target RNA.

1626. The oligomeric compound of any of embodiments 1621-1625, wherein the target RNA is a target mRNA or a target pre-mRNA.

1627. The oligomeric compound of embodiment 1626, wherein the target mRNA or target pre-mRNA is not a mouse, rat, monkey, or human PTEN RNA.

1628. The oligomeric compound of embodiment 1626 or 1627, wherein the target mRNA or target pre-mRNA is not a mouse, rat, monkey, or human SRB-1 RNA.

1629. The oligomeric compound of any of embodiments 1626-1628, wherein the target mRNA or target pre-mRNA is not a mouse, rat, monkey, or human MYD88 RNA.

1630. The oligomeric compound of any of embodiments 1626-1629, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

1631. The oligomeric compound of any of embodiments 1621-1630, wherein the target RNA is a human RNA.

1632. The oligomeric compound of any of embodiments 1621-1631, wherein the target RNA is expressed in the liver.

1633. The oligomeric compound of any of embodiments 1621-1632, wherein the target RNA is a liver target.

1634. The oligomeric compound of any of embodiments 1621-1631, wherein the target RNA is not expressed in the liver.

1635. The oligomeric compound of any of embodiments 1621-1631 or 1634, wherein the target RNA is not a liver target.

1636. The oligomeric compound of any of embodiments 1621-1635, wherein modulation of the expression of the target RNA in the liver is associated with treating a disorder or condition.

1637. The oligomeric compound of embodiment 1636, wherein the disorder or condition is a liver disorder or condition.

1638. The oligomeric compound of any of embodiments 1621-1637, wherein the target RNA is expressed in the central nervous system.

1639. The oligomeric compound of any of embodiments 1621-1637, wherein the target RNA is not expressed in the central nervous system.

1640. The oligomeric compound of any of embodiments 1621-1638, wherein the target RNA is a central nervous system target.

1641. The oligomeric compound of any of embodiments 1621-1639, wherein the target RNA is not a central nervous system target.

1642. The oligomeric compound of any of embodiments 1621-1641, wherein the target RNA is expressed in white fat cells.

1643. The oligomeric compound of any of embodiments 1621-1641, wherein the target RNA is expressed in brown fat cells.

1644. The oligomeric compound of any of embodiments 1621-1641, wherein the target RNA is expressed in adipocytes.

1645. The oligomeric compound of any of embodiments 1621-1641, wherein the target RNA is expressed in macrophages.

1646. The oligomeric compound of any of embodiments 1621-1641, wherein the target RNA is expressed in cancer cells.

1647. The oligomeric compound of any of embodiments 1621-1641, wherein the target RNA is expressed in tumor cells.

1648. The oligomeric compound of any of embodiments 1621-1641, wherein the target RNA is expressed in smooth muscle cells.

1649. The oligomeric compound of any of embodiments 1621-1641, wherein the target RNA is expressed in lymphocytes.

1650. The oligomeric compound of any of embodiments 1621-1641, wherein the target RNA is expressed in pulmonary cells.

1651. The oligomeric compound of any of embodiments 1621-1641, wherein the target RNA is expressed in heart muscle cells.

1652. The oligomeric compound of any of embodiments 1621-1641, wherein the target RNA is expressed in cardiomyocytes.

1653. The oligomeric compound of any of embodiments 1621-1641, wherein the target RNA is expressed in endothelial cells.

1654. The oligomeric compound of any of embodiments 1621-1641, wherein the target RNA is expressed in fibroblasts.

1655. The oligomeric compound of any of embodiments 1621-1641, wherein the target RNA is expressed in glial cells.

1656. The oligomeric compound of any of embodiments 1621-1641, wherein the target RNA is expressed in Schwann cells.

1657. The oligomeric compound of any of embodiments 1621-1641, wherein the target RNA is expressed in pancreatic cells.

1658. The oligomeric compound of any of embodiments 1621-1641, wherein the target RNA is expressed in kidney cells.

1659. The oligomeric compound of any of embodiments 1621-1641, wherein the target RNA is expressed in beta cells.

1660. The oligomeric compound of any of embodiments 1621-1641, wherein the target RNA is expressed in non-parenchymal cells.

1661. The oligomeric compound of any of embodiments 1621-1641, wherein the target RNA is expressed in hepatocytes.

1662. The oligomeric compound of any of embodiments 1621-1641, wherein the target RNA is expressed in oligodendrocytes.

1663. The oligomeric compound of any of embodiments 1621-1641, wherein the target RNA is expressed in astrocytes.

1664. The oligomeric compound of any of embodiments 1621-1641, wherein the target RNA is expressed in microglia.

1665. The oligomeric compound of any of embodiments 1621-1641, wherein the target RNA is expressed in ependymal cells.

1666. The oligomeric compound of any of embodiments 1621-1641, wherein the target RNA is expressed in sensory neurons.

1667. The oligomeric compound of any of embodiments 1621-1641, wherein the target RNA is expressed in motor neurons.

1668. The oligomeric compound of any of embodiments 1621-1641, wherein the target RNA is expressed in skeletal muscle.

1669. The oligomeric compound of any of embodiments 1621-1641, wherein the target RNA is expressed in cardiac muscle.

1670. The oligomeric compound of any of embodiments 1621-1641, wherein the target RNA is expressed in smooth muscle.

1671. The oligomeric compound of any of embodiments 1621-1641, wherein the target RNA is expressed in adipose tissue.

1672. The oligomeric compound of any of embodiments 1621-1641, wherein the target RNA is expressed in white adipose tissue.

1673. The oligomeric compound of any of embodiments 1621-1641, wherein the target RNA is expressed in the spleen.

1674. The oligomeric compound of any of embodiments 1621-1641, wherein the target RNA is expressed in the bone.

1675. The oligomeric compound of any of embodiments 1621-1641, wherein the target RNA is expressed in the bone marrow.

1676. The oligomeric compound of any of embodiments 1621-1641, wherein the target RNA is expressed in the intestine.

1677. The oligomeric compound of any of embodiments 1621-1641, wherein the target RNA is expressed in the adrenal glands.

1678. The oligomeric compound of any of embodiments 1621-1641, wherein the target RNA is expressed in the testes.

1679. The oligomeric compound of any of embodiments 1621-1641, wherein the target RNA is expressed in the ovaries.

1680. The oligomeric compound of any of embodiments 1621-1641, wherein the target RNA is expressed in the pancreas.
1681. The oligomeric compound of any of embodiments 1621-1641, wherein the target RNA is expressed in the pituitary gland.
1682. The oligomeric compound of any of embodiments 1621-1641, wherein the target RNA is expressed in the prostate gland.
1683. The oligomeric compound of any of embodiments 1621-1641, wherein the target RNA is expressed in the skin.
1684. The oligomeric compound of any of embodiments 1621-1641, wherein the target RNA is expressed in the epidermis.
1685. The oligomeric compound of any of embodiments 1621-1641, wherein the target RNA is expressed in the uterus.
1686. The oligomeric compound of any of embodiments 1621-1641, wherein the target RNA is expressed in the bladder.
1687. The oligomeric compound of any of embodiments 1621-1641, wherein the target RNA is expressed in the brain.
1688. The oligomeric compound of any of embodiments 1621-1641, wherein the target RNA is expressed in the glomerulus.
1689. The oligomeric compound of any of embodiments 1621-1641, wherein the target RNA is expressed in the distal tubular epithelium.
1690. The oligomeric compound of any of embodiments 1621-1641, wherein the target RNA is expressed in breast tissue.
1691. The oligomeric compound of any of embodiments 1621-1641, wherein the target RNA is expressed in the lung.
1692. The oligomeric compound of any of embodiments 1621-1641, wherein the target RNA is expressed in the heart.
1693. The oligomeric compound of any of embodiments 1621-1641, wherein the target RNA is expressed in the kidney.
1694. The oligomeric compound of any of embodiments 1621-1641, wherein the target RNA is expressed in the ganglion.
1695. The oligomeric compound of any of embodiments 1621-1641, wherein the target RNA is expressed in the frontal cortex.
1696. The oligomeric compound of any of embodiments 1621-1641, wherein the target RNA is expressed in the spinal cord.
1697. The oligomeric compound of any of embodiments 1621-1641, wherein the target RNA is expressed in the trigeminal ganglion.
1698. The oligomeric compound of any of embodiments 1621-1641, wherein the target RNA is expressed in the sciatic nerve.
1699. The oligomeric compound of any of embodiments 1621-1641, wherein the target RNA is expressed in the dorsal root ganglion.
1700. The oligomeric compound of any of embodiments 1621-1641, wherein the target RNA is expressed in the epidymal fat.
1701. The oligomeric compound of any of embodiments 1621-1641, wherein the target RNA is expressed in the diaphragm.
1702. The oligomeric compound of any of embodiments 1621-1641, wherein the target RNA is expressed in the colon.
1703. The oligomeric compound of any of embodiments 1621-1641, wherein the target RNA is a white fat cell target.
1704. The oligomeric compound of any of embodiments 1621-1641, wherein the target RNA is a brown fat cell target.
1705. The oligomeric compound of any of embodiments 1621-1641, wherein the target RNA is an adipocyte target.
1706. The oligomeric compound of any of embodiments 1621-1641, wherein the target RNA is a macrophage target.
1707. The oligomeric compound of any of embodiments 1621-1641, wherein the target RNA is a cancer cell target.
1708. The oligomeric compound of any of embodiments 1621-1641, wherein the target RNA is a tumor cell target.
1709. The oligomeric compound of any of embodiments 1621-1641, wherein the target RNA is a smooth muscle cell target.
1710. The oligomeric compound of any of embodiments 1621-1641, wherein the target RNA is a lymphocyte target.
1711. The oligomeric compound of any of embodiments 1621-1641, wherein the target RNA is a pulmonary cell target.
1712. The oligomeric compound of any of embodiments 1621-1641, wherein the target RNA is a heart muscle cell target.
1713. The oligomeric compound of any of embodiments 1621-1641, wherein the target RNA is a cardiomyocyte target.
1714. The oligomeric compound of any of embodiments 1621-1641, wherein the target RNA is a endothelial cell target.
1715. The oligomeric compound of any of embodiments 1621-1641, wherein the target RNA is a fibroblast target.
1716. The oligomeric compound of any of embodiments 1621-1641, wherein the target RNA is a glial cell target.
1717. The oligomeric compound of any of embodiments 1621-1641, wherein the target RNA is a Schwann cell target.
1718. The oligomeric compound of any of embodiments 1621-1641, wherein the target RNA is a pancreatic cell target.
1719. The oligomeric compound of any of embodiments 1621-1641, wherein the target RNA is a kidney cell target.
1720. The oligomeric compound of any of embodiments 1621-1641, wherein the target RNA is a beta cell target.
1721. The oligomeric compound of any of embodiments 1621-1641, wherein the target RNA is a non-parenchymal cell target.
1722. The oligomeric compound of any of embodiments 1621-1641, wherein the target RNA is a hepatocyte target.
1723. The oligomeric compound of any of embodiments 1621-1641, wherein the target RNA a oligodendrocyte target.
1724. The oligomeric compound of any of embodiments 1621-1641, wherein the target RNA is a astrocyte target.
1725. The oligomeric compound of any of embodiments 1621-1641, wherein the target RNA is a microglia target.
1726. The oligomeric compound of any of embodiments 1621-1641, wherein the target RNA is a ependymal cell target.

1727. The oligomeric compound of any of embodiments 1621-1641, wherein the target RNA is a sensory neuron target.
1728. The oligomeric compound of any of embodiments 1621-1641, wherein the target RNA is a motor neuron target.
1729. The oligomeric compound of any of embodiments 1621-1641, wherein the target RNA is a skeletal muscle target.
1730. The oligomeric compound of any of embodiments 1621-1641, wherein the target RNA is a cardiac muscle target.
1731. The oligomeric compound of any of embodiments 1621-1641, wherein the target RNA is a smooth muscle target.
1732. The oligomeric compound of any of embodiments 1621-1641, wherein the target RNA is a adipose tissue target.
1733. The oligomeric compound of any of embodiments 1621-1641, wherein the target RNA is a white adipose tissue target.
1734. The oligomeric compound of any of embodiments 1621-1641, wherein the target RNA is a spleen target.
1735. The oligomeric compound of any of embodiments 1621-1641, wherein the target RNA is a bone target.
1736. The oligomeric compound of any of embodiments 1621-1641, wherein the target RNA is a bone marrow target.
1737. The oligomeric compound of any of embodiments 1621-1641, wherein the target RNA is an intestinal target.
1738. The oligomeric compound of any of embodiments 1621-1641, wherein the target RNA is an adrenal gland target.
1739. The oligomeric compound of any of embodiments 1621-1641, wherein the target RNA is a testicular target.
1740. The oligomeric compound of any of embodiments 1621-1641, wherein the target RNA is an ovarian target.
1741. The oligomeric compound of any of embodiments 1621-1641, wherein the target RNA is a pancreatic target.
1742. The oligomeric compound of any of embodiments 1621-1641, wherein the target RNA is a pituitary gland target.
1743. The oligomeric compound of any of embodiments 1621-1641, wherein the target RNA is a prostate gland target.
1744. The oligomeric compound of any of embodiments 1621-1641, wherein the target RNA is a skin target.
1745. The oligomeric compound of any of embodiments 1621-1641, wherein the target RNA is an epidermal target.
1746. The oligomeric compound of any of embodiments 1621-1641, wherein the target RNA is a uterine target.
1747. The oligomeric compound of any of embodiments 1621-1641, wherein the target RNA is a bladder target.
1748. The oligomeric compound of any of embodiments 1621-1641, wherein the target RNA is a brain target.
1749. The oligomeric compound of any of embodiments 1621-1641, wherein the target RNA is a glomerulus target.
1750. The oligomeric compound of any of embodiments 1621-1641, wherein the target RNA is a distal tubular epithelium target.
1751. The oligomeric compound of any of embodiments 1621-1641, wherein the target RNA is a breast tissue target.
1752. The oligomeric compound of any of embodiments 1621-1641, wherein the target RNA is a lung target.
1753. The oligomeric compound of any of embodiments 1621-1641, wherein the target RNA is a heart target.
1754. The oligomeric compound of any of embodiments 1621-1641, wherein the target RNA is a kidney target.
1755. The oligomeric compound of any of embodiments 1621-1641, wherein the target RNA is a ganglion target.
1756. The oligomeric compound of any of embodiments 1621-1641, wherein the target RNA is a frontal cortex target.
1757. The oligomeric compound of any of embodiments 1621-1641, wherein the target RNA is a spinal cord target.
1758. The oligomeric compound of any of embodiments 1621-1641, wherein the target RNA is a trigeminal ganglion target.
1759. The oligomeric compound of any of embodiments 1621-1641, wherein the target RNA is a sciatic nerve target.
1760. The oligomeric compound of any of embodiments 1621-1641, wherein the target RNA is a dorsal root ganglion target.
1761. The oligomeric compound of any of embodiments 1621-1641, wherein the target RNA is a epidymal fat target.
1762. The oligomeric compound of any of embodiments 1621-1641, wherein the target RNA is a diaphragm target.
1763. The oligomeric compound of any of embodiments 1621-1641, wherein the target RNA is a colon target.
1764. The oligomeric compound of any of embodiments 1621-1763, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.
1765. The oligomeric compound of any of embodiments 1621-1763, wherein the target RNA is a HTT RNA.
1766. The oligomeric compound of embodiment 1764, wherein the target RNA is a MeCP2 RNA.
1767. The oligomeric compound of embodiment 1764, wherein the target RNA is a DUX4 RNA.
1768. The oligomeric compound of embodiment 1764, wherein the target RNA is a HDAC2 RNA.
1769. The oligomeric compound of embodiment 1764, wherein the target RNA is a Ataxin 1 RNA.
1770. The oligomeric compound of embodiment 1764, wherein the target RNA is a Ataxin 2 RNA.
1771. The oligomeric compound of embodiment 1764, wherein the target RNA is a Ataxin 3 RNA.
1772. The oligomeric compound of embodiment 1764, wherein the target RNA is a Ataxin 6 RNA.
1773. The oligomeric compound of embodiment 1764, wherein the target RNA is a Ataxin 7 RNA.
1774. The oligomeric compound of embodiment 1764, wherein the target RNA is a C9ORF72 RNA.
1775. The oligomeric compound of embodiment 1621-1763, wherein the target RNA is an alpha-synuclein RNA.
1776. The oligomeric compound of embodiment 1764, wherein the target RNA is an UBE3A RNA.
1777. The oligomeric compound of any of embodiments 1621-1763, wherein the target RNA is a SOD1 RNA.
1778. The oligomeric compound of embodiment 1764, wherein the target RNA is a Prion RNA.
1779. The oligomeric compound of embodiment 1764, wherein the target RNA is a PMP22 RNA.
1780. The oligomeric compound of any of embodiments 1621-1764, wherein the target RNA is a Tau RNA.
1781. The oligomeric compound of embodiment 1764, wherein the target RNA is a LRRK2 RNA.

1782. The oligomeric compound of embodiment 1764, wherein the target RNA is an APP RNA.
1783. The oligomeric compound of 1764, wherein the target RNA is a LINGO2 RNA.
1784. The oligomeric compound of any of embodiments 1764, wherein the target RNA is a GYS1 RNA.
1785. The oligomeric compound of any of embodiments 1764, wherein the target RNA is a KCNT1 RNA.
1786. The oligomeric compound of any of embodiments 1764, wherein the target RNA is a IRF8 RNA.
1787. The oligomeric compound of any of embodiments 1764, wherein the target RNA is a Progranulin RNA.
1788. The oligomeric compound of any of embodiments 1764, wherein the target RNA is a GFAP RNA.
1789. The oligomeric compound of any of embodiments 1621-1788, wherein modulation of the expression of the target RNA is associated with treating a disorder or condition.
1790. The oligomeric compound of embodiment 1789, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.
1791. The oligomeric compound of embodiment 1790, wherein the disorder or condition is Alzheimer's Disease.
1792. The oligomeric compound of embodiment 1790, wherein the disorder or condition is Amyotrophic Lateral Sclerosis.
1793. The oligomeric compound of embodiment 1790, wherein the disorder or condition is Parkinson's Disease.
1794. The oligomeric compound of embodiment 1790 wherein the disorder or condition is a Spinocerebellar ataxia.
1795. The oligomeric compound of embodiment 1790 wherein the disorder or condition is Angelman Syndrome.
1796. The oligomeric compound of embodiment 1790, wherein the disorder or condition is Alexander's Disease.
1797. The oligomeric compound of embodiment 1790, wherein the disorder or condition is Lafora Disease.
1798. The oligomeric compound of embodiment 1790, wherein the disorder or condition is Charcot-Marie Tooth Disease.
1799. The oligomeric compound of embodiment 1790, wherein the disorder or condition is Prion Disease.
1800. The oligomeric compound of embodiment 1790, wherein the disorder or condition is a dementia.
1801. The oligomeric compound of embodiment 1790, wherein the disorder or condition is neurodegeneration.
1802. The oligomeric compound of embodiment 1790, wherein the disorder or condition is MeCP2 Duplication Syndrome.
1803. The oligomeric compound of embodiment 1790, wherein the disorder or condition is encephalopathy.
1804. The oligomeric compound of embodiment 1790, wherein the disorder or condition is neuroinflammation.
1805. The oligomeric compound of embodiment 1790, wherein the disorder or condition is multiple sclerosis.
1806. The oligomeric compound of any of embodiments 1461-1805, wherein the parent oligomeric compound of the oligomeric compound of any of embodiments 1461-1805 is cytotoxic in vitro.
1807. The oligomeric compound of embodiment 1806, wherein the parent oligomeric compound is cytotoxic in a standard in vitro cytotoxicity assay.
1808. The oligomeric compound of any of embodiments 1461-1805 wherein administration to a mouse of the parent oligomeric compound of the oligomeric compound of any of embodiments 1461-1805 is hepatotoxic to the mouse.
1809. The oligomeric compound of embodiment 1808, wherein the administration of the parent oligomeric compound to the mouse is systemic administration.
1810. The oligomeric compound of embodiment 1809, wherein the systemic administration is subcutaneous administration.
1811. The oligomeric compound of any of embodiments 1808-1810, wherein the mouse is a CD-1 mouse.
1812. The oligomeric compound of any of embodiments 1808-1810, wherein the mouse is a C57BL/6 mouse.
1813. The oligomeric compound of any of embodiments 1808-1810, wherein the mouse is a BALB/c mouse.
1814. The oligomeric compound of any of embodiments 1807-1813, wherein the plasma ALT level in the mouse is higher than 500 units per liter following the administration of the parent oligomeric compound.
1815. The oligomeric compound of any of embodiments 1807-1814, wherein the plasma AST level in the mouse is higher than 500 units per liter following the administration of the parent oligomeric compound.
1816. The oligomeric compound of any of embodiments 1807-1815, wherein the plasma ALT level in the mouse is higher than 1000 units per liter following the administration of the parent oligomeric compound.
1817. The oligomeric compound of any of embodiments 1807-1816, wherein the plasma AST level in the mouse is higher than 1000 units per liter following the administration of the parent oligomeric compound.
1818. The oligomeric compound of any of embodiments 1807-1817, wherein the hepatotoxicity is measured 24-48 hours following the administration of the parent oligomeric compound.
1819. The oligomeric compound of any of embodiments 1807-1817, wherein the hepatotoxicity is measured 72 hours following the administration of the parent oligomeric compound.
1820. The oligomeric compound of any of embodiments 1807-1817, wherein the hepatotoxicity is measured 3 days following the administration of the parent oligomeric compound.
1821. The oligomeric compound of any of embodiments 1807-1817, wherein the hepatotoxicity is measured 5 days following the administration of the parent oligomeric compound.
1822. The oligomeric compound of any of embodiments 1807-1817, wherein the hepatotoxicity is measured 7 days following the administration of the parent oligomeric compound.
1823. The oligomeric compound of any of embodiments 1807-1817, wherein the hepatotoxicity is measured 10 days following the administration of the parent oligomeric compound.
1824. The oligomeric compound of any of embodiments 1807-1817, wherein the hepatotoxicity is measured 14 days following the administration of the parent oligomeric compound.
1825. The oligomeric compound of any of embodiments 1807-1817, wherein 1-10 mg/kg of the parent oligomeric compound is administered to the mouse.
1826. The oligomeric compound of any of embodiments 1807-1817, wherein 10-25 mg/kg of the parent oligomeric compound is administered to the mouse.

1827. The oligomeric compound of any of embodiments 1807-1817, wherein 25-50 mg/kg of the parent oligomeric compound is administered to the mouse.

1828. The oligomeric compound of any of embodiments 1807-1817, wherein 50-100 mg/kg of the parent oligomeric compound is administered to the mouse.

1829. The oligomeric compound of any of embodiments 1807-1817, wherein 100-150 mg/kg of the parent oligomeric compound is administered to the mouse.

1830. The oligomeric compound of any of embodiments 1807-1817, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

1831. The oligomeric compound of any of embodiments 1461-1830, wherein administration of 50 mg/kg of the oligomeric compound of any of embodiments 1461-1830 to a mouse is not hepatotoxic to the mouse.

1832. The oligomeric compound of embodiment 1831, wherein plasma ALT level in the mouse is lower than 100 units per liter following the administration of the oligomeric compound of embodiment 1831.

1833. The oligomeric compound of embodiment 1831 or 1832, wherein plasma ALT level in the mouse is at least 10-fold lower than plasma ALT level in a mouse administered the parent oligomeric compound of the oligomeric compound of embodiment 1831 or 1832, wherein the administrations and plasma ALT measurements of both the oligomeric compound of embodiment 1831 or 1832 and the parent oligomeric compound are completed in the same way.

1834. The oligomeric compound of embodiment 1833, wherein the plasma ALT level in the mouse is at least 100-fold lower than the plasma ALT level in the mouse administered the parent oligomeric compound.

1835. The oligomeric compound of embodiment 1833, wherein the plasma ALT level in the mouse is at least 500-fold lower than the plasma ALT level in the mouse administered the parent oligomeric compound.

1836. The oligomeric compound of any of embodiments 1807-1835, wherein the therapeutic index in a mouse of the oligomeric compound of any of embodiments 1807-1835 is increased relative to the therapeutic index of the parent oligomeric compound.

1837. The oligomeric compound of embodiment 1836, wherein the therapeutic index in a mouse of the oligomeric compound of embodiment 1836 is at least two-fold greater than the therapeutic index of the parent oligomeric compound.

1838. The oligomeric compound of any of embodiments 1461-1805, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;
and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

1839. The oligomeric compound of embodiment 1838, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

1840. The oligomeric compound of embodiment 1839, wherein the 2'-O-methyl modified sugar moiety is at position 2 of the central region.

1841. The oligomeric compound of embodiment 1838-1840, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

1842. The oligomeric compound of any of embodiments 1838-1841, wherein the nucleobase sequence of the otherwise identical oligomeric compound is 100% complementary to the target RNA.

1843. The oligomeric compound of any of embodiments 1838-1842, wherein the otherwise identical oligomeric compound is a parent oligomeric compound of the oligomeric compound of any of embodiments 1838-1842.

1844. The oligomeric compound of any of embodiments 1621-1843, wherein the oligomeric compound inhibits the target RNA with an $IC_{50}$ lower than 100 nM in a standard in vitro activity assay.

1845. The oligomeric compound of any of embodiments 1621-1843, wherein the parent oligomeric compound of the oligomeric compound of any of embodiments 1621-1843 inhibits the target RNA with an $IC_{50}$ lower than 100 nM in a standard in vitro activity assay.

1846. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 4-fold.

1847. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 3-fold.

1848. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 2-fold.

1849. The oligomeric compound of any of embodiments 1621-1848, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1850. The oligomeric compound of any of embodiments 1621-1849, wherein the nucleobase sequence of the parent oligomeric compound is 100% complementary to the target RNA.

1851. The oligomeric compound of any of embodiments 1461-1850, wherein administration of 10-50 mg of the oligomeric compound to a human is not hepatotoxic to the human.

1852. The oligomeric compound of any of embodiments 1461-1850, wherein administration of 50-100 mg of the oligomeric compound to a human is not hepatotoxic to the human.

1853. The oligomeric compound of any of embodiments 1461-1850, wherein administration of 100-300 mg of the oligomeric compound to a human is not hepatotoxic to the human.
1854. The oligomeric compound of any of embodiments 1851-1853, wherein the administration is systemic administration.
1855. A composition comprising the oligomeric compound of any of embodiments 1461-1854, and a second oligomeric compound, wherein the second oligomeric compound is complementary to the oligomeric compound of any of embodiments 1461-1854.
1856. The composition of embodiment 1855, wherein the second oligomeric compound comprises at least 14 contiguous linked nucleosides that are at least 90% complementary to the oligomeric compound of any of embodiments 1851-1853.
1857. The composition of embodiment 1855, wherein the second oligomeric compound comprises at least 14 contiguous linked nucleosides that are 100% complementary to the oligomeric compound of any of embodiments 1461-1854.
1858. A pharmaceutical composition comprising the oligomeric compound of any of embodiments 1461-1854 or the composition of any of embodiments 1855-1857, comprising a pharmaceutically acceptable carrier or diluent.
1859. A method comprising administering the oligomeric compound or composition of any of embodiments 1461-1858 to a human subject.
1860. A method of treating a disease or disorder comprising administering the oligomeric compound or composition of any of embodiments 1461-1858 to a human subject.
1861. A method of modulating the amount or activity of a target RNA in a human subject comprising administering the oligomeric compound or composition of any of embodiments 1461-1858 to the human subject; and thereby modulating the amount or activity of the target RNA in the human subject.
1862. A method of treating a disease or disorder in a human subject comprising administering the oligomeric compound or composition of any of embodiments 1461-1858 to the human subject having the disease or disorder; and thereby treating the disease or disorder in the human subject.
1863. The method of embodiment 1861 or 1862, wherein the disease or disorder is a liver disease, and wherein the oligomeric compound modulates the amount or activity of a liver target RNA.
1864. The method of embodiment 1861 or 1862, wherein the disease or disorder is a central nervous system disease, and wherein the oligomeric compound modulates the amount or activity of a central nervous system target RNA.
1865. The method of any of embodiments 1861-1864, wherein the disease or disorder is a cancer, a neurodegenerative disease, a cardiovascular disease, an immunological disease, a hereditary disease, a repeat expansion disease, a muscle-wasting disease, or a metabolic disease.
1866. The method of embodiment 1861 or 1862, wherein the oligomeric compound modulates the amount or activity of a white fat cell target.
1867. The method of embodiment 1861 or 1862, wherein the oligomeric compound modulates the amount or activity of a brown fat cell target.
1868. The method of embodiment 1861 or 1862, wherein the oligomeric compound modulates the amount or activity of an adipocyte target.
1869. The method of embodiment 1861 or 1862, wherein the oligomeric compound modulates the amount or activity of a macrophage target.
1870. The method of embodiment 1861 or 1862, wherein the oligomeric compound modulates the amount or activity of a cancer cell target.
1871. The method of embodiment 1861 or 1862, wherein the oligomeric compound modulates the amount or activity of a tumor cell target.
1872. The method of embodiment 1861 or 1862, wherein the oligomeric compound modulates the amount or activity of a smooth muscle cell target.
1873. The method of embodiment 1861 or 1862, wherein the oligomeric compound modulates the amount or activity of a lymphocyte target.
1874. The method of embodiment 1861 or 1862, wherein the oligomeric compound modulates the amount or activity of a pulmonary cell target.
1875. The method of embodiment 1861 or 1862, wherein the oligomeric compound modulates the amount or activity of a heart muscle cell target.
1876. The method of embodiment 1861 or 1862, wherein the oligomeric compound modulates the amount or activity of a cardiomyocyte target.
1877. The method of embodiment 1861 or 1862, wherein the oligomeric compound modulates the amount or activity of a endothelial cell target.
1878. The method of embodiment 1861 or 1862, wherein the oligomeric compound modulates the amount or activity of a fibroblast target.
1879. The method of embodiment 1861 or 1862, wherein the oligomeric compound modulates the amount or activity of a glial cell target.
1880. The method of embodiment 1861 or 1862, wherein the oligomeric compound modulates the amount or activity of a Schwann cell target.
1881. The method of embodiment 1861 or 1862, wherein the oligomeric compound modulates the amount or activity of a pancreatic cell target.
1882. The method of embodiment 1861 or 1862, wherein the oligomeric compound modulates the amount or activity of a kidney cell target.
1883. The method of embodiment 1861 or 1862, wherein the oligomeric compound modulates the amount or activity of a beta cell target.
1884. The method of embodiment 1861 or 1862, wherein the oligomeric compound modulates the amount or activity of a non-parenchymal cell target.
1885. The method of embodiment 1861 or 1862, wherein the oligomeric compound modulates the amount or activity of a hepatocyte target.
1886. The method of embodiment 1861 or 1862, wherein the oligomeric compound modulates the amount or activity of a oligodendrocyte target.
1887. The method of embodiment 1861 or 1862, wherein the oligomeric compound modulates the amount or activity of a astrocyte target.
1888. The method of embodiment 1861 or 1862, wherein the oligomeric compound modulates the amount or activity of a microglia target.
1889. The method of embodiment 1861 or 1862, wherein the oligomeric compound modulates the amount or activity of a ependymal cell target.
1890. The method of embodiment 1861 or 1862, wherein the oligomeric compound modulates the amount or activity of a sensory neuron target.

1891. The method of embodiment 1861 or 1862, wherein the oligomeric compound modulates the amount or activity of a motor neuron target.
1892. The method of embodiment 1861 or 1862, wherein the oligomeric compound modulates the amount or activity of a skeletal muscle target.
1893. The method of embodiment 1861 or 1862, wherein the oligomeric compound modulates the amount or activity of a cardiac muscle target.
1894. The method of embodiment 1861 or 1862, wherein the oligomeric compound modulates the amount or activity of a smooth muscle target.
1895. The method of embodiment 1861 or 1862, wherein the oligomeric compound modulates the amount or activity of a adipose tissue target.
1896. The method of embodiment 1861 or 1862, wherein the oligomeric compound modulates the amount or activity of a white adipose tissue target.
1897. The method of embodiment 1861 or 1862, wherein the oligomeric compound modulates the amount or activity of a spleen target.
1898. The method of embodiment 1861 or 1862, wherein the oligomeric compound modulates the amount or activity of a bone target.
1899. The method of embodiment 1861 or 1862, wherein the oligomeric compound modulates the amount or activity of a bone marrow target.
1900. The method of embodiment 1861 or 1862, wherein the oligomeric compound modulates the amount or activity of an intestinal target.
1901. The method of embodiment 1861 or 1862, wherein the oligomeric compound modulates the amount or activity of an adrenal gland target.
1902. The method of embodiment 1861 or 1862, wherein the oligomeric compound modulates the amount or activity of a testicular target.
1903. The method of embodiment 1861 or 1862, wherein the oligomeric compound modulates the amount or activity of an ovarian target.
1904. The method of embodiment 1861 or 1862, wherein the oligomeric compound modulates the amount or activity of a pancreatic target.
1905. The method of embodiment 1861 or 1862, wherein the oligomeric compound modulates the amount or activity of a pituitary gland target.
1906. The method of embodiment 1861 or 1862, wherein the oligomeric compound modulates the amount or activity of a prostate gland target.
1907. The method of embodiment 1861 or 1862, wherein the oligomeric compound modulates the amount or activity of a skin target.
1908. The method of embodiment 1861 or 1862, wherein the oligomeric compound modulates the amount or activity of an epidermal target.
1909. The method of embodiment 1861 or 1862, wherein the oligomeric compound modulates the amount or activity of a uterine target.
1910. The method of embodiment 1861 or 1862, wherein the oligomeric compound modulates the amount or activity of a bladder target.
1911. The method of embodiment 1861 or 1862, wherein the oligomeric compound modulates the amount or activity of a brain target.
1912. The method of embodiment 1861 or 1862, wherein the oligomeric compound modulates the amount or activity of a glomerulus target.
1913. The method of embodiment 1861 or 1862, wherein the oligomeric compound modulates the amount or activity of a distal tubular epithelium target.
1914. The method of embodiment 1861 or 1862, wherein the oligomeric compound modulates the amount or activity of a breast tissue target.
1915. The method of embodiment 1861 or 1862, wherein the oligomeric compound modulates the amount or activity of a lung target.
1916. The method of embodiment 1861 or 1862, wherein the oligomeric compound modulates the amount or activity of a heart target.
1917. The method of embodiment 1861 or 1862, wherein the oligomeric compound modulates the amount or activity of a kidney target.
1918. The method of embodiment 1861 or 1862, wherein the oligomeric compound modulates the amount or activity of a ganglion target.
1919. The method of embodiment 1861 or 1862, wherein the oligomeric compound modulates the amount or activity of a frontal cortex target.
1920. The method of embodiment 1861 or 1862, wherein the oligomeric compound modulates the amount or activity of a spinal cord target.
1921. The method of embodiment 1861 or 1862, wherein the oligomeric compound modulates the amount or activity of a trigeminal ganglion target.
1922. The method of embodiment 1861 or 1862, wherein the oligomeric compound modulates the amount or activity of a sciatic nerve target.
1923. The method of embodiment 1861 or 1862, wherein the oligomeric compound modulates the amount or activity of a dorsal root ganglion target.
1924. The method of embodiment 1861 or 1862, wherein the oligomeric compound modulates the amount or activity of a epidymal fat target.
1925. The method of embodiment 1861 or 1862, wherein the oligomeric compound modulates the amount or activity of a diaphragm target.
1926. The method of embodiment 1861 or 1862, wherein the oligomeric compound modulates the amount or activity of a colon target.
1927. The method of any of embodiments 1802-1926, wherein the plasma ALT level of the human subject after the administration is not more than three times higher than it was prior to the administration.
1928. The method of any of embodiments 1802-1926, wherein the plasma ALT level of the human subject after the administration is not more than 150 units per liter.
1929. The method of any of embodiments 1802-1928, wherein the human subject is susceptible to liver damage.
1930. The method of any of embodiments 1802-1928, wherein the human subject is susceptible to liver degeneration.
1931. The method of any of embodiments 1802-1930, wherein the human subject is susceptible to elevated apoptosis in the liver.
1932. The method of any of embodiments 1802-1931, wherein the human subject has a liver disease.
1933. The method of any of embodiments 1802-1932, wherein the human subject has kidney disease.
1934. The method of any of embodiments 1802-1933, wherein the human subject is susceptible to kidney damage.
1935. The method of any of embodiments 1802-1934, wherein the human subject has heart disease.

1936. The method of any of embodiments 1802-1935, wherein the human subject is susceptible to heart damage.
1937. The method of any of embodiments 1802-1936, wherein the human subject has pancreatitis.
1938. The method of any of embodiments 1802-1937, wherein the human subject is susceptible to pancreatic damage.
1939. The method of any of embodiments 1802-1938, wherein the human subject has a neurological disease.
1940. The method of any of embodiments 1802-1939, wherein the human subject is susceptible to neurological damage.
1941. The method of any of embodiments 1859-1940, comprising administering the parent oligomeric compound of the oligomeric compound of any of embodiments 1461-1858 to a mouse.
1942. The method of any of embodiments 1859-1940, comprising contacting a cell with the parent oligomeric compound of the oligomeric compound of any of embodiments 1461-1858.
1943. The method of embodiment 1941 or 1942, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.
1944. A method of designing an oligomeric compound comprising starting with a parent oligomeric compound and changing the design of that compound in order to arrive at an oligomeric compound of any one of embodiments 1461-1858.
1945. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1461-1858.
1946. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1461-1858.
1947. The method of embodiment 1945 or 1946, wherein the method designs an oligomeric compound with improved therapeutic index relative to the parent oligomeric compound.
1948. The method of embodiment 1945 or 1946, wherein the method designs an oligomeric compound with lower hepatotoxicity relative to the parent oligomeric compound.
1949. The method of embodiment 1945, wherein the second oligomeric compound has an improved therapeutic index relative to the parent oligomeric compound.
1950. The method of embodiment 1945 or 1946, wherein the second oligomeric compound has reduced hepatotoxicity in a mouse relative to the parent oligomeric compound.
1951. The method of embodiment 1945, wherein the oligomeric compound according to any one of embodiments 1461-1858 has reduced hepatotoxicity relative to the parent oligomeric compound.
1952. A method comprising administering an oligomeric compound of any of embodiments 1461-1858 to a mouse and separately administering the parent oligomeric compound of the oligomeric compound of any of embodiments 1461-1858 to a second mouse, wherein the therapeutic index of the oligomeric compound of any of embodiments 1461-1858 is improved relative to the therapeutic index of the parent oligomeric compound.
1953. The method of any of embodiments 1859-1952, wherein the level of p21 RNA is measured in the mouse, the cell, and/or the human subject.
1954. A method comprising administering an oligomeric compound of any of embodiments 1461-1858 to a subject and measuring the level of p21 RNA in the subject.
1955. The method of embodiment 1954, wherein the subject is a mouse.
1956. The method of embodiment 1954, wherein the subject is a human.
1957. The method of any of embodiments 1954-1956, wherein the p21 RNA level is measured within 24 hours of the administration.
1958. The method of any of embodiments 1954-1956, wherein the p21 RNA level is measured 24-48 hours following the administration.
1959. An oligomeric compound or composition of any one of embodiments 1461-1858, for use in medical therapy.
1960. The oligomeric compound of any of embodiments 1461-1858, wherein the oligomeric compound is not toxic.
1961. The oligomeric compound of any of embodiment 1461-1858, wherein a comparator compound is toxic; wherein the comparator compound is identical to the oligomeric compound except that each nucleoside of the central region of the comparator compound is a nucleoside comprising 2'-β-D-deoxyribosyl sugar moiety.
1962. The oligomeric compound of embodiment 1961, wherein administering a dose of the oligomeric compound to an animal results in a circulating ALT level that is at least 3-fold lower than the ALT level that results from administering the same dose of the comparator compound to an animal for at least one matched dose.
1963. The oligomeric compound of embodiment 1961 or 1962, wherein the lowest dose of the oligomeric compound that raises circulating ALT to over 300 units per liter is at least three-fold higher than the lowest dose of the comparator compound that raises circulating ALT to over 300 units per liter.
1964. The oligomeric compound of any of embodiments 1961-1963, wherein the oligomeric compound is capable of reducing the target RNA in a cell.
1965. The oligomeric compound of embodiment 1964, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.
1966. The oligomeric compound of embodiment 1965 having RNA-reducing activity that is no more than 2-fold worse than the RNA-reducing activity of the comparator compound.
1967. A method of modulating the amount or activity of a target RNA in a human subject comprising administering the oligomeric compound or composition of any of embodiments 1461-1858 to the human subject; and thereby modulating the amount or activity of the target RNA in the human subject.
1968. A method of treating a disease or disorder in a human subject comprising administering the oligomeric compound or composition of any of embodiments 1461-1858 to the human subject having the disease or disorder; and thereby treating the disease or disorder in the human subject.

1969. The method of embodiment 1967 or 1968, wherein the disease or disorder is a liver disease, and wherein the oligomeric compound modulates the amount or activity of a liver target RNA.
1970. The method of embodiment 1967 or 1968, wherein the disease or disorder is a central nervous system disease, and wherein the oligomeric compound modulates the amount or activity of a central nervous system target RNA.
1971. The method of any of embodiments 1967-1970, wherein the disease or disorder is a cancer, a neurodegenerative disease, a cardiovascular disease, an immunological disease, a hereditary disease, a repeat expansion disease, a muscle-wasting disease, or a metabolic disease.
1972. The method of any of embodiments 1967-1971, wherein the plasma ALT level of the human subject after the administration is not more than three times higher than it was prior to the administration.
1973. The method of any of embodiments 1967-1972, wherein the plasma ALT level of the human subject after the administration is not more than 150 units per liter.
1974. A method of treating a disease or disorder in a human subject comprising administering the oligomeric compound or composition of any of embodiments 1461-1858 to the human subject having the disease or disorder; and thereby treating the disease or disorder in the human subject.
1975. The method of embodiment 1974, wherein the disease or disorder is not a CNS disease or disorder.
1976. The method of embodiment 1974, wherein the disease or disorder is a disease or disorder of the white fat cells.
1977. The method of embodiment 1974, wherein the disease or disorder is a disease or disorder of the brown fat cells.
1978. The method of embodiment 1974, wherein the disease or disorder is a disease or disorder of the adipocytes.
1979. The method of embodiment 1974, wherein the disease or disorder is a disease or disorder of the macrophages.
1980. The method of embodiment 1974, wherein the disease or disorder is a disease or disorder of the cancer cells.
1981. The method of embodiment 1974, wherein the disease or disorder is a disease or disorder of the tumor cells.
1982. The method of embodiment 1974, wherein the disease or disorder is a disease or disorder of the smooth muscle cells.
1983. The method of embodiment 1974, wherein the disease or disorder is a disease or disorder of the lymphocytes.
1984. The method of embodiment 1974, wherein the disease or disorder is a disease or disorder of the pulmonary cells.
1985. The method of embodiment 1974, wherein the disease or disorder is a disease or disorder of the heart muscle cells.
1986. The method of embodiment 1974, wherein the disease or disorder is a disease or disorder of the cardiomyocytes.
1987. The method of embodiment 1974, wherein the disease or disorder is a disease or disorder of the endothelial cells.
1988. The method of embodiment 1974, wherein the disease or disorder is a disease or disorder of the fibroblasts.
1989. The method of embodiment 1974, wherein the disease or disorder is a disease or disorder of the glial cells.
1990. The method of embodiment 1974, wherein the disease or disorder is a disease or disorder of the Schwann cells.
1991. The method of embodiment 1974, wherein the disease or disorder is a disease or disorder of the pancreatic cells.
1992. The method of embodiment 1974, wherein the disease or disorder is a disease or disorder of the kidney cells.
1993. The method of embodiment 1974, wherein the disease or disorder is a disease or disorder of the beta cells.
1994. The method of embodiment 1974, wherein the disease or disorder is a disease or disorder of the non-parenchymal cells.
1995. The method of embodiment 1974, wherein the disease or disorder is a disease or disorder of the hepatocytes.
1996. The method of embodiment 1974, wherein the disease or disorder is a disease or disorder of the oligodendrocytes.
1997. The method of embodiment 1974, wherein the disease or disorder is a disease or disorder of the astrocytes.
1998. The method of embodiment 1974, wherein the disease or disorder is a disease or disorder of the microglia.
1999. The method of embodiment 1974, wherein the disease or disorder is a disease or disorder of the ependymal cells.
2000. The method of embodiment 1974, wherein the disease or disorder is a disease or disorder of the sensory neurons.
2001. The method of embodiment 1974, wherein the disease or disorder is a disease or disorder of the motor neurons.
2002. The method of embodiment 1974, wherein the disease or disorder is a disease or disorder of the skeletal muscle.
2003. The method of embodiment 1974, wherein the disease or disorder is a disease or disorder of the cardiac muscle.
2004. The method of embodiment 1974, wherein the disease or disorder is a disease or disorder of the smooth muscle.
2005. The method of embodiment 1974, wherein the disease or disorder is a disease or disorder of the adipose tissue.
2006. The method of embodiment 1974, wherein the disease or disorder is a disease or disorder of the white adipose tissue.
2007. The method of embodiment 1974, wherein the disease or disorder is a disease or disorder of the spleen.
2008. The method of embodiment 1974, wherein the disease or disorder is a disease or disorder of the bone.
2009. The method of embodiment 1974, wherein the disease or disorder is a disease or disorder of the bone marrow.
2010. The method of embodiment 1974, wherein the disease or disorder is a disease or disorder of the intestine.
2011. The method of embodiment 1974, wherein the disease or disorder is a disease or disorder of the adrenal glands.
2012. The method of embodiment 1974, wherein the disease or disorder is a disease or disorder of the testes.
2013. The method of embodiment 1974, wherein the disease or disorder is a disease or disorder of the ovaries.
2014. The method of embodiment 1974, wherein the disease or disorder is a disease or disorder of the pancreas.
2015. The method of embodiment 1974, wherein the disease or disorder is a disease or disorder of the pituitary gland.
2016. The method of embodiment 1974, wherein the disease or disorder is a disease or disorder of the prostate gland.
2017. The method of embodiment 1974, wherein the disease or disorder is a disease or disorder of the skin.
2018. The method of embodiment 1974, wherein the disease or disorder is a disease or disorder of the epidermis.
2019. The method of embodiment 1974, wherein the disease or disorder is a disease or disorder of the uterus.
2020. The method of embodiment 1974, wherein the disease or disorder is a disease or disorder of the bladder.
2021. The method of embodiment 1974, wherein the disease or disorder is a disease or disorder of the brain.
2022. The method of embodiment 1974, wherein the disease or disorder is a disease or disorder of the glomerulus.
2023. The method of embodiment 1974, wherein the disease or disorder is a disease or disorder of the distal tubular epithelium.
2024. The method of embodiment 1974, wherein the disease or disorder is a disease or disorder of the breast tissue.

2025. The method of embodiment 1974, wherein the disease or disorder is a disease or disorder of the lung.
2026. The method of embodiment 1974, wherein the disease or disorder is a disease or disorder of the heart.
2027. The method of embodiment 1974, wherein the disease or disorder is a disease or disorder of the kidney.
2028. The method of embodiment 1974, wherein the disease or disorder is a disease or disorder of the ganglion.
2029. The method of embodiment 1974, wherein the disease or disorder is a disease or disorder of the frontal cortex.
2030. The method of embodiment 1974, wherein the disease or disorder is a disease or disorder of the spinal cord.
2031. The method of embodiment 1974, wherein the disease or disorder is a disease or disorder of the trigeminal ganglion.
2032. The method of embodiment 1974, wherein the disease or disorder is a disease or disorder of the sciatic nerve.
2033. The method of embodiment 1974, wherein the disease or disorder is a disease or disorder of the dorsal root ganglion.
2034. The method of embodiment 1974, wherein the disease or disorder is a disease or disorder of the epidymal fat.
2035. The method of embodiment 1974, wherein the disease or disorder is a disease or disorder of the diaphragm.
2036. The method of embodiment 1974, wherein the disease or disorder is a disease or disorder of the colon.
2037. A method of screening a library of oligomeric compounds for activity against a target RNA, wherein the library of oligomeric compounds comprises a plurality of oligomeric compounds of any of embodiments 1461-1858.

Certain Compounds

In certain embodiments, compounds described herein are oligomeric compounds comprising or consisting of oligonucleotides consisting of linked nucleosides. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety and/or a modified nucleobase) and/or at least one modified internucleoside linkage).

I. Modifications

A. Modified Nucleosides

Modified nucleosides comprise a modified sugar moiety, a modified nucleobase, or both a modified sugar moiety and a modified nucleobase.

1. Certain Modified Sugar Moieties

In certain embodiments, sugar moieties are non-bicyclic, modified furanosyl sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 3', 4', and/or 5' positions. In certain embodiments, the furanosyl sugar moiety is a ribosyl sugar moiety. In certain embodiments, the furanosyl sugar moiety is a β-D-ribofuranosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("2'-OMe" or "2'-O-methyl"), and 2'-O(CH$_2$)$_2$OCH$_3$ ("2'-MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, C$_1$-C$_{10}$ alkyl, C$_1$-C$_{10}$ substituted alkyl, S-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 3'-substituent groups include 3'-methyl (see Frier, et al., The ups and downs of nucleic acid duplex stability: structure-stability studies on chemically-modified DNA:RNA duplexes. Nucleic Acids Res., 25, 4429-4443, 1997.) Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-allyl, 5'-ethyl, 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836. 2',4'-difluoro modified sugar moieties have been described in Martinez-Montero, et al., Rigid 2',4'-difluororibonucleosides: synthesis, conformational analysis, and incorporation into nascent RNA by HCV polymerase. *J. Org. Chem.*, 2014, 79:5627-5635. Modified sugar moieties comprising a 2'-modification (OMe or F) and a 4'-modification (OMe or F) have also been described in Malek-Adamian, et al., *J. Org. Chem*, 2018, 83: 9839-9849.

In certain embodiments, a 2'-substituted nucleoside or non-bicyclic 2'-modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R11 is, independently, H, an amino protecting group, or substituted or unsubstituted C$_1$-C$_{10}$ alkyl.

In certain embodiments, a 2'-substituted nucleoside or non-bicyclic 2'-modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or non-bicyclic 2'-modified nucleoside comprises a sugar moiety comprising a non-bridging 2'-substituent group selected from: F, OCH$_3$, and OCH$_2$CH$_2$OCH$_3$.

In certain embodiments, the 4' O of 2'-deoxyribose can be substituted with a S to generate 4'-thio DNA (see Takahashi, et al., *Nucleic Acids Research* 2009, 37: 1353-1362). This modification can be combined with other modifications detailed herein. In certain such embodiments, the sugar moiety is further modified at the 2' position. In certain embodiments the sugar moiety comprises a 2'-fluoro. A thymidine with this sugar moiety has been described in Watts, et al., *J. Org. Chem.* 2006, 71(3): 921-925 (4'-S-fluoro5-methylarauridine or FAMU).

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-CH$_2$-2',4'-(CH$_2$)$_2$-2',4'-(CH$_2$)$_3$-2',4'-CH$_2$—O-2' ("LNA"), 4'-CH$_2$—S-2',4'-(CH$_2$)$_2$-0-2' ("ENA"), 4'-CH(CH$_3$)—O-2' (referred to as "constrained ethyl" or "cEt" when in the S configuration), 4'-CH$_2$—O—CH$_2$-2',4'-CH$_2$—N(R)-2',4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N (OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2',4'-C(R$_a$R$_b$)—O—N(R)-2',4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672), 4'-C(=O)—N(CH$_3$)$_2$-2',4'-C(=O)—N(R)$_2$-2',4'-C(=S)—N(R)$_2$-2' and analgos thereof (see, e.g., Obika et al., WO2011052436A1, Yusuke, WO2017018360A1).

In certain embodiments, such 4' to 2' bridges independently comprise from 1 to 4 linked groups independently selected from: 4C(R$_a$)(R$_b$)$_n$—, 4C(R$_a$)(R$_b$)$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2017, 129, 8362-8379; Elayadi et al., Christiansen, et al., *J. Am. Chem. Soc.* 1998, 120, 5458-5463; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

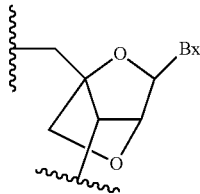

LNA (β-D-configuration)
bridge = 4'-CH$_2$—O-2'

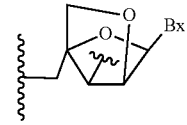

α-L-LNA (α-L-configuration)
bridge = 4'-CH$_2$—O-2'

α-L-methyleneoxy (4'-CH$_2$—O-2') or α-L-LNA bicyclic nucleosides have been incorporated into antisense oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars). Nucleosides comprising modified furanosyl sugar moieties and modified furanosyl sugar moieties may be referred to by the position(s) of the substitution(s) on the sugar moiety of the nucleoside. The term "modified" following a position of the furanosyl ring, such as "2'-modified", indicates that the sugar moiety comprises the indicated modification at the 2' position and may comprise additional modifications and/or substituents. A 4'-2' bridged sugar moiety is 2'-modified and 4'-modified, or, alternatively, "2',4'-modified". The term "substituted" following a position of the furanosyl ring, such as "2'-substituted" or "2'-4'-substituted", indicates that is the only position(s) having a substituent other than those found in unmodified sugar moieties in oligonucleotides. Accordingly, the following sugar moieties are represented by the following formulas.

In the context of a nucleoside and/or an oligonucleotide, a non-bicyclic, modified furanosyl sugar moiety is represented by formula I:

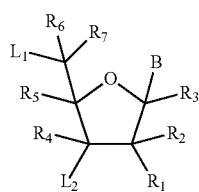

I wherein B is a nucleobase; and $L_1$ and $L_2$ are each, independently, an internucleoside linkage, a terminal group, a conjugate group, or a hydroxyl group. Among the R groups, at least one of $R_{3-7}$ is not H and/or at least one of $R_1$ and $R_2$ is not H or OH. In a 2'-modified furanosyl sugar moiety, at least one of $R_1$ and $R_2$ is not H or OH and each of $R_{3-7}$ is independently selected from H or a substituent other than H. In a 4'-modified furanosyl sugar moiety, $R_5$ is not H and each of $R_{1-4, 6, 7}$ are independently selected from H and a substituent other than H; and so on for each position of the furanosyl ring. The stereochemistry is not defined unless otherwise noted.

In the context of a nucleoside and/or an oligonucleotide, a non-bicyclic, modified, substituted fuarnosyl sugar moiety is represented by formula I, wherein B is a nucleobase; and $L_1$ and $L_2$ are each, independently, an internucleoside linkage, a terminal group, a conjugate group, or a hydroxyl group. Among the R groups, either one (and no more than one) of $R_{3-7}$ is a substituent other than H or one of $R_1$ or $R_2$ is a substituent other than H or OH. The stereochemistry is not defined unless otherwise noted. Examples of non-bicyclic, modified, substituted furanosyl sugar moieties include 2'-substituted ribosyl, 4'-substituted ribosyl, and 5'-substituted ribosyl sugar moieties, as well as substituted 2'-deoxyfuranosyl sugar moieties, such as 4'-substituted 2'-deoxyribosyl and 5'-substituted 2'-deoxyribosyl sugar moieties.

In the context of a nucleoside and/or an oligonucleotide, a 2'-substituted ribosyl sugar moiety is represented by formula II:

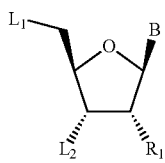

II wherein B is a nucleobase; and $L_1$ and $L_2$ are each, independently, an internucleoside linkage, a terminal group, a conjugate group, or a hydroxyl group. $R_1$ is a substituent other than H or OH. The stereochemistry is defined as shown.

In the context of a nucleoside and/or an oligonucleotide, a 4'-substituted ribosyl sugar moiety is represented by formula III:

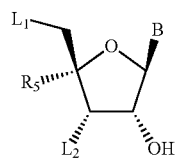

III wherein B is a nucleobase; and $L_1$ and $L_2$ are each, independently, an internucleoside linkage, a terminal group, a conjugate group, or a hydroxyl group. $R_5$ is a substituent other than H. The stereochemistry is defined as shown.

In the context of a nucleoside and/or an oligonucleotide, a 5'-substituted ribosyl sugar moiety is represented by formula IV:

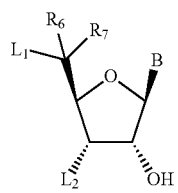

IV wherein B is a nucleobase; and $L_1$ and $L_2$ are each, independently, an internucleoside linkage, a terminal group, a conjugate group, or a hydroxyl group. $R_6$ or $R_7$ is a substituent other than H. The stereochemistry is defined as shown.

In the context of a nucleoside and/or an oligonucleotide, a 2'-deoxyfuranosyl sugar moiety is represented by formula V:

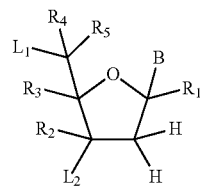

V wherein B is a nucleobase; and $L_1$ and $L_2$ are each, independently, an internucleoside linkage, a terminal group, a conjugate group, or a hydroxyl group. Each of $R_{1-5}$ are independently selected from H and a non-H substituent. If all of $R_{1-5}$ are each H, the sugar moiety is an unsubstituted 2'-deoxyfuranosyl sugar moiety. The stereochemistry is not defined unless otherwise noted.

In the context of a nucleoside and/or an oligonucleotide, a 4'-substituted 2'-deoxyribosyl sugar moiety is represented by formula VI:

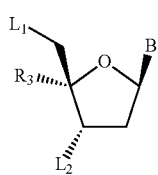

wherein B is a nucleobase; and $L_1$ and $L_2$ are each, independently, an internucleoside linkage, a terminal group, a conjugate group, or a hydroxyl group. $R_3$ is a substituent other than H. The stereochemistry is defined as shown.

In the context of a nucleoside and/or an oligonucleotide, a 5'-substituted 2'-deoxyribosyl sugar moiety is represented by formula VII:

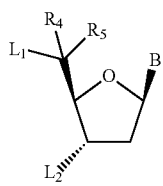

wherein B is a nucleobase; and $L_1$ and $L_2$ are each, independently, an internucleoside linkage, a terminal group, a conjugate group, or a hydroxyl group. $R_4$ or $R_5$ is a substituent other than H. The stereochemistry is defined as shown.

Unsubstituted 2'-deoxyfuranosyl sugar moieties may be unmodified (β-D-2'-deoxyribosyl) or modified. Examples of modified, unsubstituted 2'-deoxyfuranosyl sugar moieties include β-L-2'-deoxyribosyl, α-L-2'-deoxyribosyl, α-D-2'-deoxyribosyl, and β-D-xylosyl sugar moieties. For example, in the context of a nucleoside and/or an oligonucleotide, a β-L-2'-deoxyribosyl sugar moiety is represented by formula VIII:

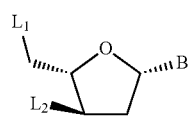

wherein B is a nucleobase; and $L_1$ and $L_2$ are each, independently, an internucleoside linkage, a terminal group, a conjugate group, or a hydroxyl group. The stereochemistry is defined as shown. Synthesis of α-L-ribosyl nucleotides and β-D-xylosyl nucleotides has been described by Gaubert, et al., *Tetehedron* 2006, 62: 2278-2294. Additional isomers of DNA and RNA nucleosides are described by Vester, et. al., "Chemically modified oligonucleotides with efficient RNase H response," Bioorg. Med. Chem. Letters, 2008, 18: 2296-2300.

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), mannitol nucleic acid ("MNA") (see, e.g., Leumann, C J. *Bioorg. & Med. Chem.* 2002, 10, 841-854), fluoro HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), F-CeNA, and 3'-ara-HNA, having the formulas below, where $L_1$ and $L_2$ are each, independently, an internucleoside linkage linking the modified THP nucleoside to the remainder of an oligonucleotide or one of $L_1$ and $L_2$ is an internucleoside linkage linking the modified THP nucleoside to the remainder of an oligonucleotide and the other of $L_1$ and $L_2$ is H, a hydroxyl protecting group, a linked conjugate group, or a 5' or 3'-terminal group.

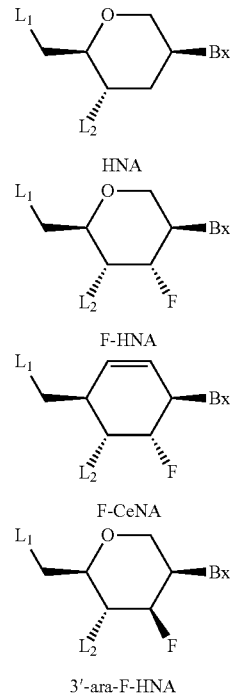

Additional sugar surrogates comprise THP compounds having the formula:

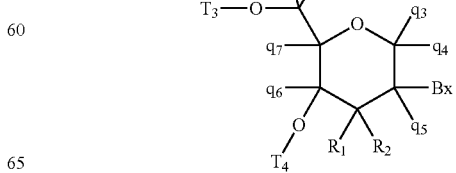

wherein, independently, for each of said modified THP nucleoside:

Bx is a nucleobase moiety;

$T_3$ and $T_4$ are each, independently, an internucleoside linkage linking the modified THP nucleoside to the remainder of an oligonucleotide or one of T3 and T4 is an internucleoside linkage linking the modified THP nucleoside to the remainder of an oligonucleotide and the other of T3 and T4 is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having no heteroatoms. For example, nucleosides comprising bicyclo [3.1.0]-hexane have been described (see, e.g., Marquez, et al., J. Med. Chem. 1996, 39:3739-3749).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate comprising the following structure:

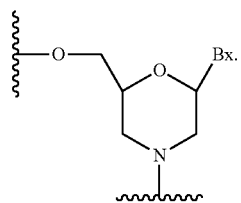

In certain embodiments, morpholinos may be modified, for example by adding or altering various substituent groups from the above morpholino structure. Such sugar surrogates are referred to herein as "modified morpholinos." In certain embodiments, morpholino residues replace a full nucleotide, including the internucleoside linkage, and have the structures shown below, wherein Bx is a heterocyclic base moiety.

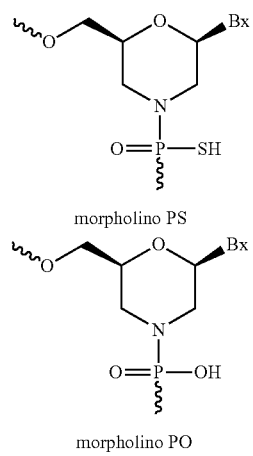

morpholino PS morpholino PO

In certain embodiments, sugar surrogates comprise acyclic moieites. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), glycol nucleic acid ("GNA", see Schlegel, et al., J. Am. Chem. Soc. 2017, 139:8537-8546) and nucleosides and oligonucleotides described in Manoharan et al., WO2011/133876.

Many other bicyclic and tricyclic sugar and sugar surrogate ring systems are known in the art that can be used in modified nucleosides. Certain such ring systems are described in Hanessian, et al., J. Org. Chem., 2013, 78: 9051-9063 and include bcDNA and tcDNA. Modifications to bcDNA and tcDNA, such as 6'-fluoro, have also been described (Dogovic and Leumann, J. Org. Chem., 2014, 79: 1271-1279).

In certain embodiments, modified nucleosides are DNA mimics. "DNA mimic" means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms. In certain embodiments, a DNA mimic comprises a structure represented by the formula below:

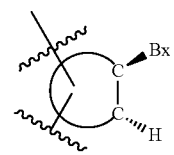

Wherein Bx represents a heterocyclic base moiety.
In certain embodiments, a DNA mimic comprises a structure represented by one of the formulas below:

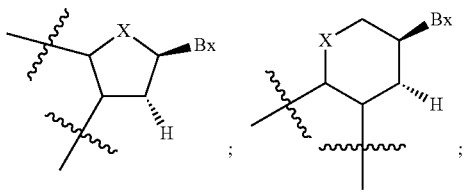

-continued

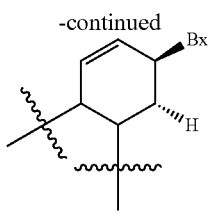

wherein X is O or S and Bx represents a heterocyclic base moiety.

In certain embodiments, a DNA mimic is a sugar surrogate. In certain embodiments, a DNA mimic is a cycohexenyl or hexitol nucleic acid. In certain embodiments, a DNA mimic is described in FIG. 1 of Vester, et. al., "Chemically modified oligonucleotides with efficient RNase H response," *Bioorg. Med. Chem. Letters*, 2008, 18: 2296-2300, incorporated by reference herein. In certain embodiments, a DNA mimic nucleoside has a formula selected from:

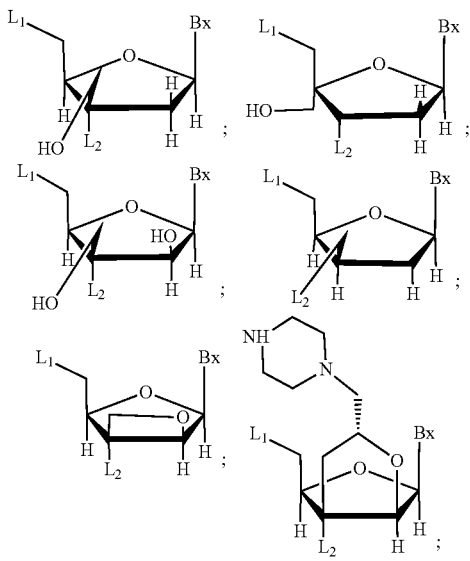

wherein Bx is a heterocyclic base moiety, and $L_1$ and $L_2$ are each, independently, an internucleoside linkage linking the modified THP nucleoside to the remainder of an oligonucleotide or one of $L_1$ and $L_2$ is an internucleoside linkage linking the modified nucleoside to the remainder of an oligonucleotide and the other of $L_1$ and $L_2$ is H, a hydroxyl protecting group, a linked conjugate group, or a 5' or 3'-terminal group. In certain embodiments, a DNA mimic is α,β-constrained nucleic acid (CAN), 2',4'-carbocyclic-LNA, or 2',4'-carbocyclic-ENA. In certain embodiments, a DNA mimic has a sugar moiety selected from among: 4'-C-hydroxymethyl-2'-deoxyribosyl, 3'-C-hydroxymethyl-2'-deoxyribosyl, 3'-C-hydroxymethyl-arabinosyl, 3'-C-2'-O-arabinosyl, 3'-C-methylene-extended-xyolosyl, 3'-C-2'-O-piperazino-arabinosyl. In certain embodiments, a DNA mimic has a sugar moiety selected from among: 2'-methyl-ribosyl, 2'-S-methylribosyl, 2'-aminoribosyl, 2'-NH(CH$_2$)-ribosyl, 2'-NH(CH$_2$)$_2$-ribosyl, 2'-CH$_2$—F-ribosyl, 2'-CHF2-ribosyl, 2'-CF$_3$-ribosyl, 2'=CF$_2$ ribosyl, 2'-ethylribosyl, 2'-alkenylribosyl, 2'-alkynylribosyl, 2'-O-4'-C-methyleneribosyl, 2'-cyanoarabinosyl, 2'-chloroarabinosyl, 2'-fluoroarabinosyl, 2'-bromoarabinosyl, 2'-azidoarabinosyl, 2'-methoxyarabinosyl, and 2'-arabinosyl. In certain embodiments, a DNA mimic has a sugar moiety selected from 4'-methyl-modified deoxyfuranosyl, 4'-F-deoxyfuranosyl, 4'-OMe-deoxyfuranosyl. In certain embodiments, a DNA mimic has a sugar moiety selected from among: 5'-methyl-2'-β-D-deoxyribosyl, 5'-ethyl-2'-β-D-deoxyribosyl, 5'-allyl-2'-β-D-deoxyribosyl, 2'-fluoro-β-D-arabinofuranosyl. In certain embodiments, DNA mimics are listed on page 32-33 of PCT/US00/267929 as B-form nucleotides, incorporated by reference herein in its entirety.

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443. In certain embodiments, modified nucleosides comprise double-headed nucleosides having two nucleobases. Such compounds are described in detail in Sorinaset al., *J. Org. Chem*, 2014 79: 8020-8030.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

In certain embodiments, compounds comprise or consist of a modified oligonucleotide complementary to an target nucleic acid comprising one or more modified nucleobases. In certain embodiments, the modified nucleobase is 5-methylcytosine. In certain embodiments, each cytosine is a 5-methylcytosine.

B. Modified Internucleoside Linkages

In certain embodiments, compounds described herein having one or more modified internucleoside linkages are selected over compounds having only phosphodiester internucleoside linkages because of desirable properties such as, for example, enhanced cellular uptake, enhanced affinity for target nucleic acids, and increased stability in the presence of nucleases.

In certain embodiments, compounds comprise or consist of a modified oligonucleotide complementary to a target nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, nucleosides of modified oligonucleotides may be linked together using any internucleoside linkage. The two main classes of internucleoside linkages are defined by the presence or absence of a phosphorus atom. Representative phosphorus-containing internucleoside linkages include unmodified phosphodiester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, phosphorothioate, and phosphorodithioate ("HS-P=S"). Representative non-phosphorus containing internucleoside linkages include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); formacetal, thioacetamido (TANA), alt-thioformacetal, glycine amide, and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. All phosphorothioate linkages described herein are stereorandom unless otherwise specified. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

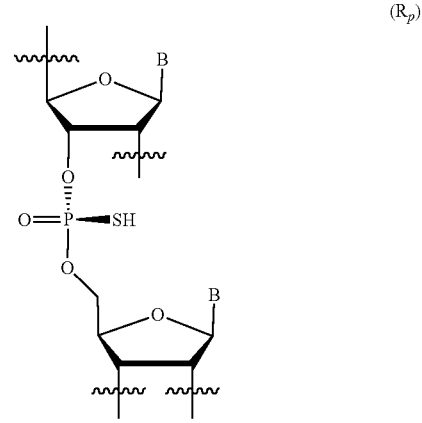

(R$_p$)

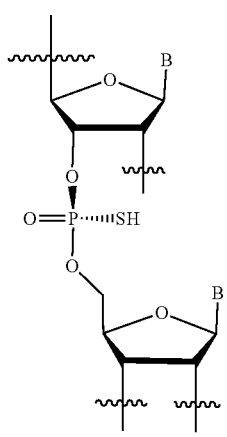

(S_p)

Unless otherwise indicated, chiral internucleoside linkages of modified oligonucleotides described herein can be stereorandom or in a particular stereochemical configuration.

Neutral internucleoside linkages include, without limitation, phosphotriesters, phosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

In certain embodiments, nucleic acids can be linked 2' to 5' rather than the standard 3' to 5' linkage. Such a linkage is illustrated below.

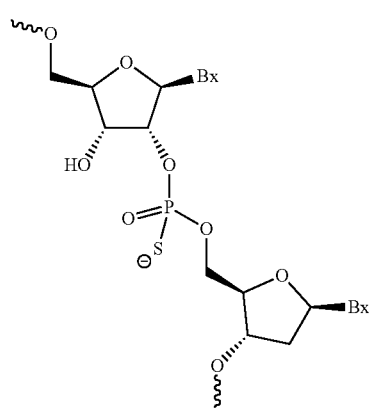

In the context of a nucleoside and/or an oligonucleotide, a non-bicyclic, 2'-linked modified furanosyl sugar moiety is represented by formula IX:

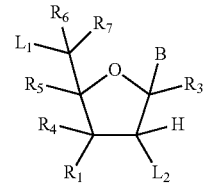

IX wherein B is a nucleobase; L$_1$ is an internucleoside linkage, a terminal group, a conjugate group, or a hydroxyl group and L$_2$ is an internucleoside linkage. The stereochemistry is not defined unless otherwise noted.

In certain embodiments, nucleosides can be linked by vinicinal 2',3'-phosphodiester bonds. In certain such embodiments, the nucleosides are threofuranosyl nucleosides (TNA; see Bala, et al., *J Org. Chem.* 2017, 82:5910-5916). A TNA linkage is shown below.

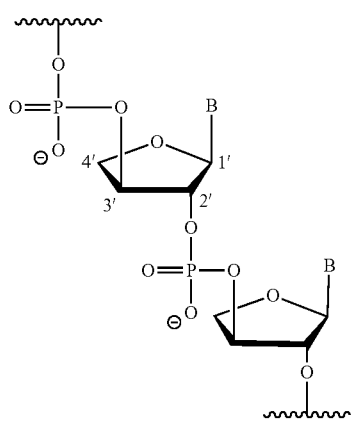

threose nucleic acid
(TNA)

Additional modified linkages include α,β-D-CNA type linkages and related conformationally-constrained linkages, shown below. Synthesis of such molecules has been described previously (see Dupouy, et al., *Angew. Chem. Int, Ed. Engl.,* 2014, 45: 3623-3627, Bursting, et al. *Tetahedron,* 2004, 60:10955-10966; Ostergaard, et al., *ACS Chem. Biol.* 2014, 9: 1975-1979, Dupouy, et al., *Eur. J Org. Chem.,* 2008, Ser. No. 12/851,294; Martinez, et al., *PLoS One,* 2011, 6:e25510; Dupouy, et al., *Eur. J. Org. Chem.* 2007, 5256-5264; Boissonnet, et al. *New J. Chem.,* 2011 35: 1528-1533.)

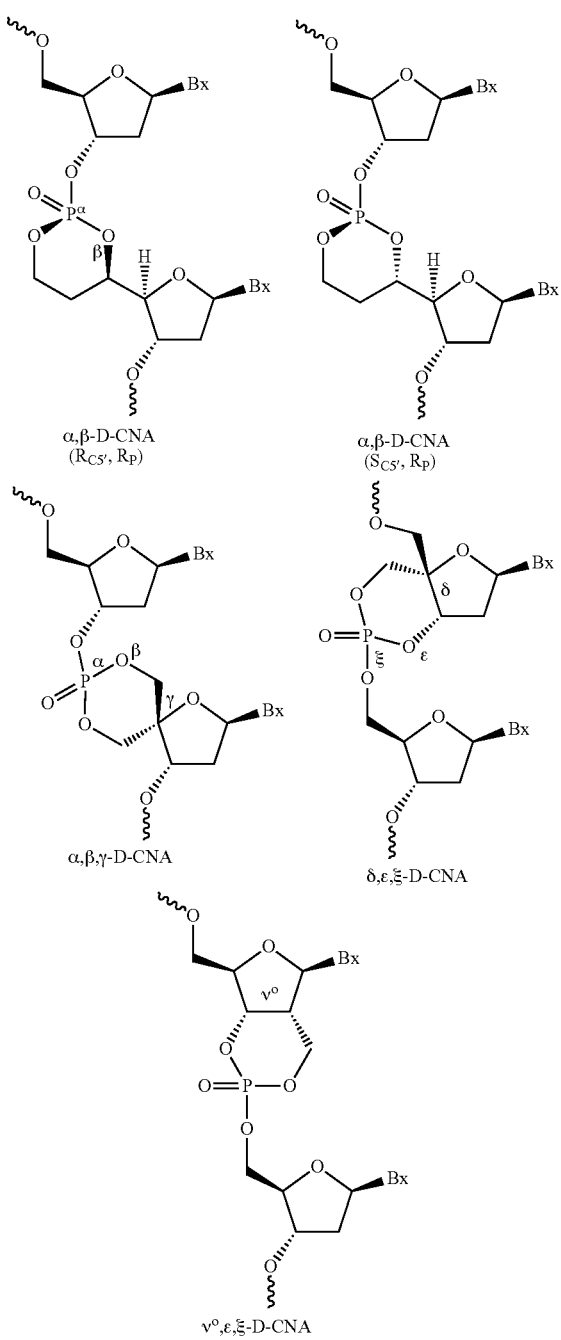

II. Certain Motifs

In certain embodiments, oligomeric compounds described herein comprise or consist of oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, oligomeric compounds described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, a modified oligonucleotide comprises or consists of a gapmer. The sugar motif of a gapmer defines the regions of the gapmer: 5'-region, central region, and 3'-region. The positions of the nucleosides within each region are counted beginning at the 5'-end of each region. Each region of a gapmer is connected by an internucleoside linkage, as are the nucleosides within each region. Each nucleoside of the 5'-region and each nucleoside of the 3'-region comprise a 2'-modified furanosyl sugar moiety. The nucleoside at the first position (position 1) of the central region and the nucleoside at the last position of the central region are adjacent to the 5'-region and 3'-region, respectively, and each comprise a sugar moiety independently selected from a 2'-deoxyfuranosyl sugar moiety or a sugar surrogate. Unlike the nucleosides at the first and last positions of the central region, the nucleosides at the other positions within the central region may comprise a 2'-modified furanosyl sugar moiety. In certain embodiments, the 2'-modified furanosyl sugar moiety in the 5' and 3'-regions is a 4'-2'-bicyclic sugar moiety. In certain embodiments, the 2'-modified furanosyl sugar moiety in the 5' and 3' regions is a cEt. In certain embodiments, the 2'-modified furanosyl sugar moiety is a 2'-MOE furanosyl sugar moiety. In certain embodiments, each nucleoside within the gap supports RNase H cleavage. In certain embodiments, a plurality of nucleosides within the gap support RNase H cleavage. In certain embodiments, the nucleoside at the first and last positions of the central region adjacent to the 5' and 3' regions are DNA nucleosides.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification of each sugar moiety of each wing and the gap nucleosides comprise 2'-β-D-deoxyribosyl sugar moieties. Thus, a 5-10-5 MOE gapmer consists of 5 linked nucleosides comprising 2'-MOE-β-D-ribofuranosyl sugar moieties in the 5'-wing, 10 linked nucleosides comprising a 2'-β-D-deoxyribosyl sugar moiety in the gap, and 5 linked nucleosides comprising 2'-MOE-β-D-ribofuranosyl sugar moieties in the 3'-wing. A 3-10-3 cEt gapmer consists of 3 linked nucleosides comprising a cEt in the 5'-wing, 10 linked nucleosides comprising a 2'-β-D-deoxyribosyl sugar moiety in the gap, and 3 linked nucleosides comprising a cEt in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

The sugar motif of a 3-10-3 cEt gapmer may also be denoted by the notation kkk-d(10)-kkk, wherein each "k" represents a cEt and each "d" represents a 2'-β-D-deoxyribosyl sugar moiety. This sugar motif is independent of the nucleobase sequence, the internucleoside linkage motif, and any nucleobase modifications. A 5-10-5 MOE gapmer may be denoted by the notation eeeee-d(10)-eeeee or e(5)-d(10)-e(5), wherein each "e" represents a 2'-MOE-β-D-ribofuranosyl sugar moiety, and each "d" represents a 2'-β-D-deoxyribosyl sugar moiety.

B. Certain Nucleobase Motifs

In certain embodiments, oligomeric compounds described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, one nucleoside comprising a modified nucleobase is in the central region of a modified oligonucleotide. In certain such embodiments, the sugar moiety of said nucleoside is a 2'-β-D-deoxyribosyl moiety. In certain such embodiments, the modified nucleobase is selected from: 5-methyl cytosine, 2-thiopyrimidine, 2-thiothymine, 6-methyladenine, inosine, pseudouracil, or 5-propynepyrimidine.

C. Certain Internucleoside Linkage Motifs

In certain embodiments, oligomeric compounds described herein comprise or consist of oligonucleotides. In certain embodiments, oligonucleotides comprise modified and/or unmodified internucleoside linkages arranged along the oligonucleotide or region thereof in a defined pattern or motif. In certain embodiments, each internucleoside linkage is a phosphodiester internucleoside linkage (P=O). In certain embodiments, each internucleoside linkage of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the internucleoside linkages within the central region of a modified oligonucleotide are all modified. In certain such embodiments, some or all of the internucleoside linkages in the 5'-region and 3'-region are unmodified phosphate linkages. In certain embodiments, the terminal internucleoside linkages are modified. In certain embodiments, the internucleoside linkage motif comprises at least one phosphodiester internucleoside linkage in at least one of the 5'-region and the 3'-region, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the 5'-region and 3'-region are (Sp) phosphorothioates, and the central region comprises at least one Sp, Sp, Rp motif. In certain embodiments, populations of modified oligonucleotides are enriched for modified oligonucleotides comprising such internucleoside linkage motifs.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are phosphorothioate internucleoside linkages. In certain embodiments, all of the internucleoside linkages of the oligonucleotide are phosphorothioate internucleoside linkages. In certain embodiments, each internucleoside linkage of the oligonucleotide is selected from phosphodiester or phosphate and phosphorothioate. In certain embodiments, each internucleoside linkage of the oligonucleotide is selected from phosphodiester or phosphate and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, modified oligonucleotides comprise a linkage motif comprising all phosphorothioate linkages except for one or two methylphosphonate linkages. In certain embodiments, one methylphosphonate linkage is in the central region of an oligonucleotide.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

III. Certain Modified Oligonucleotides

In certain embodiments, oligomeric compounds described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of a modified oligonucleotide may be modified or unmodified and may or may not follow the modification pattern of the sugar moieties. Likewise, such modified oligonucleotides may comprise one or more modified nucleobase independent of the pattern of the sugar modifications. Furthermore, in certain instances, a modified oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar moiety, region or segment B consists of 6-10 linked nucleosides having a specified sugar moiety, and region or segment C consists of 2-6 linked nucleosides having a specified sugar moiety. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a "C" in an oligonucleotide sequence. In certain embodiments, when a DNA nucleoside or DNA-like nucleoside that comprises a T in a DNA sequence is replaced with a RNA-like nucleoside, including a nucleoside comprising a 2'-OMe modified sugar moiety, the nucleobase T is replaced with the nucleobase U. Each of these compounds has an identical target RNA.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. Certain Conjugated Compounds

In certain embodiments, the oligomeric compounds described herein comprise or consist of an oligonucleotide (modified or unmodified) and optionally one or more conjugate groups and/or terminal groups. Conjugate groups consist of one or more conjugate moiety and a conjugate linker that links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO* 1, 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate linkers

Conjugate moieties are attached to oligonucleotides through conjugate linkers. In certain oligomeric compounds, a conjugate linker is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an oligomeric compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the compound has been taken up, it is desirable that the conjugate group be cleaved to release the unconjugated oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides.

In certain such embodiments, one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is a nucleoside comprising a 2'-deoxyfuranosyl that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage. In certain such embodiments, the cleavable moiety is a nucleoside comprising a 2'-β-D-deoxyribosyl sugar moiety. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

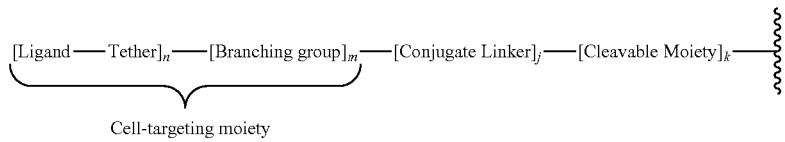

Cell-targeting moiety wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," Bioconjugate Chemistry, 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," J Med. Chem. 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, (3-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-0-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds described herein comprise a conjugate group found in any of the following references: Lee, Carbohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycobiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromb Vasc Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; U52006/0148740; US2008/0281044; US2010/0240730; US2003/0119724; US2006/0183886; U52008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Oligomeric compounds described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more oligomeric compounds or a salt thereof. In certain embodiments, the oligomeric compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more oligomeric compound. In certain embodiments, such pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS.

Compositions and methods for the formulation of pharmaceutical compositions are dependent upon a number of criteria, including, but not limited to, route of administration, extent of disease, or dose to be administered.

An oligomeric compound described herein complementary to a target nucleic acid can be utilized in pharmaceutical compositions by combining the oligomeric compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising an oligomeric compound complementary to a target nucleic acid and a pharmaceutically acceptable diluent. In certain embodiments, the pharmaceutically acceptable diluent is phosphate buffered saline. In certain embodiments, the oligomeric compound comprises or consists of a modified oligonucleotide provided herein.

Pharmaceutical compositions comprising oligomeric compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the oligomeric compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Certain Mechanisms

In certain embodiments, oligomeric compounds described herein comprise or consist of modified oligonucleotides. In certain such embodiments, the oligomeric compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Nucleosides that are sufficiently "DNA-like" to elicit RNase H activity are referred to as DNA mimics herein. Further, in certain embodiments, one or more non-DNA-like nucleoside in in the RNA:DNA duplex is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Certain Toxicities

For a compound to be a viable therapeutic agent, it must be safe at therapeutically relevant doses. It has become clear that toxicity of oligonucleotides can arise from one or more of several mechanisms. For example, some oligonucleotides hybridize an unintended RNA (or "off-target RNA") resulting in reduction of the off-target RNA and the protein encoded by that off-target RNA. Such unintended protein reduction may have toxic consequences. The data disclosed herein demonstrate that toxicity can result from oligonucleotides binding certain proteins and subsequent sub-cellular localization of the oligonucleotide/protein complex. Other mechanisms of toxicity may also contribute. Of course, for an oligonucleotide to be a suitable drug for use in therapy, all of the forms or mechanisms of toxicity must be acceptably low.

Since toxicity can result from multiple mechanisms, the observed toxicity for a particular compound will typically be the most toxic mechanism or the mechanism that results in toxicity at the lowest dose for that particular compound (the "limiting toxicity"). Changes to a compound that reduce the limiting toxicity will result in a compound having an observable improvement in toxic profile. Changes that reduce a form of toxicity that is not the limiting toxicity may not result in an observable improvement in toxicity, because the improvement may be masked by the limiting toxicity. In such instances, the improvement to a non-limiting toxicity can nonetheless have value. For example, the limiting toxicity might be controlled through additional changes to the compound or through changes in dose or dose frequency or through use of a separate therapy that mitigates the limiting toxicity; at that point, a previously masked toxicity would become limiting. Alternatively, in certain circumstances, the limiting toxicity might be less relevant (for example, if the drug is intended for delivery to specific tissues not affected by the limiting toxicity or if the compound is for the treatment of severe or life-threatening indications where a certain degree of the limiting toxicity may be acceptable). In such instances, improvements to a non-limiting toxicity can have significant benefit. Further, the various forms and mechanisms of toxicity may have a cumulative effect, particularly over time. Accordingly, the beneficial effects of improvements to a particular mechanism of toxicity might be masked at an early time point where another mechanism is the limiting toxicity, but over time such masked toxicity may contribute or even predominate the overall safety profile.

In certain embodiments, oligomeric compounds of the invention have improved toxicity profiles compared to standard gapmer compounds having a gap comprising only nucleosides having 2'-β-D-deoxyribosyl sugar moieties and the same nucleobase sequence. It should be noted that some standard gapmers are suitable therapeutic agents. Toxicity is driven in part by nucleobase sequence (oligonucleotides having identical chemical modification patterns but different sequences can have vastly different safety profiles). When one attempts to modulate a particular target RNA, one might find an antisense oligonucleotide that has an acceptable safety profile at therapeutic doses. On other occasions, however, the most active/potent oligonucleotides have unacceptable toxicity. In such instances, it is desirable to modify such compounds to reduce their toxicity, ideally with no loss or only modest loss in activity/potency. In certain embodiments, modification motifs described herein reduce toxicity with little or no loss in activity/potency.

Without limitation to any particular mechanism, it is believed that certain modification motifs described herein may reduce interactions between an oligomeric compound and certain proteins. In certain embodiments, such interactions result in the limiting toxicity and so disruption of these interactions results in observable improvements in the toxicity profile. In certain embodiments, the motifs described herein may alter off-target cleavage. In certain embodiments, the disclosed motifs improve toxicity through an undefined mechanism. In certain embodiments, the motifs may improve toxicity through multiple mechanisms, including, but not limited to those described here.

Disclosed herein for comparison are certain gapmer oligonucleotides that are notably more toxic than other gapmers. These toxic gapmer oligonucleotides cause rapid delocalization of paraspeckle proteins, including p54nrb, to nucleoli, possibly due to the binding of these toxic oligonucleotides to the p54nrb protein and/or other paraspeckle proteins. Certain such toxic oligonucleotides have both more global protein binding than their nontoxic (or less toxic) counterparts and have higher binding affinities (i.e., lower Kd values) for key paraspeckle proteins, including p54nrb and RNase H1. Certain such toxic oligonucleotides, but not nontoxic (or less toxic) oligonucleotides, cause the paraspeckle proteins PSF, PSPC1, and FUS to localize to the nucleoli as well, as observed across a number of mouse and human cell types. In certain instances, the nucleolar delocalization of paraspeckle proteins is mediated by RNase H1. Importantly, in some instances, nontoxic (or less toxic) modified oligonucleotides with the same chemical modification pattern (gapmer motif) and a different sequence do not cause the delocalization of p54nrb to nucleoli. This early event leads to nucleolar stress, p53 activation, and apoptotic cell death, both in vitro across a number of mammalian cell types and in vivo in mice. These results were consistent for gapmers with toxic sequences and containing several different commonly-used chemical modifications of modified oligonucleotides, including LNA, cEt, and 2'-MOE.

In certain embodiments, the instant invention is directed towards modified oligonucleotides having chemical modifications that can alleviate the observed toxicity. In certain embodiments, such toxicity is related to protein binding and the resulting nucleolar mislocalization of proteins, such as paraspeckle proteins described above. In certain embodiments, the incorporation of a safety-enhancing nucleoside at position 2, 3 or 4 of the central region (or "gap") of the modified oligonucleotide can reduce both global protein binding and the associated toxicity. In certain embodiments, the safety-enhancing nucleoside is a nucleoside comprising a 2'-OMe β-D-deoxyribosyl sugar moiety at position 2 of the central region. Incorporation of a nucleoside comprising a 2'-OMe-β-D-deoxyribosyl sugar moiety at position 2 of the central region in a toxic 3-10-3, 3-10-4, 4-10-3 cEt gapmer, a 3-10-3 LNA gapmer, a 5-10-5 MOE gapmer, or several cEt/MOE mixed wing gapmers reduced cellular toxicity and apoptosis in vitro and hepatoxicity in vivo across a wide variety of sequences, while having only a modest effect, if any, on antisense activity. In certain embodiments, incorporation of a nucleoside comprising a 2'-OMe-β-D-deoxyribosyl sugar moiety at position 2 of the central region also reduced delayed neurotoxicity, suggesting a common mechanism for delayed neurotoxicity and hepatoxicity. In certain embodiments, the safety-enhancing nucleoside is a nucleoside comprising a 5'-alkyl or 5'-allyl modified β-D-deoxyribosyl sugar moiety at position 3 or position 4 of the central region. In certain instances, incorporation of a nucleoside comprising a 5'-alkyl β-D-deoxyribosyl sugar moiety at position 3 or position 4 of the central region of a 3-10-3 cEt gapmer reduces cellular toxicity and apoptosis in vitro and hepatoxicity in vivo across a variety of sequences, while having a modest effect, if any, on antisense activity. In certain embodiments, the incorporation of a safety-enhancing internucleoside linkage between the nucleosides at positions 2-3 or positions 3-4 of the central region can reduce toxicity. In certain embodiments, one or more of a safety-enhancing linkages linking the nucleosides from positions 2-4 of the central region is a neutral linkage. In certain embodiments, one or more of a safety-enhancing linkages linking the nucleosides from positions 2-4 of the central region is a 2'-5' internucleoside linkage. The instant invention extends to any chemical modification introduced at positions 2, 3 or 4 of the central region, including modifications to nucleosides and to internucleoside linkages. In certain embodiments, such modification reduces in vitro toxicity (compared to the modified oligonucleotide lacking the safety enhancing nucleoside at positions 2, 3 or 4 of the central region or lacking the safety enhancing internucleoside linkage between positions 2-3 or 3-4 of the central region) as measured by the caspase 3/7 assay and/or in vivo hepatotoxicity, as measured by ALT or AST, and/or in vivo neurotoxicity, as measured by an FOB score or accumulation of markers of glial inflammation, Aifl and GFAP.

In certain embodiments, introducing chemical modifications at positions 2, 3 or 4 of the central region can significantly reduce toxicity with only a modest loss in potency, if any. This leads to an improvement in therapeutic index for a given target sequence. In certain cases, such improvements in therapeutic index are large enough to allow further drug development based on a compound targeted to a previously-toxic (but potent) sequence.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron.

Certain Compounds Having Central Region Modifications

In certain embodiments, the oligomeric compounds herein comprise a gapmer comprising one or more an altered nucleotides in the central region of the gapmer. Each of such oligomeric compounds has a corresponding parent oligomeric compound that is identical to the first oligomeric compound except that is lacking the one or more altered nucleotides in the central region of the gapmer. Examples of such parent oligomeric compounds and their corresponding identical oligomeric compounds lacking the altered nucleotide are found in Tables 1 and 2 of Example 1 as well as throughout the Examples section. In Example 1, 558807 is the parent oligonucleotide. In certain embodiments, the central region of a parent oligomeric compound comprises only phosphodiester and/or phosphorothioate internucleoside linkages, unmodified nucleobases and/or 5-methylcytosine, and unmodified, 2'β-D-deoxyribosyl sugar moieties.

In certain embodiments, the present disclosure provides oligomeric compounds that comprise a gapmer comprising one or more altered nucleotides in the central region of the gapmer that have an increased therapeutic index an/or increased tolerability compared to the corresponding parent oligomeric compounds. In certain such embodiments, the modification or modifications of the central region of the oligomeric compounds with increased therapeutic index and/or increased tolerability are particularly useful in providing oligomeric compounds having reduced toxicity without significantly altering the potency. The modifications in the central region described herein can be at any position in the central region, and examples of embodiments comprising modifications at such positions are disclosed in the numbered embodiments and Examples. In certain embodiments, the altered nucleotide is an altered nucleoside attached to a phosphorothioate or phosphodiester internucleoside linkage. In a preferred embodiment, the altered nucleotide is at positions 1-4 of the central region of the modified oligonucleotide. In another preferred embodiment, the altered nucleotide comprises a nucleoside comprising a 2'-modified sugar moiety at position 2 of the central region of the modified oligonucleotide. In another preferred embodiment, the altered nucleotide comprises a nucleoside comprising a 5'-modified sugar moiety at positions 3 or 4 of the central region of the modified oligonucleotide. In another preferred embodiment, the altered nucleotide comprises a neutral internucleoside linkage between positions 2-3 or positions 3-4 of the central region of the modified oligonucleotide.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}$H hydrogen atoms. Isotopic substitutions encompassed by the compounds herein include but are not limited to: $^{2}$H or $^{3}$H in place of $^{1}$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine nucleobase could be described as a DNA having an RNA sugar, or as an RNA having a DNA nucleobase.

Accordingly, nucleic acid sequences provided herein, including, but not limited to those in the sequence listing, are intended to encompass nucleic acids containing any combination of unmodified or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^{m}$CGAUCG," wherein mC indicates a cytosine base comprising a methyl group at the 5-position. In certain cases, compounds comprising a uridine nucleobase and a 2'-OMe sugar moiety are compared to compounds comprising a thymidine nucleobase with a 2'-β-D-deoxyribosyl sugar moiety at the same position. While these compounds have different SEQ ID NO:, they are not considered distinct sequences, and they have identical target RNA. In certain cases, compounds comprising a cytosine nucleobase and a 2'-OMe sugar moiety are compared to compounds comprising a 5-methylcytosine nucleobase and a 2'-β-D-deoxyribosyl sugar moiety at the same position.

In the Examples below, modified oligonucleotides are represented by a chemistry notation, always shown in the 5'-to-3' direction, of the format $B_{sl}B_{sl}{}^{m}B_{s}$, where "B" or "$^{m}$B" represents the nucleobase, with a superscript "m" before "B" representing a 5-methyl modification, the subscript in position "s" represents the sugar moiety, and the subscript in position "l" represents the 5'-to-3' internucleoside linkage.

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1 Effect of Position-Specific
2'-Modifications on In Vitro Activity and In Vivo
Liver Toxicity of Modified Oligonucleotides
Complementary to CXCL12

Modified oligonucleotides were synthesized with kkk-x-d(9)-kkk, kkk-d-x-d(8)-kkk, kkk-dd-x-d(7)-kkk or kkk-d(3)-x-d(6)-kkk sugar motifs, respectively, where "x" represents a sugar moiety having the modification indicated in the table below, "k" represents a cEt, and "d" represents an unmodified, 2'-β-D-deoxyribosyl sugar moiety. These modified oligonucleotides were compared to the otherwise identical modified oligonucleotide lacking an altered nucleotide in the central region, a 3-10-3 cEt gapmer, having three cEt nucleosides in each of the 5' and 3' regions and 10 DNA nucleosides in the central region. Each internucleoside linkage is a phosphorothioate. The compounds in the table below are 100% complementary to mouse CXCL12, GEN-BANK NT_039353.7 truncated from 69/430,515 to 69/445,350 (SEQ ID NO: 1), at position 6877 to 6892.

13; probe sequence: CCATCGGTGCAAACCTA-CAGAAGCAGTATG, SEQ ID NO: 14). RAPTOR is a sentinel gene that can be indicative of toxicity, as described in US 20160160280, hereby incorporated by reference.

For acute in vivo toxicity studies, three BALB/C mice per group were administered 150 mg/kg modified oligonucleotide by subcutaneous injection and sacrificed 72 hours later. Three mice were administered an injection of saline as a control. Plasma levels of ALT were measured using an automated clinical chemistry analyzer. Increased ALT is indicative of acute liver toxicity.

TABLE 1

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936049 | 1 | 2'-OMe | $G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 828910 | 1 | 2'-MOE | $G_{ks}{}^mC_{ks}A_{ks}T_{es}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936050 | 1 | cEt | $G_{ks}{}^mC_{ks}A_{ks}T_{ks}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 936054 | 1 | 2'-FANA | $G_{ks}{}^mC_{ks}A_{ks}U_{(FANA)s}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936048 | 1 | 2'-ribo-F | $G_{ks}{}^mC_{ks}A_{ks}U_{fs}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936053 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 828911 | 2 | 2'-MOE | $G_{ks}{}^mC_{ks}A_{ks}T_{ds}G_{es}T_{ds}T_{ds}{}^mC_{ds}T_{ds}{}^mC_{ds}A_{ds}{}^mC_{ds}A_{ds}T_{ks}T_{ks}A_k$ | 18 |
| 1070041 | 2 | cEt | $G_{ks}{}^mC_{ks}A_{ks}T_{ds}G_{ks}T_{ds}T_{ds}{}^mC_{ds}T_{ds}{}^mC_{ds}A_{ds}{}^mC_{ds}A_{ds}T_{ks}T_{ds}A_k$ | 18 |
| 1061314 | 2 | 2'-OH (RNA) | $G_{ks}{}^mC_{ks}A_{ks}T_{ds}G_{rs}T_{ds}T_{ds}{}^mC_{ds}T_{ds}{}^mC_{ds}A_{ds}{}^mC_{ds}A_{ds}T_{ks}T_{ks}A_k$ | 18 |
| 936051 | 2 | 2'-FANA | $G_{ks}{}^mC_{ks}A_{ks}T_{ds}G_{(FANA)s}T_{ds}T_{ds}{}^mC_{ds}T_{ds}{}^mC_{ds}A_{ds}{}^mC_{ds}A_{ds}T_{ks}T_{ks}A_k$ | 18 |
| 936052 | 2 | 2'-ribo-F | $G_{ks}{}^mC_{ks}A_{ks}T_{ds}G_{fs}T_{ds}T_{ds}{}^mC_{ds}T_{ds}{}^mC_{ds}A_{ds}{}^mC_{ds}A_{ds}T_{ks}T_{ks}A_k$ | 18 |
| 892826 | 3 | 2'-OMe | $G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_k$ | 20 |
| 828912 | 3 | 2'-MOE | $G_{ks}{}^mC_{ks}A_{ks}T_{ds}G_{ds}T_{es}T_{ds}{}^mC_{ds}T_{ds}{}^mC_{ds}A_{ds}{}^mC_{ds}A_{ds}T_{ks}T_{ks}A_k$ | 18 |
| 892816 | 3 | cEt | $G_{ks}{}^mC_{ks}A_{ks}T_{ds}G_{ds}T_{ks}T_{ds}{}^mC_{ds}T_{ds}{}^mC_{ds}A_{ds}{}^mC_{ds}A_{ds}T_{ks}T_{ks}A_k$ | 18 |
| 895596 | 3 | 2'-FANA | $G_{ks}{}^mC_{ks}A_{ks}T_{ds}G_{ds}U_{(FANA)s}T_{ds}{}^mC_{ds}T_{ds}{}^mC_{ds}A_{ds}{}^mC_{ds}A_{ds}T_{ks}T_{ks}A_k$ | 20 |
| 892821 | 3 | 2'-ribo-F | $G_{ks}{}^mC_{ks}A_{ks}T_{ds}G_{ds}U_{fs}T_{ds}{}^mC_{ds}T_{ds}{}^mC_{ds}A_{ds}{}^mC_{ds}A_{ds}T_{ks}T_{ks}A_k$ | 20 |
| 892819 | 4 | 2'-OMe | $G_{ks}{}^mC_{ks}A_{ks}T_{ds}G_{ds}T_{ds}U_{ms}{}^mC_{ds}T_{ds}{}^mC_{ds}A_{ds}{}^mC_{ds}A_{ds}T_{ks}T_{ks}A_k$ | 21 |
| 828913 | 4 | 2'-MOE | $G_{ks}{}^mC_{ks}A_{ks}T_{ds}G_{ds}T_{ds}T_{es}{}^mC_{ds}T_{ds}{}^mC_{ds}A_{ds}{}^mC_{ds}A_{ds}T_{ks}T_{ks}A_k$ | 18 |
| 892817 | 4 | cEt | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ds}A_k$ | 18 |
| 895595 | 4 | 2'-FANA | $G_{ks}{}^mC_{ks}A_{ks}T_{ds}G_{ds}T_{ds}U_{(FANA)s}{}^mC_{ds}T_{ds}{}^mC_{ds}A_{ds}{}^mC_{ds}A_{ds}T_{ks}T_{ks}A_k$ | 21 |
| 892822 | 4 | 2'-ribo-F | $G_{ks}{}^mC_{ks}A_{ks}T_{ds}G_{ds}T_{ds}U_{fs}{}^mC_{ds}T_{ds}{}^mC_{ds}A_{ds}{}^mC_{ds}A_{ds}T_{ks}T_{ks}A_k$ | 21 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, approximately 20,000 mouse 3T3-L1 cells were electroporated with 0, 27 nM, 82 nM, 247 nM, 740 nM, 2,220 nM, 6,660 nM or 20,000 nM antisense oligonucleotide. mRNA was harvested and analyzed by RT-qPCR. CXCL12 mRNA was detected with primer probe set RTS2605 (forward sequence CCAGAGCCAACGT-CAAGCAT, SEQ ID NO: 9; reverse sequence: CAGCCGTGCAACAATCTGAA, SEQ ID NO: 10; probe sequence: TGAAAATCCTCAACACTCCAAACTGTGCC, SEQ ID NO: 11) and RAPTOR mRNA was detected with primer probe set RTS3420 (forward sequence GCCCTCAGAAAGCTCTGGAA, SEQ ID NO: 12; reverse sequence: TAGGGTCGAGGCTCTGCTTGT, SEQ ID NO:

TABLE 2

Activity and toxicity of modified oligonucleotides complementary CXCL12

| Compound ID | position of altered nucleotide in central region | sugar modification of altered nucleotide | in vitro CXCL12 IC$_{50}$ (µM) | in vitro RAPTOR IC$_{50}$ (µM) | ALT @ 150 mg/kg (IU/L) |
|---|---|---|---|---|---|
| PBS | n/a | n/a | n/a | n/a | 23 |
| 558807 | n/a | n/a | 0.2 | 1.26 | n.d.** |
| 936049 | 1 | 2'-OMe | 0.17 | 4.8 | 8622 |
| 828910 | 1 | 2'-MOE | 0.12 | 7.2 | 2175 |
| 936050 | 1 | cEt | 0.15 | 6.5 | 912 |
| 936054 | 1 | 2'-FANA | 0.12 | 9.9 | 5755 |
| 936048 | 1 | 2'-ribo-F | 0.15 | 1.9 | death |
| 936053 | 2 | 2'-OMe | 0.17 | >>10 | 46 |
| 828911 | 2 | 2'-MOE | 0.42 | >>10 | 27 |
| 1070041 | 2 | cEt | 0.52 | n.d. | 96 |
| 1061314 | 2 | 2'-OH (RNA) | n.d. | n.d. | 26 |
| 936051 | 2 | 2'-FANA | 0.12 | 2.34 | death |
| 936052 | 2 | 2'-ribo-F | 0.19 | 13.5 | 1110 |
| 892826 | 3 | 2'-OMe | 0.21 | 7.1 | 10463 |
| 828912 | 3 | 2'-MOE | 0.28 | 10 | 701 |
| 892816 | 3 | cEt | 0.17 | 11 | 278 |
| 895596 | 3 | 2'-FANA | 0.12 | 7.4 | 17369 |
| 892821 | 3 | 2'-ribo-F | 0.18 | 4.5 | 6333 |
| 892819 | 4 | 2'-OMe | 0.18 | >10 | 565 |

TABLE 2-continued

Activity and toxicity of modified oligonucleotides complementary CXCL12

| Compound ID | position of altered nucleotide in central region | sugar modification of altered nucleotide | in vitro CXCL12 IC$_{50}$ (μM) | in vitro RAPTOR IC$_{50}$ (μM) | ALT @ 150 mg/kg (IU/L) |
|---|---|---|---|---|---|
| 828913 | 4 | 2'-MOE | 0.22 | 10 | 2474 |
| 892817 | 4 | cEt | 0.23 | 9 | 5264 |
| 895595 | 4 | 2'-FANA | 0.08 | 8.8 | 22082 |
| 892822 | 4 | 2'-ribo-F | 0.04 | 4.85 | 4020 |

**558807 treatment at 16.7 mg/kg leads to an ALT of 586 IU/L in this experiment; mice that are treated with 558807 at 150 mg/kg typically experience death before 72 hours post-treatment.

For the in vitro study reported in the tables below, 3T3-L1 cells were electroporated with 27 nM, 80 nM, 250 nM, 740 nM, 2,222 nM, 6,667 nM, or 20,000 nM of modified oligonucleotide and levels of P21 and Gadd45a were measured by RT-qPCR. Levels of Gadd45a were analyzed using primer probe set Mm00432802_m1 (ThermoFisher). Levels of P21 were analyzed using primer probe set Mm04207341_m1 (ThermoFisher).

TABLE 2b in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 110 | 98 | 69 | 99 | 117 | 228 | 488 |
| 936049 | 63 | 116 | 96 | 93 | 121 | 151 | 199 |
| 936053 | 151 | 144 | 158 | 160 | 152 | 143 | 155 |
| 892826 | 140 | 104 | 104 | 128 | 138 | 181 | 177 |

TABLE 2c in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 558807 | 115 | 120 | 111 | 136 | 155 | 237 | 298 |
| 936049 | 101 | 124 | 131 | 158 | 172 | 212 | 276 |
| 936053 | 144 | 227 | 175 | 203 | 197 | 201 | 193 |
| 892826 | 132 | 114 | 134 | 152 | 147 | 163 | 158 |

For the in vitro study reported in the tables below, b.END cells were electroporated with 27 nM, 80 nM, 250 nM, 740 nM, 2,222 nM, 6,667 nM, or 20,000 nM of modified oligonucleotide and levels of P21 were measured by RT-qPCR using primer probe set Mm04207341_m1 (ThermoFisher).

TABLE 2d in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 138 | 117 | 93 | 73 | 107 | 160 | 226 |
| 936053 | 108 | 112 | 96 | 90 | 111 | 101 | 118 |
| 892826 | 112 | 112 | 114 | 107 | 117 | 116 | 137 |
| 1061314 | 126 | 128 | 103 | 115 | 128 | 122 | 112 |
| 936051 | 114 | 113 | 109 | 118 | 117 | 123 | 178 |
| 936052 | 109 | 116 | 102 | 100 | 112 | 119 | 138 |
| 828911 | 115 | 108 | 120 | 113 | 114 | 115 | 122 |
| 1070041 | 101 | 100 | 109 | 104 | 104 | 120 | 132 |

TABLE 2e in vitro Gadd45a Expression in b.END cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 558807 | 558807 | 86 | 132 | 93 | 101 | 178 | 220 |
| 936053 | 936053 | 111 | n.d. | 148 | 150 | 200 | 215 |
| 892826 | 892826 | 134 | 177 | 160 | 170 | 177 | 162 |
| 1061314 | 1061314 | 135 | 149 | 150 | 197 | 199 | 184 |
| 936051 | 936051 | 136 | 132 | 152 | 185 | 199 | 193 | 258 |
| 936052 | 936052 | 125 | 160 | 146 | 173 | 210 | 201 | 228 |
| 828911 | 828911 | 121 | 154 | 158 | 193 | 190 | 189 | 249 |
| 1070041 | 1070041 | 118 | 139 | 163 | 194 | 225 | 301 | 313 |

For the in vivo activity and toxicity study in the table below, 2 or 3 BALB/C mice per group were administered modified oligonucleotide at 1.8 mg/kg, 5.5 mg/kg, or 16.7 mg/kg by subcutaneous injection and sacrificed after 72 hours.

TABLE 2f in vivo Activity and Toxicity

| Compound ID | position of altered nucleotide in central region | sugar modification of altered nucleotide | in vivo CXCL12 ED50 (mg/kg) | ALT @5.5 mg/kg (IU/L) | ALT @ 16.7 mg/kg (IU/L) |
|---|---|---|---|---|---|
| PBS | n/a | n/a | n/a | 30 (@0 mg/kg) | |
| 558807 | n/a | n/a | 1.6 | 40 | 1721 |
| 936051 | 2 | 2'-FANA | 0.15 | 44 | 4285 |
| 936053 | 2 | 2'-OMe | 5.5 | 27 | 25 |
| 828911 | 2 | 2'-MOE | 14 | 36 | 25 |
| 936052 | 2 | 2'-ribo-F | 2.9 | 26 | 29 |

For in vivo activity and toxicity study in the table below, 3 BALB/C mice per group were administered modified oligonucleotide by subcutaneous injection and sacrificed after 72 hours. Compound 558807 was dosed at 1.8, 5.5, or 16.7 mg/kg, compounds 828911, 936052 and 936053 were dosed at 1.8, 5.5, 16.7 and 50 mg/kg, and compounds 1061315 and 1070041 were dosed at 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_m1 (ThermoFisher). Levels of P21 were analyzed using primer probe set Mm04207341_m1 (ThermoFisher). Levels of Tnfrsf10b were analyzed using primer probe set Mm00457866_m1 (ThermoFisher). Expression levels were normalized with Ribogreen® and are presented relative to levels in mice treated with PBS.

TABLE 2g

In Vivo Activity and Toxicity of modified oligonucleotides complementary to CXCL12

| Compound ID | position of altered nucleotide in central region | sugar modification of altered nucleotide | in vivo CXCL12 ED50 (mg/kg) | ALT @50 mg/kg (IU/L) | ALT @ 150 mg/kg (IU/L) |
|---|---|---|---|---|---|
| PBS | n/a | n/a | n/a | 28 (@0 mg/kg) | |
| 558807 | n/a | n/a | 2.7 | n.d.** | |
| 936053 | 2 | 2'-OMe | 4.9 | 23 | n.d. |
| 828911 | 2 | 2'-MOE | 14 | 27 | n.d. |
| 1070041 | 2 | cEt | 29 | 25 | 78 |
| 1061314 | 2 | 2'-OH (RNA) | 78 | 21 | 24 |
| 936052 | 2 | 2'-ribo-F | 4.2 | 39 | n.d. |

**558807 treatment at 16.7 mg/kg leads to an ALT of 586 IU/L; mice that are treated with 558807 at 150 mg/kg typically experience death before 72 hours post-treatment.

TABLE 2h

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 100 | 172 | 856 | n/a | n/a |
| 936053 | 61 | 99 | 91 | 92 | n/a |
| 828911 | 80 | 100 | 96 | 100 | n/a |
| 1070041 | 128 | 225 | 139 | 177 | 169 |
| 1061314 | 112 | 84 | 89 | 105 | 180 |
| 936052 | 84 | 80 | 134 | 126 | n/a |

TABLE 2i

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 102 | 267 | 790 | n/a | n/a |
| 936053 | 106 | 111 | 130 | 100 | n/a |
| 828911 | 120 | 116 | 95 | 102 | n/a |
| 1070041 | 106 | 139 | 252 | 483 | 1021 |
| 1061314 | 79 | 66 | 81 | 136 | 220 |
| 936052 | 82 | 101 | 183 | 138 | n/a |

TABLE 2j

In Vivo Dose-response of P21 mRNA upon treatment with modified oligonucleotides complementary to CXCL12

| | Expression level of P21 mRNA (% Control) | | | | |
|---|---|---|---|---|---|
| Compound ID | 1.8 mg/kg | 5.5 mg/kg | 16.7 mg/kg | 50 mg/kg | 150 mg/kg |
| 558807 | 100 | 61 | 609 | n/a | n/a |
| 936053 | 104 | 94 | 104 | 89 | n/a |
| 828911 | 90 | 145 | 52 | 92 | n/a |
| 1070041 | 28 | 93 | 83 | 132 | 264 |
| 1061314 | 45 | 59 | 30 | 34 | 178 |
| 936052 | 70 | 71 | 51 | 101 | n/a |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in above. Expression levels were normalized with Ribogreen® and are expressed relative to PBS-treated control mice.

TABLE 2k

Activity and toxicity of modified oligonucleotides complementary to CXCL12

| Compound ID | position of altered nucleotide in central region | sugar modification of altered nucleotide | ALT (IU/L) at 100 mg/kg | ALT (IU/L) at 33 mg/kg |
|---|---|---|---|---|
| 558807 | n/a | n/a | death | 3740 |
| 936049 | 1 | 2'-OMe | 3060 | 612 |
| 936053 | 2 | 2'-OMe | 42 | 21 |
| 892826 | 3 | 2'-OMe | 1127 | 2281 |

TABLE 2l

In Vivo Dose-response of CXCL12 mRNA upon treatment with modified oligonucleotides complementary to CXCL12

| | Expression level of CXCL12 mRNA (% Control) | | | |
|---|---|---|---|---|
| Compound ID | 3.37 mg/kg | 11 mg/kg | 33 mg/kg | 100 mg/kg |
| 558807 | 95 | 29 | 12 | n.d. |
| 936049 | 102 | 50 | 22 | 14 |
| 936053 | 100 | 70 | 40 | 31 |
| 892826 | 100 | 49 | 16 | 10 |

TABLE 2m

In Vivo Dose-response of P21 mRNA upon treatment with modified oligonucleotides complementary to CXCL12

| | Expression level of P21 mRNA (% Control) | | | |
|---|---|---|---|---|
| Compound ID | 3.37 mg/kg | 11 mg/kg | 33 mg/kg | 100 mg/kg |
| 558807 | 194 | 186 | 32700 | n.d. |
| 936049 | 126 | 127 | 3156 | 21746 |
| 936053 | 100 | 49 | 89 | 185 |
| 892826 | 60 | 60 | 2401 | 12981 |

Example 2 Effect of Position-Specific 5'-Modifications on In Vitro Activity and In Vivo Liver Toxicity of Modified Oligonucleotides Complementary CXCL12

Modified oligonucleotides containing 5'-methyl, 5'-allyl, and 5'-ethyl modifications at various positions were synthesized. Procedures for the synthesis of 5'-methyl and 5'-allyl analogs are detailed in WO2013022967. Procedures for the synthesis of 5'-ethyl analogs are detailed herein below in Example 39. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

TABLE 3

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^mC_{ks}A_{ks}T_{as}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1123320 | 2 | 5'-(S)-Me | $G_{ks}{}^mC_{ks}A_{ks}T_{as}G_{[(S)-\mu]s}T_{ds}T_{ds}{}^mC_{ds}T_{ds}{}^mC_{ds}A_{ds}{}^mC_{ds}A_{ds}T_{ks}T_{ks}A_k$ | 18 |
| 1123322 | 2 | 5'-(R)-Me | $G_{ks}{}^mC_{ks}A_{ks}T_{as}G_{[(R)-\mu]s}T_{ds}T_{ds}{}^mC_{ds}T_{ds}{}^mC_{ds}A_{ds}{}^mC_{ds}A_{ds}T_{ks}T_{ks}A_k$ | 18 |
| 1123479 | 2 | 55'-(R,S)-allyl | $G_{ks}{}^mC_{ks}A_{ks}T_{as}G_{[\gamma]s}T_{ds}T_{ds}{}^mC_{ds}T_{ds}{}^mC_{ds}A_{ds}{}^mC_{ds}A_{ds}T_{ks}T_{ks}A_k$ | 18 |
| 942943 | 3 | 55'-(R)-Me | $G_{ks}{}^mC_{ks}A_{ks}T_{as}G_{ds}T_{[(R)-\mu]s}T_{ds}{}^mC_{ds}T_{ds}{}^mC_{ds}A_{ds}{}^mC_{ds}A_{ds}T_{ks}T_{ks}A_k$ | 18 |
| 957908 | 3 | 5'-(S)-Me | $G_{ks}{}^mC_{ks}A_{ks}T_{as}G_{ds}T_{[(S)-\mu]s}T_{ds}{}^mC_{ds}T_{ds}{}^mC_{ds}A_{ds}{}^mC_{ds}A_{ds}T_{ks}T_{ks}A_k$ | 18 |
| 957910 | 3 | 5'-(R)-allyl | $G_{ks}{}^mC_{ks}A_{ks}T_{as}G_{ds}T_{[(R)-\gamma]s}T_{ds}{}^mC_{ds}T_{ds}{}^mC_{ds}A_{ds}{}^mC_{ds}A_{ds}T_{ks}T_{ks}A_k$ | 18 |
| 957912 | 3 | 5'-(S)-allyl | $G_{ks}{}^mC_{ks}A_{ks}T_{as}G_{ds}T_{[(S)-\gamma]s}T_{ds}{}^mC_{ds}T_{ds}{}^mC_{ds}A_{ds}{}^mC_{ds}A_{ds}T_{ks}T_{ks}A_k$ | 18 |
| 1175787 | 3 | 5'-(R)-Et | $G_{ks}{}^mC_{ks}A_{ks}T_{as}G_{ds}T_{[(R)-\epsilon]s}T_{ds}{}^mC_{ds}T_{ds}{}^mC_{ds}A_{ds}{}^mC_{ds}A_{ds}T_{ks}T_{ks}A_k$ | 18 |
| 1175785 | 3 | 5'-(S)-Et | $G_{ks}{}^mC_{ks}A_{ks}T_{as}G_{ds}T_{[(S)-\epsilon]s}T_{ds}{}^mC_{ds}T_{ds}{}^mC_{ds}A_{ds}{}^mC_{ds}A_{ds}T_{ks}T_{ks}A_k$ | 18 |
| 942944 | 4 | 5'-(R)-Me | $G_{ks}{}^mC_{ks}A_{ks}T_{as}G_{ds}T_{ds}T_{[(R)-\mu]s}{}^mC_{ds}T_{ds}{}^mC_{ds}A_{ds}{}^mC_{ds}A_{ds}T_{ks}T_{ks}A_k$ | 18 |
| 957909 | 4 | 5'-(S)-Me | $G_{ks}{}^mC_{ks}A_{ks}T_{as}G_{ds}T_{ds}T_{[(S)-\mu]s}{}^mC_{ds}T_{ds}{}^mC_{ds}A_{ds}{}^mC_{ds}A_{ds}T_{ks}T_{ks}A_k$ | 18 |
| 957911 | 4 | 5'-(R)-allyl | $G_{ks}{}^mC_{ks}A_{ks}T_{as}G_{ds}T_{ds}T_{[(R)-\gamma]s}{}^mC_{ds}T_{ds}{}^mC_{ds}A_{ds}{}^mC_{ds}A_{ds}T_{ks}T_{ks}A_k$ | 18 |
| 957913 | 4 | 5'-(S)-allyl | $G_{ks}{}^mC_{ks}A_{ks}T_{as}G_{ds}T_{ds}T_{[(S)-\gamma]s}{}^mC_{ds}T_{ds}{}^mC_{ds}A_{ds}{}^mC_{ds}A_{ds}T_{ks}T_{ks}A_k$ | 18 |
| 1175786 | 4 | 5'-(R)-Et | $G_{ks}{}^mC_{ks}A_{ks}T_{as}G_{ds}T_{ds}T_{[(R)-\epsilon]s}{}^mC_{ds}T_{ds}{}^mC_{ds}A_{ds}{}^mC_{ds}A_{ds}T_{ks}T_{ks}A_k$ | 18 |
| 1175782 | 4 | 5'-(S)-Et | $G_{ks}{}^mC_{ks}A_{ks}T_{as}G_{ds}T_{ds}T_{[(S)-\epsilon]s}{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety. A subscript "k" indicates a cET. A subscript "s" indicates a phosphorothioate internucleoside linkage. A subscript "[μ]" indicates a 5'-(R,S)-Me-β-D-2'-deoxyribosyl sugar moiety. A subscript "[(R)-μ]" indicates a 5'-(R)-Me-β-D-2'-deoxyribosyl sugar moiety. A subscript "[(S)-μ]" indicates a 5'-(S)-Me-β-D-2'-deoxyribosyl sugar moiety. A subscript "[γ]" indicates a 5'-(R,S)-allyl-β-D-2'-deoxyribosyl sugar moiety. A subscript "[(R)-γ]" indicates a 5'-(R)-allyl-β-D-2'-deoxyribosyl sugar moiety. A subscript "[(S)-γ]" indicates a 5'-(S)-allyl-β-D-2'-deoxyribosyl sugar moiety. A subscript "[ε]" indicates a 5'-(R,S)-ethyl-β-D-2'-deoxyribosyl sugar moiety. A subscript "[(R)-ε]" indicates a 5'-(R)-ethyl-β-D-2'-deoxyribosyl sugar moiety. A subscript "[(S)-ε]" indicates a 5'-(S)-ethyl-β-D-2'-deoxyribosyl sugar moiety.

Experimental Procedures & Results

In vitro activity and in vivo activity and toxicity experiments were performed essentially as described in Example 1. For in vivo toxicity studies, a single BALB/C mouse per modified oligonucleotide was administered 150 mg/kg modified oligonucleotide by subcutaneous injection and sacrificed 72 hours later. For the in vivo activity study in the table below, 2 BALB/C mice per group were administered 1.8 mg/kg, 5.5 mg/kg, 16.7 mg/kg, 50 mg/kg dose of modified oligonucleotide subcutaneously and sacrificed after 72 hours. For 558807, only 1.8 mg/kg, 5.5 mg/kg, and 16.7 mg/kg doses were tested for dose response, due to acute toxicity of higher doses. Tissues were collected and liver mRNA was isolated and levels of CXCL12 were measured by RT-qPCR with primer probe set RTS2605 as described above.

TABLE 4

Activity and toxicity of modified oligonucleotides complementary CXCL12

| Compound ID | position of altered nucleotide in central region | sugar modification of altered nucleotide | In vitro IC50 CXCL12 (μM) | Raptor IC50 (tox marker) | in vivo ED50 (mg/kg) | ALT (at 150 mg/kg) |
|---|---|---|---|---|---|---|
| 558807 | n/a | Parent | 0.11 | 1.3 | 2.9 | n.d.** |
| 942943 | 3 | 5'-(R)-Me | 0.118 | 23 | 2.8 | 2466 |
| 942944 | 4 | 5'-(R)-Me | 0.169 | 22 | 3 | 233 |
| 957908 | 3 | 5'-(S)-Me | 0.193 | 33 | 3.7 | 52 |
| 957909 | 4 | 5'-(S)-Me | 0.159 | 4 | 2.2 | 1267 |
| 957910 | 3 | 5'-(R)-allyl | 0.239 | >>20 | 3.6 | 32 |
| 957911 | 4 | 5'-(R)-allyl | 0.269 | >>20 | 6.4 | 30 |
| 957912 | 3 | 5'-(S)-allyl | 0.234 | >>20 | 5.1 | 30 |
| 957913 | 4 | 5'-(S)-allyl | 0.263 | >>20 | 5.7 | 32 |

**Not tested in this experiment; mice that are treated with 558807 at 150 mg/kg typically experience death before 72 hours post-treatment.

For the in vivo activity and toxicity study reported in the table below, 2 BALB/C mice per group were administered 5 mg/kg or 150 mg/kg modified oligonucleotide subcutaneously and sacrificed 72 hours later. Plasma levels of ALT were measured and liver mRNA was analyzed for target reduction as in example 1 above.

TABLE 5

Activity and toxicity of modified oligonucleotides complementary CXCL12

| Compound ID | position of altered nucleotide in central region | sugar modification of altered nucleotide | CXCL12 mRNA (% control) 5 mg/kg | CXCL12 mRNA (% control) 150 mg/kg | ALT 5 mg/kg (IU/L) | ALT 150 mg/kg (IU/L) |
|---|---|---|---|---|---|---|
| 558807 | n/a | n/a | n.d. | n.d. | n.d. | n.d.** |
| 942943 | 3 | 5'-(R)-Me | 28 | 3 | 27 | 4407 |
| 957910 | 3 | 5'-(R)-allyl | 53 | 7 | 24 | 38 |
| 1175787 | 3 | 5'-(R)-Et | 57 | 6 | 27 | 39 |
| 1175785 | 3 | 5'-(S)-Et | 46 | 8 | 25 | 45 |
| 957909 | 4 | 5'-(S)-Me | 30 | 7 | 22 | 7133 |
| 957913 | 4 | 5'-(S)-allyl | 59 | 10 | 30 | 37 |
| 1175786 | 4 | 5'-(R)-Et | 44 | 35 | 24 | 44 |
| 1175782 | 4 | 5'-(S)-Et | 52 | 7 | 26 | 131 |

**Not tested in this experiment; mice that are treated with 558807 at 150 mg/kg typically experience death before 72 hours post-treatment.

For the results in the tables below, in vivo activity and toxicity experiments were performed essentially as described in Example 1. For in vivo toxicity studies, two BALB/C mice per group was administered 50 or 150 mg/kg modified oligonucleotide by subcutaneous injection and sacrificed 72 hours later. One animal was administered an injection of saline as a control. Plasma levels of ALT were measured using an automated clinical chemistry analyzer.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 6

Activity and toxicity of modified oligonucleotides complementary CXCL12

| Compound ID | position of altered nucleotide in central region | sugar modification of altered nucleotide | in vivo $ED_{50}$ (mg/kg) | ALT (IU/L) at 150 mg/kg | ALT (IU/L) at 50 mg/kg |
|---|---|---|---|---|---|
| 558807 | n/a | n/a | 1.7* | n.d.** | n.d.** |
| 1123320 | 2 | 5'-(R)-Me | 2.8 | 7448 | 3987 |
| 1123322 | 2 | 5'-(S)-Me | 2.1 | 5181 | 1912 |
| 1123479 | 2 | 5'-(R,S)-allyl | 6.1 | 2562 | 56 |

*Compound 558807 was only dosed at 1.8, 5.5, and 16.7 mg/kg
**Not tested in this experiment; mice that are treated with 558807 150 mg/kg typically experience death within 72 hours post-treatment.

Table 6b In Vivo Dose-Response of Gadd45a mRNA Upon Treatment with Modified Oligonucleotides Complementary to CXCL12

TABLE 6b

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | | Expression level of Gadd45a mRNA (% Control) | | | |
| 558807 | 83 | 143 | 188 | n/a | n/a |
| 1123320 | 68 | 80 | 114 | 387 | 683 |
| 1123322 | 105 | 61 | 169 | 141 | 575 |
| 1123479 | 88 | 70 | 75 | 273 | 141 |

TABLE 6c

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 115 | 119 | 195 | n/a | n/a |
| 1123320 | 78 | 115 | 77 | 1,802 | 6,928 |
| 1123322 | 95 | 75 | 231 | 1,036 | 8,281 |
| 1123479 | 174 | 132 | 125 | 303 | 1,423 |

TABLE 6d

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 144 | 123 | 1212 | n/a | n/a |
| 1123320 | 109 | 224 | 114 | 17,332 | 51,431 |
| 1123322 | 218 | 92 | 303 | 10,383 | 75,226 |
| 1123479 | 271 | 209 | 295 | 838 | 12,248 |

TABLE 7

Activity and toxicity of modified oligonucleotides complementary CXCL12

| Compound ID | position of altered nucleotide in central region | sugar modification of altered nucleotide | in vivo $EC_{50}$ (mg/kg) | ALT (IU/L) at 150 mg/kg | ALT (IU/L) at 50 mg/kg |
|---|---|---|---|---|---|
| 936053 | 2 | 2'-OMe | 4.9 | 49 | 23 |
| 1175782 | 4 | 5'-(S)-Et | 3.7 | 153 | 37 |
| 1175785 | 3 | 5'-(S)-Et | 6.6 | 34 | 24 |
| 1175786 | 4 | 5'-(R)-Et | 3.5 | 33 | 26 |
| 1175787 | 3 | 5'-(R)-Et | 5.8 | 39 | 28 |

Example 3 Effect of Position-Specific 2'-Modifications on In Vitro Activity and In Vivo Liver Toxicity of Modified Oligonucleotides Complementary to Factor XI Modified oligonucleotides were synthesized as indicated in the table below, comprising an altered nucleotide at positions 1-3 of the central region. These modified oligonucleotides were compared to the otherwise identical modified oligonucleotide lacking an altered nucleotide in the central region, a 3-10-3 cEt gapmer, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to the complement of mouse Factor XI, GENBANK NT_039460.6 truncated from 6086000 to 6111000 (SEQ ID NO: 2), at position 11699 to 11714.

TABLE 8

Modified oligonucleotides complementary to Factor XI

| Compound ID | position of altered nucleotide in central region | sugar modification of altered nucleotide | Chemistry Notation (5'-3') | SEQ ID NO |
|---|---|---|---|---|
| 464917 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 982033 | 1 | 2'-OMe | $G_{ks}T_{ks}{}^mC_{ks}U_{ms}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 143 |
| 982034 | 2 | 2'-OMe | $G_{ks}T_{ks}{}^mC_{ks}T_{ds}G_{ms}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 985292 | 2 | 2'-MOE | $G_{ks}T_{ks}{}^mC_{ks}T_{ds}G_{es}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 985293 | 2 | cEt | $G_{ks}T_{ks}{}^mC_{ks}T_{ds}G_{ks}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1011274 | 2 | 2'-FANA | $G_{ks}T_{ks}{}^mC_{ks}T_{ds}G_{(FANA)s}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 604581 | 2 | 2'-ribo-F | $G_{ks}T_{ks}{}^mC_{ks}T_{ds}G_{fs}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 982035 | 3 | 2'-OMe | $G_{ks}T_{ks}{}^mC_{ks}T_{ds}G_{ds}U_{ms}G_{ds}{}^mC_{ds}A_{ds}T_{ds}{}^mC_{ds}T_{ds}{}^mC_{ds}T_{ks}{}^mC_{ks}{}^mC_k$ | 23 |
| 985294 | 3 | 2'-MOE | $G_{ks}T_{ks}{}^mC_{ks}T_{ds}G_{ds}T_{es}G_{ds}{}^mC_{ds}A_{ds}T_{ds}{}^mC_{ds}T_{ds}{}^mC_{ds}T_{ks}{}^mC_{ks}{}^mC_k$ | 22 |
| 985295 | 3 | cEt | $G_{ks}T_{ks}{}^mC_{ks}T_{ds}G_{ds}T_{ks}G_{ds}{}^mC_{ds}A_{ds}T_{ds}{}^mC_{ds}T_{ds}{}^mC_{ds}T_{ks}{}^mC_{ks}{}^mC_k$ | 22 |
| 1011276 | 3 | 2'-FANA | $G_{ks}T_{ks}{}^mC_{ks}T_{ds}G_{ds}U_{(FANA)s}G_{ds}{}^mC_{ds}A_{ds}T_{ds}{}^mC_{ds}T_{ds}{}^mC_{ds}T_{ks}{}^mC_{ks}{}^mC_k$ | 23 |
| 605933 | 3 | 2'-ribo-F | $G_{ks}T_{ks}{}^mC_{ks}T_{ds}G_{ds}U_{fs}G_{ds}{}^mC_{ds}A_{ds}T_{ds}{}^mC_{ds}T_{ds}{}^mC_{ds}T_{ks}{}^mC_{ks}{}^mC_k$ | 23 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

Experimental Procedures & Results

For in vitro toxicity studies, 3T3-L1 cells were electroporated with 27, 80, 250, 740, 2, 222, 6,667, or 20,000 nM of modified oligonucleotide and levels of Raptor were measured by RT-qPCR as in Example 1.

For in vivo toxicity studies, two BALB/C mice per group were administered 100 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 8b

Toxkity of modified oligonucleotides complementary Factor XI position of

| Compound ID | position of altered nucleotide in central region | sugar modification of altered nucleotide | Raptor IC50 (μM) | ALT at 100 mg/kg (IU/L) |
|---|---|---|---|---|
| 464917 | n/a | n/a | 1.6 | 18751* |
| 982034 | 2 | 2'-OMe | >20 | 1363 |

TABLE 8b-continued

Toxkity of modified oligonucleotides complementary Factor XI position of

| Compound ID | position of altered nucleotide in central region | sugar modification of altered nucleotide | Raptor IC50 (μM) | ALT at 100 mg/kg (IU/L) |
|---|---|---|---|---|
| 985292 | 2 | 2'-MOE | 15.5 | 2406 |
| 985293 | 2 | cEt | 9.3 | 15141 |
| 1011274 | 2 | 2'-FANA | 2.3 | death |
| 604581 | 2 | 2'-ribo-F | 6 | 14957 |
| 982035 | 3 | 2'-OMe | 1.8 | 6411 |
| 985294 | 3 | 2'-MOE | 6.2 | 2836 |
| 985295 | 3 | cEt | 5.2 | 3669 |
| 1011276 | 3 | 2'-FANA | >20 | death |
| 605933 | 3 | 2'-ribo-F | 4.6 | 18570 |

*ALT for 464917 is for a 50 mg/kg dose

For the in vitro study reported in the tables below, 3T3-L1 cells were electroporated with 27, 80, 250, 740, 2, 222, 6,667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8c in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 464917 | 108 | 124 | 122 | 169 | 228 | 478 | 749 |
| 982033 | 119 | 120 | 128 | 128 | 218 | 498 | 895 |
| 982034 | 115 | 121 | 110 | 102 | 136 | 266 | 840 |
| 982035 | 162 | 157 | 175 | 206 | 466 | 768 | 661 |

TABLE 8d in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 464917 | 130 | 150 | 115 | 179 | 321 | 632 | 633 |
| 982033 | 120 | 117 | 126 | 203 | 331 | 767 | 798 |
| 982034 | 89 | 111 | 103 | 102 | 173 | 678 | 800 |
| 982035 | 161 | 120 | 140 | 181 | 557 | 779 | 497 |

For the in vitro study reported in the tables below, b.END cells were electroporated with 27, 80, 250, 740, 2, 222, 6,667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8e in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 464917 | 111 | 115 | 124 | 120 | 139 | 192 | 446 |
| 982033 | 105 | 102 | 107 | 110 | 125 | 171 | 414 |
| 982034 | 106 | 102 | 109 | 112 | 120 | 132 | 208 |
| 982035 | 102 | 97 | 111 | 115 | 129 | 168 | 392 |

TABLE 8f in vitro Gadd45a Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 464917 | 101 | 83 | 85 | 87 | 129 | 236 | 380 |
| 982033 | 89 | 76 | 101 | 91 | 177 | 347 | 731 |
| 982034 | 58 | 73 | 86 | 88 | 115 | 202 | 373 |
| 982035 | 68 | 72 | 81 | 103 | 166 | 298 | 620 |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in Example 1 above. Expression levels were normalized with Ribogreen® and are expressed relative to PBS-treated control mice.

TABLE 8g

Activity and toxicity of modified oligonucleotides complementary FXI

| Compound ID | position of altered nucleotide in central region | sugar modification of altered nucleotide | ALT (IU/L) at 100 mg/kg | ALT (IU/L) at 33 mg/kg |
|---|---|---|---|---|
| 464917 | n/a | n/a | 11816 | 11682 |
| 982033 | 1 | OMe | 26992 | 3951 |
| 982034 | 2 | OMe | 7954 | 920 |
| 982035 | 3 | OMe | 28994 | 3848 |

TABLE 8h

In Vivo Dose-response of FXI mRNA upon treatment with modified oligonucleotides complementary to FXI

| Compound ID | 3.37 mg/kg | 11 mg/kg | 33 mg/kg | 100 mg/kg |
|---|---|---|---|---|
| | Expression level of FXI mRNA (% Control) | | | |
| 464917 | 47 | 12 | 8.0 | 1.8 |
| 982033 | 53 | 18 | 10 | 5.5 |
| 982034 | 53 | 24 | 9.9 | 3.5 |
| 982035 | 36 | 20 | 11 | 5.3 |

TABLE 8i

In Vivo Dose-response of P21 mRNA upon treatment with modified oligonucleotides complementary to FXI

| Compound ID | 3.37 mg/kg | 11 mg/kg | 33 mg/kg | 100 mg/kg |
|---|---|---|---|---|
| | Expression level of P21 mRNA (% Control) | | | |
| 464917 | 230 | 4143 | 4678 | 5289 |
| 982033 | 122 | 1106 | 2926 | 5653 |
| 982034 | 93 | 297 | 1694 | 4294 |
| 982035 | 418 | 1283 | 4759 | 6960 |

Example 4 Effect of Position-Specific 2' and 5'-Modifications on In Vivo Activity and Liver Toxicity of Modified Oligonucleotides Complementary to Factor XI Modified oligonucleotides were synthesized with 2' or 5' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse Factor XI, the complement of GENBANK NT_039460.6 truncated from 6086000 to 6111000 (SEQ ID NO: 2), at position 11699 to 11714.

TABLE 9

Modified oligonucleotides complementary to Factor XI

| Compound ID | position of altered nucleotide in central region | sugar modification of altered nucleotide | Chemistry Notation(5'-3') | SEQ ID NO |
|---|---|---|---|---|
| 464917 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 443919 | n/a | n/a | $G_{es}T_{es}{}^mC_{es}T_{ds}G_{ds}T_{ds}G_{ds}{}^mC_{ds}A_{ds}T_{ds}{}^mC_{ds}T_{ds}{}^mC_{ds}T_{es}{}^mC_{es}{}^mC_e$ | 22 |
| 465977 | n/a | n/a | $G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{es}{}^mC_{es}{}^mC_e$ | 22 |
| 483706 | n/a | n/a | $G_{es}T_{es}{}^mC_{es}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183062 | 2 | 5'-(R)-Me | $G_{ks}T_{ks}{}^mC_{ks}T_{ds}G_{[(R)-\mu]s}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183059 | 2 | 5'-(S)-Me | $G_{ks}T_{ks}{}^mC_{ks}T_{ds}G_{[(S)-\mu]s}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183065 | 2 | 5'-(R)-allyl | $G_{ks}T_{ks}{}^mC_{ks}T_{ds}G_{[(R)-\gamma]s}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183063 | 3 | 5'-(R)-Me | $G_{ks}T_{ks}{}^mC_{ks}T_{ds}G_{ds}T_{[(R)-\mu]s}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183060 | 3 | 5'-(S)-Me | $G_{ks}T_{ks}{}^mC_{ks}T_{ds}G_{ds}T_{[(S)-\mu]s}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183066 | 3 | 5'-(R)-allyl | $G_{ks}T_{ks}{}^mC_{ks}T_{ds}G_{ds}T_{[(R)-\gamma]s}G_{ds}{}^mC_{ds}A_{ds}T_{ds}{}^mC_{ds}T_{ds}{}^mC_{ds}T_{ks}{}^mC_{ks}{}^mC_k$ | 22 |
| 1183064 | 4 | 5'-(R)-Me | $G_{ks}T_{ks}{}^mC_{ks}T_{ds}G_{ds}T_{ds}G_{[(R)-\mu]s}{}^mC_{ds}A_{ds}T_{ds}{}^mC_{ds}T_{ds}{}^mC_{ds}T_{ks}{}^mC_{ks}{}^mC_k$ | 22 |
| 1183061 | 4 | 5'-(S)-Me | $G_{ks}T_{ks}{}^mC_{ks}T_{ds}G_{ds}T_{ds}G_{[(S)-\mu]s}{}^mC_{ds}A_{ds}T_{ds}{}^mC_{ds}T_{ds}{}^mC_{ds}T_{ks}{}^mC_{ks}{}^mC_k$ | 22 |
| 1183067 | 4 | 5'-(R)-allyl | $G_{ks}T_{ks}{}^mC_{ks}T_{ds}G_{ds}T_{ds}G_{[(R)-\gamma]s}{}^mC_{ds}A_{ds}T_{ds}{}^mC_{ds}T_{ds}{}^mC_{ds}T_{ks}{}^mC_{ks}{}^mC_k$ | 22 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[β]" indicates a 5'-(R,S)-Me-β-D-2'-deoxyribosyl sugar moiety. A subscript "[(R)-μ]" indicates a 5'-(R)-Me-β-D-2'-deoxyribosyl sugar moiety. A subscript "[(S)-μ]" indicates a 5'-(S)-Me-β-D-2'-deoxyribosyl sugar moiety. A subscript "[γ]" indicates a 5'-(R,S)-allyl-β-D-2'-deoxyribosyl sugar moiety. A subscript "[(R)-γ]" indicates a 5'-(R)-allyl-β-D-2'-deoxyribosyl sugar moiety. A subscript "[(S)-γ]" indicates a 5'-(S)-allyl-β-D-2'-deoxyribosyl sugar moiety. A subscript "[ε]" indicates a 5'-(R,S)-ethyl-β-D-2'-deoxyribosyl sugar moiety. A subscript "[(R)-ε]" indicates a 5'-(R)-ethyl-β-D-2'-deoxyribosyl sugar moiety. A subscript "[(S)-ε]" indicates a 5'-(S)-ethyl-β-D-2'-deoxyribosyl sugar moiety.

Experimental Procedures & Results

For the in vivo activity and toxicity study below, two BALB/C mice per group were administered 33 or 100 mg/kg modified oligonucleotide by subcutaneous injection and sacrificed 72 hours later. Expression levels of FXI were measured by RT-qPCR using primer probe set RTS2898 (forward sequence: ACATGACAGGCGCGATCTCT, SEQ ID NO: 78; reverse sequence: TCTAGGTTCACGTACA-CATCTTTGC, SEQ ID NO: 79; probe sequence: TTCCTT-CAAGCAATGCCCTCAGCAAT, SEQ ID NO: 80). Plasma levels of ALT were measured using an automated clinical chemistry analyzer. Increased ALT is indicative of acute liver toxicity.

TABLE 10

Toxicity and activity of modified oligonucleotides complementary Factor XI

| Compound ID | position of altered nucleotide in central region | sugar modification of altered nucleotide | FXI mRNA (% control) 33 mg/kg | FXI mRNA (% control) 100 mg/kg | ALT (IU/L) at 33 mg/kg | ALT (IU/L) at 100 mg/kg |
|---|---|---|---|---|---|---|
| 464917 | n/a | n/a | 11 | 0.9 | 7511 | 31066* |
| 443919 | n/a | n/a | 27 | 7.9 | 24 | 57 |
| 465977 | n/a | n/a | 5.6 | n.d. | 11575 | death |
| 483706 | n/a | n/a | 20.3 | 4.9 | 52 | 732 |
| 1183062 | 2 | 5'-(R)-Me | 5.7 | n.d. | 12083 | death |
| 1183059 | 2 | 5'-(S)-Me | 4.0 | 2.4 | 662 | 7894 |

TABLE 10-continued

Toxicity and activity of modified oligonucleotides complementary Factor XI

| Compound ID | position of altered nucleotide in central region | sugar modification of altered nucleotide | FXI mRNA (% control) 33 mg/kg | FXI mRNA (% control) 100 mg/kg | ALT (IU/L) at 33 mg/kg | ALT (IU/L) at 100 mg/kg |
|---|---|---|---|---|---|---|
| 1183065 | 2 | 5'-(R)-allyl | 5.2 | 1.5 | 4707 | 24000 |
| 1183063 | 3 | 5'-(R)-Me | 4.9 | 2.0 | 2458 | 14891 |
| 1183060 | 3 | 5'-(S)-Me | 8.2 | 2.1 | 8710 | 23995 |
| 1183066 | 3 | 5'-(R)-allyl | 5.1 | 2.0 | 524 | 6473 |
| 1183064 | 4 | 5'-(R)-Me | 4.0 | 1.5 | 4357 | 11342 |
| 1183061 | 4 | 5'-(S)-Me | 4.1 | 2.3 | 1891 | 20557 |
| 1183067 | 4 | 5'-(R)-allyl | 11 | 3.6 | 184 | 2536 |

*One of two mke died

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 10b in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 464917 | 100 | 100 | 116 | 139 | 216 | 496 | 1232 |
| 443919 | 122 | 116 | 99 | 86 | 114 | 105 | 184 |
| 465977 | 104 | 117 | 103 | 106 | 139 | 220 | 578 |
| 483706 | 105 | 92 | 116 | 125 | 135 | 165 | 376 |

TABLE 10c in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 464917 | 89 | 93 | 106 | 113 | 157 | 324 | 599 |
| 443919 | 163 | 166 | 147 | 129 | 145 | 126 | 178 |
| 465977 | 101 | 110 | 119 | 100 | 135 | 150 | 334 |
| 483706 | 89 | 133 | 185 | 194 | 197 | 217 | 459 |

TABLE 10d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | | | Caspase Activation | | | | |
| 464917 | 4388 | 4428 | 4656 | 6208 | 20274 | 48106 | 82324 |
| 443919 | 4200 | 4802 | 4986 | 4605 | 4714 | 4552 | 9385 |
| 465977 | 4017 | 4133 | 4253 | 4465 | 6983 | 34156 | 61008 |
| 483706 | 4155 | 4595 | 4020 | 4476 | 4585 | 6565 | 16766 |

For the in vivo study in the table below, three BALB/C mice per group were administered 11 or 33 mg/kg of modified oligonucleotide and sacrificed after 72 hours.

TABLE 10e in vivo Activity and toxicity of modified oligonucleotides complementary FXI

| Compound ID | 2' sugar modification of nucleosides in 5' region | 2' sugar modification of nucleosides in 3' region | P21 mRNA @ 33 mg/kg (% control) | Tnfrsf10b mRNA @ 33 mg/kg (% control) | FXI mRNA @ 33 mg/kg (% control) | ALT @ 33 mg/kg |
|---|---|---|---|---|---|---|
| 464917 | kkk | kkk | 24040 | 108884 | 1.4 | 18316 |
| 443919 | kkk | eee | 109 | 110 | 16 | 68 |
| 465977 | eee | kkk | n.d. | n.d. | n.d. | death |
| 483706 | eee | eee | 1195 | 733 | 2.7 | 1424 |

Example 5 Effect of Position-Specific 2'-Modifications on In Vitro Activity and In Vivo Liver Toxicity of Modified Oligonucleotides Complementary to PTEN Modified oligonucleotides were synthesized with 2' modifications as indicated in the table below.

These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse PTEN, GENBANK NC_000085.6, truncated from 32755001 to 32829000 (SEQ ID NO: 3), at position 2635 to 2650.

TABLE 11

Modified oligonucleotides complementary to PTEN

| Compound ID | position of altered nucleotide in central region | sugar modification of altered nucleotide | Chemistry Notation(5'-3') | SEQ ID NO |
|---|---|---|---|---|
| 482050 | n/a | n/a | $A_{ks}T_{ks}{}^mC_{ks}A_{ds}T_{ds}G_{ds}G_{ds}{}^mC_{ds}T_{ds}G_{ds}{}^mC_{ds}A_{ds}G_{ds}{}^mC_{ks}T_{ks}T_k$ | 24 |
| 982036 | 1 | 2'-OMe | $A_{ks}T_{ks}{}^mC_{ks}A_{ms}T_{ds}G_{ds}G_{ds}{}^mC_{ds}T_{ds}G_{ds}{}^mC_{ds}A_{ds}G_{ds}{}^mC_{ks}T_{ks}T_k$ | 24 |
| 982037 | 2 | 2'-OMe | $A_{ks}T_{ks}{}^mC_{ks}A_{ds}U_{ms}G_{ds}G_{ds}{}^mC_{ds}T_{ds}G_{ds}{}^mC_{ds}A_{ds}G_{ds}{}^mC_{ks}T_{ks}T_k$ | 25 |
| 985297 | 2 | 2'-MOE | $A_{ks}T_{ks}{}^mC_{ks}A_{ds}T_{es}G_{ds}G_{ds}{}^mC_{ds}T_{ds}G_{ds}{}^mC_{ds}A_{ds}G_{ds}{}^mC_{ks}T_{ks}T_k$ | 24 |
| 985298 | 2 | cEt | $A_{ks}T_{ks}{}^mC_{ks}A_{ds}T_{ks}G_{ds}G_{ds}{}^mC_{ds}T_{ds}G_{ds}{}^mC_{ds}A_{ds}G_{ds}{}^mC_{ks}T_{ks}T_k$ | 24 |
| 1011277 | 2 | 2'-FANA | $A_{ks}T_{ks}{}^mC_{ks}A_{ds}U_{(FANA)s}G_{ds}G_{ds}{}^mC_{ds}T_{ds}G_{ds}{}^mC_{ds}A_{ds}G_{ds}{}^mC_{ks}T_{ks}T_k$ | 25 |
| 985296 | 2 | 2'-ribo-F | $A_{ks}T_{ks}{}^mC_{ks}A_{ds}U_{fs}G_{ds}G_{ds}{}^mC_{ds}T_{ds}G_{ds}{}^mC_{ds}A_{ds}G_{ds}{}^mC_{ks}T_{ks}T_k$ | 25 |
| 982038 | 3 | 2'-OMe | $A_{ks}T_{ks}{}^mC_{ks}A_{ds}T_{ds}G_{ms}G_{ds}{}^mC_{ds}T_{ds}G_{ds}{}^mC_{ds}A_{ds}G_{ds}{}^mC_{ks}T_{ks}T_k$ | 24 |
| 985301 | 3 | 2'-MOE | $A_{ks}T_{ks}{}^mC_{ks}A_{ds}T_{ds}G_{es}G_{ds}{}^mC_{ds}T_{ds}G_{ds}{}^mC_{ds}A_{ds}G_{ds}{}^mC_{ks}T_{ks}T_k$ | 24 |
| 985302 | 3 | cEt | $A_{ks}T_{ks}{}^mC_{ks}A_{ds}T_{ds}G_{ks}G_{ds}{}^mC_{ds}T_{ds}G_{ds}{}^mC_{ds}A_{ds}G_{ds}{}^mC_{ks}T_{ks}T_k$ | 24 |
| 1011278 | 3 | 2'-FANA | $A_{ks}T_{ks}{}^mC_{ks}A_{ds}T_{ds}G_{(FANA)s}G_{ds}{}^mC_{ds}T_{ds}G_{ds}{}^mC_{ds}A_{ds}G_{ds}{}^mC_{ks}T_{ks}T_k$ | 24 |
| 985300 | 3 | 2'-ribo-F | $A_{ks}T_{ks}{}^mC_{ks}A_{ds}T_{ds}G_{fs}G_{ds}{}^mC_{ds}T_{ds}G_{ds}{}^mC_{ds}A_{ds}G_{ds}{}^mC_{ks}T_{ks}T_k$ | 24 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated and transfected with 16, 80, 400, 2,000, and 10,000 nM modified oligonucleotide by electroporation. mRNA was harvested and analyzed by RT-qPCR. PTEN mRNA was detected and RAPTOR mRNA was detected.

For in vivo toxicity studies, 2-4 BALB/C mice per group were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 12

Activity and toxicity of modified oligonucleotides complementary PTEN

| Compound ID | position of altered nucleotide in central region | sugar modification of altered nucleotide | PTEN IC$_{50}$ (μM) | RAPTOR IC$_{50}$ (μM) | ALT @ 200 mg/kg (IU/L) |
|---|---|---|---|---|---|
| 482050 | n/a | n/a | 3.9 | 2.4 | 2458 |
| 982037 | 2 | 2'-OMe | 2.7 | 10 | 133 |
| 985297 | 2 | 2'-MOE | 3 | 9.4 | 242 |
| 985298 | 2 | cEt | 1.4 | 2.1 | 890 |
| 1011277 | 2 | 2'-FANA | 3.1 | 3.5 | 1488 |
| 985296 | 2 | 2'-ribo-F | 2.2 | 6 | 1884 |
| 982038 | 3 | 2'-OMe | 1.8 | 3.7 | 327 |
| 985301 | 3 | 2'-MOE | 1.5 | 5 | 261 |
| 985302 | 3 | cEt | 2 | 3.3 | 87 |
| 1011278 | 3 | 2'-FANA | 1.7 | 1.1 | 14073 |
| 985300 | 3 | 2'-ribo-F | 2.2 | 6 | 107 |

For the in vitro study reported in the tables below, 3T3-L1 cells were transfected with 27, 80, 250, 740, 2, 222, 6,667, or 20,000 nM of modified oligonucleotide by electroporation and levels of P21 and Gadd45a were measured by RT-qPCR as described in example 1.

TABLE 12b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 482050 | 111 | 107 | 113 | 124 | 113 | 130 | 157 |
| 982036 | 92 | 95 | 93 | 95 | 91 | 110 | 162 |
| 982037 | 112 | 108 | 99 | 105 | 112 | 120 | 113 |
| 982038 | 108 | 105 | 111 | 111 | 114 | 99 | 108 |

TABLE 12c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 482050 | 65 | 64 | 70 | 67 | 79 | 176 | 276 |
| 982036 | 81 | 62 | 62 | 71 | 113 | 189 | 467 |
| 982037 | 107 | 90 | 79 | 75 | 79 | 100 | 165 |
| 982038 | 110 | 112 | 104 | 131 | 118 | 129 | 266 |

Example 6 Effect of Position-Specific 2'-Modifications on In Vitro Activity and In Vivo Liver Toxicity of Modified Oligonucleotides Complementary to SOD1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse SOD1, GENBANK NT_039625.7 truncated from 24924000 to 24933000 (SEQ ID NO: 4), at position 5685 to 5880.

TABLE 13

Modified oligonucleotides complementary to SOD1

| Compound ID | position of altered nucleotide in central region | sugar modification of altered nucleotide | Chemistry Notation(5'-3') | SEQ ID NO |
|---|---|---|---|---|
| 508031 | n/a | n/a | $T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 508034 | n/a | n/a | $T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{es}G_{es}G_{e}$ | 26 |
| 508037 | n/a | n/a | $T_{es}G_{es}A_{es}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 529933 | n/a | n/a | $T_{es}G_{es}A_{es}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{e}$ | 26 |
| 895154 | 1 | 2'-OMe | $T_{ks}G_{ks}A_{ks}G_{ms}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 895155 | 2 | 2'-OMe | $T_{ks}G_{ks}A_{ks}G_{ds}G_{ms}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985305 | 2 | 2'-MOE | $T_{ks}G_{ks}A_{ks}G_{ds}G_{es}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985306 | 2 | cEt | $T_{ks}G_{ks}A_{ks}G_{ds}G_{ks}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 1011279 | 2 | 2'-FANA | $T_{ks}G_{ks}A_{ks}G_{ds}G_{(FANA)s}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 985304 | 2 | 2'-ribo-F | $T_{ks}G_{ks}A_{ks}G_{ds}G_{fs}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 895156 | 3 | 2'-OMe | $T_{ks}G_{ks}A_{ks}G_{ds}G_{ds}U_{ms}{}^mC_{ds}{}^mC_{ds}T_{ds}G_{ds}{}^mC_{ds}A_{ds}{}^mC_{ds}T_{ks}G_{ks}G_{k}$ | 27 |
| 985309 | 3 | 2'-MOE | $T_{ks}G_{ks}A_{ks}G_{ds}G_{ds}T_{es}{}^mC_{ds}{}^mC_{ds}T_{ds}G_{ds}{}^mC_{ds}A_{ds}{}^mC_{ds}T_{ks}G_{ks}G_{k}$ | 26 |
| 985310 | 3 | cEt | $T_{ks}G_{ks}A_{ks}G_{ds}G_{ds}T_{ks}{}^mC_{ds}{}^mC_{ds}T_{ds}G_{ds}{}^mC_{ds}A_{ds}{}^mC_{ds}T_{ks}G_{ks}G_{k}$ | 26 |
| 1011280 | 3 | 2'-FANA | $T_{ks}G_{ks}A_{ks}G_{ds}G_{ds}U_{(FANA)s}{}^mC_{ds}{}^mC_{ds}T_{ds}G_{ds}{}^mC_{ds}A_{ds}{}^mC_{ds}T_{ks}G_{ks}G_{k}$ | 27 |
| 985308 | 3 | 2'-ribo-F | $T_{ks}G_{ks}A_{ks}G_{ds}G_{ds}U_{fs}{}^mC_{ds}{}^mC_{ds}T_{ds}G_{ds}{}^mC_{ds}A_{ds}{}^mC_{ds}T_{ks}G_{ks}G_{k}$ | 27 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated at 20,000 cells/well and transfected with 16, 80, 400, 2,000, and 10,000 nM modified oligonucleotide by electroporation. mRNA was harvested and analyzed by RT-qPCR. SOD1 mRNA was detected using primer probe set RTS3025 (forward sequence: TTTTTTGCGCGGTCCTTTC (SEQ ID NO: 119); reverse sequence: GAGGGACCAGAGAGAGCAAGAC (SEQ ID NO: 120); probe sequence: CGCCTTCCGTCCGTCGGCT (SEQ ID NO:121)) and RAPTOR mRNA was detected as in Example 1 above.

For the in vivo toxicity study in the table below, two BALB/C mice per modified oligonucleotide were administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 14

Activity and toxicity of modified oligonucleotides complementary SOD1

| Compound ID | position of altered nucleotide in central region | sugar modification of altered nucleotide | SOD1 IC50 (µM) | RAPTOR IC$_{50}$ (µM) | ALT @ 150 mg/kg (IU/L) |
|---|---|---|---|---|---|
| 508031 | n/a | n/a | 0.03 | 0.46 | 21934 |
| 895155 | 2 | 2'-OMe | 0.04 | 1 | 112 |
| 985305 | 2 | 2'-MOE | 0.21 | n/a | 63 |
| 985306 | 2 | cEt | 1.61 | 10.2 | 826 |
| 1011279 | 2 | 2'-FANA | 0.28 | 1 | death |
| 985304 | 2 | 2'-ribo-F | 0.04 | 0.8 | 182 |
| 895156 | 3 | 2'-OMe | 0.48 | 4.5 | 1371 |
| 985309 | 3 | 2'-MOE | 0.61 | 6 | 1629 |
| 985310 | 3 | cEt | 1.46 | 11.9 | 178 |
| 1011280 | 3 | 2'-FANA | 0.6 | 4 | death |
| 985308 | 3 | 2'-ribo-F | 0.24 | 0.92 | 887 |

For in vitro activity studies, 3T3-L1 cells were plated at 20,000 cells/well and transfected with 30 nM, 80 nM, 250 nM, 740 nM, 2,222 nM, 6,667 nM, or 20,000 nM modified oligonucleotide by electroporation. P21 and Gadd45a mRNA were analyzed as in Example 1 above and caspase activation was measured as in Example 4 above. Results were normalized with Ribogreen® and are presented relative to the average of untreated control cells.

TABLE 14b in vitro P21 Expression

| Compound ID | 30 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 508031 | 104 | 96 | 104 | 91 | 99 | 180 | 366 |
| 895154 | 94 | 117 | 85 | 93 | 105 | 159 | 181 |
| 895155 | 98 | 110 | 92 | 88 | 88 | 101 | 137 |
| 895156 | 95 | 104 | 74 | 97 | 125 | 139 | 283 |

TABLE 14c in vitro Gadd45a Expression

| Compound ID | 30 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 508031 | 103 | 99 | 113 | 103 | 139 | 564 | 844 |
| 895154 | 110 | 125 | 114 | 106 | 130 | 297 | 669 |

TABLE 14c-continued in vitro Gadd45a Expression

| Compound ID | 30 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 895155 | 129 | 139 | 120 | 126 | 122 | 145 | 340 |
| 895156 | 122 | 132 | 94 | 125 | 223 | 490 | 856 |

TABLE 14d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | Caspase Activation | | | | | | |
| 508031 | 10871 | 11667 | 12107 | 14458 | 46619 | 101512 | 177873 |
| 895154 | 11681 | 11503 | 11656 | 11422 | 17167 | 70398 | 124774 |
| 895155 | 11669 | 11005 | 11479 | 11156 | 12487 | 20199 | 77630 |
| 895156 | 11980 | 10646 | 10616 | 11178 | 24226 | 72844 | 153302 |

For the in vivo toxicity study in the table below, three BALB/C mice per modified oligonucleotide were administered 100 mg/kg modified oligonucleotide by subcutaneous injection and sacrificed 72 hours later. One animal was administered an injection of saline as a control. Plasma levels of ALT and AST were measured using an automated clinical chemistry analyzer. Increased ALT and AST are indicative of acute liver toxicity.

For the in vivo study in the table below, three BALB/C mice per group were administered 33 or 100 mg/kg of modified oligonucleotide and sacrificed after 24 hours.

TABLE 15

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) |
|---|---|---|---|---|---|---|
| 508031 | n/a | n/a | 823 | 399 | 321 | 36 |
| 895154 | 1 | 2'-OMe | 125 | 176 | 345 | 56 |
| 895155 | 2 | 2'-OMe | 67 | 147 | 365 | 75 |
| 895156 | 3 | 2'-OMe | 538 | 351 | 525 | 51 |

For the in vivo study in the table below, three BALB/C mice per group were administered 33 or 100 mg/kg of modified oligonucleotide and sacrificed after 72 hours.

TABLE 15b

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) | ALT @ 100 mg/kg (IU/L) |
|---|---|---|---|---|---|---|---|
| 508031 | n/a | n/a | 6007 | 9032 | 392 | 13 | 16,317 |
| 895154 | 1 | 2'-OMe | 561 | 1042 | 129 | 19 | 206 |
| 895155 | 2 | 2'-OMe | 165 | 233 | 18 | 26 | 41 |
| 895156 | 3 | 2'-OMe | 3218 | 8189 | 190 | 9.6 | 1,242 |

TABLE 15c

Activity and toxicity of modified oligonucleotides complementary to SOD1

| Compound ID | 2' sugar modification in 5' region | 2' sugar modification in 3' region | P21 mRNA @ 100 mg/kg (% control) | Tnfrsf10b mRNA @ 100 mg/kg (% control) | SOD1 mRNA @ 100 mg/kg (% control) | ALT @ 100 mg/kg (IU/L) |
|---|---|---|---|---|---|---|
| 508031 | kkk | kkk | 3478 | 4593 | 9 | 14526 |
| 508034 | kkk | eee | 11365 | 7288 | 3 | 22396* |
| 508037 | eee | kkk | 130 | 225 | 17 | 20 |
| 529933 | eee | eee | 90 | 142 | 18 | 11 |

*2/3 animals were found dead

For the in vitro study reported in the tables below, 3T3-L1 cells were electroporated with 27 nM, 80 nM, 250 nM, 740 nM, 2,222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 15d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | Caspase Activation | | | | | | |
| 508031 | 5969 | 6550 | 5986 | 8376 | 22499 | 56695 | 91450 |
| 508034 | 5652 | 5258 | 6555 | 7590 | 17098 | 49473 | 73813 |
| 508037 | 4027 | 4000 | 4222 | 4104 | 4208 | 3899 | 7869 |
| 529933 | 5904 | 5393 | 5595 | 5677 | 4772 | 4914 | 11918 |

TABLE 15e in vitro P21 mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 508031 | 132 | 116 | 119 | 108 | 121 | 185 | 692 |
| 508034 | 119 | 115 | 120 | 117 | 125 | 174 | 344 |
| 508037 | 120 | 119 | 121 | 121 | 117 | 122 | 149 |
| 529933 | 106 | 110 | 101 | 120 | 108 | 108 | 100 |

TABLE 15f in vitro Gadd45a mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 508031 | 202 | 132 | 198 | 137 | 215 | 570 | 1046 |
| 508034 | 132 | 132 | 167 | 161 | 185 | 475 | 842 |
| 508037 | 175 | 164 | 181 | 175 | 195 | 215 | 416 |
| 529933 | 136 | 136 | 148 | 167 | 169 | 130 | 155 |

For the in vivo dose-response study in the table below, three BALB/C mice per group were administered 3.7, 11.1, 33, or 100 mg/kg 508031 or 3.7, 11.1, 33, 100, or 300 mg/kg 895155 by subcutaneous injection and sacrificed. Levels of Gadd45a, P21, and Tnfrsf1b mRNA were measured by RT-PCR as described in Example 1.

TABLE 15g

Activity and toxicity of modified oligonucleotides complementary to SOD1

| Compound ID | position of altered nucleotide in central region | sugar modification of altered nucleotide | ED$_{50}$ (mg/kg) |
|---|---|---|---|
| 508031 | n/a | n/a | 13.12 |
| 895155 | 2 | 2'-OMe | 38.8 |

TABLE 15h

In Vivo Dose-response of Tnfrsf10b mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of Tnfrsf10b mRNA (% Control) | | | | |
| 508031 | 99 | 276 | 3443 | 6446 | n/a |
| 895155 | 81 | 105 | 115 | 193 | 2215 |

TABLE 15i

In Vivo Dose-response of P21 mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of P21 mRNA (% Control) | | | | |
| 508031 | 163 | 222 | 1867 | 3788 | n/a |
| 895155 | 162 | 167 | 167 | 199 | 1467 |

Example 7 Effect of Position-Specific 2'-Modifications on In Vitro Activity and In Vivo Liver Toxicity of Modified Oligonucleotides Complementary to SRB1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate. The compounds in the table below are 100% complementary to the complement of mouse SRB1, GENBANK NT_039313.7 truncated from 566000 to 632000 (SEQ ID NO: 5), at position 64840 to 64855.

TABLE 16

Modified oligonucleotides complementary to SRB1

| Compound ID | position of altered nucleotide in central region | sugar modification of altered nucleotide | Chemistry Notation(5'-3') | SEQ ID NO |
|---|---|---|---|---|
| 449093 | n/a | n/a | $T_{ks}T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982030 | 1 | 2'-OMe | $T_{ks}T_{ks}{}^mC_{ks}A_{ms}G_{ds}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982031 | 2 | 2'-OMe | $T_{ks}T_{ks}{}^mC_{ks}A_{ds}G_{ms}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042573 | 2 | 2'-MOE | $T_{ks}T_{ks}{}^mC_{ks}A_{ds}G_{es}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042574 | 2 | cEt | $T_{ks}T_{ks}{}^mC_{ks}A_{ds}G_{ks}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042575 | 2 | 2'-FANA | $T_{ks}T_{ks}{}^mC_{ks}A_{ds}G_{(FANA)s}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 1042572 | 2 | 2'-ribo-F | $T_{ks}T_{ks}{}^mC_{ks}A_{ds}G_{fs}T_{ds}{}^mC_{ds}A_{ds}T_{ds}G_{ds}A_{ds}{}^mC_{ds}T_{ds}T_{ks}{}^mC_{ks}{}^mC_k$ | 28 |
| 982032 | 3 | 2'-Me | $T_{ks}T_{ks}{}^mC_{ks}A_{ds}G_{ds}U_{ms}{}^mC_{ds}A_{ds}T_{ds}G_{ds}A_{ds}{}^mC_{ds}T_{ds}T_{ks}{}^mC_{ks}{}^mC_k$ | 29 |
| 1042577 | 3 | 2'-MOE | $T_{ks}T_{ks}{}^mC_{ks}A_{ds}G_{ds}T_{es}{}^mC_{ds}A_{ds}T_{ds}G_{ds}A_{ds}{}^mC_{ds}T_{ds}T_{ks}{}^mC_{ks}{}^mC_k$ | 28 |
| 1042578 | 3 | cEt | $T_{ks}T_{ks}{}^mC_{ks}A_{ds}G_{ds}T_{ks}{}^mC_{ds}A_{ds}T_{ds}G_{ds}A_{ds}{}^mC_{ds}T_{ds}T_{ks}{}^mC_{ks}{}^mC_k$ | 28 |
| 1042580 | 3 | 2'-FANA | $T_{ks}T_{ks}{}^mC_{ks}A_{ds}G_{ds}U_{(FANA)s}{}^mC_{ds}A_{ds}T_{ds}G_{ds}A_{ds}{}^mC_{ds}T_{ds}T_{ks}{}^mC_{ks}{}^mC_k$ | 29 |
| 1042576 | 3 | 2'-ribo-F | $T_{ks}T_{ks}{}^mC_{ks}A_{ds}G_{ds}U_{fs}{}^mC_{ds}A_{ds}T_{ds}G_{ds}A_{ds}{}^mC_{ds}T_{ds}T_{ks}{}^mC_{ks}{}^mC_k$ | 29 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vivo toxicity studies, two BALB/C mice per modified oligonucleotide was administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 17

Toxicity of modified oligonucleotides complementary SRB1

| Compound ID | position of altered nucleotide in central region | sugar modification of altered nucleotide | ALT @ 150 mg/kg (IU/L) |
|---|---|---|---|
| 449093 | n/a | n/a | 2009 |
| 982031 | 2 | 2'-OMe | 2168 |
| 1042573 | 2 | 2'-MOE | 3368 |
| 1042574 | 2 | cEt | 1972 |
| 1042575 | 2 | 2'-FANA | 16335 |
| 1042572 | 2 | 2'-ribo-F | 3563 |
| 982032 | 3 | 2'-OMe | 1630 |
| 1042577 | 3 | 2'-MOE | 2965 |
| 1042578 | 3 | cEt | 3650 |
| 1042580 | 3 | 2'-FANA | 6622 |
| 1042576 | 3 | 2'-ribo-F | 3521 |

For the in vitro study reported in the tables below, 3T3-L1 cells were transfected with 27, 80, 250, 740, 2, 222, 6,667, or 20,000 nM of modified oligonucleotide by electroporation and levels of P21 and Gadd45a were measured by RT-qPCR as described in example 1.

TABLE 17b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 449093 | 99 | 107 | 101 | 104 | 175 | 212 | 255 |
| 982030 | 102 | 100 | 108 | 125 | 172 | 215 | 288 |
| 982031 | 115 | 116 | 114 | 137 | 174 | 204 | 330 |
| 982032 | 107 | 97 | 106 | 112 | 134 | 183 | 224 |

TABLE 17c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 449093 | 124 | 105 | 120 | 105 | 122 | 215 | 350 |
| 982030 | 105 | 103 | 107 | 104 | 126 | 249 | 551 |
| 982031 | 88 | 79 | 86 | 80 | 95 | 182 | 447 |
| 982032 | 82 | 69 | 73 | 76 | 89 | 172 | 366 |

Example 8 Effect of Inosine Substitution on In Vitro Activity and In Vivo Liver Toxicity of Modified Oligonucleotides Complementary to CXCL12 and Factor XI

TABLE 18

Modified oligonucleotides

| Compound ID | position of altered nucleotide in central region | nucleobase of altered nucleotide | Chemistry Notation (5'-3') | SEQ ID NO |
|---|---|---|---|---|
| 1061955 | 2 | Inosine | $G_{ks}{}^mC_{ks}A_{ks}T_{ds}I_{ds}T_{ds}T_{ds}{}^mC_{ds}T_{ds}{}^mC_{ds}A_{ds}{}^mC_{ds}A_{ds}T_{ks}T_{ks}A_k$ | 30 |
| 1154233 | 2 | Inosine | $G_{ks}T_{ks}{}^mC_{ks}T_{ds}I_{ds}T_{ds}G_{ds}{}^mC_{ds}A_{ds}T_{ds}{}^mC_{ds}T_{ks}{}^mC_{ds}T_{ks}{}^mC\text{-}{}_{ks}{}^mC_k$ | 40 |

A subscript "d" indicates a nucleoside comprising an unmodified, 2'-β-D-deoxyribosyl sugar moiety. A subscript "k" indicates a cEt. A subscript "s" indicates a phosphorothioate internucleoside linkage. A superscript "m" before C indicates 5-methyl Cytosine. I indicates inosine.

For in vitro activity studies, 3T3-L1 cells were plated at 20,000 cells/well and transfected with 27 nM, 80 nM, 250 nM, 740 nM, 2,222 nM, 6,667 nM, or 20,000 nM modified oligonucleotide by electroporation. mRNA was harvested and analyzed by RT-qPCR. CXCL12 mRNA and P21 mRNA were analyzed as in example 1.

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide.

For the in vivo activity and toxicity study in the table below, two BALB/C mice per group were administered 16.7, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 19

Effect of Inosine on activity and toxicity

| Compound ID | position of altered nucleotide in central region | nucleobase of altered nucleotide | CXCL12 IC$_{50}$ (μM) | in vivo CXCL12 ED$_{50}$ (mg/kg) | ALT @ 16.7 mg/kg (IU/L) | ALT @ 50 mg/kg (IU/L) | ALT @ 150 mg/kg (IU/L) |
|---|---|---|---|---|---|---|---|
| 558807* | n/a | n/a | 0.2 | 1.7 | 209 | death | death |
| 1061955 | 2 | Inosine | 0.3 | 4.2 | 20.5 | 26 | 86 |

*Data presented above in Example 4

TABLE 19b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 102 | 104 | 105 | 101 | 133 | 191 | 301 |
| 1061955 | 117 | 116 | 106 | 104 | 104 | 121 | 149 |

TABLE 19c in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 135 | 110 | 131 | 115 | 147 | 476 | 462 |
| 1061955 | 75 | 81 | 134 | 120 | 121 | 162 | 170 |

For the study in the tables below, two BALB/C mice per group were administered 1.8 mg/kg, 5.5 mg/kg, 16.7 mg/kg, 50 mg/kg, or 150 mg/kg modified oligonucleotide by subcutaneous injection and sacrificed after 72 hours. 558807 was administered at 1.8 mg/kg, 5.5 mg/kg, 16.7 mg/kg due to acute toxicity at higher doses. Expression levels of Gadd45a, Tnfrsf10b, and P21 mRNA were measured as described in Example 1. Data for 558807 was also presented in Example 2, Tables 6b-6d.

TABLE 19d

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 122 | 211 | 278 | n/a | n/a |
| 1061955 | 109 | 86 | 93 | 84 | 123 |

TABLE 19e

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 160 | 166 | 271 | n/a | n/a |
| 1061955 | 158 | 77 | 126 | 134 | 192 |

TABLE 19f

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 173 | 148 | 1456 | n/a | n/a |
| 1061955 | 36 | 8.6 | 16 | 33 | 72 |

For the in vivo activity and toxicity study in the table below, two BALB/C mice per group were administered 33 or 100 mg/kg modified oligonucleotide by subcutaneous injection and sacrificed 72 hours later. Four mice were administered an injection of saline as a control. FXI mRNA expression was measured by RT-qPCR as described in Example 3. Plasma levels of ALT were measured using an automated clinical chemistry analyzer. Increased ALT is indicative of acute liver toxicity.

TABLE 19g

Effect of Inosine on activity and toxicity

| Compound ID | position of altered nucleotide in central region | nucleobase of altered nucleotide | FXI mRNA @ 33 mg/kg (% control) | FXI mRNA @ 100 mg/kg (% control) | ALT @33 mg/kg (IU/L) | ALT @ 100 mg/kg (IU/L) |
|---|---|---|---|---|---|---|
| 464917* | n/a | n/a | 10.9 | 0.9 | 7511 | 31066 |
| 1154233 | 2 | Inosine | 5.0 | 1.2 | 315 | 4553 |

*Data presented above in Example 4

Example 9 Effect of Position-Specific Nucleobase Substitutions on In Vitro Activity and In Vivo Liver Toxicity of Modified Oligonucleotides Complementary to CXCL12

Modified oligonucleotides containing nucleobase modifications at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

Nucleobase modifications:

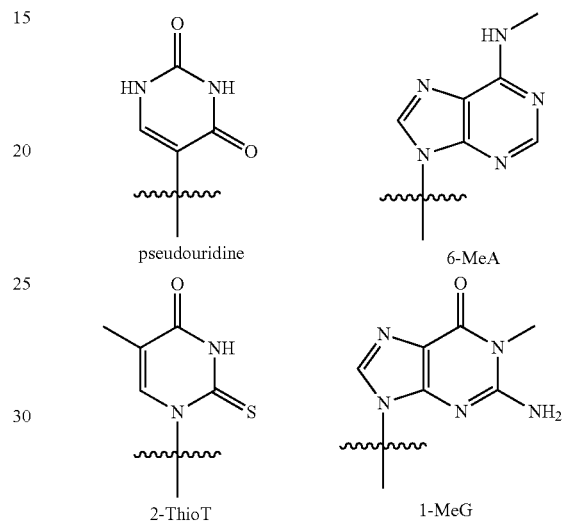

pseudouridine, 6-MeA, 2-ThioT, 1-MeG

TABLE 20

Modified oligonucleotides

| Compound ID | position of altered nucleotide in central region | nucleobase of altered nucleotide | Chemistry Notation (5'-3') | SEQ ID NO |
|---|---|---|---|---|
| 1076587 | 2 | 6-MeA, 2'-OH | $G_{ks}{}^mC_{ks}A_{ks}{}^{m6}A_{rs}T_{ds}T_{ds}{}^mC_{ds}T_{ds}{}^mC_{ds}A_{ds}{}^mC_{ds}A_{ds}T_{ks}T_{ks}A_k$ | 31 |
| 1076588 | 3 | 6-MeA, 2'-OH | $G_{ks}{}^mC_{ks}A_{ks}T_{ds}G_{ds}{}^{m6}A_{rs}T_{ds}{}^mC_{ds}T_{ds}{}^mC_{ds}A_{ds}{}^mC_{ds}A_{ds}T_{ks}T_{ks}A_k$ | 32 |
| 1069852 | 2 | pseudouridine, 2'-OH | $G_{ks}{}^mC_{ks}A_{ks}T_{ds}\Psi_{rs}T_{ds}T_{ds}{}^mC_{ds}T_{ds}{}^mC_{ds}A_{ds}{}^mC_{ds}A_{ds}T_{ks}T_{ks}A_k$ | 33 |
| 1061328 | 3 | pseudouridine, 2'-OH | $G_{ks}{}^mC_{ks}A_{ks}T_{ds}G_{ds}\Psi_{rs}T_{ds}{}^mC_{ds}T_{ds}{}^mC_{ds}A_{ds}{}^mC_{ds}A_{ds}T_{ks}T_{ks}A_k$ | 34 |
| 1016673 | 1 | pseudouridine, 2'-H | $G_{ks}{}^mC_{ks}A_{ks}\Psi_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 35 |
| 1004684 | 3 | pseudouridine, 2'-H | $G_{ks}{}^mC_{ks}A_{ks}T_{ds}T_{ds}\Psi_{ds}T_{ds}{}^mC_{ds}T_{ds}{}^mC_{ds}A_{ds}{}^mC_{ds}A_{ds}T_{ks}T_{ks}A_k$ | 36 |
| 1004685 | 4 | pseudouridine, 2'-H | $G_{ks}{}^mC_{ks}A_{ks}T_{ds}G_{ds}T_{ds}\Psi_{ds}{}^mC_{ds}T_{ds}{}^mC_{ds}A_{ds}{}^mC_{ds}A_{ds}T_{ks}T_{ks}A_k$ | 37 |
| 1016674 | 6 | pseudouridine, 2'-H | $G_{ks}{}^mC_{ks}A_{ks}T_{ds}G_{ds}T_{ds}{}^mC_{ds}T_{ds}\Psi_{ds}{}^mC_{ds}A_{ds}{}^mC_{ds}A_{ds}T_{ks}T_{ks}A_k$ | 38 |
| 863089 | 1 | 2-thioT | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 863090 | 3 | 2-thioT | $G_{ks}{}^mC_{ks}A_k{}^sT_{ds}G_{ds}{}^sT_{ds}T_{ds}{}^mC_{ds}T_{ds}{}^mC_{ds}A_{ds}{}^mC_{ds}A_{ds}T_{ks}T_{ks}A_k$ | 18 |
| 863091 | 4 | 2-thioT | $G_{ks}{}^mC_{ks}A_{ks}T_{ds}G_{ds}T_{ds}{}^sT_{ds}{}^mC_{ds}T_{ds}{}^mC_{ds}A_{ds}{}^mC_{ds}A_{ds}T_{ks}T_{ks}A_k$ | 18 |
| 863092 | 6 | 2-thioT | $G_{ks}{}^mC_{ks}A_{ks}T_{ds}G_{ds}T_{ds}{}^sT_{ds}{}^mC_{ds}T_{ds}{}^mC_{ds}A_{ds}{}^mC_{ds}A_{ds}T_{ks}T_{ks}A_k$ | 18 |
| 1061964 | 2 | 1-MeG, 2'-OH | $G_{ks}{}^mC_{ks}A_{ks}T_{ds}{}^{m1}G_{rs}T_{ds}T_{ds}{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety. A subscript "r" indicates a unmodified,β-D-ribofuranosyl sugar moiety. A subscript "k" indicates a cEt. A subscript "s" indicates a phosphorothioate internucleoside linkage. A superscript "m" before C indicates 5-methyl Cytosine. A subscript "s" indicates a phosphorothioate internucleoside linkage. A superscript "m" before a nucleobase indicator indicates that the nucleobase has a 5-methyl group, such as methyl Cytosine, methyl Adenosine, or methyl Guanosine. A superscript "m6" before a A indicates 6-methyl Adenosine Ψ represents the nucleobase pseudouridine. ST represents the nucleobase 2-thiothymidine.

For in vitro activity studies, 3T3-L1 cells were plated at 20,000 cells/well and transfected with 10 nM, 30 nM, 250 nM, 740 nM, 2,220 nM, 6, 667 nM, or 20,000 nM modified oligonucleotide by electroporation. mRNA was harvested and analyzed by RT-qPCR. CXCL12 and RAPTOR mRNA was analyzed as in Example 1. The in vitro caspase assay was performed as described in Example 4.

For the in vivo toxicity study in the table below, two BALB/C mice per modified oligonucleotide were administered 50 or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 21

Effect of modified nucleobases on activity and toxicity

| Compound ID | position of altered nucleotide in central region | nucleobase of altered nucleotide | CXCL12 IC$_{50}$ (nM) | RAPTOR IC$_{50}$ (nM) | ALT @ 50 mg/kg (IU/L) | ALT @ 150 mg/kg (IU/L) |
|---|---|---|---|---|---|---|
| 558807 | n/a | n/a | 47 | 800 | 6303 | death |
| 1076587 | 2 | 6-MeA | 300 | 18 | n.d. | n.d. |
| 1076588 | 3 | 6-MeA | 1400 | 13 | n.d. | n.d. |
| 1016673 | 1 | pseudouridine, 2'-H | 156 | 3600 | n.d. | n.d. |
| 1004684 | 2 | pseudouridine, 2'-H | 105 | 2600 | n.d. | n.d. |
| 1004685 | 3 | pseudouridine, 2'-H | 157 | 4100 | n.d. | n.d. |
| 1016674 | 4 | pseudouridine, 2'-H | 142 | 3800 | n.d. | n.d. |
| 863089 | 1 | 2-thioT | 48 | 8800 | 390 | 3620 |
| 863090 | 3 | 2-thioT | 130 | 1400 | death | death |
| 863091 | 4 | 2-thioT | 155 | 1700 | 6237 | death |
| 863092 | 6 | 2-thioT | 110 | 1900 | 14514.5 | death |
| 1061964 | 2 | 1-MeG | 5200 | 8600 | n.d. | n.d. |

TABLE 21b in vitro Caspase Activation

| Compound ID | 27 nM | 80 nM | 250 nM | 740 nM | 2222 nM | 6667 nM | 20,000 nM |
|---|---|---|---|---|---|---|---|
| | Relative Caspase Activation (% Control) | | | | | | |
| 558807 | 100 | 100 | 100 | 97 | 110 | 202 | 298 |
| 1076587 | 90 | 86 | 80 | 82 | 81 | 77 | 94 |
| 1076588 | 91 | 91 | 96 | 91 | 96 | 97 | 114 |
| 1069852 | 97 | 87 | 105 | 100 | 89 | 79 | 85 |
| 1061328 | 92 | 95 | 96 | 98 | 102 | 153 | 199 |

TABLE 21c in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 135 | 110 | 131 | 115 | 147 | 476 | 462 |
| 1061964 | 107 | 142 | 140 | 149 | 135 | 123 | 125 |

TABLE 21d in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 102 | 104 | 105 | 101 | 133 | 191 | 301 |
| 1061964 | 121 | 110 | 115 | 90 | 107 | 102 | 90 |

For in vivo activity and toxicity study in the table below, 2 BALB/C mice per group were administered modified oligonucleotide by subcutaneous injection and sacrificed after 72 hours. Compounds were dosed at 0.6, 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_ml (ThermoFisher). Levels of P21 were analyzed using primer probe set Mm04207341_ml (ThermoFisher). Levels of Tnfrsf10b were analyzed using primer probe set Mm00457866_ml (ThermoFisher). Expression levels were normalized with Ribogreen® and are presented relative to levels in mice treated with PBS.

TABLE 21e

In Vivo of modified oligonucleotides complementary to CXCL12 containing 2-Thio-T

| Compound ID | 2-Thio-T position in central region | ALT@16.7 mg/kg (IU/L) | ALT @50 mg/kg (IU/L) | ALT @ 150 mg/kg (IU/L) |
|---|---|---|---|---|
| PBS | n/a | | 27 (@0 mg/kg) | |
| 558807 | n/a | | 2002 | 6303 | death |

TABLE 21e-continued

In Vivo of modified oligonucleotides complementary to CXCL12 containing 2-Thio-T

| Compound ID | 2-Thio-T position in central region | ALT@16.7 mg/kg (IU/L) | ALT @50 mg/kg (IU/L) | ALT @ 150 mg/kg (IU/L) |
|---|---|---|---|---|
| 863089 | 1 | 60 | 390 | 3620 |
| 863090 | 3 | 4929 | death | death |
| 863091 | 4 | 1894 | 6237 | death |
| 863092 | 6 | 1073 | 14515 | death |

TABLE 21f

In Vivo Activity of modified oligonucleotides complementary to CXCL12 containing 2-Thio-T

| Compound ID | 0.6 mg/kg | 1.8 mg/kg | 5.5 mg/kg | 16.7 mg/kg | 50 mg/kg | 150 mg/kg |
|---|---|---|---|---|---|---|
| | Expression level of CXCL12 mRNA (% Control) | | | | | |
| 558807 | 65 | 34 | 14 | 4 | 7 | n.d. |
| 863089 | 72 | 51 | 33 | 16 | 14 | 8 |
| 863090 | 58 | 31 | 11 | 11 | 0 | 0 |
| 863091 | 66 | 28 | 24 | 12 | 12 | 0 |
| 863092 | 59 | 42 | 20 | 5 | 6 | 0 |

Example 10 Effect of Position-Specific Morpholinos on In Vitro Activity and In Vivo Liver Toxicity of Modified Oligonucleotides Complementary to CXCL12

Modified oligonucleotides containing morpholinos at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892. Morpholino residues replace a full nucleotide, including the internucleoside linkage, and have the structures shown below.

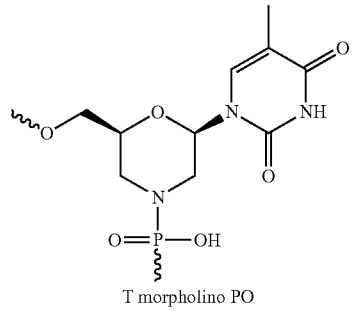

T morpholino PO

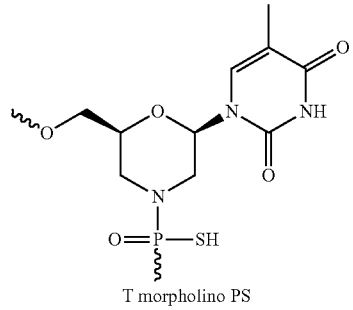

T morpholino PS

TABLE 22

| Compound ID | morpholino position in central region | morpholino type | Chemistry Notation (5'-3') | SEQ ID NO |
|---|---|---|---|---|
| 1044689 | 1 | T-PO | $G_{ks}{}^mC_{ks}A_{ks}(MP^T{}_0)$ $G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1044690 | 3 | T-PO | $G_{ks}{}^mC_{ks}A_{ks}T_{ds}G_{ds}(MP^T{}_0)$ $T_{ds}{}^mC_{ds}T_{ds}{}^mC_{ds}A_{ds}{}^mC_{ds}A_{ds}T_{ks}T_{ks}A_k$ | 18 |
| 1044691 | 4 | T-PO | $G_{ks}{}^mC_{ks}A_{ks}T_{ds}G_{ds}T_{ds}(MP^T{}_0)$ ${}^mC_{ds}T_{ds}{}^mC_{ds}A_{ds}{}^mC_{ds}A_{ds}T_{ks}T_{ks}A_k$ | 18 |
| 1044692 | 6 | T-PO | $G_{ks}{}^mC_{ks}A_{ks}T_{ds}G_{ds}T_{ds}T_{ds}{}^mC_{ds}(MP^T{}_0)$ ${}^mC_{ds}A_{ds}{}^mC_{ds}A_{ds}T_{ks}T_{ks}A_k$ | 18 |
| 1048416 | 1 | T-PS | $G_{ks}{}^mC_{ks}A_{ks}(MP^T{}_s)$ $G_{ds}T_{ds}T_{ds}{}^mC_{ds}T_{ds}{}^mC_{ds}A_{ds}{}^mC_{ds}A_{ds}T_{ks}T_{ks}Ak$ | 18 |
| 1048417 | 3 | T-PS | $G_{ks}{}^mC_{ks}A_{ks}T_{ds}G_{ds}(MP^T{}_s)$ $T_{ds}{}^mC_{ds}T_{ds}{}^mC_{ds}A_{ds}{}^mC_{ds}A_{ds}T_{ks}T_{ks}A_k$ | 18 |
| 1048418 | 4 | T-PS | $G_{ks}{}^mC_{ks}A_{ks}T_{ds}G_{ds}T_{ds}(MP^T{}_s)$ ${}^mC_{ds}T_{ds}{}^mC_{ds}A_{ds}{}^mC_{ds}A_{ds}T_{ks}T_{ks}A_k$ | 18 |
| 1048419 | 6 | T-PS | $G_{ks}{}^mC_{ks}A_{ks}T_{ds}G_{ds}T_{ds}T_{ds}{}^mC_{ds}(MP^T{}_s)$ ${}^mC_{ds}A_{ds}{}^mC_{ds}A_{ds}T_{ks}T_{ks}A_k$ | 18 |

A subscript "d" indicates a nucleoside comprising an unmodified, 2'-β-D-deoxyribosyl sugar moiety. A subscript "r" indicates a nucleoside comprising an unmodified, β-D-ribofuranosyl sugar moiety. A subscript "k" indicates a cEt. A subscript "s" indicates a phosphorothioate internucleoside linkage. A superscript "m" before C indicates 5-methyl Cytosine. A $(MP^T_o)$ represents a phosphate thymidine morpholino, while $(MP^T_s)$ represents a phosphorothioate thymidine morpholino.

TABLE 22

Effect of morpholinos on in vitro activity and toxicity

| Compound ID | morpholino position in central region | morpholino type | CXCL12 $IC_{50}$ (nM) | RAPTOR $IC_{50}$ (nM) |
|---|---|---|---|---|
| 558807 | n/a | n/a | 47 | 800 |
| 1044689 | 1 | T-PO | 405 | >20000 |
| 1044690 | 3 | T-PO | 182 | 4100 |
| 1044691 | 4 | T-PO | 128 | 4400 |
| 1044692 | 6 | T-PO | 145 | 1900 |
| 1048416 | 1 | T-PS | 333 | >20000 |
| 1048417 | 3 | T-PS | 159 | 3300 |
| 1048418 | 4 | T-PS | 134 | 5200 |
| 1048419 | 6 | T-PS | 119 | 1100 |

Example 11 Effect of Position-Specific MOP on In Vitro Activity and In Vivo Toxicity of Modified Oligonucleotides Complementary CXCL12, Factor XI, PTEN, and SOD-1

Modified oligonucleotides were synthesized with MOP neutral backbone linkages at specific positions in place of phosphorothioate linkages. These modified oligonucleotides were compared to the otherwise identical modified oligonucleotide lacking the altered nucleotide in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12, Factor XI, PTEN, or SOD-1, with sequences described above.

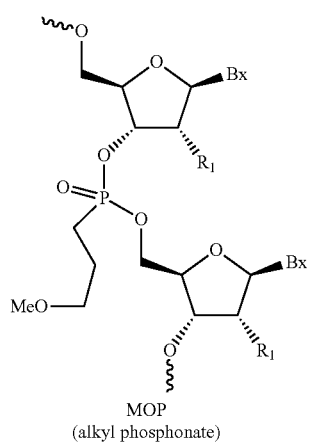

MOP
(alkyl phosphonate)

TABLE 23

Modified oligonucleotides containing MOP linkages

| Compound ID | MOP position in central region | Target | Chemistry Notation (5'-3') | SEQ ID NO |
|---|---|---|---|---|
| 766676 | 1 | CXCL12 | $G_{ks}{}^mC_{ks}A_{ks}T_{ds}G_{dx}T_{ds}T_{ds}{}^mC_{ds}T_{ds}{}^mC_{ds}A_{ds}{}^mC_{ds}A_{ds}T_{ks}T_{ks}A_k$ | 18 |
| 766677 | 2 | CXCL12 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 766678 | 3 | CXCL12 | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 766679 | 4 | CXCL12 | $G_{ks}{}^mC_{ks}A_{ks}T_{ds}G_{ds}T_{ds}T_{ds}{}^mC_{dx}T_{ds}{}^mC_{ds}A_{ds}{}^mC_{ds}A_{ds}T_{ks}T_{ks}A_k$ | 18 |
| 766680 | 5 | CXCL12 | $G_{ks}{}^mC_{ks}A_{ks}T_{ds}G_{ds}T_{ds}T_{ds}{}^mC_{ds}T_{dx}{}^mC_{ds}A_{ds}{}^mC_{ds}A_{ds}T_{ks}T_{ks}A_k$ | 18 |
| 766681 | 6 | CXCL12 | $G_{ks}{}^mC_{ks}A_{ks}T_{ds}G_{ds}T_{ds}T_{ds}{}^mC_{ds}T_{ds}{}^mC_{dx}A_{ds}{}^mC_{ds}A_{ds}T_{ks}T_{ks}A_k$ | 18 |
| 766682 | 7 | CXCL12 | $G_{ks}{}^mC_{ks}A_{ks}T_{ds}G_{ds}T_{ds}T_{ds}{}^mC_{ds}T_{ds}{}^mC_{dx}A_{ds}{}^mC_{ds}A_{ds}T_{ks}T_{ks}A_k$ | 18 |
| 766683 | 8 | CXCL12 | $G_{ks}{}^mC_{ks}A_{ks}T_{ds}G_{ds}T_{ds}T_{ds}{}^mC_{ds}T_{ds}{}^mC_{ds}A_{dx}{}^mC_{ds}A_{ds}T_{ks}T_{ks}A_k$ | 18 |
| 766684 | 9 | CXCL12 | $G_{ks}{}^mC_{ks}A_{ks}T_{ds}G_{ds}T_{ds}T_{ds}{}^mC_{ds}T_{ds}{}^mC_{ds}A_{ds}{}^mC_{dx}A_{ds}T_{ks}T_{ks}A_k$ | 18 |
| 766685 | 10 | CXCL12 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{dx}T_{ks}T_{ks}A_k$ | 18 |
| 965605 | 2 | FactorXI | $G_{ks}T_{ks}{}^mC_{ks}T_{ds}G_{dx}T_{ds}G_{ds}{}^mC_{ds}A_{ds}T_{ds}{}^mC_{ds}T_{ds}{}^mC_{ds}T_{ks}{}^mC_{ks}{}^mC_k$ | 22 |
| 965606 | 3 | FactorXI | $G_{ks}T_{ks}{}^mC_{ks}T_{ds}G_{ds}T_{dx}G_{ds}{}^mC_{ds}A_{ds}T_{ds}{}^mC_{ds}T_{ds}{}^mC_{ds}T_{ks}{}^mC_{ks}{}^mC_k$ | 22 |
| 985299 | 2 | PTE' | $A_{ks}T_{ks}{}^mC_{ks}A_{ds}T_{dx}G_{ds}G_{ds}{}^mC_{ds}T_{ds}G_{ds}{}^mC_{ds}A_{ds}G_{ds}{}^mC_{ks}T_{ks}T_k$ | 24 |
| 985303 | 3 | PTEN | $A_{ks}T_{ks}{}^mC_{ks}A_{ds}T_{ds}G_{dx}G_{ds}{}^mC_{ds}T_{ds}G_{ds}{}^mC_{ds}A_{ds}G_{ds}ksT_{ks}T_k$ | 24 |
| 985307 | 2 | SOD1 | $T_{ks}G_{ks}A_{ks}G_{ds}G_{dx}T_{ds}{}^mC_{ds}{}^mC_{ds}T_{ds}G_{ds}{}^mC_{ds}A_{ds}{}^mC_{ds}T_{ks}G_{ks}G_k$ | 26 |
| 985311 | 3 | SOD1 | $T_{ks}G_{ks}A_{ks}G_{ds}G_{ds}T_{dx}{}^mC_{ds}{}^mC_{ds}T_{ds}G_{ds}{}^mC_{ds}A_{ds}{}^mC_{ds}T_{ks}G_{ks}G_k$ | 26 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP or methoxypropyl internucleoside linkage. The position of the internucleoside linkage is designated as the position of the nucleoside that is on the 5' end of the linkage.

For in vitro activity studies for compounds complementary to CXCL12, b.END cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. CXCL12 and raptor mRNA was analyzed as in previous examples.

modified oligonucleotide by subcutaneous injection and sacrificed 24 hours later. Mice were administered 1.9 mg/kg, 5.6 mg/kg, 16.7 mg/kg, 50 mg/k or 150 mg/kg of compound 558807 or 766676-766685. Mice were administered 6.25 mg/kg, 12.5 mg/kg, 25 mg/kg, 50 mg/kg, or 100 mg/kg modified oligonucleotide for compounds 965605 and 965606. Mice were administered 6.25 mg/kg, 12.5 mg/kg, 25 mg/kg, or 100 mg/kg modified oligonucleotide for 464917. Mice were administered 6.25 mg/kg, 12.5 mg/kg, 25 mg/kg, or 150 mg/kg modified oligonucleotide for 482050. Mice were administered 6.25 mg/kg, 12.5 mg/kg, 25 mg/kg, 50 mg/kg or 150 mg/kg modified oligonucleotide for 985299 and 985303. Mice were administered 12.5 mg/kg, 25 mg/kg, 50 mg/kg or 150 mg/kg modified oligonucleotide for 508031, 985307, and 985311. Two animals were administered an injection of saline as a control.

TABLE 24

Effect of MOP backbone modifications on activity and toxicity

| Compound ID | MOP position in central region | Complementary mRNA | Complementary mRNA $IC_{50}$ (µM) | RAPTOR $IC_{50}$ (µM) | in vivo Complementary mRNA $ED_{50}$ (mg/kg) | ALT @ Max dose* (IU/L) |
|---|---|---|---|---|---|---|
| PBS | n/a | n/a | n/a | n/a | n/a | 23 |
| 558807 | n/a | CXCL12 | 0.095 | 1.26 | 2.9 | death |
| 766676 | 1 | CXCL12 | 0.100 | 5.8 | 4.5 | 7764 |
| 766677 | 2 | CXCL12 | 0.110 | >>10 | 6.8 | 46 |
| 766678 | 3 | CXCL12 | 0.115 | >>10 | 6.2 | 44 |
| 766679 | 4 | CXCL12 | 0.080 | 7.2 | 5.7 | 4481 |
| 766680 | 5 | CXCL12 | 0.085 | 3.5 | 5.1 | 9139 |
| 766681 | 6 | CXCL12 | 0.080 | 3.0 | 3.6 | 17846 |
| 766682 | 7 | CXCL12 | 0.090 | 3.8 | 4.4 | 12510 |
| 766683 | 8 | CXCL12 | 0.070 | 2.2 | 4.3 | death |
| 766684 | 9 | CXCL12 | 0.090 | 2.2 | 3.1 | death |
| 766685 | 10 | CXCL12 | 0.090 | 2.0 | 2.1 | death |
| 464917 | n/a | Factor XI | n.d. | 1.6 | 6.9 | 33848 |
| 965605 | 2 | Factor XI | n.d. | 3.7 | 10.2 | 3464 |
| 965606 | 3 | Factor XI | n.d. | 7.7 | 12.3 | 1160 |
| 482050 | n/a | PTEN | 3.9 | 2.4 | 67 | 2458 |
| 985299 | 2 | PTEN | 1.1 | 4 | 120 | 767 |
| 985303 | 3 | PTEN | 1.7 | 3.7 | 194 | 43 |
| 508031 | n/a | SOD1 | 0.03 | 0.46 | 63 | 21934 |
| 985307 | 2 | SOD1 | 0.17 | 3.6 | 157 | 57 |
| 985311 | 3 | SOD1 | 0.78 | 5.1 | 173 | 71 |

*ALT at 150 mg/kg for CXCL12 oligonucleotides, 100 mg/kg for Factor XI oligonucleotides, 200 mg/kg for PTEN oligonucleotides 985299 and 985303, 100 mg/kg for PTEN oligonucleotide 482050 and 150 mg/kg for SOD1 oligonucleotides 985307 and 985311, and 100 mg/kg for SOD1 oligonucleotide 508031.
**Value represents the average of two independent experiments For in vitro activity studies for compounds complementary to Factor XI, PTEN or SOD1, 3T3-L1 cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. Complementary mRNA and raptor mRNA was analyzed as in previous examples.

For the in vivo toxicity study in the table below, one or two BALB/C mice per modified oligonucleotide were administered modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

For the in vivo activity study in the table below, two to four BALB/C mice per dosing group were administered Relative caspase activation in 3T3-L1 cells was determined as described in Example 4.

For the in vitro study reported in the tables below, b.END cells were electroporated with 27 nM, 80 nM, 250 nM, 740 nM, 2, 222 nM, 6,667 nM, or 20,000 nM of modified oligonucleotide and levels of P21 were measured by RT-qPCR using primer probe set Mm04207341_ml (ThermoFisher).

Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted.

TABLE 24a

Effect of MOP backbone modifications on activity and toxicity

| Compound ID | MOP position in central region | Complementary mRNA | Caspase (% mock) | in vitro p21 mRNA (% saline) | % nucleolar p54nrb |
|---|---|---|---|---|---|
| 558807 | n/a | CXCL12 | 313 | 243 | 82 |
| 766676 | 1 | CXCL12 | 243 | 187 | 32 |
| 766677 | 2 | CXCL12 | 121 | 179 | 25 |
| 766678 | 3 | CXCL12 | 136 | 180 | 32 |
| 766679 | 4 | CXCL12 | 240 | 195 | 39 |
| 766680 | 5 | CXCL12 | 351 | 263 | 86 |
| 766681 | 6 | CXCL12 | 315 | 309 | 79 |
| 766682 | 7 | CXCL12 | 345 | 236 | 71 |
| 766683 | 8 | CXCL12 | 257 | 260 | 91 |
| 766684 | 9 | CXCL12 | 314 | 247 | 88 |
| 766685 | 10 | CXCL12 | 308 | 291 | 90 |

For the in vivo toxicity study in the table below, two BALB/C mice per dosing group were administered modified oligonucleotide by subcutaneous injection and sacrificed 72 hours later. Mice were administered 10 mg/kg, 33 mg/kg, or 100 mg/kg modified oligonucleotide for compounds 464917, 965605, and 965606 and 10 mg/kg, 100 mg/kg, or 200 mg/kg for 482050, 985299, and 985303. Two animals were administered an injection of saline as a control. Plasma levels of ALT were measured using an automated clinical chemistry analyzer. Increased ALT is indicative of acute liver toxicity. Therapeutic index was calculated as the ratio of maximum non-toxic dose (MNTD)/ED$_{50}$, where ED$_{50}$ was determined via the in vivo activity study reported in the table above.

TABLE 24b

In vivo Toxicity improvement for modified oligonucleotides complementary to Factor XI

| Compound ID | ALT @ 10 mg/kg | ALT @ 33 mg/kg | ALT @ 100 mg/kg | TI (MNTD/ED50) |
|---|---|---|---|---|
| 464917 | 239 | 8199 | 33848 | 1.4 |
| 965605 | 46 | 125 | 3464 | 3.2 |
| 965606 | 55 | 77 | 1160 | 2.7 |

TABLE 24c in vivo Toxicity improvement for modified oligonucleotides complementary to PTEN

| Compound ID | ALT @ 10 mg/kg | ALT @ 100 mg/kg | ALT @ 200 mg/kg | TI (MNTD/ED50) |
|---|---|---|---|---|
| 482050 | 55 | 9496 | 5329 | 0.15 |
| 985299 | 45 | 164 | 767 | 0.8 |
| 985303 | 33 | 39 | 43 | 1.0 |

TABLE 24d in vivo Toxicity improvement for modified oligonucleotides complementary to SOD1

| Compound ID | ALT @ 50 mg/kg | ALT @ 150 mg/kg | TI (MNTD/ED50) |
|---|---|---|---|
| 482050 | 2189 | n.d. | <0.8 |
| 985307 | n.d. | 57 | >1.0 |
| 985311 | n.d. | 71 | >0.9 |

Example 12 Effect of Position-Specific MOP in Combination with 2'-Modifications Modified oligonucleotides were synthesized with MOP neutral backbone linkages at specific positions in place of phosphorothioate linkages in combination with 2'-FANA or 2'-OMe modified sugar moieties. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12 or SOD1, with sequences as described above.

3'-HPPO-GalNAc refers to the structure below, wherein the phosphate group is attached to the 3'-oxygen atom of the 3' nucleoside:

TABLE 25

Modified oligonucleotides containing MOP linkages and 2'-Modifications

| Compound ID | MOP position in central region | 2'-altered nucleotide position in central region | sugar modification of 2'-altered nucleotide | Target | Chemistry Notation (5'-3') | SEQ ID NO |
|---|---|---|---|---|---|---|
| 1061302 | 1 | 1 | 2'-OMe | CXCL12 | $G_{ks}{}^mC_{ks}A_{ks}T_{mx}G_{ds}T_{ds}T_{ds}{}^mC_{ds}T_{ds}{}^mC_{ds}A_{ds}{}^mC_{ds}A_{ds}T^{ks}T_{ks}A_k$ | 18 |
| 1061303 | 2 | 2 | 2'-OMe | CXCL12 | $G_{ks}{}^mC_{ks}A_{ks}T_{ds}G_{mx}T_{ds}T_{ds}{}^mC_{ds}T_{ds}{}^mC_{ds}A_{ds}{}^mC_{ds}A_{ds}T_{ks}T_{ks}A_k$ | 18 |
| 1061304 | 3 | 3 | 2'-OMe | CXCL12 | $G_{ks}{}^mC_{ks}A_{ks}T_{ds}G_{ds}T_{mx}T_{ds}{}^mC_{ds}T_{ds}{}^mC_{ds}A_{ds}{}^mC_{ds}A_{ds}T_{ks}T_{ks}A_k$ | 18 |
| 1061305 | 4 | 4 | 2'-OMe | CXCL12 | $G_{ks}{}^mC_{ks}A_{ks}T_{ds}G_{ds}T_{ds}T_{mx}{}^mC_{ds}T_{ds}{}^mC_{ds}A_{ds}{}^mC_{ds}A_{ds}T_{ks}T_{ks}A_k$ | 18 |
| 1061306 | 1 | 1 | 2'-OMe | SOD1 | $T_{ks}A_{ks}G_{mx}G_{ds}T_{ds}{}^mC_{ds}{}^mC_{ds}T_{ds}G_{ds}{}^mC_{ds}A_{ds}{}^mC_{ds}T_{ks}G_{ks}G_k$ | 26 |
| 1061307 | 2 | 2 | 2'-OMe | SOD1 | $T_{ks}G_{ks}A_{ks}G_{ds}G_{mx}T_{ds}{}^mC_{ds}{}^mC_{ds}T_{ds}G_{ds}{}^mC_{ds}A_{ds}{}^mC_{ds}T_{ks}G_{ks}G_k$ | 26 |
| 1061308 | 3 | 3 | 2'-OMe | SOD1 | $T_{ks}G_{ks}A_{ks}G_{ds}G_{ds}T_{mx}{}^mC_{ds}{}^mC_{ds}T_{ds}G_{ds}{}^mC_{ds}A_{ds}{}^mC_{ds}T_{ks}G_{ks}G_k$ | 26 |
| 955900 | 3 | 1 | 2'-FANA | CXCL12 | $G_{ks}{}^mC_{ks}A_{ks}U_{(FANA)s}G_{ds}T_{dx}T_{ds}{}^mC_{ds}T_{ds}{}^mC_{ds}A_{ds}{}^mC_{ds}A_{ds}T_{ks}T_{ks}A_k$ | 19 |
| 955901 | 3 | 2 | 2'-FANA | CXCL12 | $G_{ks}{}^mC_{ks}A_{ks}T_{ds}G_{(FANA)s}T_{dx}T_{ds}{}^mC_{ds}T_{ds}{}^mC_{ds}A_{ds}{}^mC_{ds}A_{ds}T_{ks}T_{ks}A_k$ | 18 |
| 955902 | 3 | 4 | 2'-FANA | CXCL12 | $G_{ks}{}^mC_{ks}A_{ks}T_{ds}G_{ds}T_{dx}U_{(FANA)s}{}^mC_{ds}T_{ds}{}^mC_{ds}A_{ds}{}^mC_{ds}A_{ds}T_{ks}T_{ks}A_k$ | 21 |
| 955903 | 3 | 5 | 2'-FANA | CXCL12 | $G_{ks}{}^mC_{ks}A_{ks}T_{ds}G_{ds}T_{dx}T_{ds}{}^mC_{(FANA)s}T_{ds}{}^mC_{ds}A_{ds}{}^mC_{ds}A_{ds}T_{ks}T_{ks}A_k$ | 18 |
| 955904 | 3 | 6 | 2'-FANA | CXCL12 | $G_{ks}{}^mC_{ks}A_{ks}T_{ds}G_{ds}T_{dx}T_{ds}{}^mC_{ds}U_{(FANA)s}{}^mC_{ds}A_{ds}{}^mC_{ds}A_{ds}T_{ks}T_{ks}A_k$ | 39 |
| 955905 | 3 | 7 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}{}^mC_{(FANA)s}A_{ds}{}^mC_{ds}A_{ds}T_{ks}T_{ks}A_k$ | 18 |
| 955906 | 3 | 8 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}D_{ds}A_{(FANA)s}{}^mC_{ds}A_{ds}T_{ks}T_{ks}A_k$ | 18 |
| 955907 | 3 | 9 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}A_{ds}{}^mC_{(FANA)s}A_{ds}T_{ks}T_{ks}A_k$ | 18 |
| 955908 | 3 | 10 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{(FANA)s}T_{ks}T_{ks}A_k$ | 18 |
| 855156 | n/a | n/a | n/a | CXCL12 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$-HPPO-GalNac | 18 |
| 855161 | 3 | n/a | n/a | CXCL12 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$-HPPO-GalNac | 18 |
| 855160 | 1, 2 | n/a | n/a | CXCL12 | $G_{ks}{}^mC_{ks}A_{ks}T_{dx}G_{dx}T_{ds}T_{ds}{}^mC_{ds}T_{ds}{}^mC_{ds}A_{ds}{}^mC_{ds}A_{ds}T_{ks}T_{ks}A_k$-HPPO-GalNac | 18 |
| 895571 | n/a | 3 | 2'-MOE | CXCL12 | $G_{ks}{}^mC_{ks}A_{ks}T_{ds}G_{ds}T_{es}T_{ds}{}^mC_{ds}T_{ds}{}^mC_{ds}A_{ds}{}^mC_{ds}A_{ds}T_{ks}T_{ks}A_k$-HPPO-GalNac | 18 |
| 978782 | 3 | 2 | 2'-FANA | CXCL12 | $G_{ks}{}^mC_{ks}A_{ks}T_{ds}G_{(FANA)s}T_{dx}T_{ds}{}^mC_{ds}T_{ds}{}^mC_{ds}A_{ds}{}^mC_{ds}A_{ds}T_{ks}T_{ks}A_k$-HPPO-GalNac | 18 |
| 978783 | 3 | 4 | 2'-FANA | CXCL12 | $G_{ks}{}^mC_{ks}A_{ks}T_{ds}G_{ds}T_{dx}U_{(FANA)s}{}^mC_{ds}T_{ds}{}^mC_{ds}A_{ds}{}^mC_{ds}A_{ds}T_{ks}T_{ks}A_k$-HPPO-GalNac | 21 |
| 978784 | 3 | 5 | 2'-FANA | CXCL12 | $G_{ks}{}^mC_{ks}A_{ks}T_{ds}G_{ds}T_{dx}T_{ds}{}^mC_{(FANA)s}T_{ds}{}^mC_{ds}A_{ds}{}^mC_{ds}A_{ds}T_{ks}T_{ks}A_k$-HPPO-GalN | 18 |
| 978785 | 3 | 6 | 2'-FANA | CXCL12 | $G_{ks}{}^mC_{ks}A_{ks}T_{ds}G_{ds}T_{dx}T_{ds}{}^mC_{ds}U_{(FANA)s}{}^mC_{ds}A_{ds}{}^mC_{ds}A_{ds}T_{ks}T_{ks}A_k$-HPPO-GalNac | 39 |
| 978786 | 3 | 10 | 2'-FANA | CXCL12 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{(FANA)s}T_{ks}T_{ks}A_k$-HPPO-GalNac | 18 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated at 20,000 cells/well and transfected with 0, 27 nM, 82 nM, 247 nM, 740 nM, 2,220 nM, 6,660 nM or 20,000 nM of modified oligonucleotide by electroporation. After X hours, mRNA was harvested and analyzed by RT-qPCR. Target and raptor mRNA was analyzed as previous examples.

TABLE 26

Effect of MOP backbone modifications combined with ara-F modifications on in vitro activity and toxicity

| Compound ID | MOP position in central region | FANA position in central region | Target IC$_{50}$ (nM) | RAPTOR IC$_{50}$ (nM) |
|---|---|---|---|---|
| 558807 | n/a | n/a | 34 | 1000 |
| 766678 | 3 | n/a | 67 | >20,000 |
| 955900 | 3 | 1 | 58 | >20,000 |
| 955901 | 3 | 2 | 43 | >20,000 |
| 955902 | 3 | 4 | 27 | >20,000 |
| 955903 | 3 | 5 | 27 | >20,000 |
| 955904 | 3 | 6 | 65 | >20,000 |
| 955905 | 3 | 7 | 93 | 16000 |
| 955906 | 3 | 8 | 99 | >20,000 |
| 955907 | 3 | 9 | 154 | >20,000 |
| 955908 | 3 | 10 | 171 | >20,000 |

For the in vivo toxicity study in the table below, three male BALB/C mice per modified oligonucleotide were administered 0.2, 0.6, 1.8 or 50 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 27

Effect of MOP backbone modifications combined with 2' modifications on in vivo activity and toxicity

| Compound ID | MOP position in central region | position of 2'-altered nucleotide in central region | sugar modification of 2'-altered nucleotide | in vivo CXCL12 ED$_{50}$ (mg/kg) | ALT @ 50 mg/kg |
|---|---|---|---|---|---|
| 855156 | n/a | n/a | n/a | 0.13 | 2938* |
| 855161 | 3 | n/a | n/a | 0.36 | 40 |
| 855160 | 2, 3 | n/a | n/a | 0.37 | 28 |
| 895571 | n/a | 3 | 2'-MOE | 0.43 | 319 |
| 978782 | 3 | 2 | 2'-FANA | 0.47 | 56 |
| 978783 | 3 | 4 | 2'-FANA | 0.43 | 39 |

*Value represents the ALT at 1.8 mg/kg

For the in vivo toxicity study in the table below, male BALB/C mice per modified oligonucleotide were administered 5, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. The caspase assay was performed in vitro as described in Example 8.

TABLE 28

Effect of MOP backbone modifications combined with 2'-OMe modified sugar moieties

| Compound ID | MOP position in central region | 2'-OMe position in central region | CXCL12 IC$_{50}$ (μM) | in vivo CXCL12 ED$_{50}$ (mg/kg) | ALT @ 50 mg/kg (IU/L) | ALT @ 150 mg/kg (IU/L) |
|---|---|---|---|---|---|---|
| 558807 | n/a | n/a | 0.18 | 2.88 | 8329 | death |
| 936053 | n/a | 2 | 0.17 | 1.75 | 75 | 40 |
| 1061302 | 1 | 1 | 0.09 | 0.39 | 101 | 2253 |
| 1061303 | 2 | 2 | 0.13 | 11 | 49 | 34 |
| 1061304 | 3 | 3 | 0.09 | 4.6 | 31 | 52 |
| 1061305 | 4 | 4 | 0.09 | 15.4 | 22 | 31 |

TABLE 28b in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | Relative Caspase Activation (% Control) | | | | |
| 558807 | 98 | 106 | 112 | 139 | 288 | 587 | 1977 |
| 936053 | 106 | 111 | 113 | 91 | 98 | 107 | 153 |
| 1061302 | 98 | 90 | 106 | 111 | 149 | 456 | 1555 |
| 1061303 | 104 | 99 | 104 | 84 | 102 | 86 | 125 |
| 1061304 | 91 | 97 | 82 | 96 | 85 | 105 | 269 |
| 1061305 | 90 | 96 | 72 | 91 | 84 | 103 | 348 |

TABLE 28c

In Vivo Dose-response of Gadd45a mRNA upon treatment with modified oligonucleotides complementary to CXCL12

| Compound ID | 5.0 mg/kg | 50 mg/kg | 150 mg/kg |
|---|---|---|---|
| | Expression level of Gadd45a mRNA (% Control) | | |
| 558807 | 120 | 473 | n.d. |
| 936053 | 76 | 169 | 219 |
| 1061302 | 188 | 178 | 357 |
| 1061303 | 55 | 66 | 66 |
| 1061304 | 58 | 66 | 97 |
| 1061305 | 67 | 18 | 20 |

TABLE 28d

In Vivo Dose-response of Tnfrsf10b mRNA upon treatment with modified oligonucleotides complementary to CXCL12

| Compound ID | 5.0 mg/kg | 50 mg/kg | 150 mg/kg |
|---|---|---|---|
| | Expression level of Tnfrs10b mRNA (% Control) | | |
| 558807 | 137 | 8022 | n.d. |
| 936053 | 91 | 104 | 180 |
| 1061302 | 104 | 137 | 1217 |
| 1061303 | 90 | 92 | 110 |
| 1061304 | 70 | 75 | 149 |
| 1061305 | 79 | 60 | 50 |

TABLE 28e

In Vivo Dose-response of P21 mRNA upon treatment with modified oligonucleotides complementary to CXCL12

| Compound ID | 5.0 mg/kg | 50 mg/kg | 150 mg/kg |
|---|---|---|---|
| | Expression level of P21 mRNA (% Control) | | |
| 558807 | 84 | 58138 | n.d. |
| 936053 | 239 | 81 | 299 |
| 1061302 | 87 | 315 | 14680 |
| 1061303 | 293 | 495 | 480 |
| 1061304 | 182 | 400 | 353 |
| 1061305 | 353 | 321 | 223 |

Example 13 Effect of Position-Specific 2'-OMe on In Vitro Activity and Toxicity of Modified Oligonucleotides with a Variety of Sequences Modified oligonucleotides were synthesized as indicated in the table below. The compounds have the sugar motif kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^m$C at position 5 (from the 5' end) in the parent kkk-d(10)-kkk oligonucleotide, the kkk-d-m-d(8)-kkk contains a 2'-OMe modified C at this position, with no 5-Me group.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe sets described in Table 30 below. Results were normalized with Ribogreen® and are reported normalized to PBS-treated animals.

Levels of mRNA for Gadd45a, P21, and Tnfrsf10b were analyzed as in Example 1 for mice administered 150 mg/kg modified oligonucleotide. Results are normalized with Ribogreen® and presented relative to PBS-treated control animals.

The caspase assay was performed in vitro as described in Example 8.

TABLE 29

Targets and Sequences

| Parent Compound ID | Corresponding compound with 2'-OMe at position 2 of the central region | Complementary mRNA | Sequence | SEQ ID NO |
|---|---|---|---|---|
| 546006 | 1133071 | HDAC2 | GAGGATGGCAAGCACA | 41 |
| 549334 |  | AR | CACCTGCGGGAAGCTC | 42 |
|  | 1200896 | AR | CACCUGCGGGAAGCTC | 126 |
| 562920 | 1201379 | VWF | TGTGCCCCAGCCCATT | 43 |
| 572912 | 1200898 | PABPN1 | CTTCCACAGTATATCT | 44 |
| 576095 | 1200899 | EGLN2 | TACTGGTAGTGTTGCT | 45 |
| 597605 | 1200900 | HEGFL | TTGACACAAAGGGAGT | 46 |
| 601840 | 1201381 | MTDH | GAATCTCCTTTTCCAG | 47 |
| 640599 | 1201862 | EZH2 | TTTACACGCTTCCGCC | 48 |
| 694804 |  | DNM2 | AGACTCTCGGTTCCGA | 49 |
|  | 1202810 |  | AGACUCTCGGTTCCGA | 127 |
| 738431 | 1200905 | Nestin | CTTTTCTATCAGTCTC | 51 |
| 739428 |  | WWTR1/TNS | CTTCTTGATGTCTTTC | 52 |
|  | 1201694 |  | CTTCUTGATGTCTTTC | 129 |
| 747137 | 1200907 | FOXO1A | AAGTGTCACTAAAACC | 53 |
| 747149 |  | FOXO1A | GGACTGAAATAGCAGA | 54 |
|  | 1203759 |  | GGACUGAAATAGCAGA | 130 |
| 747190 |  | FOXO1A | AGGCTGGCCCCCACTG | 55 |
|  | 1203759 |  | AGGCUGGCCCCCACTG | 131 |
| 758252 |  | CHOP/DDIT3 | GGTTTTTGATTCTTCC | 56 |
|  | 1203759 |  | GGTTUTTGATTCTTCC | 132 |
| 797793 | 1201073 | DLL4 | GCATGCCGCCCCGTCC | 57 |
| 808013 | 1203761 | CYBB | TCTTCATACAATAGCA | 58 |
| 813942 | 1203762 | CDK9 | CGTTCAAATTCCGTCT | 59 |
| 832311 | 1201199 | PEMT | TCCGGCTGCGGCTCAG | 60 |

TABLE 30

Primer Probe Sets

| Transcript | PP Set Name | Primer | Sequence | SEQ ID NO: |
|---|---|---|---|---|
| HDAC2 | RTS3500 | Forward | TGATGGTGTTGAGGAAGCTTTTT | 15 |
|  |  | Reverse | TCCCTCAAGTCTCCTGTTCCA | 16 |
|  |  | Probe | ACAACAGATCGCGTGATGACCGTCTC | 17 |
| DNM2 | RTS36436 | Forward | AGAGGAGACCGAGCGAAT | 61 |
|  |  | Reverse | CATGGTTTGTGTTGATGTACGAC | 62 |
|  |  | Probe | CCTACATCAGGGAGCGAGAAGGGA | 63 |
| FOXO1A | RTS4973 | Forward | GTCAAGACTACAACACACAGC | 64 |
|  |  | Reverse | AAAACTATAAGGAGGGGTGAAGG | 65 |
|  |  | Probe | CTGAAGGACTTTTAAATGTAGCCTGCTCACTAA | 66 |
| PABPN1 | n/a | Forward | CCGGAGCTAGAAGCGATCAA | 70 |
|  |  | Reverse | CCTTTAGCTTCTCAGCCTCTTCCT | 71 |
|  |  | Probe | CTCGAGTCAGGGAGATG | 72 |

TABLE 31

Toxicity and Activity

| Compound ID | Position of 2'-altered nucleotide in central region | sugar modification of altered nucleotide | Gadd45a mRNA (% Control) | Tnfrsf10b mRNA (% Control) | P21 mRNA (% Control) | ALT @ 150 mg/kg | Relative Caspase Activation (% Control) @ 20 µM | Complementary mRNA* (% Control) |
|---|---|---|---|---|---|---|---|---|
| PBS | n/a | n/a | 100 | 100 | 111 | 28 @ 0 | n.d. | 100 |
| 546006 | n/a | n/a | 1885 | 4660 | 6556 | 131 | 291 | 38 |
| 1133071 | 2 | 2'-Ome | 1357 | 5569 | 6541 | 245 | 279 | 37 |
| 549334 | n/a | n/a | 187 | 225 | 182 | 30 | n.d. | n.d. |
| 1200896 | 2 | 2'-Ome | 165 | 126 | 130 | 28 | n.d. | n.d. |
| 562920 | n/a | n/a | 498 | 568 | 1336 | 109 | 473 | n.d. |
| 1201379 | 2 | 2'-Ome | 171 | 200 | 402 | 32 | 473 | n.d. |
| 572912 | n/a | n/a | 357 | 7503 | 5043 | 3883 | 205 | n.d. |
| 1200898 | 2 | 2'-Ome | 155 | 170 | 301 | 41 | 84 | n.d. |
| 576095 | n/a | n/a | 147 | 121 | 154 | 39 | n.d. | n.d. |
| 1200899 | 2 | 2'-Ome | 401 | 154 | 169 | 32 | n.d. | n.d. |
| 597605 | n/a | n/a | 353 | 1965 | 2263 | 488 | 328 | n.d. |
| 1200900 | 2 | 2'-Ome | 121 | 227 | 228 | 32 | 126 | n.d. |
| 601840 | n/a | n/a | 221 | 365 | 840 | 98 | 287 | n.d. |
| 1201381 | 2 | 2'-Ome | 103 | 123 | 72 | 24 | 274 | n.d. |
| 640599 | n/a | n/a | 111 | 286 | 376 | 26 | 184 | n.d. |
| 1201862 | 2 | 2'-Ome | 96 | 262 | 276 | 22 | 99 | n.d. |
| 694804 | n/a | n/a | 336 | 916 | 1297 | 1090 | 257 | 6 |
| 1202810 | 2 | 2'-Ome | 106 | 238 | 257 | 36 | 166 | 16 |
| 715415 | n/a | n/a | 186 | 1211 | 1249 | 420 | 137 | n.d. |
| 1203758 | 2 | 2'-Ome | 78 | 150 | 115 | 41 | 141 | n.d. |
| 738431 | n/a | n/a | 229 | 507 | 448 | 608 | 220 | n.d. |
| 1200905 | 2 | 2'-Ome | 141 | 193 | 197 | 69 | 181 | n.d. |
| 739428 | n/a | n/a | 234 | 1975 | 2107 | 533 | 269 | n.d. |
| 1201694 | 2 | 2'-Ome | 154 | 593 | 388 | 42 | 114 | n.d. |
| 747137 | n/a | n/a | 155 | 1379 | 1851 | 50 | 512 | 19 |
| 1200907 | 2 | 2'-Ome | 99 | 716 | 824 | 39 | 168 | 27 |
| 747149 | n/a | n/a | 454 | 5765 | 4892 | 606 | 166 | 9 |
| 1203759 | 2 | 2'-Ome | 105 | 119 | 211 | 33 | 109 | 22 |
| 747190 | n/a | n/a | 162 | 2856 | 4677 | 1315 | 393 | 2 |
| 1200961 | 2 | 2'-Ome | 129 | 237 | 345 | 71 | 305 | 7 |
| 758252 | n/a | n/a | 158 | 989 | 861 | 725 | 355 | n.d. |
| 1233760 | 2 | 2'-Ome | 94 | 106 | 182 | 47 | 187 | n.d. |
| 797793 | n/a | n/a | 190 | 1175 | 1181 | 1318 | 229 | n.d. |
| 1201073 | 2 | 2'-Ome | 184 | 230 | 201 | 78 | 125 | n.d. |
| 808013 | n/a | n/a | 126 | 2153 | 4617 | 169 | 437 | n.d. |
| 1203761 | 2 | 2'-Ome | 154 | 163 | 147 | 25 | 113 | n.d. |
| 813942 | n/a | n/a | 351 | 3758 | 4638 | 127 | 340 | n.d. |
| 1203762 | 2 | 2'-Ome | 103 | 89 | 257 | 28 | 88 | n.d. |
| 832311 | n/a | n/a | 305 | 1059 | 878 | 739 | 288 | n.d. |
| 1201199 | 2 | 2'-Ome | 294 | 720 | 597 | 208 | 256 | n.d. |

*Value represents the reduction of the mRNA that is complementary to the modified oligonucleotide as indicated in Table 29 above.

Example 14 Dose-Response of Position-Specific 2'-OMe on In Vitro and In Vivo Activity and Toxicity of Modified Oligonucleotides with a Variety of Sequences On target in vivo activity and toxicity was measured for a subset of compounds described in Example 13 above. Two male BALB/c mice per group were administered 1.85, 5.55, 16.67, 50, or 150 mg/kg modified oligonucleotide once via subcutaneous injection, as indicated in the tables below. Mice were sacrificed after 1 week and mRNA was isolated from the liver and measured by RT-qPCR using the primer probe sets described in Table 30 above. Levels of mRNA for Gadd45a, P21, and Tnfrsf10b were analyzed as in Example 1. Results were normalized with Ribogreen and are reported normalized to PBS-treated animals. Plasma levels of ALT was measured using an automated clinical chemistry analyzer. Increased ALT is indicative of acute liver toxicity. The therapeutic index is calculated as a ratio of the maximum non-toxic dose divided by the in vivo ED50. The maximum non-toxic dose is the highest dose at which the ALT value remains less than 5× increased compared to PBS-treated mice, typically 150 IU/L.

TABLE 33 in vivo dose response activity

| | Target Expression (% Control) | | | | | |
|---|---|---|---|---|---|---|
| Compound Number | 1.9 mg/kg | 5.6 mg/kg | 16.7 mg/kg | 50 mg/kg | 150 mg/kg | ED50 (ng/g) |
| 546006 | 86.8 | 75.6 | 78.1 | 56.2 | 41.4 | 87.9 |
| 1133071 | 81.6 | 74.5 | 61.4 | 52.9 | 37.6 | 53.9 |
| 572912 | 80.7 | 58.2 | 34.6 | 26.2 | 21.7 | 10.0 |
| 1200898 | 84.8 | 80.2 | 67.4 | 42.4 | 16.3 | 31.5 |
| 694804 | 62.8 | 38.2 | 15.3 | 7.8 | 7.6 | 3.2 |
| 1202810 | 71.0 | 46.7 | 33.2 | 21.0 | 10.1 | 5.8 |
| 747137 | 45.3 | 42.5 | 28.7 | 21.4 | 14.0 | 1.5 |
| 1200907 | 42.1 | 35.3 | 40.2 | 30.6 | 18.8 | 0.53 |
| 747149 | 72.8 | 42.2 | 23.6 | 14.6 | 7.3 | 6.0 |
| 1203759 | 52.9 | 40.6 | 24.4 | 21.5 | 18.3 | 2.1 |
| 715415 | 61.5 | 56.9 | 41.9 | 19.9 | 12.0 | 6.5 |
| 1203758 | 71.6 | 68.8 | 61.1 | 34.8 | 20.9 | 20.0 |

TABLE 34 in vivo dose response toxicity (ALT)

| Compound Number | ALT (IU/L) | | | | |
|---|---|---|---|---|---|
| | 1.9 mg/kg | 5.6 mg/kg | 16.7 mg/kg | 50 mg/kg | 150 mg/kg |
| 546006 | 29 | 29 | 22 | 26 | 173 |
| 1133071 | 24 | 25 | 25 | 44 | 356 |
| 572912 | 23 | 27 | 112 | 730 | 4674 |
| 1200898 | 23 | 24 | 25 | 28 | 32 |
| 694804 | 29 | 24 | 24 | 143 | 2160 |
| 1202810 | 22 | 24 | 24 | 23 | 61 |
| 747137 | 24 | 22 | 24 | 25 | 86 |
| 1200907 | 23 | 21 | 21 | 31 | 32 |
| 747149 | 26 | 26 | 38 | 157 | 1867 |
| 1203759 | 25 | 21 | 23 | 27 | 27 |
| 715415 | 23 | 21 | 25 | 77 | 1384 |
| 1203758 | 25 | 23 | 23 | 23 | 54 |

TABLE 34b

In Vivo Dose-response of Gadd45a mRNA upon treatment with modified oligonucleotides complementary to HDAC2

| | 1.9 mg/kg | 5.6 mg/kg | 16.7 mg/kg | 50 mg/kg | 150 mg/kg |
|---|---|---|---|---|---|
| | Expression level of Gadd45a mRNA (% Control) | | | | |
| 546006 | 122 | 112 | 77 | 302 | 1070 |
| 1133071 | 94 | 134 | 154 | 396 | 873 |
| 572912 | 94 | 95 | 187 | 196 | 227 |
| 1200898 | 103 | 80 | 112 | 109 | 99 |
| 694804 | 126 | 106 | 161 | 163 | 459 |
| 1202810 | 115 | 93 | 91 | 188 | 169 |
| 747137 | 94 | 67 | 80 | 96 | 153 |
| 1200907 | 79 | 86 | 142 | 88 | 140 |
| 747149 | 123 | 172 | 146 | 283 | 575 |
| 1203759 | 100 | 147 | 102 | 172 | 154 |
| 715415 | 91 | 118 | 201 | 159 | 393 |
| 1203758 | 143 | 114 | 206 | 162 | 197 |

TABLE 34c

In Vivo Dose-response of Tnfrsf10b mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of Tnfrsf10b mRNA (% Control) | | | | |
| 546006 | 87 | 78 | 161 | 248 | 4235 |
| 1133071 | 95 | 96 | 157 | 622 | 5166 |
| 572912 | 210 | 190 | 551 | 4070 | 5847 |
| 1200898 | 135 | 116 | 105 | 170 | 179 |
| 694804 | 81 | 98 | 116 | 284 | 1775 |
| 1202810 | 88 | 110 | 88 | 128 | 241 |
| 747137 | 56 | 74 | 115 | 273 | 1013 |
| 1200907 | 99 | 86 | 15 | 239 | 453 |
| 747149 | 73 | 70 | 116 | 636 | 6027 |
| 1203759 | 87 | 55 | 57 | 97 | 105 |
| 715415 | 62 | 57 | 111 | 259 | 999 |
| 1203758 | 67 | 72 | 64 | 79 | 126 |

TABLE 34d

In Vivo Dose-response of P21 mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of P21 mRNA (% Control) | | | | |
| 546006 | 103 | 90 | 172 | 342 | 5193 |
| 1133071 | 97 | 68 | 197 | 773 | 6571 |
| 572912 | 224 | 228 | 762 | 2787 | 3182 |
| 1200898 | 98 | 106 | 70 | 164 | 172 |
| 694804 | 108 | 76 | 72 | 172 | 2212 |
| 1202810 | 91 | 125 | 245 | 51 | 162 |
| 747137 | 43 | 59 | 122 | 294 | 1220 |
| 1200907 | 108 | 97 | 110 | 383 | 708 |
| 747149 | 95 | 44 | 207 | 985 | 3869 |
| 1203759 | 61 | 30 | 47 | 71 | 95 |
| 715415 | 46 | 24 | 45 | 213 | 757 |
| 1203758 | 36 | 34 | 18 | 26 | 35 |

TABLE 34e

Therapeutic Index

| Compound ID | 2'-altered nucleotide position in central region | sugar modification of altered nucleotide | MNTD (mg/kg) | TI (MNTD/ED$_{50}$) | Fold-TI improvement |
|---|---|---|---|---|---|
| 546006 | n/a | n/a | 50 | 0.6 | 1.5 |
| 1133071 | 2 | 2'-OMe | 50 | 0.9 | |
| 572912 | n/a | n/a | 16.7 | 2 | >2.4 |
| 1200898 | 2 | 2'-OMe | >150 | >4.8 | |
| 694804 | n/a | n/a | 50 | 16 | >1.6 |
| 1202810 | 2 | 2'-OMe | >150 | >26 | |
| 747137 | n/a | n/a | >150 | >99 | ~2.9 |
| 1200907 | 2 | 2'-OMe | >150 | >284 | |
| 747149 | n/a | n/a | 50 | 11 | >6.5 |
| 1203759 | 2 | 2'-OMe | >150 | >72 | |
| 715415 | n/a | n/a | 50 | 8 | n/a |
| 1203758 | 2 | 2'-OMe | >150 | >7.5 | |

Example 15 Effect of Modified Oligonucleotides on Nucleolar Localization of p54nrb Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. ALT data presented were previously described in Example 13 above.

TABLE 35

Nucleolar mislocalization of p54nrb and correlation with hepatoxicity

| Compound ID | 2'-altered nucleotide position in central region | sugar modification of altered nucleotide | % cells with mislocalization of p54nrb | ALT @ 150 mg/kg |
|---|---|---|---|---|
| 546006 | n/a | n/a | 56 | 131 |
| 1133071 | 2 | 2'-OMe | 67 | 245 |
| 572912 | n/a | n/a | 75 | 3883 |
| 1200898 | 2 | 2'-OMe | 3 | 41 |
| 758252 | n/a | n/a | 71 | 725 |
| 1233760 | 2 | 2'-OMe | 4 | 47 |

Example 16 Effect of Position-Specific 2'-OMe on In Vitro Activity and Toxicity of Modified Oligonucleotides with Various Sequences Modified oligonucleotides with the sugar motifs lll-d(10)-lll and lll-d-m-d(8)-lll were synthesized, where "l" indicates a β-D-locked nucleic acid (β-D-LNA), "d" represents a 2'-β-D-deoxyribosyl sugar moiety and "m" represents a 2'-OMe-β-D-ribofuranosyl sugar moiety. Each internucleoside linkage is a phosphorothioate internucleoside linkage. For sequences with a T at position 5 (from the 5' end) in the parent lll-d(10)-lll oligonucleotide, the lll-d-m-d(8)-lll contains a 2'-OMe modified U at this position. For sequences with a mC at position 5 (from the 5' end) in the parent lll-d(10)-lll oligonucleotide, the lll-d-m-d(8)-lll contains a 2'-OMe modified C at this position lacking a 5-Me group.

TABLE 36

Modified Oligonucleotides

| lll-d(10)-lll compound ID | lll-d-m-d(8)-lll compound ID | Complementary mRNA | Sequence (5'-3') | SEQ ID NO |
|---|---|---|---|---|
| 1247569 | 1247570 | HDAC2 | GAGGATGGCAAGCACA | 41 |
| 1247571 | 1247572 | PABPN1 | CTTCCACAGTATATCT | 44 |
| 1247573 |  | DNM2 | AGACTCTCGGTTCCGA | 49 |
|  | 1247574 |  | AGACUCTCGGTTCCGA | 127 |
| 1247575 | 1247576 | FOXO1A | AAGTGTCACTAAAACC | 53 |
| 1247577 | 1247578 | FOXO1A | GGACTGAAATAGCAGA | 54 |
|  | 1247578 |  | GGACUGAAATAGCAGA | 130 |

In vivo toxicity and on target in vivo activity was measured for the compounds described above. Two male balb/c mice per group were administered 16.67 or 150 mg/kg modified oligonucleotide once via subcutaneous injection, as indicated in the tables below. Mice were sacrificed after 72 hours and mRNA was isolated from the liver and measured by RT-qPCR using the primer probe sets described in Table 30 above. Levels of mRNA for P21, and Tnfrsf10b were analyzed as in Example 1. Results were normalized with Ribogreen and are reported normalized to PBS-treated animals.

Example 17 Effect of Position-Specific 2'-Modifications on In Vitro Activity and In Vivo Liver Toxicity of Modified Oligonucleotides Complementary to CPT1A Modified oligonucleotides were synthesized as indicated in the table below. These modified oligonucleotides were compared to the otherwise identical modified oligonucleotide lacking an altered nucleotide in the central region, a 5-10-5 MOE modified oligonucleotide, containing five nucleosides each comprising a 2'-MOE-β-D-ribofuranosyl sugar moiety in each of the 5' and 3' regions and 10 unmodified DNA nucleosides in the central region. Each internucleoside linkage is a phosphorothioate internucleoside linkage. The compounds in the table below are 100% complementary to mouse CPT1A, GENBANK NC_000085.6 truncated from 3319001 to 3389000 (SEQ ID NO: 6), at position 49870 to 49889. In certain instances, a modified oligonucleotide comprising a T at position 5 is compared to a modified oligonucleotide comprising a 2'-OMe U at position 5.

TABLE 37 in vivo activity and toxicity

| Compound | Complementary mRNA Expression (% Control) | | ALT (IU/L) | | P21 mRNA (% Control) | | Tnfrsf10b mRNA (% Control) | |
|---|---|---|---|---|---|---|---|---|
| Number | 16.7 mg/kg | 150 mg/kg | 16.7 mg/kg | 150 mg/kg | 16.7 mg/kg | 150 mg/kg | 16.7 mg/kg | 150 mg/kg |
| 1247569 | 70 | 35 | 37 | 2368 | 163 | 12778 | 158 | 7046 |
| 1247570 | 72 | 46 | 34 | 867 | 444 | 11860 | 320 | 6772 |
| 1247571 | 40 | 26 | 460 | 10838 | 3061 | 7588 | 2216 | 8133 |
| 1247572 | 54 | 16 | 26 | 330 | 90 | 928 | 124 | 679 |
| 1247573 | 7 | 19 | 59 | 20665 | 153 | 10379 | 157 | 4858 |
| 1247574 | 19 | 6 | 25 | 284 | 139 | 839 | 123 | 575 |
| 1247575 | 51 | 30 | 50 | 2404 | 390 | 11275 | 334 | 6365 |
| 1247576 | 57 | 27 | 25 | 85 | 142 | 1850 | 218 | 2033 |
| 1247577 | 52 | 25 | 34 | 2460 | 256 | 11736 | 193 | 14610 |
| 1247578 | 60 | 21 | 25 | 39 | 124 | 133 | 178 | 143 |
| 1247579 | 48 | 14 | 23 | 1696 | 95 | 3704 | 176 | 108 |
| 1247580 | 77 | 21 | 28 | 232 | 78 | 265 | 2850 | 307 |

TABLE 38

Modified oligonucleotides complementary to CPT1A

| Compound ID | position of altered nucleotide in central region | sugar modification of altered nucleotide | Chemistry Notation | SEQ ID NO |
|---|---|---|---|---|
| 147420 | n/a | n/a | $A_{es}A_{es}T_{es}G_{es}T_{es}G_{ds}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |
| 994947 | n/a | OMe | $A_{es}A_{es}T_{es}G_{ms}T_{es}G_{ds}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |
| 994948 | n/a | OMe | $A_{es}A_{es}T_{es}G_{es}U_{ms}G_{ds}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 74 |
| 994949 | 1 | OMe | $A_{es}A_{es}T_{es}G_{es}T_{es}G_{ms}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |
| 994950 | 2 | OMe | $A_{es}A_{es}T_{es}G_{es}T_{es}G_{ds}{}^mC_{ms}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |
| 994951 | 3 | OMe | $A_{es}A_{es}T_{es}G_{es}T_{es}G_{ds}{}^mC_{ds}{}^mC_{ms}T_{ds}G_{ds}{}^mC_{ds}T_{ds}G_{ds}T_{ds}{}^mC_{ds}{}^mC_{es}T_{es}T_{es}G_{es}A_e$ | 73 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "(FANA)" indicates a nucleoside comprising an ara 2'-F modified sugar moiety.

For the in vivo toxicity and activity study in the table below, BALB/C mice per modified oligonucleotide were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. Liver mRNA was harvested and analyzed by RT-qPCR. Cpt1a mRNA was detected using primer probe set RTS40014 (forward sequence: AGATCAATCGGACCCTAGACA, SEQ ID NO: 75; reverse sequence: CAGCACCTTCAGCGAGTA; SEQ ID NO: 76; probe sequence: AAGAGGACGCCACTCACGATGTTC, SEQ ID NO: 77) and P21 and Tnfrsf10b mRNA were detected as described in Example 1.

For the in vivo activity study in the table below, three BALB/C mice per modified oligonucleotide were administered 2.5, 7.4, 22.2, 66.7, 200 mg/kg 147420 or 994950 by subcutaneous injection and sacrificed after 72 hours. Plasma levels of ALT were measured using an automated clinical chemistry analyzer. Increased ALT is indicative of acute liver toxicity. Cpt1a mRNA was detected using RT-qPCR as described above.

TABLE 40

In Vivo Toxicity of modified oligonucleotides complementary CPT1A

| Compound Number | ALT (IU/L) | | | | |
|---|---|---|---|---|---|
| | 2.5 mg/kg | 7.4 mg/kg | 22.2 mg/kg | 66.7 mg/kg | 200 mg/kg |
| 147420 | 51 | 23 | 23 | 106 | 7794 |
| 994950 | 25 | 25 | 21 | 23 | 53 |

TABLE 41

In Vivo Activity of modified oligonucleotides complementary CPT1A

| Compound Number | CPT1 mRNA (% Control) | | | | |
|---|---|---|---|---|---|
| | 2.5 mg/kg | 7.4 mg/kg | 22.2 mg/kg | 66.7 mg/kg | 200 mg/kg |
| 147420 | 115.9 | 93.1 | 78.2 | 33.7 | 4.6 |
| 994950 | 116.0 | 117.2 | 105.6 | 55.9 | 21.9 |

TABLE 39

Activity and toxicity of modified oligonucleotides complementary CPT1A

| Compound ID | position of altered nucleotide in central region | sugar modification of altered nucleotide | Cpt1a (% control) | P21 (% control) | Tnfrsf10b (% control) | ALT @ 200 mg/kg (IU/L) |
|---|---|---|---|---|---|---|
| 147420 | n/a | n/a | 6.42 | 6616 | 8796 | 15308 |
| 994947 | n/a | 2'-Ome | 6.49 | 6984 | 11499 | 18395 |
| 994948 | n/a | 2'-Ome | 8.99 | 7085 | 10520 | 10535 |
| 994949 | 1 | 2'-Ome | 5.90 | 6370 | 9595 | 12370 |
| 994950 | 2 | 2'-Ome | 12.19 | 2219 | 2146 | 52 |
| 994951 | 3 | 2'-Ome | 6.72 | 6275 | 10555 | 2991 |

TABLE 42

In Vivo Dose-response of Tnfrsf10b mRNA upon treatment with modified oligonucleotides

| Compound Number | Tnfrsf10b mRNA (% Control) | | | | |
|---|---|---|---|---|---|
| | 2.5 mg/kg | 7.4 mg/kg | 22.2 mg/kg | 66.7 mg/kg | 200 mg/kg |
| 147420 | 132 | 141 | 162 | 2341 | 8622 |
| 994950 | 119 | 133 | 125 | 153 | 1026 |

TABLE 43

In Vivo Dose-response of P21 mRNA upon treatment with modified oligonucleotides

| Compound Number | P21 mRNA (% Control) | | | | |
|---|---|---|---|---|---|
| | 2.5 mg/kg | 7.4 mg/kg | 22.2 mg/kg | 66.7 mg/kg | 200 mg/kg |
| 147420 | 141 | 94 | 240 | 4305 | 15334 |
| 994950 | 105 | 89 | 103 | 208 | 2413 |

Example 18 Effect of 2'-OMe Modification in Modified Oligonucleotides Complementary to Factor XI Modified oligonucleotides were synthesized as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents a 2'-OMe-ribofuranosyl sugar moiety. For sequences with a Tat position 5 (from the 5' end) in the parent kkk-d(10)-kkk oligonucleotide, the kkk-d-m-d(8)-kkk contains a 2'-OMe modified U at this position. For sequences with a mC at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for FXI and RAPTOR as described above.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS2898, described in Example 4 above. Results were normalized with Ribogreen® and are reported normalized to PBS-treated animals.

TABLE 44

Sequences

| kkk-d(10)-kkk compound ID | kkk-d-m-d(8)-kkk compound ID | Sequence (5'-3') | SEQ ID NO |
|---|---|---|---|
| 464917 | 982034 | GTCTGTGCATCTCTCC | 22 |
| 464924 | | GTTATTGTGGTTGGCG | 81 |
| | 1133247 | GTTAUTGTGGTTGGCG | 133 |
| 465156 | | ATTCTGTGTGCACTGC | 82 |
| | 1133310 | ATTCUGTGTGCACTGC | 134 |
| 465162 | 1133316 | TCTTGTCTGACATTCT | 83 |
| 465163 | 1133317 | TTTTGTGTCTTCTGTA | 84 |
| 465172 | | CTGTTTGAGTTTTCTC | 85 |
| | 1133326 | CTGTUTGAGTTTTCTC | 135 |
| 465174 | 1133328 | CAAAGTGATACCAGTT | 86 |
| 465175 | | AATCTTCCAGGGCCAC | 87 |
| | 1133329 | AATCUTCCAGGGCCAC | 136 |
| 465176 | | TCATTTCTATGGAATA | 88 |
| | 1133330 | TCATUTCTATGGAATA | 137 |
| 465178 | 1133332 | GTCAGTATCCCAGTGT | 89 |
| 465179 | 1133333 | GGTTACAGTGGAAGAG | 90 |
| 465181 | 1133335 | TCTGGGTGTTCTTACG | 91 |
| 465186 | 1133340 | TTTCCTTGAGTAGTAG | 92 |
| 465187 | 1133341 | TCTCCTTGCTGTATTT | 93 |

TABLE 45

Activity and Toxicity of Modified oligonucleotides complementary to Factor XI

| Compound ID | altered nucleotide position in central region | sugar modification of altered nucleotide | in vitro FXI IC$_{50}$ (nM) | in vitro RAPTOR IC$_{50}$ (nM) | Relative Caspase Activation (% Control) @ 20 µM | p21 @ 150 mg/kg | FXI @ 10 mg/kg | ALT @ 150 mg/kg (IU/L) |
|---|---|---|---|---|---|---|---|---|
| 464917 | n/a | n/a | 101 | 44 | 700 | death | 25.4 | death |
| 982034 | 2 | 2'-OMe | 221 | 119 | 122 | 31922 | 40.8 | 13172 |
| 464924 | n/a | n/a | 115 | >2000 | 332 | 19340 | 8.6 | 5365 |

TABLE 45-continued

Activity and Toxicity of Modified oligonucleotides complementary to Factor XI

| Compound ID | altered nucleotide position in central region | sugar modification of altered nucleotide | in vitro FXI IC$_{50}$ (nM) | in vitro RAPTOR IC$_{50}$ (nM) | Relative Caspase Activation (% Control) @ 20 μM | p21 @ 150 mg/kg | FXI @ 10 mg/kg | ALT @ 150 mg/kg (IU/L) |
|---|---|---|---|---|---|---|---|---|
| 1133247 | 2 | 2'-OMe | 189 | >2000 | 190 | 753 | 12.1 | 33 |
| 465156 | n/a | n/a | 98 | 129 | 934 | 82279 | 14.4 | 24858 |
| 1133310 | 2 | 2'-OMe | 354 | 465 | 603 | 127 | 14.7 | 7034 |
| 465162 | n/a | n/a | 99 | >2000 | 758 | death | 15.1 | death |
| 1133316 | 2 | 2'-OMe | 144 | >2000 | 189 | 4660 | 34.2 | 60 |
| 465163 | n/a | n/a | 163 | >2000 | 115 | 34117 | 41.5 | 2347 |
| 1133317 | 2 | 2'-OMe | 272 | >2000 | 67 | 11844 | 79.4 | 478 |
| 465172 | n/a | n/a | 106 | >2000 | 429 | 512 | 57.6 | 23 |
| 1133326 | 2 | 2'-OMe | 176 | >2000 | 157 | 237 | 64.8 | 20 |
| 465174 | n/a | n/a | 69 | >2000 | 130 | 276 | 21.7 | 21 |
| 1133328 | 2 | 2'-OMe | 393 | >2000 | 113 | 167 | 33.8 | 23 |
| 465175 | n/a | n/a | 50 | 125 | 523 | 6957 | 37.8 | 1564 |
| 1133329 | 2 | 2'-OMe | 99 | 170 | 501 | 1564 | 59.8 | 60 |
| 465176 | n/a | n/a | 111 | >2000 | 219 | 344 | 98.6 | 27 |
| 1133330 | 2 | 2'-OMe | 89 | >2000 | 135 | 190 | 95.1 | 22 |
| 465178 | n/a | n/a | 11 | 115 | 364 | 900086 | 8.1 | 13168 |
| 1133332 | 2 | 2'-OMe | 24 | 1653 | 247 | 5982 | 27.0 | 75 |
| 465179 | n/a | n/a | 74 | >2000 | 188 | 4046 | 23.0 | 344 |
| 1133333 | 2 | 2'-OMe | 82 | >2000 | 102 | 122 | 62.4 | 23 |
| 465181 | n/a | n/a | 75 | 1571 | 487 | 17469 | 25.4 | 7087 |
| 1133335 | 2 | 2'-OMe | 56 | >2000 | 214 | 929 | 61.7 | 26 |
| 465186 | n/a | n/a | 75 | >2000 | 200 | 42551 | 17.3 | 3709 |
| 1133340 | 2 | 2'-OMe | 208 | >2000 | 125 | 513 | 42.8 | 34 |
| 465187 | n/a | n/a | 35 | 475 | 393 | 778834* | 10.4 | 11752* |
| 1133341 | 2 | 2'-OMe | 28 | >2000 | 167 | 1984 | 38.6 | 36 |

*½ animals were found dead

Example 19 Effect of 2'-OMe Incorporation on Toxicity of Modified Oligonucleotides Complementary to HDAC2

Modified oligonucleotides were synthesized as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents a 2'-OMe-β-D-ribofuranosylsugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a mC at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for HDAC2 and RAPTOR as described above. For the in vivo toxicity study in the table below, two male BALB/C mice per modified oligonucleotide were administered 10 or 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS3500 described above in Example 13. Results were normalized with Ribogreen® and are reported normalized to PBS-treated animals.

TABLE 46

Sequences

| kkk-d(10)-kkk compound ID | kkk-d-m-d(8)-kkk compound ID | Sequence (5'-3') | SEQ ID NO |
|---|---|---|---|
| 545984 | 1133060 | TTGCCAATATCACCAT | 94 |
| 545996 |  | CAACUGAACCACCCGT | 95 |
|  | 1133066 | CAACTGAACCACCCGT | 138 |
| 546004 | 1133070 | GCACAATATCATTAAC | 96 |
| 546009 | 1132933 | GACTCTCTGATGATAC | 97 |
| 546023 | 1132940 | CTATACCATCTCTCAT | 98 |
| 546024 | 1133080 | CATCATCTATACCATC | 99 |
| 546034 | 1133085 | ACACATTTAGCATGAC | 100 |
| 546045 |  | ATTATATGGCAACTCA | 101 |
|  | 1132951 | ATTAUATGGCAACTCA | 139 |
| 546049 | 1132953 | GACTAATATGCAGTTT | 102 |
| 546075 | 1132966 | GTCAAATTCAAGGGTT | 103 |
| 546095 | 1132976 | CATAAAGCATGGTGGA | 104 |
| 546108 | 1133122 | TAGTCTCTGTCAGTTA | 105 |
| 546109 | 1132983 | GTACCTATAGTCTCTG | 106 |
| 546110 | 1133123 | TCATGTACCTATAGTC | 107 |

TABLE 46-continued

Sequences

| kkk-d(10)-kkk compound ID | kkk-d-m-d(8)-kkk compound ID | Sequence (5'-3') | SEQ ID NO |
|---|---|---|---|
| 546112 | 1133124 | TCTTAATTTCATGTAC | 108 |
| 546118 | 1133127 | ACCCTCAAGTCTCCTG | 109 |

TABLE 47

In vitro Activity and Toxicity of Modified oligonucleotides complementary to HDAC2

| Compound ID | altered nucleotide position in central region | sugar modification of altered nucleotide | in vitro HDAC 2 IC$_{50}$ (nM) | in vitro RAPTOR IC$_{50}$ (nM) | Relative Caspase Activation (% Control) @ 20 µM |
|---|---|---|---|---|---|
| 546009 | n/a | n/a | 44 | 773 | 632 |
| 1132933 | 2 | 2'-OMe | 89 | >2000 | 193 |
| 546023 | n/a | n/a | 79 | 1643 | 825 |
| 1132940 | 2 | 2'-OMe | 156 | >2000 | 980 |
| 546045 | n/a | n/a | 72 | 460 | 469 |
| 1132951 | 2 | 2'-OMe | 98 | >2000 | 326 |
| 546049 | n/a | n/a | 82 | >2000 | 127 |
| 1132953 | 2 | 2'-OMe | 144 | >2000 | 132 |
| 546075 | n/a | n/a | 81 | >2000 | 149 |
| 1132966 | 2 | 2'-OMe | 135 | >2000 | 143 |
| 546095 | n/a | n/a | 78 | >2000 | 126 |
| 1132976 | 2 | 2'-OMe | 128 | >2000 | 98 |
| 546109 | n/a | n/a | 30 | >2000 | 396 |
| 1132983 | 2 | 2'-OMe | 44 | >2000 | 117 |
| 545984 | n/a | n/a | 89 | 452 | 1235 |
| 1133060 | 2 | 2'-OMe | 126 | >2000 | 270 |
| 545996 | n/a | n/a | 297 | >2000 | 776 |
| 1133066 | 2 | 2'-OMe | 111 | >2000 | 327 |
| 546004 | n/a | n/a | 181 | >2000 | 124 |
| 1133070 | 2 | 2'-OMe | 164 | >2000 | 90 |
| 546024 | n/a | n/a | 85 | >2000 | 124 |
| 1133080 | 2 | 2'-OMe | 45 | >2000 | 123 |
| 546034 | n/a | n/a | 125 | >2000 | 107 |
| 1133085 | 2 | 2'-OMe | 125 | >2000 | 104 |
| 546108 | n/a | n/a | 21 | 144 | 1265 |
| 1133122 | 2 | 2'-OMe | 34 | >2000 | 176 |
| 546110 | n/a | n/a | 17 | >2000 | 82 |
| 1133123 | 2 | 2'-OMe | 30 | >2000 | 95 |
| 546112 | n/a | n/a | 178 | >2000 | 106 |
| 1133124 | 2 | 2'-OMe | 106 | >2000 | 98 |
| 546118 | n/a | n/a | 6 | 181 | 425 |
| 1133127 | 2 | 2'-OMe | 11 | >2000 | 158 |

TABLE 48

In vivo Activity and Toxicity of Modified oligonucleotides complementary to HDAC2

| Compound ID | HDAC2 @ 10 mg/kg | HDAC2 @ 150 mg/kg | P21 mRNA @ 150 mg/kg | Tnfrsf10b @ 150 mg/kg | ALT @ 150 mg/kg (IU/L) |
|---|---|---|---|---|---|
| 546009 | 22 | 7.5 | 5739 | 7162 | 14907 |
| 1132933 | 40 | 7.5 | 98 | 176 | 31 |
| 546023 | 57 | 9.9 | 1586 | 754 | 820 |
| 1132940 | 61 | 12.7 | 1348 | 565 | 224 |
| 546045 | 68 | 17.2 | 5601 | 2362 | 1031 |
| 1132951 | 60 | 15.3 | 1726 | 970 | 183 |
| 546049 | 50 | 8.9 | 294 | 133 | 29 |
| 1132953 | 71 | 15.2 | 282 | 150 | 27 |
| 546075 | 71 | 16.2 | 282 | 232 | 21 |
| 1132966 | 61 | 27.7 | 741 | 621 | 86 |
| 546095 | 39 | 12.7 | 3303 | 2314 | 1063 |
| 1132976 | 50 | 15.3 | 685 | 512 | 94 |
| 546109 | 29 | 4.3 | 684 | 706 | 182 |
| 1132983 | 37 | 5.2 | 217 | 190 | 34 |
| 545984 | 31 | 4.9 | 14070 | 10327 | 37277 |
| 1133060 | 42 | 9.0 | 183 | 138 | 39 |
| 545996 | 56 | 14.7 | 613 | 458 | 433 |
| 1133066 | 60 | 24.2 | 215 | 156 | 28 |
| 546004 | 64 | 13.4 | 499 | 203 | 35 |
| 1133070 | 69 | 17.6 | 286 | 192 | 30 |
| 546024 | 34 | 6.2 | 381 | 169 | 25 |
| 1133080 | 41 | 8.1 | 452 | 201 | 26 |
| 546034 | 52 | 7.5 | 181 | 140 | 32 |
| 1133085 | 68 | 10.6 | 127 | 143 | 27 |
| 546108 | 3 | n.d. | n.d. | n.d. | death |
| 1133122 | 7 | 1.9 | 1524 | 1353 | 131 |
| 546110 | 15 | 6.2 | 23642 | 6298 | 5132 |
| 1133123 | 35 | 3.3 | 221 | 155 | 29 |
| 546112 | 52 | 14.3 | 817 | 350 | 34 |
| 1133124 | 59 | 13.9 | 822 | 571 | 29 |
| 546118 | 13 | 5.7 | 3853 | 3854 | 3894 |
| 1133127 | 15 | 4.8 | 470 | 473 | 139 |

For the FOB scores reported in the table below, mice per group were administered 100 µg modified oligonucleotide by intracerebroventricular (ICV) injection. At 3 hours and 2 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

Two weeks after injection of modified oligonucleotide, mice were sacrificed and levels of HDAC, p21 and Aifl were measured in the cortex and the spinal cord by RT-PCR as described above. Aifl is a marker for inflammation. Results are presented below relative to control animals.

TABLE 48b

In vivo Activity and Toxicity of Modified oligonucleotides complementary to HDAC2

| Compound ID | 3 hr FOB | 2 week FOB | HDAC mRNA Cortex | HDAC mRNA Spinal Cord | p21 mRNA Cortex | p21 mRNA Spinal Cord | Aif1 mRNA Cortex | Aif1 mRNA Spinal cord |
|---|---|---|---|---|---|---|---|---|
| 546009 | 5.5 | 5.5 | n.d. | n.d. | n.d. | n.d. | n.d. | n.d. |
| 1132933 | 3.5 | 0 | 45.3 | 45.3 | 148 | 227 | 96 | 129 |
| 546023 | 0 | 0 | 36.3 | 31.3 | 120 | 144 | 117 | 156 |
| 1132940 | 0 | 0 | 59.2 | 39.3 | 135 | 166 | 94 | 174 |
| 546045 | 4.5 | 0 | 43.4 | 39.2 | 136 | 284 | 113 | 161 |
| 1132951 | 3 | 0 | 61.4 | 42.6 | 128 | 200 | 86 | 121 |
| 546049 | 1 | 0 | 95.3 | 68.8 | 111 | 116 | 90 | 110 |
| 1132953 | 3 | 0 | 67.1 | 47.8 | 126 | 138 | 82 | 103 |
| 546075 | 7 | 7 | n.d. | n.d. | n.d. | n.d. | n.d. | n.d. |
| 1132966 | 2.5 | 0 | 39.9 | 40.9 | 129 | 174 | 116 | 130 |
| 546095 | 5.5 | 0 | 66.7 | 44.2 | 124 | 321 | 90 | 189 |
| 1132976 | 6 | 0 | 55 | 36 | 132 | 427 | 87 | 248 |
| 546109 | 7 | 7 | n.d. | n.d. | n.d. | n.d. | n.d. | n.d. |
| 1132983 | 7 | 7 | n.d. | n.d. | n.d. | n.d. | n.d. | n.d. |
| 545984 | 2.5 | 6.5 | n.d. | n.d. | n.d. | n.d. | n.d. | n.d. |
| 1133060 | 1 | 0 | 71.0 | 39.8 | 107 | 130 | 92 | 112 |
| 545996 | 3 | 0 | 59.1 | 48.9 | 122 | 220 | 104 | 171 |
| 1133066 | 7 | 7 | n.d. | n.d. | n.d. | n.d. | n.d. | n.d. |
| 546004 | 0 | 0 | 55.3 | 47.6 | 136 | 261 | 116 | 176 |
| 1133070 | 0 | 0 | 58.7 | 50.0 | 127 | 173 | 81 | 99 |
| 546024 | 6.5 | 0 | 20.2 | 20.5 | 134 | 211 | 115 | 140 |
| 1133080 | 1 | 0 | 34.6 | 18.4 | 109 | 139 | 88 | 112 |
| 546034 | 3 | 0 | 58.9 | 46.6 | 96 | 149 | 98 | 146 |
| 1133085 | 3 | 0 | 79.0 | 42.0 | 114 | 126 | 101 | 137 |
| 546108 | 2 | 6.5 | n.d. | n.d. | n.d. | n.d. | n.d. | n.d. |
| 1133122 | 3.5 | 1 | 25.4 | 17.7 | 97 | 166 | 120 | 178 |
| 546110 | 2.5 | 3 | 55.0 | 23.5 | 88 | 294 | 93 | 342 |
| 1133123 | 0 | 0 | 57.4 | 49.8 | 112 | 149 | 85 | 105 |
| 546112 | 3 | 0 | 68.5 | 46.6 | 108 | 119 | 97 | 420 |
| 1133124 | 1.5 | 0 | 70.8 | 52.8 | 122 | 107 | 157 | 873 |
| 546118 | 7 | 7 | n.d. | n.d. | n.d. | n.d. | n.d. | n.d. |
| 1133127 | 7 | 7 | n.d. | n.d. | n.d. | n.d. | n.d. | n.d. |

Example 20 Incorporation of 2'-OMe at Various Positions

Modified oligonucleotides were synthesized with kkk-m-d(9)-kkk, kkk-d-m-d(8)-kkk, kkk-dd-m-d(7)-kkk or kkk-d(3)-m-d(6)-kkk sugar motifs, respectively, where "m" represents a 2'-OMe-β-D-ribofuranosylsugar moiety, "k" represents a cEt, and "d" represents an unmodified, 2'-β-D-deoxyribosyl sugar moiety. In certain instances, 2'-OMeU replaces 2'-deoxyT. These modified oligonucleotides were compared to the otherwise identical modified oligonucleotide lacking an altered nucleotide in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

TABLE 49

Modified Oligonucleotides

| Compound ID | altered nucleotide position in central region | sugar moiety of altered nucleotide | Chemistry Notation | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1061877 | 1 | 2'-OMe | $G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_k$ | 19 |
| 936053 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 1061879 | 3 | 2'-OMe | $G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_k$ | 20 |
| 1061981 | 4 | 2'-OMe | $G_{ks}{}^mC_{ks}A_{ks}T_{ds}G_{ds}G_{ds}U_{ms}{}^mC_{ds}T_{ds}{}^mC_{ds}A_{ds}{}^mC_{ds}A_{ds}T_{ks}T_{ks}A_k$ | 21 |
| 1244110 | 5 | 2'-OMe | $G_{ks}{}^mC_{ks}A_{ks}T_{ds}G_{ds}T_{ds}T_{ds}{}^mC_{ms}T_{ds}{}^mC_{ds}A_{ds}{}^mC_{ds}A_{ds}T_{ks}T_{ks}A_k$ | 18 |

TABLE 49-continued

Modified Oligonucleotides

| Compound ID | altered nucleotide position in central region | sugar moiety of altered nucleotide | Chemistry Notation | SEQ ID NO |
|---|---|---|---|---|
| 1244111 | 6 | 2'-OMe | $G_{ks}{}^mC_{ks}A_{ks}T_{ds}G_{ds}T_{ds}T_{ds}{}^mC_{ds}U_{ms}{}^m$ $C_{ds}A_{ds}{}^mC_{ds}A_{ds}T_{ks}T_{ks}A_k$ | 39 |
| 1244112 | 7 | 2'-OMe | $G_{ks}{}^mC_{ks}A_{ks}T_{ds}G_{ds}T_{ds}T_{ds}{}^mC_{ds}T_{ds}$ $C_{ms}A_{ds}{}^mC_{ds}A_{ds}T_{ks}T_{ks}A_k$ | 18 |
| 1244113 | 8 | 2'-OMe | $G_{ks}{}^mC_{ks}A_{ks}T_{ds}G_{ds}T_{ds}T_{ds}{}^mC_{ds}T_{ds}{}^m$ $C_{ds}A_{ms}{}^mC_{ds}A_{ds}T_{ks}T_{ks}A_k$ | 18 |
| 1244114 | 9 | 2'-OMe | $G_{ks}{}^mC_{ks}A_{ks}T_{ds}G_{ds}T_{ds}T_{ds}{}^mC_{ds}T_{ds}{}^m$ $C_{ds}A_{ds}C_{ms}A_{ds}T_{ks}T_{ks}A_k$ | 18 |
| 1244115 | 10 | 2'-OMe | $G_{ks}{}^mC_{ks}A_{ks}T_{ds}G_{ds}T_{ds}T_{ds}{}^mC_{ds}T_{ds}{}^m$ $C_{ds}A_{ds}{}^mC_{ds}A_{ms}T_{ks}T_{ks}A_k$ | 18 |

A subscript "d" indicates an unmodified, 2'-β-D-deoxyribosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 50

In vitro activity and toxicity of modified oligonucleotides complementary to CXCL12

| Compound ID | in vitro CXCL12 IC$_{50}$ (nM) | in vitro Caspase (% control) @ 20 μM | in vitro p21 (% control) @ 20 μM | % nucleolar p54nrb |
|---|---|---|---|---|
| 558807 | 47 | 641 | 307 | 92 |
| 1061877 | 13 | 519 | 266 | 43 |
| 936053 | 67 | 173 | 143 | 8 |
| 1061879 | 59 | 416 | 192 | 59 |
| 1061981 | 112 | 325 | 129 | 46 |
| 1244110 | 21 | 386 | 390 | 60 |
| 1244111 | 53 | 380 | 430 | 69 |
| 1244112 | 42 | 345 | 344 | 92 |
| 1244113 | 114 | 361 | 373 | 54 |
| 1244114 | 17 | 399 | 440 | 78 |
| 1244115 | 70 | 372 | 400 | 67 |

Example 21 Stereochemical Isomers of Nucleosides

Modified oligonucleotides containing modified nucleotides with various stereochemical configurations at positions 1', 3', and 5' of the 2'-deoxyfuranosyl sugar were synthesized. Amidites for the synthesis of β-L-DNA-containing nucleotides are commercially available (ChemGenes) and the synthesis of both α-L and β-L dT phosphoramidites has been reported (Morvan, *Biochem and Biophys Research Comm*, 172(2): 537-543, 1990). The altered nucleotides were contained within the central region of the oligonucleotide.

These modified oligonucleotides were compared to the otherwise identical modified oligonucleotide lacking a an altered nucleotide in the central region, 558807, described in Table 1, Example 1 above. The compounds in Table 51 each comprise a 5' wing and a 3' wing each consisting of three linked cEt nucleosides and a central region comprising nucleosides each comprising 2'-β-D-deoxyribosyl sugar moieites aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

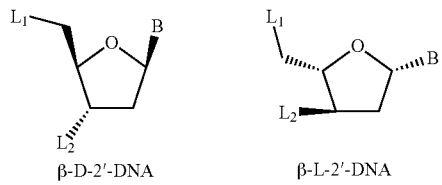

β-D-2'-DNA          β-L-2'-DNA

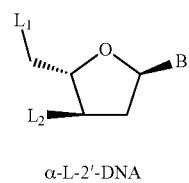

α-L-2'-DNA

B is any nucleobase and L$_1$ and L$_2$ are internucleoside linkages

TABLE 51 modified oligonucleotides with stereochemical modifications

| Compound ID | position of altered nucleotide in central region | stereochemical configuration of altered nucleotide | Chemistry Notation (5' to 3') | SEQ ID NO |
|---|---|---|---|---|
| 1215458 | 2 | β-L-DNA | $G_{ks}{}^mC_{ks}A_{ks}T_{ds}[_{β-L}G_{ds}]T_{ds}T_{ds}{}^mC_{ds}T_{ds}{}^mC_{ds}A_{ds}{}^mC_{ds}A_{ds}T_{ks}T_{ks}A_k$ | 18 |
| 1215459 | 3 | β-L-DNA | $G_{ks}{}^mC_{ks}A_{ks}T_{ds}G_{ds}[_{β-L}T_{ds}]T_{ds}{}^mC_{ds}T_{ds}{}^mC_{ds}A_{ds}{}^mC_{ds}A_{ds}T_{ks}T_{ks}A_k$ | 18 |
| 1215460 | 4 | β-L-DNA | $G_{ks}{}^mC_{ks}A_{ks}T_{ds}G_{ds}T_{ds}[_{β-L}T_{ds}]{}^mC_{ds}T_{ds}{}^mC_{ds}A_{ds}{}^mC_{ds}A_{ds}T_{ks}T_{ks}A_k$ | 18 |
| 1215461 | 3 | α-L-DNA | $G_{ks}{}^mC_{ks}A_{ks}T_{ds}G_{ds}[_{α-L}T_{ds}]T_{ds}{}^mC_{ds}T_{ds}{}^mC_{ds}A_{ds}{}^mC_{ds}A_{ds}T_{ks}T_{ks}A_k$ | 18 |
| 1215462 | 4 | α-L-DNA | $G_{ks}{}^mC_{ks}A_{ks}T_{ds}G_{ds}T_{ds}[_{α-L}T_{ds}]{}^mC_{ds}T_{ds}{}^mC_{ds}A_{ds}{}^mC_{ds}A_{ds}T_{ks}T_{ks}A_k$ | 18 |

A subscript "d" indicates an unmodified, 2'-β-D-deoxyribosyl sugar moiety. A subscript "k" indicates a cEt. A subscript "s" indicates a phosphorothioate internucleoside linkage. [$_{β-L}B_{ds}$] indicates a modified β-L-DNA nucleotide with a 2'-deoxyribosyl moiety, a phosphorothioate linkage, and base B. [$_{α-L}B_{ds}$] indicates a modified, α-L DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 52

Activity and toxicity of modified oligonucleotides complementary CXCL12

| Compound ID | in vitro CXCL12 IC$_{50}$ (μM) | in vitro RAPTOR IC$_{50}$ (μM) | in vivo CXCL12 ED$_{50}$ (mg/kg) | ALT @ 50 mg/kg (IU/L) | ALT @ 150 mg/kg (IU/L) |
|---|---|---|---|---|---|
| PBS | n/a | n/a | n/a | 25 @ 0 mg/kg | |
| 558807 | 0.10 | 1 | 2.9 | n.d.** | |
| 1215458 | 0.41 | >20 | 11 | 32 | 42 |
| 1215459 | 0.44 | >20 | 13 | 31 | 37 |
| 1215460 | 0.41 | >20 | 13 | 29 | 43 |
| 1215461 | 0.14 | 3 | 2.8 | 1725 | 6301 |
| 1215462 | 0.13 | 3 | 3.6 | 45 | 3652 |

**558807 treatment at 16.7 mg/kg leads to an ALT of 586 IU/L; mice that are treated with 558807 at 150 mg/kg typically experience death before 72 hours post-treatment.

TABLE 53 in vitro Caspase Activation

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Relative Caspase Activation (% Control)} | | | | | | |
| 558807 | 106 | 113 | 117 | 169 | 250 | 396 | 343 |
| 1215458 | 81 | 88 | 98 | 95 | 74 | 78 | 95 |
| 1215459 | 96 | 88 | 111 | 98 | 98 | 81 | 102 |
| 1215460 | 89 | 98 | 96 | 111 | 91 | 113 | 130 |
| 1215461 | 90 | 94 | 89 | 117 | 142 | 201 | 250 |
| 1215462 | 96 | 93 | 95 | 119 | 150 | 192 | 240 |

TABLE 53b in vitro P21 Expression

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Expression level of P21 mRNA (% Control)} | | | | | | |
| 558807 | 98 | 116 | 122 | 115 | 115 | 135 | 184 |
| 1215458 | 104 | 127 | 135 | 153 | 139 | 140 | 130 |
| 1215459 | 99 | 116 | 134 | 154 | 158 | 141 | 147 |
| 1215460 | 85 | 109 | 118 | 120 | 118 | 122 | 109 |
| 1215461 | 105 | 107 | 128 | 136 | 139 | 147 | 153 |
| 1215462 | 110 | 127 | 143 | 150 | 139 | 124 | 143 |

TABLE 53c in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Expression level of Tnfrsf10b mRNA (% Control)} | | | | | | |
| 558807 | 107 | 108 | 105 | 99 | 113 | 102 | 68 |
| 1215458 | 90 | 88 | 92 | 87 | 81 | 78 | 80 |
| 1215459 | 97 | 108 | 108 | 100 | 103 | 94 | 83 |
| 1215460 | 92 | 100 | 99 | 102 | 95 | 95 | 84 |
| 1215461 | 86 | 91 | 99 | 98 | 97 | 97 | 114 |
| 1215462 | 101 | 97 | 98 | 56 | 82 | 101 | 108 |

TABLE 53d in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | \multicolumn{7}{c}{Expression level of Gadd45a mRNA (% Control)} | | | | | | |
| 558807 | 123 | 134 | 135 | 136 | 164 | 180 | 223 |
| 1215458 | 132 | 142 | 141 | 135 | 125 | 104 | 87 |
| 1215459 | 163 | 167 | 183 | 190 | 179 | 150 | 110 |
| 1215460 | 127 | 142 | 140 | 141 | 143 | 120 | 95 |

TABLE 53d-continued in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 1215461 | 117 | 141 | 150 | 165 | 168 | 167 | 128 |
| 1215462 | 110 | 139 | 143 | 138 | 133 | 150 | 137 |

Example 22 Stereochemical Isomers of Nucleosides

Modified oligonucleotides containing β-L-DNA nucleotides (described in Example 21 above) at various positions were synthesized. These modified oligonucleotides were compared to compound 558807, described in Table 1, Example 1 above. Compound 558807 contains 5-methyl cytosine for all cytosine nucleosides, as do compounds 1215458-1215460 described in the table below. The compounds in Table 54 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. Compounds 1244441-1244447 in the table below contain unmethylated cytosine in the central region of the compounds. The compounds in the table below are 100% complementary to mouse CXCL12, GENBANK NT_039353.7 truncated from 69/430,515 to 69/445,350 (SEQ ID NO: 1), at position 6877 to 6892.

TABLE 55

In vitro activity and toxicity of modified oligonucleotides complementary to CXCL12

| Compound ID | in vitro CXCL12 $IC_{50}$ (nM) | in vitro Caspase (% control) @ 20 μM |
|---|---|---|
| 558807 | 0.029 | 321 |
| 1244441 | 0.471 | 108 |
| 1215458 | 0.200 | 104 |
| 1215459 | 0.191 | 111 |
| 1215460 | 0.130 | 133 |
| 1244442 | 0.134 | 185 |
| 1244443 | 0.083 | 279 |
| 1244444 | 0.109 | 213 |
| 1244445 | 0.198 | 249 |
| 1244446 | 0.127 | 243 |
| 1244447 | 0.080 | 333 |

Example 23 Stereochemical Isomers of Nucleosides

Modified oligonucleotides containing α-D-DNA nucleotides (see below) at various positions were synthesized. These modified oligonucleotides were compared to the otherwise identical modified oligonucleotide lacking an altered nucleotide in the central region. The compounds in Table 54 each comprise a 5' wing and a 3' wing each consisting of three linked cEt nucleosides and a central region comprising nucleosides each comprising 2'-β-D-de-

TABLE 54 modified oligonucleotides with stereochemical modifications

| Compound ID | position of altered nucleotide in central region | stereochemical configuration of altered nucleotide | Chemistry Notation | SEQ ID NO |
|---|---|---|---|---|
| 1244441 | 1 | β-L-DNA | $G_{ks}{}^mC_{ks}A_{ks}[_{β-L}T_{ds}]G_{ds}T_{ds}T_{ds}C_{ds}T_{ds}C_{ds}A_{ds}C_{ds}A_{ds}T_{ks}T_{ks}A_k$ | 18 |
| 1215458 | 2 | β-L-DNA | $G_{ks}{}^mC_{ks}A_{ks}T_{ds}[_{β-L}G_{ds}]T_{ds}T_{ds}{}^mC_{ds}T_{ds}{}^mC_{ds}A_{ds}{}^mC_{ds}A_{ds}T_{ks}T_{ks}A_k$ | 18 |
| 1215459 | 3 | β-L-DNA | $G_{ks}{}^mC_{ks}A_{ks}T_{ds}G_{ds}[_{β-L}T_{ds}]T_{ds}{}^mC_{ds}T_{ds}{}^mC_{ds}A_{ds}{}^mC_{ds}A_{ds}T_{ks}T_{ks}A_k$ | 18 |
| 1215460 | 4 | β-L-DNA | $G_{ks}{}^mC_{ks}A_{ks}T_{ds}G_{ds}T_{ds}[_{β-L}T_{ds}]{}^mC_{ds}T_{ds}{}^mC_{ds}A_{ds}{}^mC_{ds}A_{ds}T_{ks}T_{ks}A_k$ | 18 |
| 1244442 | 5 | β-L-DNA | $G_{ks}{}^mC_{ks}A_{ks}T_{ds}G_{ds}T_{ds}T_{ds}[_{β-L}C_{ds}]T_{ds}C_{ds}A_{ds}C_{ds}A_{ds}T_{ks}T_{ks}A_k$ | 18 |
| 1244443 | 6 | β-L-DNA | $G_{ks}{}^mC_{ks}A_{ks}T_{ds}G_{ds}T_{ds}T_{ds}C_{ds}[_{β-L}T_{ds}]C_{ds}A_{ds}C_{ds}A_{ds}T_{ks}T_{ks}A_k$ | 18 |
| 1244444 | 7 | β-L-DNA | $G_{ks}{}^mC_{ks}A_{ks}T_{ds}G_{ds}T_{ds}T_{ds}C_{ds}T_{ds}[_{β-L}C_{ds}]A_{ds}C_{ds}A_{ds}T_{ks}T_{ks}A_k$ | 18 |
| 1244445 | 8 | β-L-DNA | $G_{ks}{}^mC_{ks}A_{ks}T_{ds}G_{ds}T_{ds}T_{ds}C_{ds}T_{ds}C_{ds}[_{β-L}A_{ds}]C_{ds}A_{ds}T_{ks}T_{ks}A_k$ | 18 |
| 1244446 | 9 | β-L-DNA | $G_{ks}{}^mC_{ks}A_{ks}T_{ds}G_{ds}T_{ds}T_{ds}C_{ds}T_{ds}C_{ds}A_{ds}[_{β-L}C_{ds}]A_{ds}T_{ks}T_{ks}A_k$ | 18 |
| 1244447 | 10 | β-L-DNA | $G_{ks}{}^mC_{ks}A_{ks}T_{ds}G_{ds}T_{ds}T_{ds}C_{ds}T_{ds}C_{ds}A_{ds}C_{ds}[_{β-L}A_{ds}]T_{ks}T_{ks}A_k$ | 18 |

A subscript "d" indicates a nucleoside comprising an unmodified, 2-β-D-deoxyribosyl sugar moiety. A subscript "k" indicates a cEt. A subscript "s" indicates a phosphorothioate internucleoside linkage. [$_{β-L}B_{ds}$] indicates a modified β-L-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells. Localization of p54nrb in HeLa cells was quantitated as described in Example 15.

oxyribosyl sugar moieties aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

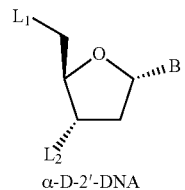

α-D-2'-DNA

TABLE 56 modified oligonucleotides with stereochemical modifications

| Compound ID | position of altered nucleotide in central region | stereochemical configuration of altered nucleotide | Chemistry Notation | SEQ ID NO |
|---|---|---|---|---|
| 1244458 | none | none | $G_{ks}{}^mC_{ks}A_{ks}T_{ds}G_{ds}T_{ds}T_{ds}C_{ds}T_{ds}C_{ds}A_{ds}C_{ds}A_{ds}T_{ks}T_{ks}A_k$ | 18 |
| 1244448 | 1 | α-D-DNA | $G_{ks}{}^mC_{ks}A_{ks}[\alpha_{-D}T_{ds}]G_{ds}T_{ds}T_{ds}C_{ds}T_{ds}C_{ds}A_{ds}C_{ds}A_{ds}T_{ks}T_{ks}A_k$ | 18 |
| 1244449 | 2 | α-D-DNA | $G_{ks}{}^mC_{ks}A_{ks}T_{ds}[\alpha_{-D}G_{ds}]T_{ds}T_{ds}C_{ds}T_{ds}C_{ds}A_{ds}C_{ds}A_{ds}T_{ks}T_{ks}A_k$ | 18 |
| 1244450 | 3 | α-D-DNA | $G_{ks}{}^mC_{ks}A_{ks}T_{ds}G_{ds}[\alpha_{-D}T_{ds}]T_{ds}C_{ds}T_{ds}C_{ds}A_{ds}C_{ds}A_{ds}T_{ks}T_{ks}A_k$ | 18 |
| 1244451 | 4 | α-D-DNA | $G_{ks}{}^mC_{ks}A_{ks}T_{ds}G_{ds}T_{ds}[\alpha_{-D}T_{ds}]C_{ds}T_{ds}C_{ds}A_{ds}C_{ds}A_{ds}T_{ks}T_{ks}A_k$ | 18 |
| 1244452 | 5 | α-D-DNA | $G_{ks}{}^mC_{ks}A_{ks}T_{ds}G_{ds}T_{ds}T_{ds}[\alpha_{-D}C_{ds}]T_{ds}C_{ds}A_{ds}C_{ds}A_{ds}T_{ks}T_{ks}A_k$ | 18 |
| 1244453 | 6 | α-D-DNA | $G_{ks}{}^mC_{ks}A_{ks}T_{ds}G_{ds}T_{ds}T_{ds}C_{ds}[\alpha_{-D}T_{ds}]C_{ds}A_{ds}C_{ds}A_{ds}T_{ks}T_{ks}A_k$ | 18 |
| 1244454 | 7 | α-D-DNA | $G_{ks}{}^mC_{ks}A_{ks}T_{ds}G_{ds}T_{ds}T_{ds}C_{ds}T_{ds}[\alpha_{-D}C_{ds}]A_{ds}C_{ds}A_{ds}T_{ks}T_{ks}A_k$ | 18 |
| 1244455 | 8 | α-D-DNA | $G_{ks}{}^mC_{ks}A_{ks}T_{ds}G_{ds}T_{ds}T_{ds}C_{ds}T_{ds}C_{ds}[\alpha_{-D}A_{ds}]C_{ds}A_{ds}T_{ks}T_{ks}A_k$ | 18 |
| 1244456 | 9 | α-D-DNA | $G_{ks}{}^mC_{ks}A_{ks}T_{ds}G_{ds}T_{ds}T_{ds}C_{ds}T_{ds}C_{ds}A_{ds}[\alpha_{-D}C_{ds}]A_{ds}T_{ks}T_{ks}A_k$ | 18 |
| 1244457 | 10 | α-D-DNA | $G_{ks}{}^mC_{ks}A_{ks}T_{ds}G_{ds}T_{ds}T_{ds}C_{ds}T_{ds}C_{ds}A_{ds}C_{ds}[\alpha_{-D}A_{ds}]T_{ks}T_{ks}A_k$ | 18 |

A subscript "d" indicates a nucleoside comprising an unmodified, 2'-β-D-deoxyribosyl sugar moiety. A subscript "k" indicates a cEt. A subscript "s" indicates a phosphorothioate internucleoside linkage. $[_{\alpha\text{-}D}\text{-}B_{ds}]$ indicates a modified, α-D-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 57

In vitro activity and toxicity of modified oligonucleotides complementary CXCL12

| Compound ID | in vitro CXCL12 IC$_{50}$ (nM) | in vitro Caspase (% control) @ 20 μM | in vitro p21 (% control) @ 20 μM | % nucleolar p54nrb |
|---|---|---|---|---|
| 1244458 | 19 | 785 | 327 | 86 |
| 1244448 | 35 | 269 | 135 | 66 |
| 1244449 | 169 | 111 | 101 | 8 |
| 1244450 | 103 | 96 | 169 | 11 |
| 1244451 | 45 | 261 | 206 | 78 |
| 1244452 | 393 | 295 | 146 | 83 |
| 1244453 | 80 | 417 | 255 | 92 |
| 1244454 | 512 | 287 | 240 | 65 |
| 1244455 | 125 | 409 | 310 | 83 |
| 1244456 | 247 | 233 | 269 | 96 |
| 1244457 | 31 | 854 | 400 | 100 |

Example 24 4'-methyl and Xylo DNA

Modified oligonucleotides containing an altered nucleotide with a 4'-methyl modified sugar moiety or a 2'-deoxy-β-D-xylofuranosyl (2'deoxy-β-D-XNA) sugar moiety at various positions were synthesized (see Table 58 below). Synthesis of oligonucleotides comprising 2'deoxy-β-D-XNA nucleosides has been described previously (Wang, et. al., *Biochemistry*, 56(29): 3725-3732, 2017). Synthesis of oligonucleotides comprising 4'-methyl modified nucleosides has been described previously (e.g., Detmer et. al., *European J. Org. Chem*, 1837-1846, 2003). The compounds in Table 58 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. These compounds were compared to a compound comprising a 2'-OMe modified sugar moiety at position 2 of the central region, 936053, described in Example 1 above. The compounds in the table below are 100% complementary to mouse CXCL12, GENBANK NT_039353.7 truncated from 69/430,515 to 69/445,350 (SEQ ID NO: 1), at position 6877 to 6892.

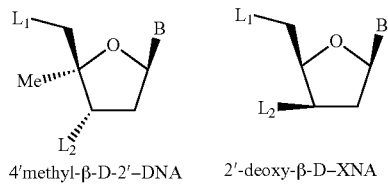

4'methyl-β-D-2'-DNA  2'-deoxy-β-D-XNA

TABLE 58 modified oligonucleotides with stereochemical modifications

| Compound ID | position of altered nucleotide in central region | modification of altered nucleotide | Chemistry Notation | SEQ ID NO |
|---|---|---|---|---|
| 936053 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}Tk_{ks}A_k$ | 18 |
| 1244461 | 3 | 4'-Me | $G_{ks}{}^mC_{ks}A_{ks}T_{ds}G_{ds}T_{[4m]s}T_{ds}{}^mC_{ds}T_{ds}{}^mC_{ds}A_{ds}{}^mC_{ds}A_{ds}T_{ks}Tk_{ks}A_k$ | 18 |

TABLE 58-continued modified oligonucleotides with stereochemical modifications

| Compound ID | position of altered nucleotide in central region | modification of altered nucleotide | Chemistry Notation | SEQ ID NO |
|---|---|---|---|---|
| 1244462 | 4 | 4'-Me | $G_{ks}{}^mC_{ks}A_{ks}T_{ds}G_{ds}T_{ds}T_{[4m]s}{}^mC_{ds}T_{ds}{}^mC_{ds}A_{ds}{}^mC_{ds}A_{ds}T_{ks}Tk_{ks}A_k$ | 18 |
| 1263776 | 3 | β-D-XNA | $G_{ks}{}^mC_{ks}A_{ks}T_{ds}G_{ds}[_{\beta\text{-}D}T_{xs}]T_{ds}{}^mC_{ds}T_{ds}{}^mC_{ds}A_{ds}{}^mC_{ds}A_{ds}T_{ks}Tk_{ks}A_k$ | 18 |
| 1263777 | 4 | β-D-XNA | $G_{ks}{}^mC_{ks}A_{ks}T_{ds}G_{ds}T_{ds}[_{\beta\text{-}D}T_{xs}]{}^mC_{ds}T_{ds}{}^mC_{ds}A_{ds}{}^mC_{ds}A_{ds}T_{ks}Tk_{ks}A_k$ | 18 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" indicates 5-methyl Cytosine. A subscript "[4m]" indicates a 4'-methyl-2'-β-D-deoxyribosyl sugar moiety. [$_\beta$-D-B$_{xs}$] indicates a modified, β-D-XNA (xylo) nucleotide with a 2'-deoxyxylosyl sugar moiety, a phosphorothioate linkage, and base B.

For in vivo activity and toxicity studies, 3 BALB/c mice per group were administered 10 or 150 mg/kg modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

TABLE 59

In vivo activity and toxicity of modified oligonucleotides complementary to CXCL12

| Compound ID | in vivo CXCL12 @ 10 mg/kg (% control) | in vivo CXCL12 @ 150 mg/kg (% control) | in vivo P21 @ 150 mg/kg (% control) | in vivo Tnfrsf10b @ 150 mg/kg (% control) | in vivo Gadd45a @ 150 mg/kg (% control) | in vivo ALT @ 10 mg/kg (IU/L) | in vivo ALT @ 150 mg/kg (IU/L) |
|---|---|---|---|---|---|---|---|
| PBS | 100 | 100 | 100 | 100 | 100 | 26 (@ 0 mg/kg) | |
| 936053 | 37 | 13 | 175 | 448 | 216 | 23 | 83 |
| 1244461 | 22 | 5 | 2994 | 4663 | 1124 | 31 | 5080 |
| 1244462 | 30 | 7* | 1038 | 717* | 407* | 28 | 1789* |
| 1263776 | 19 | 11 | 4846 | 10686 | 1032 | 27 | 9234 |
| 1263777 | 13 | n.d. | n.d. | n.d. | n.d. | 58 | death |

*Value represents the average of 2 samples.

Example 25 Microscopy

Selected modified nucleotides described in the Examples above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells.

For experiments reported in the tables below, the number of cells with nucleolar p54nrb and the total number of cells in the images were counted and a percentage of cells with mislocalization of p54nrb was calculated. Where the same compound appears in multiple tables, these represent the results from independent experiments.

TABLE 60

Nucleolar mislocalization of p54nrb

| Compound ID | Cells with nucleolar p54nrb | Total cells | % cells with mislocalization |
|---|---|---|---|
| Mock | 0 | 74 | 0 |
| 558807 | 45 | 51 | 88 |

TABLE 61

Nucleolar mislocalization of p54nrb

| Compound ID | Sugar Motif | % cells with mislocalization | ALT @ 150 mg/kg (IU/L) |
|---|---|---|---|
| 464917 | kkk-d(10)-kkk | 75 | death |
| 982034 | kkk-d-m-(8)-kkk | <7 | 13,172 |
| 465175 | kkk-d(10)-kkk | 57 | 1,564 |
| 1133329 | kkk-d-m-(8)-kkk | 48 | 60 |
| 465181 | kkk-d(10)-kkk | 58 | 7,087 |
| 1133335 | kkk-d-m-(8)-kkk | <1 | 26 |
| 545984 | kkk-d(10)-kkk | 98 | 37,277 |
| 1133060 | kkk-d-m-(8)-kkk | 0 | 39 |

For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalizization to the nucleolus was observed in most or all cells.

TABLE 62

Nucleolar mislocalization of p54nrb and correlation with toxicity

| Compound ID | Complementary mRNA | Mislocalization of p54nrb | ALT @ max dose* |
|---|---|---|---|
| 558807 | CXCL12 | ++ | death |
| 936049 | CXCL12 | ++ | 8,622 |
| 936053 | CXCL12 | − | 46 |
| 892826 | CXCL12 | − | 10,463 |
| 766677 | CXCL12 | − | 23 |
| 828911 | CXCL12 | − | 27 |
| 936051 | CXCL12 | + | death |
| 936052 | CXCL12 | − | 1,110 |
| 1070041 | CXCL12 | + | 96 |
| 1061314 | CXCL12 | − | 26 |
| 1061302 | CXCL12 | + | 2,253 |
| 1061303 | CXCL12 | − | 34 |
| 1061304 | CXCL12 | − | 52 |
| 1061305 | CXCL12 | − | 31 |
| 1076587 | CXCL12 | − | n.d. |
| 1076588 | CXCL12 | + | n.d. |
| 1069852 | CXCL12 | − | n.d. |
| 1061328 | CXCL12 | + | n.d. |
| 1061955 | CXCL12 | − | 86 |
| 1061964 | CXCL12 | − | n.d. |
| 1244441 | CXCL12 | − | n.d. |
| 1215458 | CXCL12 | − | n.d. |
| 1215459 | CXCL12 | − | n.d. |
| 1215460 | CXCL12 | − | n.d. |
| 1244442 | CXCL12 | − | n.d. |
| 1244443 | CXCL12 | + | n.d. |
| 1244444 | CXCL12 | ++ | n.d. |
| 1244445 | CXCL12 | ++ | n.d. |
| 1244446 | CXCL12 | ++ | n.d. |
| 1244447 | CXCL12 | ++ | n.d. |
| 464917 | FXI | + | 18,316 |
| 465977 | FXI | + | death |
| 483706 | FXI | + | 1,424 |
| 443919 | FXI | − | 68 |
| 820685** | FXI | − | 59 |
| 508031 | SOD1 | ++ | 16,317 |
| 895154 | SOD1 | + | 206 |
| 895155 | SOD1 | − | 41 |
| 895156 | SOD1 | + | 1,242 |
| 508034 | SOD1 | + | 22,396 |
| 508037 | SOD1 | − | 20 |
| 529933 | SOD1 | − | 11 |

*Data presented in previous examples; maximum administered dose is 150 mg/kg for modified oligonucleotides complementary to CXCL12, 100 mg/kg for modified oligonucleotides complementary to SOD1, and 33 mg/kg for compounds complementary to FXI, except that the ALT for 820685 is at 100 mg/kg.
**820685 has the same sequence as 464917 and a sugar motif of kkk-m(10)-kkk.

*Data presented in previous examples; maximum administered dose is 150 mg/kg for modified oligonucleotides complementary to CXCL12, 100 mg/kg for modified oligonucleotides complementary to SOD1, and 33 mg/kg for compounds complementary to FXI, except that the ALT for 820685 is at 100 mg/kg. **820685 has the same sequence as 464917 and a sugar motif of kkk-m(10)-kkk.

Example 26 Nucleolar Mislocalization of p54nrb with Fluorescently-Labeled Modified Oligonucleotides Modified oligonucleotides described in the tables above were conjugated to Cy3 or FAM on the 3'-end via a phosphorothioate linker or on the 5'-end via a phosphorothioate linker to generate a compound comprising a conjugate group that comprises a fluorophore, resulting in a fluorescently labeled modified oligonucleotide. Fluorescently labeled modified oligonucleotides were incubated with HeLa cells at 200 nM for 2 hours and cells were imaged by fluorescent microscopy. Cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalization to the nucleolus was observed in most or all cells.

TABLE 63

Fluorescently Labeled Modified Oligonucleotides

| Unlabelled compound ID | Fluorescently-labelled compound ID | Chemistry notation for Fluorescently-labelled compound | SEQ ID NO: |
|---|---|---|---|
| 558807 | 925819 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766676 | 925820 | $G_{ks}{}^mC_{ks}A_{ks}T_{dx}G_{ds}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766677 | 925821 | $G_{ks}{}^mC_{ks}A_{ks}T_{ds}G_{dx}T_{ds}T_{ds}{}^mC_{ds}T_{ds}{}^mC_{ds}A_{ds}{}^mC_{ds}A_{ds}T_{ks}T_{ks}A_{ks}$-Cy3 | 18 |
| 766678 | 925822 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_{ks}$-Cy3 | 18 |
| 766679 | 925826 | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_{ks}$-Cy3 | 18 |
| 766684 | 925824 | $G_{ks}{}^mC_{ks}A_{ks}T_{ds}G_{ds}T_{ds}T_{ds}{}^mC_{ds}T_{ds}{}^mC_{ds}A_{ds}{}^mC_{dx}A_{ds}T_{ks}T_{ks}A_{ks}$-Cy3 | 18 |
| 936049 | 958339 | Cy3-$G_{ks}{}^mC_{ks}A_{ks}U_{ms}G_{ds}T_{ds}T_{ds}{}^mC_{ds}T_{ds}{}^mC_{ds}A_{ds}{}^mC_{ds}A_{ds}T_{ks}T_{ks}A_{k}$ | 19 |
| 936053 | 958340 | Cy3-$G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_{k}$ | 18 |
| 892826 | 958341 | Cy3-$G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ks}T_{ks}A_{k}$ | 20 |
| 558807 | 1189295 | FAM-$G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}$ | 18 |
| 1061955 | 1189310 | FAM-$G_{ks}{}^mC_{ks}A_{ks}T_{ds}T_{ds}T_{ds}T_{ds}{}^mC_{ds}T_{ds}{}^mC_{ds}A_{ds}{}^mC_{ds}A_{ds}T_{ks}T_{ks}A_{ks}$ | 30 |
| 766677 | 1215929 | FAM-$G_{ks}{}^mC_{ks}A_{ks}T_{ds}G_{dx}T_{ds}T_{ds}{}^mC_{ds}T_{ds}{}^mC_{ds}A_{ds}{}^mC_{ds}A_{ds}T_{ks}T_{ks}A_{ks}$ | 18 |
| 936053 | 1189369 | FAM-$G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_{k}$ | 18 |
| 942944 | 1215928 | FAM-$G_{ks}{}^mC_{ks}A_{ks}T_{ds}G_{ds}T_{ds}{}^{(R)-m}T_{ds}{}^mC_{ds}T_{ds}{}^mC_{ds}A_{ds}{}^mC_{ds}A_{ds}T_{ks}T_{ks}A_{k}$ | 18 |
| 464917 | 813223 | Cy3-$G_{ks}T_{ks}{}^mC_{ks}T_{ds}G_{ds}T_{ds}G_{ds}{}^mC_{ds}A_{ds}T_{ds}{}^mC_{ds}T_{ds}{}^mC_{ds}T_{ks}{}^mC_{ks}{}^mC_{k}$ | 22 |
| 508031 | 828939 | Cy3-$T_{ks}G_{ks}A_{ks}G_{ds}G_{ds}T_{ds}{}^mC_{ds}{}^mC_{ds}T_{ds}G_{ds}{}^mC_{ds}A_{ds}{}^mC_{ds}T_{ks}G_{ks}G_{k}$ | 26 |
| 482050 | 841864 | Cy3-$A_{ks}T_{ks}{}^mC_{ks}A_{ds}T_{ds}G_{ds}G_{ds}{}^mC_{ds}T_{ds}G_{ds}{}^mC_{ds}A_{ds}G_{ds}{}^mC_{ks}T_{ks}T_{k}$ | 24 |
| 449093 | 489982 | FAM-$T_{ks}T_{ks}{}^mC_{ks}A_{ds}G_{ds}T_{ds}{}^mC_{ds}A_{ds}T_{ds}G_{ds}A_{ds}{}^mC_{ds}T_{ds}T_{ks}{}^mC_{ks}{}^mC_{k}$ | 28 |
| 465178 | 869208 | Cy3-$G_{ks}T_{ks}{}^mC_{ks}A_{ds}G_{ds}T_{ds}A_{ds}T_{ds}{}^mC_{ds}{}^mC_{ds}{}^mC_{ds}A_{ds}G_{ds}T_{ks}G_{ks}T_{k}$ | 89 |

TABLE 63-continued

Fluorescently Labeled Modified Oligonucleotides

| Unlabelled compound ID | Fluorescently-labelled compound ID | Chemistry notation for Fluorescently-labelled compound | SEQ ID NO: |
|---|---|---|---|
| 575013 | 869198 | Cy3-$^mC_{ks}A_{ks}G_{ks}A_{ds}T_{ds}A_{ds}T_{ds}A_{ds}G_{ds}G_{ds}A_{ds}{}^mC_{ds}T_{ds}G_{ks}G_{ks}A_k$ | 110 |
| 549139 | 869199 | Cy3-$G_{ks}A_{ks}{}^mC_{ks}G_{ds}{}^mC_{ds}G_{ds}{}^mC_{ds}{}^mC_{ds}T_{ds}G_{ds}A_{ds}A_{ds}G_{ds}G_{ks}T_{ks}T_k$ | 111 |
| 508032 | 869200 | Cy3-$G_{ks}G_{ks}A_{ks}{}^mC_{ds}A_{ds}{}^mC_{ds}A_{ds}T_{ds}T_{ds}G_{ds}G_{ds}{}^mC_{ds}{}^mC_{ds}A_{ks}{}^mC_{ks}A_k$ | 112 |
| 464932 | 869201 | Cy3-$G_{ks}G_{ks}{}^mC_{ks}{}^mC_{ds}A_{ds}{}^mC_{ds}{}^mC_{ds}A_{ds}{}^mC_{ds}G_{ds}{}^mC_{ds}T_{ds}G_{ds}T_{ks}{}^mC_{ks}A_k$ | 113 |
| 465131 | 869202 | Cy3-$T_{ks}G_{ks}{}^mC_{ks}{}^mC_{ds}A_{ds}{}^mC_{ds}{}^mC_{ds}G_{ds}T_{ds}A_{ds}G_{ds}A_{ds}{}^mC_{ds}A_{ks}{}^mC_{ks}G_k$ | 114 |
| 147420 | 841863 | Cy3-$A_{es}A_{es}T_{es}G_{es}T_{es}G_{ds}{}^mC_{ds}{}^mC_{ds}T_{ds}G_{ds}{}^mC_{ds}T_{ds}G_{ds}T_{ds}{}^mC_{ds}{}^mC_{es}T_{es}T_{es}G_{es}A_e$ | 73 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 64

Nucleolar mislocalization of p54nrb

| Unlabelled compound ID | Fluorescently-labelled Compound ID | Complementary mRNA | Mislocalization of p54nrb | ALT @ 150 mg/kg of unlabelled modified oligonucleotide |
|---|---|---|---|---|
| 558807 | 925819 | CXCL12 | ++ | death |
| 766676 | 925820 | CXCL12 | ++ | 5,475 |
| 766677 | 925821 | CXCL12 | − | 23 |
| 766678 | 925822 | CXCL12 | − | 67 |
| 766679 | 925823 | CXCL12 | + | 3,347 |
| 766684 | 925824 | CXCL12 | ++ | death |
| 936049 | 958339 | CXCL12 | ++ | 8,622 |
| 936053 | 958340 | CXCL12 | − | 46 |
| 892826 | 958341 | CXCL12 | + | 10,463 |
| 558807 | 1189295 | CXCL12 | ++ | death |
| 1061955 | 1189310 | CXCL12 | − | 86 |
| 766677 | 1215929 | CXCL12 | − | 23 |
| 936053 | 1189369 | CXCL12 | − | 46 |
| 942944 | 1215928 | CXCL12 | + | 233 |

TABLE 65

Nucleolar mislocalization of p54nrb

| Unlabelled compound ID | Fluorescently-labelled Compound ID | Complementary mRNA | Mislocalization of p54nrb | ALT @ 200 mg/kg of unlabelled modified oligonucleotide |
|---|---|---|---|---|
| 147420 | 841863 | CPT1A | ++ | 7,794 |

For in vivo maximum tolerated doses reported in the table below, 2-4 BALB/C mice per group were administered modified oligonucleotide at 3.7, 11, 33, 100, or 300 mg/kg by subcutaneous injection and sacrificed after 72 hours. Maximum tolerated dose is the highest dose at which ALT is below 5× that in PBS-treated control mice, or ~150 IU/L.

TABLE 67

Nucleolar mislocalization of p54nrb

| Unlabelled compound ID | Fluorescently-labelled compound ID | Complementary mRNA | Mislocalization of p54nrb, labelled modified oligonucleotide | Maximum tolerated dose unlabelled modified oligonucleotide (mg/kg, mouse) |
|---|---|---|---|---|
| 464917 | 813223 | FXI | + | 11 |
| 508031 | 828939 | SOD1 | ++ | 33 |
| 482050 | 841864 | PTEN | ++ | 33 |
| 449093 | 489982 | SRB1 | ++ | 33 |
| 465178 | 869208 | FXI | + | 100 |
| 575013 | 869198 | FXII | − | >300 |
| 549139 | 869199 | none | − | >300 |
| 508032 | 869200 | SOD1 | − | >300 |
| 464932 | 869201 | FXI | − | >300 |
| 465131 | 869202 | FXI | − | >300 |

TABLE 68

Nucleolar mislocalization of p54nrb

| Unlabelled compound ID | Fluorescently-labelled compound ID | Cells with nucleolar p54nrb | Total cells | % cells with p54nrb mislocalization |
|---|---|---|---|---|
| 558807 | 925819 | 57 | 74 | 77 |
| 936049 | 958339 | 51 | 72 | 71 |
| 936053 | 958340 | 6 | 65 | 9 |
| 892826 | 958341 | 30 | 53 | 57 |

Example 27 In Vivo and In Vitro Toxicity of LNA-Containing Modified Oligonucleotides Modified oligonucleotides in the table below have a 3-10-3 sugar motif with LNA nucleosides on the 5' and 3' ends and DNA nucleosides in the central region.

TABLE 69

Modified Oligonucleotides

| Compound ID | Chemistry notation | SEQ ID NO: |
|---|---|---|
| 569713 | $G_{ls}A_{ls}{}^mC_{ds}G_{ds}{}^mC_{ds}G_{ds}{}^mC_{ds}{}^mC_{ds}T_{ds}G_{ds}A_{ds}A_{ds}G_{ds}G_{ls}T_{ls}T_l$ | 111 |
| 569717 | $A_{ls}T_{ls}{}^mC_{ls}A_{ds}T_{ds}G_{ds}G_{ds}{}^mC_{ds}T_{ds}G_{ds}{}^mC_{ds}A_{ds}G_{ds}{}^mC_{ls}T_{ls}T_l$ | 24 |
| 569719 | $G_{ls}T_{ls}{}^mC_{ls}T_{ds}G_{ds}T_{ds}G_{ds}{}^mC_{ds}A_{ds}T_{ds}{}^mC_{ds}T_{ds}{}^mC_{ds}T_{ls}{}^mC_{ls}{}^mC_l$ | 22 |
| 569721 | $T_{ls}G_{ls}A_{ls}G_{ds}G_{ds}T_{ds}{}^mC_{ds}T_{ds}G_{ds}{}^mC_{ds}A_{ds}{}^mC_{ds}T_{ls}G_{ls}G_l$ | 26 |
| 814336 | $G_{ls}{}^mC_{ls}A_{ls}T_{ds}G_{ds}T_{ds}T_{ds}{}^mC_{ds}T_{ds}{}^mC_{ds}A_{ds}{}^mC_{ds}A_{ds}T_{ls}T_{ls}A_l$ | 18 |

A subscript "d" indicates an unmodified, 2'-β-D-deoxyribosyl sugar moiety. A subscript "l" indicates a β-D-LNA sugar moiety. A subscript "s" indicates a phosphorothioate internucleoside linkage. A superscript "m" before a C indicates 5-methyl Cytosine.

Modified nucleotides with 3-10-3 lll-d(10)-lll sugar motifs were tested for their effect on 3T3 cells by microscopy. 3T3 cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a scale of (+) indicating that mislocalization of p54nrb to the nucleolus was observed in some cells, or (++) indicating that p54nrb mislocalization to the nucleolus was observed in most or all cells. Modified nucleotides with 3-10-3 lll-d(10)-lll or kkk-d(10)-kkk sugar motifs were tested in vivo. For in vivo toxicity data, 2-4 BALB/C mice were administered modified oligonucleotide by subcutaneous injection at the doses indicated in the table below. Mice were sacrificed after 72 hours and mRNA was isolated and analyzed as described in Example 1 above. ALT values in plasma were obtained using a clinical chemistry analyzer.

TABLE 70

Modified oligonucleotide dosages administered to mice

| Compound ID | Dose 1 (mg/kg) | Dose 2 (mg/kg) (Maximum dose) |
|---|---|---|
| 549139 | 300 | n/a |
| 569713 | 300 | n/a |
| 482050 | 33 | 100 |
| 569717 | 33 | 100 |
| 464917 | 11 | 33 |
| 569719 | 11 | 33 |
| 508031 | 33 | 100 |
| 569721 | 33 | 100 |
| 558807 | 17 | 51 |
| 814336 | 17 | 51 |

TABLE 71

In vitro p54nrb localization and in vitro toxicity

| Compound ID | Complementary mRNA | Mislocalization of p54nrb | ALT @ maximum dose | P21 mRNA at maximum dose (% control) | Tnfrsf10b mRNA at maximum dose (% control) |
|---|---|---|---|---|---|
| 549139 | none | − | 35 | 306 | 252 |
| 569713 | none | − | 44 | 449 | 241 |
| 482050 | PTEN | n.d. | 6555 | 10,430 | 4,232 |
| 569717 | PTEN | n.d. | 270 | 17,295 | 9,568 |
| 464917 | FXI | ++ | 13,920 | 9,590 | 7,731 |
| 569719 | FXI | + | 14,449 | 13,020 | 6,569 |
| 508031 | SOD1 | ++ | 18,550 | 8,909 | 6,678 |
| 569721 | SOD1 | + | 33,246 | 12,193 | 9,169 |
| 558807 | CXCL12 | ++ | 9,510 | 11,904 | 6,831 |
| 814336 | CXCL12 | ++ | death* | n.d. | n.d. |

*At 17 mg/kg, ALT was 4725, P21 mRNA was 11,567, and Tnfrsf10b mRNA was 8,636.

*At 17 mg/kg, ALT was 4725, P21 mRNA was 11,567, and Tnfrsf10b mRNA was 8,636.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 72 in vitro Caspase Activation

| Compound ID | 27 nM | 80 nM | 250 nM | 740 nM | 2,222 nM | 6,667 nM | 20,000 nM |
|---|---|---|---|---|---|---|---|
| | | | Caspase Activation | | | | |
| 549139 | 2693 | 2272 | 2536 | 2170 | 2664 | 2128 | 2406 |
| 569713 | 2219 | 1988 | 1996 | 1892 | 2099 | 2178 | 3202 |
| 464917 | 1988 | 2116 | 1907 | 2365 | 6580 | 13268 | 24228 |
| 569719 | 2080 | 2183 | 2610 | 4225 | 10773 | 14199 | 20524 |
| 508031 | 7082 | 6602 | 7123 | 8876 | 14962 | 20060 | 29955 |
| 569721 | 7905 | 7741 | 8508 | 10364 | 20715 | 24370 | 49476 |
| 558807 | 7272 | 7887 | 8672 | 12555 | 19397 | 25124 | 28133 |
| 814336 | 7308 | 7975 | 9150 | 12927 | 21327 | 26992 | 26794 |

TABLE 73 in vitro P21 Expression

| Compound ID | 27 nM | 80 nM | 250 nM | 740 nM | 2,222 nM | 6,667 nM | 20,000 nM |
|---|---|---|---|---|---|---|---|
| | | | Expression level of P21 mRNA (% Control) | | | | |
| 549139 | 108 | 104 | 93 | 97 | 97 | 88 | 99 |
| 569713 | 116 | 105 | 94 | 127 | 129 | 139 | 166 |
| 464917 | 129 | 132 | 145 | 149 | 275 | 595 | 1044 |
| 569719 | 120 | 118 | 144 | 160 | 332 | 731 | 922 |
| 508031 | 100 | 90 | 99 | 102 | 100 | 124 | 247 |
| 569721 | 116 | 104 | 123 | 119 | 148 | 123 | 470 |
| 558807 | 95 | 126 | 123 | 123 | 104 | 119 | 193 |
| 814336 | 86 | 100 | 96 | 85 | 119 | 170 | 254 |

TABLE 74 in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | | | Expression level of Gadd45a mRNA (% Control) | | | | |
| 549139 | 113 | 125 | 105 | 83 | 72 | 61 | 35 |
| 569713 | 168 | 139 | 116 | 154 | 135 | 162 | 147 |
| 464917 | 153 | 170 | 187 | 210 | 376 | 906 | 933 |
| 569719 | 165 | 168 | 217 | 220 | 514 | 1223 | 1086 |
| 508031 | 106 | 115 | 111 | 112 | 114 | 211 | 345 |
| 569721 | 165 | 168 | 158 | 136 | 212 | 326 | 451 |
| 558807 | 200 | 198 | 222 | 216 | 200 | 235 | 263 |
| 814336 | 117 | 113 | 139 | 148 | 169 | 198 | 278 |

TABLE 75 in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | | | Expression level of Tnfrsf10b mRNA (% Control) | | | | |
| 549139 | 93 | 96 | 87 | 87 | 89 | 98 | 96 |
| 569713 | 116 | 111 | 79 | 119 | 115 | 128 | 114 |
| 464917 | 122 | 127 | 129 | 93 | 116 | 186 | 125 |
| 569719 | 105 | 107 | 117 | 88 | 119 | 151 | 36 |

Example 28 Total Protein Binding of Modified Oligonucleotides Complementary to SOD1

Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 508031, 895154, 895155, and 895156, described in Example 6 above. Eluted proteins were run on an SDS-PAGE gel. Increased total protein binding is observed for compound 508031 and 895154 compared to compound 895155 and 895156.

Example 29 Total Protein Binding of Modified Oligonucleotides Complementary to FXI Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 464917, 465977, 483706, and 820685, described in Examples 4 and 25 above. Eluted proteins were run on an SDS-PAGE gel. Increased total protein binding is observed for compound 464917 and 465977 compared to compounds 483706 and 820685. A series of western blots was done to detect SSBP1, NCL1, PCNA, p54nrb, RNase H1, and PSF.

In an independent experiment, cellular proteins were captured with 791136 and eluted with increasing concentrations of 464917, 465178, 464392, and 465131. Increased total protein binding is observed for compound 464917 compared to 465178, 464932, and 465131.

Example 30 Total Protein Binding, Activity and Toxicity with MOP Linkages

Modified oligonucleotides were evaluated for their total protein binding in cells. Cellular proteins were captured with the biotin-conjugated modified oligonucleotide 592590, which has a 5'-biotin-TEG, the sugar motif kkk-d(10)-kkk and the sequence GCTAGCCTCTGGATTT (SEQ ID NO:115) and eluted with the modified oligonucleotides described in the table below. Eluted proteins were run on an SDS-PAGE gel and visualized. Decreased protein binding is observed for compounds with decreased toxicity compared to 558807, in particular for compounds 766654, 766655, and 766666.

TABLE 76

Modified oligonucleotides containing Two MOP linkages

| Compound ID | Linkage Mod position in central region | Target | Chemistry Notation | SEQ ID NO |
|---|---|---|---|---|
| 766653 | 1, 2 | CXCL12 | $G_{ks}{}^mC_{ks}A_{ks}T_{dx}G_{dx}T_{ds}T_{ds}{}^mC_{ds}T_{ds}{}^mC_{ds}A_{ds}{}^mC_{ds}A_{ds}T_{ks}T_{ks}A_k$ | 18 |
| 766654 | 2, 3 | CXCL12 | $G_{ks}{}^mC_{ks}A_{ks}T_{ds}G_{dx}T_{dx}T_{ds}{}^mC_{ds}T_{ds}{}^mC_{ds}A_{ds}{}^mC_{ds}A_{ds}T_{ks}T_{ks}A_k$ | 18 |
| 766655 | 3, 4 | CXCL12 | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 766656 | 4, 5 | CXCL12 | $G_{ks}{}^mC_{ks}A_{ks}T_{ds}G_{ds}T_{ds}T_{dx}{}^mC_{dx}T_{ds}{}^mC_{ds}A_{ds}{}^mC_{ds}A_{ds}T_{ks}T_{ks}A_k$ | 18 |
| 766657 | 5, 6 | CXCL12 | $G_{ks}{}^mC_{ks}A_{ks}T_{ds}G_{ds}T_{ds}T_{ds}{}^mC_{dx}T_{dx}{}^mC_{ds}A_{ds}{}^mC_{ds}A_{ds}T_{ks}T_{ks}A_k$ | 18 |
| 766658 | 6, 7 | CXCL12 | $G_{ks}{}^mC_{ks}A_{ks}T_{ds}G_{ds}T_{ds}T_{ds}{}^mC_{ds}T_{dx}{}^mC_{dx}A_{ds}{}^mC_{ds}A_{ds}T_{ks}T_{ks}A_k$ | 18 |
| 766659 | 7, 8 | CXCL12 | $G_{ks}{}^mC_{ks}A_{ks}T_{ds}G_{ds}T_{ds}T_{ds}{}^mC_{ds}T_{ds}{}^mC_{dx}A_{dx}{}^mC_{ds}A_{ds}T_{ks}T_{ks}A_k$ | 18 |
| 766665 | 8, 9 | CXCL12 | $G_{ks}{}^mC_{ks}A_{ks}T_{ds}G_{ds}T_{ds}T_{ds}{}^mC_{ds}T_{ds}{}^mC_{ds}A_{dx}{}^mC_{dx}A_{ds}T_{ks}T_{ks}A_k$ | 18 |
| 766664 | 9, 10 | CXCL12 | $G_{ks}{}^mC_{ks}A_{ks}T_{ds}G_{ds}T_{ds}T_{ds}{}^mC_{ds}T_{ds}{}^mC_{ds}A_{ds}{}^mC_{dx}A_{dx}T_{ks}T_{ks}A_k$ | 18 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

In vitro activity and in vivo activity and toxicity experiments were performed essentially as described in Example 1. For in vivo toxicity studies, a single BALB/C mouse per dose of modified oligonucleotide was administered 16.7 mg/kg, 50 mg/kg, or 150 mg/kg modified oligonucleotide by subcutaneous injection and sacrificed 72 hours later. ALT levels were measured using an automated clinical chemistry analyzer. For the in vivo activity study in the table below, 1 BALB/C mouse per group was administered 1.8 mg/kg, 5.5 mg/kg, 16.7 mg/kg, 50 mg/kg or 150 mg/kg modified oligonucleotide subcutaneously and sacrificed after 24 hours.

TABLE 77 in vivo Activity and Toxicity

| Compound ID | MOP linkage positions | in vivo CXCL12 ED50 (mg/kg) | ALT @ 50 mg/kg (IU/L) | ALT @ 150 mg/kg (IU/L) |
|---|---|---|---|---|
| PBS | n/a | n/a | 26 (@0 mg/kg) | |
| 558807 | n/a | 2.9 | 19,806 | death |
| 766653 | 1, 2 | 23.6 | 32 | 33 |
| 766654 | 2, 3 | 31.6 | 28 | 30 |
| 766655 | 3, 4 | 32.7 | 28 | 27 |
| 766656 | 4, 5 | 26.7 | 25 | 29 |
| 766657 | 5, 6 | 7.0 | 213 | 5,503 |
| 766658 | 6, 7 | 6.2 | 64 | 1,380 |
| 766659 | 7, 8 | 10.6 | 51 | 3,423 |
| 766665 | 8, 9 | 5.5 | 3,437 | 11,954 |
| 766664 | 9, 10 | 6.2 | 4,045 | death |

Example 31 Self-Structure of Modified Oligonucleotides Complementary to CXCL12

Tm was determined for self-structures of modified oligonucleotides described in the examples above. Compounds in the table below are complementary to CXCL12 and have sequences corresponding to SEQ ID NO: 18-21. Tm was also determined for duplexes of the modified oligonucleotides described in the examples above in complex with a RNA 20-mer with the sequence GAUAAUGUGAGAACAUGCCU (SEQ ID NO: 116).

TABLE 78

Tm of Modified Oligonucleotides complementary to CXCL12, Self-Structure and Duplex

| Compound ID | linkage-altered nucleotide (position in central region) | Sugar-modification of altered nucleotide (position in central region) | Tm (° C.) Self structure | Tm (° C.) duplex |
|---|---|---|---|---|
| 558807 | none | none | 48.6 | 65.1 |
| 1061955 | none | inosine (2) | 32.9 | 57.5 |
| 766676 | MOP(1) | none | 44.6 | 63.3 |
| 766677 | MOP(2) | none | 45.3 | 63.5 |
| 766678 | MOP(3) | none | 47.9 | 63.1 |
| 766679 | MOP(4) | none | 47.1 | 62.6 |
| 766680 | MOP(5) | none | n.d. | 63 |
| 766681 | MOP(6) | none | n.d. | 62.9 |
| 766682 | MOP(7) | none | n.d. | 63.8 |
| 766683 | MOP(8) | none | n.d. | 63.3 |
| 766684 | MOP(9) | none | n.d. | 64.1 |
| 766685 | MOP(10) | none | n.d. | 63.9 |
| 936053 | none | 2'-OMe (2) | 49.0 | 67.0 |
| 828911 | none | 2'-MOE (2) | 48.2 | 66.8 |
| 1070041 | none | cEt (2) | 52.7 | 69.5 |
| 936051 | none | 2'-FANA (2) | 46.1 | 64.8 |
| 936052 | none | 2'-ribo-F (2) | 47.2 | 66.0 |
| 1123320 | none | 5'-(R)-Me (2) | 49.4 | 65.5 |
| 1123322 | none | 5'-(S)-Me (2) | 43.0 | 62.0 |
| 942943 | none | 5'-(R)--Me (3) | 47.3 | 62.3 |
| 957908 | none | 5'-(S)-Me (3) | 45.1 | 65.1 |
| 942944 | none | 5'-(R)--Me (4) | 49.5 | 62.3 |
| 957909 | none | 5'-(S)-Me (4) | 46.2 | 66.3 |
| 957910 | none | 5'-(R)-allyl (3) | 44.4 | 62.1 |
| 957911 | none | 5'-(R)-allyl (4) | 47.3 | 62.4 |
| 957912 | none | 5'-(S)--allyl (3) | 41.7 | 64.0 |
| 957913 | none | 5'-(S)-allyl (4) | 47.1 | 64.6 |
| 1069852 | none | pseudoU (2) | 24.4 | 54.4 |
| 1061328 | none | pseudoU (3) | 44.6 | 55.3 |
| 1215458 | none | β-L-DNA (2) | n.d. | 58 |
| 1215459 | none | β-L-DNA (3) | 43 | 59 |
| 1215460 | none | β-L-DNA (4) | 45 | 62 |
| 1215461 | none | α-L-DNA (3) | 41 | 63 |
| 1215462 | none | α-L-DNA (4) | 49 | 65 |

TABLE 79

Tm of Modified Oligonucleotide Self-Structure

| Compound ID | Target | Tm (° C.) |
|---|---|---|
| 449093 | SRB1 | <40 |
| 464917 | FXI | <40 |
| 482050 | PTEN | 33.4 |
| 508031 | SOD-1 | 58.9 |

Example 32 2'-Modifications in 5' and 3'-Regions of Modified Oligonucleotides

Modified oligonucleotides containing various sugar modification motifs were synthesized as indicated in the table below. The compounds in the table below are 100% complementary to mouse CXCL12, GENBANK NT_039353.7 truncated from 69/430,515 to 69/445,350 (SEQ ID NO: 1) at positions 6877 to 6892 (16-mers) or 6875 to 6894 (20-mers).

TABLE 80 modified oligonucleotides with 2'-sugar modifications

| Compound ID | 2'-modified sugars on 5'-end | 2'-modified sugars on 3'-end | Chemistry Notation | SEQ ID NO |
|---|---|---|---|---|
| 558807 | kkk | kkk | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1035522 | kkk | eee | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{es}T_{es}A_e$ | 18 |
| 1035523 | eee | kkk | $G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 985648 | eee | eee | $G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_e$ | 18 |
| 1069842 | kkeee | eeekk | $A_{ks}G_{ks}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{ks}{}^mC_k$ | 117 |
| 1069843 | kkeee | kkkkk | $A_{ks}G_{ks}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{ks}{}^mC_k$ | 117 |
| 1069844 | kkkkk | eeekk | $A_{ks}G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{ks}{}^mC_k$ | 117 |
| 386864 | eeeee | eeeee | $A_{es}G_{es}G_{es}{}^mC_{es}A_{es}T_{ds}G_{ds}T_{ds}T_{ds}{}^mC_{ds}T_{ds}{}^mC_{ds}A_{ds}{}^mC_{ds}A_{ds}T_{es}T_{es}A_{es}T_{es}{}^mC_e$ | 117 |
| 1069845 | kkkkk | kkkkk | $A_{ks}G_{ks}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}T_{ks}{}^mC_k$ | 117 |
| 1069846 | eekkk | kkkkk | $A_{es}G_{es}G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{ks}{}^mC_k$ | 117 |
| 1069847 | kkkkk | kkkee | $A_{ks}G_{ks}G_{ks}{}^mC_{ks}A_{ss}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_{es}{}^mC_e$ | 117 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "e" indicates a 2'-MOE-β-D-ribofuranosyl sugar moiety. A subscript "m" indicates a 2'-O-methyl-β-D-ribofuranosyl sugar moiety.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of CXCL12 were measured by RT-qPCR as described in Example 1 above. Caspase activation was measured as described in Example 4 above. Results are presented relative to the caspase activation in control cells not treated with modified oligonucleotide. Mislocalization of p54nrb was analyzed as described in Example 15 above. For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalizization to the nucleolus was observed in most or all cells. Treatment of HeLa cells with certain modified oligonucleotides caused a filamentous appearance of p54nrb in cells. This is indicated by a "f" in the table below.

TABLE 81 in vitro Activity and Toxicity

| Compound ID | Caspase (% control) | CXCL12 IC$_{50}$ (nM) | p54nrb mislocalization |
|---|---|---|---|
| 558807 | 1135 | 30 | ++ |
| 1035522 | 1261 | 35 | +, f |
| 1035523 | 244 | 100 | +, f |
| 985648 | 207 | 200 | −, f |
| 1069842 | 353 | 350 | +, f |
| 1069843 | 670 | 100 | ++ |
| 1069844 | 748 | 350 | + |
| 386864 | 1104 | 200 | −, f |
| 1069845 | 213 | 350 | ++ |
| 1069846 | 963 | 100 | + |
| 1069847 | 923 | 250 | + |

Example 33 Effect of Treatment of b.END Cells with Modified Oligonucleotides

For the in vitro study reported in the tables below, b.END.3 cells were electroporated with 3.125, 6.25, 12.5, 25, or 50 nM of modified oligonucleotide 464917 (heptatotoxic) or 549148 (nontoxic). 549148 is a 3-10-3 cEt modified oligonucleotide with the sequence GGCTACTACGCCGTCA (SEQ ID NO: 118), which is not complementary to any known mouse gene. Expression levels of p21 and Gadd45a mRNA were measured after 0, 1, 2, 4, and 6 hours by RT-qPCR as described in Example 1.

TABLE 82

Relative mp21 mRNA dose response/time course in b.END cells

| Compound | Dose (nM) | % Control mp21 mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 102 | 134 | 147 | 174 |
| 464917 | 6.25 | 113 | 149 | 169 | 242 |
| 464917 | 12.50 | 107 | 141 | 199 | 250 |
| 464917 | 25.0 | 122 | 183 | 330 | 394 |
| 464917 | 50.0 | 113 | 210 | 399 | 427 |
| 549148 | 0 | 100 | 100 | 100 | 100 |
| 549148 | 3.125 | 111 | 42 | 140 | 107 |
| 549148 | 6.25 | 88 | 90 | 128 | 126 |
| 549148 | 12.50 | 120 | 86 | 119 | 109 |
| 549148 | 25.0 | 114 | 111 | 147 | 107 |
| 549148 | 50.0 | 111 | 94 | 126 | 119 |

TABLE 82a

Relative mGadd45a mRNA dose response/time course in b.END cells

| Compound | Dose (nM) | % Control mGadd45a mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 87 | 88 | 203 | 396 |
| 464917 | 6.25 | 81 | 154 | 259 | 565 |
| 464917 | 12.50 | 85 | 173 | 331 | 905 |
| 464917 | 25.0 | 102 | 247 | 715 | 1586 |
| 464917 | 50.0 | 132 | 420 | 1376 | 3339 |
| 549148 | 0 | 100 | 100 | 100 | 100 |
| 549148 | 3.125 | 85 | 31 | 106 | 109 |
| 549148 | 6.25 | 72 | 95 | 103 | 125 |
| 549148 | 12.50 | 85 | 87 | 106 | 127 |
| 549148 | 25.0 | 85 | 103 | 144 | 123 |
| 549148 | 50.0 | 97 | 107 | 131 | 198 |

Example 34 Nucleolar Delocalization of p54nrb in Various Cell Lines

Cells were plated at 20,000 cells/well and transfected with Lipofectamine 2,000 and 60 nM of modified oligonucleotide 791143, compound 464917 labeled on the 3'-end with Cy3. Cells were visualized 6 hours after transfection.

TABLE 83 p54nrb nucleolar mislocalization

| Compound ID | Cell line | p54nrb nucleolar mislocalization |
|---|---|---|
| 791143 | U2OS | + |
| 791143 | NIH3T3 | ++ |

Cells were plated at 20,000 cells/well and transfected by free uptake with modified oligonucleotide 791143 as indicated in the table below. Cells were visualized 5 hours after transfection.

TABLE 84 p54nrb nucleolar mislocalization

| Compound ID | Cell line | p54nrb nucleolar mislocalization |
|---|---|---|
| 791143 | MHT | + |
| 791143 | HeLa | ++ |

Cells were plated at 20,000 cells/well and transfected by NEON electroporation at 1400V, 20 ms, 2 pulses with 60 nM modified oligonucleotide 813223, compound 464917 labeled on the 5'-end with Cy3. Cells were visualized 5 hours after transfection.

TABLE 85 p54nrb nucleolar mislocalization

| Compound ID | Cell line | p54nrb nucleolar mislocalization |
|---|---|---|
| 813223 | HeLa | ++ |

Cells were transfected with 60 nM modified oligonucleotide 813223 or compound 813225. Compound 813225 is the control oligonucleotide 549148 described above labeled on the 5'-end with Cy3. Cells were visualized 4 hours after transfection.

TABLE 85b p54nrb nucleolar mislocalization

| Compound ID | Cell line | p54nrb nucleolar mislocalization |
|---|---|---|
| 813223 | b.END3 | ++ |
| 813225 | b.END3 | − |
| 813223 | NIH3T3 | + |
| 813223 | primary neuron | + |
| 813223 | primary hepatocyte | ++ |

Example 35 Effect of Depletion of RNaseH1 on Toxicity of Modified Oligonucleotides HeLa cells were plated at 150,000 cells/well and transfected with control siRNA targeting luciferase or siRNA targeted to RNaseH1 (s48357 or s48358 from ThermoFisher) at a final concentration of 3 nM using Lipofectamine RNAiMAX for 48 hours. Modified oligonucleotides 464917 and 549148 were added to the cells by free uptake. 549148 is a 3-10-3 cEt modified oligonucleotide with the sequence GGCTACTACGCCGTCA (SEQ ID NO: 118), which is not complementary to any known mouse gene. Confocal microscopy was used to visualize p54nrb localization as described in Example 15 above.

TABLE 86 in vitro p54nrb mislocalization

| Compound ID | siRNA | p54nrb nucleolar mislocalization |
|---|---|---|
| 464917 | mock | ++ |
| 464917 | RNaseH1a | − |
| 464917 | RNaseH1b | − |

TABLE 87 in vitro P21 Expression in HeLa cells

| Compound ID | siRNA | 0 nM | 3.125 nM | 6.25 nM | 12.5 nM | 25 nM | 50 nM |
|---|---|---|---|---|---|---|---|
| | | Expression level of P21 mRNA (% Control) | | | | | |
| 464917 | Luci | 90 | 134 | 141 | 143 | 171 | 201 |
| 464917 | H1 | 78 | 79 | 82 | 83 | 84 | 95 |
| 549148 | Luci | 100 | 119 | 105 | 84 | 94 | 82 |
| 549148 | H1 | 99 | 86 | 92 | 81 | 79 | 85 |

TABLE 88 in vitro Gadd45a Expression in HeLa cells

| Compound ID | siRNA | 0 nM | 3.125 nM | 6.25 nM | 12.5 nM | 25 nM | 50 nM |
|---|---|---|---|---|---|---|---|
| | | Expression level of P21 mRNA (% Control) | | | | | |
| 464917 | Luci | 73 | 119 | 126 | 179 | 270 | 463 |
| 464917 | H1 | 65 | 82 | 110 | 117 | 154 | 260 |
| 549148 | Luci | 100 | 89 | 107 | 102 | 97 | 83 |
| 549148 | H1 | 72 | 83 | 103 | 103 | 105 | 96 |

Example 36 Protein Binding of Modified Oligonucleotides

Modified oligonucleotides described in the examples above were evaluated for their protein binding in cells. Cellular proteins were captured with the biotin-conjugated modified oligonucleotide 791136, which has a 5'-biotin-TEG, the sugar motif kkk-d(10)-kkk, a full phosphorothioate backbone, and the same sequence as 464917, GTCTGTG-CATCTCTCC (SEQ ID NO: 22). Proteins were eluted with increasing concentrations of 464917 or 549148. Eluted proteins were run on an SDS-PAGE gel and analyzed by western blot for p54nrb, FUS, RNaseH1, SSBP1, Ku70, PSPC1, SND1, FUBP, NCL1, and Ku80. Band intensities are represented in the table below: −, no band; +, faint band; ++, medium band; +++, intense band.

TABLE 89

Protein binding of modified oligonucleotides

| Protein | Relative band intensity 464917 | | Relative band intensity 549148 | |
|---|---|---|---|---|
| | 0.625 μM | 5 μM | 0.625 μM | 5 μM |
| p54nrb | − | +++ | − | + |
| FUS | − | ++ | − | − |
| RNaseH1 | − | ++ | − | + |
| SSBP1 | ++ | ++ | + | + |
| Ku70 | + | ++ | + | + |
| PSPC1 | − | + | − | + |
| SND1 | ++ | +++ | + | ++ |
| FUBP | + | ++ | + | + |
| NCL1 | + | ++ | + | + |
| Ku80 | + | ++ | ++ | ++ |

Total protein binding to 464917 and 549418 was tested using biotin-464917 or biotin-549148 to capture cellular proteins, which were then eluted with increasing concentrations of 464917 or 549148. The hepatotoxic compound 464917 shows increased global protein binding compared to 549148.

Example 37 In Vitro Activity and Toxicity of Modified Oligonucleotides Comprising Modified Internucleoside Linkages Modified oligonucleotides were designed based on the control oligonucleotide 558807, described in Example 1 herein and synthesized using standard procedures. Modified internucleoside linkages (1 or 2) were positioned at various positions within the central region of the oligonucleotides as illustrated below. The resulting modified oligonucleotides were tested for their ability to inhibit CXCL12 (Chemokine ligand 12) and Raptor expression levels. The potency of the modified oligonucleotides was evaluated and compared to the control oligonucleotide.

The modified oligonucleotides were tested in vitro in mouse b.END cells by electroporation. Cells at a density of 20,000 cells per well are transfected using electroporation with 0.027, 0.082, 0.25, 0.74, 2.22, 6.67 and 20 uM concentrations of each of the oligonucleotides listed below. After a treatment period of approximately 24 hours, RNA is isolated from the cells and mRNA levels are measured by quantitative real-time PCR and the CXCL12 mRNA and Raptor mRNA levels are adjusted according to total RNA content, as measured by RIBOGREEN®.

TABLE 90

Modified Oligonucleotides

| Compound ID | Linkage-altered nucleotide position in central region | Linkage mod "x" | Chemistry Notation | SEQ ID NO |
|---|---|---|---|---|
| 558807 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 857528 | 3 | THP phosphotriester | $G_{ks}{}^mC_{ks}A_{ks}T_{ds}G_{ds}T_xT_{ds}{}^mC_{ds}T_{ds}{}^mC_{ds}A_{ds}{}^mC_{ds}A_{ds}T_{ks}T_{ks}A_k$ | 18 |
| 857529 | 3 | isopropylphosphotriester | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 857530 | 3 | isobutylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 857505 | 3 | isopropylphosphonate | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 883401 | 3 | amide-3 | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 883521 | 3 | formacetal | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_k$ | 18 |
| 857532 | 4 | THP phosphotriester | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857533 | 4 | isopropylphosphotriester | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857531 | 4 | isopropylphosphonate | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857534 | 4 | isobutylphosphonate | $G_{ks}{}^mC_{ks}A_{ks}T_{ds}G_{ds}T_{ds}T_{dx}{}^mC_{ds}T_{ds}{}^mC_{ds}A_{ds}{}^mC_{ds}A_{ds}T_{ks}T_{ks}A_k$ | 18 |
| 857537 | 3, 4 | isopropylphosphonate | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 857540 | 3, 4 | isobutylphosphonate | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |
| 857538 | 3, 4 | THP phosphotriester | $G_{ks}{}^mC_{ks}A_{ks}T_{ds}G_{ds}T_{dx}T_{dx}{}^mC_{ds}T_{ds}{}^mC_{ds}A_{ds}{}^mC_{ds}A_{ds}T_{ks}T_{ks}A_k$ | 18 |

A subscript "d" indicates a an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a modified internucleoside linkage as indicated in the "linkage mod x" column. These linkages are illustrated below.

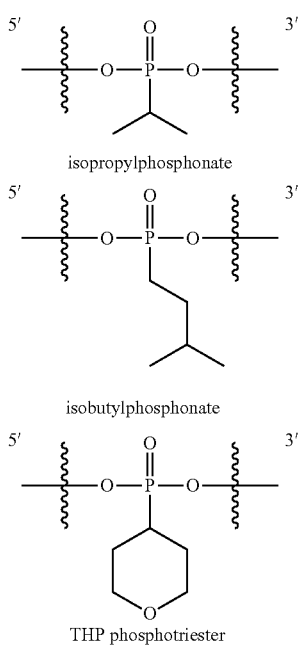

isopropylphosphonate isobutylphosphonate

THP phosphotriester

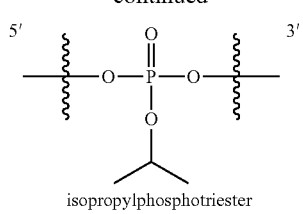

isopropylphosphotriester

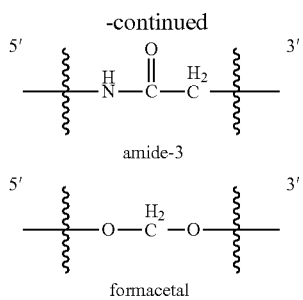

amide-3 formacetal

The half maximal inhibitory concentration (IC$_{50}$) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control. The results are presented in the table below.

TABLE 91

In vitro Activity and Toxicity

| Compound ID | IC$_{50}$ (μM) CXCL12 | Raptor % Control (4 μM) | Raptor IC50* (μM) |
|---|---|---|---|
| 558807 | 0.17 | 47 | 3.7 |
| 857505 | 0.15 | 82 | >4 |
| 857530 | 0.32 | 87 | >4 |
| 857528 | 0.23 | 110 | >4 |
| 857529 | 1.09 | 74 | >4 |
| 883401 | 30 | 65 | >4 |
| 883521 | 0.40 | 94 | >4 |

TABLE 91-continued

In vitro Activity and Toxicity

| Compound ID | IC$_{50}$ (μM) CXCL12 | Raptor % Control (4 μM) | Raptor IC50* (μM) |
|---|---|---|---|
| 857531 | 0.27 | 99 | >4 |
| 857534 | 0.12 | 57 | >4 |
| 857532 | 0.16 | 69 | >4 |
| 857533 | 0.10 | 61 | >4 |

Six week old BALB/C mice (purchased from Charles River) were injected subcutaneously once at dosage 0.2, 0.6, 1.8 or 50 mg/kg with the modified oligonucleotides shown below or with saline control. For compound 855156, mice were injected with 0.21, 0.62, 1.85,or 5.56 mg/kg modified oligonucleotide. Each treatment group consisted of 3 animals. The mice were sacrificed 72 hours following administration, and organs and plasma were harvested for further analysis.

TABLE 92

Modified Oligonucleotides

| Compound ID | Linkage-altered nucleotide position in central region | Linkage mod "x" | Chemistry Notation | SEQ ID NO |
|---|---|---|---|---|
| 895566 | 3 | isopropylphosphonate | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 895567 | 3 | THP phosphotriester | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 895568 | 3 | isopropylphosphotriester | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 895569 | 3 | isobutylphosphonate | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 895570 | 3 | formacetal | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 913196 | 3 | amide-3 | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 920046 | 3 | TANA | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 951972 | 3 | (R)-MOP | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 951973 | 3 | (S)-MOP | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 974343 | 3 | alt-thioformacetal | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 974344 | 3 | glycine amide | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 1011295 | 3 | thioformacetal | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |
| 1011296 | 3 | MMI | G$_{ks}$$^m$C$_{ks}$A$_{ks}$T$_{ds}$G$_{ds}$T$_{dx}$T$_{ds}$$^m$C$_{ds}$T$_{ds}$$^m$C$_{ds}$A$_{ds}$$^m$C$_{ds}$A$_{ds}$T$_{ks}$T$_{ks}$A$_k$-HPPO-GalNAc | 18 |

TABLE 91-continued

In vitro Activity and Toxicity

| Compound ID | IC$_{50}$ (μM) CXCL12 | Raptor % Control (4 μM) | Raptor IC50* (μM) |
|---|---|---|---|
| 857537 | 1.4 | 82 | >4 |
| 857540 | 0.48 | 65 | >4 |
| 857538 | 0.33 | 110 | >4 |
| 857539 | 0.13 | 74 | >4 |

*IC50 values can only be calculated when less than the highest dose in the experiment, in this case, 4 μM

Example 38

Modified oligonucleotides were designed based on 558807. Each modified oligonucleotide has a modified internucleoside linkage positioned between nucleosides 3 and 4 counting from the 5'-gap junction (not including the 3 cEt modified nucleosides in the 5'-wing) as illustrated below. Each of the modified oligonucleotides is conjugated with a HPPO-GalNAc conjugate group at the 3'-end as illustrated below. The oligonucleotides were evaluated for reduction in CXCL12 (Chemokine ligand 12) mRNA expression levels in vivo. The transaminase levels (ALT and AST) for each dose were also measured.

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a modified internucleoside linkage as indicated in the "linkage mod x" column. These linkages are illustrated above and below.

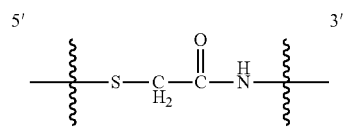

TANA

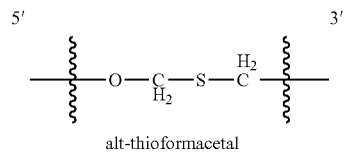

alt-thioformacetal

-continued

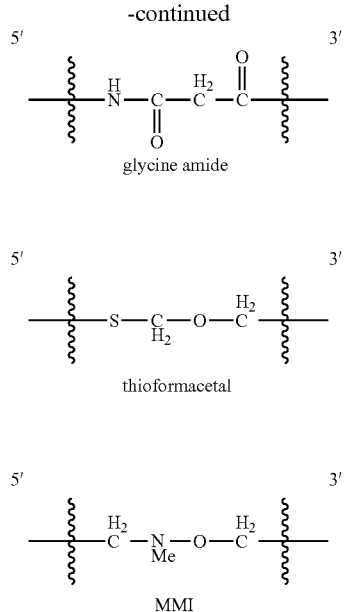

glycine amide thioformacetal

MMI

Each modified oligonucleotide in the study includes a 3'-HPPO-GalNAc conjugate group which is attached to the 3'-oxygen of the oligomeric compound. The 3'-HPPO-GalNAc conjugate group is illustrated below wherein the phosphate group is attached to the 3'-oxygen atom:

at which 50% inhibition of CXCL12 mRNA expression was achieved compared to the control.

TABLE 93

In vivo Toxicity

| Compound ID | Linkage-altered nucleotide position in Central region | Linkage Mod | ALT (at 50 mg/kg) |
|---|---|---|---|
| 855156* | n/a | n/a | 4298** |
| 855161 | 3 | MOP | 31 |
| 895566 | 3 | isopropylphosphonate | 24 |
| 895567 | 3 | THP phosphotriester | 25 |
| 895568 | 3 | isopropylphosphotriester | 38 |
| 895569 | 3 | isobutylphosphonate | 28 |
| 895570 | 3 | formacetal | 31 |
| 913196 | 3 | amide-3 | 29 |
| 920046 | 3 | TANA | 24 |
| 951972 | 3 | (R)-MOP | 47 |
| 951973 | 3 | (S)-MOP | 45 |
| 974343 | 3 | alt-thioacetal | 39 |
| 974344 | 3 | glycine amide | 30 |
| 1011295 | 3 | thioacetal | 38 |
| 1011296 | 3 | MMI | 56 |

*Described in Table 25 above
**Values determined in an independent experiment and shown for comparison; ALT value is at 5.56 mg/kg modified oligonucleotide

**Values determined in an independent experiment and shown for comparison; ALT value is at 5.56 mg/kg modified oligonucleotide

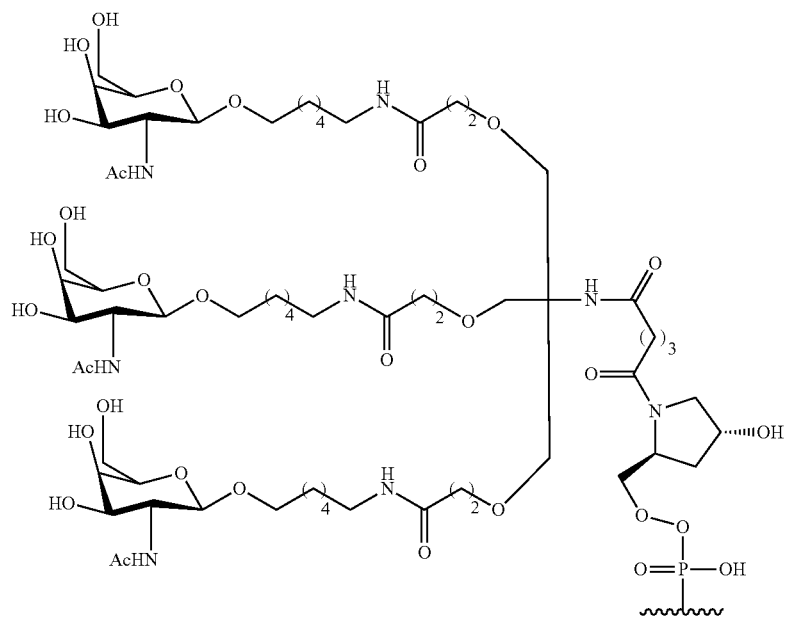

Liver tissues were homogenized and mRNA levels were quantitated using real-time PCR and normalized to RIBOGREEN as described herein. Plasma chemistry markers such as liver transaminase levels, alanine aminotransferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide TABLE 93b In Vivo CXCL12 mRNA levels

| Compound ID | 0.21 mg/kg | 0.62 mg/kg | 1.85 mg/kg | 5.56 mg/kg | 50 mg/kg |
|---|---|---|---|---|---|
| | Expression level of CXCL12 mRNA (% Control) | | | | |
| 855156* | 81 | 63 | 45 | 31 | n.d. |
| 895566 | 68 | 55 | 42 | n.d. | 22 |

TABLE 93b-continued

| | In Vivo CXCL12 mRNA levels | | | | |
|---|---|---|---|---|---|
| Compound ID | 0.21 mg/kg | 0.62 mg/kg | 1.85 mg/kg | 5.56 mg/kg | 50 mg/kg |
| | Expression level of CXCL12 mRNA (% Control) | | | | |
| 895567 | 59 | 50 | 36 | n.d. | 18 |
| 895568 | 69 | 49 | 37 | n.d. | 17 |
| 895569 | 72 | 51 | 41 | n.d. | 18 |
| 895570 | 68 | 50 | 38 | n.d. | 17 |
| 913196 | 62 | 48 | 44 | n.d. | 19 |
| 920046 | 80 | 58 | 58 | n.d. | 25 |
| 855161 | 67 | 51 | 38 | 32 | 21 |
| 951972 | 77 | 61 | 39 | 29 | 20 |
| 951973 | 81 | 59 | 37 | 32 | 19 |
| 974343 | 86 | 56 | 37 | 27 | 16 |
| 974344 | 79 | 69 | 44 | 34 | 23 |
| 1011295 | 78 | 62 | 44 | 31 | 30 |
| 1011296 | 77 | 63 | 49 | 51 | 29 |

Example 39 Synthesis of 5'-(R)-Ethyl and 5'-(S)-Ethyl Phosphoramidites

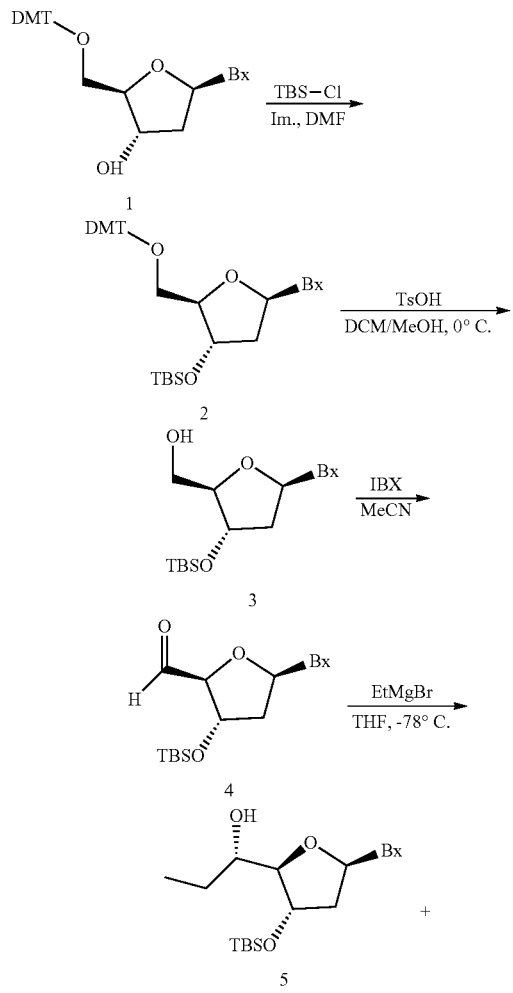

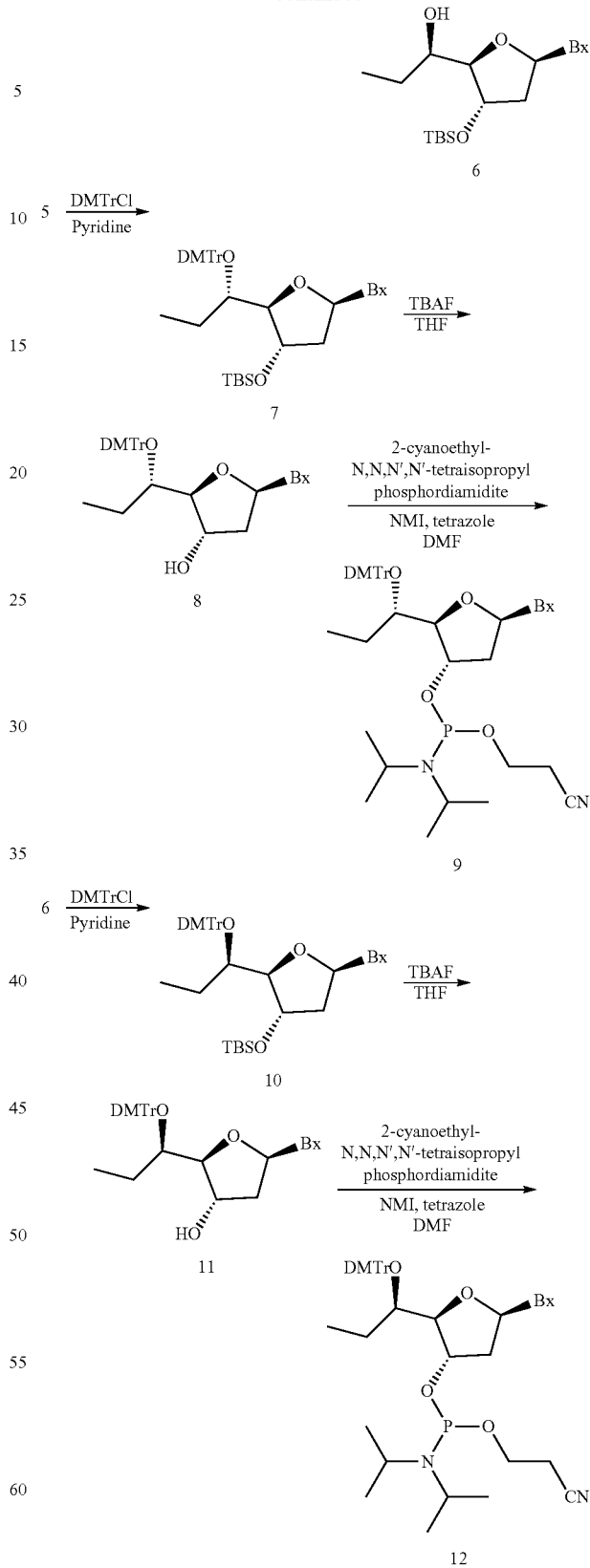

1 was synthesized by The National Institutes of Pharmaceutical R&D Bx = N(Bz)-A, N(iBu)-G, N(Bz)MeC, T
5'-(R)-ethyl and 5'-(S)-ethyl phosphordiamidtes were prepared as per the scheme illustrated above.

Example 40 Time Course of Modified Oligonucleotides in HeLa Cells

HeLa cells were transfected with a modified oligonucleotide listed in the tables below. At 0, 0.5, 1, 2, 4, and 6 hours after transfection, cells were lysed and mRNA was isolated and analyzed by RT-qPCR. Primer probe set HTS3934 (forward sequence: TGGAGACTCTCAGGGTCGAAA, SEQ ID NO: 122; reverse sequence: GGCGTTTG-GAGTGGTAGAAATC, SEQ ID NO: 123; probe sequence: CGGCGGCAGACCAGCATGAC, SEQ ID NO: 124) was used to detect human p21 mRNA, and primer probe set HS00169255_ml (ThermoFisher)) was used to detect human Gadd45a mRNA. Results are normalized to untreated cells.

TABLE 94

Relative hp21 mRNA timecourse in HeLa cells

| | % Control human p21 mRNA | | | | | |
|---|---|---|---|---|---|---|
| Compound | 0 hrs | 0.5 hrs | 1 hrs | 2 hrs | 4 hrs | 6 hrs |
| 464917 | 100 | 123 | 133 | 241 | 259 | 557 |
| 558807 | 97.8 | 113 | 135 | 187 | 253 | 528 |
| 549148 | 120 | 120 | 129 | 187 | 138 | 147 |
| 549139 | 102 | 125 | 124 | 143 | 133 | 213 |

TABLE 95

Relative hGadd45a mRNA timecourse in HeLa cells

| | % Control human Gadd45a mRNA | | | | | |
|---|---|---|---|---|---|---|
| Compound | 0 hrs | 0.5 hrs | 1 hrs | 2 hrs | 4 hrs | 6 hrs |
| 464917 | 100 | 157 | 281 | 375 | 632 | 746 |
| 558807 | 105 | 188 | 227 | 297 | 261 | 412 |
| 549148 | 106 | 156 | 200 | 231 | 156 | 180 |
| 549139 | 94 | 157 | 213 | 229 | 167 | 237 |

HeLa cells were transfected with various concentrations of modified oligonucleotide as indicated in the table below. At 0, 1, 2, 4, 6, and 8 hours after transfection, cells were lysed and mRNA was isolated and analyzed by RT-qPCR as described above.

TABLE 96

Relative hp21 mRNA dose response/time course in HeLa cells

| | | % Control human p21 mRNA | | | | | |
|---|---|---|---|---|---|---|---|
| Compound | Dose (nM) | 0 hrs | 1 hrs | 2 hrs | 4 hrs | 6 hrs | 8 hrs |
| 464917 | 0 | 100 | 114 | 87 | 105 | 107 | 97 |
| 464917 | 3.125 | 100 | 109 | 76 | 111 | 179 | 126 |
| 464917 | 6.25 | 100 | 110 | 86 | 113 | 219 | 159 |
| 464917 | 12.50 | 100 | 112 | 86 | 126 | 287 | 239 |
| 464917 | 25.0 | 100 | 110 | 98 | 153 | 313 | 399 |
| 464917 | 50.0 | 100 | 96 | 94 | 165 | 392 | 490 |
| 464917 | 100.0 | 100 | 108 | 106 | 191 | 450 | 600 |
| 464917 | 200.0 | 100 | 99 | 100 | 230 | 510 | 660 |
| 549148 | 0 | 100 | 89 | 106 | 113 | 106 | 79 |
| 549148 | 3.125 | 100 | 105 | 100 | 117 | 126 | 96 |
| 549148 | 6.25 | 100 | 88 | 99 | 128 | 115 | 84 |
| 549148 | 12.50 | 100 | 95 | 108 | 107 | 115 | 107 |
| 549148 | 25.0 | 100 | 95 | 123 | 130 | 140 | 111 |
| 549148 | 50.0 | 100 | 101 | 111 | 122 | 131 | 114 |
| 549148 | 100.0 | 100 | 98 | 89 | 131 | 104 | 100 |
| 549148 | 200.0 | 100 | 93 | 95 | 163 | 102 | 99 |

TABLE 97

Relative hGadd45a mRNA dose response/time course in HeLa cells

| | | % Control human p21 mRNA | | | | | |
|---|---|---|---|---|---|---|---|
| Compound | Dose (nM) | 0 hrs | 1 hrs | 2 hrs | 4 hrs | 6 hrs | 8 hrs |
| 464917 | 0 | 100 | 97 | 80 | 109 | 110 | 88 |
| 464917 | 3.125 | 100 | 117 | 95 | 156 | 208 | 170 |
| 464917 | 6.25 | 100 | 121 | 111 | 176 | 176 | 205 |
| 464917 | 12.50 | 100 | 139 | 126 | 165 | 271 | 261 |
| 464917 | 25.0 | 100 | 147 | 136 | 176 | 279 | 420 |
| 464917 | 50.0 | 100 | 130 | 171 | 203 | 368 | 700 |
| 464917 | 100.0 | 100 | 143 | 194 | 261 | 835 | 1234 |
| 464917 | 200.0 | 100 | 113 | 198 | 213 | 890 | 1111 |
| 549148 | 0 | 100 | 98 | 104 | 104 | 111 | 99 |
| 549148 | 3.125 | 100 | 124 | 133 | 120 | 132 | 133 |
| 549148 | 6.25 | 100 | 151 | 140 | 155 | 160 | 142 |
| 549148 | 12.50 | 100 | 159 | 159 | 131 | 120 | 144 |
| 549148 | 25.0 | 100 | 173 | 172 | 148 | 156 | 180 |
| 549148 | 50.0 | 100 | 155 | 170 | 164 | 104 | 164 |
| 549148 | 100.0 | 100 | 140 | 129 | 141 | 160 | 190 |
| 549148 | 200.0 | 100 | 121 | 115 | 128 | 107 | 185 |

Example 41 Time Course of Toxicity of Modified Oligonucleotide 464917 In Vivo The modified oligonucleotide 464917 was administered subcutaneously at 11, 33, or 100 mg/kg to 9 BALB/C mice per dosing group. Three mice from each group were sacrificed at 24 hours, three at 48 hours, and the last three at 72 hours after dosing. mRNA was isolated and analyzed as described in Example 1. ALT values in plasma were obtained using a clinical chemistry analyzer.

TABLE 98

Time Course of Activity and Toxicity in mice

| Compound | Dose (mg/kg) | 24 hrs ALT | 48 hrs ALT | 72 hrs ALT | 24 hrs mFXI mRNA | 48 hrs mFXI mRNA | 72 hrs mFXI mRNA |
|---|---|---|---|---|---|---|---|
| 464917 | 0 | 44 | 58 | 29 | 100 | 100 | 100 |
| 464917 | 11 | 40 | 132 | 311* | 20 | 17 | 11* |
| 464917 | 33 | 98 | 2015 | 8072 | 2.7 | 2.6 | 5.7 |
| 464917 | 100 | 168 | 12261 | 26659* | 1.7 | 0.5 | 0.07** |

*Data represents a single mouse
**Data represents the average of two mice

TABLE 99

Time Course of Toxicity in mice

| Compound | Dose (mg/kg) | 24 hrs mP21 mRNA | 48 hrs mP21 mRNA | 72 hrs mP21 mRNA | 24 hrs mTnfrsf10b mRNA | 48 hrs mTnfrsf10b mRNA | 72 hrs mTnfrsf10b mRNA |
|---|---|---|---|---|---|---|---|
| 464917 | 0 | 100 | 100 | 100 | 100 | 100 | 100 |
| 464917 | 11 | 518 | 607 | 2060* | 272 | 845 | 3401* |
| 464917 | 33 | 6451 | 1846 | 5221 | 2071 | 5333 | 7013 |
| 464917 | 100 | 163667 | 4067 | 4910** | 5451 | 12293 | 7402** |

*Data represents a single mouse
**Data represents the average of two mice

Example 42 Nucleolar Delocalization of p54nrb In Vivo

Compound 959265 is compound 464917 conjugated to a Cy3 on the 5'-end and HPPO-GalNAc on the 3'-end. Balb/c mice were administered 15 mg/kg of 959265 by subcutaneous injection. Hepatocytes were isolated and purified 40 hours after administration of modified oligonucleotide and plated on a confocal dish for 6-7 hours. After 6-7 hours, cells were fixed with formaldehyde and stained for p54nrb with immunofluorescent staining for p54nrb. Levels of FXI and p21 were detected by RT-qPCR as described above.

A single dose of 959265 at 15 mg/kg reduced FXI to 10.6% of control values. Levels of p21 mRNA were upregulated 1,046%. Isolated hepatocytes were observed to contain p54nrb that had been localized to the nucleolus or no detectable p54nrb.

Example 43 Nucleolar Delocalization of p54nrb In Vivo

Balb/c mice were administered 100 mg/kg of 464917 or 549148 by subcutaneous injection. Hepatocytes were isolated and purified 16 hours after administration of modified oligonucleotide and plated on a confocal dish for 1-2 hours. After 1-2 hours, cells were fixed with formaldehyde and stained for p54nrb with immunofluorescent staining for p54nrb.

Localization of p54nrb to the nucleolus of hepatocytes was observed for compound 464917 but not for compound 549148.

Example 44 In Vivo Activity and Toxicity of Compounds Containing a MOP Neutral Linkage Six week old BALB/C mice (purchased from Charles River) were injected subcutaneously once at dosage 0.2, 0.6, 1.8 5.4,or 50 mg/kg with the modified oligonucleotides shown below or with saline control. For compound 855156, mice were injected with 0.2, 0.6, 1.8, 5.4, or 15 mg/kg modified oligonucleotide. Each treatment group consisted of 3 animals. The mice were sacrificed 72 hours following administration, and organs and plasma were harvested for further analysis.

Liver tissues were homogenized and mRNA levels were quantitated using real-time PCR and normalized to RIBOGREEN as described herein. Plasma chemistry markers such as liver transaminase levels, alanine aminotranferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide at which 50% inhibition of CXCL12 mRNA expression was achieved compared to the control.

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 101

In vivo Toxicity

| Compound ID | Linkage Mod position in Central region | Linkage Mod | ALT at 15 mg/kg | ALT at 50 mg/kg |
|---|---|---|---|---|
| 855156 | n/a | n/a | 9,639 | n/a |
| 869742 | n/a | n/a | 2,001 | n/a |
| 898384 | 3 | MOP | 30 | 32 |
| 898385 | 2, 3 | MOP | 32 | 30 |

TABLE 102

In Vivo CXCL12 mRNA levels

| Compound ID | 0.2 mg/kg | 0.6 mg/kg | 1.8 mg/kg | 5.4 mg/kg | 15 mg/kg | 50 mg/kg |
|---|---|---|---|---|---|---|
| | Expression level of CXCL12 mRNA (% Control) | | | | | |
| 855156 | 64 | 42 | 23 | 19 | 16 | n/a |
| 869742 | 87 | 58 | 32 | 23 | 18 | n/a |
| 898384 | 87 | 91 | 49 | 40 | 36 | 31 |
| 898385 | 91 | 90 | 64 | 64 | 55 | 41 |

Example 45

Modified oligonucleotides were tested for toxicity in vivo in Balb/c mice.

TABLE 103

Modified Oligonucleotides

| Compound ID | Chemistry notation | SEQ ID NO: |
|---|---|---|
| 575013 | $^mC_{ks}A_{ks}G_{ks}A_{ds}T_{ds}A_{ds}T_{ds}A_{ds}G_{ds}G_{ds}A_{ds}{}^mC_{ds}T_{ds}G_{ks}G_{ks}A_k$ | 110 |

TABLE 100

Modified Oligonucleotides

| Compound ID | position of linkage-altered nucleotide in central region | Linkage mod | Chemistry Notation | SEQ ID NO |
|---|---|---|---|---|
| 869742 | n/a | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_{ks}T_k$-HPPO-GalNAc | 125 |
| 898384 | 3 | MOP | $G_{ks}{}^mC_{ks}A_{ks}T_{ds}G_{ds}T_{dx}T_{ds}{}^mC_{ds}T_{ds}{}^mC_{ds}A_{ds}{}^mC_{ds}A_{ds}T_{ks}T_{ks}A_{ks}T_k$-HPPO-GalNAc | 125 |
| 898385 | 2, 3 | MOP | $G_{ks}{}^mC_{ks}A_{ks}T_{ds}G_{dx}T_{dx}T_{ds}{}^mC_{ds}T_{ds}{}^mC_{ds}A_{ds}{}^mC_{ds}A_{ds}T_{ks}T_{ks}A_{ks}T_k$-HPPO-GalNAc | 125 |

TABLE 103-continued

Modified Oligonucleotides

| Compound ID | Chemistry notation | SEQ ID NO: |
|---|---|---|
| 465131 | $T_{ks}G_{ks}{}^mC_{ks}{}^mC_{ds}A_{ds}{}^mC_{ds}{}^mC_{ds}G_{ds}T_{ds}A_{ds}G_{ds}A_{ds}{}^mC_{ds}A_{ks}{}^mC_{ds}A_{ks}{}^mC_{ks}G_k$ | 114 |
| 549139 | $G_{ks}A_{ks}{}^mC_{ks}G_{ds}{}^mC_{ds}G_{ds}G_{ds}{}^mC_{ds}{}^mC_{ds}T_{ds}G_{ds}A_{ds}A_{ds}G_{ds}G_{ks}T_{ks}T_k$ | 111 |
| 464932 | $G_{ks}G_{ks}A_{ks}{}^mC_{ds}A_{ds}{}^mC_{ds}A_{ds}T_{ds}T_{ds}G_{ds}G_{ds}{}^mC_{ds}{}^mC_{ds}A_{ks}{}^mC_{ks}A_k$ | 112 |

A subscript "d" indicates an unmodified, 2'-β-D-deoxyribosyl sugar moiety. A subscript "k" indicates a cEt modified sugar moiety. A subscript "s" indicates a phosphorothioate internucleoside linkage. A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT were measured using an automated clinical chemistry analyzer. Increased ALT is indicative of acute liver toxicity.

For the in vitro toxicity study in the table below, the caspase assay was performed essentially as described in Example 8 in 3T3-L1 cells. The caspase assay was performed in HeLa cells by free uptake at 2 μM modified oligonucleotide and in b.END3 cells by free uptake at 50 μM modified oligonucleotide.

TABLE 104

In vivo and in vitro toxicity of modified oligonucleotides

| Compound ID | in vivo Dose (mg/kg) | ALT (IU/L) | in vivo P21 (% control) | in vivo Tnfrsf10b (% control) | in vitro caspase @20 μM, 3T3-L1 (% control) | in vitro caspase @2 μM, HeLa (% control) | in vitro caspase @50 μM, b.END (% control) |
|---|---|---|---|---|---|---|---|
| 575013 | 100 | 12 | 54 | 105 | 237 | 100 | 140 |
| 465131 | 100 | 21 | 111 | 164 | 114 | 119 | n.d. |
| 549139 | 100 | 24 | 118 | 135 | 125 | 111 | 113 |
| 549148 | 100 | 24 | 72 | 83 | 184 | 121 | 159 |
| 464932 | 100 | 5 | 150 | 180 | 280 | 113 | 187 |
| 449093 | 33 | 2324 | 42802 | 3835 | 2703 | 306 | 783 |
|  | 100 | 9983 | 150994 | 3744 |  |  |  |
| 482050 | 33 | 1470 | 7890 | 4725 | 1502 | 203 | 439 |
|  | 100 | 6555 | 10430 | 4232 |  |  |  |
| 508031 | 33 | 648 | 2980 | 2239 | 1082 | 255 | 357 |
|  | 100 | 18550 | 8909 | 6678 |  |  |  |
| 558807 | 17 | 1877 | 2763 | 1168 | 910 | 408 | 413 |
|  | 51 | 9510 | 11904 | 6831 |  |  |  |
| 464917 | 11 | 601 | 6098 | 3516 | 1724 | 219 | 552 |
|  | 33 | 13920 | 9590 | 7731 |  |  |  |

Example 46 Time Course of Toxicity and Activity of Modified Oligonucleotide 464932 or 464917 In Vivo The modified oligonucleotide 464932, described in Example 45 above, or 464917, described in Example 4 above, was administered subcutaneously at 33 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 105

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 20 | 41 | 40 | 40 | 44 | 41 |
| 464932 | ALT | 49 | 64 | 58 | 47 | 39 | 108 |
|  | mFXI | 174 | 104 | 40 | 53 | 19 | 12 |
|  | mP21 | 94 | 115 | 71 | 182 | 47 | 185 |
|  | mTnfrsf10b | 133 | 101 | 112 | 108 | 117 | 140 |
| 464917 | ALT | 39 | 49 | 53 | 41 | 1903 | 13917 |
|  | mFXI | 100 | 56 | 12 | 19 | 4 | 5 |
|  | mP21 | 138 | 391 | 829 | 3751 | 1854 | 12716 |
|  | mTnfrsf10b | 118 | 221 | 714 | 1250 | 6369 | 8781 |

Example 47 Time Course of Toxicity and Activity of Modified Oligonucleotide 558807 or 558765 In Vivo Modified oligonucleotide 558765 is a 3-10-3 cEt gapmer with a full phosphorothioate backbone and the sequence AmCAT${}^m$CTT${}^m$CAGAT${}^m$CATT (SEQ ID NO: 144). The modified oligonucleotide 558807 or 558765 was administered subcutaneously at 51 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 106

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 21 | 42 | 40 | 40 | 44 | 41 |
| 558765 | ALT | 34 | 53 | 46 | 92 | 33 | 36 |
|  | mCXCL12 | 109 | 94 | 20 | 54 | 29 | 26 |

TABLE 106-continued

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| | mP21 | 143 | 116 | 92 | 209 | 48 | 404 |
| | mTnfrsf10b | 106 | 70 | 118 | 98 | 154 | 215 |
| 558807 | ALT | 36 | 50 | 53 | 36 | 1888 | 7272 |
| | mCXCL12 | 43 | 18 | 5 | 10 | 3 | 3 |
| | mP21 | 136 | 142 | 86 | 580 | 1573 | 1642 |
| | mTnfrsf10b | 101 | 148 | 236 | 292 | 3375 | 7454 |

Example 48 Toxicity Improvement In Vivo with Incorporation 2'-OMe Modified-Nucleoside in the Central Region BALB/c mice were administered 1.8, 5.5, 16.7, or 50 mg/kg of 558807 or 1.8, 5.5, 16.7, 50, 100, 200, or 300 mg/kg of 936053 and sacrificed after 72 hours. Plasma levels of ALT were measured with a clinical chemistry analyzer and mRNA was isolated and analyzed as described in Example 1. Therapeutic index (TI) was calculated as the maximum non-toxic dose divided by the ED50. Compound 936053 differs from compound 558807 only in the presence of a 2'-OMe group at position 5 from the 5' end of the compound, or position 2 of the central region.

TABLE 107 in vivo dose response

| Compound ID | Dose (mg/kg) | ALT (IU/L) | in vivo P21 (% control) | in vivo Tnfrsf10b (% control) | in vivo Gadd45a (% control) | CXCL12 mRNA (% control) | ED50 (mg/kg) | MTND (mg/kg) | Therapeutic Index |
|---|---|---|---|---|---|---|---|---|---|
| 558807 | 1.8 | 24 | 118 | 120 | 147 | 67.5 | 2.75 | 5.5 | 2 |
| | 5.5 | 27 | 63 | 103 | 176 | 20.3 | | | |
| | 16.7 | 586 | 625 | 788 | 879 | 9.7 | | | |
| | 50 | death | n.d. | n.d. | n.d. | n.d. | | | |
| 936053 | 1.8 | 34 | 104 | 78 | 61 | 65.3 | 4.86 | 200 | 41 |
| | 5.5 | 26 | 94 | 137 | 99 | 47.4 | | | |
| | 16.7 | 23 | 104 | 110 | 91 | 32.7 | | | |
| | 50 | 23 | 89 | 122 | 90 | 14.4 | | | |
| | 100 | 42 | n.d. | n.d. | n.d. | n.d. | | | |
| | 200 | 109 | n.d. | n.d. | n.d. | n.d. | | | |
| | 300 | 231 | n.d. | n.d. | n.d. | n.d. | | | |

Example 49 Toxicity Improvement of Modified Oligonucleotides Targeted to FXI

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 18. Each pair of compounds, presented adjacent to each other in the table below, represents a compound with the motif kkk-d(10)-kkk (464xxx) and the same sequence with the motif kkk-d-m-d(8)-kkk (1133xxx). In instances where position 5 in the original sequence is a T, this nucleoside is a 2'-OMeU in the kkk-d-m-d(8)-kkk sequence.

TABLE 108 in vivo dose response

| Compound ID | Dose (mg/kg) | ALT (IU/L) | in vivo P21 (% control) | FXI mRNA (% control) | ED50 (mg/kg) | MTND (mg/kg) | Therapeutic Index |
|---|---|---|---|---|---|---|---|
| 464924 | 1.8 | 27 | 136 | 59.7 | 2.4 | 16.7 | 7.0 |
| | 5.5 | 27 | 144 | 20.4 | | | |
| | 16.7 | 31 | 167 | 2.5 | | | |
| | 50 | 646 | 551 | 0.4 | | | |
| | 150 | 4509 | 1160 | 0.4 | | | |
| 1133247 | 1.8 | 32 | 130 | 75.0 | 3.4 | >150 | >44 |
| | 5.5 | 30 | 67 | 29.3 | | | |
| | 16.7 | 30 | 94 | 5.4 | | | |
| | 50 | 37 | 123 | 1.9 | | | |
| | 150 | 53 | 304 | 1.4 | | | |
| 465172 | 1.8 | 26 | 131 | 73.5 | 6.7 | >150 | >22 |
| | 5.5 | 22 | 102 | 57.8 | | | |
| | 16.7 | 23 | 99 | 28.8 | | | |

TABLE 108-continued in vivo dose response

| Compound ID | Dose (mg/kg) | ALT (IU/L) | in vivo P21 (% control) | FXI mRNA (% control) | ED50 (mg/kg) | MTND (mg/kg) | Therapeutic Index |
|---|---|---|---|---|---|---|---|
| | 50 | 25 | 102 | 13.8 | | | |
| | 150 | 33 | 177 | 6.2 | | | |
| 1133326 | 1.8 | 25 | 51 | 81.1 | 16.3 | >150 | >9 |
| | 5.5 | 25 | 64 | 81.8 | | | |
| | 16.7 | 24 | 55 | 49.0 | | | |
| | 50 | 24 | 78 | 21.1 | | | |
| | 150 | 22 | 90 | 11.8 | | | |
| 465174 | 1.8 | 25 | 192 | 67.5 | 4.2 | >150 | >36 |
| | 5.5 | 29 | 172 | 46.8 | | | |
| | 16.7 | 22 | 31 | 18.0 | | | |
| | 50 | 20 | 49 | 7.5 | | | |
| | 150 | 29 | 83 | 5.7 | | | |
| 1133328 | 1.8 | 21 | 40 | 74.8 | 4.8 | >150 | >32 |
| | 5.5 | 23 | 38 | 44.3 | | | |
| | 16.7 | 28 | 42 | 18.6 | | | |
| | 50 | 26 | 25 | 13.0 | | | |
| | 150 | 31 | 38 | 10.7 | | | |
| 465178 | 1.8 | 26 | 43 | 47.2 | 1.7 | 16.7 | 10 |
| | 5.5 | 35 | 119 | 18.4 | | | |
| | 16.7 | 73 | 627 | 4.3 | | | |
| | 50 | 1067 | 3509 | 0.7 | | | |
| | 150 | 11596 | 4849 | 0.4 | | | |
| 1133332 | 1.8 | 23 | 101 | 47.8 | 1.8 | 150 | 83 |
| | 5.5 | 35 | 42 | 30.7 | | | |
| | 16.7 | 33 | 136 | 13.1 | | | |
| | 50 | 41 | 600 | 3.7 | | | |
| | 150 | 117 | 1414 | 1.3 | | | |

Example 50 Toxicity Improvement of Modified Oligonucleotides Targeted to HDAC2

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 19. Each pair of compounds, presented adjacent to each other in the table below, represents a compound with the motif kkk-d(10)-kkk (546xxx) and the same sequence with the motif kkk-d-m-d (8)-kkk (1133xxx). In instances where position 5 in the original sequence is a T, this nucleoside is a 2'-OMeU in the kkk-d-m-d(8)-kkk sequence.

TABLE 109 in vivo dose response

| Compound ID | Dose (mg/kg) | ALT (IU/L) | HDAC2 mRNA (% control) | ED50 (mg/kg) | MTND (mg/kg) | Therapeutic Index |
|---|---|---|---|---|---|---|
| 546108 | 1.8 | 33 | 74 | 3.2 | 16.7 | 5.2 |
| | 5.5 | 47 | 26.2 | | | |
| | 16.7 | 168 | 3.8 | | | |
| | 50 | 1713 | 4.8 | | | |
| | 150 | 17844 | 4.5 | | | |
| 1133122 | 1.8 | 29 | 91.6 | 5.5 | >150 | >27 |
| | 5.5 | 25 | 48.3 | | | |
| | 16.7 | 2 | 11.0 | | | |
| | 50 | 43 | 1.1 | | | |
| | 150 | 78 | 1.1 | | | |
| 546110 | 1.8 | 25 | 72.9 | 6.4 | 16.7 | 2.6 |
| | 5.5 | 27 | 57.4 | | | |
| | 16.7 | 37 | 29.4 | | | |

TABLE 109-continued in vivo dose response

| Compound ID | Dose (mg/kg) | ALT (IU/L) | HDAC2 mRNA (% control) | ED50 (mg/kg) | MTND (mg/kg) | Therapeutic Index |
|---|---|---|---|---|---|---|
| | 50 | 416 | 6.7 | | | |
| | 150 | 2817 | 6.0 | | | |
| 1133123 | 1.8 | 24 | 71.0 | 6.8 | >150 | >22 |
| | 5.5 | 80 | 49.6 | | | |
| | 16.7 | 25 | 47.8 | | | |
| | 50 | 25 | 8.0 | | | |
| | 150 | 28 | 3.0 | | | |
| 546118 | 1.8 | 30 | 69.9 | 23.8 | 16.7 | 0.7 |
| | 5.5 | 29 | 70.1 | | | |
| | 16.7 | 40 | 50.8 | | | |
| | 50 | 365 | 39.1 | | | |
| | 150 | 1681 | 36.0 | | | |
| 1133127 | 1.8 | 35 | 77.2 | 24.9 | >150 | >6 |
| | 5.5 | 25 | 60.6 | | | |
| | 16.7 | 26 | 57.1 | | | |
| | 50 | 25 | 39.9 | | | |
| | 150 | 33 | 34.4 | | | |

Example 51 Toxcity Improvement of Modified Oligonucleotides

Modified oligonucleotides were tested for toxicity in vivo in Balb/c mice. Compound 865060 has the motif kkk-d(10)-kkkk and compound 865061 has the motif kkkk-d(10)-kkk. Compounds 1269430 and 1269431 are otherwise identical compounds to 865060 and 865061, respectively, containing a 2'-OMe modified sugar moiety at the second position in the central region.

TABLE 110

Modified Oligonucleotides

| Compound ID | Chemistry notation | SEQ ID NO: |
|---|---|---|
| 865060 | $G_{kc}{}^mC_{ks}A_{ks}T_{ds}G_{ds}T_{ds}T_{ds}{}^mC_{ds}T_{ds}{}^mC_{ds}$ $A_{ds}{}^mC_{ds}A_{ds}T_{ks}T_{ks}A_{ks}T_k G_{ks}G_{ks}{}^mC_{ks}$ | 125 |
| 865061 | $A_{ks}T_{ds}G_{ds}T_{ds}T_{ds}{}^mC_{ds}T_{ds}{}^mC_{ds}$ $A_{ds}{}^mC_{ds}A_{ds}T_{ks}T_{ks}A_k$ | 141 |
| 1269430 | $G_{ks}{}^mC_{ks}A_{ks}T_{ds}G_{ms}T_{ds}T_{ds}{}^mC_{ds}$ $T_{ds}{}^mC_{ds}A_{ds}{}^mC_{ds}A_{ds}T_{ks}T_{ks}A_{ks}T_k$ | 125 |
| 1269431 | $G_{ks}G_{ks}{}^mC_{ks}A_{ks}T_{ds}G_{ms}T_{ds}T_{ds}{}^mC_{ds}$ $T_{ds}{}^mC_{ds}A_{ds}{}^mC_{ds}A_{ds}T_{ks}T_{ks}A_k$ | 141 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

For the in vitro toxicity study in the table below, the caspase assay was performed essentially as described in Example 8 in 3T3-L1 cells, the percent nucleolar p54nrb was visualized as described in Example 11, and the p21 mRNA levels were determined as described in Example 11.

TABLE 111

In vivo and in vitro toxicity of modified oligonucleotides

| Compound ID | in vitro CXCL12 IC$_{50}$ (nM) | Relative Caspase Activation (% Control) @20 µM | in vitro p21 mRNA (% Control) @20 µM | in vitro % nucleolar p54nrb | in vivo p21 @150 mg/kg | in vivo Tnfrsf10b mRNA @150 mg/kg | ALT @ 150 mg/kg (IU/L) |
|---|---|---|---|---|---|---|---|
| 558807 | 183 | 432 | 285 | 82 | 7152* | 5504* | 9928* |
| 936053 | 259 | 114 | 114 | 0 | 166 | 204 | 12 |
| 865060 | 310 | 355 | 224 | 64 | 7604* | 9339* | 11058* |
| 1269430 | 308 | 110 | 127 | 0 | 209 | 350 | 10 |
| 865061 | 510 | 738 | 198 | 75 | 12531 | 6351 | 9014 |
| 1269431 | 849 | 116 | 134 | 0 | 376 | 661 | 52 |

*Value at 50 mg/kg dose; mice administered 150 mg/kg did not survive

Example 52 Long-Term Toxicity Improvement of Modified Oligonucleotides

Modified oligonucleotides were tested for toxicity in vivo in Balb/c mice. Mice were administered 50 mg/kg modified oligonucleotide once a week for six weeks and ALT was measured using an automated clinical chemistry analyzer. Compounds in the table below are described in Example 13. Each pair of compounds represents an oligonucleotide with the sugar motif kkk-d(10)-kkk (upper) and an oligonucleotide with the same sequence having the sugar motif kkk-d-m-d(8)-kkk (lower).

TABLE 112

Long-term Toxicity

| Compound ID | Week of Dosing | | | | | |
|---|---|---|---|---|---|---|
| | 1 | 2 | 3 | 4 | 5 | 6 |
| | ALT (IU/L) | | | | | |
| PBS | 35 | 65 | 27 | 45 | 55 | 23 |
| 572912 | 398 | 1036 | 2667 | 2787 | n.d. | n.d. |
| 1200898 | 36 | 53 | 70 | 112 | 187 | 513 |
| 797793 | 1210 | 972 | 1674 | 2703 | 3831 | 3635 |
| 1201073 | 99 | 143 | 165 | 178 | 217 | 330 |
| 576095 | 46 | 83 | 1017 | 1763 | 2886 | 4118 |
| 1200899 | 50 | 57 | 129 | 550 | 1225 | 1392 | n.d. indicates that the mice were sacrificed prior to the measurement date.

Example 53

Modified oligonucleotides were designed based on 546118. Each of the modified oligonucleotides is conjugated with a THA-GalNAc conjugate group at the 3'-end. THA-GalNac refers to this structure:

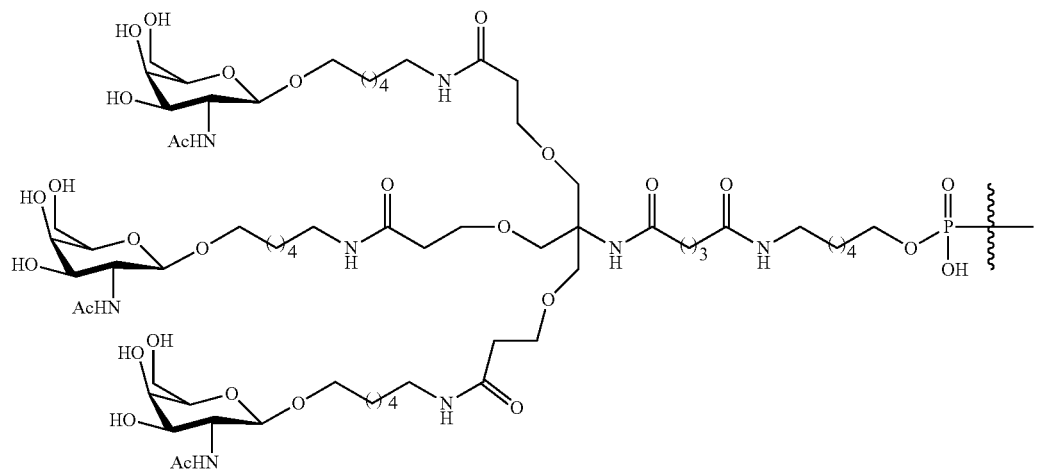

wherein the phosphate group is attached to the 3'-oxygen atom of the 3' nucleotide.

The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.023, 0.067, 0.2, 0.6, 1.8, 5.4, 15, or 50 mg/kg with the modified oligonucleotides shown below or with saline control. Each treatment group consisted of 3 animals. The mice were sacrificed 72 hours following administration, and organs and plasma were harvested for further analysis.

TABLE 113

Modified Oligonucleotides

| Compound ID | position of altered nucleotide in central region | modification of altered nucleotide | Chemistry Notation (5' to 3') | SEQ NO ID |
|---|---|---|---|---|
| 1270732 | N/A | N/A | $A_{ks}{}^mC_{ks}{}^mC_{ks}{}^mC_{ds}T_{ds}{}^mC_{ds}A_{ds}A_{ds}$ $G_{ds}T_{ds}{}^mC_{ds}T_{ds}{}^mC_{ds}{}^mC_{ks}T_{ks}G_k$-THAGalNAc | 109 |
| 1270733 | 2 | 2'-OMe | $A_{ks}{}^mC_{ks}{}^mC_{ks}{}^mC_{ds}U_{ms}{}^mC_{ds}A_{ds}A_{ds}$ $G_{ds}T_{ds}{}^mC_{ds}T_{ds}{}^mC_{ds}{}^mC_{ks}T_{ks}G_k$-THAGalNAc | 140 |
| 1270734 | 2 | MOP | $A_{ks}{}^mC_{ks}{}^mC_{ks}{}^mC_{ds}T_{dx}{}^mC_{ds}A_{ds}A_{ds}$ $G_{ds}T_{ds}{}^mC_{ds}T_{ds}{}^mC_{ds}{}^mC_{ks}T_{ks}G_k$-THAGalNAc | 109 |

A subscript "d" indicates an unmodified, 2'-β-D-deoxyribosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 114

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| 1270732 | 0.023 | 34 | 106 | n.d. | |
| | 0.067 | 7 | 74 | n.d. | |
| | 0.2 | 15 | 113 | 80 | |
| | 0.6 | 13 | 112 | 76 | |
| | 1.8 | 33 | 537 | 118 | 0.060 |
| | 5.4 | 122 | 688 | 271 | |
| | 15 | 1467 | 2606 | 1418 | |
| | 50 | 3429 | 5197 | 3064 | |
| 1270733 | 0.023 | 22 | 71 | n.d. | |

TABLE 114-continued

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| | 0.067 | 43 | 91 | n.d. | |
| | 0.2 | 18 | 89 | 80 | |

TABLE 114-continued

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| | 0.6 | 20 | 103 | 18104 | 0.066 |
| | 1.8 | 17 | 81 | 81 | |
| | 5.4 | 23 | 154 | 81 | |
| | 15 | 11 | 172 | 110 | |
| | 50 | 22 | 988 | 353 | |
| 1270734 | 0.023 | 13 | 64 | n.d. | |
| | 0.067 | 22 | 65 | n.d. | |
| | 0.2 | 31 | 158 | 93 | |
| | 0.6 | 7 | 230 | 149 | |
| | 1.8 | 12 | 64 | 93 | 0.084 |
| | 5.4 | 20 | 169 | 110 | |
| | 15 | 318 | 1513 | 608 | |
| | 50 | 1650 | 2894 | 1368 | | n.d. means a value wds not determined.

Example 54

Modified oligonucleotides were designed based on 546110, described in Example 19 above. Each of the modified oligonucleotides is conjugated with a THA-GalNAc conjugate group at the 3'-end as described in Example 53 above. The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.016, 0.08, 0.40, 2.0, or 50 mg/kg with the modified oligonucleotides shown below or with saline control. Each treatment group consisted of 3 animals. The mice were sacrificed 72 hours following administration, and organs and plasma were harvested for further analysis.

TABLE 115

Modified Oligonucleotides

| Compound ID | position of altered nucleotide in central region | modification of altered nucleotide | Chemistry Notation (5' to 3') | SEQ NO ID |
|---|---|---|---|---|
| 1270729 | n/a | n/a | $T_{ks}{}^mC_{ks}A_{ks}T_{ds}G_{ds}T_{ds}A_{ds}{}^mC_{ds}{}^mC_{ds}T_{ds}A_{ds}T_{ds}A_{ds}G_{ks}T_{ks}{}^mC_k$-THA-GalNAc | 107 |
| 1270733 | 2 | 2'-OMe | $T_{ks}{}^mC_{ks}A_{ks}T_{ds}G_{ms}T_{ds}A_{ds}{}^mC_{ds}{}^mC_{ds}T_{ds}A_{ds}T_{ds}A_{ds}G_{ks}T_{ks}{}^mC_k$-THA-GalNAc | 107 |
| 1270734 | 2 | MOP | $T_{ks}{}^mC_{ks}A_{ks}T_{ds}G_{dx}T_{ds}A_{ds}{}^mC_{ds}{}^mC_{ds}T_{ds}A_{ds}T_{ds}A_{ds}G_{ks}T_{ks}{}^mC_k$-THA-GalNAc | 107 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine. A subscript "x" indicates a MOP internucleoside linkage.

TABLE 116

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| 1270729 | 0.016 | 6 | 69 | 123 | 0.76 |
| | 0.08 | 14 | 61 | 136 | |
| | 0.40 | 13 | 71 | 142 | |
| | 2.0 | 17 | 174 | 154 | |
| | 50 | 3655 | 7927 | 5297 | |
| 1270730 | 0.016 | 31 | 107 | 124 | 1.05 |
| | 0.08 | 10 | 144 | 132 | |
| | 0.40 | 17 | 65 | 99 | |
| | 2.0 | 9 | 88 | 123 | |
| | 50 | 11 | 110 | 164 | |
| 1270731 | 0.016 | 22 | 88 | 135 | 1.28 |
| | 0.08 | 13 | 86 | 101 | |
| | 0.40 | 20 | 135 | 138 | |
| | 2.0 | 13 | 66 | 137 | |
| | 50 | 6 | 76 | 164 | | n.d. means a value wds not determined.

Example 55

Modified oligonucleotides were designed based on 747149, described in Example 13 above. Each of the modified oligonucleotides is conjugated with a THA-GalNAc conjugate group at the 3'-end as described in Example 53 above. The oligonucleotides were evaluated for reduction in FBO1A mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 117

Modified Oligonucleotides

| Compound ID | position of modi-altered nucleotide in central region | fication of altered nucleo-tide | Chemistry Notation (5' to 3') | SEQ NO ID |
|---|---|---|---|---|
| 1270738 | N/A | N/A | $G_{ks}G_{ks}A_{ks}{}^mC_{ds}T_{ds}G_{ds}A_{ds}A_{ds}A_{ds}T_{ds}A_{ds}G_{ds}{}^mC_{ds}A_{ks}G_{ks}A_{k}$-THA-GalNAc | 54 |
| 1270739 | 2 | 2'-OMe | $G_{ks}G_{ks}A_{ks}{}^mC_{ds}U_{ms}G_{ds}A_{ds}A_{ds}A_{ds}T_{ds}A_{ds}G_{ds}{}^mC_{ds}A_{ks}G_{ks}A_{k}$-THA-GalNAc | 130 |
| 1270740 | 2 | MOP | $G_{ks}G_{ks}A_{ks}{}^mC_{ds}T_{dx}G_{ds}A_{ds}A_{ds}A_{ds}T_{ds}A_{ds}G_{ds}{}^mC_{ds}A_{ks}G_{ks}A_{k}$-THA-GalNAc | 54 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "m" indicates a 2'-O-methyl-β-D-ribofuranosyl sugar moiety.

TABLE 118

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| 1270738 | 0.025 | 29 | 49 | 114 | 1.23 |
|  | 0.10 | 18 | 46 | 119 |  |
|  | 0.40 | 30 | 156 | 133 |  |
|  | 1.6 | 62 | 273 | 258 |  |
|  | 6.4 | 177 | 1020 | 1426 |  |
|  | 50 | 1467 | 4296 | 10211 |  |
| 1270739 | 0.025 | 10 | 66 | 115 | 5.16 |
|  | 0.10 | 14 | 54 | 120 |  |
|  | 0.40 | 9 | 39 | 93 |  |
|  | 1.6 | 16 | 34 | 98 |  |
|  | 6.4 | 12 | 88 | 116 |  |
|  | 50 | 26 | 163 | 115 |  |
| 1270740 | 0.025 | 25 | 59 | 94 | 3.33 |
|  | 0.10 | 20 | 79 | 143 |  |
|  | 0.40 | 22 | 81 | 110 |  |
|  | 1.6 | 7 | 68 | 146 |  |
|  | 6.4 | 27 | 195 | 165 |  |
|  | 50 | 102 | 1378 | 439 |  |

Example 56

Modified oligonucleotides were designed based on 464924, described in Example 18 above. Each of the modified oligonucleotides is conjugated with a THA-GalNAc conjugate group at the 3'-end as described in Example 53 above. The oligonucleotides were evaluated for reduction in FXI mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 119

Modified Oligonucleotides

| Compound ID | position of modi-altered nucleotide in central region | fication of altered nucleo-tide | Chemistry Notation (5' to 3') | SEQ NO ID |
|---|---|---|---|---|
| 1270735 | N/A | N/A | $G_{ks}T_{ks}T_{ks}A_{ds}T_{ds}T_{ds}G_{ds}T_{ds}G_{ds}G_{ds}T_{ds}T_{ds}G_{ds}G_{ks}{}^mC_{ks}G_{k}$-THA-GalNAc | 81 |
| 1270736 | 2 | 2'-OMe | $G_{ks}T_{ks}T_{ks}A_{ds}U_{ms}T_{ds}G_{ds}T_{ds}G_{ds}G_{ds}T_{ds}T_{ds}G_{ds}G_{ks}{}^mC_{ks}G_{k}$-THA-GalNAc | 133 |
| 1270737 | 2 | MOP | $G_{ks}T_{ks}T_{ks}A_{ds}T_{dx}T_{ds}G_{ds}T_{ds}G_{ds}G_{ds}T_{ds}T_{ds}G_{ds}G_{ks}{}^mC_{ks}G_{k}$-THA-GalNAc | 81 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine. A subscript "x" indicates a MOP internucleoside linkage.

TABLE 120

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| 1270735 | 0.025 | 9 | 86 | 93 | 0.86 |
|  | 0.10 | 8 | 26 | 66 |  |
|  | 0.40 | 10 | 94 | 81 |  |
|  | 1.6 | 22 | 69 | 95 |  |
|  | 6.4 | 3 | 114 | 137 |  |
|  | 50 | 30 | 266 | 308 |  |
| 1270736 | 0.025 | 17 | 95 | 70 | 0.81 |
|  | 0.10 | 26 | 53 | 65 |  |
|  | 0.40 | 29 | 77 | 58 |  |
|  | 1.6 | 11 | 53 | 93 |  |
|  | 6.4 | 12 | 64 | 90 |  |
|  | 50 | 28 | 92 | 125 |  |
| 1270740 | 0.025 | 17 | 63 | 77 | 105 |
|  | 0.10 | 14 | 83 | 101 |  |
|  | 0.40 | 9 | 62 | 72 |  |
|  | 1.47 | 1.6 | 21 | 98 |  |
|  | 6.4 | 12 | 33 | 104 |  |
|  | 50 | 11 | 168 | 214 |  |

Example 57 Introduction of 5'-Alkyl Modifications In Vivo

Modified oligonucleotides containing a 5'-alkyl modified nucleoside in the central region were synthesized.

The oligonucleotides were evaluated for reduction in target mRNA expression levels in vivo. The transaminase levels (ALT and AST) for each dose were measured.

For the in vitro toxicity study in the table below, the caspase assay was performed essentially as described in Example 8 in Hepa1-6 cells.

For the in vivo toxicity and activity study in the table below, six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis.

TABLE 121

Modified Oligonucleotides

| Compound ID | Chemistry notation | SEQ ID NO: |
|---|---|---|
| 546108 | $T_{ks}A_{ks}G_{ks}T_{ds}{}^mC_{ds}T_{ds}{}^mC_{ds}T_{ds}G_{ds}T_{ds}{}^mC_{ds}A_{ds}G_{ds}T_{ks}T_{ks}A_k$ | 105 |
| 1133122 | $T_{ks}A_{ks}G_{ks}T_{ds}C_{ms}T_{ds}{}^mC_{ds}T_{ds}G_{ds}T_{ds}{}^mC_{ds}A_{ds}G_{ds}T_{ks}T_{ks}A_k$ | 105 |
| 1280765 | $T_{ks}A_{ks}G_{ks}T_{ds}{}^mC_{dx}T_{ds}{}^mC_{ds}T_{ds}G_{ds}T_{ds}{}^mC_{ds}A_{ds}G_{ds}T_{ks}T_{ks}A_k$ | 105 |
| 1280766 | $T_{ks}A_{ks}G_{ks}T_{ds}{}^mC_{ds}T_{[(R)-\mu]s}{}^mC_{ds}T_{ds}G_{ds}T_{ds}{}^mC_{ds}A_{ds}G_{ds}T_{ks}T_{ks}A_k$ | 105 |
| 1280767 | $T_{ks}A_{ks}G_{ks}T_{ds}{}^mC_{ds}T_{ds}{}^mC_{[(R)-\mu]s}T_{ds}G_{ds}T_{ds}{}^mC_{ds}A_{ds}G_{ds}T_{ks}T_{ks}A_k$ | 105 |
| 1280768 | $T_{ks}A_{ks}G_{ks}T_{ds}mC_{ds}T_{[(R)-\varepsilon]s}{}^mC_{ds}T_{ds}G_{ds}T_{ds}{}^mC_{ds}A_{ds}G_{ds}T_{ks}T_{ks}A_k$ | 105 |
| 1280769 | $T_{ks}A_{ks}G_{ks}T_{ds}mC_{ds}T_{ds}{}^mC_{[(R)-\varepsilon]s}T_{ds}G_{ds}T_{ds}{}^mC_{ds}A_{ds}G_{ds}T_{ks}T_{ks}A_k$ | 105 |
| 694804 | $A_{ks}G_{ks}A_{ks}{}^mC_{ds}T_{ds}{}^mC_{ds}T_{ds}{}^mC_{ds}G_{ds}G_{ds}T_{ds}T_{ds}{}^mC_{ds}{}^mC_{ks}G_{ks}A_k$ | 49 |
| 1202810 | $A_{ks}G_{ks}A_{ks}{}^mC_{ds}U_{ds}{}^mC_{ds}T_{ds}{}^mC_{ds}G_{ds}G_{ds}T_{ds}T_{ds}{}^mC_{ds}{}^mC_{ks}G_{ks}A_k$ | 127 |
| 1280776 | $A_{ks}G_{ks}A_{ks}{}^mC_{ds}T_{dx}{}^mC_{ds}T_{ds}{}^mC_{ds}G_{ds}G_{ds}T_{ds}T_{ds}{}^mC_{ds}{}^mC_{ks}G_{ks}A_k$ | 49 |
| 1280785 | $A_{ks}G_{ks}A_{ks}mC_{ds}T_{ds}{}^mC_{[(R)-\mu]s}T_{ds}{}^mC_{ds}G_{ds}G_{ds}T_{ds}T_{ds}{}^mC_{ds}{}^mC_{ks}G_{ks}A_k$ | 49 |
| 1280795 | $A_{ks}G_{ks}A_{ks}{}^mC_{ds}T_{ds}{}^mC_{ds}T_{[(R)-\mu]s}{}^mC_{ds}G_{ds}G_{ds}T_{ds}T_{ds}{}^mC_{ds}{}^mC_{ks}G_{ks}A_k$ | 49 |
| 1280804 | $A_{ks}G_{ks}A_{ks}{}^mC_{ds}T_{ds}{}^mC_{[(R)-\varepsilon]s}T_{ds}{}^mC_{ds}G_{ds}G_{ds}T_{ds}T_{ds}{}^mC_{ds}{}^mC_{ks}G_{ks}A_k$ | 49 |
| 1280810 | $A_{ks}G_{ks}A_{ks}{}^mC_{ds}T_{ds}{}^mC_{ds}T_{[(R)-\varepsilon]s}{}^mC_{ds}G_{ds}G_{ds}T_{ds}T_{ds}{}^mC_{ds}{}^mC_{ks}G_{ks}A_k$ | 49 |
| 465178 | $G_{ks}T_{ks}{}^mC_{ks}A_{ds}G_{ds}T_{ds}A_{ds}T_{ds}{}^mC_{ds}{}^mC_{ds}{}^mC_{ds}A_{ds}G_{ds}T_{ks}G_{ks}T_k$ | 89 |
| 1133332 | $G_{ks}T_{ks}{}^mC_{ks}A_{ds}G_{ms}T_{ds}A_{ds}T_{ds}{}^mC_{ds}{}^mC_{ds}{}^mC_{ds}A_{ds}G_{ds}T_{ks}G_{ks}T_k$ | 89 |
| 1280775 | $G_{ks}T_{ks}{}^mC_{ks}A_{ds}G_{dx}T_{ds}A_{ds}T_{ds}{}^mC_{ds}{}^mC_{ds}{}^mC_{ds}A_{ds}G_{ds}T_{ks}G_{ks}T_k$ | 89 |
| 1280784 | $G_{ks}T_{ks}{}^mC_{ks}A_{ds}G_{ds}T_{[(R)-\mu]s}A_{ds}T_{ds}{}^mC_{ds}{}^mC_{ds}{}^mC_{ds}A_{ds}G_{ds}T_{ks}G_{ks}T_k$ | 89 |
| 1280794 | $G_{ks}T_{ks}{}^mC_{ks}A_{ds}G_{ds}T_{ds}A_{[(R)-\mu]s}T_{ds}{}^mC_{ds}{}^mC_{ds}{}^mC_{ds}A_{ds}G_{ds}T_{ks}G_{ks}T_k$ | 89 |
| 1280803 | $G_{ks}T_{ks}{}^mC_{ks}A_{ds}G_{ds}T_{[(R)-\varepsilon]s}A_{ds}T_{ds}{}^mC_{ds}{}^mC_{ds}{}^mC_{ds}A_{ds}G_{ds}T_{ks}G_{ks}T_k$ | 89 |
| 1281809 | $G_{ks}T_{ks}{}^mC_{ks}A_{ds}G_{ds}T_{ds}A_{[(R)-\varepsilon]s}T_{ds}{}^mC_{ds}{}^mC_{ds}{}^mC_{ds}A_{ds}G_{ds}T_{ks}G_{ks}T_k$ | 89 |
| 546110 | $T_{ks}{}^mC_{ks}A_{ks}T_{ds}G_{ds}T_{ds}A_{ds}{}^mC_{ds}{}^mC_{ds}T_{ds}A_{ds}T_{ds}A_{ds}G_{ks}T_{ks}{}^mC_k$ | 107 |
| 1133201 | $T_{ks}{}^mC_{ks}A_{ks}T_{ds}G_{ms}T_{ds}A_{ds}{}^mC_{ds}{}^mC_{ds}T_{ds}A_{ds}T_{ds}A_{ds}G_{ks}T_{ks}{}^mC_k$ | 107 |
| 1280778 | $T_{ks}{}^mC_{ks}A_{ks}T_{ds}G_{dx}T_{ds}A_{ds}{}^mC_{ds}{}^mC_{ds}T_{ds}A_{ds}T_{ds}A_{ds}G_{ks}T_{ks}{}^mC_k$ | 107 |
| 1280779 | $T_{ks}{}^mC_{ks}A_{ks}T_{ds}G_{ds}T_{[(R)-\mu]s}A_{ds}{}^mC_{ds}{}^mC_{ds}T_{ds}A_{ds}T_{ds}A_{ds}G_{ks}T_{ks}{}^mC_k$ | 107 |
| 1280789 | $T_{ks}{}^mC_{ks}A_{ks}T_{ds}G_{ds}T_{ds}A_{[(R)-\mu]s}{}^mC_{ds}{}^mC_{ds}T_{ds}A_{ds}T_{ds}A_{ds}G_{ks}T_{ks}{}^mC_k$ | 107 |
| 1280798 | $T_{ks}{}^mC_{ks}A_{ks}T_{ds}G_{ds}T_{[(R)-\varepsilon]s}A_{ds}{}^mC_{ds}{}^mC_{ds}T_{ds}A_{ds}T_{ds}A_{ds}G_{ks}T_{ks}{}^mC_k$ | 107 |
| 1281804 | $T_{ks}{}^mC_{ks}A_{ks}T_{ds}G_{ds}T_{ds}A_{[(R)-\varepsilon]s}{}^mC_{ds}{}^mC_{ds}T_{ds}A_{ds}T_{ds}A_{ds}G_{ks}T_{ks}{}^mC_k$ | 107 |
| 464924 | $G_{ks}T_{ks}T_{ks}A_{ds}T_{ds}T_{ds}G_{ds}T_{ds}G_{ds}G_{ds}T_{ds}T_{ds}G_{ds}G_{ks}{}^mC_{ks}G_k$ | 81 |
| 1133247 | $G_{ks}T_{ks}T_{ks}A_{ds}U_{ms}T_{ds}G_{ds}T_{ds}G_{ds}G_{ds}T_{ds}T_{ds}G_{ds}G_{ks}{}^mC_{ks}G_k$ | 133 |
| 1280774 | $G_{ks}T_{ks}T_{ks}A_{ds}T_{dx}T_{ds}G_{ds}T_{ds}G_{ds}G_{ds}T_{ds}T_{ds}G_{ds}G_{ks}{}^mC_{ks}G_k$ | 81 |
| 1280783 | $G_{ks}T_{ks}T_{ks}A_{ds}T_{ds}T_{[(R)-\mu]s}G_{ds}T_{ds}G_{ds}G_{ds}T_{ds}T_{ds}G_{ds}G_{ks}{}^mC_{ks}G_k$ | 81 |
| 1280793 | $G_{ks}T_{ks}T_{ks}A_{ds}T_{ds}T_{ds}G_{[(R)-\mu]s}T_{ds}G_{ds}G_{ds}T_{ds}T_{ds}G_{ds}G_{ks}{}^mC_{ks}G_k$ | 81 |
| 747149 | $G_{ks}G_{ks}A_{ks}{}^mC_{ds}T_{ds}G_{ds}A_{ds}A_{ds}A_{ds}T_{ds}A_{ds}G_{ds}{}^mC_{ds}A_{ks}G_{ks}A_k$ | 54 |
| 1203759 | $G_{ks}G_{ks}A_{ks}{}^mC_{ds}U_{ms}G_{ds}A_{ds}A_{ds}A_{ds}T_{ds}A_{ds}G_{ds}{}^mC_{ds}A_{ks}G_{ks}A_k$ | 130 |
| 1280778 | $G_{ks}G_{ks}A_{ks}{}^mC_{ds}T_{dx}G_{ds}A_{ds}A_{ds}A_{ds}T_{ds}A_{ds}G_{ds}{}^mC_{ds}A_{ks}G_{ks}A_k$ | 54 |
| 1280787 | $G_{ks}G_{ks}A_{ks}{}^mC_{ds}T_{ds}G_{[(R)-\mu]s}A_{ds}A_{ds}A_{ds}T_{ds}A_{ds}G_{ds}{}^mC_{ds}A_{ks}G_{ks}A_k$ | 54 |
| 1280797 | $G_{ks}G_{ks}A_{ks}{}^mC_{ds}T_{ds}G_{ds}A_{ds}A_{[(R)-\mu]s}A_{ds}T_{ds}A_{ds}G_{ds}{}^mC_{ds}A_{ks}G_{ks}A_k$ | 54 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[(R)-μ]" indicates a 5'-(R)-Me-β-D-2'-deoxyribosyl sugar moiety. A subscript "[(R)-ε]" indicates a 5'-(R)-ethyl-β-D-2'-deoxyribosyl sugar moiety.

TABLE 122

Activity and Toxicity in vitro and in vivo

| Compound ID | Target | position of altered nucleoside in central region | modification of altered nucleoside | in vivo Target ED$_{50}$ (mg/kg) | in vivo ALT @150 mg/kg | Relative Caspase Activation (% Control) @20 μM |
|---|---|---|---|---|---|---|
| 546108 | HDAC2 | N/A | N/A | n.d. | n.d. | 2436 |
| 1133122 | HDAC2 | 2 | 2'-OMe | 6.1 | 127 | 103 |
| 1280765 | HDAC2 | 2 | MOP | 7.7 | 29 | 157 |
| 1280766 | HDAC2 | 3 | 5'-(R)—Me | 4.5 | 61 | 158 |
| 1280767 | HDAC2 | 4 | 5'-(R)—Me | 5.9 | 79 | 122 |
| 1280768 | HDAC2 | 3 | 5'-(R)—Et | 8.6 | 39 | 70 |
| 1280769 | HDAC2 | 4 | 5'-(R)—Et | 9.6 | 55 | 90 |
| 694804 | DMN2 | N/A | N/A | n.d. | n.d. | 1443 |
| 1202810 | DMN2 | 2 | 2'-OMe | 14.7 | 50 | 70 |
| 1280776 | DMN2 | 2 | MOP | 8.6 | 24 | 214 |
| 1280785 | DMN2 | 3 | 5'-(R)—Me | 6.2 | 92 | 285 |
| 1280795 | DMN2 | 4 | 5'-(R)—Me | 7.3 | 27 | 113 |
| 1280804 | DMN2 | 3 | 5'-(R)—Et | 14.9 | 36 | 135 |
| 1280810 | DMN2 | 4 | 5'-(R)—Et | 16.2 | 26 | 211 |
| 465178 | FXI | N/A | N/A | n.d. | n.d. | 506 |
| 1133332 | FXI | 2 | 2'-OMe | 2.0 | 119 | 168 |
| 1280775 | FXI | 2 | MOP | 2.5 | 153 | 136 |
| 1280784 | FXI | 3 | 5'-(R)—Me | 1.7 | 260 | 145 |

TABLE 122-continued

Activity and Toxicity in vitro and in vivo

| Compound ID | Target | position of altered nucleoside in central region | modification of altered nucleoside | in vivo Target $ED_{50}$ (mg/kg) | in vivo ALT @150 mg/kg | Relative Caspase Activation (% Control) @20 µM |
|---|---|---|---|---|---|---|
| 1280794 | FXI | 4 | 5'-(R)—Me | 2.3 | 358 | 165 |
| 1280803 | FXI | 3 | 5'-(R)—Et | 4.9 | 122 | 104 |
| 1281809 | FXI | 4 | 5'-(R)—Et | 21.2 | 56 | 93 |
| 546110 | FXI | N/A | N/A | n.d. | n.d. | 404 |
| 1133201 | FXI | 2 | 2'-OMe | 10.6 | 127 | 96 |
| 1280778 | FXI | 2 | MOP | 26.6 | 29 | 105 |
| 1280779 | FXI | 3 | 5'-(R)—Me | 10.9 | 61 | 84 |
| 1280789 | FXI | 4 | 5'-(R)—Me | 11.7 | 79 | 74 |
| 1280798 | FXI | 3 | 5'-(R)—Et | 30.5 | 39 | 78 |
| 1281804 | FXI | 4 | 5'-(R)—Et | 31.5 | 55 | 80 |
| 464924 | FXI | N/A | N/A | n.d. | n.d. | n.d. |
| 1133247 | FXI | 2 | 2'-OMe | 4.6 | 51 | n.d. |
| 1280774 | FXI | 2 | MOP | 3.7 | 37 | n.d. |
| 1280783 | FXI | 3 | 5'-(R)—Me | 3.6 | 48 | n.d. |
| 1280793 | FXI | 4 | 5'-(R)—Me | 2.3 | 351 | n.d. |
| 747149 | FOXO1A | N/A | N/A | n.d. | n.d. | n.d. |
| 1203759 | FOXO1A | 2 | 2'-OMe | 24.9 | 30 | n.d. |
| 1280778 | FOXO1A | 2 | MOP | 8.5 | 35 | n.d. |
| 1280787 | FOXO1A | 3 | 5'-(R)—Me | 65.9 | 62 | n.d. |
| 1280797 | FOXO1A | 4 | 5'-(R)—Me | 20.4 | 22 | n.d. |

Example 58 Nucleosides with Chiral Phosphorothioate Linkages

Modified oligonucleotides containing chirally-controlled phosphorothioate linkages in the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration.

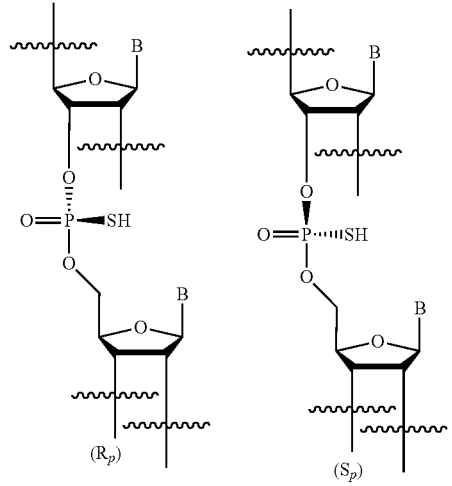

TABLE 123 modified oligonucleotides with stereochemically-controlled phosphorothioate linkages

| Compound ID | Chemistry Notation | SEQ ID NO |
|---|---|---|
| 558807 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 1220041 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dq}T_{ks}T_{ks}A_k$ | 18 |
| 1220042 | $G_{ks}{}^mC_{ks}A_{ks}T_{dr}G_{dq}T_{dq}T_{dq}{}^mC_{dq}T_{dq}{}^mC_{dq}A_{dq}{}^mC_{dq}A_{dq}T_{ks}T_{ks}A_k$ | 18 |
| 1220043 | $G_{ks}{}^mC_{ks}A_{ks}T_{dq}G_{dr}T_{dq}T_{dq}{}^mC_{dq}T_{dq}{}^mC_{dq}A_{dq}{}^mC_{dq}A_{dq}T_{ks}T_{ks}A_k$ | 18 |
| 1220044 | $G_{ks}{}^mC_{ks}A_{ks}T_{dq}G_{dq}T_{dr}T_{dq}{}^mC_{dq}T_{dq}{}^mC_{dq}A_{dq}{}^mC_{dq}A_{dq}T_{ks}T_{ks}A_k$ | 18 |
| 1220045 | $G_{ks}{}^mC_{ks}A_{ks}T_{dq}G_{dq}T_{dq}T_{dr}{}^mC_{dq}T_{dq}{}^mC_{dq}A_{dq}{}^mC_{dq}A_{dq}T_{ks}T_{ks}A_k$ | 18 |
| 1220046 | $G_{ks}{}^mC_{ks}A_{ks}T_{dq}G_{dq}T_{dq}T_{dq}{}^mC_{dr}T_{dq}{}^mC_{dq}A_{dq}{}^mC_{dq}A_{dq}T_{ks}T_{ks}A_k$ | 18 |
| 1220051 | $G_{ks}{}^mC_{ks}A_{ks}T_{dq}G_{dq}T_{dq}T_{dq}{}^mC_{dq}T_{dr}{}^mC_{dq}A_{dq}{}^mC_{dq}A_{dq}T_{ks}T_{ks}A_k$ | 18 |
| 1220047 | $G_{ks}{}^mC_{ks}A_{ks}T_{dq}G_{dq}T_{dq}T_{dq}{}^mC_{dq}T_{dq}{}^mC_{dr}A_{dq}{}^mC_{dq}A_{dq}T_{ks}T_{ks}A_k$ | 18 |
| 1220048 | $G_{ks}{}^mC_{ks}A_{ks}T_{dq}G_{dq}T_{dq}T_{dq}{}^mC_{dq}T_{dq}{}^mC_{dq}A_{dr}{}^mC_{dq}A_{dq}T_{ks}T_{ks}A_k$ | 18 |
| 1220049 | $G_{ks}{}^mC_{ks}A_{ks}T_{dq}G_{dq}T_{dq}T_{dq}{}^mC_{dq}T_{dq}{}^mC_{dq}A_{dq}{}^mC_{dr}A_{dq}T_{ks}T_{ks}A_k$ | 18 |

TABLE 123-continued modified oligonucleotides with stereochemically-controlled phosphorothioate linkages

| Compound ID | Chemistry Notation | SEQ ID NO |
|---|---|---|
| 1220050 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dr}T_{ks}T_{ks}A_k$ | 18 |
| 1237987 | $G_{ks}{}^mC_{ks}A_{ks}T_{dq}G_{dq}T_{dq}T_{dq}{}^mC_{dq}T_{dq}{}^mC_{dq}A_{dq}{}^mC_{dr}A_{dr}T_{ks}T_{ks}A_k$ | 18 |
| 1237988 | $G_{ks}{}^mC_{ks}A_{ks}T_{dq}G_{dq}T_{dq}T_{dq}{}^mC_{dq}T_{dq}{}^mC_{dr}A_{dr}{}^mC_{dq}A_{dq}T_{ks}T_{ks}A_k$ | 18 |
| 1237989 | $G_{ks}{}^mC_{ks}A_{ks}T_{dq}G_{dq}T_{dq}T_{dq}{}^mC_{dr}T_{dr}{}^mC_{dq}A_{dq}{}^mC_{dq}A_{dq}T_{ks}T_{ks}A_k$ | 18 |
| 1237990 | $G_{ks}{}^mC_{ks}A_{ks}T_{dq}G_{dq}T_{dr}T_{dr}{}^mC_{dq}T_{dq}{}^mC_{dq}A_{dq}{}^mC_{dq}A_{dq}T_{ks}T_{ks}A_k$ | 18 |
| 1237991 | $G_{ks}{}^mC_{ks}A_{ks}T_{dr}G_{dr}T_{dq}T_{dq}{}^mC_{dq}T_{dq}{}^mC_{dq}A_{dq}{}^mC_{dq}A_{dq}T_{ks}T_{ks}A_k$ | 18 |
| 1220052 | $G_{ks}{}^mC_{ks}A_{ks}T_{dr}G_{dr}T_{dr}T_{dr}{}^mC_{dr}T_{dr}{}^mC_{dr}A_{dr}{}^mC_{dr}A_{dr}T_{ks}T_{ks}A_k$ | 18 |
| 1220053 | $G_{ks}{}^mC_{ks}A_{ks}T_{dq}G_{dr}T_{dr}T_{dr}{}^mC_{dr}T_{dr}{}^mC_{dr}A_{dr}{}^mC_{dr}A_{dr}T_{ks}T_{ks}A_k$ | 18 |
| 1220054 | $G_{ks}{}^mC_{ks}A_{ks}T_{dr}G_{dq}T_{dr}T_{dr}{}^mC_{dr}T_{dr}{}^mC_{dr}A_{dr}{}^mC_{dr}A_{dr}T_{ks}T_{ks}A_k$ | 18 |
| 1220055 | $G_{ks}{}^mC_{ks}A_{ks}T_{dr}G_{dr}T_{dq}T_{dr}{}^mC_{dr}T_{dr}{}^mC_{dr}A_{dr}{}^mC_{dr}A_{dr}T_{ks}T_{ks}A_k$ | 18 |
| 1220056 | $G_{ks}{}^mC_{ks}A_{ks}T_{dr}G_{dr}T_{dr}T_{dq}{}^mC_{dr}T_{dr}{}^mC_{dr}A_{dr}{}^mC_{dr}A_{dr}T_{ks}T_{ks}A_k$ | 18 |
| 1220057 | $G_{ks}{}^mC_{ks}A_{ks}T_{dr}G_{dr}T_{dr}T_{dr}{}^mC_{dq}T_{dr}{}^mC_{dr}A_{dr}{}^mC_{dr}A_{dr}T_{ks}T_{ks}A_k$ | 18 |
| 1220058 | $G_{ks}{}^mC_{ks}A_{ks}T_{dr}G_{dr}T_{dr}T_{dr}{}^mC_{dr}T_{dq}{}^mC_{dr}A_{dr}{}^mC_{dr}A_{dr}T_{ks}T_{ks}A_k$ | 18 |
| 1220059 | $G_{ks}{}^mC_{ks}A_{ks}T_{dr}G_{dr}T_{dr}T_{dr}{}^mC_{dr}T_{dr}{}^mC_{dq}A_{dr}{}^mC_{dr}A_{dr}T_{ks}T_{ks}A_k$ | 18 |
| 1220060 | $G_{ks}{}^mC_{ks}A_{ks}T_{dr}G_{dr}T_{dr}T_{dr}{}^mC_{dr}T_{dr}{}^mC_{dr}A_{dq}{}^mC_{dr}A_{dr}T_{ks}T_{ks}A_k$ | 18 |
| 1220061 | $G_{ks}{}^mC_{ks}A_{ks}T_{dr}G_{dr}T_{dr}T_{dr}{}^mC_{dr}T_{dr}{}^mC_{dr}A_{dr}{}^mC_{dq}A_{dr}T_{ks}T_{ks}A_k$ | 18 |
| 1220062 | $G_{ks}{}^mC_{ks}A_{ks}T_{dr}G_{dr}T_{dr}T_{dr}{}^mC_{dr}T_{dr}{}^mC_{dr}A_{dr}{}^mC_{dr}A_{dq}T_{ks}T_{ks}A_k$ | 18 |
| 1220063 | $G_{ks}{}^mC_{ks}A_{ks}T_{dq}G_{dq}T_{dr}T_{dq}{}^mC_{dq}T_{dr}{}^mC_{dq}A_{dq}{}^mC_{dr}A_{dr}T_{ks}T_{ks}A_k$ | 18 |
| 1220064 | $G_{ks}{}^mC_{ks}A_{ks}T_{dr}G_{dr}T_{dq}T_{dr}{}^mC_{dr}T_{dq}{}^mC_{dr}A_{dr}{}^mC_{dq}A_{dq}T_{ks}T_{ks}A_k$ | 18 |

A subscript "d" an unmodified, 2'-β-D-deoxyribosyl sugar moiety. A subscript "k" indicates a cEt. A superscript "m" before a C indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.

For in vitro activity studies, 3T3-L1 cells were plated at 20,000 cells/well and transfected with 27 nM, 80 nM, 250 nM, 740 nM, 2,222 nM, 6,667 nM, or 20,000 nMnM modified oligonucleotide by electroporation. mRNA was harvested and analyzed by RT-qPCR. CXCL12 mRNA was detected with primer probe set RTS 2605 (forward sequence CCAGAGCCAACGTCAAGCAT, SEQ ID NO: 9; reverse sequence: CAGCCGTGCAACAATCTGAA, SEQ ID NO: 10; probe sequence: TGAAAATCCTCAACACTC-CAAACTGTGCC, SEQ ID NO: 11) and P21 mRNA was detected with primer probe set Mm04207341_m1 (ThermoFisher).

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide. Localization of p54nrb in HeLa cells was visualized with confocal microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. The self-structure Tm of each compound was determined.

TABLE 124

In vitro activity, toxicity, and Tm of modified oligonucleotides complementary to CXCL12

| Compound ID | in vitro CXCL12 IC$_{50}$ (nM) | in vitro Cdspdse (% control) @ 20 μM | P21 mRNA (% control) @ 20 μM | % nucleolar p54nrb | Tm (° C.) |
|---|---|---|---|---|---|
| 558807 | 39 | 1437 | 353 | 90 | 64.4 |
| 1220041 | 388 | 223 | 182 | 0 | 61.3 |
| 1220042 | 159 | 584 | 431 | 32 | 62.1 |
| 1220043 | 114 | 838 | 488 | 88 | 62 |
| 1220044 | 181 | 489 | 251 | 18 | 61.5 |
| 1220045 | 222 | 321 | 259 | 9.7 | 61.9 |
| 1220046 | 145 | 572 | 635 | 28 | 61.7 |
| 1220051 | 237 | 310 | 167 | 20 | 61.6 |
| 1220047 | 60 | 814 | 238 | 38 | 61.5 |
| 1220048 | 74 | 287 | 174 | 38 | 61.3 |
| 1220049 | 77 | 323 | 243 | 17 | 61.6 |
| 1220050 | 132 | 174 | 121 | 6.4 | 61.5 |
| 1237987 | 26 | 317 | 273 | 3.9 | 62.2 |
| 1237988 | 20 | 336 | 236 | 23 | 62.1 |
| 1237989 | 72 | 300 | 394 | 28 | 62.2 |
| 1237990 | 186 | 299 | 355 | 14 | 62.5 |
| 1237991 | 35 | 562 | 585 | 77 | 63 |

TABLE 125

In vitro activity, toxicity, and Tm of modified oligonucleotides complementary to CXCL12

| Compound ID | in vitro CXCL12 IC$_{50}$ (nM) | in vitro Caspase (% control) @ 20 μM | P21 mRNA (% control) @ 20 μM | % nucleolar p54nrb | Tm |
|---|---|---|---|---|---|
| 558807 | 95 | 647 | 235 | 93 | 64.4 |
| 1220052 | 63 | 484 | 272 | 98 | 67.4 |
| 1220053 | 99 | 621 | 261 | 95 | 66.2 |
| 1220054 | 197 | 495 | 192 | 96 | 66.8 |
| 1220055 | 51 | 606 | 370 | 100 | 66.9 |
| 1220056 | 103 | 569 | 369 | 97 | 67 |
| 1220057 | 104 | 593 | 330 | 92 | 67.1 |
| 1220058 | 125 | 578 | 273 | 100 | 67.3 |
| 1220059 | 109 | 525 | 351 | 62 | 66.7 |

TABLE 125-continued

In vitro activity, toxicity, and Tm of modified oligonucleotides complementary to CXCL12

| Compound ID | in vitro CXCL12 IC$_{50}$ (nM) | in vitro Caspase (% control) @ 20 μM | P21 mRNA (% control) @ 20 μM | % nucleolar p54nrb | Tm |
|---|---|---|---|---|---|
| 1220060 | 61 | 553 | 328 | 100 | 67.3 |
| 1220061 | 84 | 409 | 329 | 100 | 67.1 |
| 1220062 | 123 | 550 | 394 | 100 | 67.1 |
| 1220063 | 111 | 138 | 128 | 12 | 63.1 |
| 1220064 | 53 | 160 | 218 | 100 | 65.3 |

Example 59 Nucleosides with Chiral Phosphorothioate Linkages and 3'-GalNAc

Modified oligonucleotides containing chirally-controlled phosphorothioate linkages in the central region and a 3'-THA-GalNAc were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration.

THA-GalNAc refers to this structure at the 3' end of the molecule:

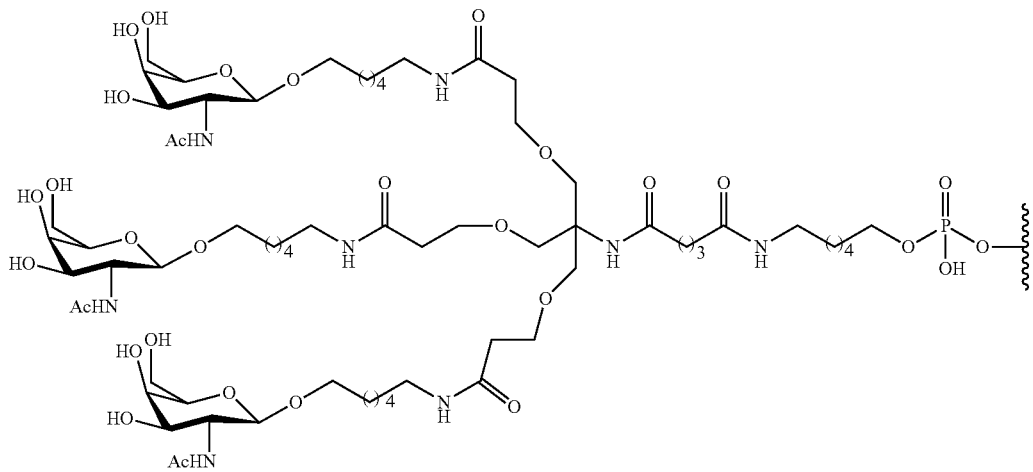

wherein the phosphate group is attached to the 3'-oxygen atom of the 3'nucleoside.

TABLE 126

Modified oligonucleotides

| Compound ID | Chemistry Notation | SEQ ID NO |
|---|---|---|
| 558807 | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 18 |
| 855156 | $G_{ksm}C_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$-THA-GalNAc | 18 |
| 1220050 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dr}T_{ks}T_{ks}A_k$ | 18 |
| 1277251 | $G_{ks}{}^mC_{ks}A_{ks}T_{dq}G_{dq}T_{dq}T_{dq}{}^mC_{dq}T_{dq}{}^mC_{dq}A_{dq}{}^mC_{dq}A_{dr}T_{ks}T_{ks}A_k$-THA-GalNAc | 18 |
| 1220059 | $G_{ks}{}^mC_{ks}A_{ks}T_{dr}G_{dr}T_{dr}T_{dr}{}^mC_{dr}T_{dr}{}^mC_{dq}A_{dr}{}^mC_{dr}A_{dr}T_{ks}T_{ks}A_k$ | 18 |
| 1277252 | $G_{ks}{}^mC_{ks}A_{ks}T_{dr}G_{dr}T_{dr}T_{dr}{}^mC_{dr}T_{dr}{}^mC_{dq}A_{dr}{}^mC_{dr}A_{dr}T_{ks}T_{ks}A_k$-THA-GalNAc | 18 |
| 1220063 | $G_{ks}{}^mC_{ks}A_{ks}T_{dq}G_{dq}T_{dr}T_{dq}{}^mC_{dq}T_{dr}{}^mC_{dq}A_{dq}{}^mC_{dr}A_{dr}T_{ks}T_{ks}A_k$ | 18 |
| 1277253 | $G_{ks}{}^mC_{ks}A_{ks}T_{dq}G_{dq}T_{dr}T_{dq}{}^mC_{dq}T_{dr}{}^mC_{dq}A_{dq}{}^mC_{dr}A_{dr}T_{ks}T_{ks}A_k$-THA-GalNAc | 18 |
| 1237988 | $G_{ks}{}^mC_{ks}T_{dq}G_{dq}T_{dq}T_{dq}{}^mC_{dq}T_{dq}{}^mC_{dr}A_{dr}{}^mC_{dq}A_{dr}T_{ks}T_{ks}A_k$ | 18 |
| 1277254 | $G_{ks}{}^mC_{ks}A_{ks}T_{dq}G_{dq}T_{dq}T_{dq}{}^mC_{dq}T_{dq}{}^mC_{dr}A_{dr}{}^mC_{dq}A_{dr}T_{ks}T_{ks}A_k$-THA-GalNAc | 18 |

A subscript "d" indicates an unmodified, 2'-β-D-deoxyribosyl sugar moiety. A subscript "k" indicates a cEt. A superscript "m" indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.

TABLE 127

In vitro toxicity and activity of modified oligonucleotides

| Compound ID | in vitro CXCL12 IC$_{50}$ (nM) | in vitro Caspase (% control) @ 20 μM | % nucleolar p54nrb |
|---|---|---|---|
| 855156 | 40 | 1437 | 90 |
| 1277251 | 130 | 174 | 6.4 |
| 1277252 | 111 | 525 | 62 |
| 1277253 | 111 | 138 | 12 |
| 1277254 | 20 | 336 | 24 |

Example 60 Nucleosides with Two Chiral Phosphate Linkages in an Otherwise Stereorandom Phosphorthioate Nucleotide Modified oligonucleotides containing chirally-controlled phosphorothioate linkages at two positions of the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound with an ID in the range of 1273959-1273967 has a kkk-d (10)-kkk sugar motif, wherein each "k" represents a 2'-constrained ethyl modified sugar moiety and each "d" represents a 2'-deoxy sugar moiety. Each compound with an ID in the range of 1276491-1276497 has a kkk-d-m-d(8)-kkk sugar motif, wherein each "k" represents a cEt and each "d" represents a nucleoside comprising an unmodified, 2'-β-D-deoxyribosyl sugar moiety and each "m" represents nucleoside comprising a 2'-Omethyl modified sugar moiety. Internucleoside linkages are as indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration. Each compound contains an "Rp/Sp" unit comprising an internucleoside linkage having the (Rp) configuration followed by an internucleoside linkage having the (Sp) configuration, from 5'-3'.

Compounds were tested in 3T3-L1 cells for caspase activation as described in Example 1 above.

TABLE 128

Modified oligonucleotides

| Compound ID | Chemistry Notation | SEQ ID NO |
|---|---|---|
| 1273959 | $G_{ks}{}^mC_{ks}A_{ks}T_{dr}G_{dq}T_{ds}T_{ds}{}^mC_{ds}T_{ds}{}^mC_{ds}A_{ds}{}^mC_{ds}A_{ds}T_{ks}T_{ks}A_k$ | 18 |
| 1273960 | $G_{ks}{}^mC_{ks}A_{ks}T_{ds}G_{dr}T_{dq}T_{ds}{}^mC_{ds}T_{ds}{}^mC_{ds}A_{ds}{}^mC_{ds}A_{ds}T_{ks}T_{ks}A_k$ | 18 |
| 1273961 | $G_{ks}{}^mC_{ks}A_{ks}T_{ds}G_{ds}T_{dr}T_{dq}{}^mC_{ds}T_{ds}{}^mC_{ds}A_{ds}{}^mC_{ds}A_{ds}T_{ks}T_{ks}A_k$ | 18 |
| 1273962 | $G_{ks}{}^mC_{ks}A_{ks}T_{ds}G_{ds}T_{ds}T_{dr}{}^mC_{dq}T_{ds}{}^mC_{ds}A_{ds}{}^mC_{ds}A_{ds}T_{ks}T_{ks}A_k$ | 18 |
| 1273963 | $G_{ks}{}^mC_{ks}A_{ks}T_{ds}G_{ds}T_{ds}T_{ds}{}^mC_{dr}T_{dq}{}^mC_{ds}A_{ds}{}^mC_{ds}A_{ds}T_{ks}T_{ks}A_k$ | 18 |
| 1273964 | $G_{ks}{}^mC_{ks}A_{ks}T_{ds}G_{ds}T_{ds}T_{ds}{}^mC_{ds}T_{dr}{}^mC_{dq}A_{ds}{}^mC_{ds}A_{ds}T_{ks}T_{ks}A_k$ | 18 |
| 1273965 | $G_{ks}{}^mC_{ks}A_{ks}T_{ds}G_{ds}T_{ds}T_{ds}{}^mC_{ds}T_{ds}{}^mC_{dr}A_{dq}{}^mC_{ds}A_{ds}T_{ks}T_{ks}A_k$ | 18 |
| 1273966 | $G_{ks}{}^mC_{ks}A_{ks}T_{ds}G_{ds}T_{ds}T_{ds}{}^mC_{ds}T_{ds}{}^mC_{ds}A_{dr}{}^mC_{dq}A_{ds}T_{ks}T_{ks}A_k$ | 18 |
| 1273967 | $G_{ks}{}^mC_{ks}A_{ks}T_{ds}G_{ds}T_{ds}T_{ds}{}^mC_{ds}T_{ds}{}^mC_{ds}A_{ds}{}^mC_{dr}A_{dq}T_{ks}T_{ks}A_k$ | 18 |
| 1276491 | $G_{ks}{}^mC_{ks}A_{ks}T_{ds}G^msT_{dr}T_{dq}{}^mC_{ds}T_{ds}{}^mC_{ds}A_{ds}{}^mC_{ds}A_{ds}T_{ks}T_{ks}A_k$ | 18 |
| 1276492 | $G_{ks}{}^mC_{ks}A_{ks}T_{ds}G^msT_{ds}T_{dr}{}^mC_{dq}T_{ds}{}^mC_{ds}A_{ds}{}^mC_{ds}A_{ds}T_{ks}T_{ks}A_k$ | 18 |
| 1276493 | $G_{ks}{}^mC_{ks}A_{ks}T_{ds}G^msT_{ds}T_{ds}{}^mC_{dr}T_{dq}{}^mC_{ds}A_{ds}{}^mC_{ds}A_{ds}T_{ks}T_{ks}A_k$ | 18 |
| 1276494 | $G_{ks}{}^mC_{ks}A_{ks}T_{ds}G^msT_{ds}T_{ds}{}^mC_{ds}T_{dr}{}^mC_{dq}A_{ds}{}^mC_{ds}A_{ds}T_{ks}T_{ks}A_k$ | 18 |
| 1276495 | $G_{ks}{}^mC_{ks}A_{ks}T_{ds}G^msT_{ds}T_{ds}{}^mC_{ds}T_{ds}{}^mC_{dr}A_{dq}{}^mC_{ds}A_{ds}T_{ks}T_{ks}A_k$ | 18 |
| 1276496 | $G_{ks}{}^mC_{ks}A_{ks}T_{ds}G^msT_{ds}T_{ds}{}^mC_{ds}T_{ds}{}^mC_{ds}A_{dr}{}^mC_{dq}A_{ds}T_{ks}T_{ks}A_k$ | 18 |
| 1276497 | $G_{ks}{}^mC_{ks}A_{ks}T_{ds}G^msT_{ds}T_{ds}{}^mC_{ds}T_{ds}{}^mC_{ds}A_{ds}{}^mC_{dr}A_{dq}T_{ks}T_{ks}A_k$ | 18 |

A subscript "d" indicates an unmodified, 2'-β-D-deoxyribosyl sugar moiety. A subscript "k" indicates a cEt. A superscript "m" before a C indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration. A subscript "m" represents a 2'-Omethyl modified sugar moiety.

TABLE 129

Caspase activation in 3T3L1 cells

| Compound ID | in vitro Caspase (% control) @ 20 μM |
|---|---|
| 1273959 | 1138 |
| 1273960 | 654 |
| 1273961 | 1036 |
| 1273962 | 752 |
| 1273963 | 1349 |
| 1273964 | 907 |
| 1273965 | 984 |
| 1273966 | 750 |
| 1273967 | 785 |
| 1276491 | 116 |
| 1276492 | 450 |
| 1276493 | 234 |
| 1276494 | 85 |
| 1276495 | 214 |

TABLE 129-continued

Caspase activation in 3T3L1 cells

| Compound ID | in vitro Caspase (% control) @ 20 μM |
|---|---|
| 1276496 | 165 |
| 1276497 | 148 |

Example 61

Modified oligonucleotides were designed based on compounds 546108, 546118, 465178, and 694804, described in Examples 18, 18, 19, and 13, respectively. For sequences with a T at position 5 (from the 5' end) in the parent kkk-d(10)-kkk oligonucleotide, the kkk-d-m-d(8)-kkk contains a 2'-OMe modified U at this position. For sequences with a mC at position 5 (from the 5' end) in the parent kkk-d(10)-kkk oligonucleotide, the kkk-d-m-d(8)-kkk contains a 2'-OMe modified C at this position, lacking the 5-methyl group. Each of the modified oligonucleotides is conjugated with a THA-GalNAc conjugate group at the 3'-end. The oligonucleotides were evaluated for in vivo toxicity at a single dose after 72 hours.

Six week old BALB/C mice (purchased from Charles River) were injected subcutaneously once at 50 mg/kg with the modified oligonucleotides shown below or with saline control. Each treatment group consisted of 3 animals. The mice were sacrificed 72 hours following administration, and organs and plasma were harvested for further analysis.

TABLE 130

Modified Oligonucleotides

| Compound ID | Target | position of altered nucleotide in central region | modification of altered nucleotide | Chemistry Notation (5' to 3') | SEQ ID NO |
|---|---|---|---|---|---|
| 1306441 | HDAC | N/A | N/A | $T_{ks}A_{ks}G_{ks}T_{ds}{}^mC_{ds}T_{ds}{}^mC_{ds}T_{ds}G_{ds}T_{ds}{}^mC_{ds}A_{ds}G_{ds}T_{ks}T_{ks}A_{ks}$-THA-GalNAc | 105 |
| 1306442 | HDAC | 2 | 2'-OMe | $T_{ks}A_{ks}G_{ks}T_{ds}C_{ds}T_{ds}{}^mC_{ds}T_{ds}G_{ds}T_{ds}{}^mC_{ds}A_{ds}G_{ds}T_{ks}T_{ks}A_{k}$-THA-GalNAc | 105 |
| 1306443 | HDAC | 2 | MOP | $T_{ks}A_{ks}G_{ks}T_{ds}{}^mC_{ds}T_{ds}\text{m}C_{ds}T_{ds}G_{ds}T_{ds}{}^mC_{ds}A_{ds}G_{ds}T_{ks}T_{ks}A_{k}$-THA-GalNAc | 105 |
| 1306444 | HDAC | 3 | MOP | $T_{ks}A_{ks}G_{ks}T_{ds}{}^mC_{ds}T_{dx}{}^mC_{ds}T_{ds}G_{ds}T_{ds}{}^mC_{ds}A_{ds}G_{ds}T_{ks}T_{ks}A_{k}$-THA-GalNAc | 105 |
| 1306445 | HDAC | 3 | MOP | $A_{ks}{}^mC_{ks}{}^mC_{ks}{}^mC_{ds}T_{ds}\text{m}C_{dx}A_{ds}A_{ds}G_{ds}T_{ds}{}^mC_{ds}T_{ds}{}^mC_{ds}{}^mC_{ks}T_{ks}G_{k}$-THA-GalNAc | 109 |
| 1306446 | FXI | N/A | N/A | $G_{ks}T_{ks}{}^mC_{ks}A_{ds}G_{ds}T_{ds}A_{ds}T_{ds}{}^mC_{ds}{}^mC_{ds}{}^mC_{ds}A_{ds}G_{ds}T_{ks}G_{ks}T_{k}$-THA-GalNAc | 89 |
| 1306447 | FXI | 2 | 2'-OMe | $G_{ks}T_{ks}{}^mC_{ks}A_{ds}G_{ms}T_{ds}A_{ds}T_{ds}{}^mC_{ds}{}^mC_{ds}{}^mC_{ds}A_{ds}G_{ds}T_{ks}G_{ks}T_{k}$-THA-GalNAc | 89 |
| 1306448 | FXI | 2 | MOP | $G_{ks}T_{ks}{}^mC_{ks}A_{ds}G_{dx}T_{ds}A_{ds}T_{ds}{}^mC_{ds}{}^mC_{ds}{}^mC_{ds}A_{ds}G_{ds}T_{ks}G_{ks}T_{k}$-THA-GalNAc | 89 |
| 1306449 | FXI | 3 | MOP | $G_{ks}T_{ks}{}^mC_{ks}A_{ds}G_{ds}T_{dx}A_{ds}T_{ds}{}^mC_{ds}{}^mC_{ds}{}^mC_{ds}A_{ds}G_{ds}T_{ks}G_{ks}Tk$-THA-GalNAc | 89 |
| 1306450 | DMN2 | N/A | N/A | $A_{ks}G_{ks}A_{ks}{}^mC_{ds}T_{ds}{}^mC_{ds}T_{ds}{}^mC_{ds}G_{ds}G_{ds}T_{ds}T_{ds}{}^mC_{ds}{}^mC_{ks}G_{ks}A_{k}$-THA-GalNAc | 49 |
| 1306451 | DMN2 | 2 | 2'-OMe | $A_{ks}G_{ks}A_{ks}{}^mC_{ds}U_{ms}{}^mC_{ds}T_{ds}{}^mC_{ds}G_{ds}G_{ds}T_{ds}T_{ds}{}^mC_{ds}{}^mC_{ks}G_{ks}A_{k}$-THA-GalNAc | 127 |
| 1306452 | DMN2 | 2 | MOP | $A_{ks}G_{ks}A_{ks}{}^mC_{ds}T_{dx}{}^mC_{ds}T_{ds}{}^mC_{ds}G_{ds}G_{ds}T_{ds}T_{ds}{}^mC_{ds}{}^mC_{ks}G_{ks}A_{k}$-THA-GalNAc | 49 |
| 1306453 | DMN2 | 3 | MOP | $A_{ks}G_{ks}A_{ks}{}^mC_{ds}T_{ds}{}^mC_{dx}T_{ds}{}^mC_{ds}G_{ds}G_{ds}T_{ds}T_{ds}{}^mC_{ds}{}^mC_{ks}G_{ks}A_{k}$-THA-GalNAc | 49 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "m" indicates a 2'-O-methyl-β-D-ribofuranosyl sugar moiety.

TABLE 131

In vivo Toxicity of Modified Oligonucleotides

| Compound ID | position of altered nucleotide in central region | modification of altered nucleotide | ALT (IU/L) |
|---|---|---|---|
| PBS | N/A | N/A | 28 |
| 1306441 | N/A | N/A | 2371 |
| 1306442 | 2 | 2'-OMe | 37 |
| 1306443 | 2 | MOP | 30 |
| 1306444 | 3 | MOP | 38 |
| 1306445 | 3 | MOP | 51 |
| 1306446 | N/A | N/A | 1555 |
| 1306447 | 2 | 2'-OMe | 53 |
| 1306448 | 2 | MOP | 43 |
| 1306449 | 3 | MOP | 43 |
| 1306450 | N/A | N/A | 1058 |
| 1306451 | 2 | 2'-OMe | 34 |
| 1306452 | 2 | MOP | 25 |
| 1306453 | 3 | MOP | 23 |

Example 62 Effect of 2'-OMe Incorporation on Delayed Toxicity of Modified Oligonucleotides Complementary to HDAC2

Modified oligonucleotides were synthesized with 2' modifications as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a mC at position 5 (from the 5' end) in the parent kkk-d(10)-kkk oligonucleotide, the kkk-d-m-d(8)-kkk contains a 2'-OMe modified C at this position, lacking the 5-methyl group. The modified oligonucleotides in the table below have a mixed backbone motif soosssssssssssos or soosossssssssos, wherein each "s" represents a phosphorothioate internucleoside linkage and each "o" represents a phosphodiester internucleoside linkage, as indicated by the chemistry notation in the table.

For the in vivo toxicity study in the table below, four female $C_{57}$/B16 mice per group were administered 300 μg modified oligonucleotide by intracerebroventricular (ICV) injection. At 8 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

TABLE 132

In vivo Activity and Toxicity of Modified oligonucleotides complementary to HDAC2

| Compound ID | Chemistry notation | HDAC2 mRNA (% control) Cortex | 8 week FOB | SEQ ID NO: |
|---|---|---|---|---|
| 1282276 | $G_{ks}A_{ko}{}^mC_{ko}T_{ds}{}^mC_{ds}T_{ds}{}^mC_{ds}T_{ds}G_{ds}A_{ds}T_{ds}G_{ds}A_{ds}T_{ko}A_{ks}{}^mC_k$ | 86 | 5 | 97 |
| 1282277 | $G_{ks}A_{ko}{}^mC_{ko}T_{ds}C_{ms}T_{ds}{}^mC_{ds}T_{ds}G_{ds}A_{ds}T_{ds}G_{ds}A_{ds}T_{ko}A_{ks}{}^mC_k$ | n.d. | 7 | 97 |
| 1282278 | $G_{ks}A_{ko}{}^mC_{ko}T_{ds}C_{mo}T_{ds}{}^mC_{ds}T_{ds}G_{ds}A_{ds}T_{ds}G_{ds}A_{ds}T_{ko}A_{ks}{}^mC_k$ | 72 | 6 | 97 |
| 1282280 | ${}^mC_{ks}T_{ko}A_{ko}T_{ds}A_{ds}{}^mC_{ds}{}^mC_{ds}A_{ds}Tds{}^mC_{ds}T_{ds}{}^mC_{ds}T_{ds}{}^mC_{ko}A_{ks}T_k$ | 44 | 2 | 98 |
| 1282296 | ${}^mC_{ks}T_{ko}A_{ko}T_{ds}A_{ms}{}^mC_{ds}{}^mC_{ds}A_{ds}T_{ds}{}^mC_{ds}T_{ds}{}^mC_{ds}T_{ds}{}^mC_{ko}A_{ks}T_k$ | n.d. | 7 | 98 |
| 1282622 | ${}^mC_{ks}T_{ko}A_{ko}T_{ds}A_{mo}{}^mC_{ds}{}^mC_{ds}A_{ds}T_{ds}{}^mC_{ds}T_{ds}{}^mC_{ds}T_{ds}{}^mC_{ko}A_{ks}T_k$ | 68 | 0 | 98 |
| 1282281 | $A_{ks}T_{ko}T_{ko}A_{ds}T_{ds}A_{ds}T_{ds}G_{ds}G_{ds}{}^mC_{ds}A_{ds}A_{ds}{}^mC_{ds}T_{ks}{}^mC_{ks}A_k$ | 70 | 4 | 101 |
| 1282627 | $A_{ks}T_{ko}T_{ko}A_{ds}U_{ms}A_{ds}T_{ds}G_{ds}G_{ds}{}^mC_{ds}A_{ds}A_{ds}mC_{ds}T_{ks}{}^mC_{ks}A_k$ | 50 | 0 | 139 |
| 1282282 | $G_{ks}A_{ko}{}^mC_{ko}T_{ds}A_{ds}A_{ds}T_{ds}A_{ds}T_{ds}G_{ds}{}^mC_{ds}A_{ds}G_{ds}T_{ko}T_{ks}T_k$ | 107 | 0 | 102 |
| 1282628 | $G_{ks}A_{ko}{}^mC_{ko}T_{ds}A_{ms}A_{ds}T_{ds}A_{ds}T_{ds}G_{ds}{}^mC_{ds}A_{ds}G_{ds}T_{ko}T_{ks}T_k$ | 86 | 0 | 102 |
| 1282283 | $G_{ks}T_{ks}{}^mC_{ko}A_{ds}A_{ds}A_{ds}T_{ds}T_{ds}{}^mC_{ds}A_{ds}A_{ds}G_{ds}G_{ds}G_{ko}T_{ks}T_k$ | n.d. | 7 | 103 |
| 1282629 | $G_{ks}T_{ks}mC_{ko}A_{ds}A_{ms}A_{ds}T_{ds}T_{ds}mC_{ds}A_{ds}A_{ds}G_{ds}G_{ds}G_{ko}T_{ks}T_k$ | n.d. | 7 | 103 |
| 1282284 | ${}^mC_{ks}A_{ko}T_{ko}A_{ds}A_{ds}A_{ds}G_{ds}{}^mC_{ds}A_{ds}T_{ds}G_{ds}G_{ds}T_{ds}G_{ko}G_{ks}A_k$ | n.d. | 7 | 104 |
| 1282630 | ${}^mC_{ks}A_{ko}T_{ko}A_{ds}A_{ms}A_{ds}G_{ds}{}^mC_{ds}A_{ds}T_{ds}G_{ds}G_{ds}T_{ds}G_{ko}G_{ks}A_k$ | n.d. | 7 | 104 |
| 1224264 | $G_{ks}T_{ko}A_{ko}{}^mC_{ds}{}^mC_{ds}T_{ds}A_{ds}T_{ds}A_{ds}G_{ds}T_{ds}{}^mC_{ds}T_{ds}{}^mC_{ko}T_{ks}G_k$ | n.d. | 7 | 106 |
| 1282631 | $G_{ks}T_{ko}A_{ko}{}^mC_{ds}C_{ms}T_{ds}A_{ds}T_{ds}A_{ds}G_{ds}T_{ds}{}^mC_{ds}T_{ds}{}^mC_{ko}T_{ks}G_k$ | n.d. | 7 | 106 |
| 1282285 | $T_{ks}T_{ko}G_{ko}{}^mC_{ds}{}^mC_{ds}A_{ds}A_{ds}T_{ds}A_{ds}T_{ds}{}^mC_{ds}A_{ds}{}^mC_{ds}{}^mC_{ko}A_{ks}T_k$ | n.d. | 7 | 94 |
| 1282632 | $T_{ks}T_{ko}G_{ko}{}^mC_{ds}C_{ms}A_{ds}A_{ds}T_{ds}A_{ds}T_{ds}{}^mC_{ds}A_{ds}{}^mC_{ds}{}^mC_{ko}A_{ks}T_k$ | 59 | 0 | 94 |
| 1282623 | $T_{ks}T_{ko}G_{ko}{}^mC_{ds}C_{mo}A_{ds}A_{ds}T_{ds}A_{ds}T_{ds}{}^mC_{ds}A_{ds}{}^mC_{ds}{}^mC_{ko}A_{ks}T_k$ | 88 | 0 | 94 |
| 1282286 | ${}^mC_{ks}A_{ko}A_{ko}{}^mC_{ds}T_{ds}G_{ds}A_{ds}A_{ds}{}^mC_{ds}{}^mC_{ds}A_{ds}{}^mC_{ds}{}^mC_{ds}{}^mC_{ko}G_{ks}T_k$ | 68 | 3 | 95 |
| 1282633 | ${}^mC_{ks}A_{ko}A_{ko}{}^mC_{ds}U_{ms}G_{ds}A_{ds}A_{ds}{}^mC_{ds}{}^mC_{ds}A_{ds}{}^mC_{ds}{}^mC_{ds}{}^mC_{ko}G_{ks}T_k$ | 71 | 0 | 138 |
| 1282287 | $G_{ks}{}^mC_{ko}A_{ko}{}^mC_{ds}A_{ds}A_{ds}T_{ds}A_{ds}T_{ds}{}^mC_{ds}A_{ds}T_{ds}A_{ko}A_{ks}{}^mC_k$ | 74 | 0 | 96 |
| 1282634 | $G_{ks}{}^mC_{ko}A_{ko}{}^mC_{ds}A_{ms}A_{ds}T_{ds}A_{ds}T_{ds}{}^mC_{ds}A_{ds}T_{ds}A_{ko}A_{ks}{}^mC_k$ | 70 | 0 | 96 |
| 1282288 | ${}^mC_{ks}A_{ko}T_{ko}{}^mC_{ds}A_{ds}T_{ds}{}^mC_{ds}T_{ds}A_{ds}T_{ds}A_{ds}{}^mC_{ds}{}^mC_{ds}A_{ko}T_{ks}{}^mC_k$ | 16 | 2 | 99 |
| 1282298 | ${}^mC_{ks}A_{ko}T_{ko}{}^mC_{ds}A_{ms}T_{ds}{}^mC_{ds}T_{ds}A_{ds}T_{ds}A_{ds}{}^mC_{ds}{}^mC_{ds}A_{ko}T_{ks}{}^mC_k$ | 18 | 4 | 99 |
| 1282624 | ${}^mC_{ks}A_{ko}T_{ko}{}^mC_{ds}A_{mo}T_{ds}{}^mC_{ds}T_{ds}A_{ds}T_{ds}A_{ds}{}^mC_{ds}{}^mC_{ds}A_{ko}T_{ks}{}^mC_k$ | 70 | 0 | 99 |

TABLE 132-continued

In vivo Activity and Toxicity of Modified oligonucleotides complementary to HDAC2

| Compound ID | Chemistry notation | HDAC2 mRNA (% control) Cortex | 8 week FOB | SEQ ID NO: |
|---|---|---|---|---|
| 1224263 | $A_{ks}{}^mC_{ko}A_{ko}{}^mC_{ds}A_{ds}T_{ds}T_{ds}T_{ds}A_{ds}G_{ds}{}^mC_{ds}A_{ds}T_{ds}G_{ko}A_{ks}{}^mC_k$ | n.d. | 2 | 100 |
| 1282635 | $A_{ks}{}^mC_{ko}A_{ko}{}^mC_{ds}A_{ms}T_{ds}T_{ds}T_{ds}A_{ds}G_{ds}{}^mC_{ds}A_{ds}T_{ds}G_{ko}A_{ks}{}^mC_k$ | 61 | 0 | 100 |
| 1282289 | $T_{ks}A_{ko}G_{ko}T_{ds}{}^mC_{ds}T_{ds}{}^mC_{ds}T_{ds}G_{ds}T_{ds}{}^mC_{ds}A_{ds}G_{ds}T_{ko}T_{ks}A_k$ | n.d. | 7 | 105 |
| 1282621 | $T_{ks}A_{ko}G_{ko}T_{ds}C_{ms}T_{ds}{}^mC_{ds}T_{ds}G_{ds}T_{ds}{}^mC_{ds}A_{ds}G_{ds}T_{ko}T_{ks}A_k$ | n.d. | 7 | 105 |
| 1282625 | $T_{ks}A_{ko}G_{ko}T_{ds}C_{mo}T_{ds}{}^mC_{ds}T_{ds}G_{ds}T_{ds}{}^mC_{ds}A_{ds}G_{ds}T_{ko}T_{ks}A_k$ | n.d | 6 | 105 |
| 1282290 | $T_{ks}{}^mC_{ko}A_{ko}T_{ds}G_{ds}T_{ds}A_{ds}{}^mC_{ds}{}^mC_{ds}T_{ds}A_{ds}T_{ds}A_{ds}G_{ko}T_{ks}{}^mC_k$ | 22 | 6 | 107 |
| 1282300 | $T_{ks}{}^mC_{ko}A_{ko}T_{ds}G_{ms}TdsA_{ds}{}^mC_{ds}mC_{ds}T_{ds}A_{ds}T_{ds}A_{ds}G_{ko}T_{ks}{}^mC_k$ | 60 | 0 | 107 |
| 1282626 | $T_{ks}{}^mC_{ko}A_{ko}T_{ds}G_{mo}T_{ds}A_{ds}mC_{ds}{}^mC_{ds}T_{ds}A_{ds}T_{ds}A_{ds}G_{ko}T_{ks}{}^mC_k$ | 107 | 0 | 107 |
| 1282291 | $T_{ks}{}^mC_{ko}T_{ko}T_{ds}A_{ds}A_{ds}T_{ds}T_{ds}T_{ds}{}^mC_{ds}AdsT_{ds}G_{ds}T_{ko}A_{ks}{}^mC_k$ | 64 | 0 | 108 |
| 1282636 | $T_{ks}{}^mC_{ko}T_{ko}T_{ds}A_{ms}A_{ds}T_{ds}T_{ds}T_{ds}{}^mC_{ds}A_{ds}T_{ds}G_{ds}T_{ko}A_{ks}{}^mC_k$ | 65 | 0 | 108 |
| 1282292 | $A_{ks}{}^mC_{ko}{}^mC_{ko}mC_{ds}T_{ds}mC_{ds}A_{ds}A_{ds}G_{ds}T_{ds}{}^mC_{ds}T_{ds}{}^mC_{ds}{}^mC_{ko}T_{ks}G_k$ | n.d. | 6 | 109 |
| 1282637 | $A_{ks}{}^mC_{ko}{}^mC_{ko}mC_{ds}U_{ms}mC_{ds}A_{ds}A_{ds}G_{ds}T_{ds}{}^mC_{ds}T_{ds}{}^mC_{ds}{}^mC_{ko}T_{ks}G_k$ | n. d. | 7 | 109 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

Example 63 Effect of Incorporation of 2'-OMe at Various Positions

Modified oligonucleotides were synthesized with 2' modifications as indicated in the table below. The compounds have the sugar motif of kkk-d-m-d(8)-kkk, kkk-d(8)-m-d-kkk, or kkk-mm-d(8)-kkk where "k" represents a cEt, "d" represents an unmodified, 2'-β-D-deoxyribosyl sugar moiety, and "m" represents a 2'-OMe-β-D-ribofuranosyl sugar moiety. For parent sequences with a T at the 2'-OMe-modified position, modified sequences contain a 2'-OMe modified U at this position. For parent sequences with a mC at the 2'-OMe-modified position, modified sequences contain a 2'-OMe modified C at this position, lacking the 5-methyl group.

TABLE 133

Modified Oligonucleotides

| Compound ID | Target | position of altered nucleotide in central region | modification of altered nucleotide | Chemistry Notation (5' to 3') | SEQ ID NO |
|---|---|---|---|---|---|
| 936053 | CXCL12 | 2 | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 18 |
| 1244114 | CXCL12 | 9 | 2'-OMe | $G_{ks}{}^mC_{ks}A_{ks}T_{ds}G_{ds}T_{ds}T_{ds}{}^mC_{ds}T_{ds}{}^mC_{ds}A_{ds}C_{ms}A_{ds}T_{ks}T_{ks}A_k$ | 18 |
| 1306760 | CXCL12 | 1, 2 | 2'-OMe | $G_{ks}{}^mC_{ks}A_{ks}U_{ms}G_{ms}T_{ds}T_{ds}mC_{ds}T_{ds}{}^mC_{ds}A_{ds}{}^mC_{ds}A_{ds}T_{ks}T_{ks}A_k$ | 19 |
| 895155 | SOD-1 | 2 | 2'-OMe | $T_{ks}G_{ks}A_{ks}G_{ds}sG_{ms}T_{ds}{}^mC_{ds}{}^mC_{ds}T_{ds}G_{ds}{}^mC_{ds}A_{ds}{}^mC_{ds}T_{ks}G_{ks}G_k$ | 26 |
| 1308544 | SOD-1 | 9 | 2'-OMe | $T_{ks}G_{ks}A_{ks}G_{ds}G_{ds}T_{ds}{}^mC_{ds}{}^mC_{ds}T_{ds}G_{ds}{}^mC_{ds}A_{ms}{}^mCdsTksGksGk$ | 26 |
| 1309002 | SOD-1 | 1, 2 | 2'-OMe | $T_{ks}G_{ks}A_{ks}G_{ms}G_{ms}T_{ds}{}^mC_{ds}{}^mC_{ds}T_{ds}G_{ds}{}^mC_{ds}A_d{}^mC_{ds}T_{ks}G_{ks}G_k$ | 26 |
| 1133122 | HDAC2 | 2 | 2'-OMe | $T_{ks}A_{ks}G_{ks}T_{ds}C_{ms}T_{ds}{}^mC_{ds}T_{ds}G_{ds}T_{ds}{}^mC_{ds}A_{ds}G_{ds}T_{ks}T_{ks}A_k$ | 105 |
| 1308545 | HDAC2 | 9 | 2'-OMe | $T_{ks}A_{ks}G_{ks}T_{ds}{}^mC_{ds}T_{ds}{}^mC_{ds}T_{ds}G_{ds}T_{ds}{}^mC_{ds}A_{ms}G_{ds}T_{ks}T_{ks}A_k$ | 105 |
| 1309073 | HDAC2 | 1, 2 | 2'-OMe | $T_{ks}A_{ks}G_{ks}U_{ms}C_{ms}T_{ds}{}^mC_{ds}T_{ds}G_{ds}T_{ds}{}^mC_{ds}A_{ds}G_{ds}T_{ks}T_{ks}A_k$ | 145 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

Six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis. The oligonucleotides were evaluated for reduction in target mRNA expression levels in vivo. P21 and Tnfrsf10b mRNA levels were also measured. The transaminase levels (ALT and AST) for each dose were also measured.

TABLE 134

In vivo Activity and Toxicity of Modified Oligonucleotides

| Compound ID | position of altered nucleotide in central region | ALT (IU/L) @ 50 mg/kg | ALT (IU/L) @ 150 mg/kg | ED50 (mg/kg) for target |
|---|---|---|---|---|
| 936053 | 2 | 11 | 109 | 3.5 |
| 1244114 | 9 | 9092 | death | 1.0 |
| 1306760 | 1, 2 | 16 | 436 | 3.0 |
| 895155 | 2 | 29 | 110 | 11.0 |
| 1308544 | 9 | 2054 | 14507 | 27.7 |
| 1309002 | 1, 2 | 6 | 64 | 47.6 |
| 1133122 | 2 | 31 | 76 | 2.7 |
| 1308545 | 9 | 24695 | death | 0.9 |
| 1309073 | 1, 2 | 28 | 128 | 3.1 |

Example 63 Effect of Incorporation of 2'-OMe in a Modified Oligonucleotide with 11 Nucleosides in the Central Region Modified oligonucleotides were synthesized with 2' modifications as indicated in the table below. The compounds have the sugar motif of kkk-d(11)-kkk, kkk-d-m-d(9)-kkk, or kkk-dd-m-d(8)-kkk, where "k" represents a cEt, "d" represents an unmodified, 2'-β-D-deoxyribosyl sugar moiety, and "m" represents a 2'-OMe-β-D-ribofuranosyl modified sugar moiety. For parent sequences with a T at the 2'-OMe-modified position, modified sequences contain a 2'-OMe modified U at this position.

TABLE 135

Modified Oligonucleotides

| Compound ID | Target | position of altered nucleoside in central region | modification of altered nucleoside | Chemistry Notation (5' to 3') | SEQ ID NO |
|---|---|---|---|---|---|
| 1280764 | CXCL12 | N/A | 2'-OMe | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ds}T_{ks}A_{ks}T_k$ | 125 |
| 1280763 | CXCL12 | 2 | 2'-OMe | $G_{ks}{}^mC_{ks}A_{ks}T_{ds}G_{ds}T_{ds}T_{ds}{}^mC_{ds}T_{ds}{}^mC_{ds}A_{ds}C_{ms}A_{ds}T_{ds}T_{ks}A_{ks}T_k$ | 125 |
| 1306440 | CXCL12 | 3 | 2'-OMe | $G_{ks}{}^mC_{ks}A_{ks}T_{ds}G_{ds}U_{ms}T_{ds}{}^mC_{ds}T_{ds}{}^mC_{ds}A_{ds}{}^mC_{ds}A_{ds}T_{ds}T_{ks}A_{ks}T_k$ | 146 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

Six week old BALB/C mice (purchased from Charles River) were injected subcutaneously once at dosage 50 or 150 mg/kg with the modified oligonucleotides shown below or with saline control. Each treatment group consisted of 3 animals. The mice were sacrificed 72 hours following administration, and organs and plasma were harvested for further analysis. P21 and Tnfrsf10b mRNA levels were measured. The transaminase levels (ALT and AST) for each dose were also measured.

TABLE 136

In vivo Activity and Toxicity of Modified Oligonucleotides with an 11-base central region

| Compound ID | position of 2'-OMe nucleotide in central region | ALT (IU/L) @ 50 mg/kg | ALT (IU/L) @ 150 mg/kg | P21 mRNA @ 50 mg/kg | Tnfrsf10b mRNA @ 150 mg/kg |
|---|---|---|---|---|---|
| 1280764 | N/A | death | death | death | death |
| 1280763 | 2 | 109 | 112 | 236 | 460 |
| 1306440 | 3 | 5109 | 7614 | 7022 | 13361 |

Example 65 Effect of Incorporation of 2'-OMe in a Modified Oligonucleotide on Kidney Toxicity Modified oligonucleotides were synthesized as indicated in the table below. The compounds have the sugar motif of kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety.

TABLE 137

Modified Oligonucleotides

| Compound ID | position of altered nucleotide in central region | modification of altered nucleotide | Chemistry Notation (5' to 3') | SEQ ID NO |
|---|---|---|---|---|
| 683702 | N/A | N/A | $A_{ks}C_{ks}A_{ks}A_{ds}G_{ds}G_{ds}A_{ds}{}^mC_{ds}A_{ds}{}^mC_{ds}{}^mC_{ds}$ $A_{ds}A_{ds}G_{ks}A_{ks}T_{ks}$ | 147 |
| 1295373 | 2 | 2'-OMe | $A_{ks}C_{ks}A_{ks}A_{ds}G_{ms}G_{ds}A_{ds}{}^mC_{ds}A_{ds}{}^mC_{ds}{}^mC_{ds}$ $A_{ds}A_{ds}G_{ks}A_{ks}T_{ks}$ | 147 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

8-10 week old Sprague Dawley rats were injected subcutaneously at dosage 50 mg/kg/week for two weeks (3 total injections) with the modified oligonucleotides shown below or with saline control. Each treatment group consisted of 3 animals. The mice were sacrificed 72 hours following administration, and organs and plasma were harvested for further analysis. KIM-1, NGAL, P21 and Tnfrsf10b mRNA levels were measured. Primer probe set rHAVCR1 (forward sequence: GGGATTACAGAGATCGTGACTGATT (SEQ ID NO: 148), reverse sequence: TGCAGCTGGAAGAAC-CAAAA (SEQ ID NO:149), probe sequence CAGAGTAAAATACCCATTCCAGCTCCTGGG (SEQ ID NO: 150)) was used to measure KIM-1 and primer probe set RTS4389 (forward sequence: GATTCGTCAGCTTTGC-CAAGT (SEQ ID NO: 151), reverse sequence: CGTCTGTTCAGTTGTCAATGCA (SEQ ID NO:152), probe sequence TCTGGGCCTCAAGGATAACAA-CATCGTTT (SEQ ID NO: 153)) was used to measure NGAL. The transaminase levels (ALT and AST) for each dose were also measured.

TABLE 138

In vivo Toxicity of Modified Oligonucleotides in kidney

| Compound ID | 2'-OMe position in central region | ALT (IU/L) | P21 mRNA (liver) | KIM-1 mRNA (kidney) | NGAL mRNA (kidney) | P21 mRNA (kidney) |
|---|---|---|---|---|---|---|
| 683702 | N/A | 393 | 1243 | 3449 | 741 | 439 |
| 1295373 | 2 | 39 | 92 | 122 | 142 | 98 |

Example 66 Nucleosides with Various Chemistries at Position 2 and 3 of the Central Region Modified oligonucleotides containing altered nucleotides at position 2 of the central region were synthesized. The compounds in the table below are 100% complementary to mouse FXI. The sequence of the oligonucleotides is GTT-ATTGTGGTTGGCG (SEQ ID NO: 81), GTTAUT-GTGGTTGGCG (SEQ ID NO: 133), or GTTATUGTGGTTGGCG (SEQ ID NO: 154) as indicated in the table below. The compounds have the sugar motif kkk-d-Z-d(8)-kkk or kkk-dd-Z-d(7)-kkk, where "k" represents a cEt, "d" represents an unmodified, 2'-β-D-deoxyribosyl sugar moiety, and "Z" represents a nucleotide comprising a modification as indicated in Table 139 below.

Compounds were tested in 3T3-L1 cells for caspase activation essentially as described in Example 1 above.

TABLE 139

Modified oligonucleotides and in vitro toxicity

| Compound ID | position of altered nucleotide in central region | modification of altered nucleotide | SEQ ID NO | in vitro Caspase (% control) @ 40 μM |
|---|---|---|---|---|
| 464924 | N/A | N/A | 81 | 246 |
| 1326529 | 2 | cEt | 81 | 593 |
| 1326530 | 3 | cEt | 81 | 376 |
| 1326531 | 2 | 2'-MOE | 81 | 146 |
| 1326532 | 3 | 2'-MOE | 81 | 121 |
| 1133247 | 2 | 2'-OMe | 133 | 133 |
| 1326533 | 3 | 2'-OMe | 154 | 126 |
| 1326534 | 2 | 2'-FANA | 133 | 65 |
| 1326535 | 3 | 2'-FANA | 154 | 158 |
| 1326536 | 2 | 2'-ribo-F | 133 | 116 |
| 1326537 | 3 | 2'-ribo-F | 154 | 103 |
| 1326538 | 2 | F-HNA | 81 | 115 |
| 1326539 | 3 | F-HNA | 81 | 298 |
| 1351257 | 2 | LNA | 81 | 665 |
| 1351258 | 3 | LNA | 81 | 136 |
| 1351259 | 2 | α-L-LNA | 133 | 217 |
| 1351260 | 3 | α-L-LNA | 154 | 114 |
| 1351261 | 2 | ENA | 81 | 175 |
| 1351262 | 3 | ENA | 81 | 209 |

"cEt" has the meaning set forth herein. "2'-MOE" has the meaning set forth herein. "2'-OMe" has the meaning set forth herein. "2'-FANA" indicates a 2'-F-β-D-arabinofuranosyl modified sugar moiety. "F-HNA" has the meaning set forth herein. "2'-ribo-F" indicates a 2'-fluororibose. "LNA" has the meaning set forth herein. "α-L-LNA" has the meaning set forth herein. "ENA" has the meaning set forth herein.

Example 67 Nucleosides with Various Chemistries at Position 2 and 3 of the Central Region Modified oligonucleotides with 2'-5' internucleoside linkages in the central region were synthesized as indicated in the table below, "k" represents a cEt, and "d" represents an unmodified, 2'-β-D-deoxyribosyl sugar moiety, and "25s" represents a 2'-5' internucleoside linkage. An example of a 2'-5' internucleoside linkage is shown below:

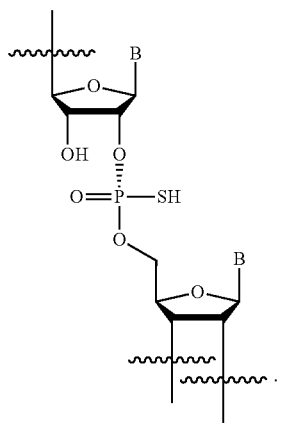

These modified oligonucleotides were compared to the otherwise identical modified oligonucleotide lacking an altered internucleoside linkage nucleotide in the central region, a 3-10-3 cEt gapmer, having three cEt nucleosides in each of the 5' and 3' regions and 10 DNA nucleosides in the central region (compound 558807). The modified oligonucleotides were also compared to a modified oligonucleotide having a 2'OMe at position 2 of the central region (Compound 936053). As demonstrated by the caspase activity, placement of a 2'-5' internucleoside linkage at certain positions in the central region reduces caspase activity compared to the otherwise identical modified oligonucleotide lacking an altered internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

The compounds were tested in Hepa1-6 cells for caspase activation essentially as described in Example 1 above and the results are shown in the table below.

TABLE 140

Modified oligonucleotides complementary to CXCL12

| Compound ID | position of altered linkage in central region | Chemistry Notation (5'-3') | in vitro Caspase (% control) @ 20 μM | SEQ ID NO |
|---|---|---|---|---|
| 558807 | n/a | $G_{ks}{}^mC_{ks}A_{ks}T_{ds}G_{ds}T_{ds}T_{ds}{}^mC_{ds}T_{ds}{}^mC_{ds}A_{ds}{}^mC_{ds}A_{ds}T_{ks}T_{ks}A_k$ | 3843 | 18 |
| 936053 | n/a | $G_{ks}{}^mC_{ks}A_{ks}T_{ds}G_{ms}T_{ds}T_{ds}{}^mC_{ds}T_{ds}{}^mC_{ds}A_{ds}{}^mC_{ds}A_{ds}T_{ks}T_{ks}A_k$ | 148 | 18 |
| 1273969 | 1 | $G_{ks}{}^mC_{ks}A_{ks}U_{d25s}G_{ms}T_{ds}T_{ds}{}^mC_{ds}T_{ds}{}^mC_{ds}A_{ds}{}^mC_{ds}A_{ds}T_{ks}T_{ks}A_k$ | 538 | 19 |
| 1306771 | 2 | $G_{ks}{}^mC_{ks}A_{ks}T_{ds}G_{m25s}T_{ds}T_{ds}{}^mC_{ds}T_{ds}{}^mC_{ds}A_{ds}{}^mC_{ds}A_{ds}T_{ks}T_{ks}A_k$ | 526 | 18 |
| 1307546 | 3 | $G_{ks}{}^mC_{ks}A_{ks}T_{ds}G_{ms}U_{d25s}T_{ds}{}^mC_{ds}T_{ds}{}^mC_{ds}A_{ds}{}^mC_{ds}A_{ds}T_{ks}T_{ks}A_k$ | 164 | 20 |
| 1306773 | 4 | $G_{ks}{}^mC_{ks}A_{ks}T_{ds}G_{ms}T_{ds}U_{d25s}{}^mC_{ds}T_{ds}{}^mC_{ds}A_{ds}{}^mC_{ds}A_{ds}T_{ks}T_{ks}A_k$ | 210 | 21 |
| 1306777 | 5 | $G_{ks}{}^mC_{ks}A_{ks}T_{ds}G_{ms}T_{ds}T_{ds}{}^mC_{d25s}T_{ds}{}^mC_{ds}A_{ds}{}^mC_{ds}A_{ds}T_{ks}T_{ks}A_k$ | 4293 | 18 |
| 1309496 | 6 | $G_{ks}{}^mC_{ks}A_{ks}T_{ds}G_{ms}T_{ds}T_{ds}{}^mC_{ds}U_{d25s}{}^mC_{ds}A_{ds}{}^mC_{ds}A_{ds}T_{ks}T_{ks}A_k$ | 3744 | 39 |
| 1306759 | 7 | $G_{ks}{}^mC_{ks}A_{ks}T_{ds}G_{ms}T_{ds}T_{ds}{}^mC_{ds}T_{ds}{}^mC_{d25s}A_{ds}{}^mC_{ds}A_{ds}T_{ks}T_{ks}A_k$ | 3408 | 18 |
| 1306738 | 8 | $G_{ks}{}^mC_{ks}A_{ks}T_{ds}G_{ms}T_{ds}T_{ds}{}^mC_{ds}T_{ds}{}^mC_{ds}A_{d25s}{}^mC_{ds}A_{ds}T_{ks}T_{ks}A_k$ | 2162 | 18 |
| 1306931 | 9 | $G_{ks}{}^mC_{ks}A_{ks}T_{ds}G_{ms}T_{ds}T_{ds}{}^mC_{ds}T_{ds}{}^mC_{ds}A_{ds}{}^mC_{d25s}A_{ds}T_{ks}T_{ks}A_k$ | 4384 | 18 |
| 1306769 | 10 | $G_{ks}{}^mC_{ks}A_{ks}T_{ds}G_{ms}T_{ds}T_{ds}{}^mC_{ds}T_{ds}{}^mC_{ds}A_{ds}{}^mCdsA_{d25s}T_{ks}T_{ks}A_k$ | 4769 | 18 |

What is claimed:

1. An oligomeric compound comprising a modified oligonucleotide consisting of 16 linked nucleosides, wherein the modified oligonucleotide has a 5'-region, a central region, and a 3'-region, wherein:
the 5'-region consists of 3 linked nucleosides, each comprising a 4'-to-2' linked bicyclic sugar moiety;
the 3' region consists of 3 linked nucleosides, each comprising a 4'-to-2' linked bicyclic sugar moiety;
and the central region consists of 10 linked nucleosides, wherein the central region has the following formula:

$(N_d)(N_x)(N_d)_n$ wherein $N_x$ is a nucleoside comprising a 2'-OMe-β-D-ribofuranosyl sugar moiety and each $N_d$ is a nucleoside comprising a 2'-β-D-deoxyribosyl sugar moiety;
and n is 8.

2. The oligomeric compound of claim 1, wherein each 4'-to-2' linked bicyclic sugar moiety of each nucleoside of the 5' region is independently selected from cEt, LNA, and ENA.

3. The oligomeric compound of claim 1, wherein each 4'-to-2' linked bicyclic sugar moiety of each nucleoside of the 3' region is independently selected from cEt, LNA, and ENA.

4. The oligomeric compound of claim 1, wherein each 4'-to-2' linked bicyclic sugar moiety of each nucleoside of the 3' region and the 5' region is independently selected from cEt and LNA.

5. The oligomeric compound of claim 1, wherein each nucleobase of each nucleoside of the modified oligonucleotide is independently selected from thymine, uracil, guanine, cytosine, 5-methylcytosine, and adenine.

6. The oligomeric compound of claim 1, wherein each internucleoside linkage is independently selected from phosphodiester and phosphorothioate internucleoside linkages.

7. The oligomeric compound of claim 1, wherein at least one internucleoside linkage within the central region is a modified internucleoside linkage other than phosphorothioate and each remaining internucleoside linkage in the modified oligonucleotide is independently selected from phosphodiester and phosphorothioate internucleoside linkages.

8. The oligomeric compound of claim 1, wherein the nucleobase sequence of the modified oligonucleotide is at least 85%, at least 90%, at least 95%, or 100% complementary to a target RNA.

9. The oligomeric compound of claim 8, wherein the target RNA is a target mRNA or a target pre-mRNA.

10. The oligomeric compound of claim 8, wherein the target RNA is expressed in the liver, in the central nervous system, and/or in muscle cells.

11. The oligomeric compound of claim 8, wherein the target RNA is expressed in cancer cells.

12. The oligomeric compound of claim 8, wherein the target RNA is selected from a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

13. The oligomeric compound of claim 7, wherein the modified internucleoside linkage other than phosphorothioate is a methoxypropyl internucleoside linkage.

14. The oligomeric compound of claim 7, wherein the central region contains exactly one modified internucleoside linkage other than phosphorothioate.

15. The oligomeric compound of claim 1, comprising a conjugate group.

16. The oligomeric compound of claim 15, wherein the conjugate group comprises GalNAc.

17. A method comprising administering the oligomeric compound of claim 1 to a subject.

18. The oligomeric compound of claim 1, wherein the modified oligonucleotide consists of the motif kkk-d-m-d(8)-kkk, wherein each k is a nucleoside comprising a cEt sugar moiety, wherein each d is a nucleoside comprising a 2'-β-D-deoxyribosyl sugar moiety, and wherein m is a nucleoside comprising a 2'-OMe-β-D-ribofuranosyl sugar moiety.

19. The oligomeric compound of claim 18, wherein each nucleobase of each nucleoside of the modified oligonucleotide is independently selected from thymine, uracil, guanine, cytosine, 5-methylcytosine, and adenine.

20. The oligomeric compound of claim 18, wherein each internucleoside linkage is independently selected from phosphodiester and phosphorothioate internucleoside linkages.

21. The oligomeric compound of claim 18, comprising a conjugate group.

22. The oligomeric compound of claim 21, wherein the conjugate group comprises GalNAc.

23. A method comprising administering the oligomeric compound of claim 18 to a subject.

24. The oligomeric compound of claim 1, wherein the modified oligonucleotide consists of the motif lll-d-m-d(8)-lll, wherein each l is a nucleoside comprising a β-D-LNA sugar moiety, wherein each d is a nucleoside comprising a 2'-β-D-deoxyribosyl sugar moiety, and wherein m is a nucleoside comprising a 2'-OMe-β-D-ribofuranosyl sugar moiety.

25. The oligomeric compound of claim 24, wherein each nucleobase of each nucleoside of the modified oligonucleotide is independently selected from thymine, uracil, guanine, cytosine, 5-methylcytosine, and adenine.

26. The oligomeric compound of claim 24, wherein each internucleoside linkage is independently selected from phosphodiester and phosphorothioate internucleoside linkages.

27. The oligomeric compound of claim 24, comprising a conjugate group.

28. The oligomeric compound of claim 27, wherein the conjugate group comprises GalNAc.

29. A method comprising administering the oligomeric compound of claim 24 to a subject.

* * * * *